(12) United States Patent
Molteni et al.

(10) Patent No.: US 7,592,349 B2
(45) Date of Patent: *Sep. 22, 2009

(54) DIARYLAMINE-CONTAINING COMPOUNDS AND COMPOSITIONS, AND THEIR USE AS MODULATORS OF C-KIT RECEPTORS

(75) Inventors: Valentina Molteni, San Diego, CA (US); Shuli You, Shanghai (CN); Juliet Nabakka, Santee, CA (US); Yi Liu, San Diego, CA (US); Xiaolin Li, San Diego, CA (US); Donatella Chianelli, San Diego, CA (US); Jon Loren, San Diego, CA (US); Xiaodong Liu, San Diego, CA (US); Shifeng Pan, San Diego, CA (US); Donald S. Karanewsky, Escondido, CA (US); Pascal Furet, Thann (FR); Vito Guagnano, Basel (CH)

(73) Assignees: IRM LLC, Hamilton (BM); Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/933,056

(22) Filed: Oct. 31, 2007

(65) Prior Publication Data

US 2008/0139559 A1 Jun. 12, 2008

Related U.S. Application Data

(63) Continuation of application No. 11/535,455, filed on Sep. 26, 2006, now Pat. No. 7,514,447.

(60) Provisional application No. 60/721,015, filed on Sep. 27, 2005.

(51) Int. Cl.
*A61K 31/505* (2006.01)
*A61K 31/506* (2006.01)
*C07D 239/42* (2006.01)
*C07D 403/04* (2006.01)
*C07D 403/14* (2006.01)
*A61P 35/00* (2006.01)

(52) U.S. Cl. .................. 514/275; 544/330; 544/331; 544/332

(58) Field of Classification Search .................. 544/300, 544/330, 331, 332; 514/275
See application file for complete search history.

(56) References Cited

U.S. PATENT DOCUMENTS

2003/0191312 A1 10/2003 Ding et al.
2004/0102453 A1 5/2004 Buerger et al.

FOREIGN PATENT DOCUMENTS

EP 0164204 A1 12/1985

OTHER PUBLICATIONS

Biegon, A., "Effects of Steroid Hormones on the Serotonergic System," Ann. NY Acad. Sci. 600:427-431 (1990).
Carroll, B.J. et al., "A Specific Laboratory Test for the Diagnosis of Melancholia," Arch. Gen. Psychiat. 38:15-22 (1981).
CAS Search, Jun. 7, 2005.
Fedorak et al., "A novel, colon-specific steroid prodrug enhances sodium chloride absorption in rat colitis," Am. J. Physiol. 269:G210-G218 (1995).
Hochhaus et al., A Selective HPLC/RIA for Dexamethasone and its Prodrug.
Dexamethasone-21-sulphobenzoate Sodium in Biological Fluids, Biomed. Chrom. 6:283-286 (1992).
Kapur, S. et al., "Role of the Dopaminergic System in Depression," Biol. Psychiat. 32:1-17 (1992).
Larsen, J. et al., "Prodrug forms for the sulfonamide group. II. Water-soluble amino acid derivatives of N-methylsulfonamides as possible prodrugs," Int. J. Pharmaceutics 47:103-110 (1988).
Larsen, J. and Bundgaard, H., "Prodrug forms for the sulfonamide group. I. Evaluation of N-acyl derivatives, N-sulfonylamidines, N-sulfonylsulfilimines and sulfonylureas as possible prodrug derivatives," Int. J. Pharmaceutics 37:87-95 (1987).
Lloyd, K.G. et al., "The Gabaergic Hypothesis of Depression," Prog. Neuro-Psycopharmacol. Biol. Psychiat. 13:341-351 (1989).
McLeod et al., A Glucocorticoid Prodrug Facilitates Normal Mucosal Function in Rat Colitis Without Adrenal Suppression,: Gastroenterol. 106:405-413 (1994).
Munemura, M. et al., "Chronis Estrogen Treatment Promotes a Functional Uncoupling of the $D_2$ Dopamine Receptor in Rat Anterior Pituitary Gland," Endocrinology 124:346-355 (1989).
Pinder, R.M. et al., "Third-Generation Antidepressants," Med. Res. Rev. 13:259-325 (1993).
Rasmussen, K. and Aghajanian, G.K., "Effect of hallucinogens on spontaneous and sensory-evoked locus coeruleus unit activity in the rat: reversal by selective $5-HT_2$ antagonists," Brain Res. 385:395-400 (1986).
Roy, E.J. et al., "Estradiol in the Striatum: Effects on Behavior and Dopamine Receptors but no Evidence for Membrane Steroid Receptors," Brain. Res. Bull. 25:221-227 (1990).
Saulnier et al., "An Efficient Method for the Synthesis of Guanidino Prodrugs," Bioorganic and Medicinal Chemistry Letters 4:1985-1990 (1994).
Shildkraut, J. et al., "The Catecholamine Hypothesis of Affective Disorders: A Review of Supporting Evidence," Am. J. Psychiat. 12:509-522 (1965).

(Continued)

Primary Examiner—Venkataraman Balasubramanian
(74) Attorney, Agent, or Firm—Daniel E. Raymond; Genomics Institute of the Novartis Research Foundation

(57) ABSTRACT

Described herein are compounds that include a diarylamine structural feature. Also described herein are methods for making such compounds, methods for using such compounds to modulate the activity of c-kit receptors, and pharmaceutical compositions and medicaments comprising such compounds. Also described herein are methods of using such compounds, pharmaceutical compositions and medicaments to treat and/or prevent and/or inhibit and/or ameliorate the pathology and/or symptomology diseases or conditions associated with the activity of c-kit receptors.

14 Claims, No Drawings

OTHER PUBLICATIONS

Siever, L.J. and Davis, K.L., "Overview: Toward a Dysregulatio Hypothesis of Depression," Am. J. Psychiat. 142:1017-1031 (1985).
Sinkula, A.A. and Yalkowsky, S.H., "Rationale for Design of Biologically Reversible Drug Derivatives: Prodrugs," J. Pharm. Sci. 64:181-210 (1975).
Sugrue, M.F. et al., "Current Concepts on the Mechanisms of Action of Antidepressant Drugs," Pharmacol. Ther. 13:219-247 (1981).
Sulser,F. et al., "Commentary. Mode of Action of Antidepressant Drugs," Biochem. Pharmacol. 27:257-261 (1978).
Mol, C.D. et al., "Structure of a c-Kit Product Complex Reveals the Basis for Kinase Transactivation," J. Biol. Chem. 278(34):31461-31464 (2003).
Zhang, Z. et al., "Crystal structure of human stem cell factor: Implication for stem cell factor receptor dimerization and activation," PNAS 97(14):7732-7737 (2000).
PCT/US06/37820 Search Report dated Sep. 5, 2007.
Kitamura et al., Cell. Mol. Life Sci. 61:2924-2931 (2004).
Cecil Textbook of Medicine, eds. Bennet, J.C. and Plum, F., $20^{th}$ ed. vol. 1, pp. 1004-1010, 1996.
Wolft, Manfred E., "Burger's Medicinal Chemistry," $5^{th}$ ed., Part 1, John Wiley & Sons, 1995, pp. 975-977.
Banker, G. S. et al., "Modern Pharmaceutics," 3rd ed., Marcel Dekker, NY, 1996, pp. 451 and 596.
West, A.R., "Solid State Chemistry and its Applications," Wiley, NY 1988, pp. 358 and 365.
Vippagunta et al., Advanced Drug Delivery Reviews 48:3-26 (2001).

US 7,592,349 B2

DIARYLAMINE-CONTAINING COMPOUNDS AND COMPOSITIONS, AND THEIR USE AS MODULATORS OF C-KIT RECEPTORS

CROSS-REFERENCE

This application is a continuation application of U.S. patent application Ser. No. 11/535,455, filed Sep. 26, 2006, now U.S. Pat. No. 7,514,447 and published as U.S. Patent Application Publication No. 2007/0149538, which claims the benefit, of provisional application Ser. No. 60/721,015 filed Sep. 27, 2005, the disclosures of which are herein incorporated by reference in their entirety for all purposes.

FIELD OF THE INVENTION

Compounds, methods of making such compounds, pharmaceutical compositions and medicaments comprising such compounds, and methods of using such compounds to treat or prevent diseases or conditions associated with c-kit receptor activity are described.

BACKGROUND OF THE INVENTION

The c-kit gene encodes a receptor tyrosine kinase and the ligand for the c-kit receptor is called the stem cell factor (SCF), which is the principal growth factor for mast cells. The activity of the c-kit receptor protein tyrosine kinase is regulated in normal cells, and the normal functional activity of the c-kit gene product is essential for maintenance of normal hematopoeisis, melanogenesis, genetogensis, and growth and differentiation of mast cells. Mutations that cause constitutive activation of c-kit kinase activity in the absence of SCF binding are implicated in various diseases including malignant human cancers.

SUMMARY OF THE INVENTION

In one aspect are compounds having a diarylamine structure. In another aspect is the method of using such compounds having a diarylamine structure for the modulation of a c-kit receptor.

In another aspect is the use of such compounds having a diarylamine structure in the treatment of a disease or condition, or to produce a medicament for the treatment of a disease or condition, in which modulation of c-kit receptor activity can prevent, inhibit or ameliorate the pathology and/or symptoms of the disease or condition. In further or alternative embodiments, such diarylamine compounds comprise at least one heterocycle group. In further or alternative embodiments, such heterocycle groups contain at least one nitrogen. In further or alternative embodiments, such heterocycle groups are pyrimidines. In further or alternative embodiments, such diarylamines further comprise multicyclic aryl groups. In further or alternative embodiments, such diarylamines further comprise at least one tricyclic aryl groups. In further or alternative embodiments, such diarylamines further comprise at least one bicyclic aryl groups. In further or alternative embodiments, such diarylamines further comprise at least one monocyclic aryl groups. In further or alternative embodiments, the multicyclic aryl groups comprise at least one heterocycle. In further or alternative embodiments, the tricyclic aryl groups comprise at least one heterocycle. In further or alternative embodiments, the bicyclic aryl groups comprise at least one heterocycle. In further or alternative embodiments, the monocyclic aryl group is a heterocycle.

In another aspect are pharmaceutical compositions comprising such a compound having a diarylamine structure. In further or alternative embodiments, such diarylamine compounds comprise at least one heterocycle group. In further or alternative embodiments, such heterocycle groups contain at least one nitrogen. In further or alternative embodiments, such heterocycle groups are pyrimidines. In further or alternative embodiments, such diarylamines further comprise multicyclic aryl groups. In further or alternative embodiments, such diarylamines further comprise at least one tricyclic aryl groups. In further or alternative embodiments, such diarylamines further comprise at least one bicyclic aryl groups. In further or alternative embodiments, such diarylamines further comprise at least one monocyclic aryl groups. In further or alternative embodiments, the multicyclic aryl groups comprise at least one heterocycle. In further or alternative embodiments, the tricyclic aryl groups comprise at least one heterocycle. In further or alternative embodiments, the bicyclic aryl groups comprise at least one heterocycle. In further or alternative embodiments, the monocyclic aryl group is a heterocycle.

In another aspect are methods for making such compounds having a diarylamine structure. In further or alternative embodiments, such diarylamine compounds comprise at least one heterocycle group. In further or alternative embodiments, such heterocycle groups contain at least one nitrogen. In further or alternative embodiments, such heterocycle groups are pyrimidines. In further or alternative embodiments, such diarylamines further comprise multicyclic aryl groups. In further or alternative embodiments, such diarylamines further comprise at least one tricyclic aryl groups. In further or alternative embodiments, such diarylamines further comprise at least one bicyclic aryl groups. In further or alternative embodiments, such diarylamines further comprise at least one monocyclic aryl groups. In further or alternative embodiments, the multicyclic aryl groups comprise at least one heterocycle. In further or alternative embodiments, the tricyclic aryl groups comprise at least one heterocycle. In further or alternative embodiments, the bicyclic aryl groups comprise at least one heterocycle. In further or alternative embodiments, the monocyclic aryl group is a heterocycle.

In another aspect are compounds having the structure of Formula (A) or Formula (B):

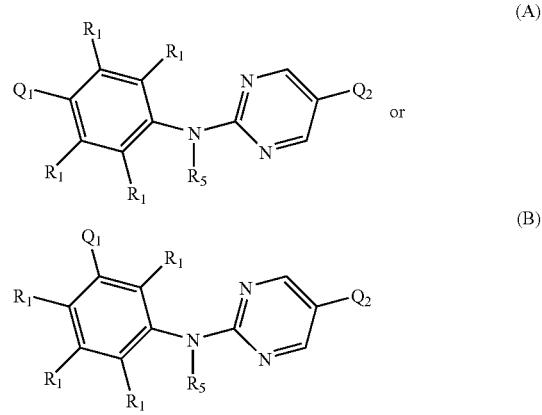

wherein:
  $Q_1$ is H, halogen, a group comprising a non-aromatic tertiary amine, a group comprising a non-aromatic secondary amine, or is an optionally substituted moiety selected from the group consisting of: -L-alkyl, -L-cycloalkyl, -L-heteroalkyl, -L-haloalkyl, -L-aryl, -L-heterocycloalkyl, and -L-heteroaryl; wherein L is selected from a bond, —O—, —NH—, —S—, —C(O)—, —C(S)—, —C(O)O—, —C(O)NH—, —S(O)—, —S(O)$_2$—, —OC(O)—, —C(O)NR" (CR"$_2$)$_{1-6}$C(O)O—, —CR"$_2$NR"CR"$_2$C(O)O—, —C(O)—NR"YC(O)O—, —C(O)NR"NR"C(O)O—, and —S(O)NH—; and Y is optionally substituted arylene or heteroarylene;

each $R_1$ is independently selected from the group consisting of H, halogen, and an optionally substituted moiety selected from -$L_1$-alkyl, -$L_1$-cycloalkyl, -$L_1$-heteroalkyl, -$L_1$-haloalkyl, -$L_1$-aryl, -$L_1$-heterocycloalkyl, and -$L_1$-heteroaryl; wherein $L_1$ is selected from a bond, —O—, —NH—, —S—, —C(O)—, —C(S)—, —C(O)O—, —C(O)NH—, —S(O)—, —S(O)$_2$—, —C(O)NR'(CR"$_2$)$_{1-6}$C(O)O—, —OC(O)—, —CR"$_2$NR"CR"$_2$C(O)O—, —C(O)—NR"Y'C(O)O—, —C(O)NR"NR"C(O)O—, and —S(O)NH—; and Y' is optionally substituted arylene or heteroarylene;

$Q_2$ is selected from the group consisting of H, halogen, and a group comprising an optionally substituted moiety selected from -$L_6$-alkyl, -$L_6$-cycloalkyl, -$L_6$-heteroalkyl, -$L_6$-haloalkyl, -$L_6$-aromatic carbocycle, -$L_6$-heterocycloalkyl, and -$L_6$-aromatic heterocycle; wherein $L_6$ is selected from a bond, —O—, —NH—, —S—, —C(O)—, —C(S)—, —C(O)O—, —C(O)NH—, —S(O)—, —S(O)$_2$—, —C(O)NR' (CR"$_2$)$_{1-6}$C(O)O—, —OC(O)—, —CR"$_2$NR"CR"$_2$C(O)O—, —C(O)—NR"Y'C(O)O—, —C(O)NR"NR"C(O)O—, and —S(O)NH—; and Y" is optionally substituted arylene or heteroarylene;

each R" is independently H, OH, halogen, $C_{1-6}$alkyl, substituted $C_{1-6}$alkyl, $C_{1-6}$alkoxy, halo-$C_{1-6}$alkyl, halo-$C_{1-6}$alkoxy, aryl, haloaryl, or heteroaryl;

any two $R_1$ groups together may form an optionally substituted 5 to 8-membered heterocyclic, cycloalkyl, or aryl ring;

$R_5$ is selected from the group consisting of H, and an optionally substituted moiety selected from -$L_5$-H, -$L_5$-alkyl, -$L_5$-cycloalkyl, -$L_5$-heteroalkyl, -$L_5$-haloalkyl, -$L_5$-aryl, -$L_5$-heterocycloalkyl, and -$L_5$-heteroaryl, wherein $L_5$ is selected from a bond, —R'O—, —R'N(H)—, —R'S—, —R'C(O)—, —R'C(S)—, —R'C(O)O—, and —R'C(O)NH—;

each R' is independently selected from the group consisting of a bond, alkylene, substituted alkylene, heteroalkylene, substituted heteroalkylene, alkenylene, substituted alkenylene, cycloalkylene, substituted cycloalkylene, heteroalkylene, substituted heteroalkylene, heterocycloalkylene, substituted heterocycloalkylene, arylene, substituted arylene, heteroarylene, substituted heteroarylene, alkarylene, substituted alkarylene, aralkylene, and substituted aralkylene; and any $R_1$ and $R_5$ taken together may form an optionally substituted 5 to 8-membered heterocyclic, cycloalkyl, or aryl ring;

or a pharmaceutically acceptable salt, pharmaceutically acceptable N-oxide, pharmaceutically active metabolite, pharmaceutically acceptable prodrug, or pharmaceutically acceptable solvate thereof.

In further or alternative embodiments, $Q_1$ is selected from the group consisting of H, halogen, and an optionally substituted moiety selected from -L-alkyl, -L-cycloalkyl, -L-heteroalkyl, -L-haloalkyl, -L-aryl, -L-heterocycloalkyl, and -L-heteroaryl; wherein L is selected from a bond, —O—, —S—,
and, —C(O)O—; wherein said optional substituents are selected from halogen, OH, $C_{1-6}$alkyl, $C_{1-6}$alkoxy, halo-$C_{1-6}$alkyl, halo-$C_{1-6}$alkoxy, aryl, haloaryl, and heteroaryl.

In further or alternative embodiments, $Q_1$ is an optionally substituted moiety selected from -L-alkyl, -L-heteroalkyl, and -L-heterocycloalkyl; wherein L is selected from a bond, —O—, —S—, and, —C(O)O—; wherein said optional substituents are selected from halogen, OH, $C_{1-6}$alkyl, $C_{1-6}$alkoxy, halo-$C_{1-6}$alkyl, halo-$C_{1-6}$alkoxy, aryl, haloaryl, and heteroaryl.

In further or alternative embodiments, $Q_1$ is -L-R, wherein R is a group comprising a tertiary amine and L is optionally substituted and selected from a bond, —O—, —S—, and, —C(O)O—; wherein said optional substituents are selected from halogen, OH, $C_{1-6}$alkyl, $C_{1-6}$alkoxy, halo-$C_{1-6}$alkyl, halo-$C_{1-6}$alkoxy, aryl, haloaryl, and heteroaryl.

In further or alternative embodiments, $Q_2$ is an optionally substituted moiety selected from, -$L_6$-cycloalkyl, -$L_6$-aromatic carbocycle, -$L_6$-heterocycloalkyl, and -$L_6$-aromatic heterocycle; wherein $L_6$ is selected from a bond, —O—, —NH—, —S—, —C(O)—, —C(S)—, —C(O)O—, —C(O)NH—, —S(O)—, —S(O)$_2$—, —C(O)NH(CR"$_2$)$_{1-6}$C(O)O—, —C(O)NR"NR"C(O)O—, and —S(O)NH—; wherein said optional substituents are selected from halogen, OH, $C_{1-6}$alkyl, $C_{1-6}$alkoxy, halo-$C_{1-6}$alkyl, halo-$C_{1-6}$alkoxy, aryl, haloaryl, and heteroaryl.

In further or alternative embodiments, $Q_2$ is selected from the group consisting of an optionally substituted cycloalkyl, optionally substituted aromatic carbocycle, optionally substituted heterocycloalkyl, and optionally substituted aromatic heterocycle; wherein said optional substituents are selected from halogen, OH, $C_{1-6}$alkyl, $C_{1-6}$alkoxy, halo-$C_{1-6}$alkyl, halo-$C_{1-6}$alkoxy, aryl, haloaryl, and heteroaryl.

In another aspect are compounds having the structure of Formula (1) or Formula (46):

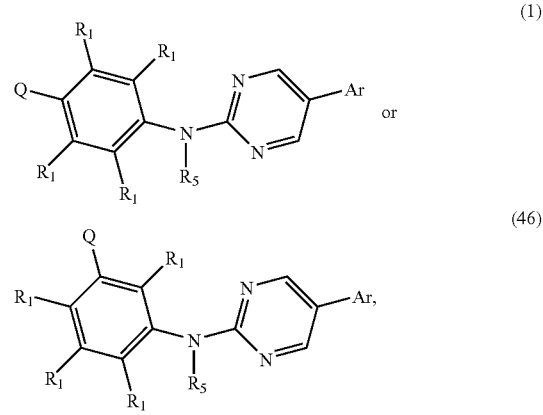

wherein:
Ar is a group comprising a moiety selected from an optionally substituted five-membered aromatic heterocycle, an optionally substituted five-membered aromatic carbocycle, an optionally substituted six-membered aromatic heterocycle, and a substituted, optionally further substituted six-membered aromatic carbocycle;

Q is a group comprising a non-aromatic tertiary amine or a non-aromatic secondary amine, with the proviso that Q is not —NR$_a$R$_b$ or —SO$_2$NR$_a$R$_b$; wherein each of R$_a$ and R$_b$ is independently H or $C_{1-6}$alkyl optionally substituted by mono- or di-alkyl ($C_{1-6}$) amino;

each $R_1$ is independently selected from the group consisting of H, halogen, and an optionally substituted moiety selected from -$L_1$-alkyl, -$L_1$-cycloalkyl, -$L_1$-heteroalkyl, -$L_1$-haloalkyl, -$L_1$-aryl, -$L_1$-heterocycloalkyl, and -$L_1$-heteroaryl; wherein $L_1$ is selected from a bond, —O—, —NH—, —S—, —C(O)—, —C(S)—, —C(O)O—, —C(O)NH—, —S(O)—, —S(O)$_2$—, —C(O)NH(CR"$_2$)$_{1-6}$C(O)O—, —C(O)NR"NR"C(O)O—, and —S(O)NH—;

each R" is independently H, OH, halogen, $C_{1-6}$alkyl, substituted $C_{1-6}$alkyl, $C_{1-6}$alkoxy, halo-$C_{1-6}$alkyl, halo-$C_{1-6}$alkoxy, aryl, haloaryl, or heteroaryl;

or any two adjacent $R_1$ groups together may form an optionally substituted 5 to 8-membered heterocyclic, cycloalkyl, or aryl ring;

$R_5$ is selected from the group consisting of H, and an optionally substituted moiety selected from -$L_5$-H, -$L_5$-alkyl, -$L_5$-cycloalkyl, -$L_5$-heteroalkyl, -$L_5$-haloalkyl, -$L_5$-aryl, -$L_5$-heterocycloalkyl, and -$L_5$-heteroaryl; wherein $L_5$ is selected from a bond, —R'O—, —R'N(H)—, —R'S—, —R'C(O)—, —R'C(S)—, —R'C(O)O—, and —R'C(O)NH—;

each R' is independently selected from the group consisting of a bond, alkylene, substituted alkylene, heteroalkylene, substituted heteroalkylene, alkenylene, substituted alkenylene, cycloalkylene, substituted cycloalkylene, heteroalkylene, substituted heteroalkylene, heterocycloalkylene, substituted heterocycloalkylene, arylene, substituted arylene, heteroarylene, substituted heteroarylene, alkarylene, substituted alkarylene, aralkylene, and substituted aralkylene; and any $R_1$ and $R_5$ taken together may form an optionally substituted 5 to 8-membered heterocyclic, cycloalkyl, or aryl ring;

or a pharmaceutically acceptable salt, pharmaceutically acceptable N-oxide, pharmaceutically active metabolite, pharmaceutically acceptable prodrug, or pharmaceutically acceptable solvate thereof.

In further or alternative embodiments are compounds having the structure of Formula (1) or Formula (46):

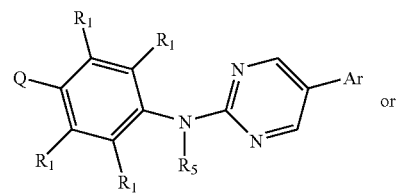

(1)

or

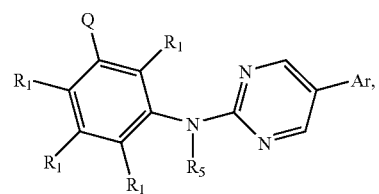

(46)

wherein:
Ar is a group comprising a moiety selected from an optionally substituted five-membered aromatic heterocycle, an optionally substituted five-membered aromatic carbocycle, an optionally substituted six-membered aromatic heterocycle, and a substituted, optionally further substituted phenyl;

Q is a group comprising a non-aromatic tertiary amine or a non-aromatic secondary amine, with the proviso that Q is not —NR$_a$R$_b$ or —SO$_2$NR$_a$R$_b$; wherein each of R$_a$ and R$_b$ is independently H or $C_{1-6}$alkyl optionally substituted by mono- or di-alkyl ($C_{1-6}$) amino;

each $R_1$ is independently selected from the group consisting of H, halogen, and an optionally substituted moiety selected from -$L_1$-alkyl, -$L_1$-cycloalkyl, -$L_1$-heteroalkyl, -$L_1$-haloalkyl, -$L_1$-aryl, -$L_1$-heterocycloalkyl, and -$L_1$-heteroaryl; wherein $L_1$ is selected from a bond, —O—, —NH—, —S—, —C(O)—, —C(S)—, —C(O)O—, —C(O)NH—, —S(O)—, —S(O)$_2$—, —C(O)NH(CR"$_2$)$_{1-6}$C(O)O—, —C(O)NR"NR"C(O)O—, and —S(O)NH—;

each R" is independently H, OH, halogen, $C_{1-6}$alkyl, substituted $C_{1-6}$alkyl, $C_{1-6}$alkoxy, halo-$C_{1-6}$alkyl, halo-$C_{1-6}$alkoxy, aryl, haloaryl, or heteroaryl;

or any two adjacent $R_1$, groups together may form an optionally substituted 5 to 8-membered heterocyclic, cycloalkyl, or aryl ring;

$R_5$ is selected from the group consisting of hydrogen and $C_{1-6}$alkyl;

or a pharmaceutically acceptable salt, pharmaceutically acceptable N-oxide, pharmaceutically active metabolite, pharmaceutically acceptable prodrug, or pharmaceutically acceptable solvate thereof.

In further or alternative embodiments, the Ar is a group comprising a substituted, optionally further substituted six-membered aromatic heterocycle. In further or alternative embodiments, said optional substituents are selected from halogen, OH, halogen, $C_{1-6}$alkyl, $C_{1-6}$alkoxy, halo-$C_{1-6}$alkyl, halo-$C_{1-6}$alkoxy, aryl, haloaryl, or heteroaryl.

In further or alternative embodiments, Ar is selected from the group consisting of

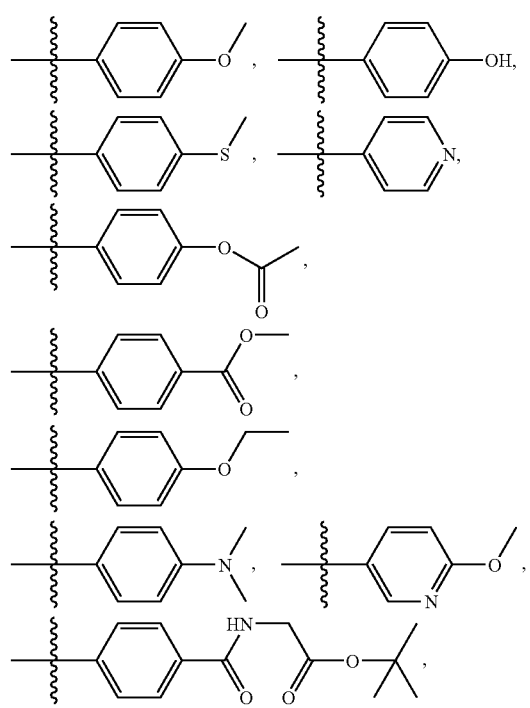

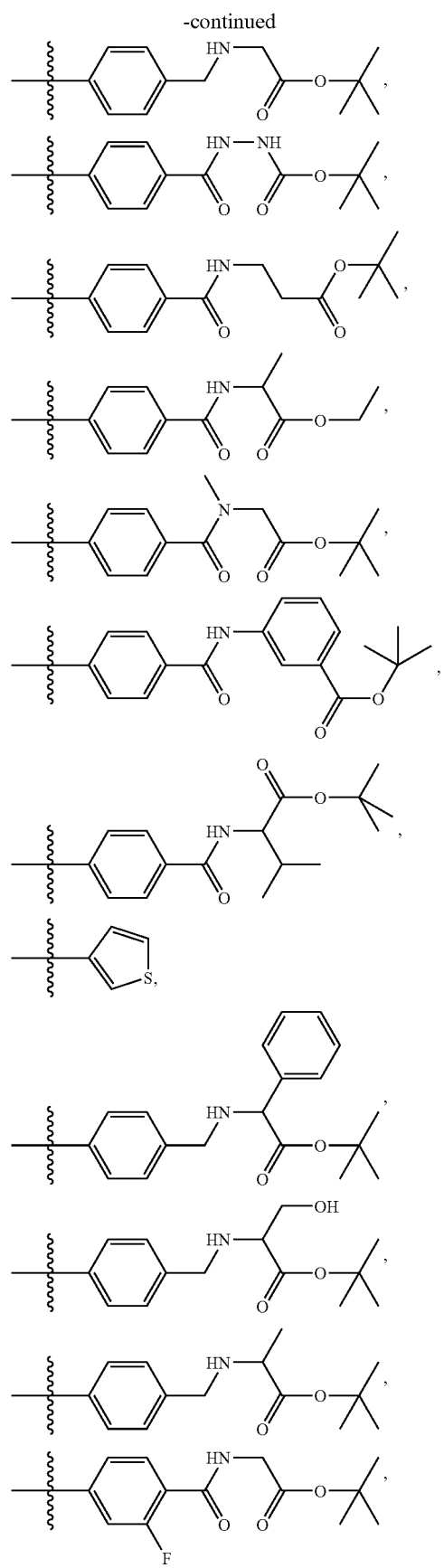
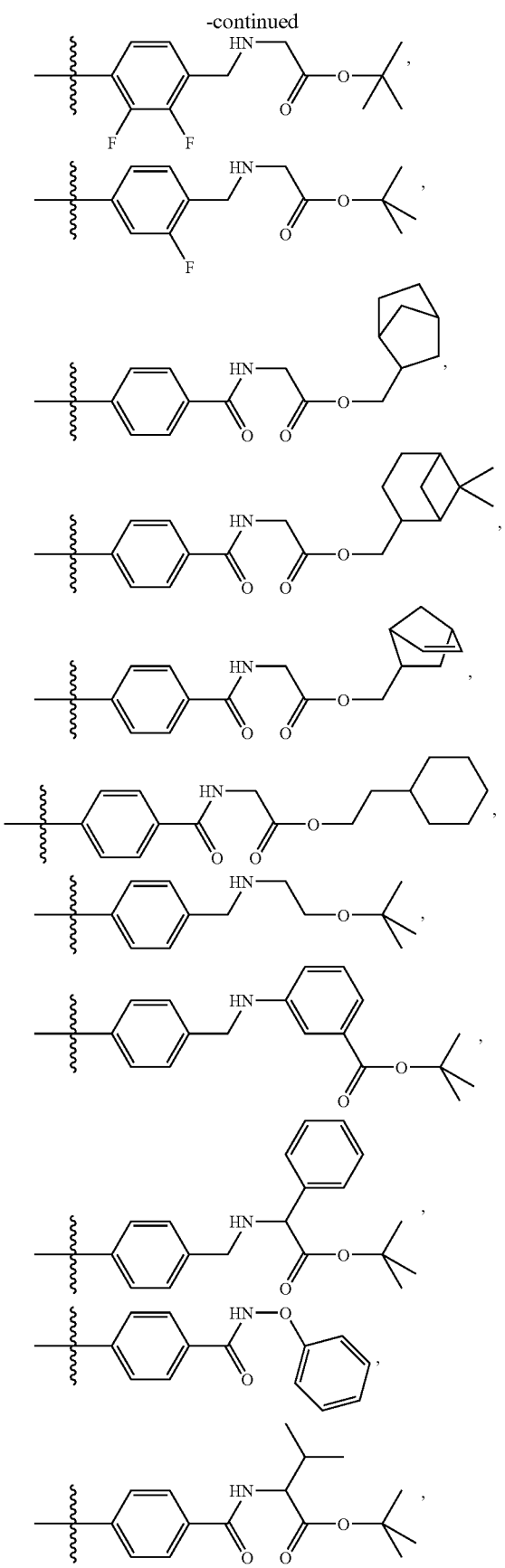

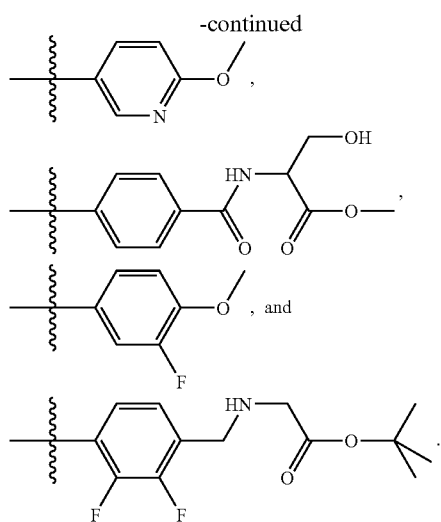
In further or alternative embodiments, Q of the compound having the structure of Formula (1) or Formula (46) is selected from the group consisting of
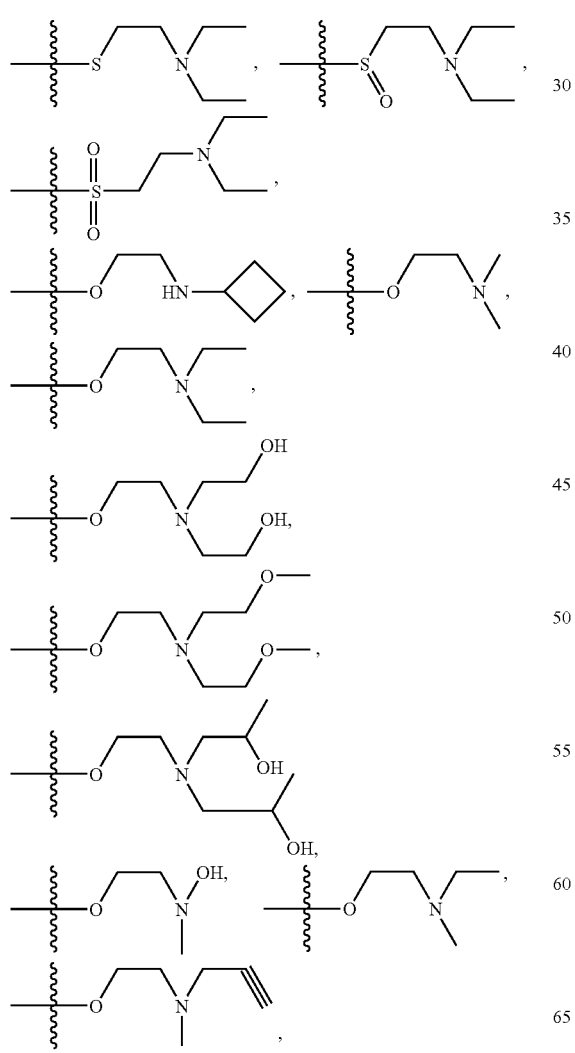
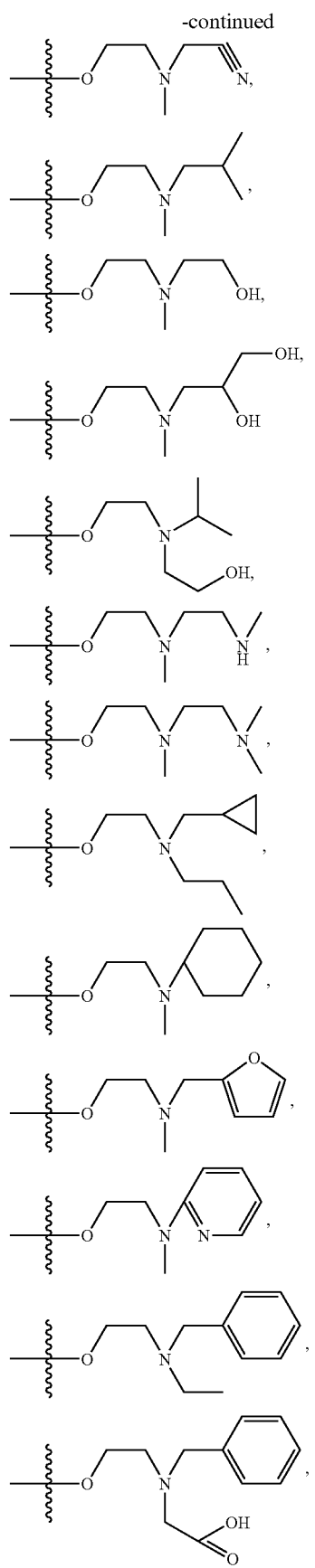

-continued
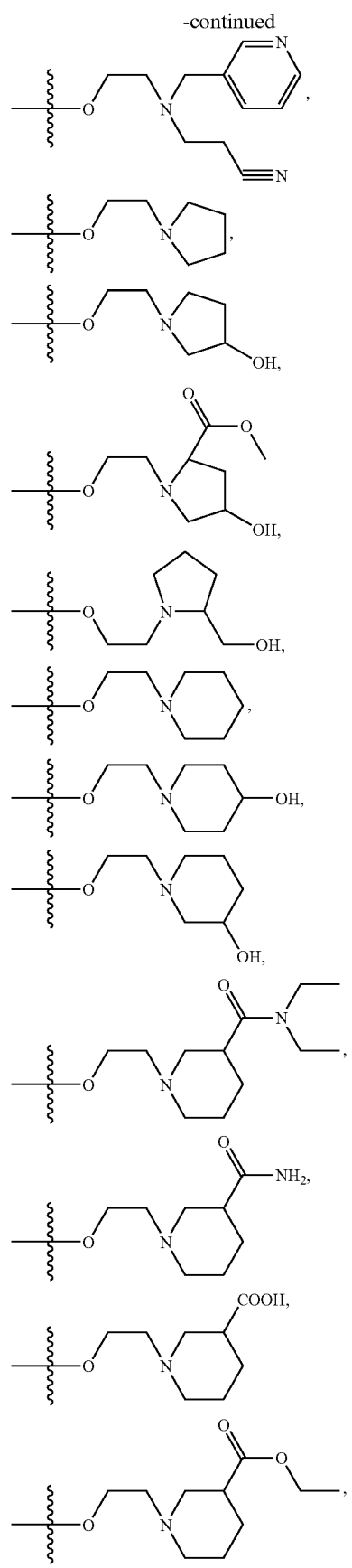
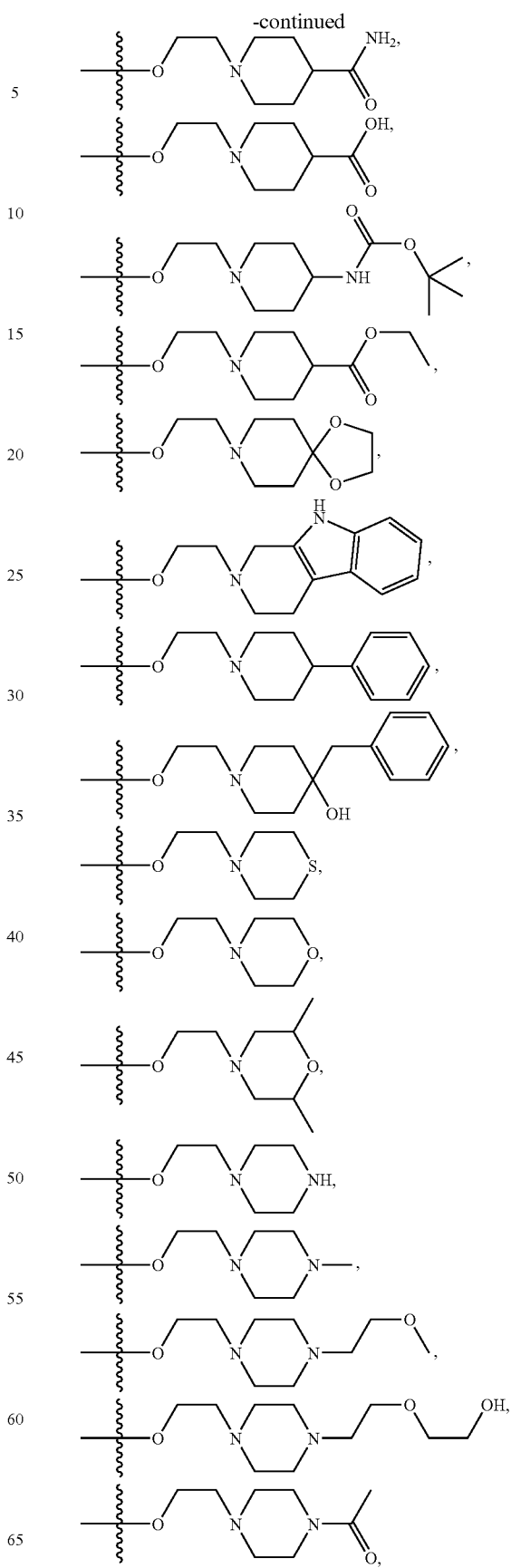

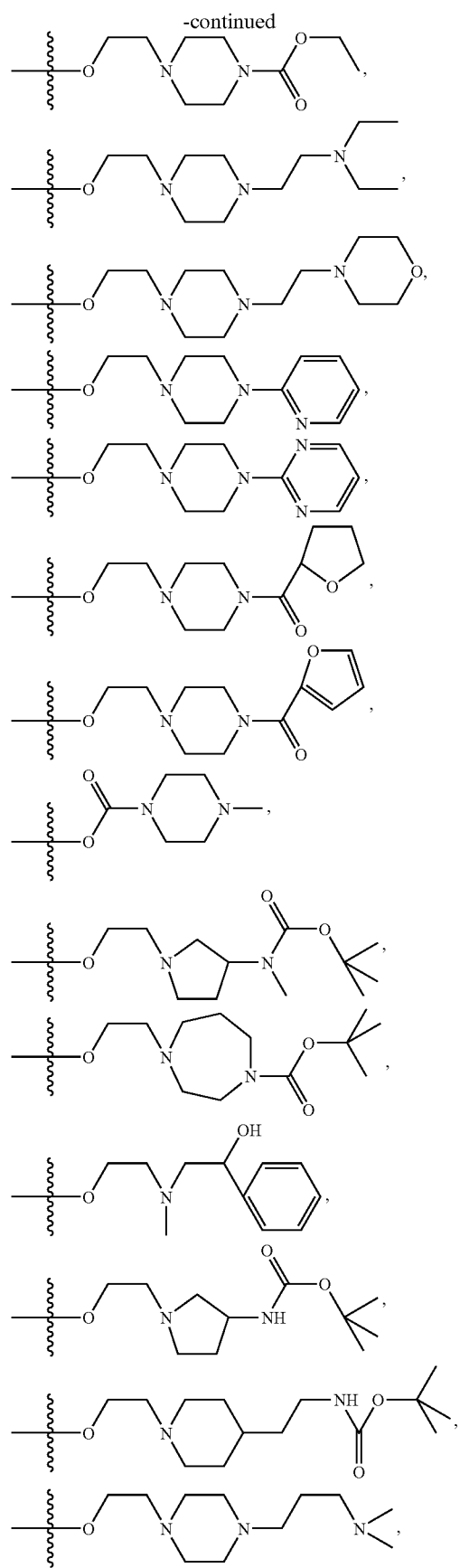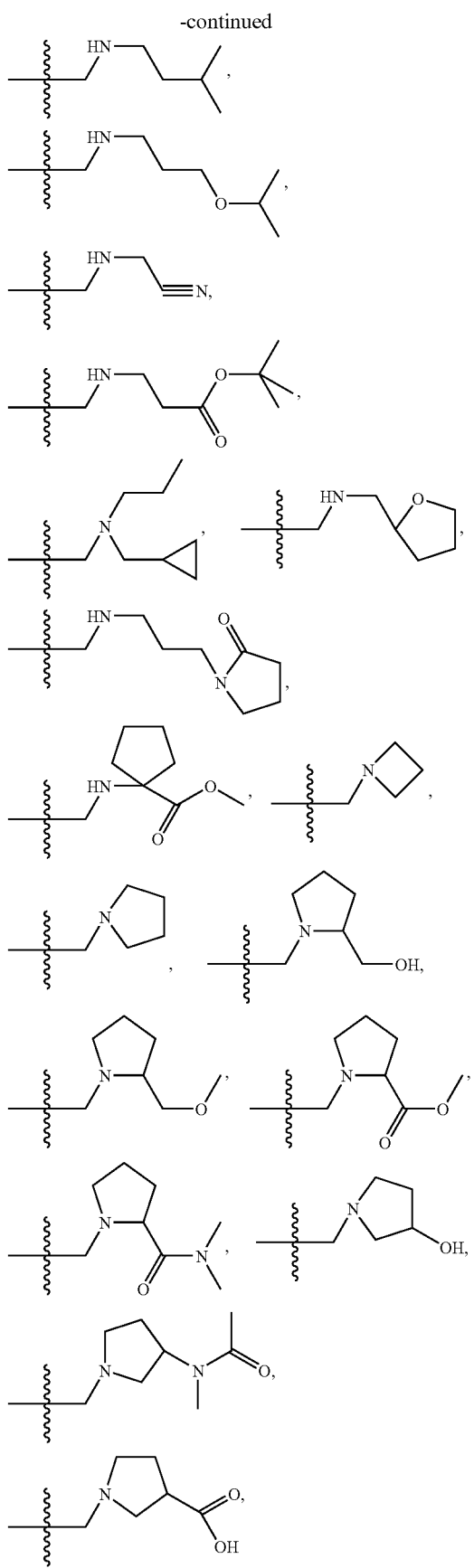

-continued
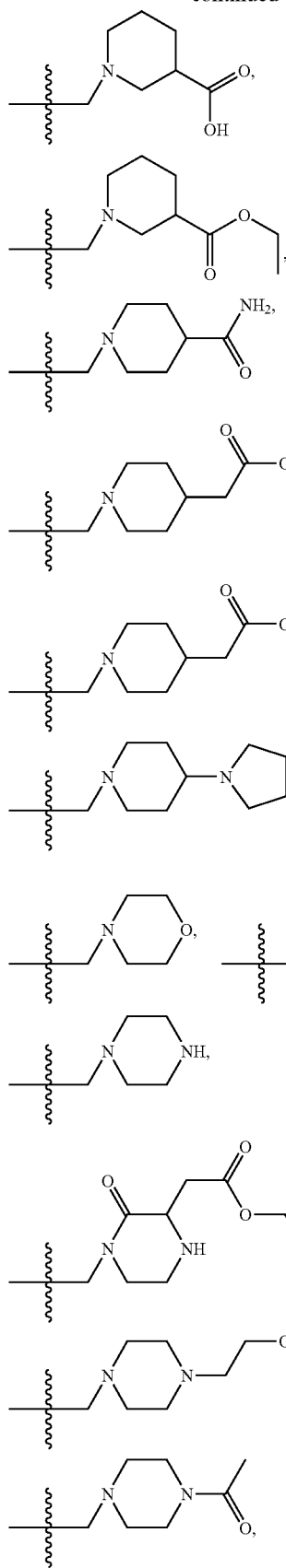
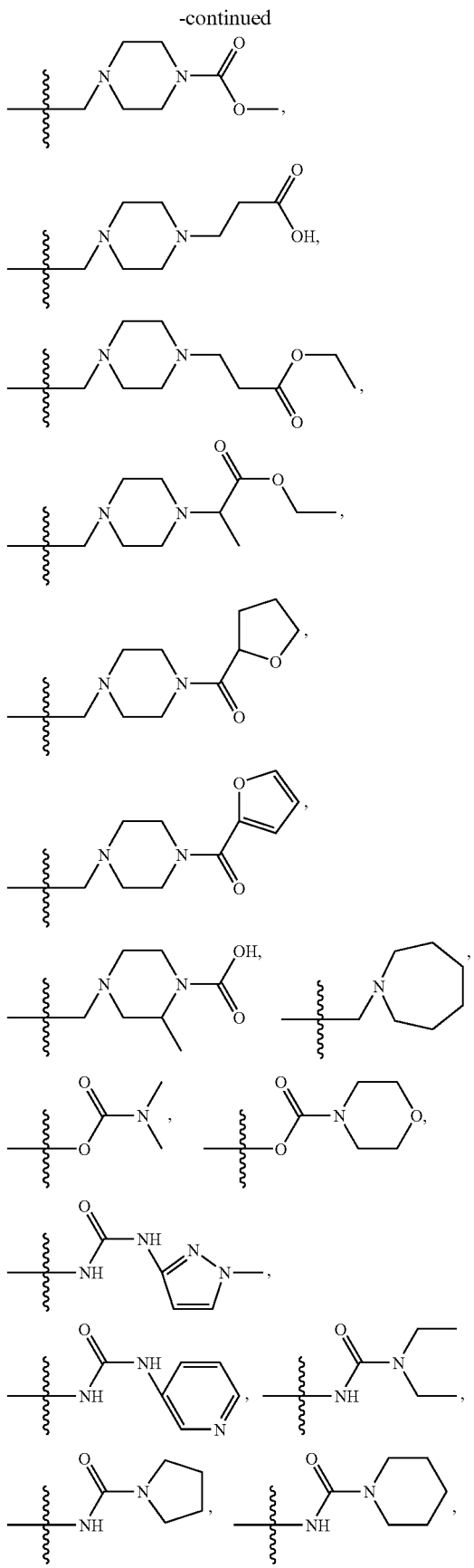

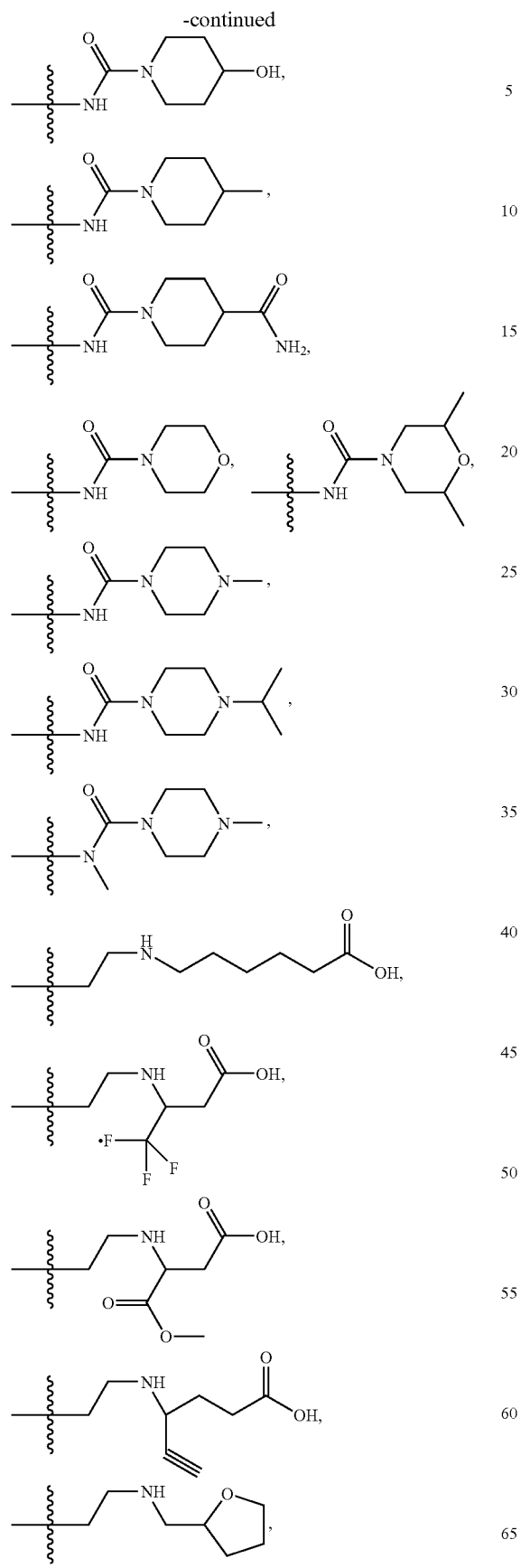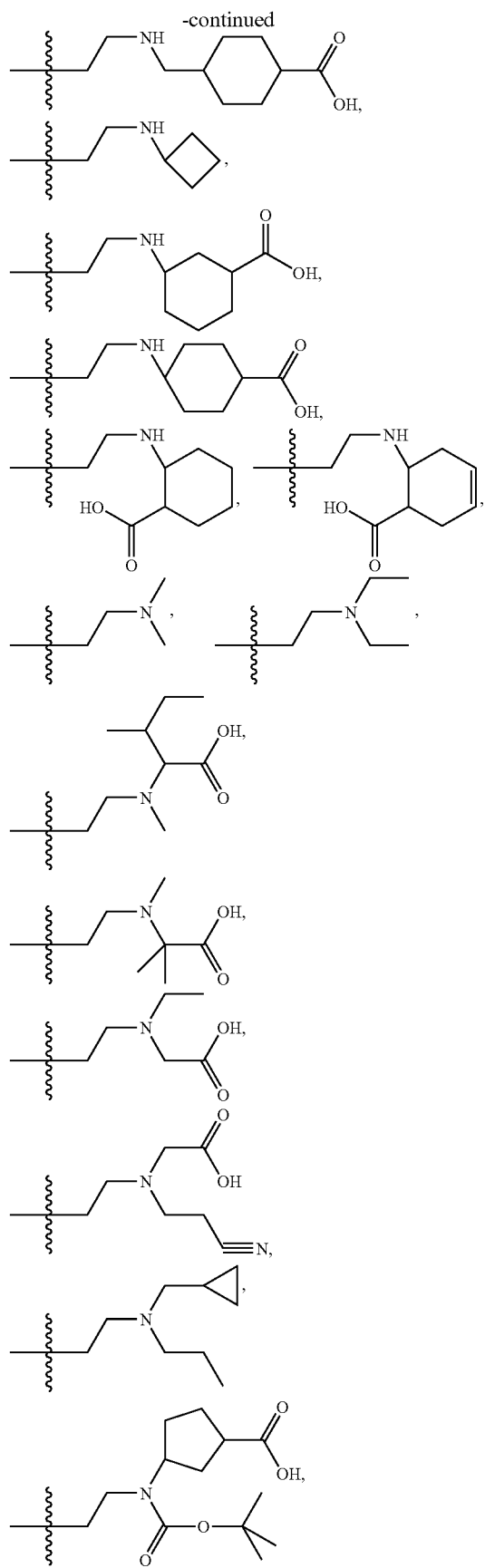

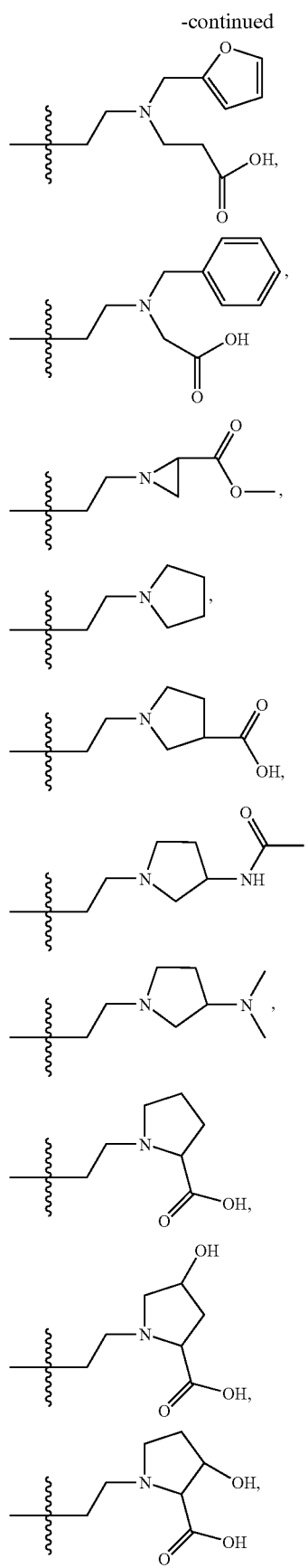

-continued
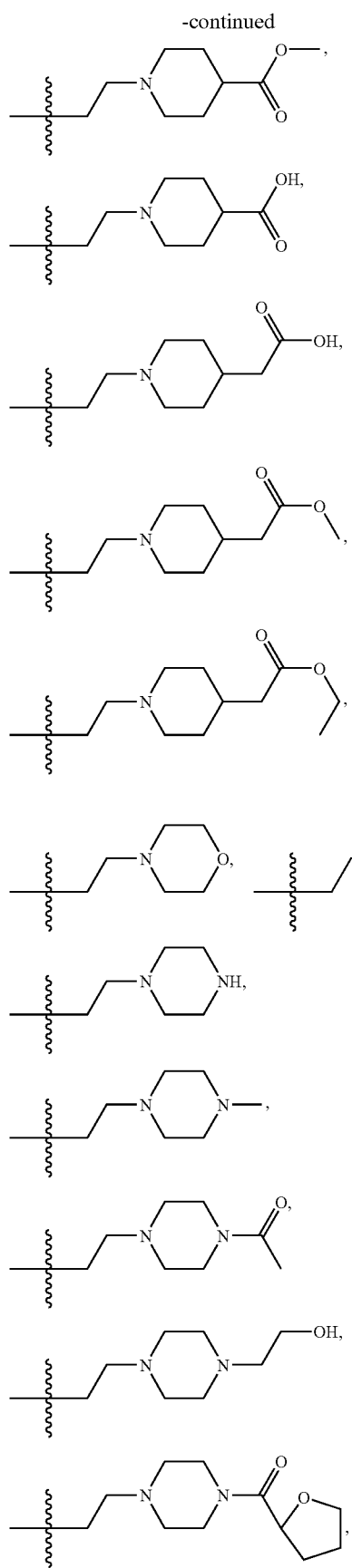
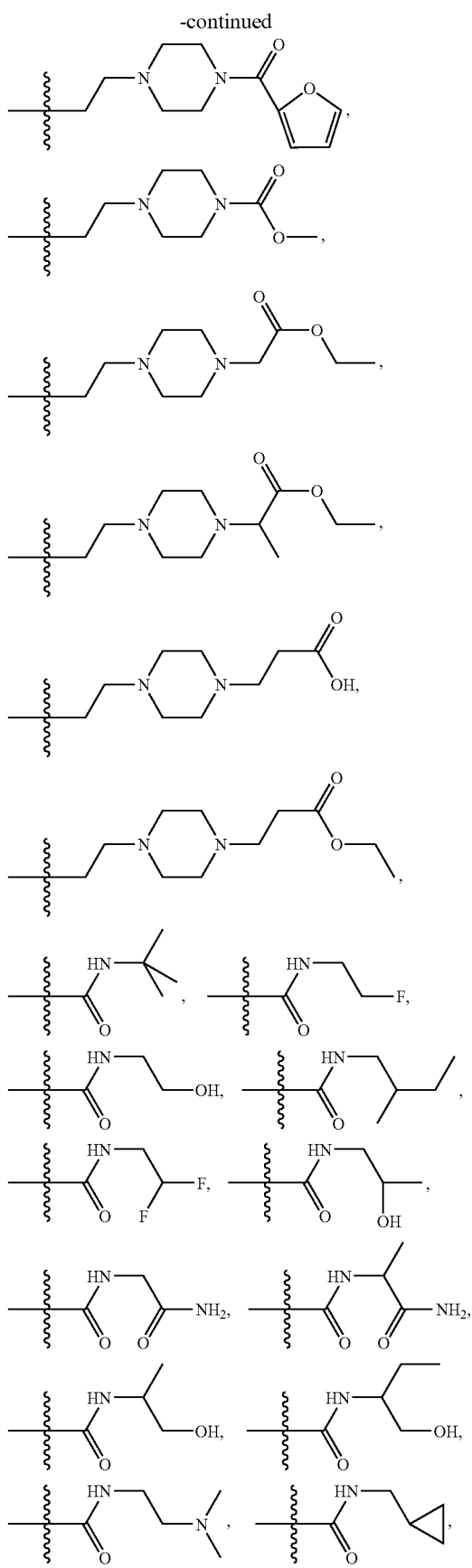

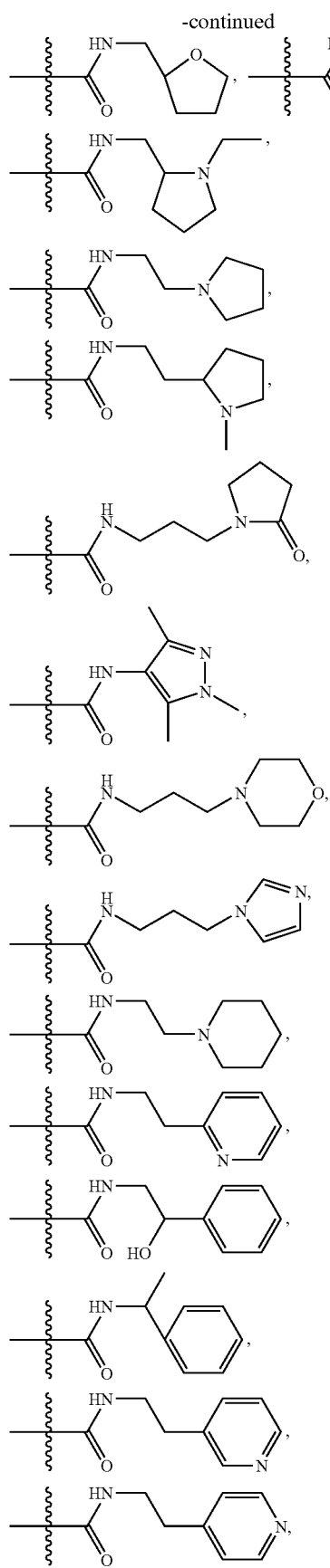
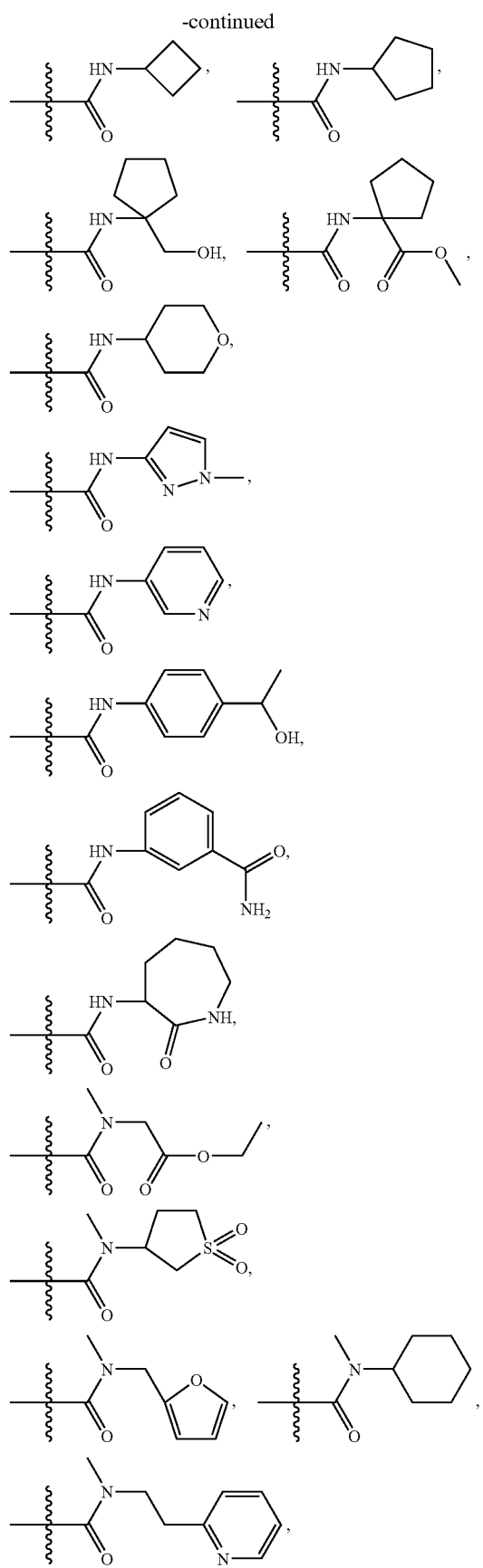

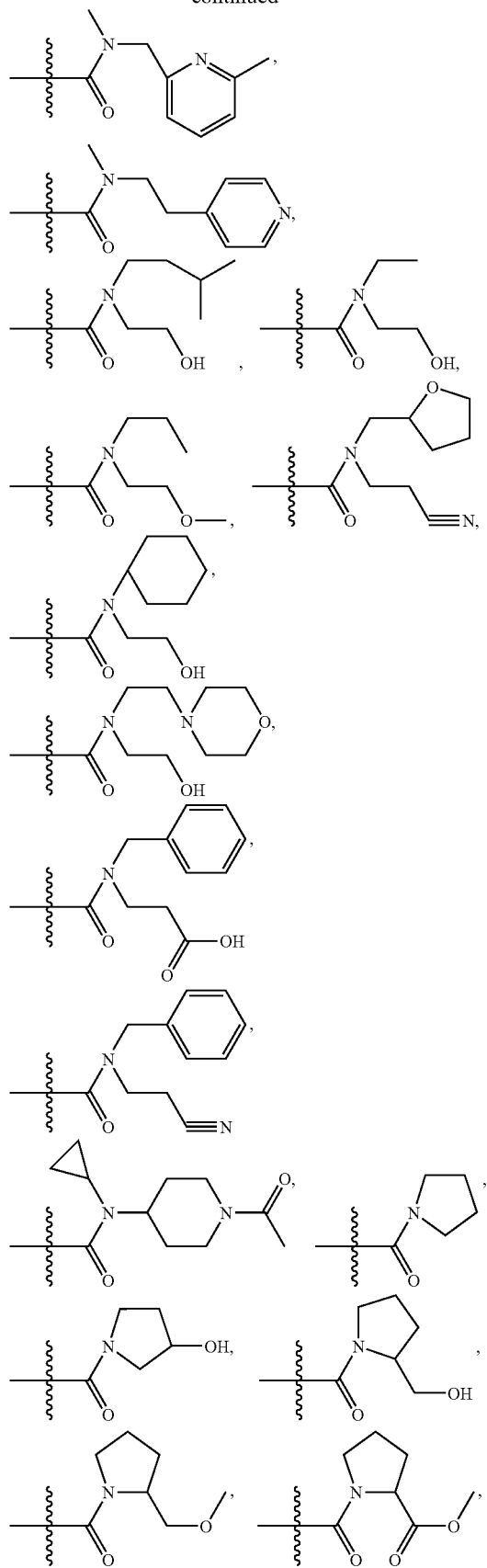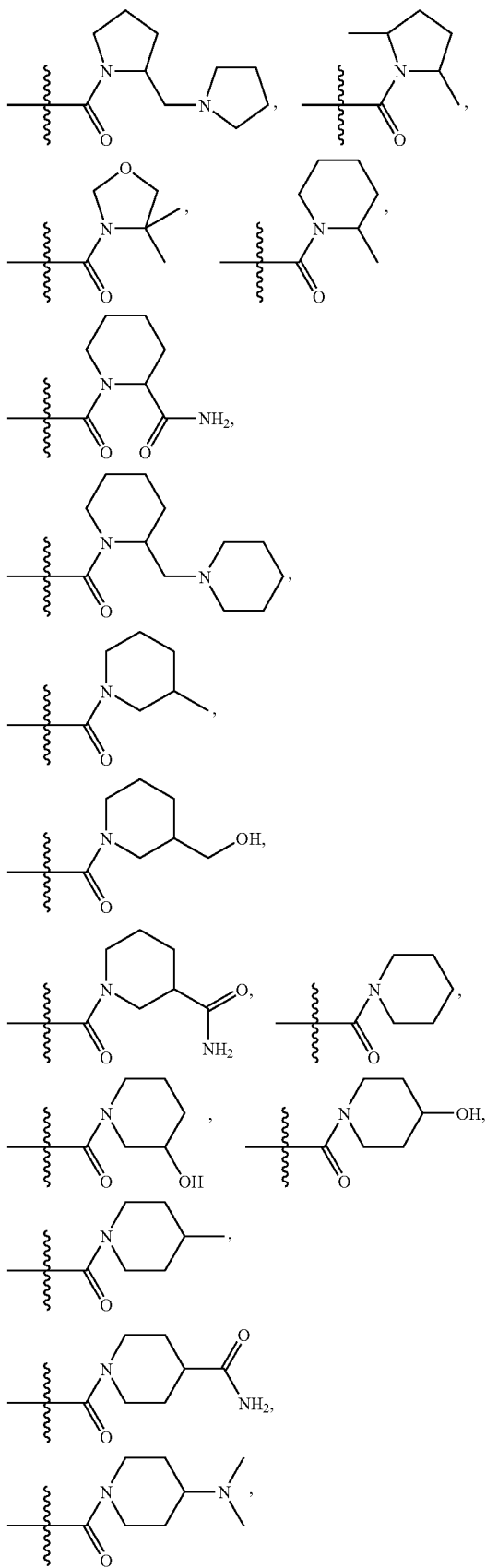

-continued
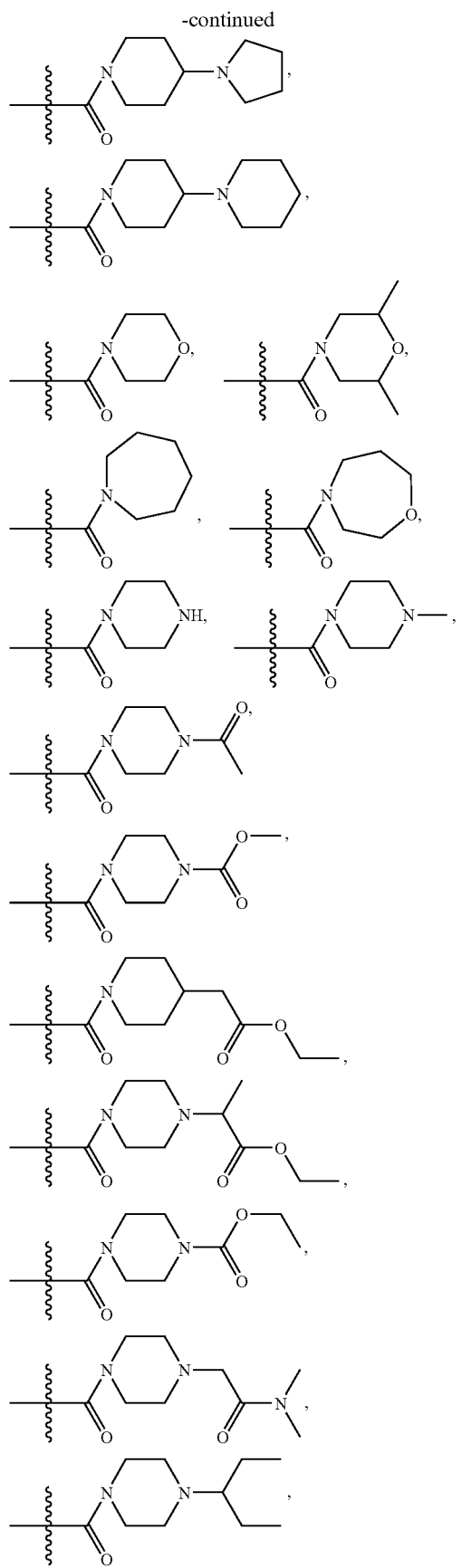
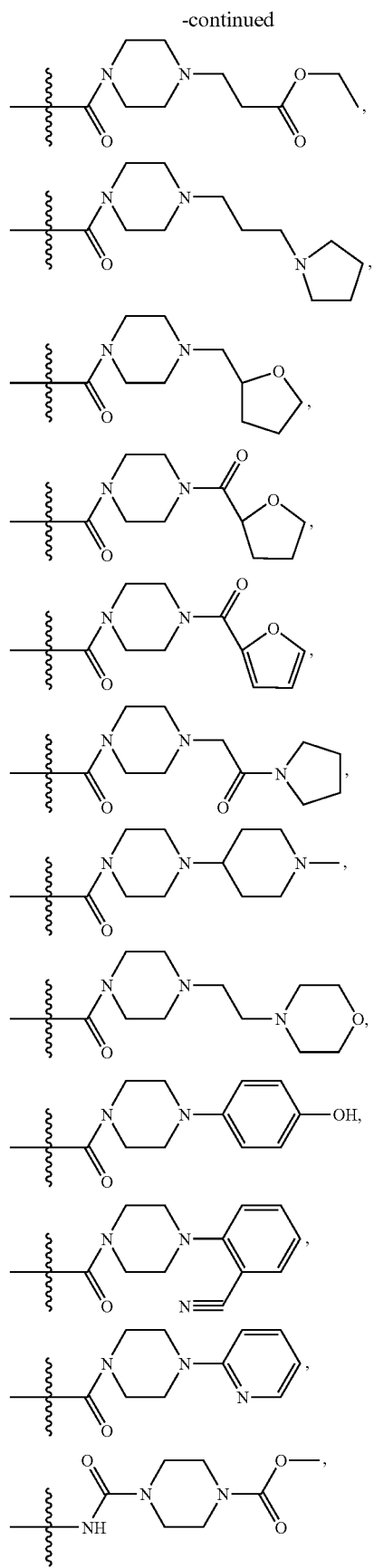

-continued
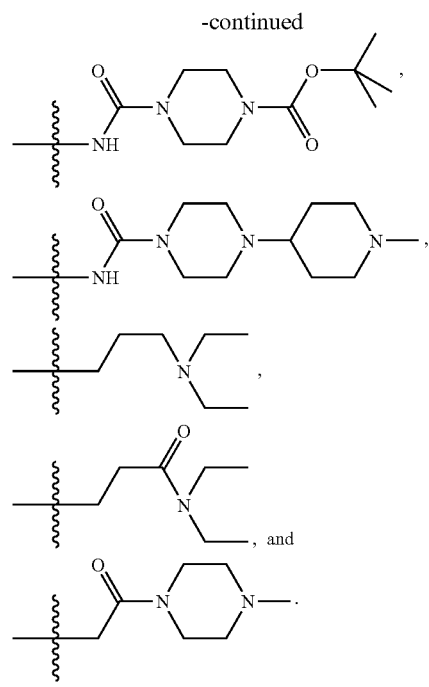
In further or alternative embodiments, Q is selected from the group consisting of
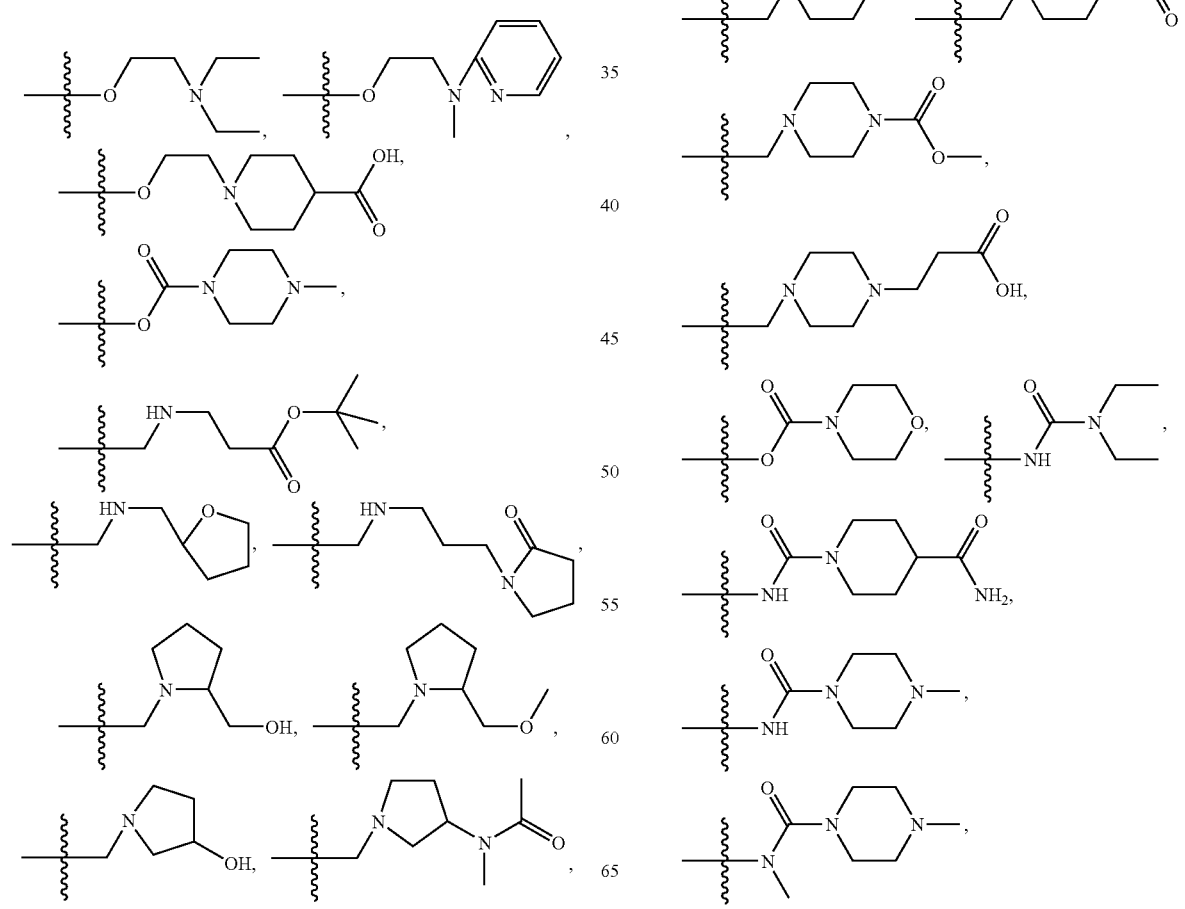

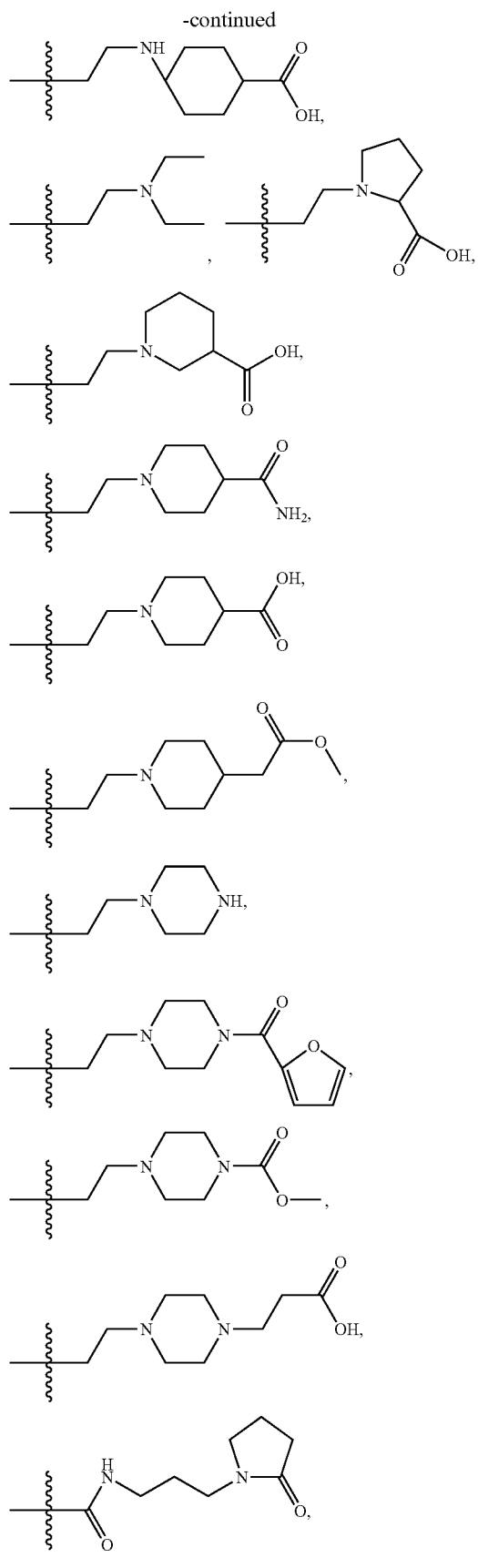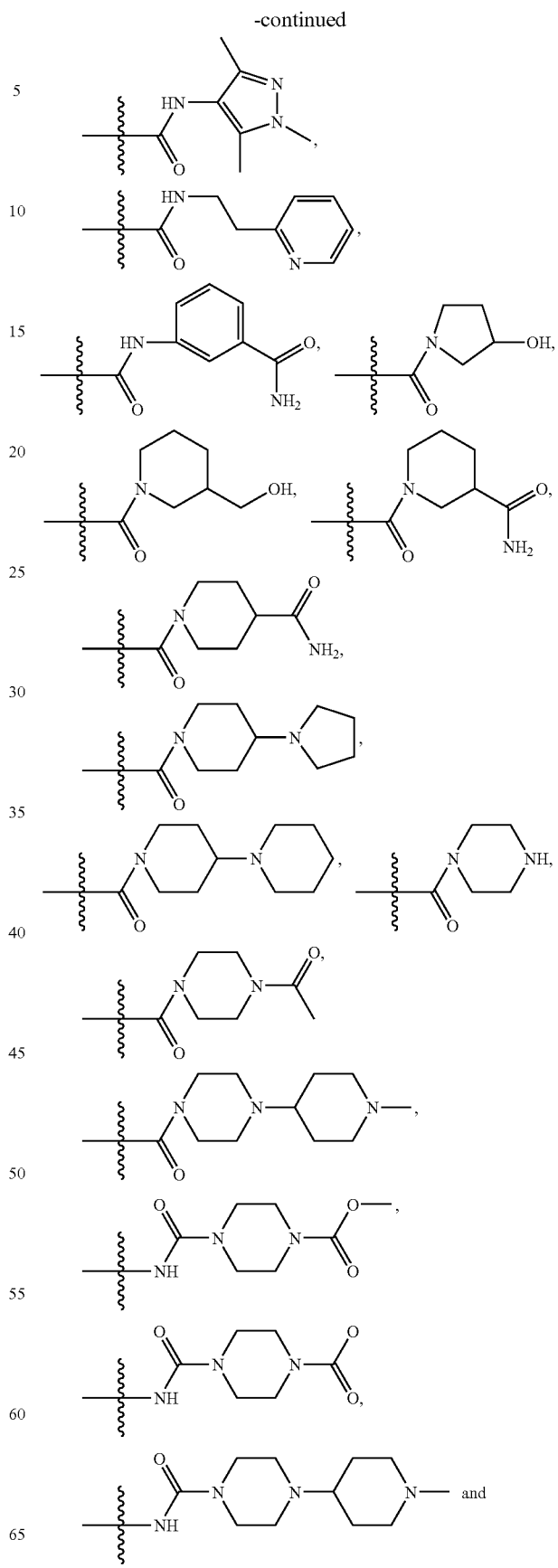

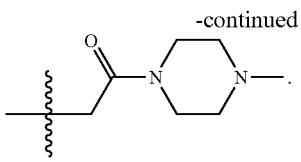

In further or alternative embodiments, Ar is selected from the group consisting of

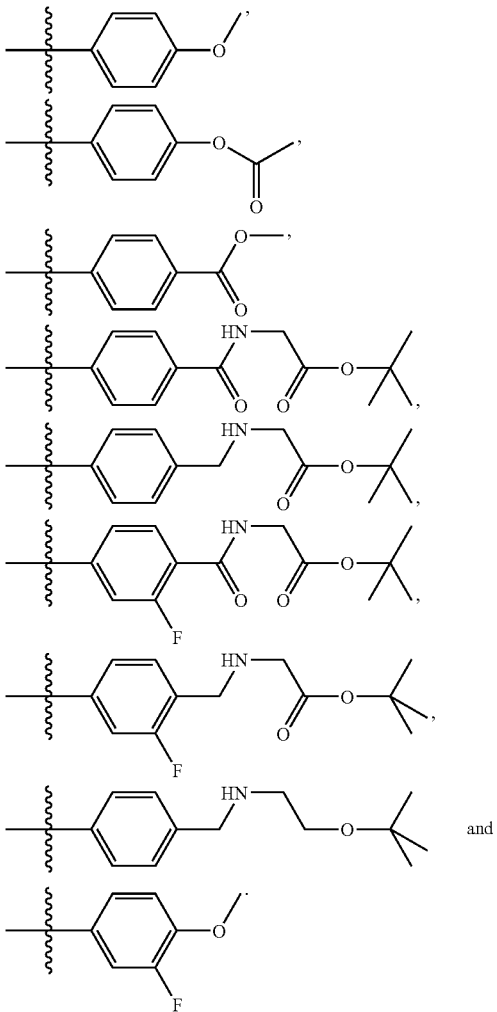

and

In further or alternative embodiments, the compound is selected from the group consisting of tert-butyl 2-(4-(2-(4-(2-(diethylamino)ethoxy)phenylamino)pyrimidin-5-yl)-2-fluorobenzamido)acetate, tert-butyl 2-(4-(2-(4-(2-(diethylamino)ethoxy)phenylamino)pyrimidin-5-yl)-2-fluorobenzylamino)acetate, tert-butyl 2-(4-(2-(4-(2-(diethylamino)ethoxy)phenylamino)pyrimidin-5-yl)benzylamino)acetate, 2,2'-(2-(4-(5-(4-methoxyphenyl)pyrimidin-2-ylamino)phenoxy)ethylazanediyl)diethanol, 1-(4-(5-(4-methoxyphenyl)pyrimidin-2-ylamino)phenethyl)piperidine-4-carboxylic acid, tert-butyl 2-(4-(2-(4-(2-(diethylamino)ethoxy)phenylamino)pyrimidin-5-yl)benzamido)acetate, methyl 1-(4-(5-(4-methoxyphenyl)pyrimidin-2-ylamino)phenethyl)piperidine-4-carboxylate, N-(4-(2-(diethylamino)ethyl)phenyl)-5-(4-methoxyphenyl)pyrimidin-2-amine, 1-(2-(4-(5-(4-methoxyphenyl)pyrimidin-2-ylamino)phenoxy)ethyl)piperidine-4-carboxylic acid, N-(4-(2-(diethylamino)ethoxy)phenyl)-5-(4-methoxyphenyl)pyrimidin-2-amine, tert-butyl 2-(4-(2-(4-(2-morpholinoethoxy)phenylamino)pyrimidin-5-yl)benzamido)acetate, tert-butyl 2-(4-(2-(4-(2-(4-carbamoylpiperidin-1-yl)ethoxy)phenylamino)pyrimidin-5-yl)benzamido)acetate, 4-(2-(4-(2-(diethylamino)ethoxy)phenylamino)pyrimidin-5-yl)phenyl acetate, ethyl 2-(2-(diethylamino)ethoxy)-5-(5-(4-methoxyphenyl)pyrimidin-2-ylamino)benzoate, 4-(5-(4-methoxyphenyl)pyrimidin-2-ylamino)phenyl 4-methylpiperazine-1-carboxylate, 5-(4-methoxyphenyl)-N-(4-(2-(methyl(pyridin-2-yl)amino)ethoxy)phenyl)pyrimidin-2-amine, methyl 4-(2-(4-(2-(diethylamino)ethoxy)phenylamino)pyrimidin-5-yl)benzoate, N-(4-(2-(diethylamino)ethoxy)phenyl)-5-(3-fluoro-4-methoxyphenyl)pyrimidin-2-amine, 2-(2-(diethylamino)ethoxy)-4-(5-(4-methoxyphenyl)pyrimidin-2-ylamino)benzoic acid, methyl 2-(2-(diethylamino)ethoxy)-4-(5-(4-methoxyphenyl)pyrimidin-2-ylamino)benzoate, N-(3-(2-(diethylamino)ethoxy)phenyl)-5-(4-methoxyphenyl)pyrimidin-2-amine, N-(3-(2-(diethylamino)ethyl)phenyl)-5-(4-methoxyphenyl)pyrimidin-2-amine, 1-(4-(5-(4-methoxyphenyl)pyrimidin-2-ylamino)benzyl)piperidine-4-carboxamide, 1-(4-(5-(4-methoxyphenyl)pyrimidin-2-ylamino)benzyl)piperidine-3-carboxamide, tert-butyl 3-(4-(5-(4-methoxyphenyl)pyrimidin-2-ylamino)benzylamino)propanoate, 5-(4-methoxyphenyl)-N-(4-(piperazin-1-ylmethyl)phenyl)pyrimidin-2-amine, 1-(4-(4-(5-(4-methoxyphenyl)pyrimidin-2-ylamino)benzyl)piperazin-1-yl)ethanone, (4-(4-(5-(4-methoxyphenyl)pyrimidin-2-ylamino)benzyl)piperazin-1-yl)(tetrahydrofuran-2-yl)methanone, 1-(3-(4-(5-(4-methoxyphenyl)pyrimidin-2-ylamino)benzylamino)propyl)pyrrolidin-2-one, (S)-(1-(4-(5-(4-methoxyphenyl)pyrimidin-2-ylamino)benzyl)pyrrolidin-2-yl)methanol, (R)—N-(4-((2-(methoxymethyl)pyrrolidin-1-yl)methyl)phenyl)-5-(4-methoxyphenyl)pyrimidin-2-amine, 1-(4-(5-(4-methoxyphenyl)pyrimidin-2-ylamino)benzyl)pyrrolidin-3-ol, methyl 1-(4-(5-(4-methoxyphenyl)pyrimidin-2-ylamino)benzylamino)cyclopentanecarboxylate, 4-(4-(5-(4-methoxyphenyl)pyrimidin-2-ylamino)benzyl)-2-methylpiperazine-1-carboxylic acid, 3-(4-(4-(5-(4-methoxyphenyl)pyrimidin-2-ylamino)benzyl)piperazin-1-yl)propanoic acid, 1-(4-(5-(4-methoxyphenyl)pyrimidin-2-ylamino)benzyl)piperidine-3-carboxylic acid, ethyl 2-(1-(4-(5-(4-methoxyphenyl)pyrimidin-2-ylamino)benzyl)piperidin-4-yl)acetate, 2-(1-(4-(5-(4-methoxyphenyl)pyrimidin-2-ylamino)benzyl)piperidin-4-yl)acetic acid, 1-(4-(5-(4-methoxyphenyl)pyrimidin-2-ylamino)benzyl)pyrrolidine-3-carboxylic acid, 3-(5-(4-methoxyphenyl)pyrimidin-2-ylamino)phenyl morpholine-4-carboxylate, 3-(5-(4-methoxyphenyl)pyrimidin-2-ylamino)phenyl 4-methylpiperazine-1-carboxylate, 3-(5-(4-((2-tert-butoxy-2-oxoethylamino)methyl)phenyl)pyrimidin-2-ylamino)phenyl 4-methylpiperazine-1-carboxylate, methyl 4-(4-(5-(4-methoxyphenyl)pyrimidin-2-ylamino)benzyl)piperazine-1-carboxylate, 4-(5-(4-((2-tert-butoxy-2-oxoethylamino)methylphenyl)pyrimidin-2-ylamino)phenyl 4-methylpiperazine-1-carboxylate, N-(3-(5-(4-methoxyphenyl)pyrimidin-2-ylamino)phenyl)-4-methylpiperazine-1-carboxamide, 2-(4-(5-(4-methoxyphenyl)pyrimidin-2-ylamino)phenyl)-1-(4-methylpiperazin-1-yl)ethanone, N1-(3-(5-(4-methoxyphenyl)pyrimidin-2-ylamino)phenyl) piperidine-1,4-dicarboxamide, 3-(5-(4-methoxyphenyl)pyrimidin-2-ylamino)benzyl 4-methylpiperazine-1-carboxylate, 4-hydroxy-N-(3-(5-(4-methoxyphenyl)

pyrimidin-2-ylamino)phenyl)piperidine-1-carboxamide, N-(4-(5-(4-methoxyphenyl)pyrimidin-2-ylamino)phenyl)-4-methylpiperazine-1-carboxamide, 1-(4-(5-(4-methoxyphenyl)pyrimidin-2-ylamino)phenethyl)piperidine-4-carboxamide, furan-2-yl(4-(4-(5-(4-methoxyphenyl)pyrimidin-2-ylamino)phenethyl)piperazin-1-yl)methanone, 5-(4-methoxyphenyl)-N-(4-(2-(piperazin-1-yl)ethyl)phenyl)pyrimidin-2-amine, N-(3-(5-(4-methoxyphenyl)pyrimidin-2-ylamino)phenyl)-N,4-dimethylpiperazine-1-carboxamide, 1-(4-(5-(4-methoxyphenyl)pyrimidin-2-ylamino)phenethyl)piperidine-3-carboxamide, 1-(4-(5-(4-methoxyphenyl)pyrimidin-2-ylamino)phenethyl)piperidine-3-carboxylic acid, methyl 4-(4-(5-(4-methoxyphenyl)pyrimidin-2-ylamino)phenethyl)piperazine-1-carboxylate, 1-(4-(5-(4-methoxyphenyl)pyrimidin-2-ylamino)phenethyl)piperidine-3-carboxylic acid, 2-(1-(4-(5-(4-methoxyphenyl)pyrimidin-2-ylamino)phenethyl)piperidin-4-yl)acetic acid, methyl 2-(1-(4-(5-(4-methoxyphenyl)pyrimidin-2-ylamino)phenethyl)piperidin-4-yl)acetate, (3-(hydroxymethyl)piperidin-1-yl)(4-(5-(4-methoxyphenyl)pyrimidin-2-ylamino)phenyl)methanone, (3-hydroxypyrrolidin-1-yl)(4-(5-(4-methoxyphenyl)pyrimidin-2-ylamino)phenyl)methanone, 1-(4-(5-(4-methoxyphenyl)pyrimidin-2-ylamino)benzoyl)piperidine-4-carboxamide, 3-(4-(4-(5-(4-methoxyphenyl)pyrimidin-2-ylamino)phenethyl)piperazin-1-yl)propanoic acid, (S)-1-(4-(5-(4-methoxyphenyl)pyrimidin-2-ylamino)phenethyl)pyrrolidine-2-carboxylic acid, 4-(4-(5-(4-methoxyphenyl)pyrimidin-2-ylamino)phenethylamino)cyclohexanecarboxylic acid, 4-(5-(4-methoxyphenyl)pyrimidin-2-ylamino)-N-(3-(2-oxopyrrolidin-1-yl)propyl)benzamide, 1-(4-(5-(4-methoxyphenyl)pyrimidin-2-ylamino)benzoyl)piperidine-3-carboxamide, N-(3-carbamoylphenyl)-4-(5-(4-methoxyphenyl)pyrimidin-2-ylamino)benzamide, 1,4'-bipiperidin-1'-yl(4-(5-(4-methoxyphenyl)pyrimidin-2-ylamino)phenyl)methanone, (4-(5-(4-methoxyphenyl)pyrimidin-2-ylamino)phenyl)(4-(pyrrolidin-1-yl)piperidin-1-yl)methanone, 4-(5-(4-methoxyphenyl)pyrimidin-2-ylamino)-N-(2-(pyridin-2-yl)ethyl)benzamide, 4-(5-(4-methoxyphenyl)pyrimidin-2-ylamino)-N-(3,5-trimethyl-1H-pyrazol-4-yl)benzamide, (4-(furan-2-carbonyl)piperazin-1-yl)(3-(5-(4-methoxyphenyl)pyrimidin-2-ylamino)phenyl)methanone, 3-(5-(4-methoxyphenyl)pyrimidin-2-ylamino)-N-(1,3,5-trimethyl-1H-pyrazol-4-yl)benzamide, (3-(5-(4-methoxyphenyl)pyrimidin-2-ylamino)phenyl)(4-(1-methylpiperidin-4-yl)piperazin-1-yl)methanone, 1-(4-(3-(5-(4-methoxyphenyl)pyrimidin-2-ylamino)benzoyl)piperazin-1-yl)ethanone, (3-(5-(4-methoxyphenyl)pyrimidin-2-ylamino)phenyl)(4-(pyrrolidin-1-yl)piperidin-1-yl)methanone, 1,4'-bipiperidin-1'-yl(3-(5-(4-methoxyphenyl)pyrimidin-2-ylamino)phenyl)methanone, 1-(3-(5-(4-methoxyphenyl)pyrimidin-2-ylamino)benzoyl)piperidine-3-carboxamide, N-(3-(5-(4-methoxyphenyl)pyrimidin-2-ylamino)phenyl)-4-(1-methylpiperidin-4-yl)piperazine-1-carboxamide, methyl 4-(3-(5-(4-methoxyphenyl)pyrimidin-2-ylamino)phenylcarbamoyl)piperazine-1-carboxylate, (R)-1-(4-(5-(4-methoxyphenyl)pyrimidin-2-ylamino)phenethyl)piperidine-3-carboxylic acid, (4-(5-(4-methoxyphenyl)pyrimidin-2-ylamino)phenyl)(piperazin-1-yl)methanone, 4-acetyl-N-(3-(5-(4-methoxyphenyl)pyrimidin-2-ylamino)phenyl)piperazine-1-carboxamide, and (3-(5-(4-methoxyphenyl)pyrimidin-2-ylamino)phenyl)(piperazin-1-yl)methanone.

In further or alternative embodiments, Q of the compound having the structure of Formula (1) is selected from the group consisting of

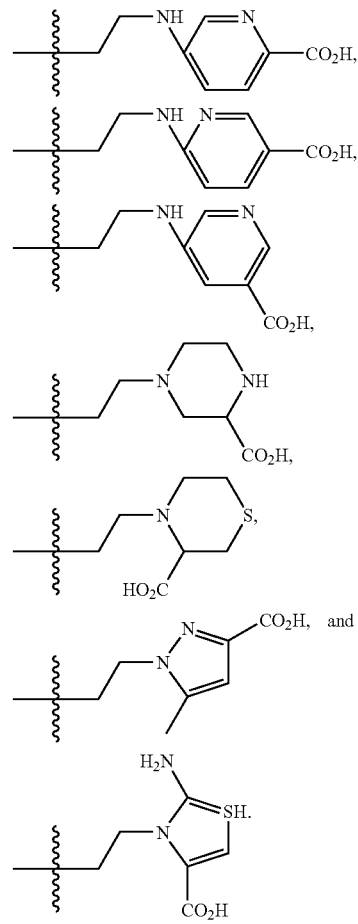

In further or alternative embodiments, Q of the compound having the structure of Formula (1) is selected from the group consisting of

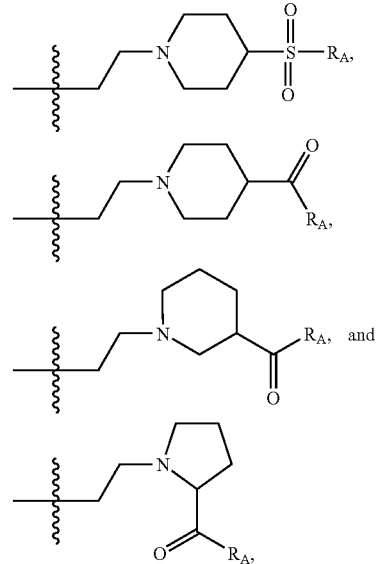

wherein $R_A$ is selected from —$NH_2$, —$NEt_2$, and —NH($CH_2$)$_n$OH; and n is 1 to 6.

In further or alternative embodiments, Q of the compound having the structure of Formula (1) is

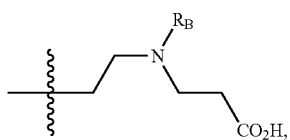

wherein $R_B$ is selected from the group consisting of

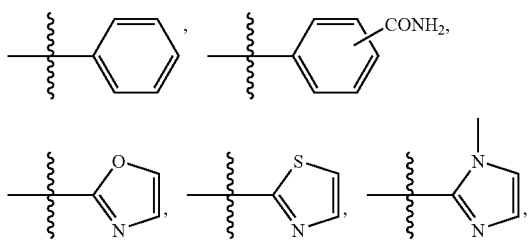

—$CH_2OH$, —$CH_2CH_2OH$, and —$CH_2CH_2CH_2OH$.

In further or alternative embodiments, Q of the compound having the structure of Formula (1) is

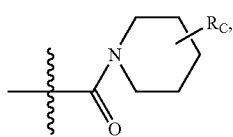

wherein $R_C$ is at 2, 3, or 4 position of the piperidine ring; and $R_C$ is selected from the group consisting of —C(O)NHEt, —C(O)NEt$_2$, c-butyl, c-pentyl, —C(O)NH-thiazole, oxazole, thiazole, —S(O)$_2$NH$_2$, —S(O)$_2$NHEt, and —S(O)$_2$NEt$_2$.

In further or alternative embodiments, Q of the compound having the structure of Formula (1) is selected from the group consisting of

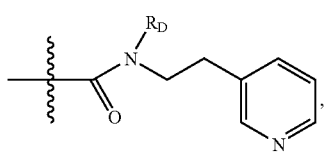

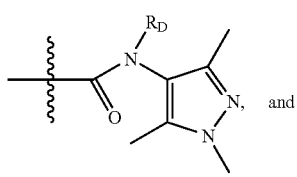
and

-continued

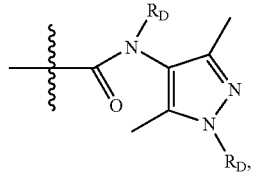

wherein each $R_D$ is independently selected from —(CH$_2$)$_k$OH or —(CH$_2$)$_k$CO$_2$H; and k is 1 to 6.

In further or alternative embodiments, Q of the compound having the structure of Formula (1) is

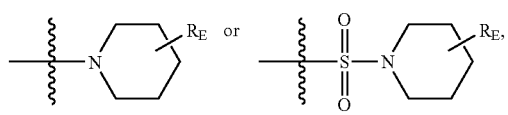

wherein $R_E$ is at 2, 3, or 4 position of the piperidine ring; and $R_E$ is selected from the group consisting of —C(O)NH$_2$, —C(O)NHEt, and —C(O)NEt$_2$.

In further or alternative embodiments, Q of the compound having the structure of Formula (1) is selected from the group consisting of

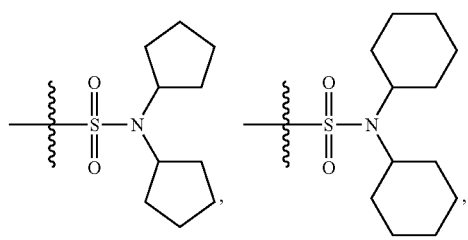

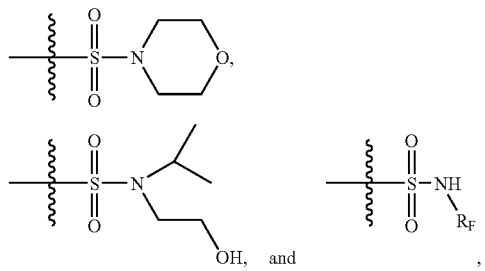

wherein $R_F$ is thiazole, pyrazole, or isoxazole.

In further or alternative embodiments, Q of the compound having the structure of Formula (46) is selected from the group consisting of

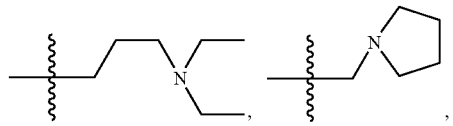

-continued
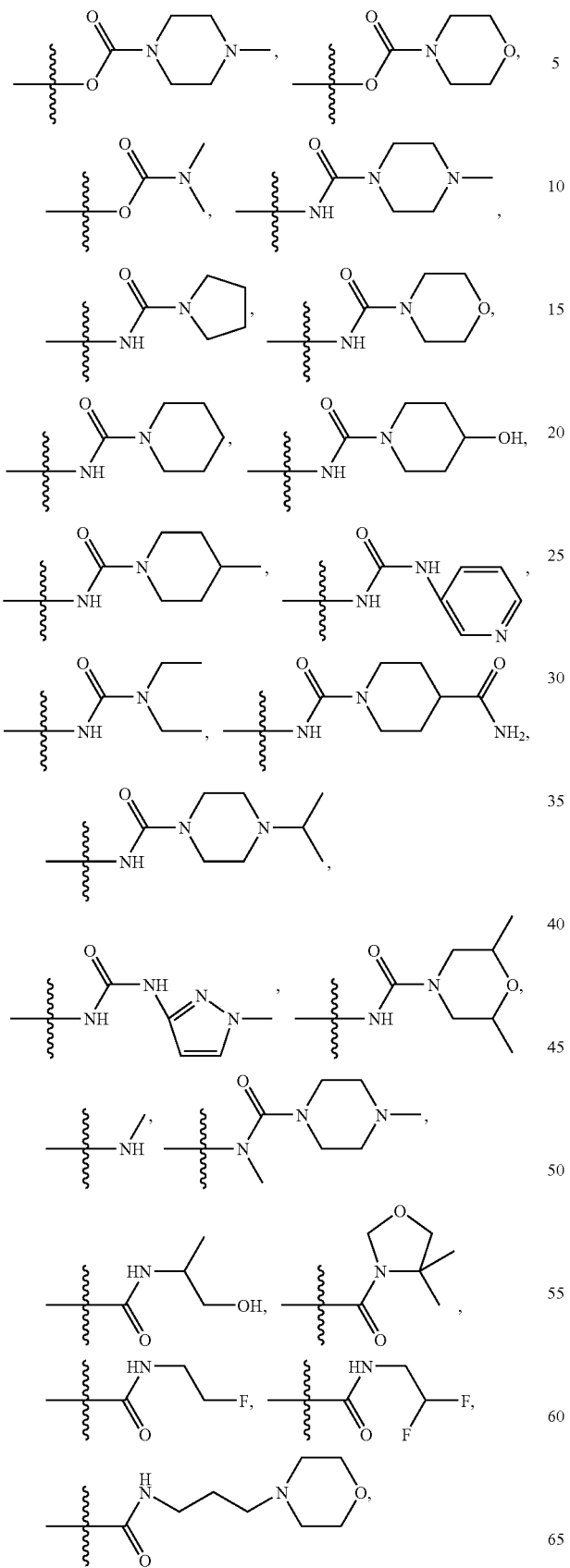
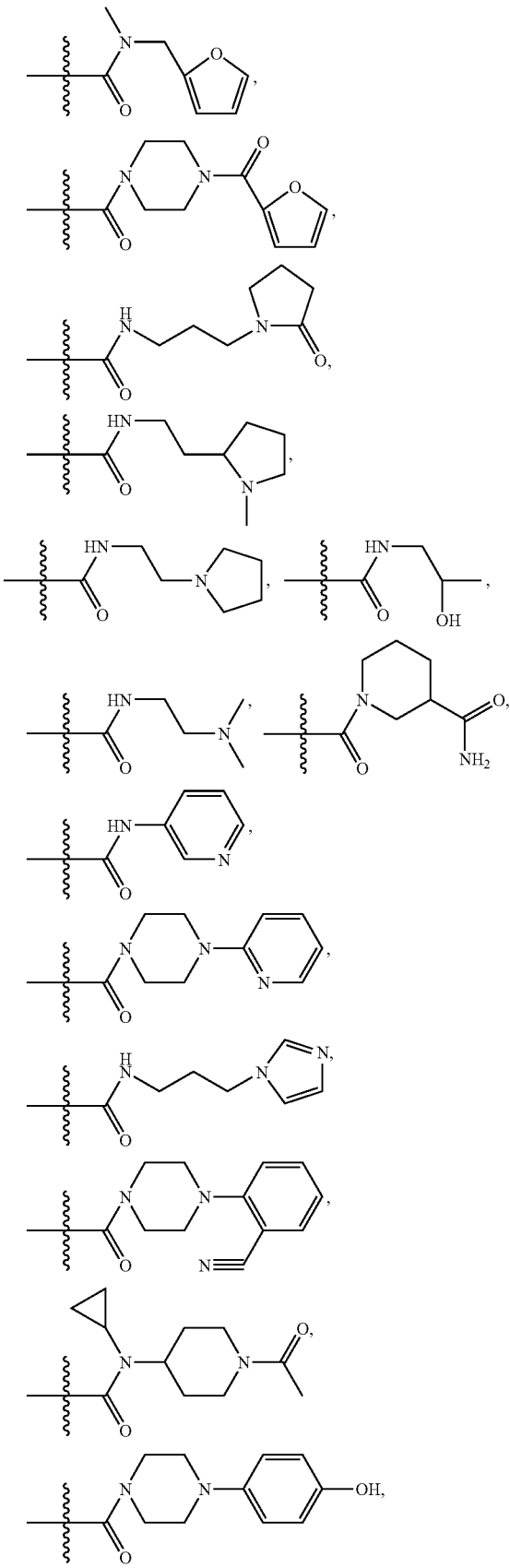

-continued
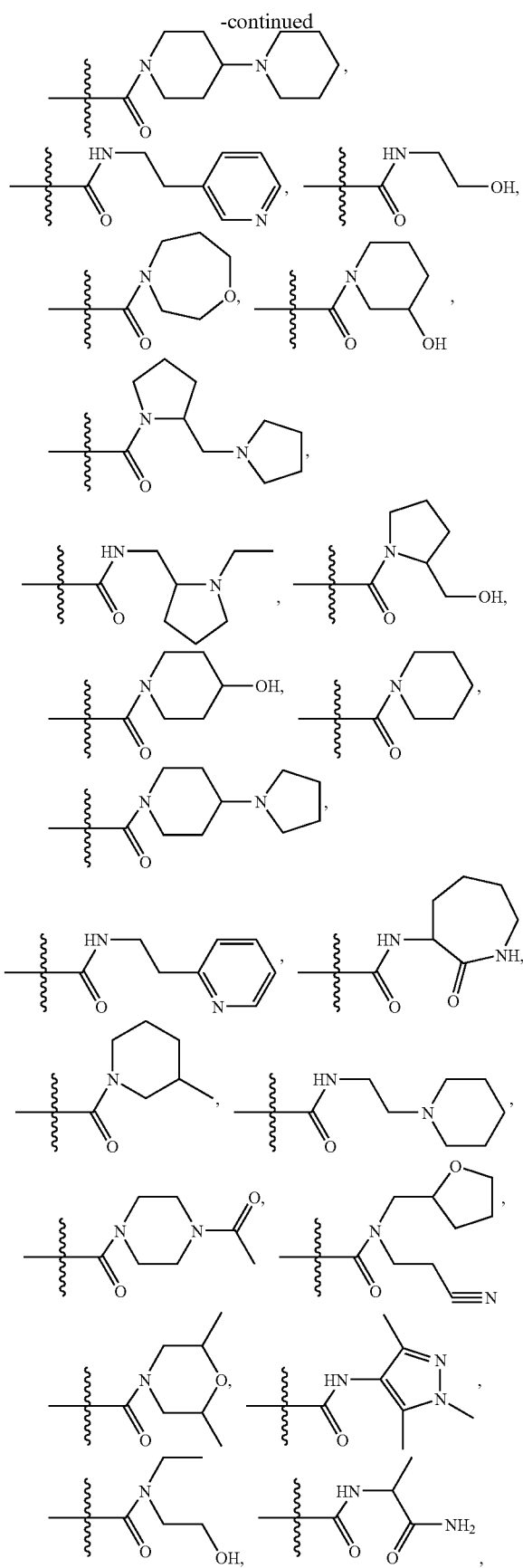
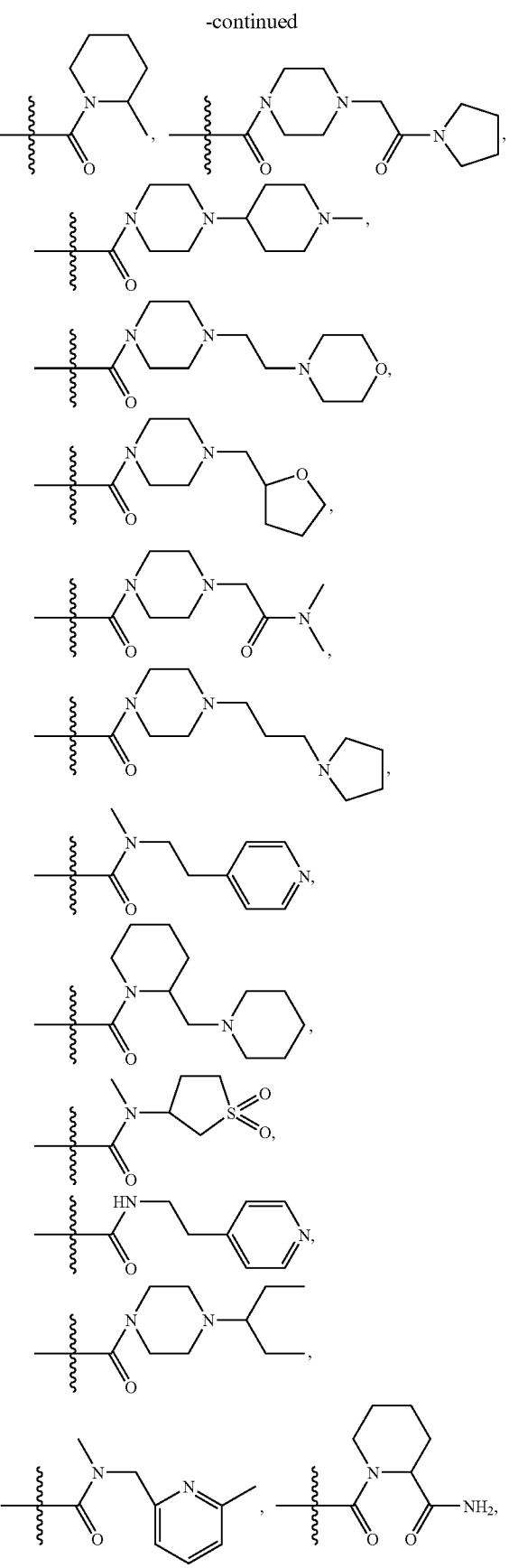

-continued

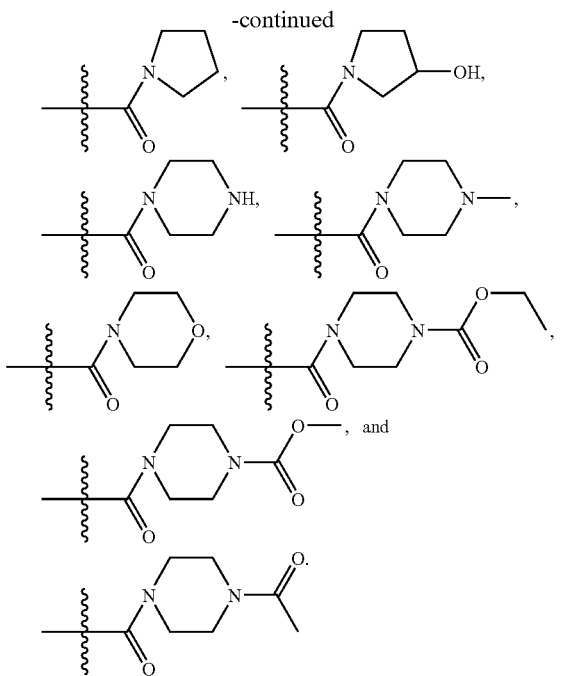

In further or alternative embodiments, Q of the compound having the structure of Formula (46) is selected from the group consisting of

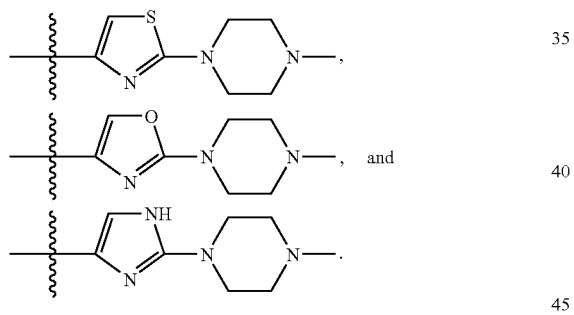

In further or alternative embodiments, $R_s$ is H. In further or alternative embodiments, each $R_1$ is H. In further or alternative embodiments, each $R_1$ is H and $R_5$ is H. In further or alternative embodiments, Q is a group comprising a non-aromatic tertiary amine.

In a further or alternative embodiment of this aspect, compounds having the structure of Formula (1) are selected from Formula (2), Formula (3), or Formula (44):

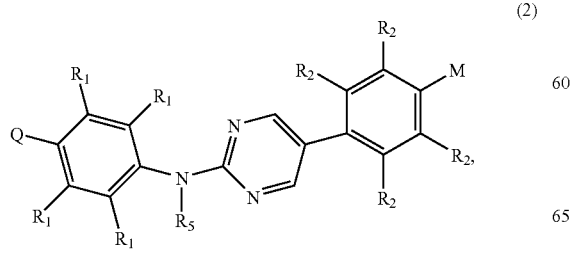

-continued

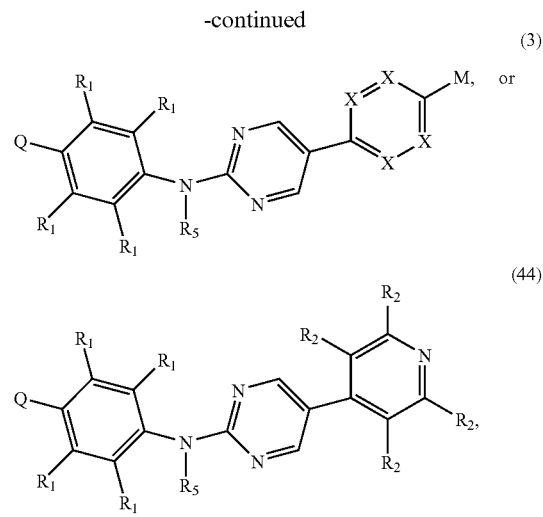

wherein:

M is selected from the group consisting of H, OH, SH, NO$_2$, CN, NR"$_2$, and an optionally substituted moiety selected from -L$_7$-alkyl, -L$_7$-cycloalkyl, -L$_7$-heteroalkyl, -L$_7$-haloalkyl, -L$_7$-aryl, -L$_7$-heterocycloalkyl, and -L$_7$-heteroaryl; wherein L$_7$ is selected from a bond, —O—, —NH—, —S—, —C(O)—, —C(S)—, —C(O)O—, —C(O)NH—, —S(O)—, —S(O)$_2$—, —OC(O)—, —C(O)NR'(CR"$_2$)$_{1-6}$C(O)O—, —CR"$_2$NR"CR"$_2$C(O)O—, —C(O)NR"Y"C(O)O—, —C(O)NR"NR"C(O)O—, —S(O)NH—, —C(O)NR"CR"$_2$C(O)W—, —CR"$_2$NR"WO—, —CR"$_2$NR"Y$^1$C(O)O—, and —C(O)NR"O—; W is C$_{1-6}$alkylene; Y$^1$ is optionally substituted arylene or optionally substituted heteroarylene; wherein said optional substituents are selected from halogen, OH, C$_{1-6}$alkyl, C$_{1-6}$alkoxy, halo-C$_{1-6}$alkyl and halo-C$_{1-6}$ alkoxy; provided that M is not H in Formula (2);

each R" is independently H, OH, halogen, C$_{1-6}$alkyl, substituted C$_{1-6}$alkyl, C$_{1-6}$alkoxy, halo-C$_{1-6}$alkyl, halo-C$_{1-6}$alkoxy, aryl, haloaryl, or heteroaryl;

each X is independently selected from N or CR$_2$, provided that at least one but no more than 2 X groups are N;

each R$_2$ is independently selected from the group consisting of H, OH, halogen, and an optionally substituted moiety selected from -L$_2$-alkyl, -L$_2$-cycloalkyl, -L$_2$-heteroalkyl, -L$_2$-haloalkyl, L$_2$-aryl, -L$_2$-heterocycloalkyl, and -L$_2$-heteroaryl; wherein L$_2$ is selected from a bond, —O—, —NH—, —S—, —C(O)—, —C(S)—, —C(O)O—, —C(O)NH—, —S(O)—, —S(O)$_2$—, —C(O)NR"(CR"$_2$)$_{1-6}$C(O)O—, —OC(O)—, —CR"$_2$NR"CR"$_2$C(O)O—, —C(O)NR"NR"C(O)O—, and —S(O)NH—; wherein said optional substituents are selected from halogen, OH, C$_{1-6}$alkyl, C$_{1-6}$alkoxy, halo-C$_{1-6}$alkyl and halo-C$_{1-6}$ alkoxy;

or any two adjacent R$_2$ groups together may form an optionally substituted 5 to 8-membered heterocyclic, cycloalkyl, or aryl ring;

or a pharmaceutically acceptable salt, pharmaceutically acceptable N-oxide, pharmaceutically active metabolite, pharmaceutically acceptable prodrug, or pharmaceutically acceptable solvate thereof.

In further or alternative embodiments, $L_7$ is selected from a bond, —O—, —NH—, —S—, —C(O)—, —C(S)—, —OC(O)—, —CH$_2$NHCH$_2$C(O)O—, —CH$_2$NH(CH$_2$)$_2$O—, —C(O)O—, —C(O)NH—, —S(O)—, —S(O)$_2$—, —C(O)NH(CR"$_2$)$_{1-6}$C(O)O—, —C(O)NR"NR"C(O)O—, and —S(O)NH—. In further or alternative embodiments, $L_2$ is selected from a bond, —C(O)—, —C(S)—, —C(O)O—, —C(O)NH—, —S(O)—, —S(O)$_2$—, —C(O)NH(CR"$_2$)$_{1-6}$C(O)O—, —C(O)NR"NR"C(O)O—, and —S(O)NH—. In further or alternative embodiments, each $R_1$ is H. In further or alternative embodiments, each $R_2$ is H. In further or alternative embodiments, $R_5$ is H. In further or alternative embodiments, each $R_1$ is H, each $R_2$ is H, and $R_5$ is H.

In a further or alternative embodiment of this aspect, compounds having the structure of Formula (46) are selected from Formula (47), Formula (48), or Formula (49):

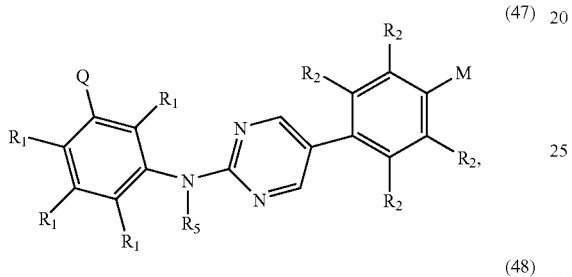

(47)

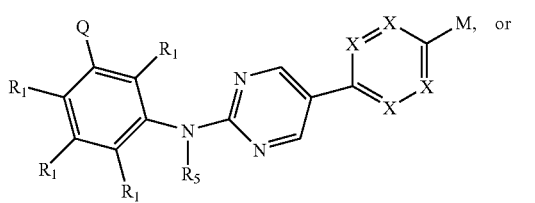

(48)

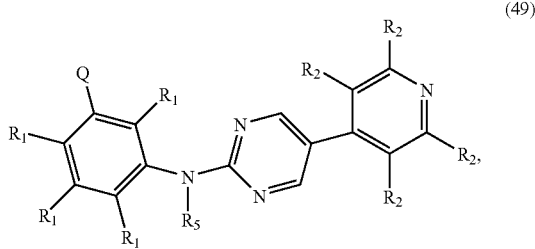

(49)

wherein:
M is selected from the group consisting of H, OH, SH, NO$_2$, CN, NR"$_2$, and an optionally substituted moiety selected from -$L_7$-alkyl, -$L_7$-cycloalkyl, -$L_7$-heteroalkyl, -$L_7$-haloalkyl, -$L_7$-aryl, -$L_7$-heterocycloalkyl, and -$L_7$-heteroaryl; wherein $L_7$ is selected from a bond, —O—, —NH—, —S—, —C(O)—, —C(S)—, —C(O)O—, —C(O)NH—, —S(O)—, —S(O)$_2$—, —OC(O)—, —C(O)NR"(CR"$_2$)$_{1-6}$C(O)O—, —CR"$_2$NR"CR"$_2$C(O)O—, —C(O)NR"Y$^1$C(O)O—, —C(O)NR"NR"C(O)O—, —S(O)NH—, —C(O)NR"CR"$_2$C(O)W—, —CR"$_2$NR"WO—, —CR"$_2$NR"Y$^1$C(O)O—, and —C(O)NR"O—; W is C$_{1-6}$alkylene; Y$^1$ is optionally substituted arylene or optionally substituted heteroarylene; wherein said optional substituents are selected from halogen, OH, C$_{1-6}$alkyl, C$_{1-6}$alkoxy, halo-C$_{1-6}$alkyl and halo-C$_{1-6}$alkoxy; provided that M is not H in Formula (47);

each R" is independently H, OH, halogen, C$_{1-6}$alkyl, substituted C$_{1-6}$alkyl, C$_{1-6}$alkoxy, halo-C$_{1-6}$alkyl, halo-C$_{1-6}$alkoxy, aryl, haloaryl, or heteroaryl;

each X is independently selected from N or CR$_2$, provided that at least one but no more than 2 X groups are N;

each $R_2$ is independently selected from the group consisting of H, OH, halogen, and an optionally substituted moiety selected from -$L_2$-alkyl, -$L_2$-cycloalkyl, -$L_2$-heteroalkyl, -$L_2$-haloalkyl, -$L_2$-aryl, -$L_2$-heterocycloalkyl, and -$L_2$-heteroaryl; wherein $L_2$ is selected from a bond, —O—, —NH—, —S—, —C(O)—, —C(S)—, —C(O)O—, —C(O)NH—, —S(O)—, —S(O)$_2$—, —C(O)NH"(CR"$_2$)$_{1-6}$C(O)O—, —OC(O)—, —CR"$_2$NR"CR"$_2$C(O)O—, —C(O)NR"NR"C(O)O—, and —S(O)NH—; wherein said optional substituents are selected from halogen, OH, C$_{1-6}$alkyl, C$_{1-6}$alkoxy, halo-C$_{1-6}$alkyl and halo-C$_{1-6}$alkoxy;

or any two adjacent $R_2$ groups together may form an optionally substituted 5 to 8-membered heterocyclic, cycloalkyl, or aryl ring;

or a pharmaceutically acceptable salt, pharmaceutically acceptable N-oxide, pharmaceutically active metabolite, pharmaceutically acceptable prodrug, or pharmaceutically acceptable solvate thereof.

In further or alternative embodiments, $L_7$ is selected from a bond, —O—, —NH—, —S—, —C(O)—, —C(S)—, —OC(O)—, —CH$_2$NHCH$_2$C(O)O—, —CH$_2$NH(CH$_2$)$_2$O—, —C(O)O—, —C(O)NH—, —S(O)—, —S(O)$_2$—, —C(O)NH(CR"$_2$)$_{1-6}$C(O)O—, —C(O)NR"NR"C(O)O—, and —S(O)NH—. In further or alternative embodiments, $L_2$ is selected from a bond, —C(O)—, —C(S)—, —C(O)O—, —C(O)NH—, —S(O)—, —S(O)$_2$—, —C(O)NH(CR"$_2$)$_{1-6}$C(O)O—, —C(O)NR"NR"C(O)O—, and —S(O)NH—. In further or alternative embodiments, each $R_1$ is H. In further or alternative embodiments, each $R_2$ is H. In further or alternative embodiments, $R_5$ is H. In further or alternative embodiments, each $R_1$ is H, each $R_2$ is H, and $R_5$ is H.

In a further or alternative embodiment of this aspect, are compounds having the structure of Formula (1) or Formula (46) in which the Ar group is a 5-membered carbocyclic bearing up to four substituents. In further or alternative embodiments, compounds having the structure of Formula (1) are selected from Formula (4), Formula (5), or Formula (6):

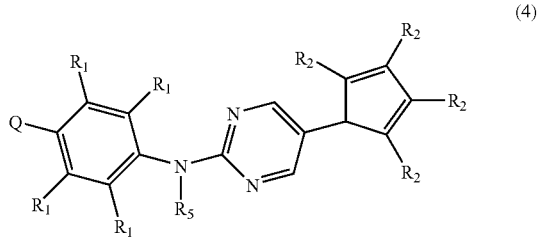

(4)

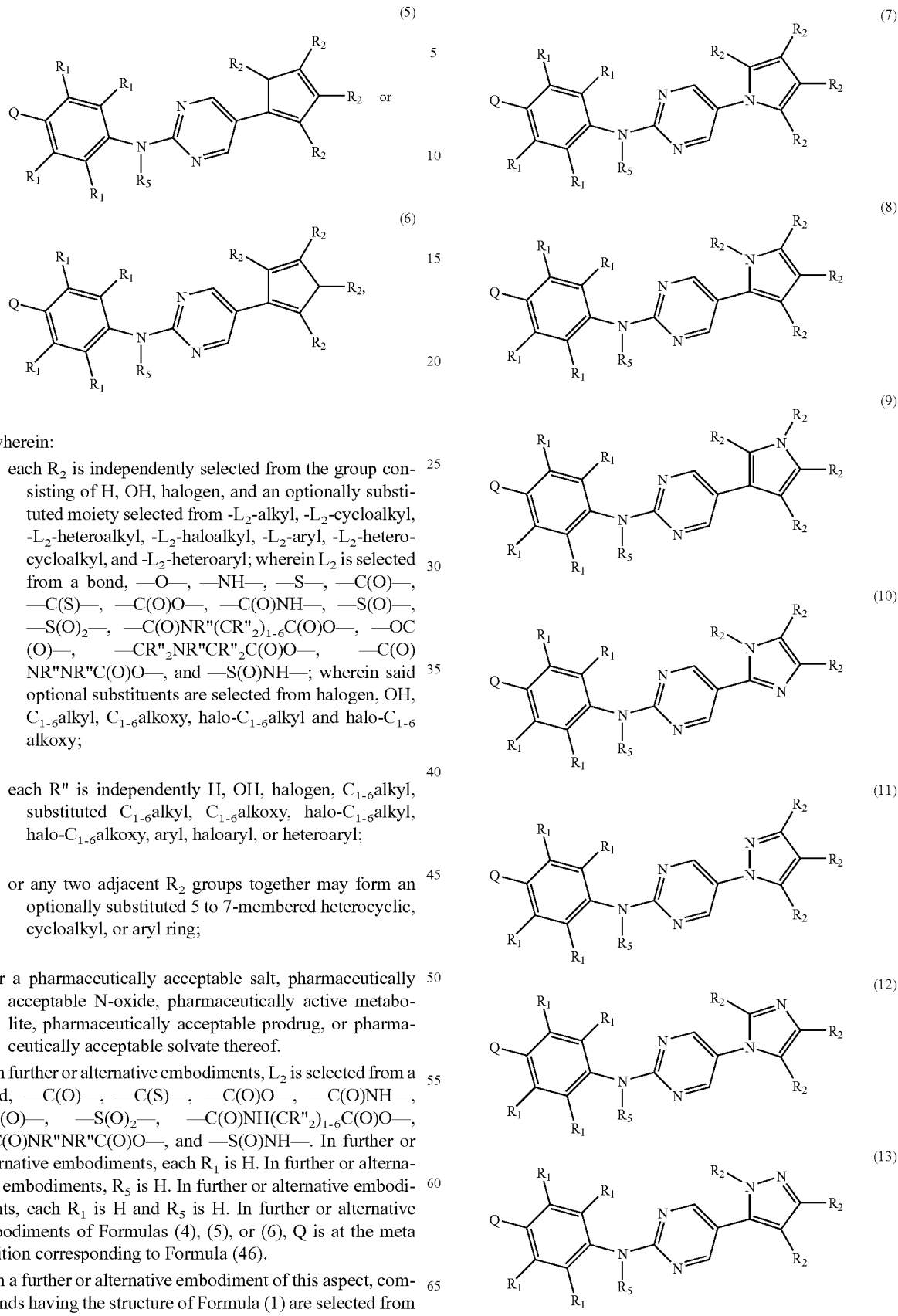

wherein:

each R₂ is independently selected from the group consisting of H, OH, halogen, and an optionally substituted moiety selected from -L₂-alkyl, -L₂-cycloalkyl, -L₂-heteroalkyl, -L₂-haloalkyl, -L₂-aryl, -L₂-heterocycloalkyl, and -L₂-heteroaryl; wherein L₂ is selected from a bond, —O—, —NH—, —S—, —C(O)—, —C(S)—, —C(O)O—, —C(O)NH—, —S(O)—, —S(O)₂—, —C(O)NR″(CR″₂)₁₋₆C(O)O—, —OC(O)—, —CR″₂NR″CR″₂C(O)O—, —C(O)NR″NR″C(O)O—, and —S(O)NH—; wherein said optional substituents are selected from halogen, OH, $C_{1-6}$alkyl, $C_{1-6}$alkoxy, halo-$C_{1-6}$alkyl and halo-$C_{1-6}$alkoxy;

each R″ is independently H, OH, halogen, $C_{1-6}$alkyl, substituted $C_{1-6}$alkyl, $C_{1-6}$alkoxy, halo-$C_{1-6}$alkyl, halo-$C_{1-6}$alkoxy, aryl, haloaryl, or heteroaryl;

or any two adjacent R₂ groups together may form an optionally substituted 5 to 7-membered heterocyclic, cycloalkyl, or aryl ring;

or a pharmaceutically acceptable salt, pharmaceutically acceptable N-oxide, pharmaceutically active metabolite, pharmaceutically acceptable prodrug, or pharmaceutically acceptable solvate thereof.

In further or alternative embodiments, L₂ is selected from a bond, —C(O)—, —C(S)—, —C(O)O—, —C(O)NH—, —S(O)—, —S(O)₂—, —C(O)NH(CR″₂)₁₋₆C(O)O—, —C(O)NR″NR″C(O)O—, and —S(O)NH—. In further or alternative embodiments, each R₁ is H. In further or alternative embodiments, R₅ is H. In further or alternative embodiments, each R₁ is H and R₅ is H. In further or alternative embodiments of Formulas (4), (5), or (6), Q is at the meta position corresponding to Formula (46).

In a further or alternative embodiment of this aspect, compounds having the structure of Formula (1) are selected from the group consisting of:

-continued

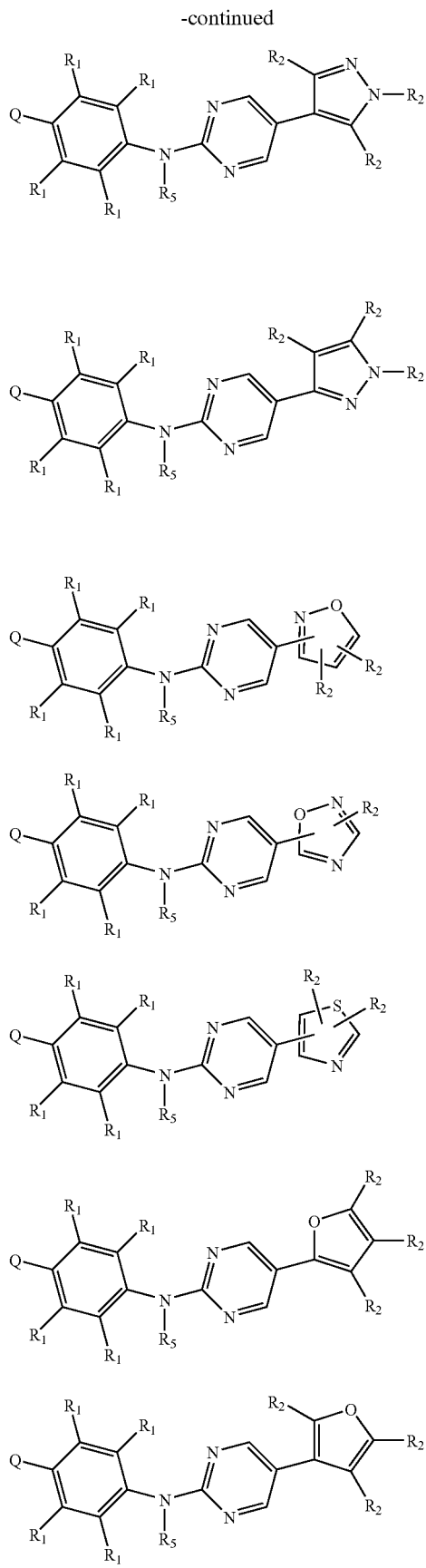

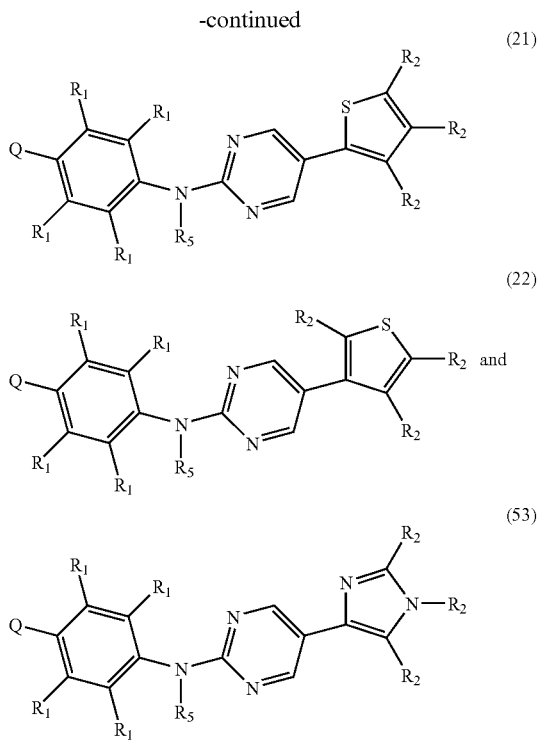

wherein;

each R₂ is independently selected from the group consisting of H, OH, halogen, and an optionally substituted moiety selected from -L₂-alkyl, -L₂-cycloalkyl, -L₂-heteroalkyl, -L₂-haloalkyl, -L₂-aryl, -L₂-heterocycloalkyl, and -L₂-heteroaryl; wherein L₂ is selected from a bond, —O—, —NH—, —S—, —C(O)—, —C(S)—, —C(O)O—, —C(O)NH—, —S(O)—, —S(O)₂—, —C(O)NR"(CR"₂)₁₋₆C(O)O—, —OC(O)—, —CR"₂NR"CR"₂C(O)O—, —C(O)NR"NR"C(O)O—, and —S(O)NH—; wherein said optional substituents are selected from halogen, OH, C₁₋₆alkyl, C₁₋₆alkoxy, halo-C₁₋₆alkyl and halo-C₁₋₆alkoxy;

each R" is independently H, OH, halogen, C₁₋₆alkyl, substituted C₁₋₆alkyl, C₁₋₆alkoxy, halo-C₁₋₁₆alkyl, halo-C₁₋₆alkoxy, aryl, haloaryl, or heteroaryl;

or any two adjacent R₂ groups together may form an optionally substituted 6 to 8-membered heterocyclic, cycloalkyl, or aryl ring;

or a pharmaceutically acceptable salt, pharmaceutically acceptable N-oxide, pharmaceutically active metabolite, pharmaceutically acceptable prodrug, or pharmaceutically acceptable solvate thereof.

In further or alternative embodiments, L₂ is selected from a bond, —C(O)—, —C(S)—, —C(O)O—, —C(O)NH—, —S(O)—, —S(O)₂—, —C(O)NH(CR"₂)₁₋₆C(O)O—, —C(O)NR"NR"C(O)O—, and —S(O)NH—. In further or alternative embodiments, each R₁ is H. In further or alternative embodiments, R₅ is H. In further or alternative embodiments, each R₁ is H and R₅ is H. In further or alternative embodiments of Formulas (7)-(22), or (53), is at the meta position corresponding to Formula (46).

In further or alternative embodiments of this aspect, Q is selected from the group consisting of

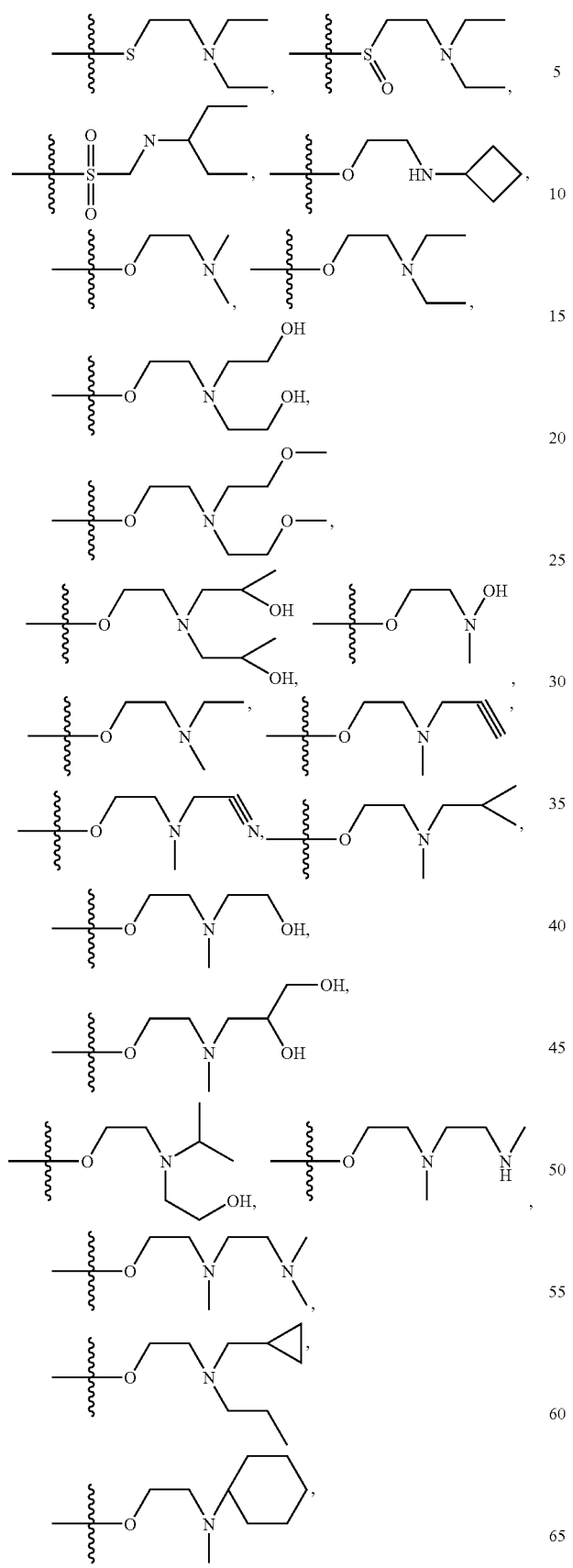
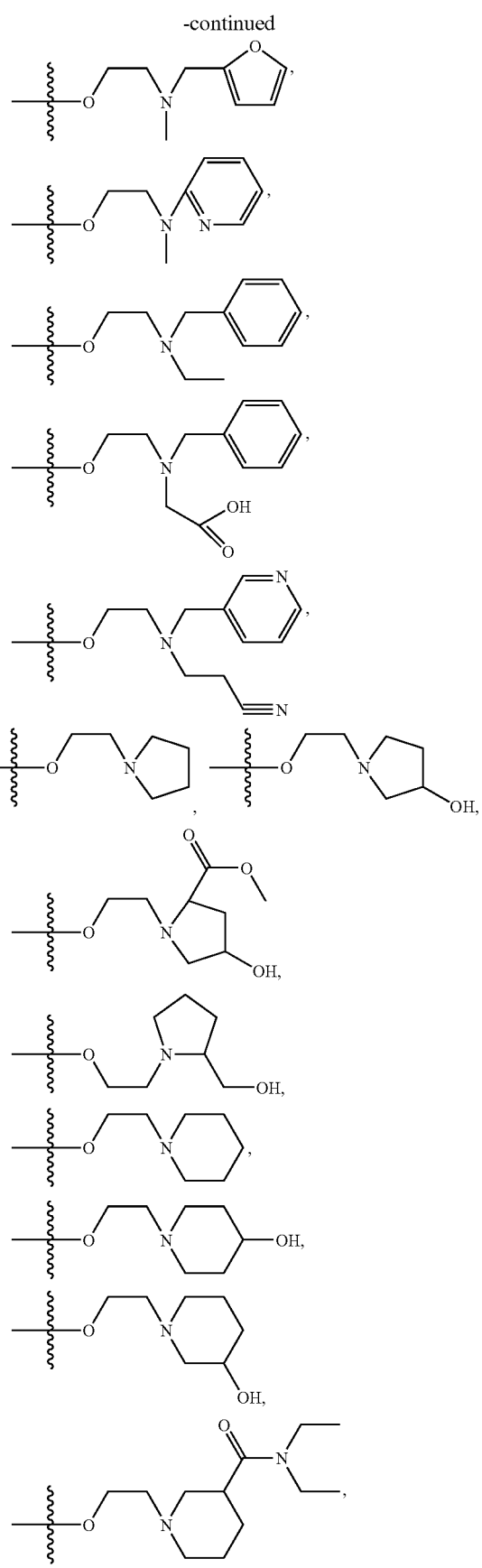

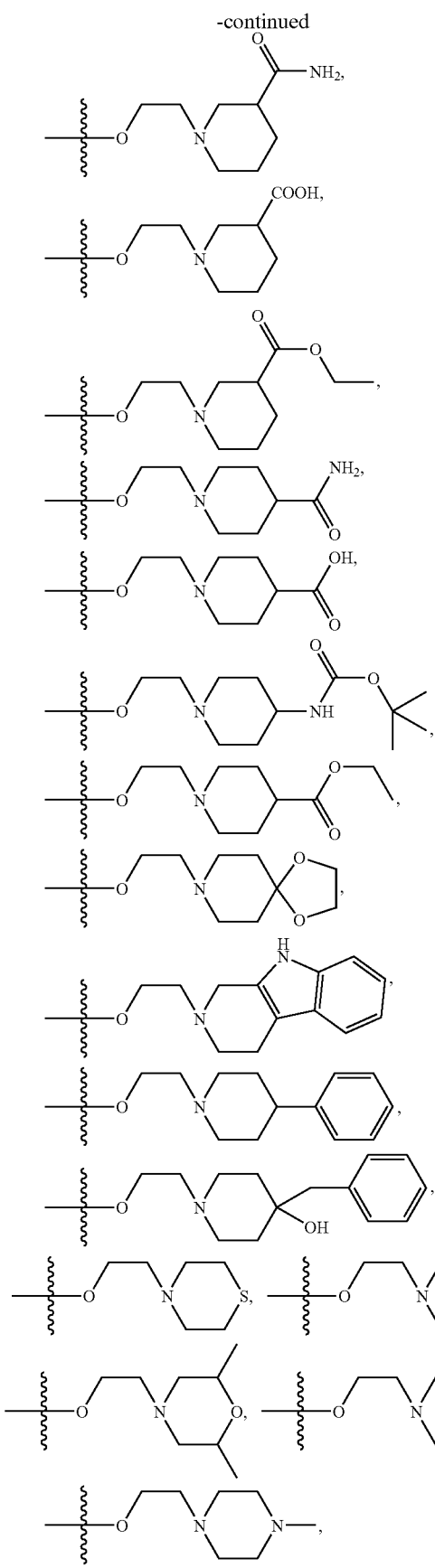
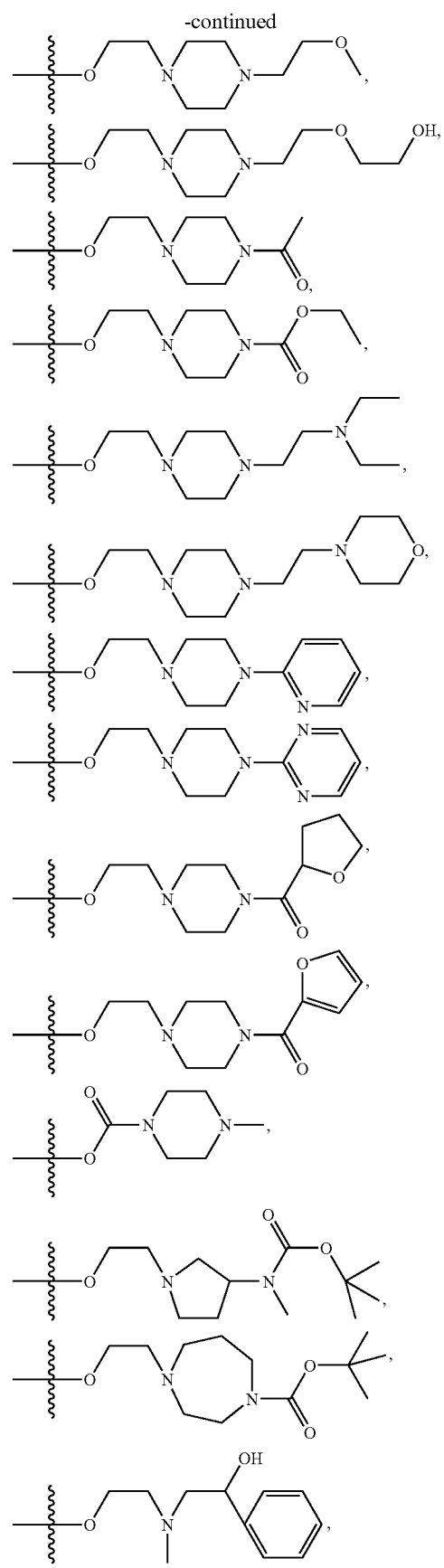

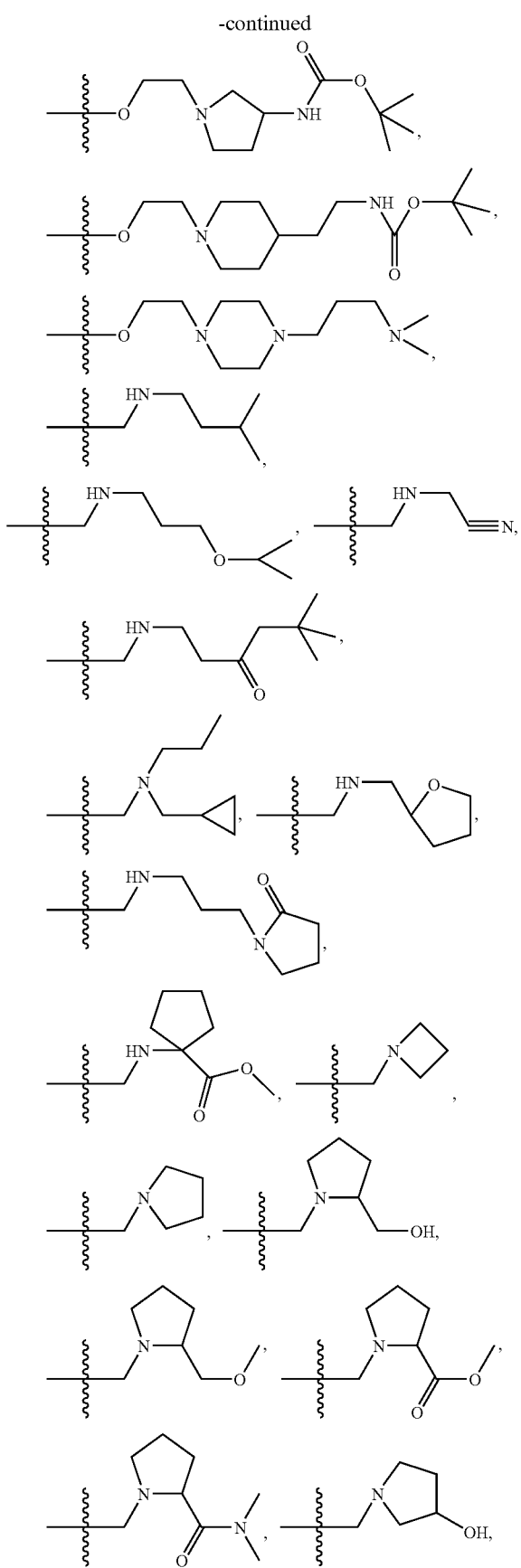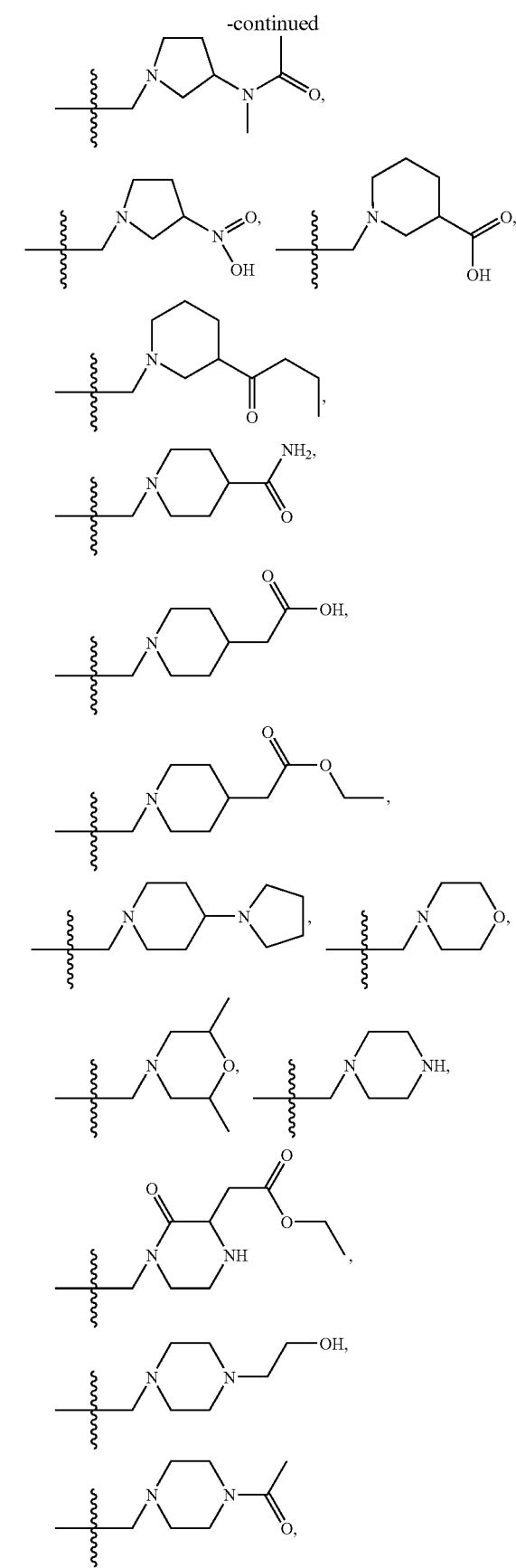

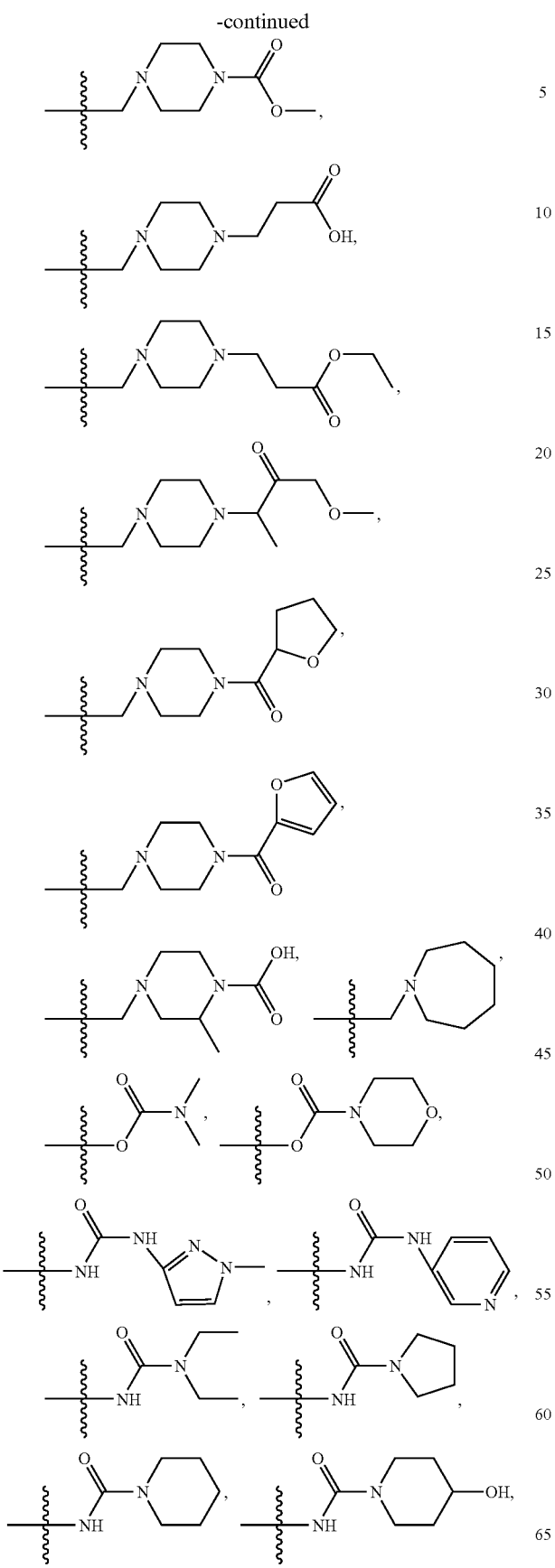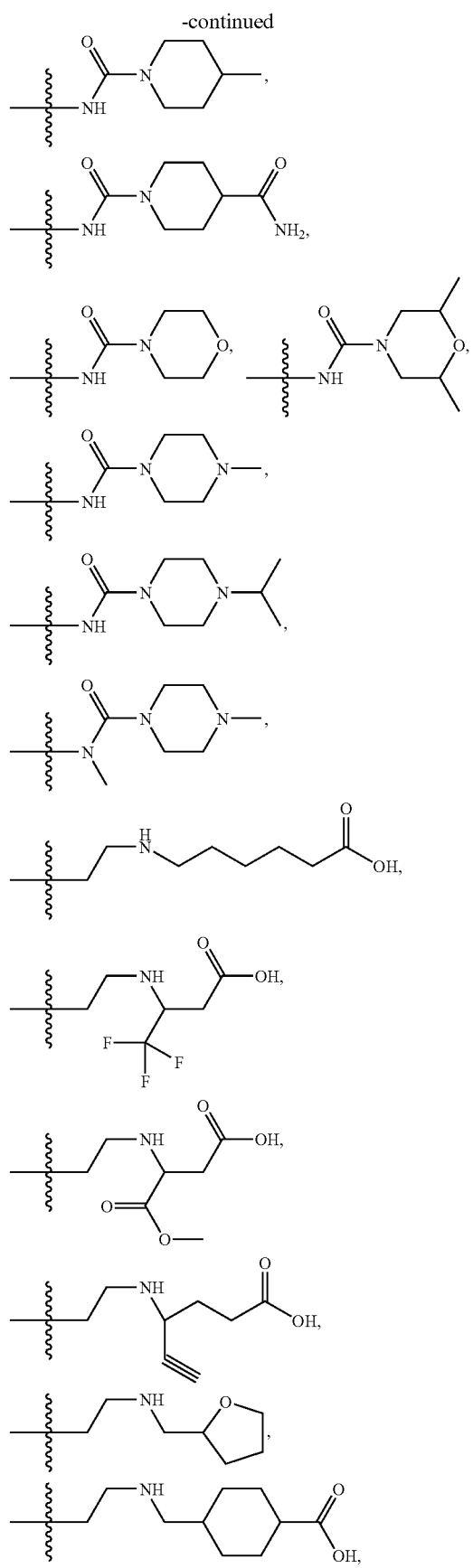

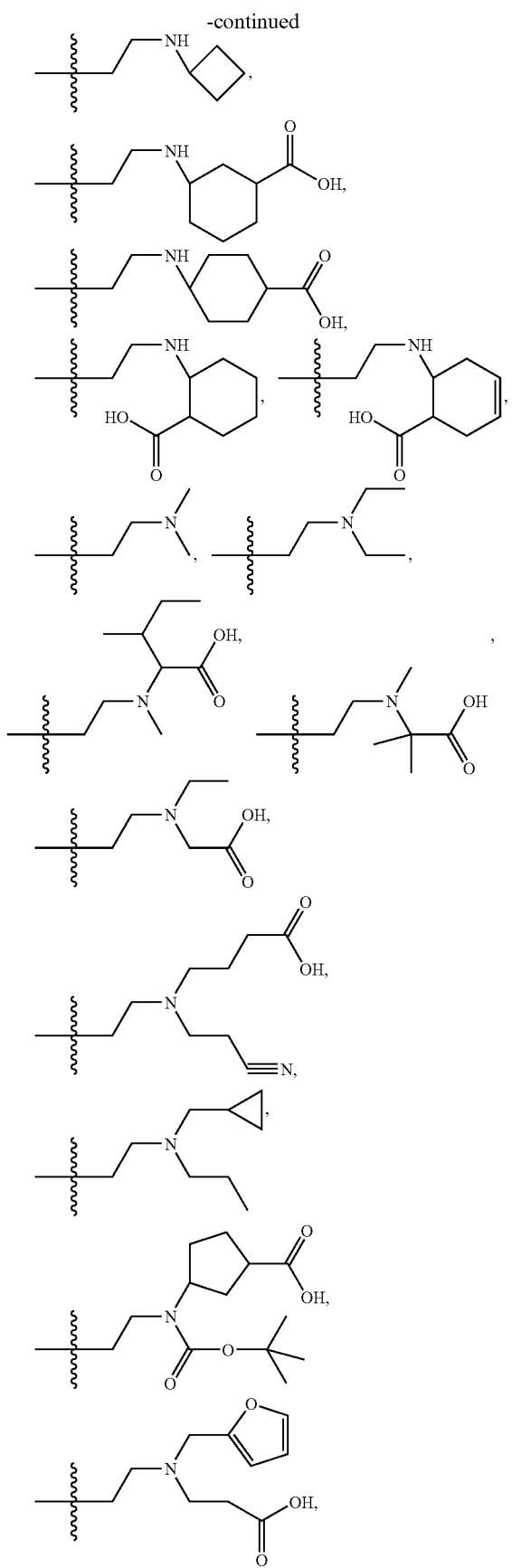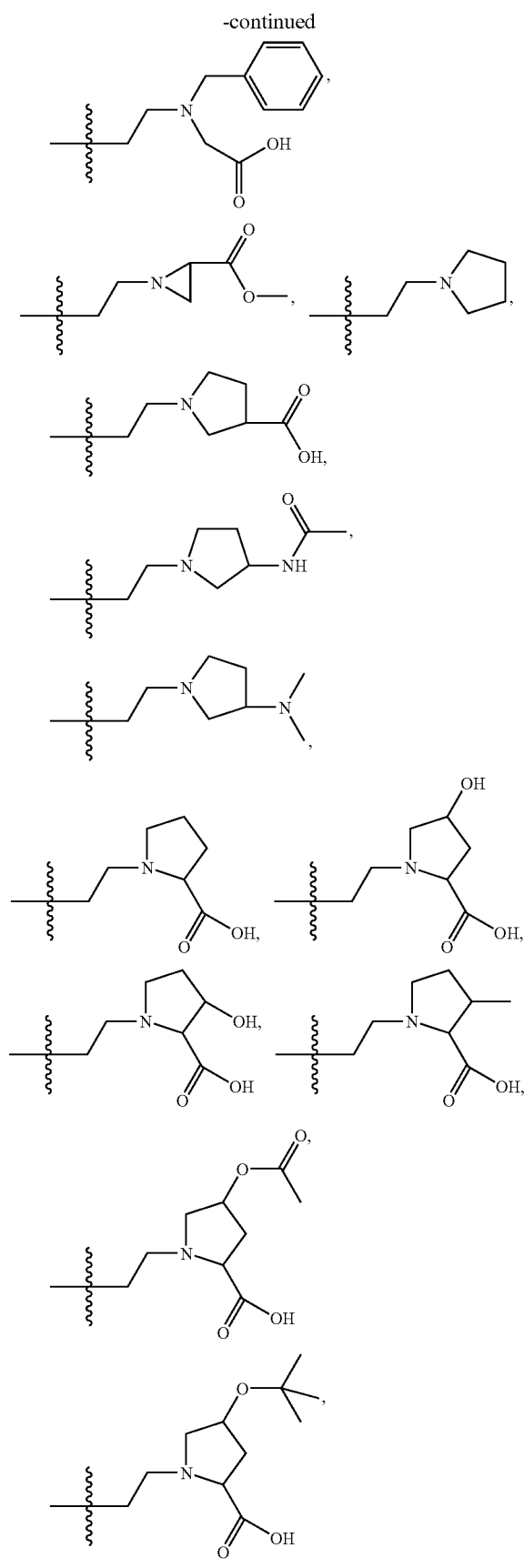

-continued
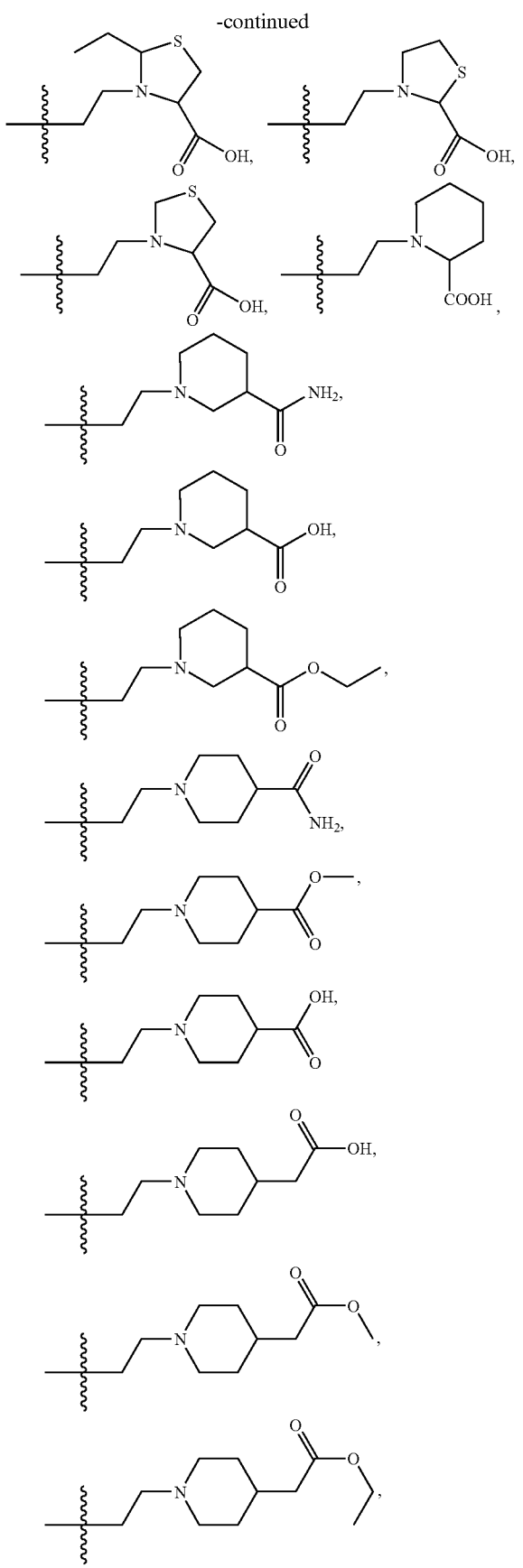
-continued
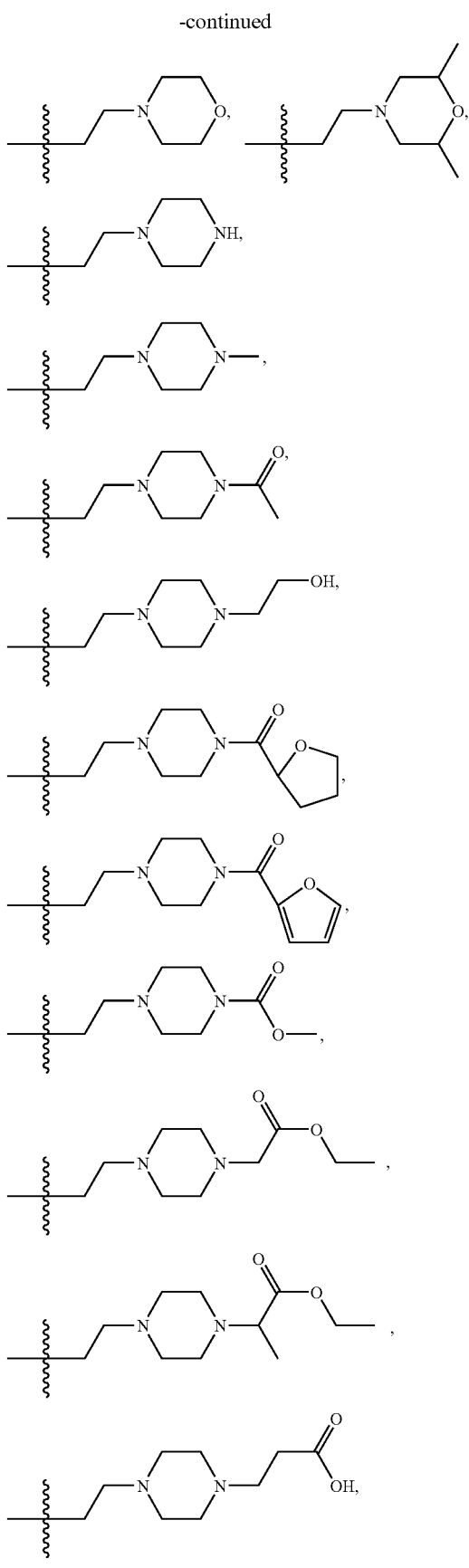

-continued
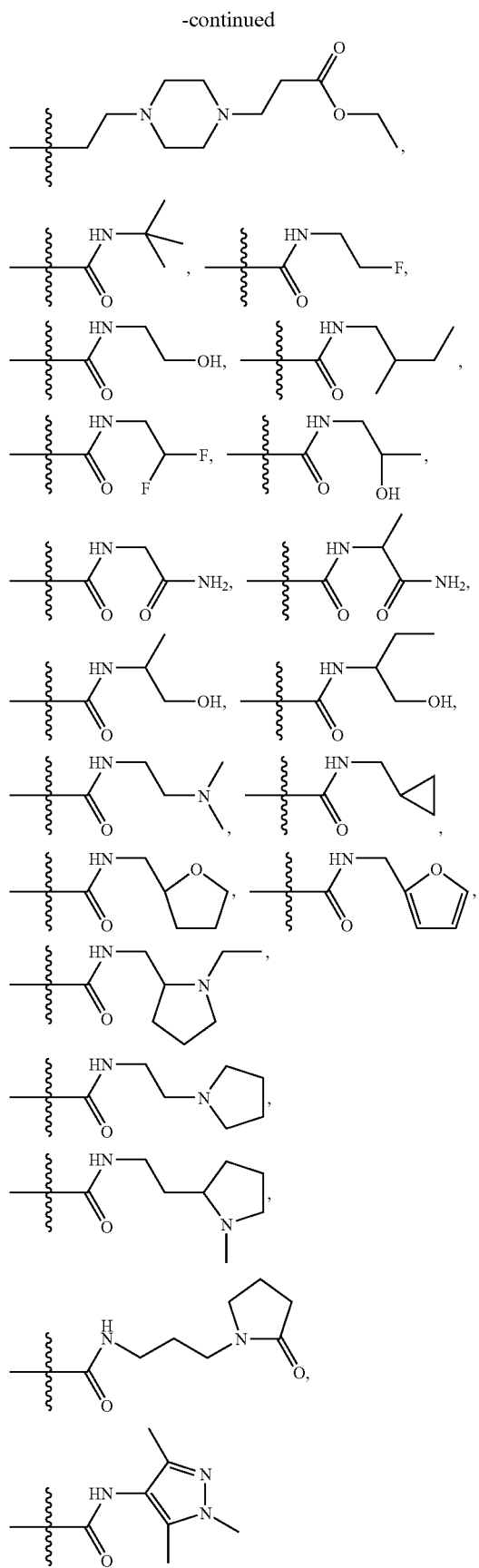
-continued
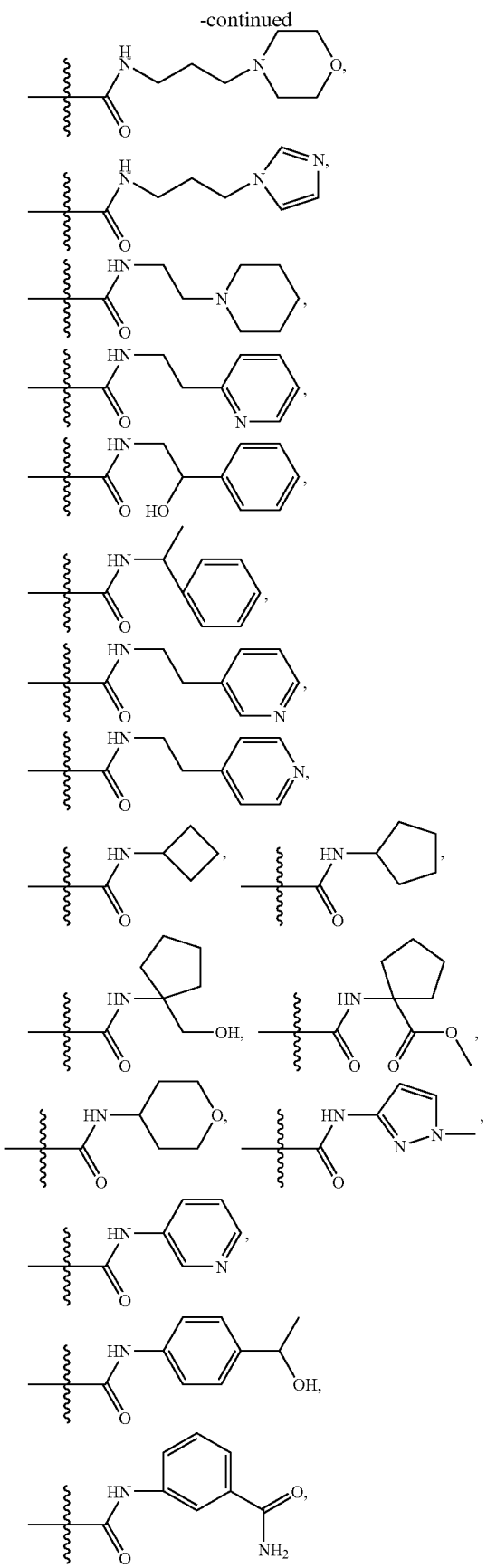

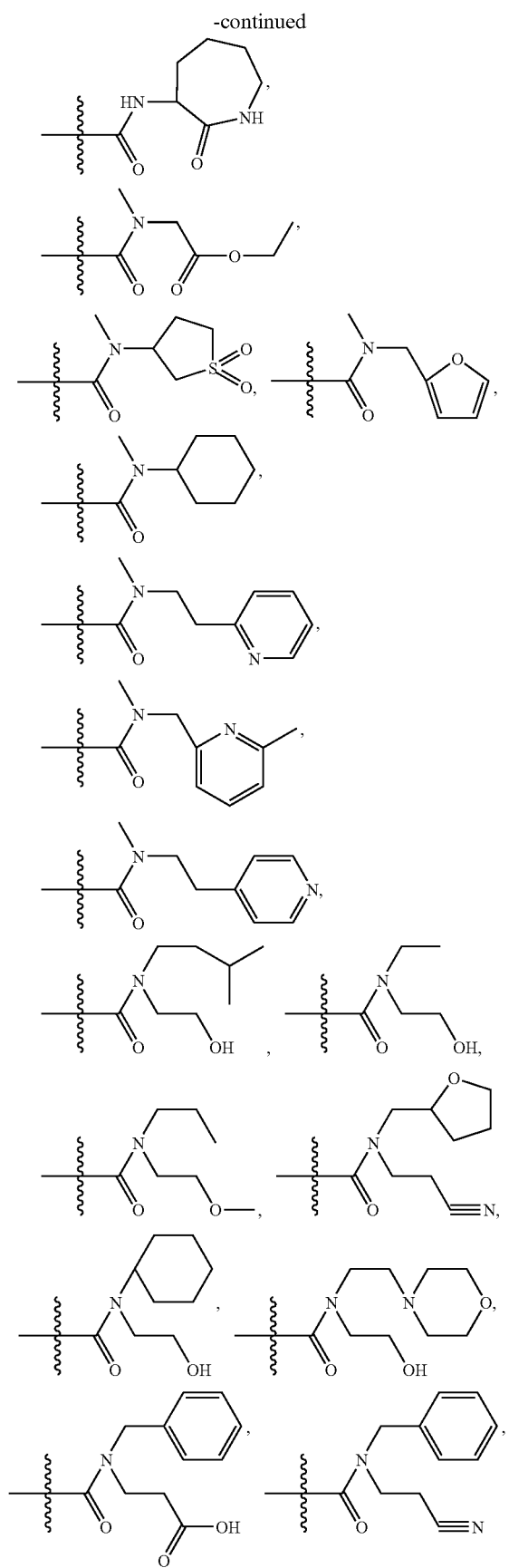
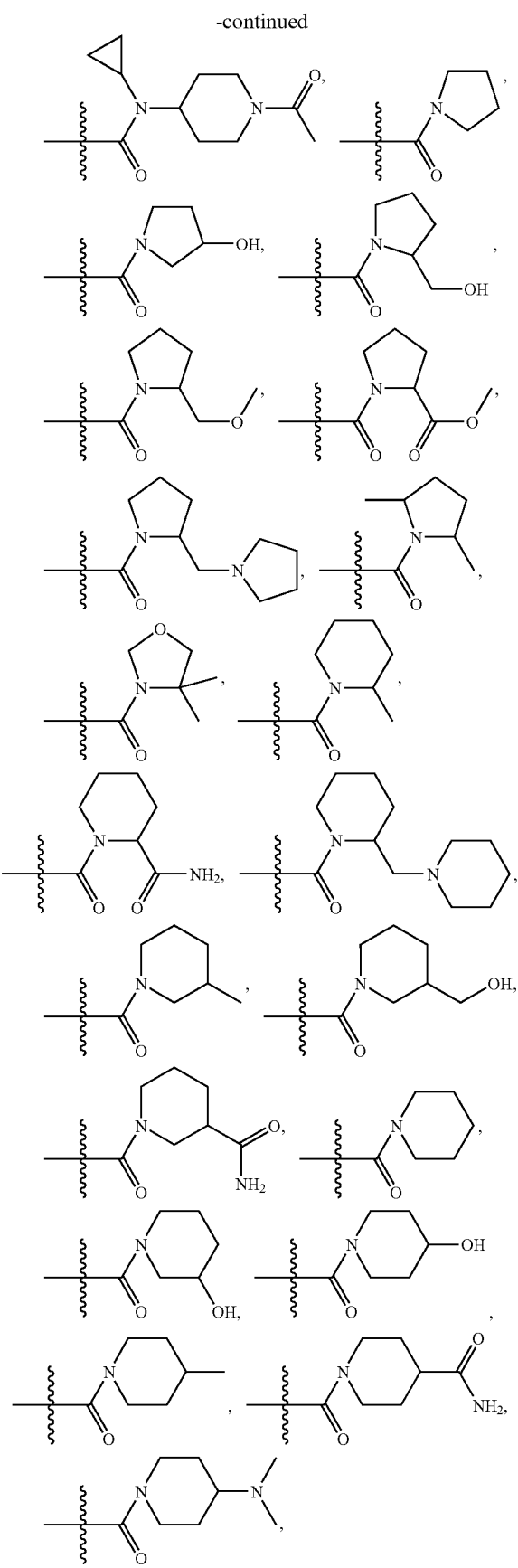

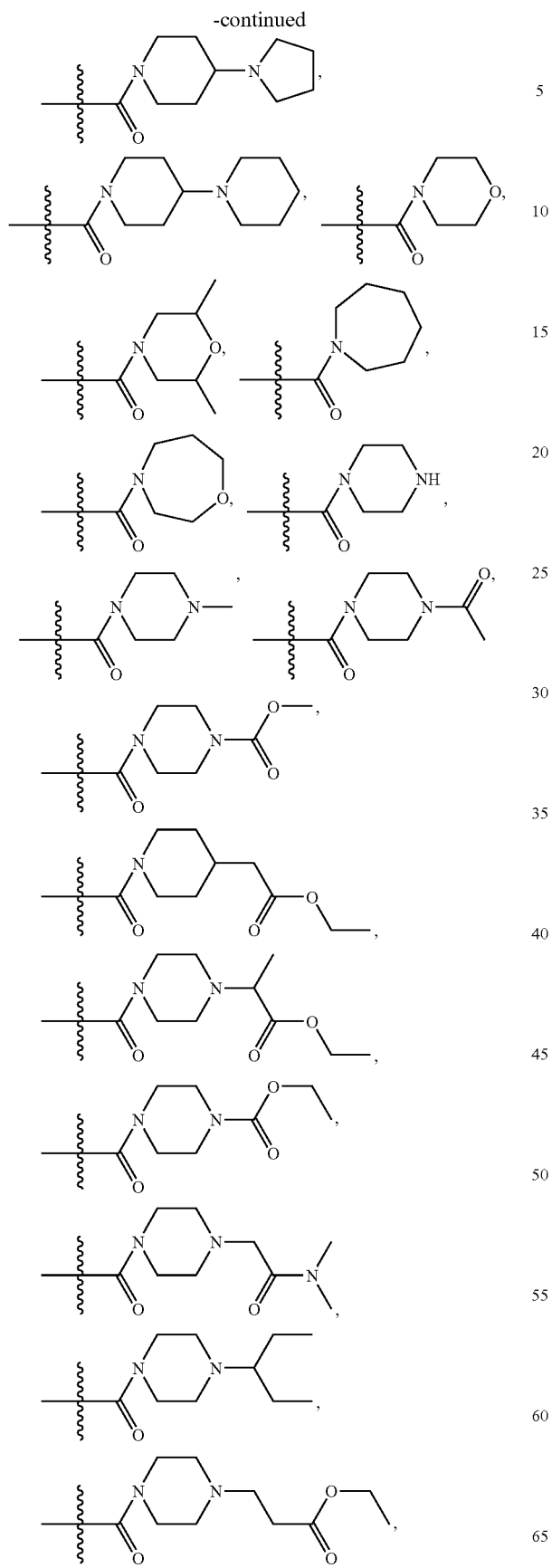
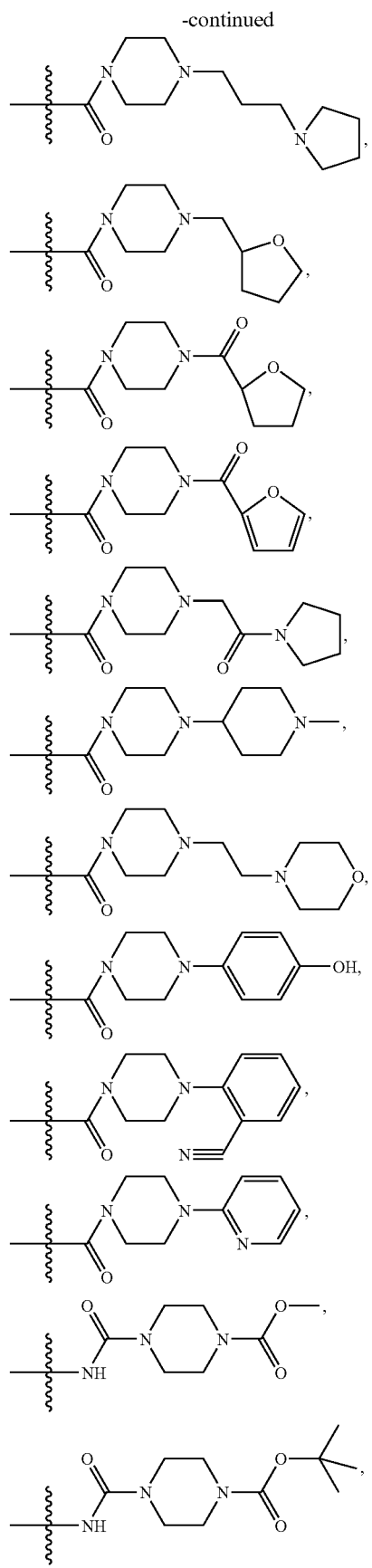

-continued

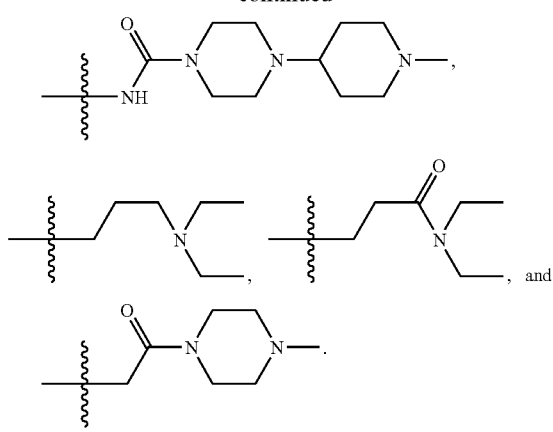

In further or alternative embodiments of this aspect, Q is selected from the group consisting of

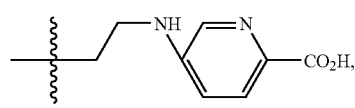

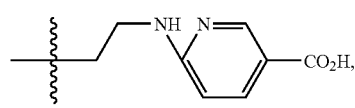

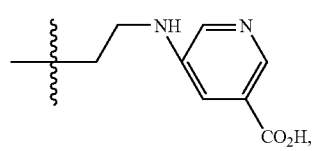

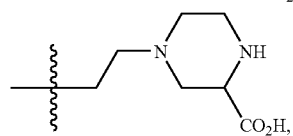

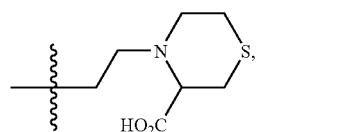

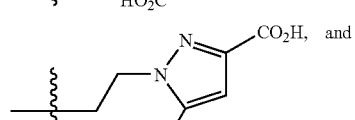

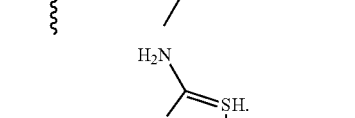

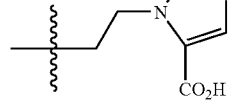

In further or alternative embodiments of this aspect, Q is selected from the group consisting of

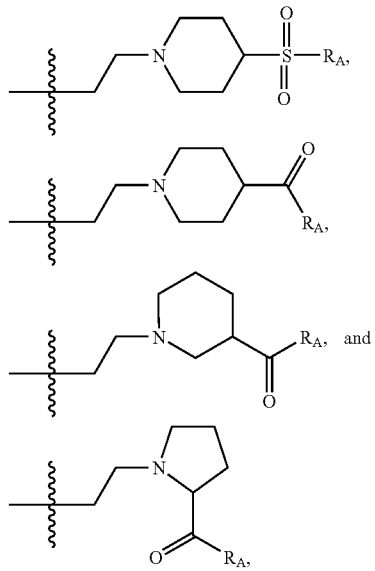

wherein $R_A$ is selected from —$NH_2$, —$NEt_2$, and —NH$(CH_2)_nOH$; and n is 1 to 6.

In further or alternative embodiments of this aspect, Q is

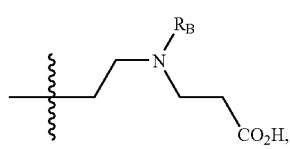

wherein $R_B$ is selected from the group consisting of

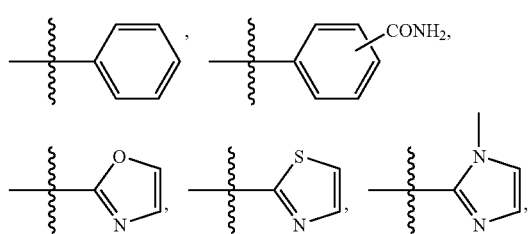

—$CH_2OH$, —$CH_2CH_2OH$, and —$CH_2CH_2CH_2OH$.

In further or alternative embodiments of this aspect, Q is

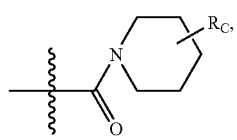

wherein $R_C$ is at 2, 3, or 4 position of the piperidine ring; and $R_C$ is selected from the group consisting of —C(O)NHEt, —C(O)NEt$_2$, c-butyl, c-pentyl, —C(O)NH-thiazole, oxazole, thiazole, —S(O)$_2$NH$_2$, —S(O)$_2$NHEt, and —S(O)$_2$NEt$_2$.

In further or alternative embodiments of this aspect, Q is selected from the group consisting of

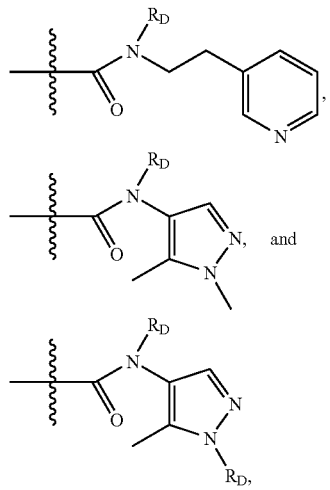

wherein each $R_D$ is independently selected from —$(CH_2)_k$OH or —$(CH_2)_kCO_2H$; and k is 1 to 6.

In further or alternative embodiments of this aspect, Q is

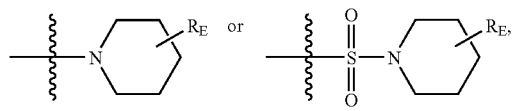

wherein $R_E$ is at 2, 3, or 4 position of the piperidine ring; and $R_E$ is selected from the group consisting of —C(O)NH$_2$, —C(O)NHEt, and —C(O)NEt$_2$.

In further or alternative embodiments of this aspect, Q is selected from the group consisting of

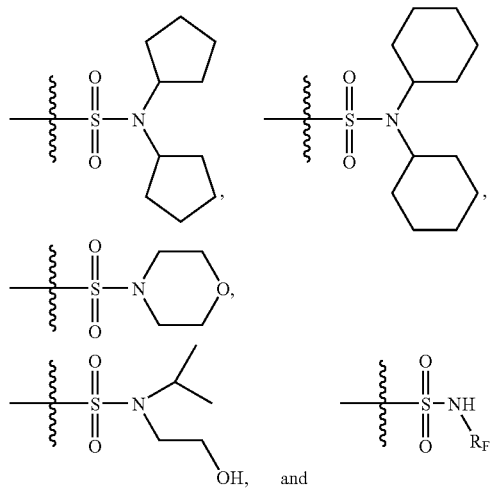

wherein $R_F$ is thiazole, pyrazole, or isoxazole.

In further or alternative embodiments of this aspect, Q is selected from the group consisting of

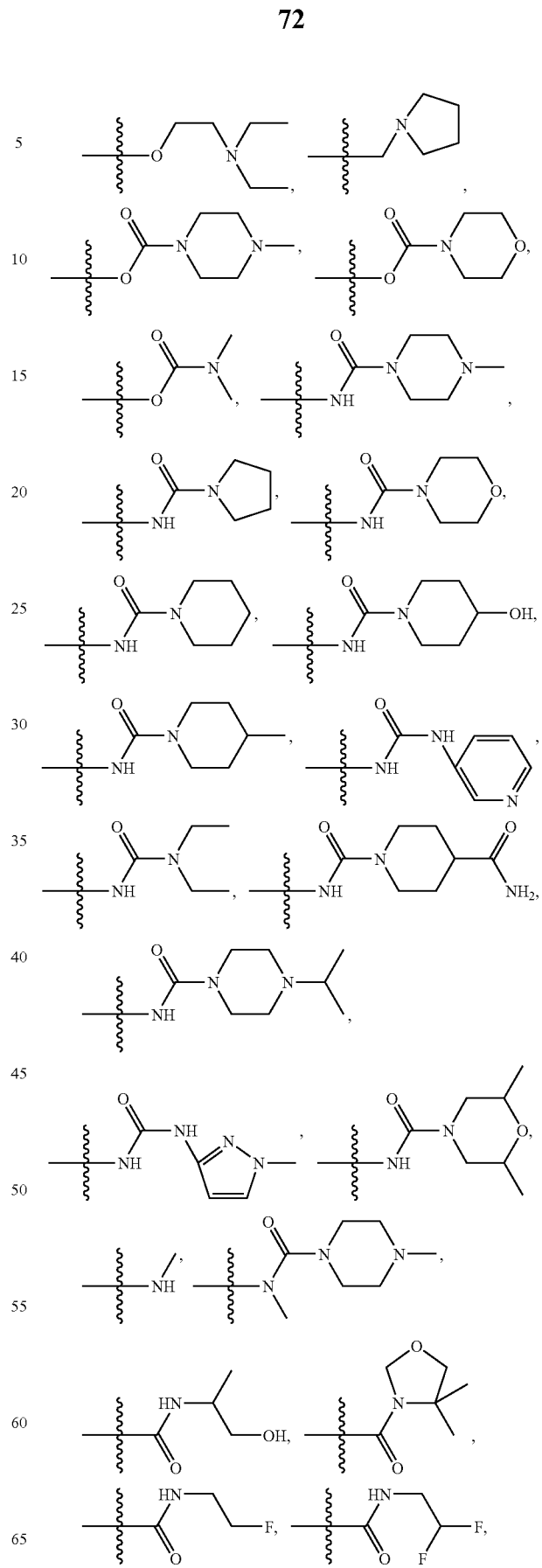

-continued
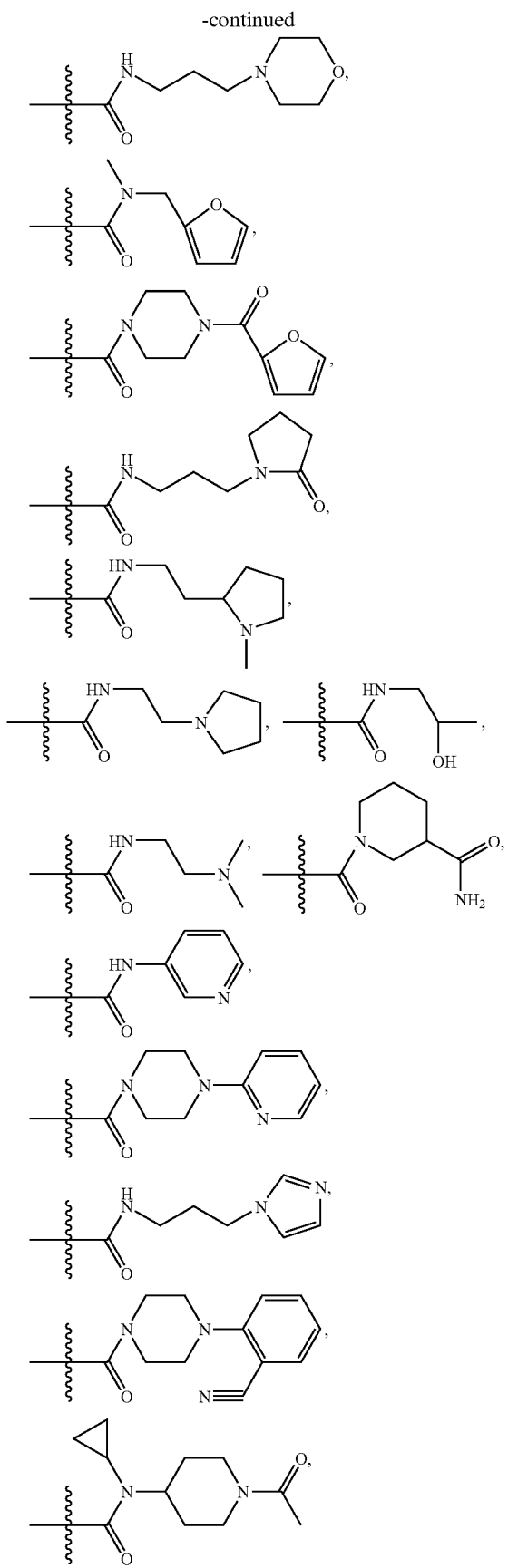
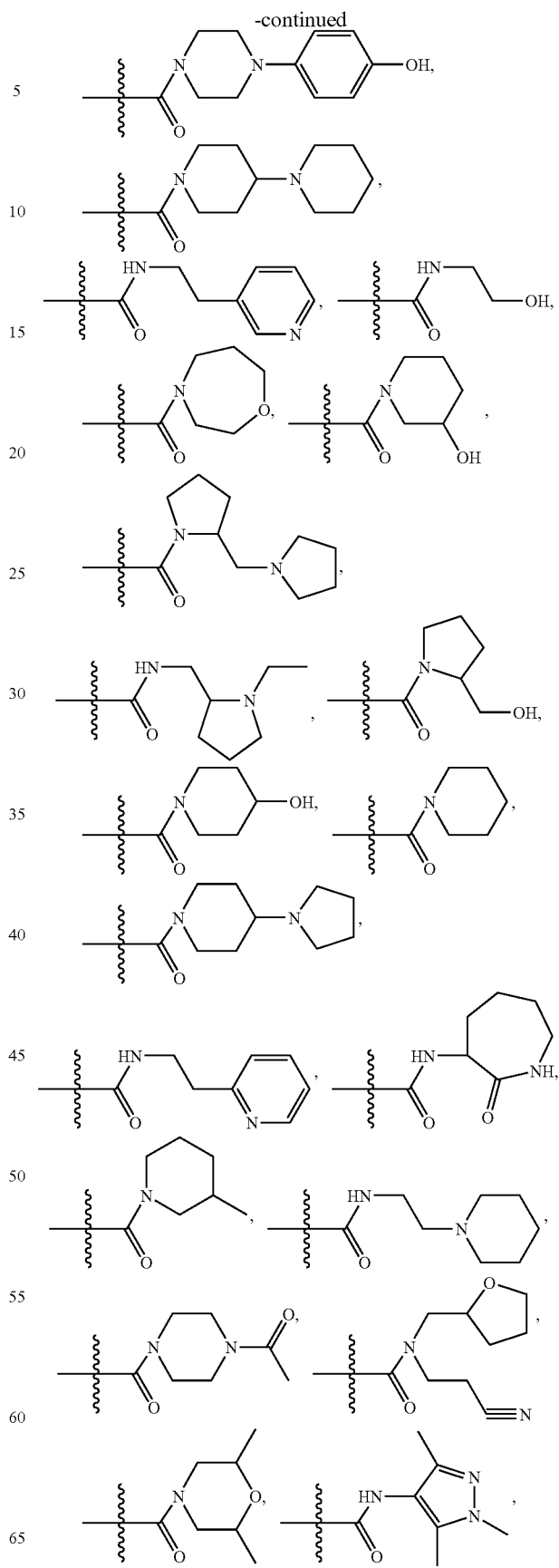

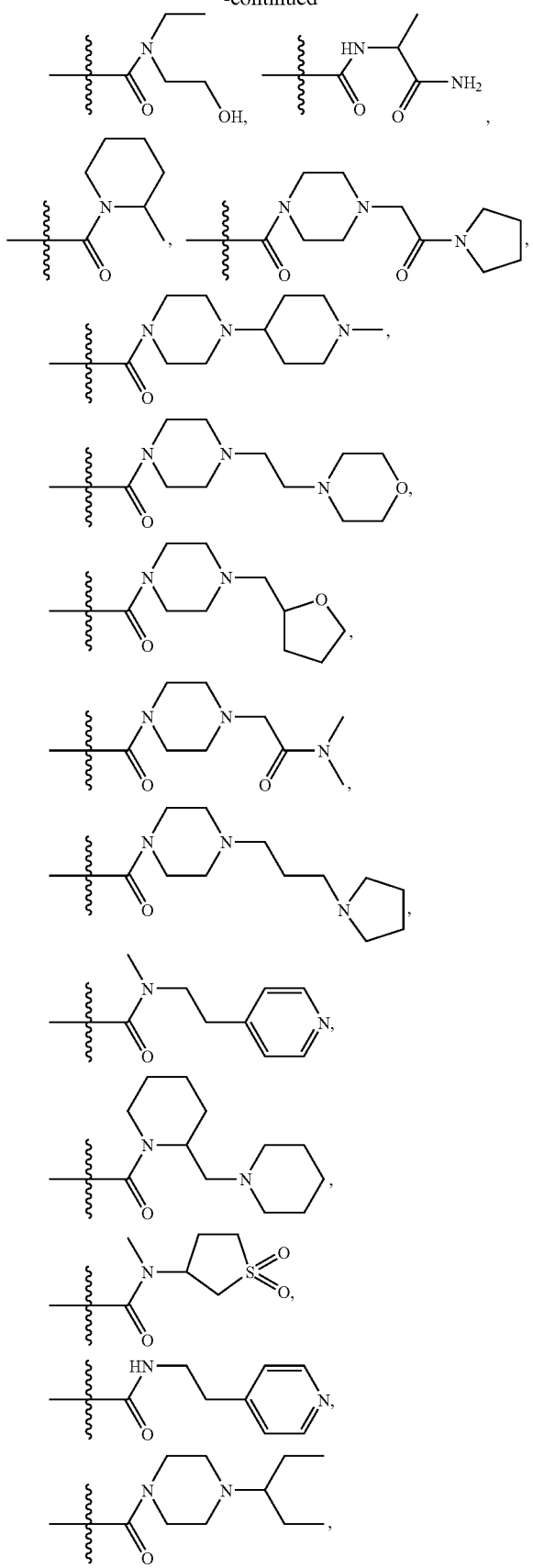
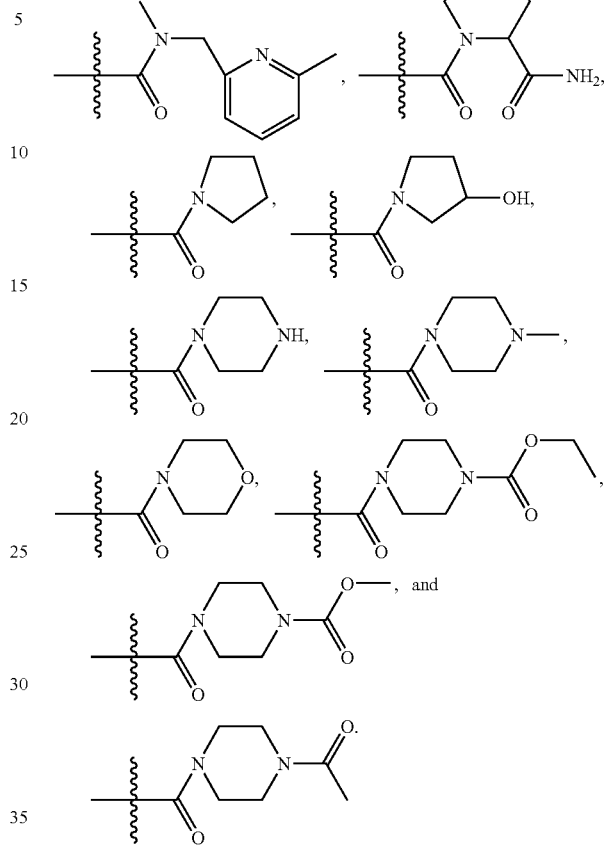

In further or alternative embodiments of this aspect, Q is selected from the group consisting of

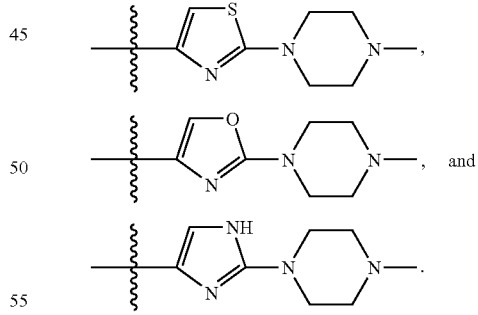

In further or alternative embodiments, $R_5$ is H. In further or alternative embodiments, each $R_1$ is H. In further or alternative embodiments, each $R_1$ is H and $R_5$ is H. In further or alternative embodiments, Q is a group comprising a non-aromatic tertiary amine.

In a further or alternative embodiment of this aspect, compounds having the structure of Formula (1) are selected from Formula (23), Formula (24), or Formula (45):

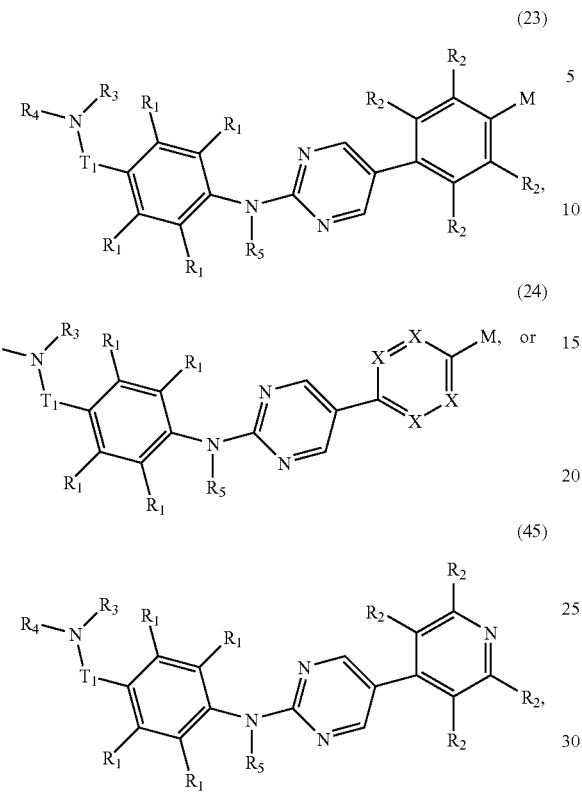

wherein:
- M is selected from the group consisting of H, OH, SH, NO$_2$, CN, NR"$_2$, and an optionally substituted moiety selected from -L$_7$-alkyl, -L$_7$-cycloalkyl, -L$_7$-heteroalkyl, -L$_7$-haloalkyl, -L$_7$-aryl, -L$_7$-heterocycloalkyl, and -L$_7$-heteroaryl; wherein L$_7$ is selected from a bond, —O—, —NH—, —S—, —C(O)—, —C(S)—, —C(O)O—, —C(O)NH—, —S(O)—, —S(O)$_2$—, —OC(O)—, —C(O)NR"(CR"$_2$)$_{1-6}$C(O)O—, —CR"$_2$NR"CR"$_2$C(O)O—, —C(O)NR"Y$^1$C(O)O—, —C(O)NR"NR"C(O)O—, —S(O)NH—, —C(O)NR"CR"$_2$C(O)W—, —CR"$_2$NR"WO—, —CR"$_2$NR"Y$^1$C(O)O—, and —C(O)NR"O—; W is C$_{1-6}$alkylene; Y$^1$ is optionally substituted arylene or optionally substituted heteroarylene; wherein said optional substituents are selected from halogen, OH, C$_{1-6}$alkyl, C$_{1-6}$alkoxy, halo-C$_{1-6}$alkyl and halo-C$_{1-6}$alkoxy; provided that M is not H in Formula (23);
- each R" is independently H, OH, halogen, C$_{1-6}$alkyl, substituted C$_{1-6}$alkyl, C$_{1-6}$alkoxy, halo-C$_{1-6}$alkyl, halo-C$_{1-6}$alkoxy, aryl, haloaryl, or heteroaryl;
- each X is independently selected from N or CR$_2$, provided that at least one but no more than 2 X groups are N;
- each R$_2$ is independently selected from the group consisting of H, OH, halogen, and an optionally substituted moiety selected from -L$_2$-alkyl, -L$_2$-cycloalkyl, -L$_2$-heteroalkyl, -L$_2$-haloalkyl, -L$_2$-aryl, -L$_2$-heterocycloalkyl, and -L$_2$-heteroaryl; wherein L$_2$ is selected from a bond, —O—, —NH—, —S—, —C(O)—, —C(S)—, —C(O)O—, —C(O)NH—, —S(O)—, —S(O)$_2$—, —C(O)NR"(CR"$_2$)$_{1-6}$C(O)O—, —OC(O)—, —CR"$_2$NR"CR"$_2$C(O)O—, —C(O)NR"NR"C(O)O—, and —S(O)NH—; wherein said optional substituents are selected from halogen, OH, C$_{1-6}$alkyl, C$_{1-6}$alkoxy, halo-C$_{1-6}$alkyl, and halo-C$_{1-6}$alkoxy;
- or any two adjacent R$_2$ groups together may form an optionally substituted 5 to 8-membered heterocyclic, cycloalkyl, or aryl ring;
- each of R$_3$ and R$_4$ is independently an optionally substituted moiety selected from -Z, -L$_3$-Z, -L$_3$-H, -L$_3$-alkyl, -L$_3$-cycloalkyl, -L$_3$-heteroalkyl, -L$_3$-haloalkyl, -L$_3$-aryl, -L$_3$-heterocycloalkyl, and -L$_3$-heteroaryl; wherein L$_3$ is selected from a bond, —C(S)—, —C(O)O—, —C(O)NR'''—, —(CR"'$_2$)$_{1-6}$—, —CR'''$_2$S(O)—, —CR'''$_2$S(O)$_2$—, —CR'''$_2$S(O)NR'''—, —CR'''$_2$C(O)NR'''—, —(CR'''$_2$)$_{1-6}$NR'''—, —(CR"'$_2$)$_{1-6}$O—, —(CR"'$_2$)$_{1-6}$C(O)O—, —Y$^2$C(O)O—, and an optionally substituted C$_{1-6}$alkylene;
wherein said optional substituents are selected from halogen, —OH, =O, —Y$^3$, C$_{1-6}$alkyl, C$_{1-6}$alkoxy, halogen or OH substituted C$_{1-6}$alkyl, halogen or OH substituted C$_{1-6}$alkoxy, —(CR"'$_2$)$_{1-6}$C(O)OR$_6$, —C(O)NR'''$_2$, —C(O)R$_6$, or —C(O)OR$_6$;
- Y$^2$ is an optionally substituted cycloalkyl ring or optionally substituted non-aromatic heterocyclic ring;
wherein said optional substituents are selected from C$_{1-6}$alkyl, halogen, —OH, =O, and —CN.
- Y$^3$ is optionally substituted aryl, optionally substituted heteroaryl, optionally substituted cycloalkyl, or optionally substituted non-aromatic heterocycle;
wherein said optional substituents are selected from C$_{1-6}$alkyl, halogen, —OH, =O, and —CN.
- Z is —H, —OH, —CN, —COOR''', —NR'''$_2$, or —C≡CR''';
- each R''' is independently H, alkyl, or substituted alkyl;
- or two R''' together may form a 3-6 membered cycloalkyl or heterocyclic ring;
- or R$_3$ and R$_4$ taken together with the N atom to which they are attached may form an optionally substituted 3 to 8-membered heterocyclic ring;
wherein said optional substituents are selected from halogen, —OH, =O, —Y$^3$, C$_{1-6}$alkyl, C$_{1-6}$alkoxy, halogen or OH substituted C$_{1-6}$alkyl, halogen or OH substituted C$_{1-6}$alkoxy, —(CR'''$_2$)$_{1-6}$Y$^4$, —(CR'''$_2$)$_{1-6}$OR$_6$, —C(O)NR'''OR$_6$, —C(O)OR$_6$, —OR$_6$, —NR'''C(O)OR$_6$, —NR'''C(O)R$_6$, —(CR'''$_2$)$_{1-6}$C(O)OR$_6$, —(CR'''$_2$)$_{1-6}$NR'''C(O)OR$_6$, —(CR'''$_2$)$_{1-6}$NR$_7$R$_8$, —S(O)$_2$NR'''$_2$, —C(O)R$_6$, —OC(O)R$_6$, —NR$_7$R$_9$, —(CR'''$_2$)$_{1-6}$C(O)NR$_7$R$_8$, —S(O)$_2$R$_4$, or —C(O)R$_4$;
- Y$^4$ is aryl, heteroaryl, cycloalkyl, or non-aromatic heterocycle;
- R$_4$ is selected from —NH$_2$, —NEt$_2$, and —NH(CH$_2$)$_{1-6}$OH;
- R$_6$ is H, alkyl, substituted alkyl, cycloalkyl, non-aromatic heterocycle, aryl, or heteroaryl;
- each of R$_7$ and R$_8$ is independently H, OH, halogen, C$_{1-6}$alkyl, C$_{1-6}$alkoxy, halo-C$_{1-6}$alkyl, or halo-C$_{1-6}$alkoxy;
- or R$_7$ and R$_8$ taken together with the N atom to which they are attached may form a 3 to 6-membered heterocyclic ring;
- T$_1$ is an optionally substituted moiety selected from -L$_4$-, -alkylene-L$_4$-, -L$_4$-alkylene-, -L$_4$-cycloalkylene-, -L$_4$-heteroalkylene-, -L$_4$-haloalkylene-, -L$_4$- arylene-, -L₄-heteroarylene-, and -L₄-heterocycloalkylene-; wherein L₄ is selected from a bond, —O—, —NH—, —S—, —CR"₂—, —NR'"C(O)—, —C(O)—, —C(S)—, —C(O)O—, —C(O)NR'"—, —S(O)—, —S(O)₂—, —OC(O)—, —C(O)NR'"(CR"₂)₁₋₆C(O)O—, —C(O)NR'"(CR"₂)₁₋₆C(O)—, —CR"₂NR'"CR"₂C(O)O—, —C(O)NR'"NR'"C(O)O—, —C(O)NR'"(CR"₂)₁₋₆—, —CR"₂C(O)—, and —S(O)NH—;

wherein said optional substituents are selected from halogen, OH, $C_{1-6}$alkyl, $C_{1-6}$alkoxy, halo-$C_{1-6}$alkyl, halo-$C_{1-6}$alkoxy, aryl, haloaryl, and heteroaryl;

or a pharmaceutically acceptable salt, pharmaceutically acceptable N-oxide, pharmaceutically active metabolite, pharmaceutically acceptable prodrug, or pharmaceutically acceptable solvate thereof.

In further or alternative embodiments, L₇ is selected from a bond, —O—, —NH—, —S—, —C(O)—, —C(S)—, —OC(O)—, —CH₂NHCH₂C(O)O—, —CH₂NH(CH₂)₂O—, —C(O)O—, —C(O)NH—, —S(O)—, —S(O)₂—, —C(O)NH(CR"₂)₁₋₆C(O)O—, —C(O)NR"NR"C(O)O—, and —S(O)NH—. In further or alternative embodiments, L₂ is selected from a bond, —C(O)—, —C(S)—, —C(O)O—, —C(O)NH—, —S(O)—, —S(O)₂—, —C(O)NH(CR"₂)₁₋₆C(O)O—, —C(O)NR"NR"C(O)O—, and —S(O)NH—.

In further or alternative embodiments, each of R₃ and R₄ is independently an optionally substituted moiety selected from -L₃-alkyl, -L₃-cycloalkyl, -L₃-heteroalkyl, -L₃-haloalkyl, -L₃-aryl, -L₃-heterocycloalkyl, and -L₃-heteroaryl;

wherein L₃ is selected from a bond, —C(S)—, —C(O)O—, —C(O)NH—, —CR'"₂S(O)—, —CR'"₂S(O)₂—, and —CR'"₂S(O)NH—; wherein said optional substituents are selected from halogen, OH, $C_{1-6}$alkyl, $C_{1-6}$alkoxy, halo-$C_{1-6}$alkyl, halo-$C_{1-6}$alkoxy, aryl, haloaryl, and heteroaryl;

or R₃ and R₄ together may form an optionally substituted 3 to 8-membered heterocyclic ring;

wherein said optional substituents are selected from halogen, OH, $C_{1-6}$alkyl, $C_{1-6}$alkoxy, halo-$C_{1-6}$alkyl, halo-$C_{1-6}$alkoxy, aryl, haloaryl, heteroaryl.

In further or alternative embodiments, T₁ is an optionally substituted moiety selected from -L₄-alkylene-, -L₄-cycloalkylene-, -L₄-heteroalkylene-, -L₄-haloalkylene-, -L₄-arylene-, -L₄-heteroarylene-, and -L₄-heterocycloalkylene-; wherein L₄ is selected from a bond, —O—, —NH—, —S—, —CR"₂—, —C(O)—, —C(S)—, —C(O)O—, —C(O)NH—, —S(O)—, —S(O)₂—, —C(O)NH(CR"₂)₁₋₆C(O)O—, —C(O)NR"NR"C(O)O—, and —S(O)NH—.

In further or alternative embodiments, each R₁ is H. In further or alternative embodiments, each R₂ is H. In further or alternative embodiments, R₅ is H. In further or alternative embodiments, each R₁ is H, each R₂ is H, and R₅ is H.

In a further or alternative embodiment of this aspect, compounds having the structure of Formula (46) are selected from Formula (50), Formula (51), or Formula (52):

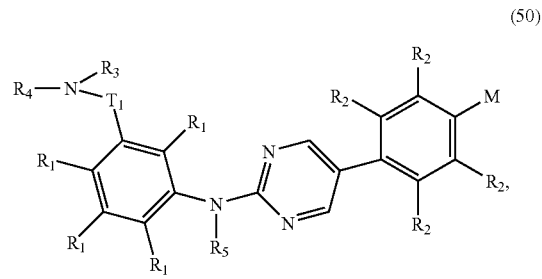
(50)

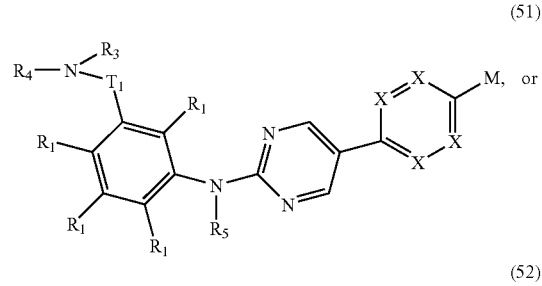
(51)

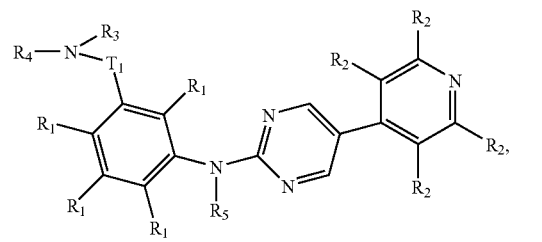
(52)

wherein:
M is selected from the group consisting of H, OH, SH, NO₂, CN, NR"₂, and an optionally substituted moiety selected from -L₇-alkyl, -L₇-cycloalkyl, -L₇-heteroalkyl, -L₇-haloalkyl, -L₇-aryl, -L₇-heterocycloalkyl, and -L₇-heteroaryl; wherein L₇ is selected from a bond, —O—, —NH—, —S—, —C(O)—, —C(S)—, —C(O)O—, —C(O)NH—, —S(O)—, —S(O)₂—, —OC(O)—, —C(O)NR"(CR"₂)₁₋₆C(O)O—, —CR"₂NR"CR"₂C(O)O—, —C(O)NR"Y¹C(O)O—, —C(O)NR"NR"C(O)O—, —S(O)NH—, —C(O)NR"CR"₂C(O)W—, —CR"₂NR"WO—, —CR"₂NR"Y¹C(O)O—, and —C(O)NR"O—; W is $C_{1-6}$alkylene; Y¹ is optionally substituted arylene or optionally substituted heteroarylene; wherein said optional substituents are selected from halogen, OH, $C_{1-6}$alkyl, $C_{1-6}$alkoxy, halo-$C_{1-6}$alkyl and halo-$C_{1-6}$alkoxy; provided that M is not H in Formula (50);

each R" is independently H, OH, halogen, $C_{1-6}$alkyl, substituted $C_{1-6}$alkyl, $C_{1-6}$alkoxy, halo-$C_{1-6}$alkyl, halo-$C_{1-6}$alkoxy, aryl, haloaryl, or heteroaryl;

each X is independently selected from N or CR₂, provided that at least one but no more than 2 X groups are N;

each R₂ is independently selected from the group consisting of H, OH, halogen, and an optionally substituted moiety selected from -L₂-alkyl, -L₂-cycloalkyl, -L₂-heteroalkyl, -L₂-haloalkyl, -L₂-aryl, -L₂-heterocycloalkyl, and -L₂-heteroaryl; wherein L₂ is selected from a bond, —O—, —NH—, —S—, —C(O)—, —C(S)—, —C(O)O—, —C(O)NH—, —S(O)—, —S(O)₂—, —C(O)NR"(CR"₂)₁₋₆C(O)O—, —OC(O)—, —CR"₂NR"CR"₂C(O)O—, —C(O)

NR"NR"C(O)O—, and —S(O)NH—; wherein said optional substituents are selected from halogen, OH, $C_{1-6}$alkyl, $C_{1-6}$alkoxy, halo-$C_{1-6}$alkyl, and halo-$C_{1-6}$alkoxy;

or any two adjacent $R_2$ groups together may form an optionally substituted 5 to 8-membered heterocyclic, cycloalkyl, or aryl ring;

each of $R_3$ and $R_4$ is independently an optionally substituted moiety selected from -Z, -$L_3$-Z, -$L_3$-H, -$L_3$-alkyl, -$L_3$-cycloalkyl, -$L_3$-heteroalkyl, -$L_3$-haloalkyl, -$L_3$-aryl, -$L_3$-heterocycloalkyl, and -$L_3$-heteroaryl;

wherein $L_3$ is selected from a bond, —C(S)—, —C(O)O—, —C(O)NR'"—, —(CR"$_2$)$_{1-6}$—, —CR'"$_2$S(O)—, —CR"$_2$S(O)$_2$—, —CR'"$_2$S(O)NR'"—, —CR'"$_2$C(O)NR'"—, —(CR"$_2$)$_{1-6}$NR$^1$—, —(CR"$_2$)$_{1-6}$O—, —(CR'"$_2$)$_{1-6}$C(O)O—, —Y$^2$C(O)O—, and an optionally substituted $C_{1-6}$alkylene;

wherein said optional substituents are selected from halogen, —OH, =O, —Y$^3$, $C_{1-6}$alkyl, $C_{1-6}$alkoxy, halogen or OH substituted $C_{1-6}$alkyl, halogen or OH substituted $C_{1-6}$alkoxy, —(CR'"$_2$)$_{1-6}$C(O)OR$_6$, —C(O)NR'"$_2$, —C(O)R$_6$, or —C(O)OR$_6$;

$Y^2$ is an optionally substituted cycloalkyl ring or optionally substituted non-aromatic heterocyclic ring;

wherein said optional substituents are selected from $C_{1-6}$alkyl, halogen, —OH, =O, and —CN.

$Y^3$ is optionally substituted aryl, optionally substituted heteroaryl, optionally substituted cycloalkyl, or optionally substituted non-aromatic heterocycle;

wherein said optional substituents are selected from $C_{1-6}$alkyl, halogen, —OH, =O, and —CN.

Z is —H, —OH, —CN, —COOR'", —NR'"$_2$, or —C≡CR'";

each R'" is independently H, alkyl, or substituted alkyl;

or two R'" together may form a 3-6 membered cycloalkyl or heterocyclic ring;

or $R_3$ and $R_4$ taken together with the N atom to which they are attached may form an optionally substituted 3 to 8-membered heterocyclic ring;

wherein said optional substituents are selected from halogen, —OH, =O, —Y$^3$, $C_{1-6}$alkyl, $C_{1-6}$alkoxy, halogen or OH substituted $C_{1-6}$alkyl, halogen or OH substituted $C_{1-6}$alkoxy, —(CR'"$_2$)$_{1-6}$Y$^4$, —(CR'"$_2$)$_{1-6}$OR$_6$, —C(O)NR'"R$_6$, —C(O)OR$_6$, —OR$_6$, —NR'"C(O)OR$_6$, —NR'"C(O)R$_6$, —(CR'"$_2$)$_{1-6}$C(O)OR$_6$, —(CR'"$_2$)$_{1-6}$NR'"C(O)OR$_6$, —(CR'"$_2$)$_{1-6}$NR$_7$R$_8$, —S(O)$_2$NR'"$_2$, —C(O)R$_6$, —OC(O)R$_6$, —NR$_7$R$_8$, —(CR'"$_2$)$_{1-6}$C(O)NR$_7$R$_5$, —S(O)$_2$R$_A$, or —C(O)R$_A$;

$Y^4$ is aryl, heteroaryl, cycloalkyl, or non-aromatic heterocycle;

$R_A$ is selected from —NH$_2$, —NEt$_2$, and —NH(CH$_2$)$_{1-6}$OH;

$R_6$ is H, alkyl, substituted alkyl, cycloalkyl, non-aromatic heterocycle, aryl, or heteroaryl;

each of $R_7$ and $R_8$ is independently H, OH, halogen, $C_{1-6}$alkyl, $C_{1-6}$alkoxy, halo-$C_{1-6}$alkyl, or halo-$C_{1-6}$alkoxy;

or $R_7$ and $R_8$ taken together with the N atom to which they are attached may form a 3 to 6-membered heterocyclic ring;

$T_1$ is an optionally substituted moiety selected from -$L_4$-, -alkylene-$L_4$-, -$L_4$-alkylene-, -$L_4$-cycloalkylene-, -$L_4$-heteroalkylene-, -$L_4$-haloalkylene-, -$L_4$-arylene-, -$L_4$-heteroarylene-, and -$L_4$-heterocycloalkylene-; wherein $L_4$ is selected from a bond, —O—, —NH—, —S—, —CR"$_2$—, —NR'"C(O)—, —C(O)—, —C(S)—, —C(O)O—, —C(O)NR'"—, —S(O)—, —S(O)$_2$—, —OC(O)—, —C(O)NR'"(CR"$_2$)$_{1-6}$C(O)O—, —C(O)NR'"(CR"$_2$)$_{1-6}$C(O)—, —CR"$_2$NR'"CR"$_2$C(O)O—, —C(O)NR'"NR"C(O)O—, —C(O)NR'"(CR"$_2$)$_{1-6}$—, —CR"$_2$C(O)—, and —S(O)NH—;

wherein said optional substituents are selected from halogen, OH, $C_{1-6}$alkyl, $C_{1-6}$alkoxy, halo-$C_{1-6}$alkyl, halo-$C_{1-6}$alkoxy, aryl, haloaryl, and heteroaryl;

or a pharmaceutically acceptable salt, pharmaceutically acceptable N-oxide, pharmaceutically active metabolite, pharmaceutically acceptable prodrug, or pharmaceutically acceptable solvate thereof.

In further or alternative embodiments, $L_7$ is selected from a bond, —O—, —NH—, —S—, —C(O)—, —C(S)—, —OC(O)—, —CH$_2$NHCH$_2$C(O)O—, —CH$_2$NH(CH$_2$)$_2$O—, —C(O)O—, —C(O)NH—, —S(O)—, —S(O)$_2$—, —C(O)NH(CR"$_2$)$_{1-6}$C(O)O—, —C(O)NR"NR"C(O)O—, and —S(O)NH—. In further or alternative embodiments, $L_2$ is selected from a bond, —C(O)—, —C(S)—, —C(O)O—, —C(O)NH—, —S(O)—, —S(O)$_2$—, —C(O)NH(CR"$_2$)$_{1-6}$C(O)O—, —C(O)NR"NR"C(O)O—, and —S(O)NH—.

In further or alternative embodiments, each of $R_3$ and $R_4$ is independently an optionally substituted moiety selected from -$L_3$-alkyl, -$L_3$-cycloalkyl, -$L_3$-heteroalkyl, -$L_3$-haloalkyl, -$L_3$-aryl, -$L_3$-heterocycloalkyl, and -$L_3$-heteroaryl;

wherein $L_3$ is selected from a bond, —C(S)—, —C(O)O—, —C(O)NH—, —CR'"$_2$S(O)—, —CR'"$_2$S(O)$_2$—, and —CR'"$_2$S(O)NH—; wherein said optional substituents are selected from halogen, OH, $C_{1-6}$alkyl, $C_{1-6}$alkoxy, halo-$C_{1-6}$alkyl, halo-$C_{1-6}$alkoxy, aryl, haloaryl, and heteroaryl;

or $R_3$ and $R_4$ together may form an optionally substituted 3 to 8-membered heterocyclic ring; wherein said optional substituents are selected from halogen, OH, $C_{1-6}$alkyl, $C_{1-6}$alkoxy, halo-$C_{1-6}$alkyl, halo-$C_{1-6}$alkoxy, aryl, haloaryl, heteroaryl.

In further or alternative embodiments, $T_1$ is an optionally substituted moiety selected from -$L_4$-alkylene-, -$L_4$-cycloalkylene-, -$L_4$-heteroalkylene-, -$L_4$-haloalkylene-, -$L_4$-arylene-, -$L_4$-heteroarylene-, and -$L_4$-heterocycloalkylene-; wherein $L_4$ is selected from a bond, —O—, —NH—, —S—, —CR"$_2$—, —C(O)—, —C(S)—, —C(O)O—, —C(O)NH—, —S(O)—, —S(O)$_2$—, —C(O)NH(CR"$_2$)$_{1-6}$C(O)O—, —C(O)NR"NR"C(O)O—, and —S(O)NH—.

In further or alternative embodiments, each $R_1$ is H. In further or alternative embodiments, each $R_2$ is H. In further or alternative embodiments, $R_5$ is H. In further or alternative embodiments, each $R_1$ is H, each $R_2$ is H, and $R_5$ is H.

In a further or alternative embodiment of this aspect, compounds having the structure of Formula (1) are selected from Formula (25), Formula (26), or Formula (27):

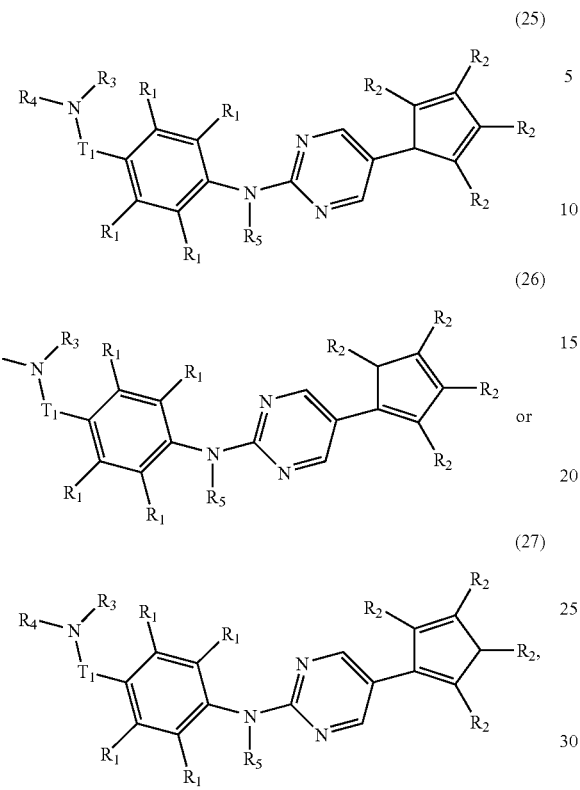

wherein;

each $R_2$ is independently selected from the group consisting of H, OH, halogen, and an optionally substituted moiety selected from -$L_2$-alkyl, -$L_2$-cycloalkyl, -$L_2$-heteroalkyl, -$L_2$-haloalkyl, -$L_2$-aryl, -$L_2$-heterocycloalkyl, and -$L_2$-heteroaryl; wherein $L_2$ is selected from a bond, —O—, —NH—, —S—, —C(O)—, —C(S)—, —C(O)O—, —C(O)NH—, —S(O)—, —S(O)$_2$—, —C(O)NR"(CR"$_2$)$_{1-6}$C(O)O—, —OC(O)—, —CR'$_2$NR"CR"$_2$C(O)O—, —C(O)NR"NR"C(O)O—, and —S(O)NH—; wherein said optional substituents are selected from halogen, OH, $C_{1-6}$alkyl, $C_{1-6}$alkoxy, halo-$C_{1-6}$alkyl and halo-$C_{1-6}$alkoxy;

each R" is independently H, OH, halogen, $C_{1-6}$alkyl, substituted $C_{1-6}$alkyl, $C_{1-6}$alkoxy, halo-$C_{1-6}$alkyl, halo-$C_{1-6}$alkoxy, aryl, haloaryl, or heteroaryl;

or any two adjacent $R_2$ groups together may form an optionally substituted 5 to 8-membered heterocyclic, cycloalkyl, or aryl ring;

each of $R_3$ and $R_4$ is independently an optionally substituted moiety selected from -Z, -$L_3$-Z, -$L_3$-H, -$L_3$-alkyl, -$L_3$-cycloalkyl, -$L_3$-heteroalkyl, -$L_3$-haloalkyl, -$L_3$-aryl, -$L_3$-heterocycloalkyl, and -$L_3$-heteroaryl; wherein $L_3$ is selected from a bond, —C(S)—, —C(O)O—, —C(O)NR'"—, —CR"$_2$S(O)—, —CR'"$_2$S(O)$_2$—, —CR'"$_2$S(O)NR'"—, —CR'"$_2$C(O)NR'"—, —(CR'"$_2$)$_{1-6}$NR'"—, —(CR'"$_2$)$_{1-6}$O—, —(CR'"$_2$)$_{1-6}$C(O)O—, —Y$^2$C(O)O—, and an optionally substituted $C_{1-6}$alkylene;

wherein said optional substituents are selected from halogen, —OH, =O, —Y$^3$, $C_{1-6}$alkyl, $C_{1-6}$alkoxy, halogen or OH substituted $C_{1-6}$alkyl, halogen or OH substituted $C_{1-6}$alkoxy, —(CR'"$_2$)$_{1-6}$C(O)OR$_6$, —C(O)NR'"$_2$, —C(O)R$_6$, or —C(O)OR$_6$;

$Y^2$ is an optionally substituted cycloalkyl ring or optionally substituted non-aromatic heterocyclic ring;
wherein said optional substituents are selected from $C_{1-6}$alkyl, halogen, —OH, =O, and —CN.

$Y^3$ is optionally substituted aryl, optionally substituted heteroaryl, optionally substituted cycloalkyl, or optionally substituted non-aromatic heterocycle;
wherein said optional substituents are selected from $C_{1-6}$alkyl, halogen, —OH, =O, and —CN.

Z is —H, —OH, —CN, —COOR'", —NR'"$_2$, or —C≡CR'";

each R'" is independently H, alkyl, or substituted alkyl;

or two R'" together may form a 3-6 membered cycloalkyl or heterocyclic ring;

or $R_3$ and $R_4$ taken together with the N atom to which they are attached may form an optionally substituted 3 to 8-membered heterocyclic ring;
wherein said optional substituents are selected from halogen, —OH, =O, —Y$^3$, $C_{1-6}$alkyl, $C_{1-6}$alkoxy, halogen or OH substituted $C_{1-6}$alkyl, halogen or OH substituted $C_{1-6}$alkoxy, —(CR'"$_2$)$_{1-6}$Y$^4$, —(CR'"$_2$)$_{1-6}$OR$_6$, —C(O)NR"R$_6$, —C(O)OR$_6$, —OR$_6$, —NR'"C(O)OR$_6$, —NR'"C(O)R$_6$, —(CR"$_2$)$_{1-6}$C(O)OR$_6$, —(CR'"$_2$)$_{1-6}$NR'"C(O)OR$_6$, —(CR'"$_2$)$_{1-6}$NR$_7$R$_8$, —S(O)$_2$NR'"$_2$, —C(O)R$_6$, —OC(O)R$_6$, —NR$_7$R$_8$, —(CR'"$_2$)$_{1-6}$C(O)NR$_7$R$_8$, —S(O)$_2$R$_A$, or —C(O)R$_A$;

$Y^4$ is aryl, heteroaryl, cycloalkyl, or non-aromatic heterocycle;

$R_A$ is selected from —NH$_2$, —NEt$_2$, and —NH(CH$_2$)$_{1-6}$OH;

$R_6$ is H, alkyl, substituted alkyl, cycloalkyl, non-aromatic heterocycle, aryl, or heteroaryl;

each of $R_7$ and $R_8$ is independently H, OH, halogen, $C_{1-6}$alkyl, $C_{1-6}$alkoxy, halo-$C_{1-6}$alkyl, or halo-$C_{1-6}$alkoxy;

or $R_7$ and $R_8$ taken together with the N atom to which they are attached may form a 3 to 6-membered heterocyclic ring;

$T_1$ is an optionally substituted moiety selected from -$L_4$-, -alkylene-$L_4$-, -$L_4$-alkylene-, -$L_4$-cycloalkylene-, -$L_4$-heteroalkylene-, -$L_4$-haloalkylene-, -$L_4$-arylene-, -$L_4$-heteroarylene-, and -$L_4$-heterocycloalkylene-; wherein $L_4$ is selected from a bond, —O—, —NH—, —S—, —CR"$_2$—, —NR'"C(O)—, —C(O)—, —C(S)—, —C(O)O—, —C(O)NR'"—, —S(O)—, —S(O)$_2$—, —OC(O)—, —C(O)NR'" (CR"$_2$)$_{1-6}$C(O)O—, —C(O)NR'"(CR"$_2$)$_{1-6}$C(O)—, —CR"$_2$NR'"CR"$_2$C(O)O—, —C(O)NR'"NR"C(O)O—, —C(O)NR'"(CR"$_2$)$_{1-6}$—, —CR"$_2$C(O)—, and —S(O)NH—;
wherein said optional substituents are selected from halogen, OH, $C_{1-6}$alkyl, $C_{1-6}$alkoxy, halo-$C_{1-6}$alkyl, halo-$C_{1-6}$alkoxy, aryl, haloaryl, and heteroaryl;

or a pharmaceutically acceptable salt, pharmaceutically acceptable N-oxide, pharmaceutically active metabolite, pharmaceutically acceptable prodrug, or pharmaceutically acceptable solvate thereof.

In further or alternative embodiments, $L_2$ is selected from a bond, —C(O)—, —C(S)—, —C(O)O—, —C(O)NH—, —S(O)—, —S(O)$_2$—, —C(O)NH(CR"$_2$)$_{1-6}$C(O)O—, —C(O)NR"NR"C(O)O—, and —S(O)NH—.

In further or alternative embodiments, each of R$_3$ and R$_4$ is independently an optionally substituted moiety selected from -L$_3$-alkyl, -L$_3$-cycloalkyl, -L$_3$-heteroalkyl, -L -haloalkyl, -L$_3$-aryl, -L$_3$-heterocycloalkyl, and -L$_3$-heteroaryl;
wherein L$_3$ is selected from a bond, —C(S)—, —C(O)O—, —C(O)NH—, —CR'"$_2$S(O)—, —CR'"$_2$S(O)$_2$—, and —CR'"$_2$S(O)NH—; wherein said optional substituents are selected from halogen, OH, C$_{1-6}$alkyl, C$_{1-6}$alkoxy, halo-C$_{1-6}$alkyl, halo-C$_{1-6}$alkoxy, aryl, haloaryl, and heteroaryl;
or R$_3$ and R$_4$ together may form an optionally substituted 3 to 8-membered heterocyclic ring; wherein said optional substituents are selected from halogen, OH, C$_{1-6}$alkyl, C$_{1-6}$alkoxy, halo-C$_{1-6}$alkyl, halo-C$_{1-6}$alkoxy, aryl, haloaryl, heteroaryl.

In further or alternative embodiments, T$_1$ is an optionally substituted moiety selected from -L$_4$-alkylene-, -L$_4$-cycloalkylene-, -L$_4$-heteroalkylene-, -L$_4$-haloalkylene-, -L$_4$-arylene-, -L$_4$-heteroarylene-, and -L$_4$-heterocycloalkylene-; wherein L$_4$ is selected from a bond, —O—, —NH—, —S—, —CR"$_2$—, —C(O)—, —C(S)—, —C(O)O—, —C(O)NH—, —S(O)—, —S(O)$_2$—, —C(O)NH(CR"$_2$)$_{1-6}$C(O)O—, —C(O)NR"NR"C(O)O—, and —S(O)NH—.

In further or alternative embodiments, each R$_1$ is H. In further or alternative embodiments, R$_5$ is H. In further or alternative embodiments, each R$_1$ is H and R$_5$ is H. In further or alternative embodiments of Formulas (25), (26), or (27), -T$_1$NR$_3$R$_4$ is at the meta position corresponding to Formula (46).

In a further or alternative embodiment of this aspect, the compounds having the structure of Formula (1) are selected from the group consisting of:

(28)


(29)

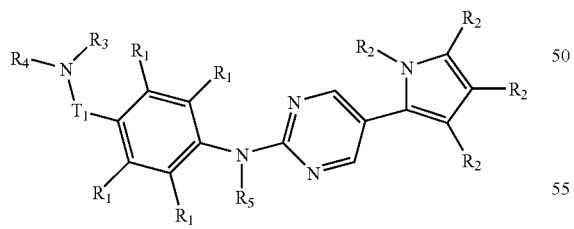

(30)

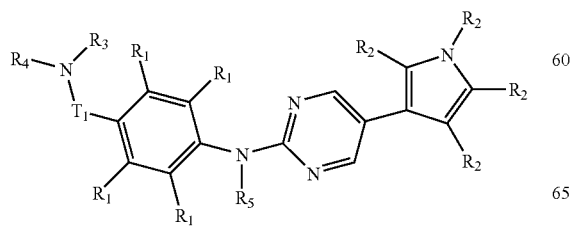

-continued (31)

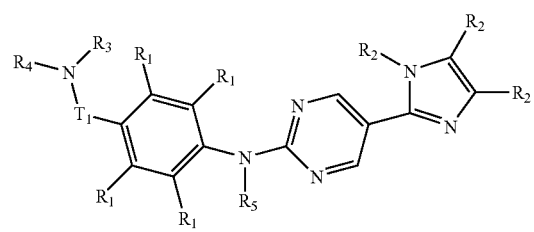

(32)

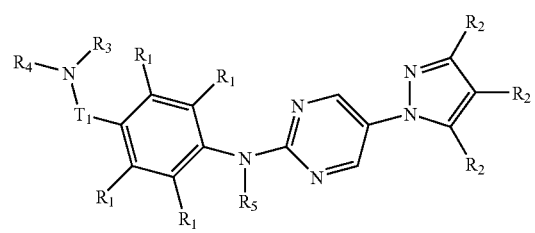

(33)

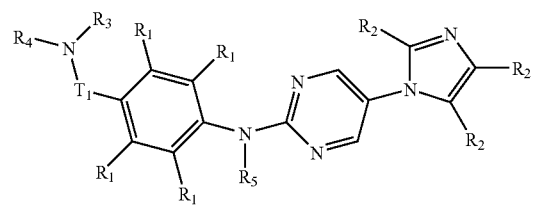

(34)

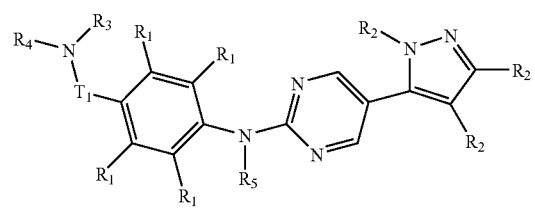

(35)

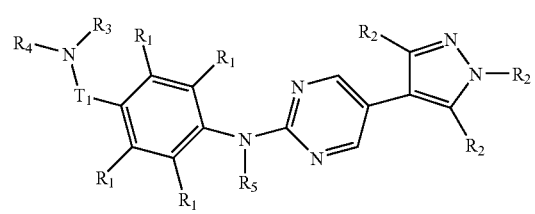

(36)

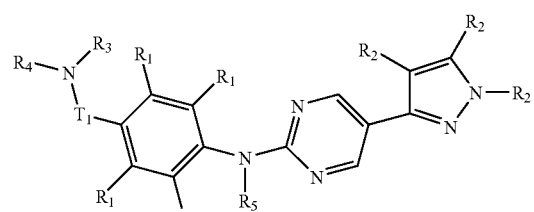

-continued

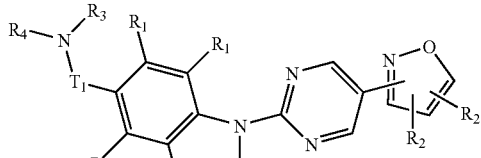
(37)

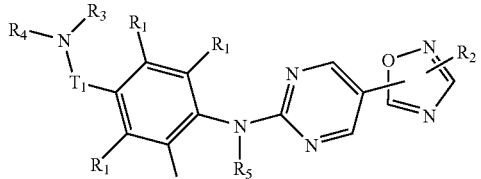
(38)

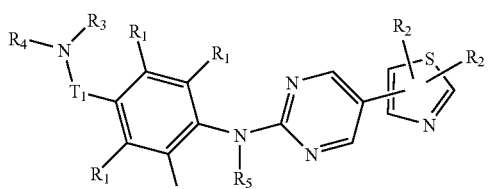
(39)

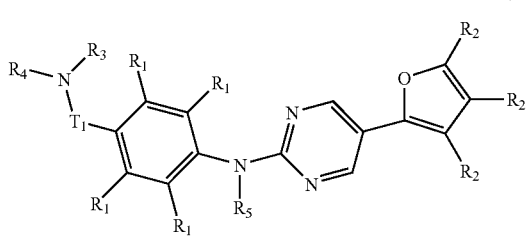
(40)

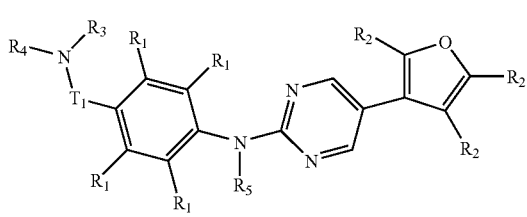
(41)

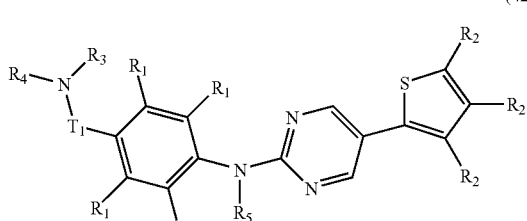
(42)

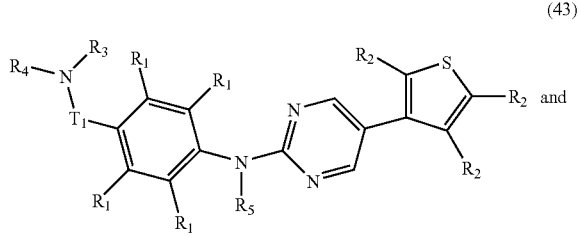
(43) and

-continued

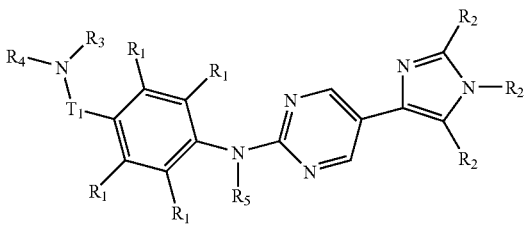
(54)

wherein;

each $R_2$ is independently selected from the group consisting of H, OH, halogen, and an optionally substituted moiety selected from -$L_2$-alkyl, -$L_2$-cycloalkyl, -$L_2$-heteroalkyl, -$L_2$-haloalkyl, -$L_2$-aryl, -$L_2$-heterocycloalkyl, and -$L_2$-heteroaryl; wherein $L_2$ is selected from a bond, —O—, —NH—, —S—, —C(O)—, —C(S)—, —C(O)O—, —C(O)NH—, —S(O)—, —S(O)$_2$—, —C(O)NR"(CR"$_2$)$_{1-6}$C(O)O—, —OC(O)—, —CR"$_2$NR"CR"$_2$C(O)O—, —C(O)NR"NR"C(O)O—, and —S(O)NH—; wherein said optional substituents are selected from halogen, OH, $C_{1-6}$alkyl, $C_{1-6}$alkoxy, halo-$C_{1-6}$alkyl and halo-$C_{1-6}$alkoxy;

each R" is independently H, OH, halogen, $C_{1-6}$alkyl, substituted $C_{1-6}$alkyl, $C_{1-6}$alkoxy, halo-$C_{1-6}$alkyl, halo-$C_{1-6}$alkoxy, aryl, haloaryl, or heteroaryl;

or any two adjacent $R_2$ groups together may form an optionally substituted 5 to 8-membered heterocyclic, cycloalkyl, or aryl ring;

each of $R_3$ and $R_4$ is independently an optionally substituted moiety selected from -Z, -$L_3$-Z, -$L_3$-H, -$L_3$-alkyl, -$L_3$-cycloalkyl, -$L_3$-heteroalkyl, -$L_3$-haloalkyl, -$L_3$-aryl, -$L_3$-heterocycloalkyl, and -$L_3$-heteroaryl; wherein $L_3$ is selected from a bond, —C(S)—, —C(O)O—, —C(O)NR'''—, —(CR"$_2$)$_{1-6}$—, —CR'''$_2$S(O)—, —CR'''$_2$S(O)$_2$—, —CR'''$_2$S(O)NR'''—, —CR'''$_2$C(O)NR'''—, —(CR'''$_2$)$_{1-6}$NR'''—, —(CR'''$_2$)$_{1-6}$O—, —(CR'''$_2$)$_{1-6}$C(O)O—, —$Y^2$C(O)O—, and an optionally substituted $C_{1-6}$alkylene;

wherein said optional substituents are selected from halogen, —OH, =O, —$Y^3$, $C_{1-6}$alkyl, $C_{1-6}$alkoxy, halogen or OH substituted $C_{1-6}$alkyl, halogen or OH substituted $C_{1-6}$alkoxy, —(CR'''$_2$)$_{1-6}$C(O)OR$_6$, —C(O)NR'''$_2$, —C(O)R$_6$, or —C(O)OR$_6$;

$Y^2$ is an optionally substituted cycloalkyl ring or optionally substituted non-aromatic heterocyclic ring;
   wherein said optional substituents are selected from $C_{1-6}$alkyl, halogen, —OH, =O, and CN.

$Y^3$ is optionally substituted aryl, optionally substituted heteroaryl, optionally substituted cycloalkyl, or optionally substituted non-aromatic heterocycle;
   wherein said optional substituents are selected from $C_{1-6}$alkyl, halogen, —OH, =O, and —CN.

Z is —H, —OH, —CN, —COOR''', —NR'''$_2$, or —C≡CR''';

each R''' is independently H, alkyl, or substituted alkyl;

or two R''' together may form a 3-6 membered cycloalkyl or heterocyclic ring;

or R₃ and R₄ taken together with the N atom to which they are attached may form an optionally substituted 3 to 8-membered heterocyclic ring;
  wherein said optional substituents are selected from halogen, —OH, =O, —Y³, $C_{1-6}$alkyl, $C_{1-6}$alkoxy, halogen or OH substituted $C_{1-6}$alkyl, halogen or OH substituted $C_{1-6}$alkoxy, —(CR'''₂)$_{1-6}$Y⁴, —(CR'''₂)$_{1-6}$OR₆, —C(O)NR'''R₆, —C(O)OR₆, —OR₆, —NR'''C(O)OR₆, —NR'''C(O)R₆, —(CR'''₂)$_{1-6}$C(O)OR₆, —(CR'''₂)$_{1-6}$NR'''C(O)OR₆, —(CR'''₂)$_{1-6}$NR₇R₈, —S(O)₂NR'''₂, —C(O)R₆, —OC(O)R₆, —NR₇R₈, —(CR'''₂)$_{1-6}$C(O)NR₇R₈, —S(O)₂R$_A$, or —C(O)R$_A$;
Y⁴ is aryl, heteroaryl, cycloalkyl, or non-aromatic heterocycle;
R$_A$ is selected from —NH₂, —NEt₂, and —NH(CH₂)$_{1-6}$OH;
R₆ is H, alkyl, substituted alkyl, cycloalkyl, non-aromatic heterocycle, aryl, or heteroaryl;
each of R₇ and R₈ is independently H, OH, halogen, $C_{1-6}$alkyl, $C_{1-6}$alkoxy, halo-$C_{1-6}$alkyl, or halo-$C_{1-6}$alkoxy;
or R₇ and R₈ taken together with the N atom to which they are attached may form a 3 to 6-membered heterocyclic ring;
T₁ is an optionally substituted moiety selected from -L₄-, -alkylene-L₄-, -L₄-alkylene-, -L₄-cycloalkylene-, -L₄-heteroalkylene-, -L₄-haloalkylene-, -L₄-arylene-, -L₄-heteroarylene-, and -L₄-heterocycloalkylene-; wherein L₄ is selected from a bond, —O—, —NH—, —S—, —CR''₂—, —NR'''C(O)—, —C(O)—, —C(S)—, —C(O)O—, —C(O)NR'''—, —S(O)—, —S(O)₂—, —OC(O)—, —C(O)NR''' (CR'''₂)$_{1-6}$C(O)O—, —C(O)NR'''(CR''₂)$_{1-6}$C(O)—, —CR''₂NR'''CR''₂C(O)O—, —C(O)NR'''NR'''C(O)O—, —C(O)NR'(CR'''₂)₁₆—, —CR''₂C(O)—, and —S(O)NH—;
  wherein said optional substituents are selected from halogen, OH, $C_{1-6}$alkyl, $C_{1-6}$alkoxy, halo-$C_{1-6}$alkyl, halo-$C_{1-6}$alkoxy, aryl, haloaryl, and heteroaryl;
or a pharmaceutically acceptable salt, pharmaceutically acceptable N-oxide, pharmaceutically active metabolite, pharmaceutically acceptable prodrug, or pharmaceutically acceptable solvate thereof.

In further alternative embodiments, L₂ is selected from a bond, —C(O)—, —C(S)—, —C(O)O—, —C(O)NH—, —S(O)—, —S(O)₂—, —C(O)NH(CR''₂)₁₆C(O)O—, —C(O)NR''NR''C(O)O—, and —S(O)NH—.

In further or alternative embodiments, each of R₃ and R₄ is independently an optionally substituted moiety selected from -L₃-alkyl, -L₃-cycloalkyl, -L₃-heteroalkyl, -L₃-haloalkyl, -L₃-aryl, -L₃-heterocycloalkyl, and -L₃-heteroaryl;
  wherein L₃ is selected from a bond, —C(S)—, —C(O)O—, —C(O)NH—, —CR'''₂S(O)—, —CR'''₂S(O)₂—, and —CR'''₂S(O)NH—; wherein said optional substituents are selected from halogen, OH, $C_{1-6}$alkyl, $C_{1-6}$alkoxy, halo-$C_{1-6}$alkyl, halo-$C_{1-6}$alkoxy, aryl, haloaryl, and heteroaryl;
or R₃ and R₄ together may form an optionally substituted 3 to 8-membered heterocyclic ring;
  wherein said optional substituents are selected from halogen, OH, $C_{1-6}$alkyl, $C_{1-6}$alkoxy, halo-$C_{1-6}$alkyl, halo-$C_{1-6}$alkoxy, aryl, haloaryl, heteroaryl.

In further or alternative embodiments, T₁ is an optionally substituted moiety selected from -L₄-alkylene-, -L₄-cycloalkylene-, -L₄-heteroalkylene-, -L₄-haloalkylene-, -L₄-arylene-, -L₄-heteroarylene-, and -L₄-heterocycloalkylene-;
wherein L₄ is selected from a bond, —O—, —NH—, —S—, —CR''₂—, —C(O)—, —C(S)—, —C(O)O—, —C(O)NH—, —S(O)—, —S(O)₂—, —C(O)NH(CR''₂)$_{1-6}$C(O)O—, —C(O)NR''NR''C(O)O—, and —S(O)NH—.

In further or alternative embodiments, each R₁ is H. In further or alternative embodiments, R₅ is H. In further or alternative embodiments, each R₁ is H and R₅ is H. In further or alternative embodiments of Formulas (28)-(43), or (54), -T₁NR₃R₄ is at the meta position corresponding to Formula (46).

In another aspect is a method for modulating the activity of a c-kit kinase receptor comprising contacting the c-kit kinase receptor with a compound having the structure of Formula (A) or Formula (B):

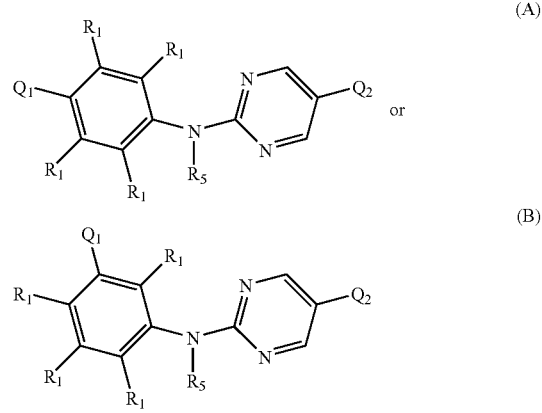

wherein:
  Q₁ is H, halogen, a group comprising a non-aromatic tertiary amine, a group comprising a non-aromatic secondary amine, or is an optionally substituted moiety selected from the group consisting of: -L-alkyl, -L-cycloalkyl, -L-heteroalkyl, -L-haloalkyl, -L-aryl, -L-heterocycloalkyl, and -L-heteroaryl; wherein L is selected from a bond, —O—, —NH—, —S—, —C(O)—, —C(S)—, —C(O)O—, —C(O)NH—, —S(O)—, —S(O)₂—, —OC(O)—, —C(O)NR'' (CR''₂)$_{1-6}$C(O)O—, —CR''₂NR''CR''₂C(O)O—, —C(O)—NR''YC(O)O—, C(O)NR''NR''C(O)O—, and —S(O)NH—; and Y is optionally substituted arylene or heteroarylene;
  each R₁ is independently selected from the group consisting of H, halogen, and an optionally substituted moiety selected from -L₁-alkyl, -L₁-cycloalkyl, -L₁-heteroalkyl, -L₁-haloalkyl, -L₁-aryl, -L₁-heterocycloalkyl, and -L₁-heteroaryl; wherein L₁ is selected from a bond, —O—, —NH—, —S—, —C(O)—, —C(S)—, —C(O)O—, —C(O)NH—, —S(O)—, —S(O)₂—, —C(O)NR'(CR''₂)$_{1-6}$C(O)O—, —OC(O)—, —CR''₂NR''CR''₂C(O)O—, —C(O)—NR''Y¹C(O)O—, —C(O)NR''NR''C(O)O—, and —S(O)NH—; and Y¹ is optionally substituted arylene or heteroarylene;
  Q₂ is selected from the group consisting of H, halogen, and a group comprising an optionally substituted moiety selected from -L₆-alkyl, -L₆-cycloalkyl, -L₆-heteroalkyl, -L₆-haloalkyl, -L₆-aromatic carbocycle, -L₆-heterocycloalkyl, and -L₆-aromatic heterocycle; wherein L₆ is selected from a bond, —O—, —NH—, —S—, —C(O)—, —C(S)—, —C(O)O—, —C(O)

NH—, —S(O)—, —S(O)₂—, —C(O)NR"(CR"₂)₁₋₆
C(O)O—, —OC(O)—, —CR"₂NR"CR"₂C(O)O—,
—C(O)—NR"Y"C(O)O—, —C(O)NR"NR"C(O)
O—, and —S(O)NH—; and Y" is optionally substituted arylene or heteroarylene;

each R" is independently H, OH, halogen, $C_{1-6}$alkyl, substituted $C_{1-6}$alkyl, $C_{1-6}$alkoxy, halo-$C_{1-6}$alkyl, halo-$C_{1-6}$alkoxy, aryl, haloaryl, or heteroaryl;

any two $R_1$ groups together may form an optionally substituted 5 to 8-membered heterocyclic, cycloalkyl, or aryl ring;

$R_5$ is selected from the group consisting of H, and an optionally substituted moiety selected from -$L_5$-H, -$L_5$-alkyl, -$L_5$-cycloalkyl, -$L_5$-heteroalkyl, -$L_5$-haloalkyl, -$L_5$-aryl, -$L_5$-heterocycloalkyl, and -$L_5$-heteroaryl, wherein $L_4$ is selected from a bond, —R'O—, —R'N(H)—, —R'S—, —R'C(O)—, —R'C(S)—, —R'C(O)O—, and —R'C(O)NH—;

each R' is independently selected from the group consisting of a bond, alkylene, substituted alkylene, heteroalkylene, substituted heteroalkylene, alkenylene, substituted alkenylene, cycloalkylene, substituted cycloalkylene, heteroalkylene, substituted heteroalkylene, heterocycloalkylene, substituted heterocycloalkylene, arylene, substituted arylene, heteroarylene, substituted heteroarylene, alkarylene, substituted alkarylene, aralkylene, and substituted aralkylene; and any $R_1$ and $R_5$ taken together may form an optionally substituted 5 to 8-membered heterocyclic, cycloalkyl, or aryl ring;

or a pharmaceutically acceptable salt, pharmaceutically acceptable N-oxide, pharmaceutically active metabolite, pharmaceutically acceptable prodrug, or pharmaceutically acceptable solvate thereof.

In further or alternative embodiments, $Q_1$ is selected from the group consisting of H, halogen, and an optionally substituted moiety selected from -L-alkyl, -L-cycloalkyl, -L-heteroalkyl, -L-haloalkyl, -L-aryl, -L-heterocycloalkyl, and -L-heteroaryl; wherein L is selected from a bond, —O—, —S—, and, —C(O)O—; wherein said optional substituents are selected from halogen, OH, $C_{1-6}$alkyl, $C_{1-6}$alkoxy, halo-$C_{1-6}$alkyl, halo-$C_{1-6}$alkoxy, aryl, haloaryl, and heteroaryl.

In further or alternative embodiments, $Q_1$ is an optionally substituted moiety selected from -L-alkyl, -L-heteroalkyl, and -L-heterocycloalkyl; wherein L is selected from a bond, —O—, —S—, and, —C(O)O—; wherein said optional substituents are selected from halogen, OH, $C_{1-6}$alkyl, $C_{1-6}$alkoxy, halo-$C_{1-6}$alkyl, halo-$C_{1-6}$alkoxy, aryl, haloaryl, and heteroaryl.

In further or alternative embodiments, $Q_1$ is -L-R, wherein R is a group comprising a tertiary amine and L is optionally substituted and selected from a bond, —O—, —S—, and, —C(O)O—; wherein said optional substituents are selected from halogen, OH, $C_{1-6}$alkyl, $C_{1-6}$alkoxy, halo-$C_{1-6}$alkyl, halo-$C_{1-6}$alkoxy, aryl, haloaryl, and heteroaryl.

In further or alternative embodiments, $Q_2$ is an optionally substituted moiety selected from, -$L_6$-cycloalkyl, -$L_6$-aromatic carbocycle, -$L_6$-heterocycloalkyl, and -$L_6$-aromatic heterocycle; wherein $L_6$ is selected from a bond, —O—, —NH—, —S—, —C(O)—, —C(S)—, —C(O)O—, —C(O)NH—, —S(O)—, —S(O)₂—, —C(O)NH(CR"₂)₁₋₆C(O)O—, —C(O)NR"NR"C(O)O—, and —S(O)NH—; wherein said optional substituents are selected from halogen, OH, $C_{1-6}$alkyl, $C_{1-6}$alkoxy, halo-$C_{1-6}$alkyl, halo-$C_{1-6}$alkoxy, aryl, haloaryl, and heteroaryl.

In further or alternative embodiments, $Q_2$ is selected from the group consisting of an optionally substituted cycloalkyl, optionally substituted aromatic carbocycle, optionally substituted heterocycloalkyl, and optionally substituted aromatic heterocycle; wherein said optional substituents are selected from halogen, OH, $C_{1-6}$alkyl, $C_{1-6}$alkoxy, halo-$C_{1-6}$alkyl, halo-$C_{1-6}$alkoxy, aryl, haloaryl, and heteroaryl.

In a further or alternative embodiment of this aspect, the compound of Formula (A) or Formula (B) is a compound having the structure of Formula (1) or Formula (46):

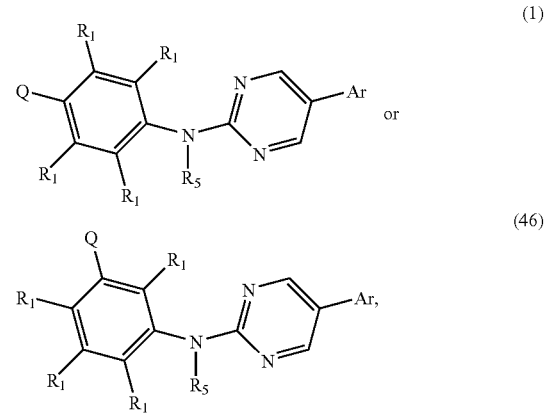

wherein:
Ar is a group comprising a moiety selected from an optionally substituted five-membered aromatic heterocycle, an optionally substituted five-membered aromatic carbocycle, an optionally substituted six-membered aromatic heterocycle, and a substituted, optionally further substituted six-membered aromatic carbocycle;

Q is a group comprising a non-aromatic tertiary amine or a non-aromatic secondary amine, with the proviso that Q is not —NR$_a$R$_b$ or —SO₂NR$_a$R$_b$; wherein each of R$_a$ and R$_b$ is independently H or $C_{1-6}$alkyl optionally substituted by mono- or di-alkyl ($C_{1-6}$) amino;

each $R_1$ is independently selected from the group consisting of H, halogen, and an optionally substituted moiety selected from -$L_1$-alkyl, -$L_1$-cycloalkyl, -$L_1$-heteroalkyl, -$L_1$-haloalkyl, -$L_1$-aryl, -$L_1$-heterocycloalkyl, and -$L_1$-heteroaryl; wherein $L_1$ is selected from a bond, O—, —NH—, —S—, —C(O)—, —C(S)—, —C(O)O—, —C(O)NH—, —S(O)—, —S(O)₂—, —C(O)NH(CR"₂)₁₋₆C(O)O—, —C(O) NR"NR"C(O)O—, and —S(O)NH—;

each R" is independently H, OH, halogen, $C_{1-6}$alkyl, substituted $C_{1-6}$alkyl, $C_{1-6}$alkoxy, halo-$C_{1-6}$alkyl, halo-$C_{1-6}$alkoxy, aryl, haloaryl, or heteroaryl;

or any two adjacent $R_1$ groups together may form an optionally substituted 5 to 8-membered heterocyclic, cycloalkyl, or aryl ring;

$R_5$ is selected from the group consisting of H, and an optionally substituted moiety selected from -$L_5$-H, -$L_5$-alkyl, -$L_5$-cycloalkyl, -$L_5$-heteroalkyl, -$L_5$-haloalkyl, -$L_5$-aryl, -$L_5$-heterocycloalkyl, and -$L_5$-heteroaryl; wherein $L_5$ is selected from a bond, —R'O—, —R'N(H)—, —R'S—, —R'C(O)—, —R'C(S)—, —R'C(O)O—, and —R'C(O)NH—;

each R' is independently selected from the group consisting of a bond, alkylene, substituted alkylene, heteroalkylene, substituted heteroalkylene, alkenylene, substituted alkenylene, cycloalkylene, substituted cycloalkylene, heteroalkylene, substituted heteroalkylene, heterocycloalkylene, substituted heterocycloalkylene, arylene, substituted arylene, heteroarylene, substituted heteroarylene, alkarylene, substituted alkarylene, aralkylene, and substituted aralkylene; and any $R_1$ and $R_5$ taken together may form an optionally substituted 5 to 8-membered heterocyclic, cycloalkyl, or aryl ring;

or a pharmaceutically acceptable salt, pharmaceutically acceptable N-oxide, pharmaceutically active metabolite, pharmaceutically acceptable prodrug, or pharmaceutically acceptable solvate thereof.

In further or alternative embodiments, the compound of Formula (A) or Formula (B), directly contacts the c-kit kinase receptor. In further or alternative embodiments, the contacting occurs in vitro. In further or alternative embodiments, the contacting occurs in vivo.

In further or alternative embodiments, the Ar is a group comprising a substituted, optionally further substituted six-membered aromatic heterocycle. In further or alternative embodiments, said optional substituents are selected from halogen, OH, halogen, $C_{1-6}$alkyl, $C_{1-6}$alkoxy, halo-$C_{1-6}$alkyl, halo-$C_{1-6}$alkoxy, aryl, haloaryl, or heteroaryl. In further or alternative embodiments, the compound is the compound of any of Formula (1) to Formula (54) in various embodiments described above.

In further or alternative embodiments, Ar is selected from the group consisting of

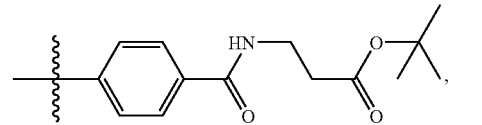

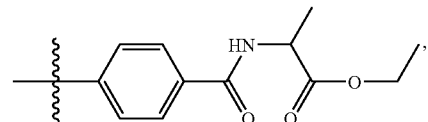

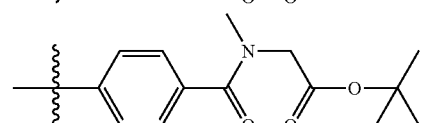

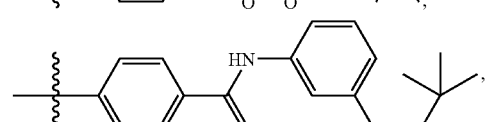

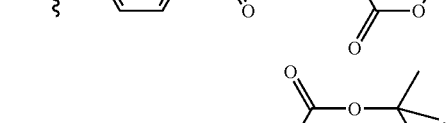

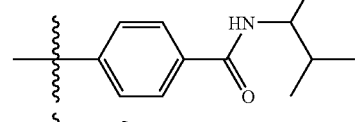

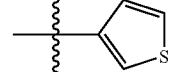

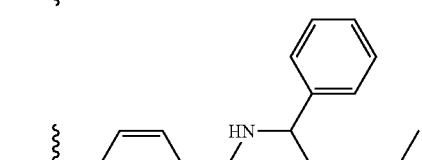

-continued

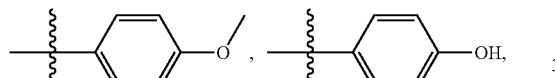

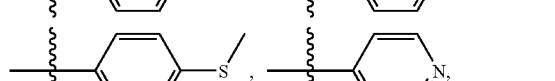

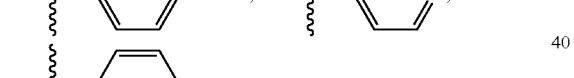

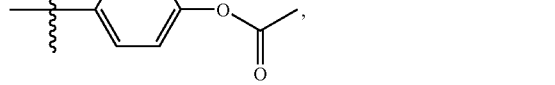


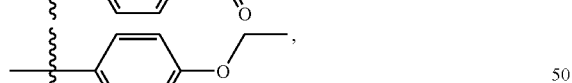

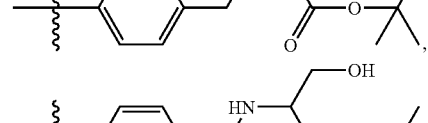

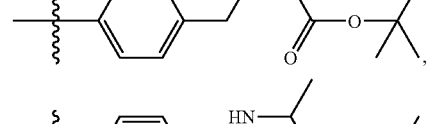

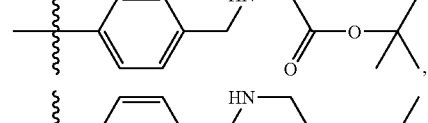

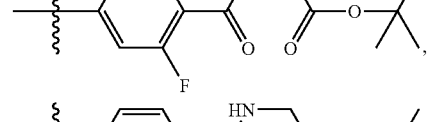

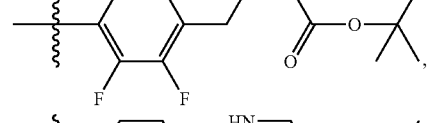

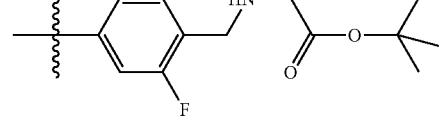

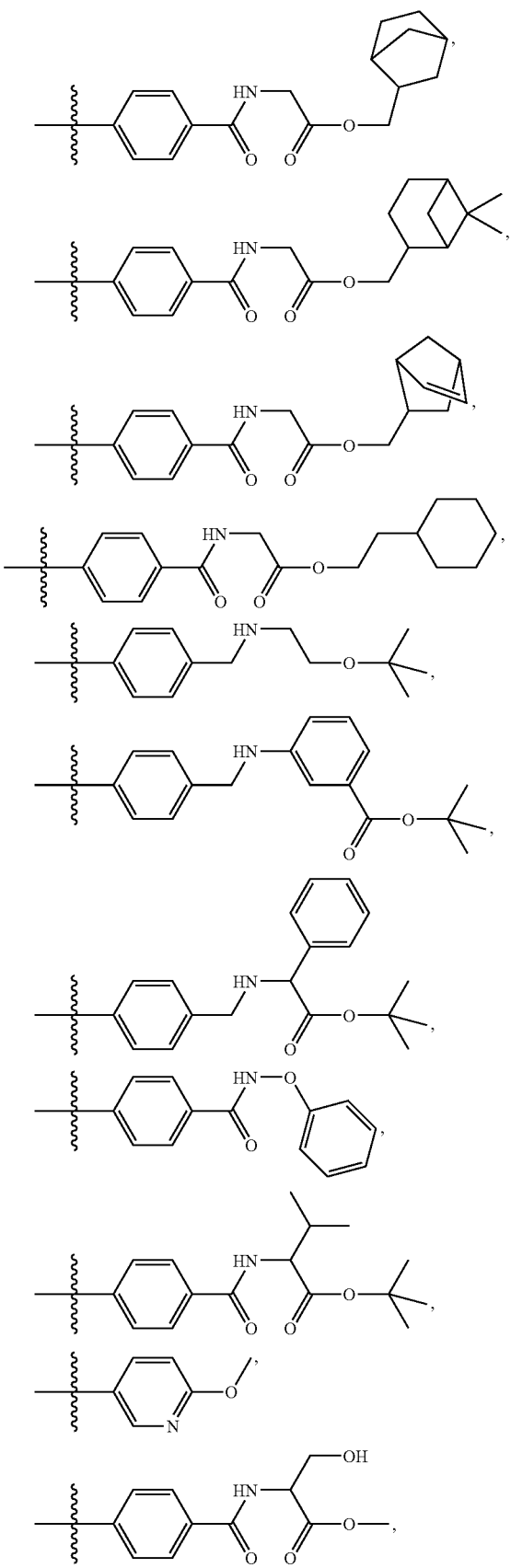
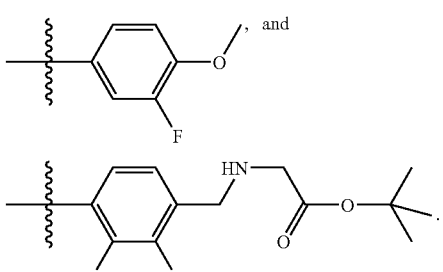
In further or alternative embodiments, Q is selected from the group consisting of

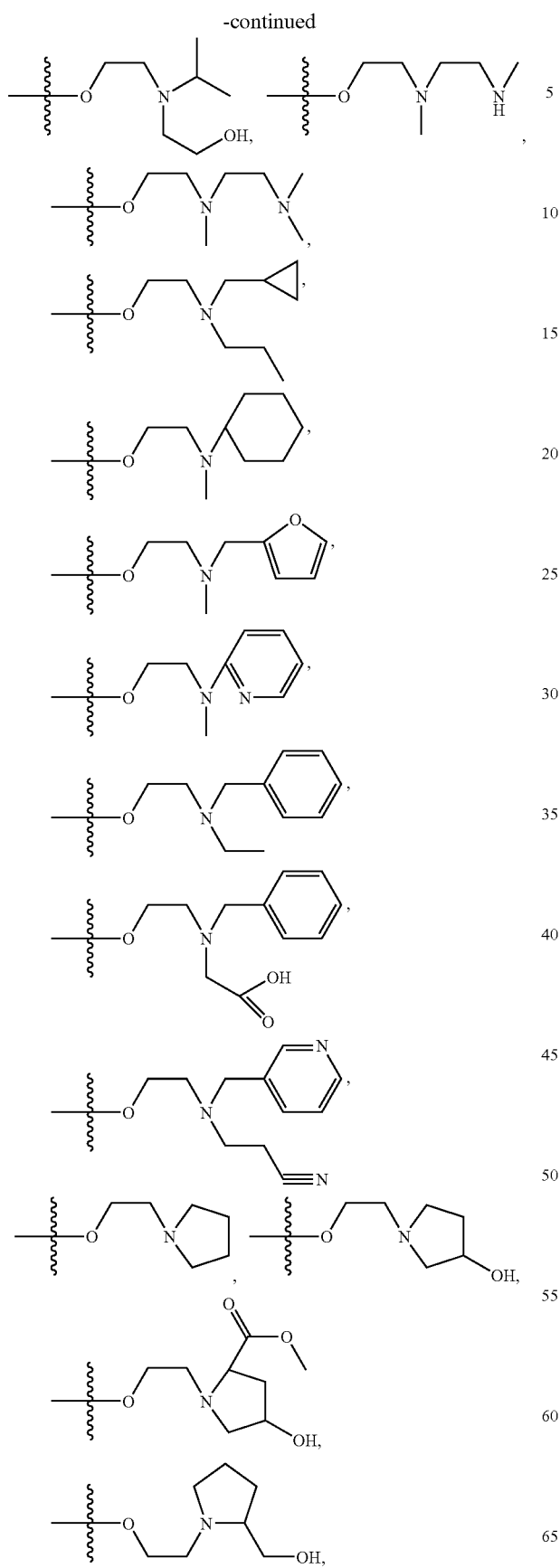
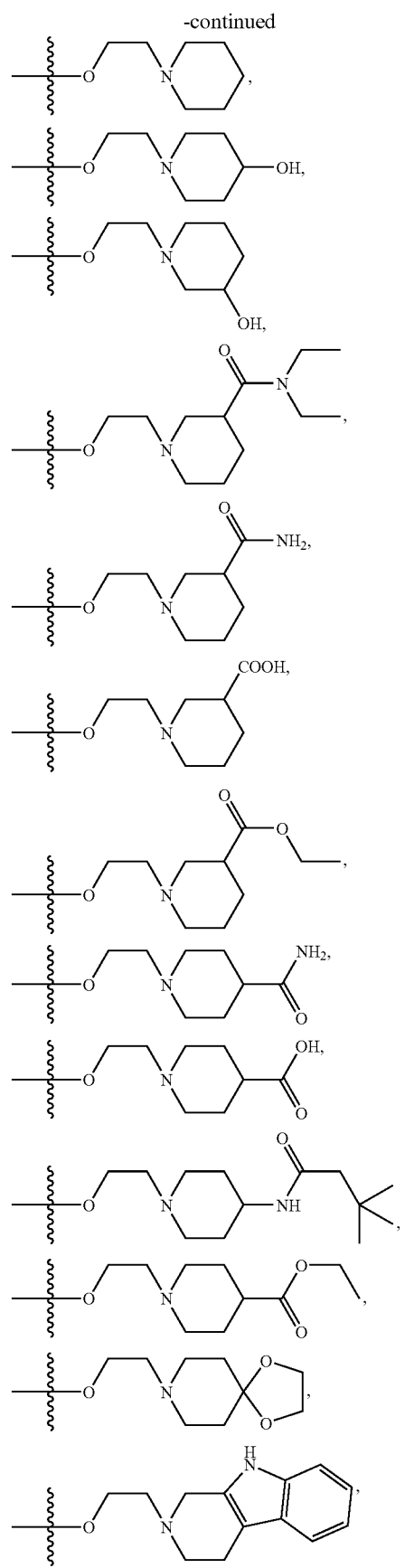

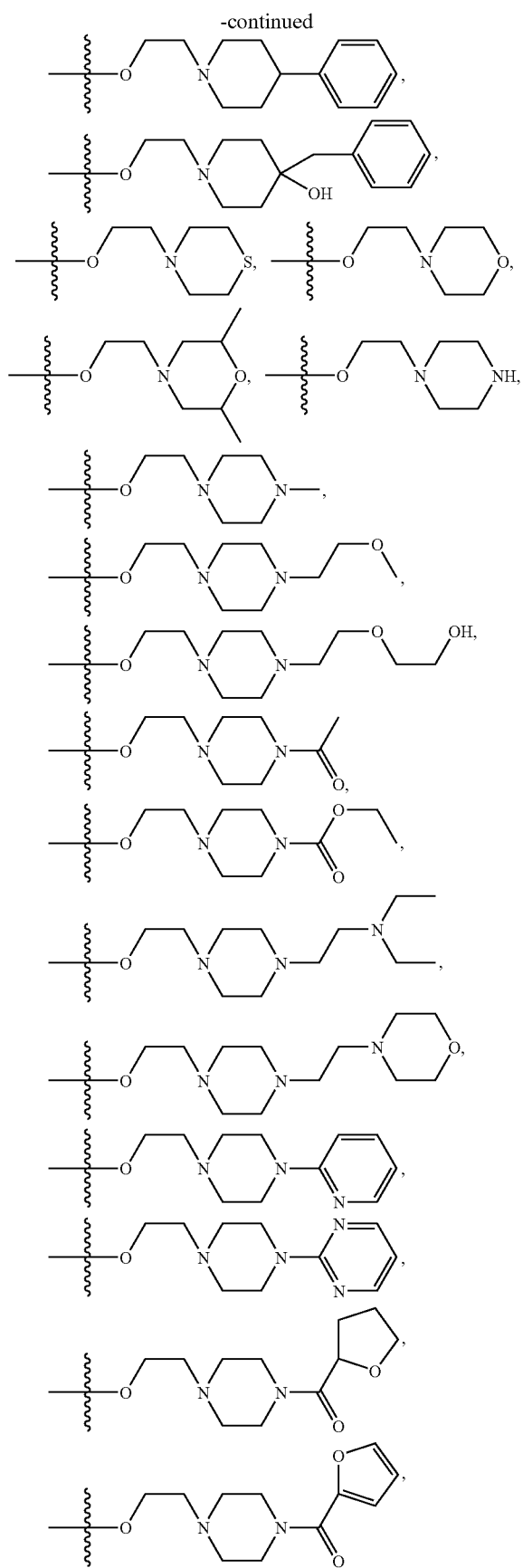
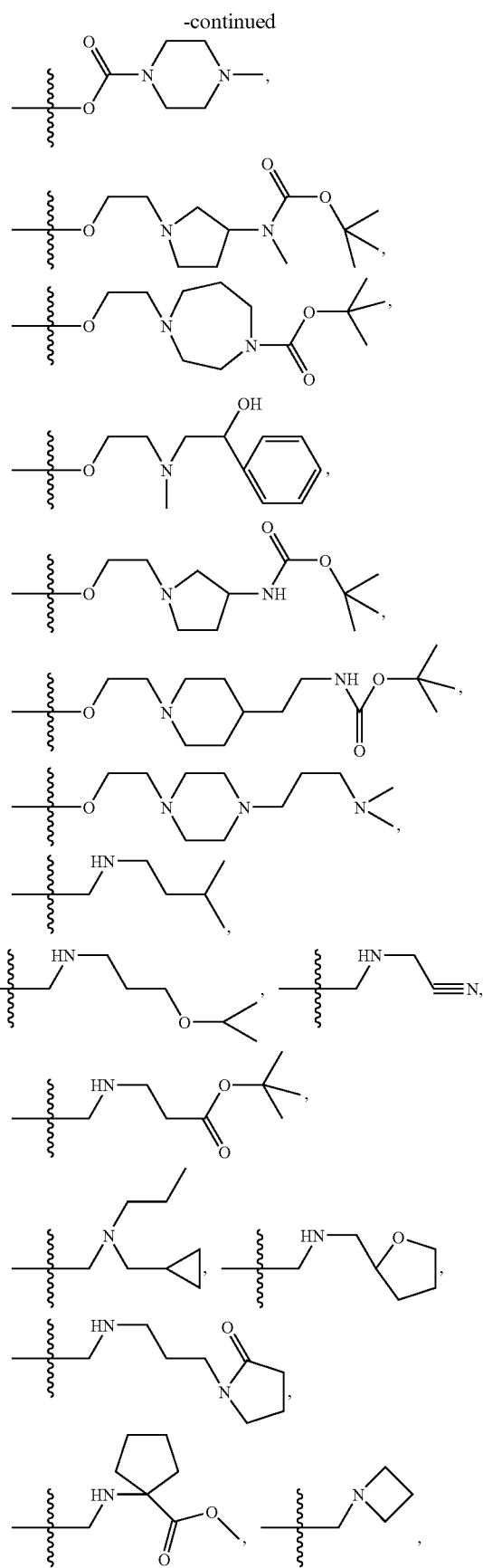

-continued
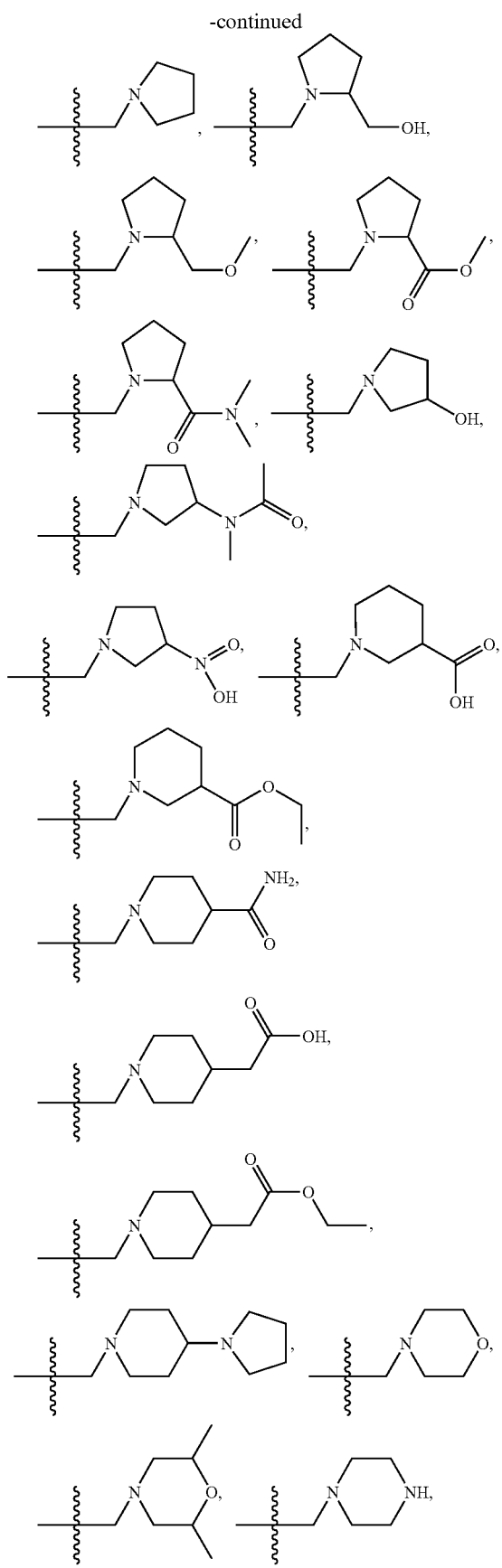
-continued
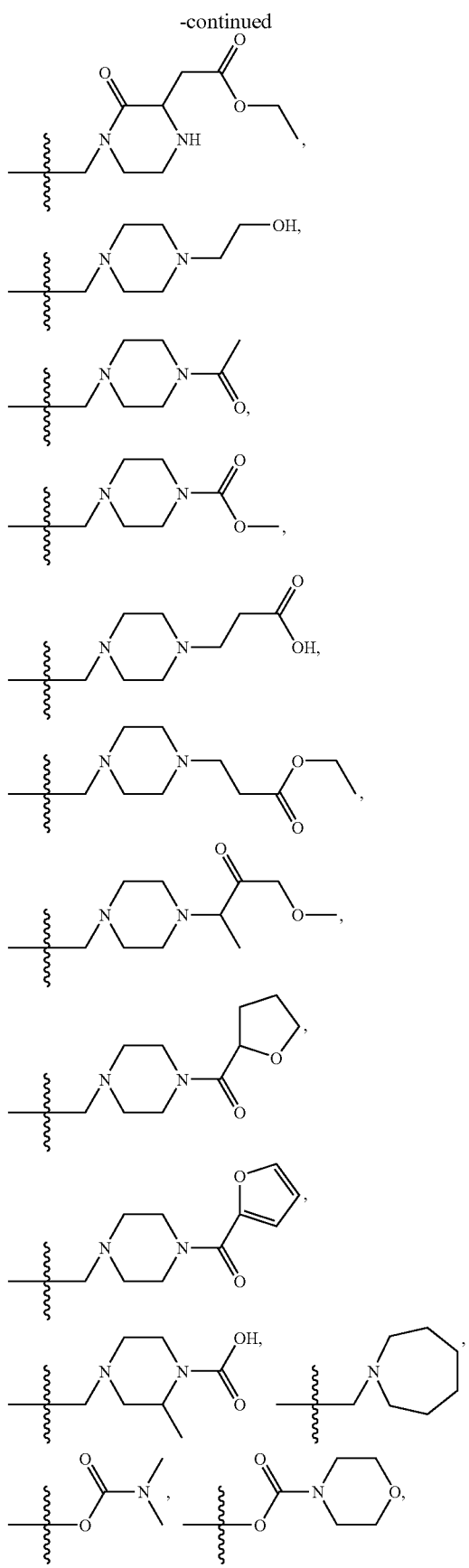

-continued
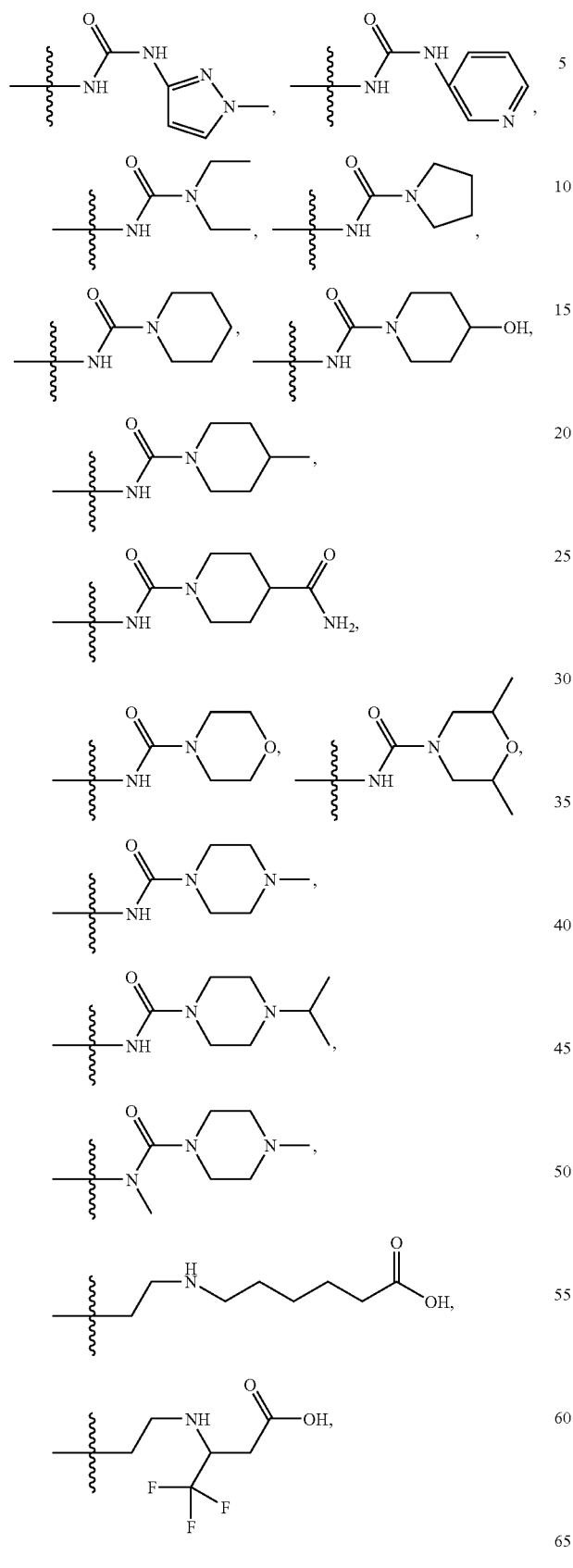
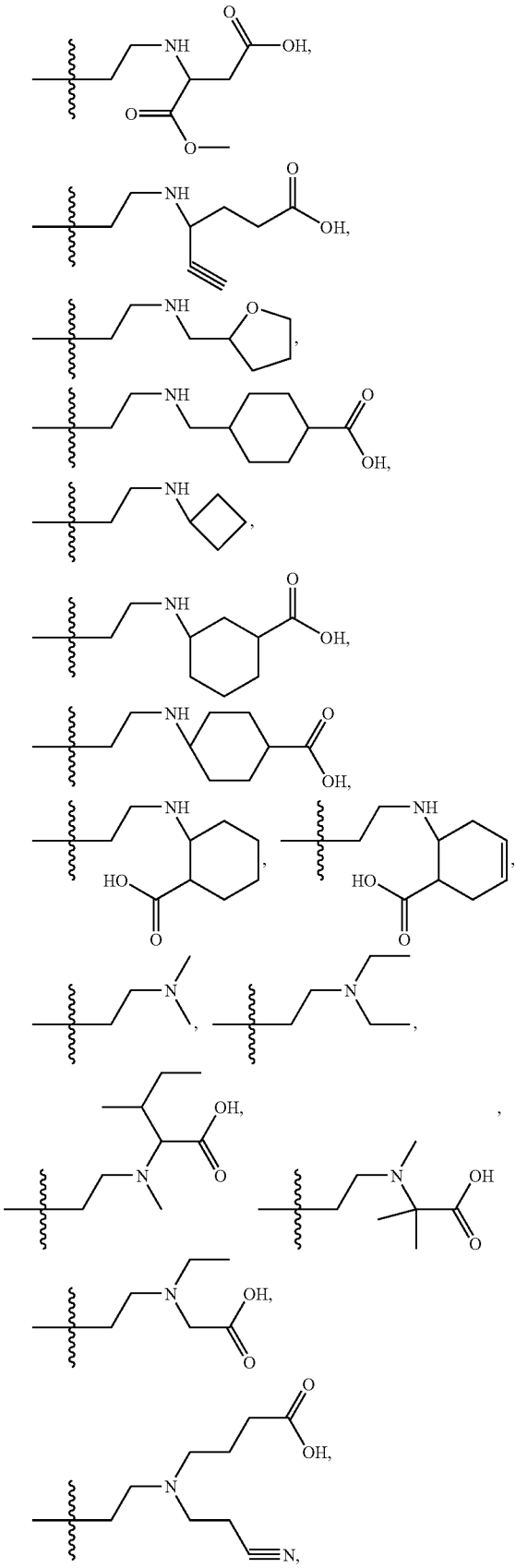

-continued
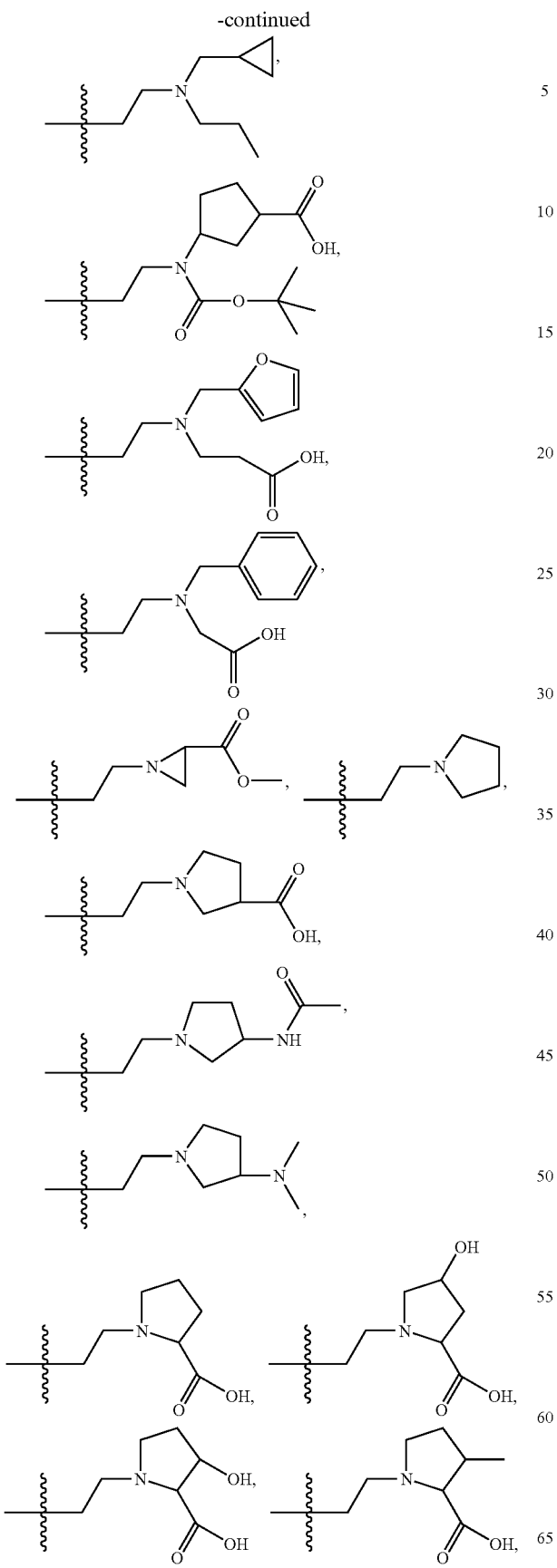
-continued
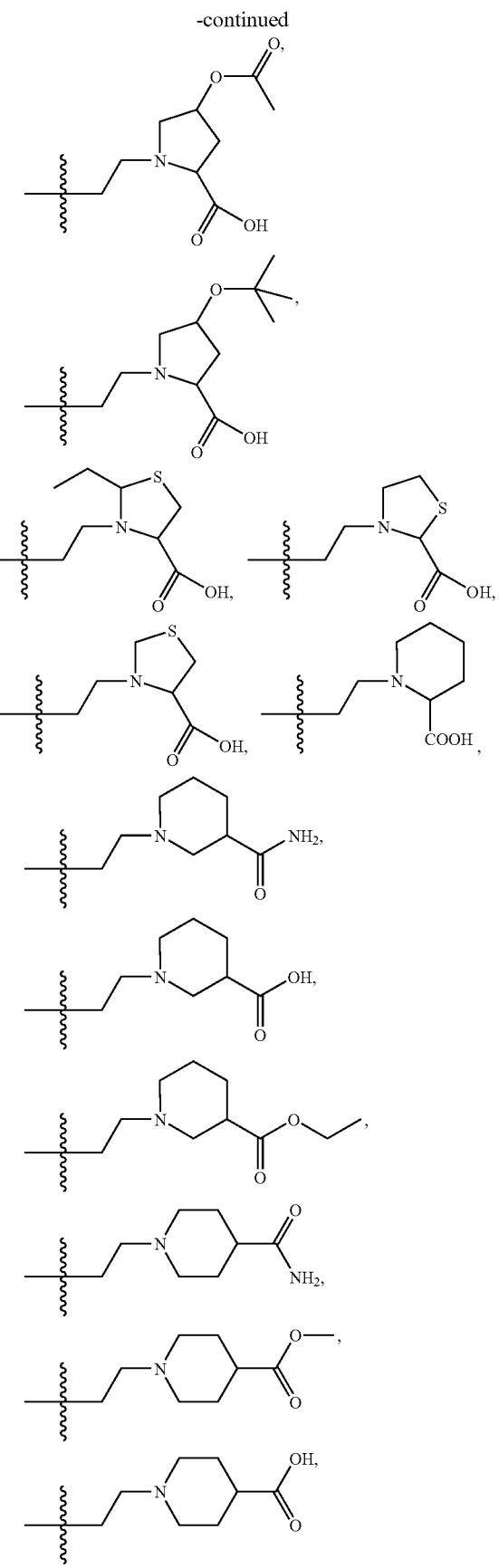

107
-continued
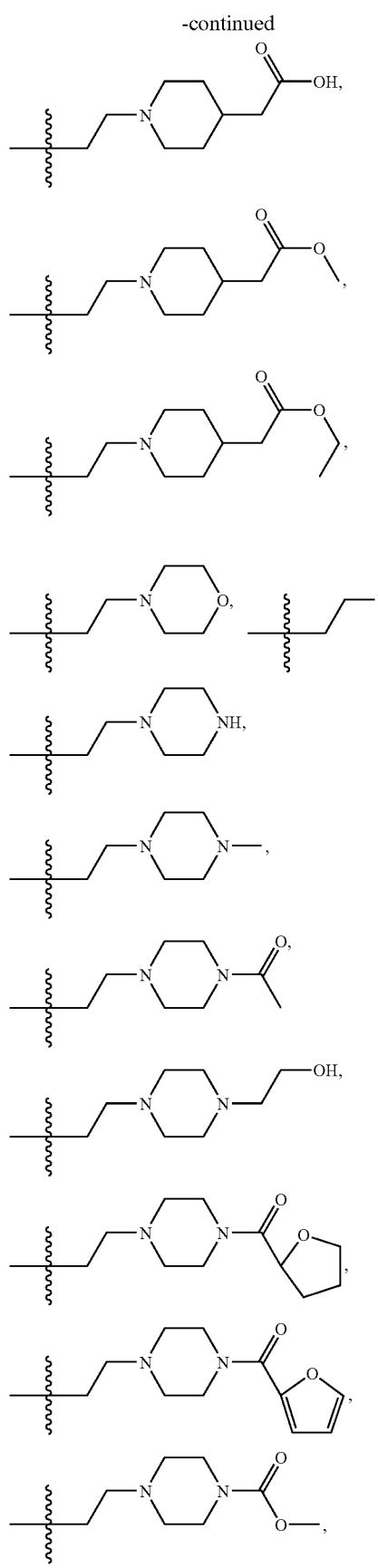
108
-continued
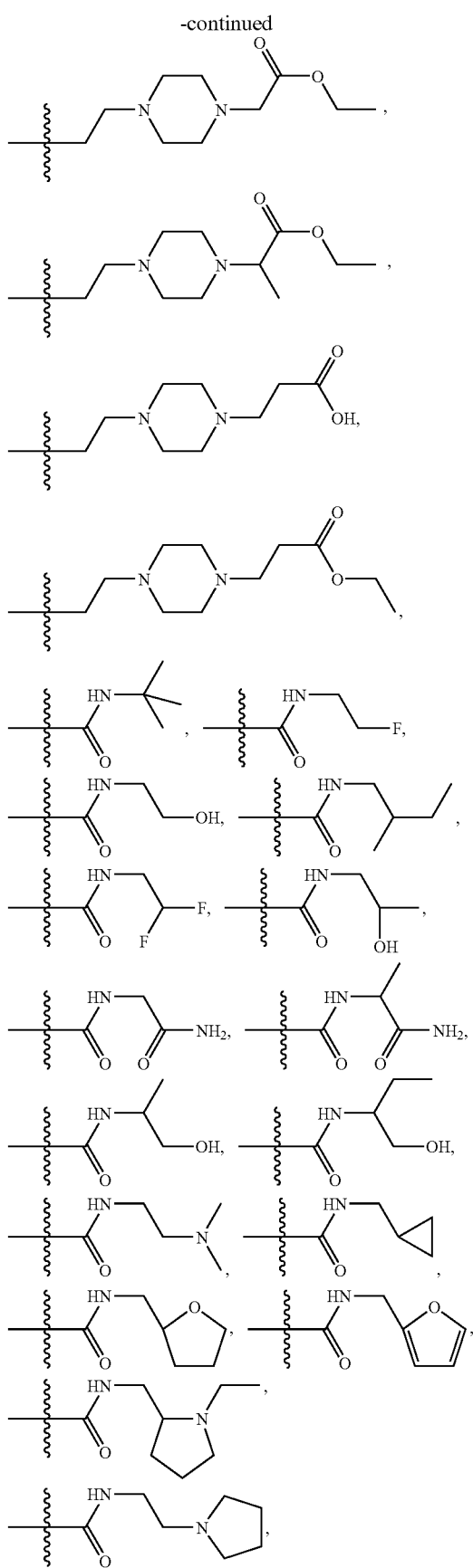

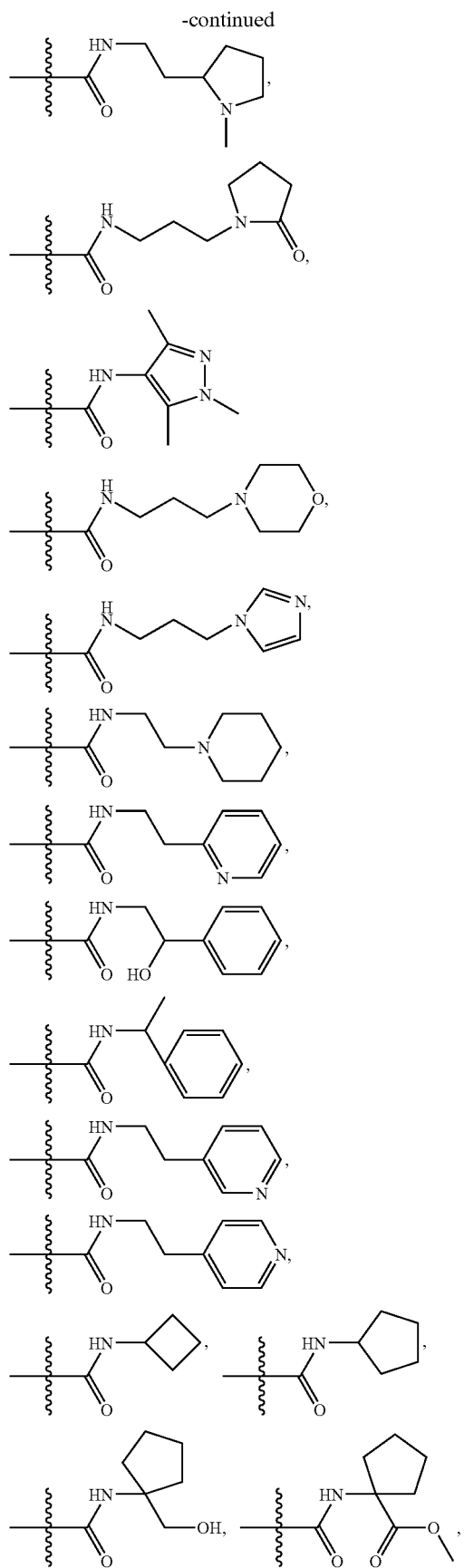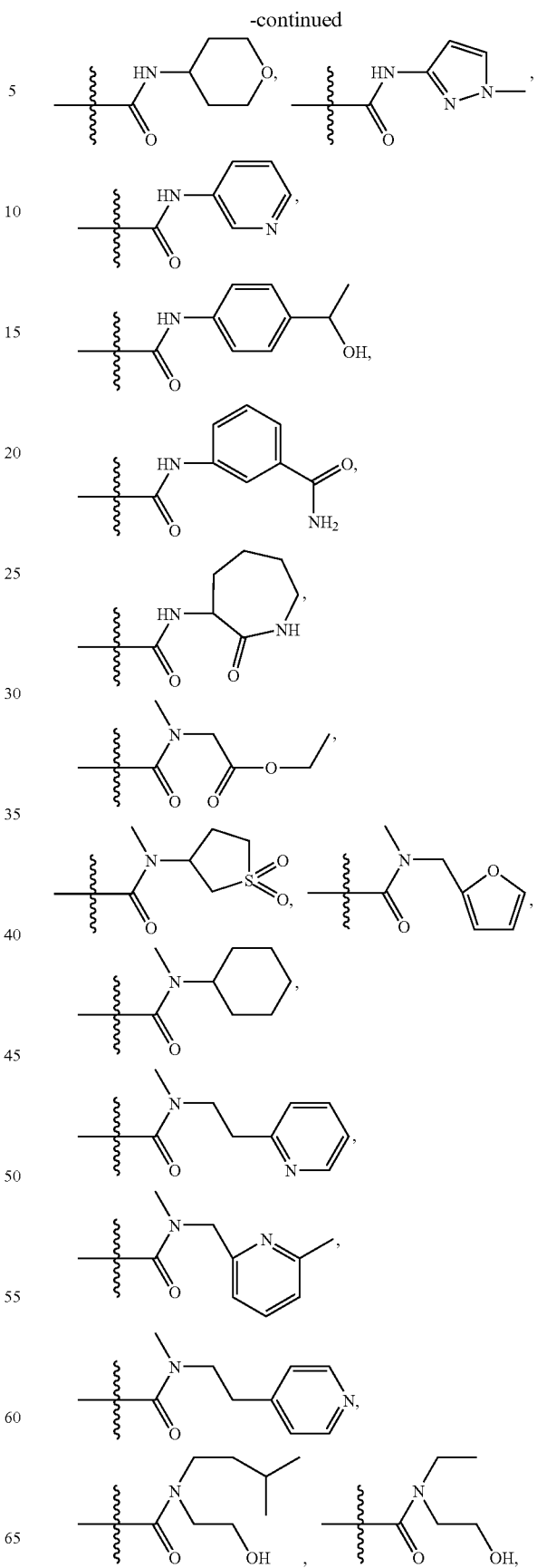

-continued
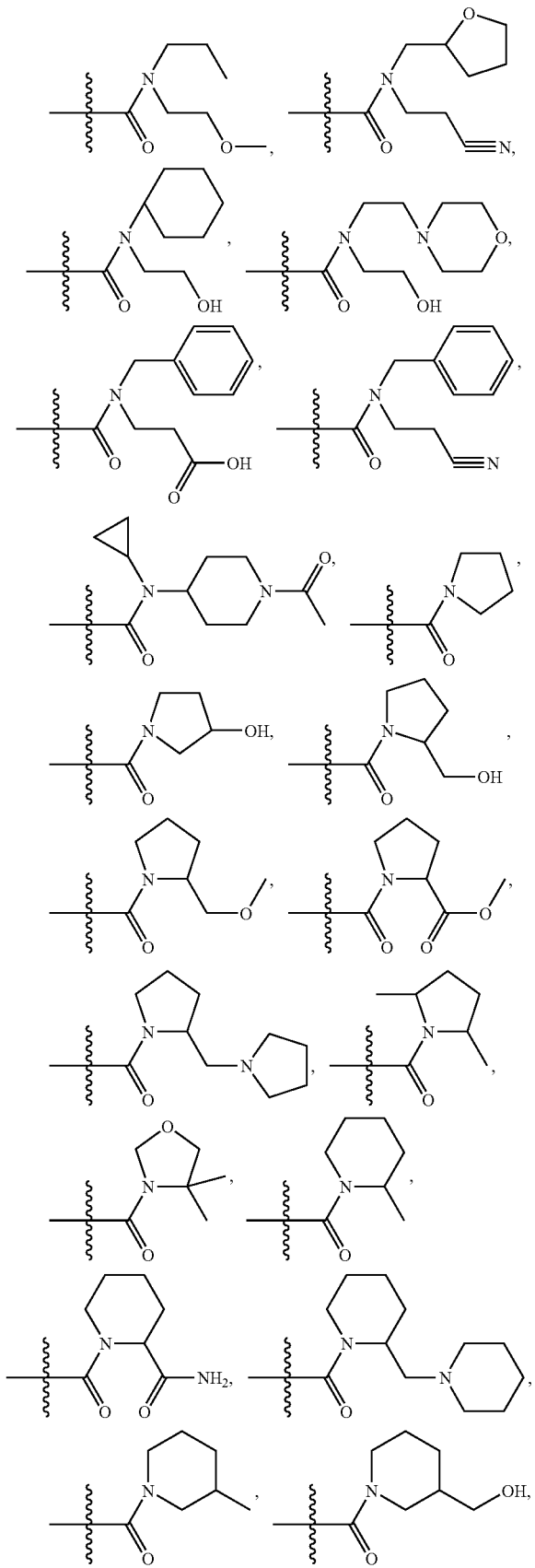
-continued
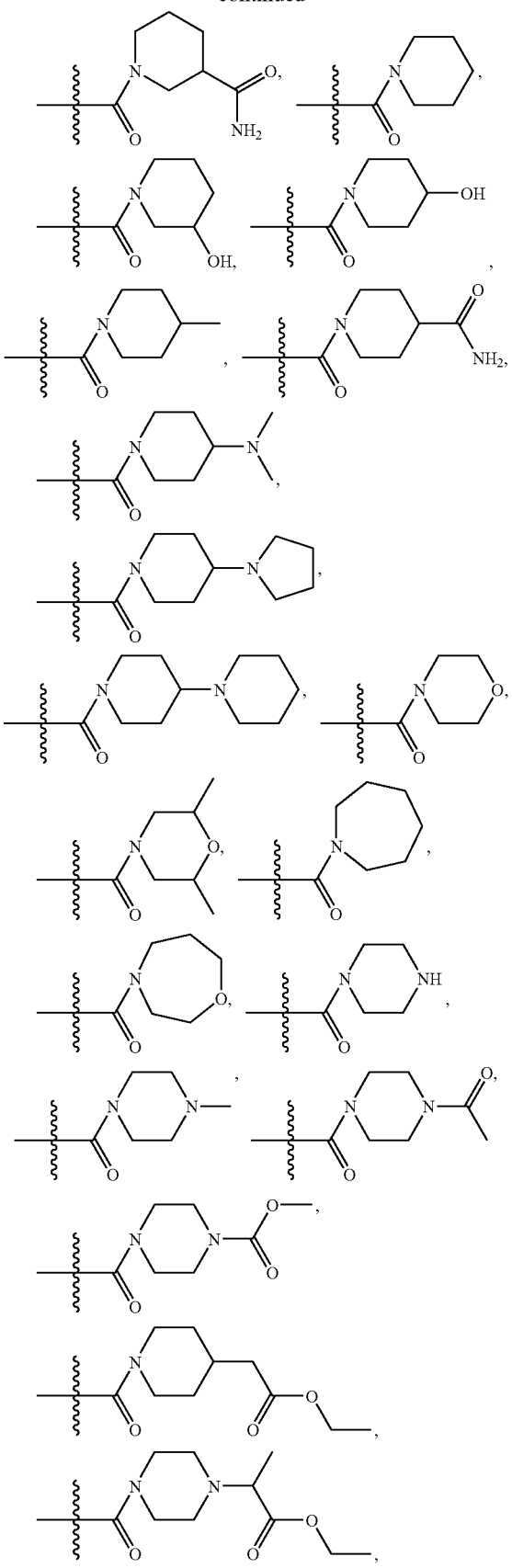

-continued
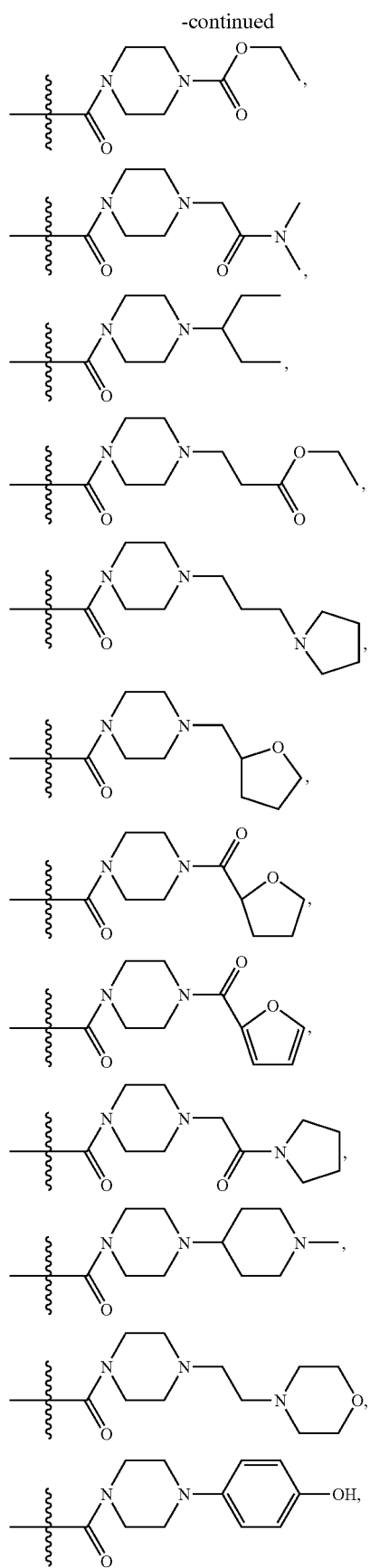
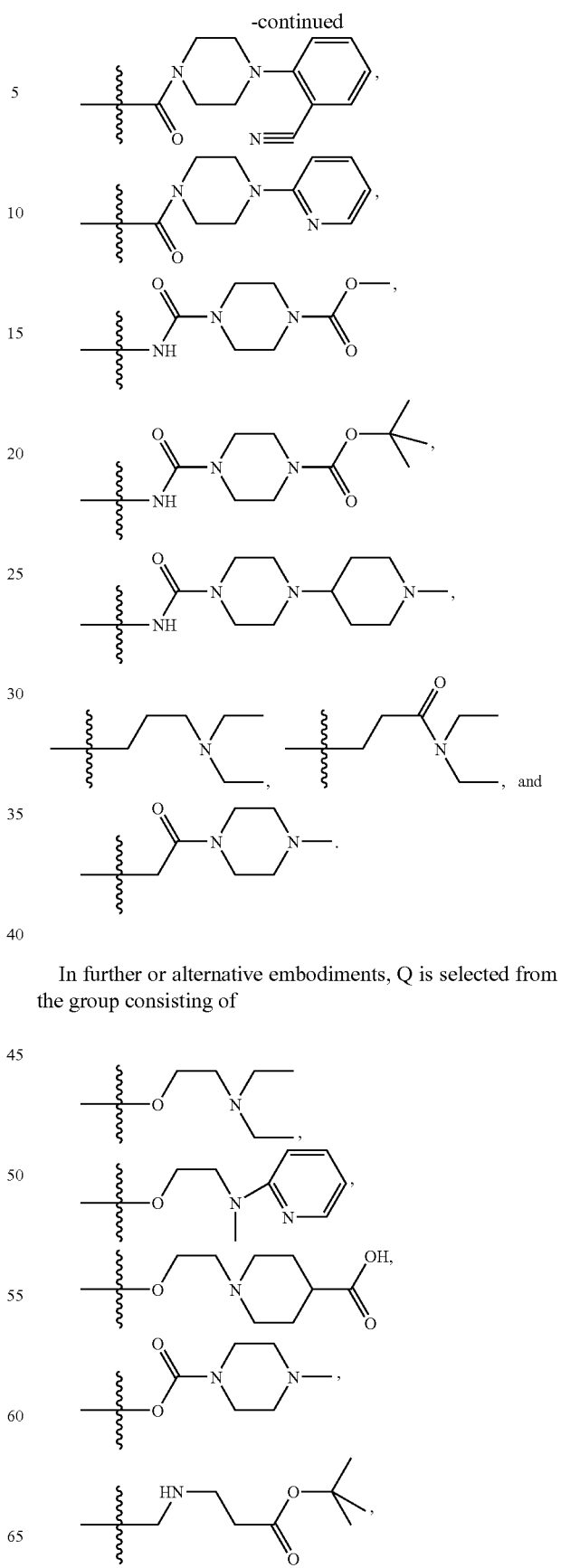
In further or alternative embodiments, Q is selected from the group consisting of
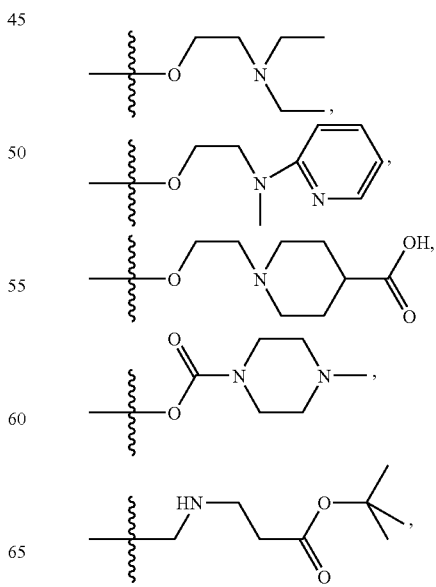

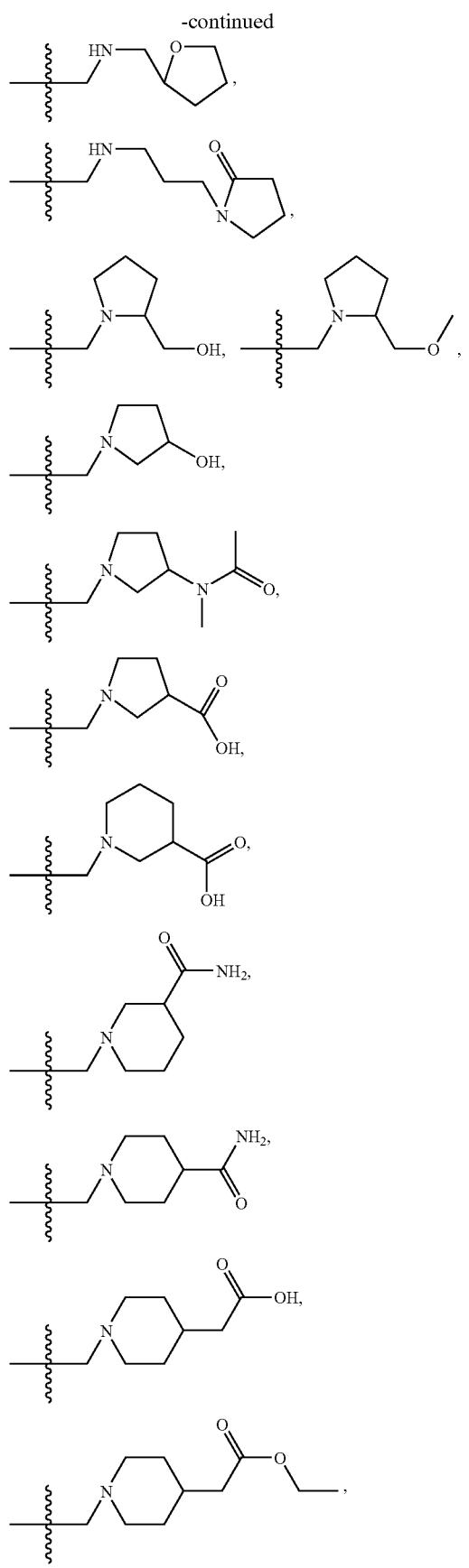
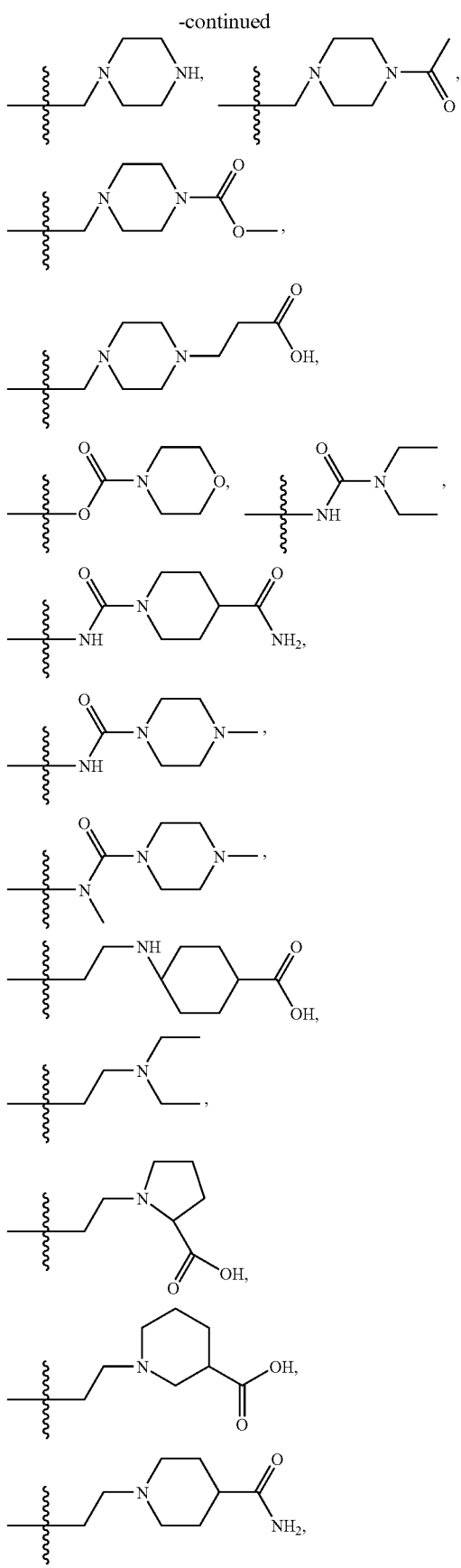

-continued
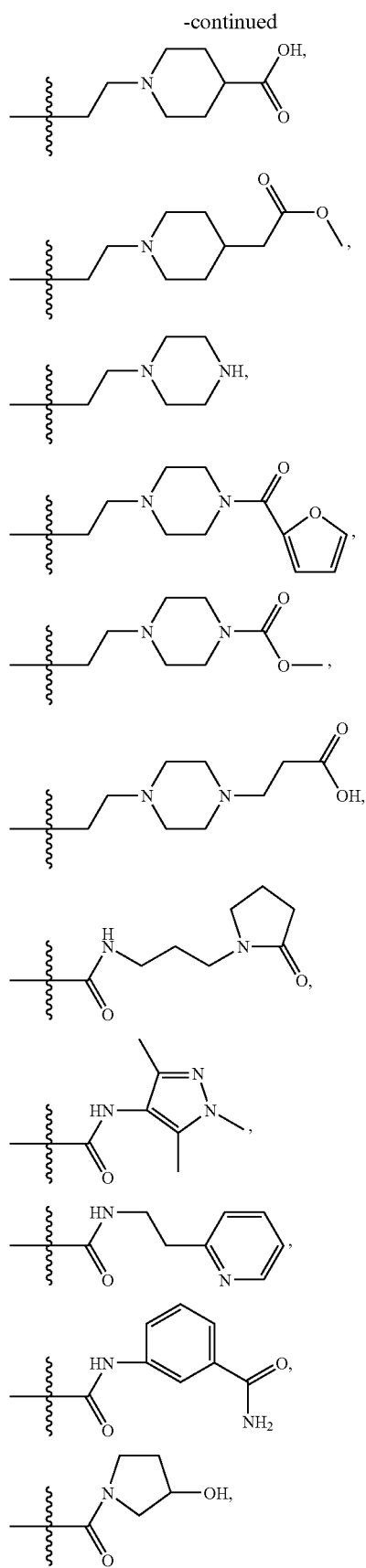
-continued
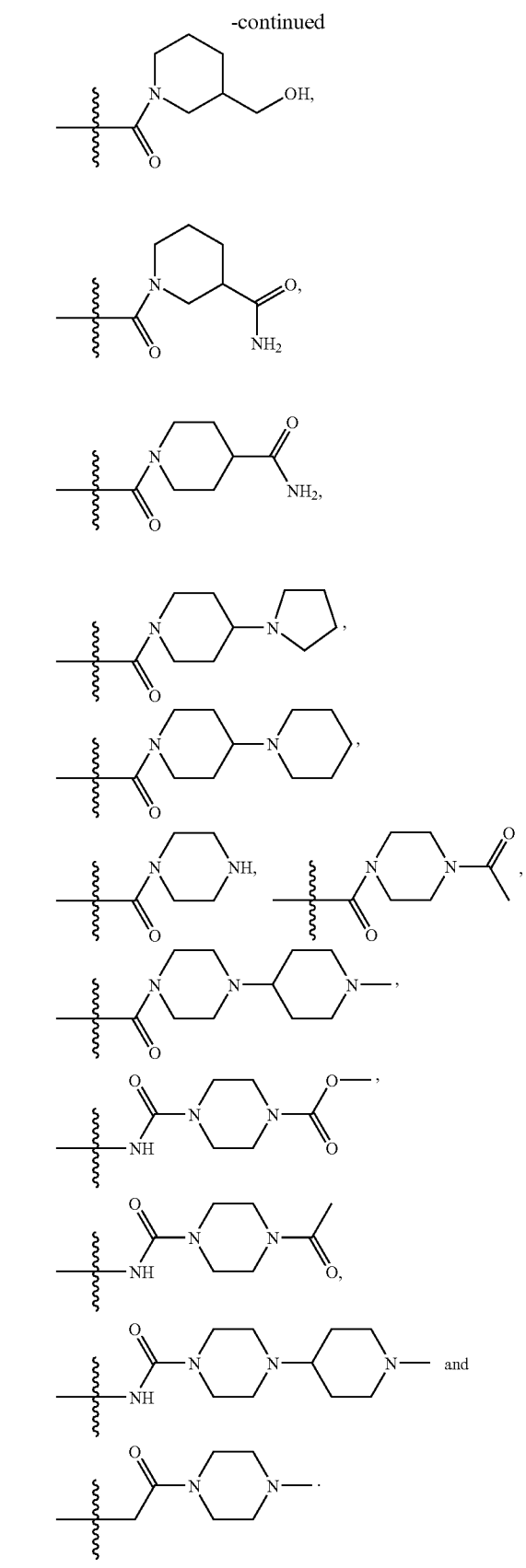

In further or alternative embodiments, Ar is selected from the group consisting of

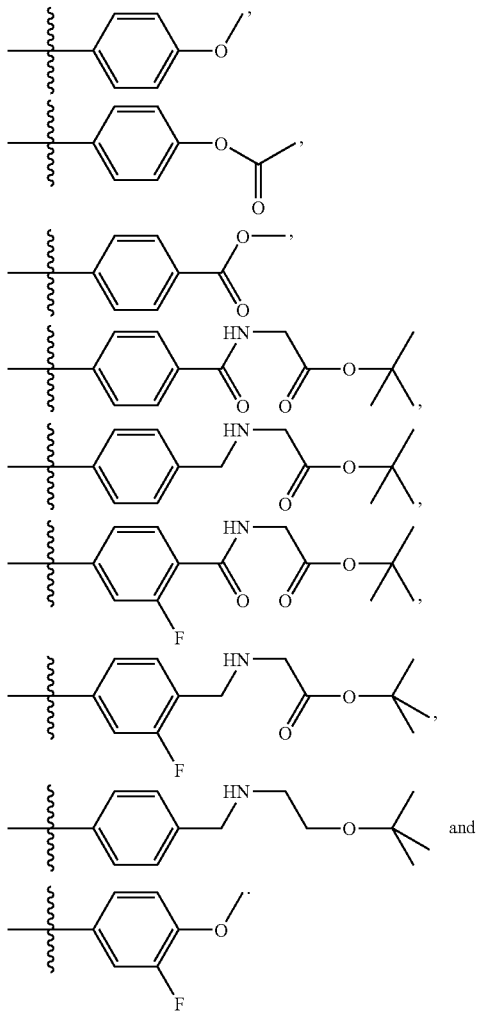

In further or alternative embodiments, the compound is selected from the group consisting of: tert-butyl 2-(4-(2-(4-(2-(diethylamino)ethoxy)phenylamino)pyrimidin-5-yl)-2-fluorobenzamido)acetate, tert-butyl 2-(4-(2-(4-(2-(diethylamino)ethoxy)phenylamino)pyrimidin-5-yl)-2-fluorobenzylamino)acetate, tert-butyl 2-(4-(2-(4-(2-(diethylamino)ethoxy)phenylamino)pyrimidin-(5-yl)benzylamino)acetate, 2,2'-(2-(4-(5-(4-methoxyphenyl)pyrimidin-2-ylamino)phenoxy)ethylazanediyl)diethanol, 1-(4-(5-(4-methoxyphenyl)pyrimidin-2-ylamino)phenethyl)piperidine-4-carboxylic acid, tert-butyl 2-(4-(2-(4-(2-(diethylamino)ethoxy)phenylamino)pyrimidin-5-yl)benzamido)acetate, methyl 1-(4-(5-(4-methoxyphenyl)pyrimidin-2-ylamino)phenethyl)piperidine-4-carboxylate, N-(4-(2-(diethylamino)ethyl)phenyl)-5-(4-methoxyphenyl)pyrimidin-2-amine, 1-(2-(4-(5-(4-methoxyphenyl)pyrimidin-2-ylamino)phenoxy)ethyl)piperidine-4-carboxylic acid, N-(4-(2-(diethylamino)ethoxy)phenyl)-5-(4-methoxyphenyl)pyrimidin-2-amine, tert-butyl 2-(4-(2-(4-(2-morpholinoethoxy)phenylamino)pyrimidin-5-yl)benzamido)acetate, tert-butyl 2-(4-(2-(4-(2-(4-carbamoylpiperidin-1-yl)ethoxy)phenylamino)pyrimidin-5-yl)benzamido)acetate, 4-(2-(4-(2-(diethylamino)ethoxy)phenylamino)pyrimidin-5-yl)phenyl acetate, ethyl 2-(2-(diethylamino)ethoxy)-5-(5-(4-methoxyphenyl)pyrimidin-2-ylamino)benzoate, 4-(5-(4-methoxyphenyl)pyrimidin-2-ylamino)phenyl 4-methylpiperazine-1-carboxylate, 5-(4-methoxyphenyl)-N-(4-(2-(methyl(pyridin-2-yl)amino)ethoxy)phenyl)pyrimidin-2-amine, methyl 4-(2-(4-(2-(diethylamino)ethoxy)phenylamino)pyrimidin-5-yl)benzoate, N-(4-(2-(diethylamino)ethoxy)phenyl)-5-(3-fluoro-4-methoxyphenyl)pyrimidin-2-amine, 2-(2-(diethylamino)ethoxy)-4-(5-(4-methoxyphenyl)pyrimidin-2-ylamino)benzoic acid, methyl 2-(2-(diethylamino)ethoxy)-4-(5-(4-methoxyphenyl)pyrimidin-2-ylamino)benzoate, N-(3-(2-(diethylamino)ethoxy)phenyl)-5-(4-methoxyphenyl)pyrimidin-2-amine, N-(3-(2-(diethylamino)ethyl)phenyl)-5-(4-methoxyphenyl)pyrimidin-2-amine, 1-(4-(5-(4-methoxyphenyl)pyrimidin-2-ylamino)benzyl)piperidine-4-carboxamide, 1-(4-(5-(4-methoxyphenyl)pyrimidin-2-ylamino)benzyl)piperidine-3-carboxamide, tert-butyl 3-(4-(5-(4-methoxyphenyl)pyrimidin-2-ylamino)benzylamino)propanoate, 5-(4-methoxyphenyl)-N-(4-(piperazin-1-ylmethyl)phenyl)pyrimidin-2-amine, 1-(4-(4-(5-(4-methoxyphenyl)pyrimidin-2-ylamino)benzyl)piperazin-1-yl)ethanone, (4-(4-(5-(4-methoxyphenyl)pyrimidin-2-ylamino)benzyl)piperazin-1-yl)(tetrahydrofuran-2-yl)methanone, 1-(3-(4-(5-(4-methoxyphenyl)pyrimidin-2-ylamino)benzylamino)propyl)pyrrolidin-2-one, (S)-(1-(4-(5-(4-methoxyphenyl)pyrimidin-2-ylamino)benzyl)pyrrolidin-2-yl)methanol, (R)—N-(4-((2-(methoxymethyl)pyrrolidin-1-yl)methyl)phenyl)-5-(4-methoxyphenyl)pyrimidin-2-amine, 1-(4-(5-(4-methoxyphenyl)pyrimidin-2-ylamino)benzyl)pyrrolidin-3-ol, methyl 1-(4-(5-(4-methoxyphenyl)pyrimidin-2-ylamino)benzylamino)cyclopentanecarboxylate, 4-(4-(5-(4-methoxyphenyl)pyrimidin-2-ylamino)benzyl)-2-methylpiperazine-1-carboxylic acid, 3-(4-(4-(5-(4-methoxyphenyl)pyrimidin-2-ylamino)benzyl)piperazin-1-yl)propanoic acid, 1-(4-(5-(4-methoxyphenyl)pyrimidin-2-ylamino)benzyl)piperidine-3-carboxylic acid, ethyl 2-(1-(4-(5-(4-methoxyphenyl)pyrimidin-2-ylamino)benzyl)piperidin-4-yl)acetate, 2-(1-(4-(5-(4-methoxyphenyl)pyrimidin-2-ylamino)benzyl)piperidin-4-yl)acetic acid, 1-(4-(5-(4-methoxyphenyl)pyrimidin-2-ylamino)benzyl)pyrrolidine-3-carboxylic acid, 3-(5-(4-methoxyphenyl)pyrimidin-2-ylamino)phenyl morpholine-4-carboxylate, 3-(5-(4-methoxyphenyl)pyrimidin-2-ylamino)phenyl 4-methylpiperazine-1-carboxylate, 3-(5-(4-((2-tert-butoxy-2-oxoethylamino)methyl)phenyl)pyrimidin-2-ylamino)phenyl 4-methylpiperazine-1-carboxylate, methyl 4-(4-(5-(4-methoxyphenyl)pyrimidin-2-ylamino)benzyl)piperazine-1-carboxylate, 4-(5-(4-((2-tert-butoxy-2-oxoethylamino)methyl)phenyl)pyrimidin-2-ylamino)phenyl 4-methylpiperazine-1-carboxylate, N-(3-(5-(4-methoxyphenyl)pyrimidin-2-ylamino)phenyl)-4-methylpiperazine-1-carboxamide, 2-(4-(5-(4-methoxyphenyl)pyrimidin-2-ylamino)phenyl)-1-(4-methylpiperazin-1-yl)ethanone, N1-(3-(5-(4-methoxyphenyl)pyrimidin-2-ylamino)phenyl)piperidine-1,4-dicarboxamide, 3-(5-(4-methoxyphenyl)pyrimidin-2-ylamino)benzyl 4-methylpiperazine-1-carboxylate, 4-hydroxy-N-(3-(5-(4-methoxyphenyl)pyrimidin-2-ylamino)phenyl)piperidine-1-carboxamide, N-(4-(5-(4-methoxyphenyl)pyrimidin-2-ylamino)phenyl)-4-methylpiperazine-1-carboxamide, 1-(4-(5-(4-methoxyphenyl)pyrimidin-2-ylamino)phenethyl)piperidine-4-carboxamide, furan-2-yl(4-(4-(5-(4-methoxyphenyl)pyrimidin-2-ylamino)phenethyl)piperazin-1-yl)methanone, 5-(4-methoxyphenyl)-N-(4-(2-(piperazin-1-yl)ethyl)phenyl)pyrimidin-2-amine, N-(3-(5-(4-methoxyphenyl)pyrimidin-2-ylamino)phenyl)-N,4-dimethylpiperazine-1-carboxamide, 1-(4-(5-(4-methoxyphenyl)pyrimidin-2-ylamino)phenethyl)piperidine-3-carboxamide, 1-(4-(5-(4-methoxyphenyl)pyrimidin-2-ylamino)phenethyl)piperidine-3-carboxylic acid, methyl 4-(4-(5-(4-methoxyphenyl)pyrimidin-2-ylamino)phenethyl)piperazine-1-carboxylate, 1-(4-(5-(4-methoxyphenyl)pyrimidin-2-ylamino)phenethyl)piperidine-3-carboxylic acid, 2-(1-(4-(5-(4-methoxyphenyl)pyrimidin-2-ylamino)phenethyl)piperidin-4-yl)acetic acid, methyl 2-(1-(4-(5-(4-methoxyphenyl)pyrimidin-2-ylamino)phenethyl)piperidin-4-yl)acetate, (3-(hydroxymethyl)piperidin-1-yl)(4-(5-(4-methoxyphenyl)pyrimidin-2-ylamino)phenyl)methanone, (3-hydroxypyrrolidin-1-yl)(4-(5-(4-methoxyphenyl)pyrimidin-2-ylamino)phenyl)methanone, 1-(4-(5-(4-methoxyphenyl)pyrimidin-2-ylamino)benzoyl)piperidine-4-carboxamide, 3-(4-(4-(5-(4-methoxyphenyl)pyrimidin-2-ylamino)phenethyl)piperazin-1-yl)propanoic acid, (S)-1-(4-(5-(4-methoxyphenyl)pyrimidin-2-ylamino)phenethyl)pyrrolidine-2-carboxylic acid, 4-(4-(5-(4-methoxyphenyl)pyrimidin-2-ylamino)phenethylamino)cyclohexanecarboxylic acid, 4-(5-(4-methoxyphenyl)pyrimidin-2-ylamino)-N-(3-(2-oxopyrrolidin-1-yl)propyl)benzamide, 1-(4-(5-(4-methoxyphenyl)pyrimidin-2-ylamino)benzoyl)piperidine-3-carboxamide, N-(3-carbamoylphenyl)-4-(5-(4-methoxyphenyl)pyrimidin-2-ylamino)benzamide, 1,4'-bipiperidin-1'-yl(4-(5-(4-methoxyphenyl)pyrimidin-2-ylamino)phenyl)methanone, (4-(5-(4-methoxyphenyl)pyrimidin-2-ylamino)phenyl)(4-(pyrrolidin-1-yl)piperidin-1-yl)methanone, 4-(5-(4-methoxyphenyl)pyrimidin-2-ylamino)-N-(2-(pyridin-2-yl)ethyl)benzamide, 4-(5-(4-methoxyphenyl)pyrimidin-2-ylamino)-N-(1,3,5-trimethyl-1H-pyrazol-4-yl)benzamide, (4-(furan-2-carbonyl)piperazin-1-yl)(3-(5-(4-methoxyphenyl)pyrimidin-2-ylamino)phenyl)methanone, 3-(5-(4-methoxyphenyl)pyrimidin-2-ylamino)-N-(1,3,5-trimethyl-1H-pyrazol-4-yl)benzamide, (3-(5-(4-methoxyphenyl)pyrimidin-2-ylamino)phenyl)(4-(1-methylpiperidin-4-yl)piperazin-1-yl)methanone, 1-(4-(3-(5-(4-methoxyphenyl)pyrimidin-2-ylamino)benzoyl)piperazin-1-yl)ethanone, (3-(5-(4-methoxyphenyl)pyrimidin-2-ylamino)phenyl)(4-(pyrrolidin-1-yl)piperidin-1-yl)methanone, 1,4'-bipiperidin-1'-yl(3-(5-(4-methoxyphenyl)pyrimidin-2-ylamino)phenyl)methanone, 1-(3-(5-(4-methoxyphenyl)pyrimidin-2-ylamino)benzoyl)piperidine-3-carboxamide, N-(3-(5-(4-methoxyphenyl)pyrimidin-2-ylamino)phenyl)-4-(1-methylpiperidin-4-yl)piperazine-1-carboxamide, methyl 4-(3-(5-(4-methoxyphenyl)pyrimidin-2-ylamino)phenylcarbamoyl)piperazine-1-carboxylate, (R)-1-(4-(5-(4-methoxyphenyl)pyrimidin-2-ylamino)phenethyl)piperidine-3-carboxylic acid, (4-(5-(4-methoxyphenyl)pyrimidin-2-ylamino)phenyl)(piperazin-1-yl)methanone, 4-acetyl-N-(3-(5-(4-methoxyphenyl)pyrimidin-2-ylamino)phenyl)piperazine-1-carboxamide, and (3-(5-(4-methoxyphenyl)pyrimidin-2-ylamino)phenyl)(piperazin-1-yl)methanone.

In further or alternative embodiments, Q of the compound having the structure of Formula (1) is selected from the group consisting of

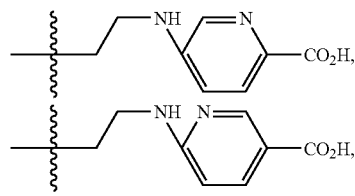

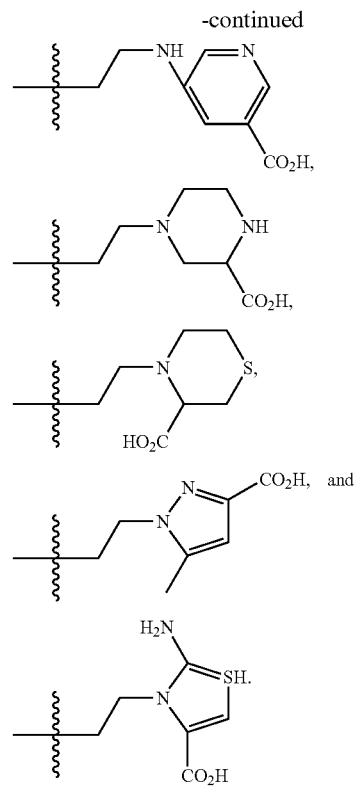

In further or alternative embodiments, Q of the compound having the structure of Formula (1) is selected from the group consisting of

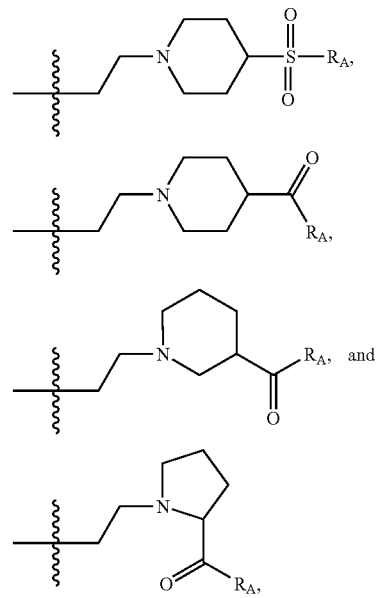

wherein $R_A$ is selected from —$NH_2$, —$NEt_2$, and —NH($CH_2$)$_n$OH; and n is 1 to 6.

In further or alternative embodiments, Q of the compound having the structure of Formula (1) is

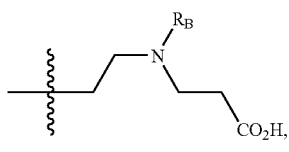

wherein $R_B$ is selected from the group consisting of

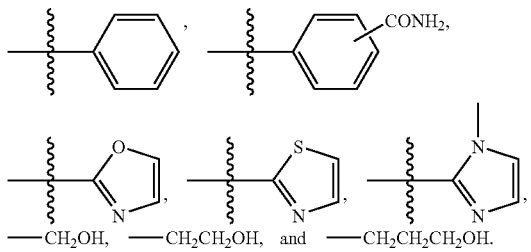
—CH$_2$OH, —CH$_2$CH$_2$OH, and —CH$_2$CH$_2$CH$_2$OH.

In further or alternative embodiments, Q of the compound having the structure of Formula (1) is

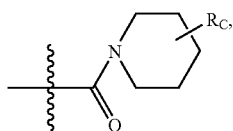

wherein $R_C$ is at 2, 3, or 4 position of the piperidine ring; and $R_C$ is selected from the group consisting of —C(O)NHEt, —C(O)NEt$_2$, c-butyl, c-pentyl, —C(O)NH-thiazole, oxazole, thiazole, —S(O)$_2$NH$_2$, —S(O)$_2$NHEt, and —S(O)$_2$NEt$_2$.

In further or alternative embodiments, Q of the compound having the structure of Formula (1) is selected from the group consisting of

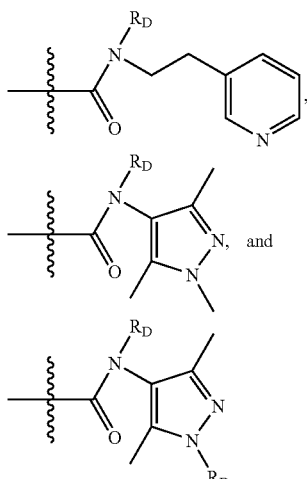

wherein each $R_D$ is independently selected from —(CH$_2$)$_k$OH or —(CH$_2$)$_k$CO$_2$H; and k is 1 to 6.

In further or alternative embodiments, Q of the compound having the structure of Formula (1) is

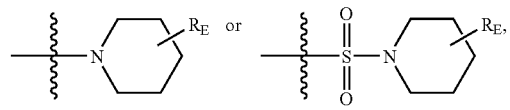

wherein $R_E$ is at 2, 3, or 4 position of the piperidine ring; and $R_B$ is selected from the group consisting of —C(O)NH$_2$, —C(O)NHEt, and —C(O)NEt$_2$.

In further or alternative embodiments, Q of the compound having the structure of Formula (1) is selected from the group consisting of

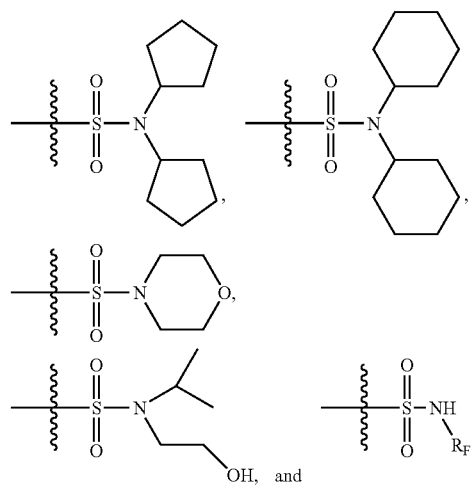

wherein $R_F$ is thiazole, pyrazole, or isoxazole.

In further or alternative embodiments, Q of the compound having the structure of Formula (46) is selected from the group consisting of

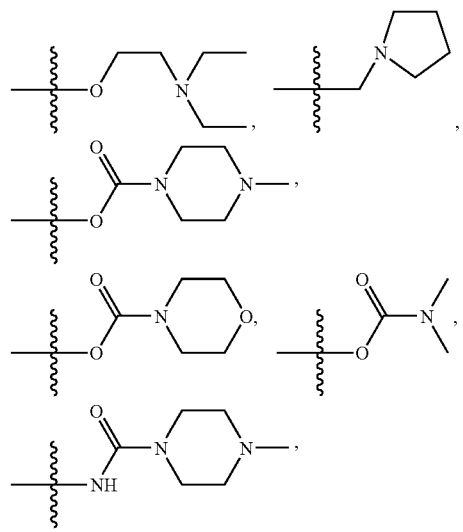

-continued
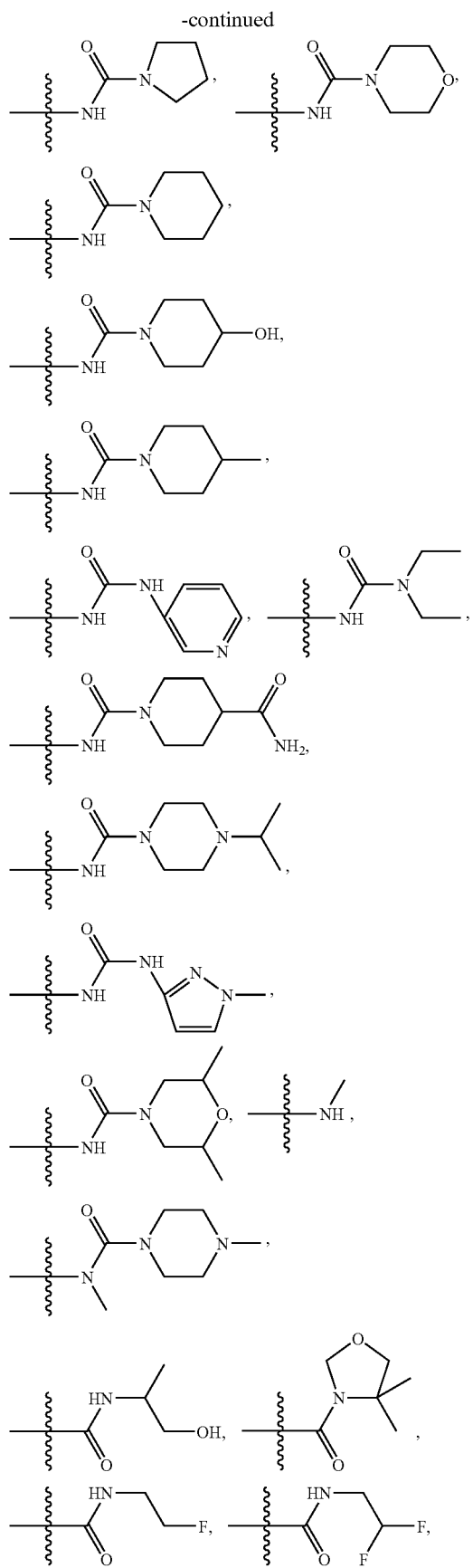
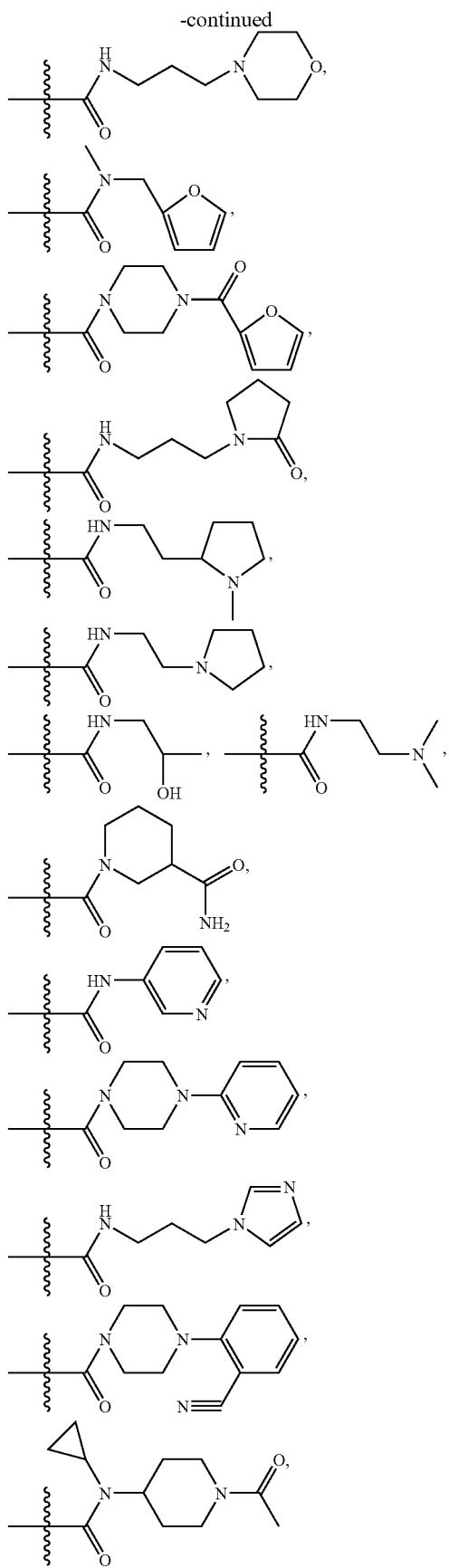

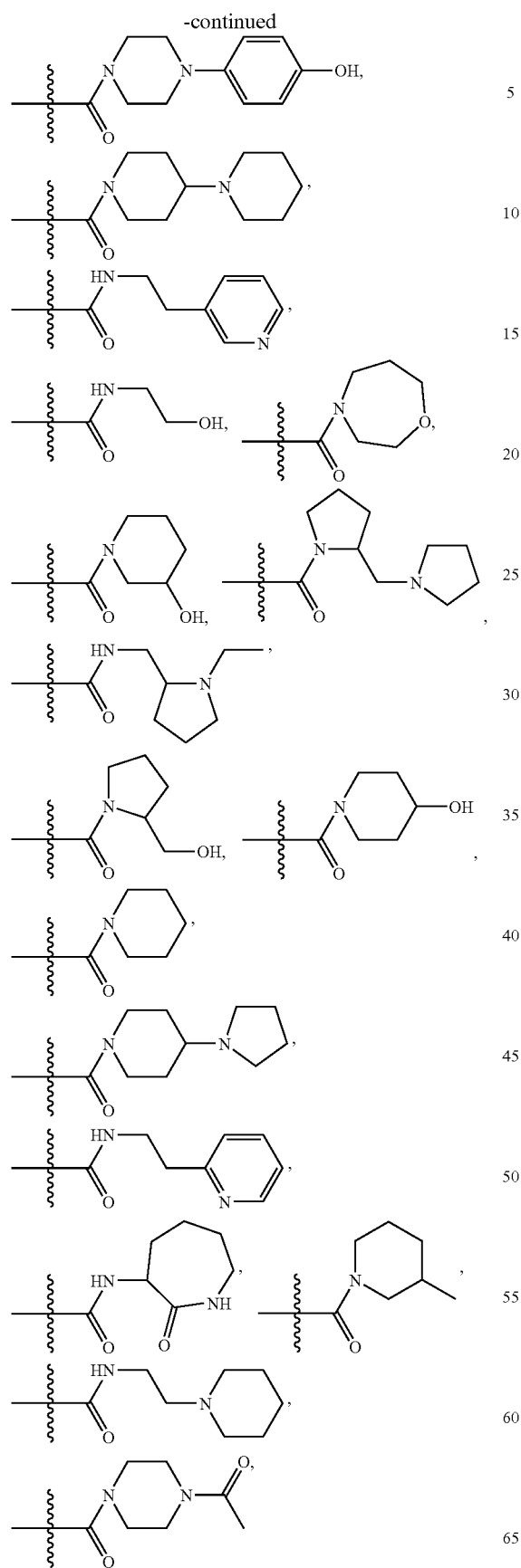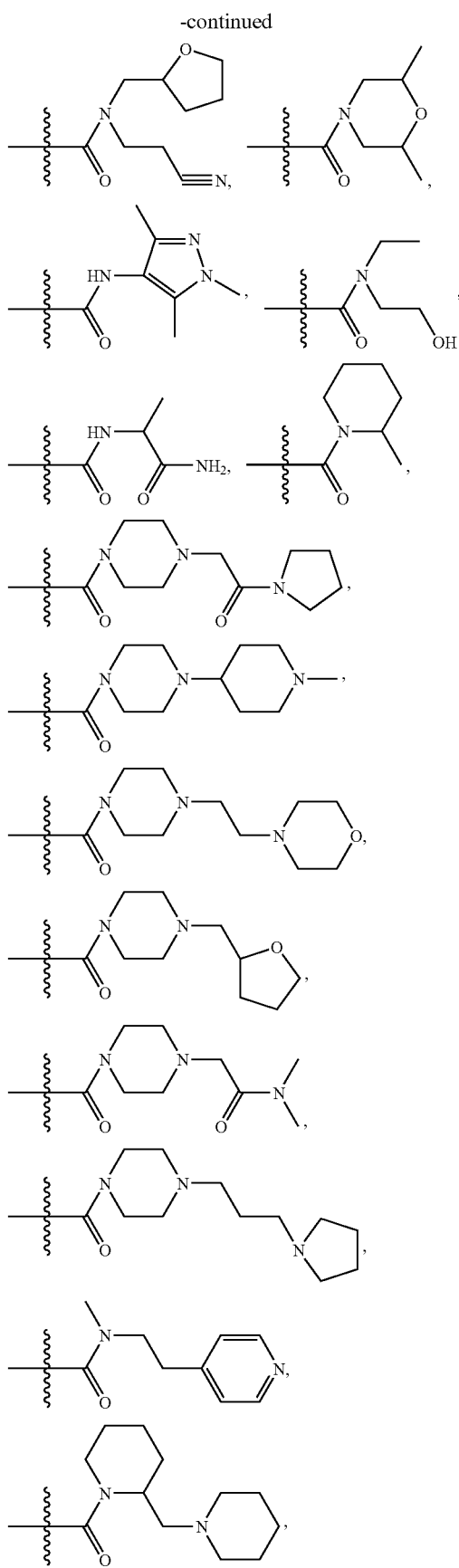

-continued

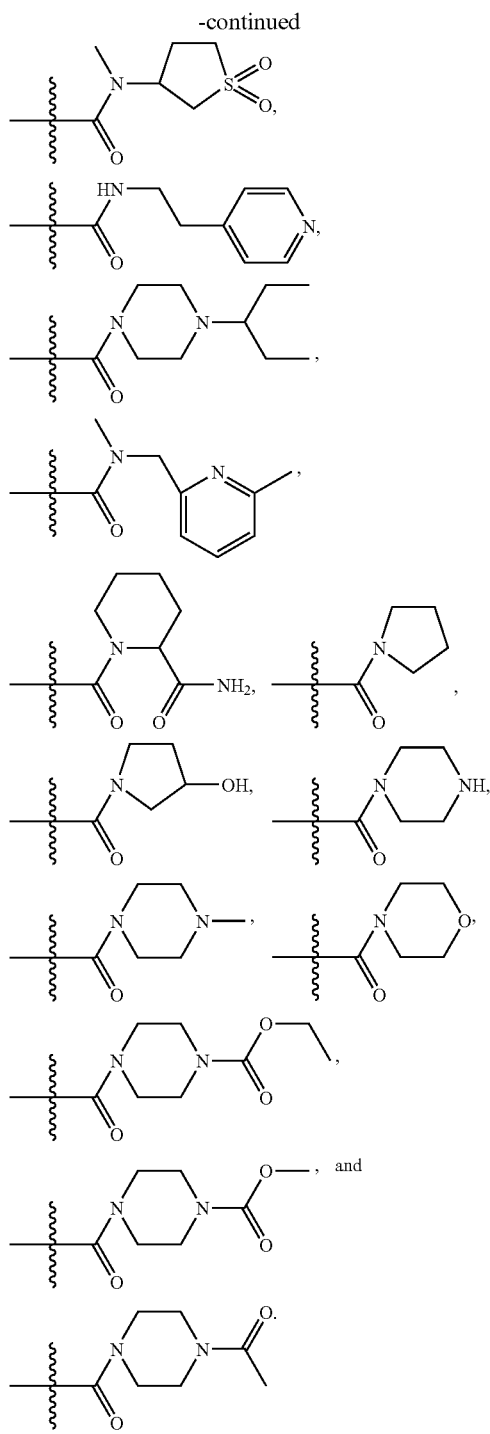

In further or alternative embodiments, Q of the compound having the structure of Formula (46) is selected from the group consisting of

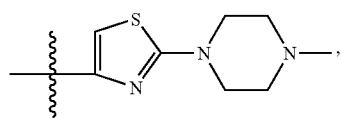

-continued

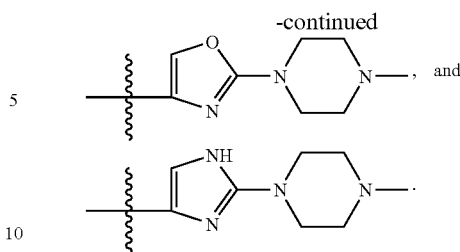

In another aspect is pharmaceutical compositions comprising at least one compound having the structure of Formula (1) or Formula (46):

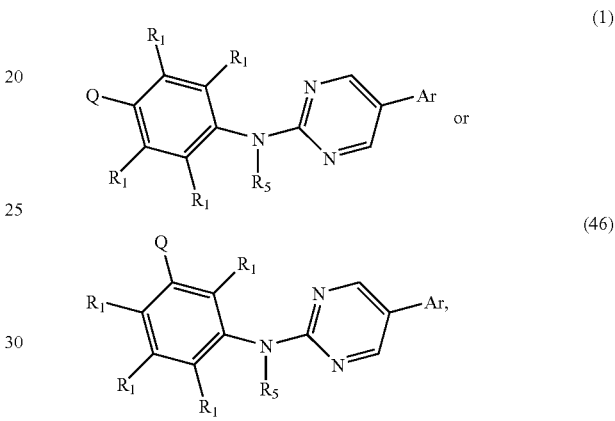

wherein:
Ar is a group comprising a moiety selected from an optionally substituted five-membered aromatic heterocycle, an optionally substituted five-membered aromatic carbocycle, an optionally substituted six-membered aromatic heterocycle, and a substituted, optionally further substituted six-membered aromatic carbocycle;

Q is a group comprising a non-aromatic tertiary amine or a non-aromatic secondary amine, with the proviso that Q is not —$NR_aR_b$ or —$SO_2NR_aR_b$; wherein each of $R_a$ and $R_b$ is independently H or $C_{1-6}$alkyl optionally substituted by mono- or di-alkyl ($C_{1-6}$) amino;

each $R_1$ is independently selected from the group consisting of H, halogen, and an optionally substituted moiety selected from -$L_1$-alkyl, -$L_1$-cycloalkyl, -$L_1$-heteroalkyl, -$L_1$-haloalkyl, -$L_1$-aryl, -$L_3$-heterocycloalkyl, and -$L_1$-heteroaryl; wherein $L_1$ is selected from a bond, —O—, —NH—, —S—, —C(O)—, —C(S)—, —C(O)O—, —C(O)NH—, —S(O)—, —$S(O)_2$—, —C(O)NH($CR''_2$)$_{1-6}$C(O)O—, —C(O)NR"NR"C(O)O—, and —S(O)NH—;

each R" is independently H, OH, halogen, $C_{1-6}$alkyl, substituted $C_{1-6}$alkyl, $C_{1-6}$alkoxy, halo-$C_{1-6}$alkyl, halo-$C_{1-6}$alkoxy, aryl, haloaryl, or heteroaryl;

or any two adjacent $R_1$ groups together may form an optionally substituted 5 to 8-membered heterocyclic, cycloalkyl, or aryl ring;

$R_5$ is selected from the group consisting of H, and an optionally substituted moiety selected from -$L_5$-H, -$L_5$-alkyl, -$L_5$-cycloalkyl, -$L_5$-heteroalkyl, -$L_5$-haloalkyl, -$L_5$-aryl, -$L_5$-heterocycloalkyl, and -$L_5$-heteroaryl; wherein $L_5$ is selected from a bond, —R'O—, —R'N(H)—, —R'S—, —R'C(O)—, —R'C(S)—, —R'C(O)O—, and —R'C(O)NH—;

- each R' is independently selected from the group consisting of a bond, alkylene, substituted alkylene, heteroalkylene, substituted heteroalkylene, alkenylene, substituted alkenylene, cycloalkylene, substituted cycloalkylene, heteroalkylene, substituted heteroalkylene, heterocycloalkylene, substituted heterocycloalkylene, arylene, substituted arylene, heteroarylene, substituted heteroarylene, alkarylene, substituted alkarylene, aralkylene, and substituted aralkylene; and
- any $R_1$ and $R_5$ taken together may form an optionally substituted 5 to 8-membered heterocyclic, cycloalkyl, or aryl ring;
- or a pharmaceutically acceptable salt, pharmaceutically acceptable N-oxide, pharmaceutically active metabolite, pharmaceutically acceptable prodrug, or pharmaceutically acceptable solvate thereof, in admixture with one or more suitable excipients.

In further or alternative embodiments, the one or more excipients are suitable for parenteral administration. In further or alternative embodiments, the one or more excipients are suitable for oral administration.

In further or alternative embodiments, the Ar is a group comprising a substituted, optionally further substituted six-membered aromatic heterocycle. In further or alternative embodiments, said optional substituents are selected from halogen, OH, halogen, $C_{1-6}$alkyl, $C_{1-6}$alkoxy, halo-$C_{1-6}$alkyl, halo-$C_{1-6}$alkoxy, aryl, haloaryl, or heteroaryl. In further or alternative embodiments, the compound is the compound of any of Formula (1) to Formula (54) in various embodiments described above.

In further or alternative embodiments, Ar is selected from the group consisting of

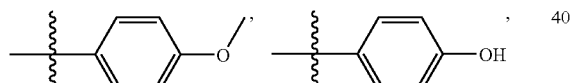

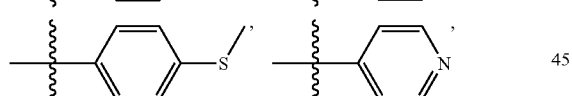

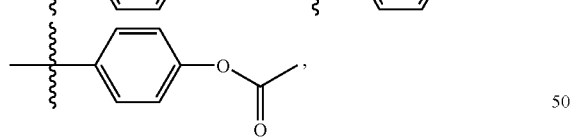

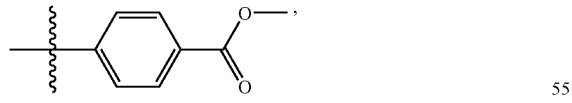

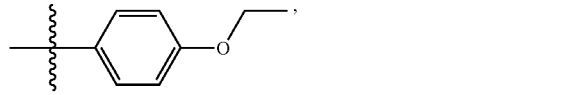

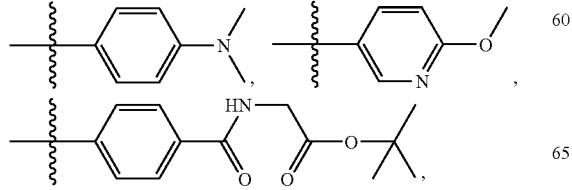

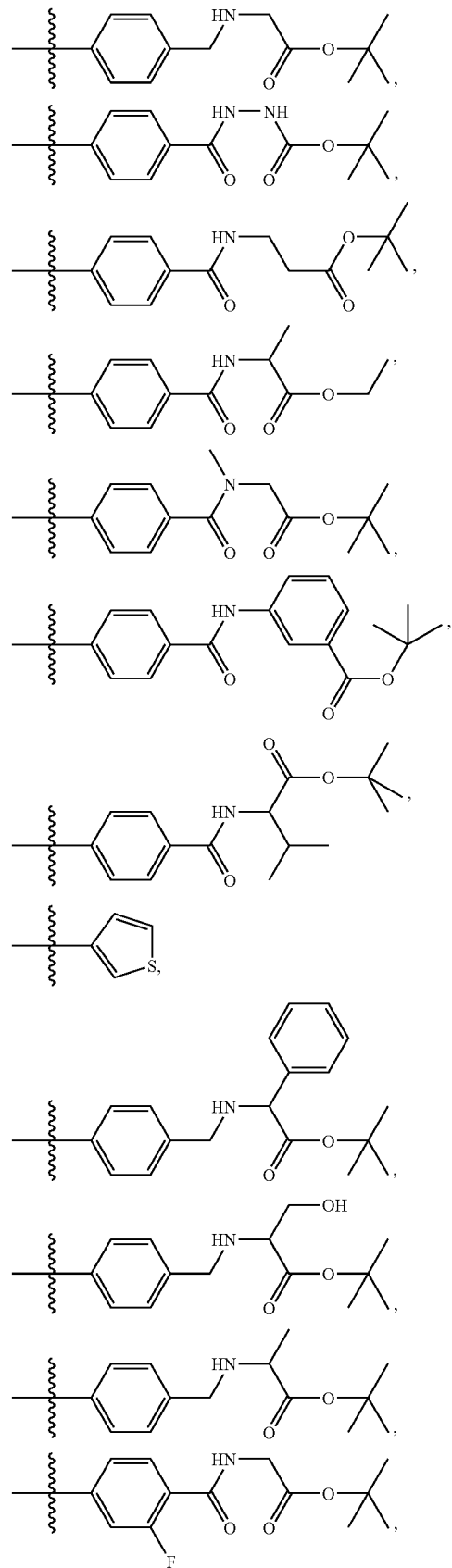

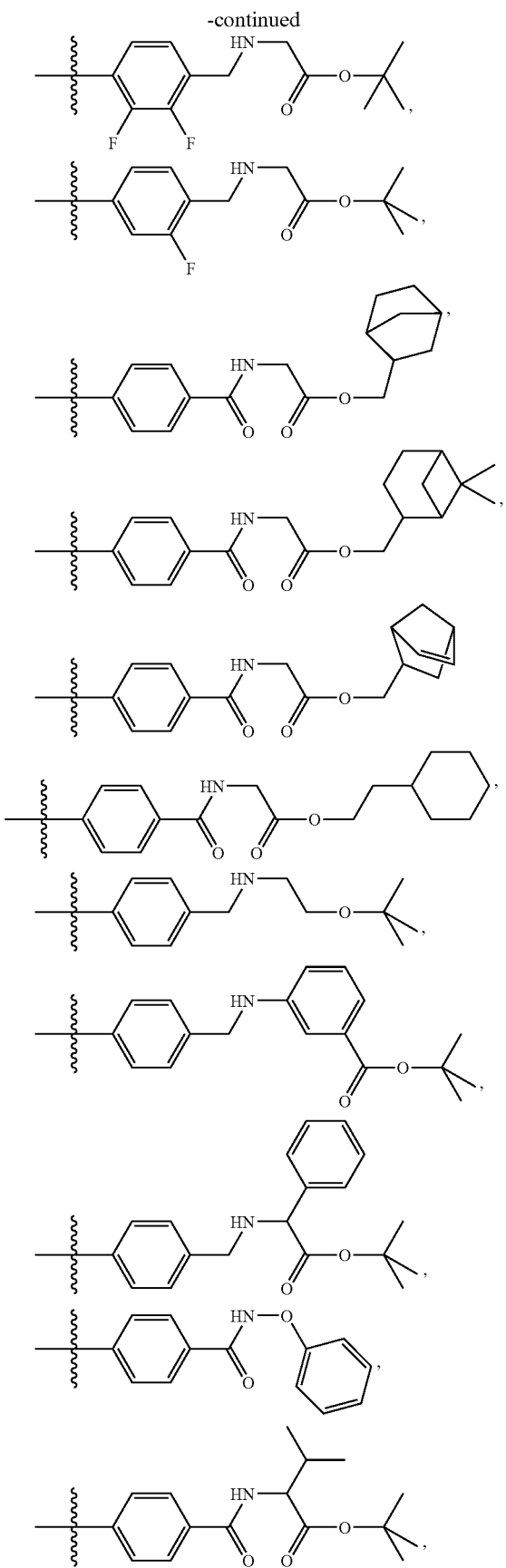
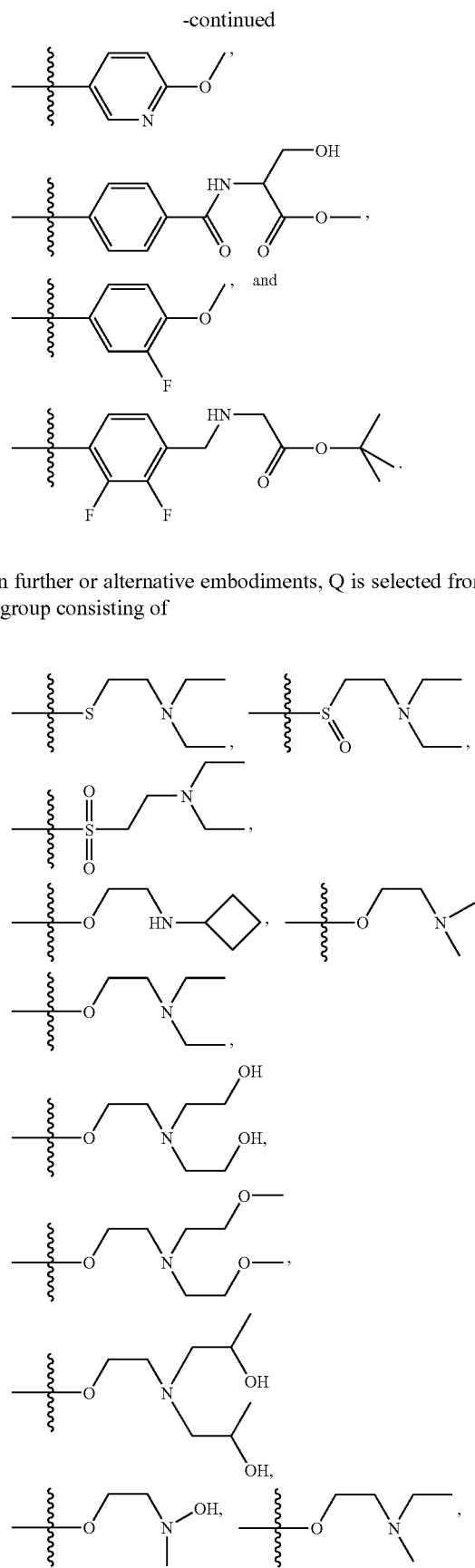
In further or alternative embodiments, Q is selected from the group consisting of -continued
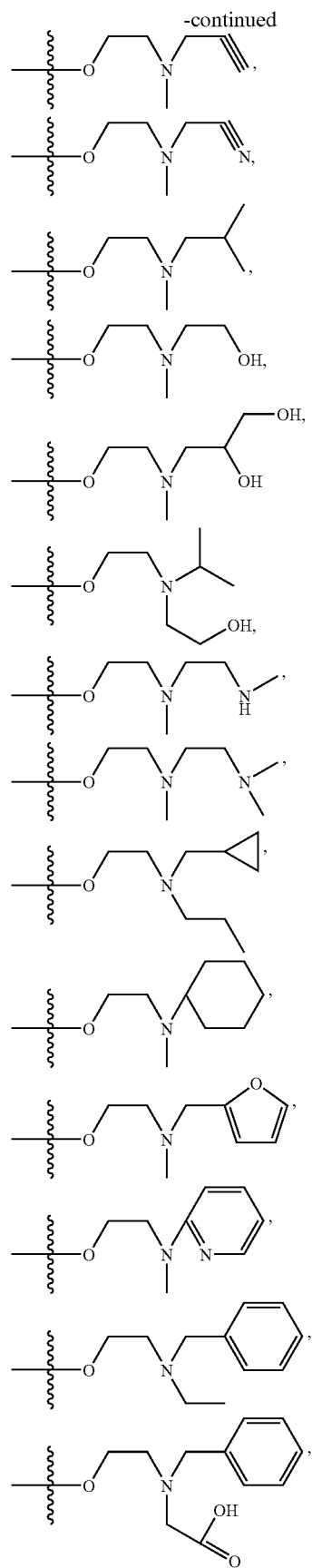
-continued
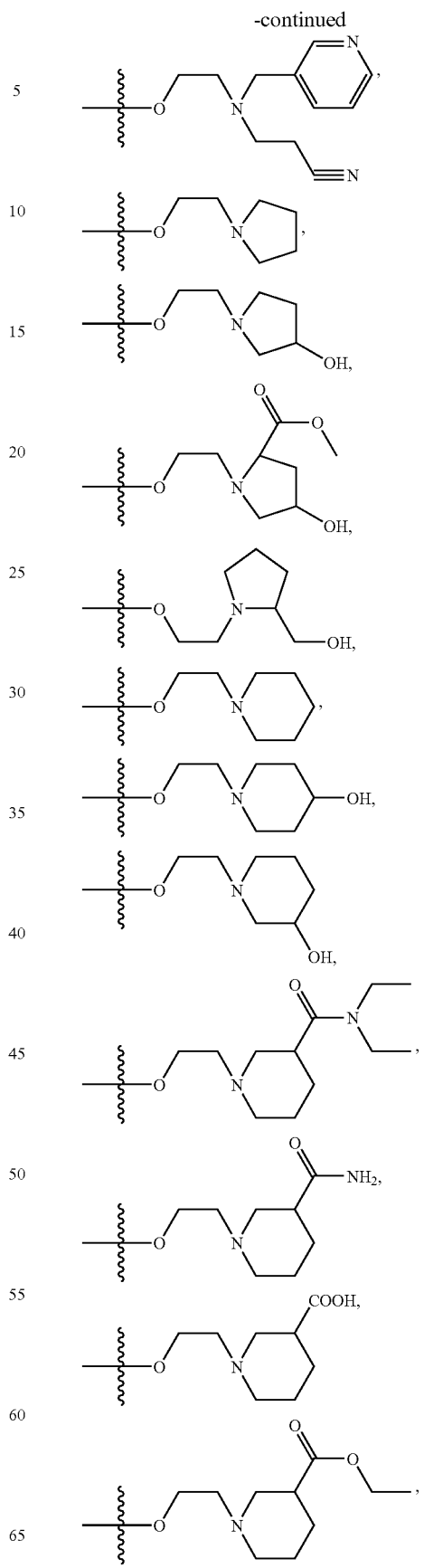

137
-continued
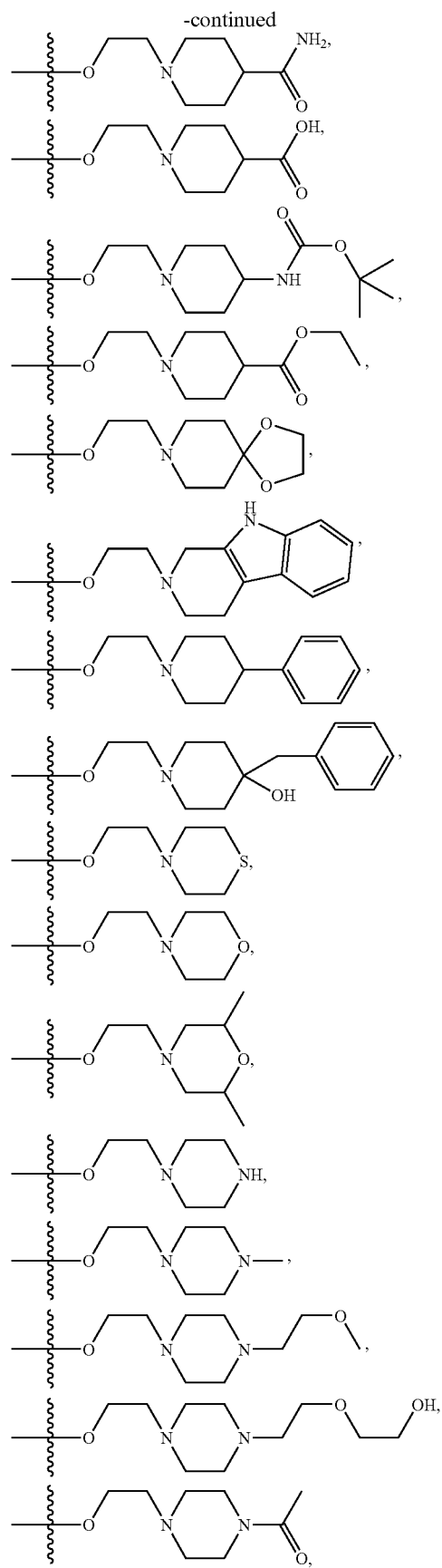
138
-continued
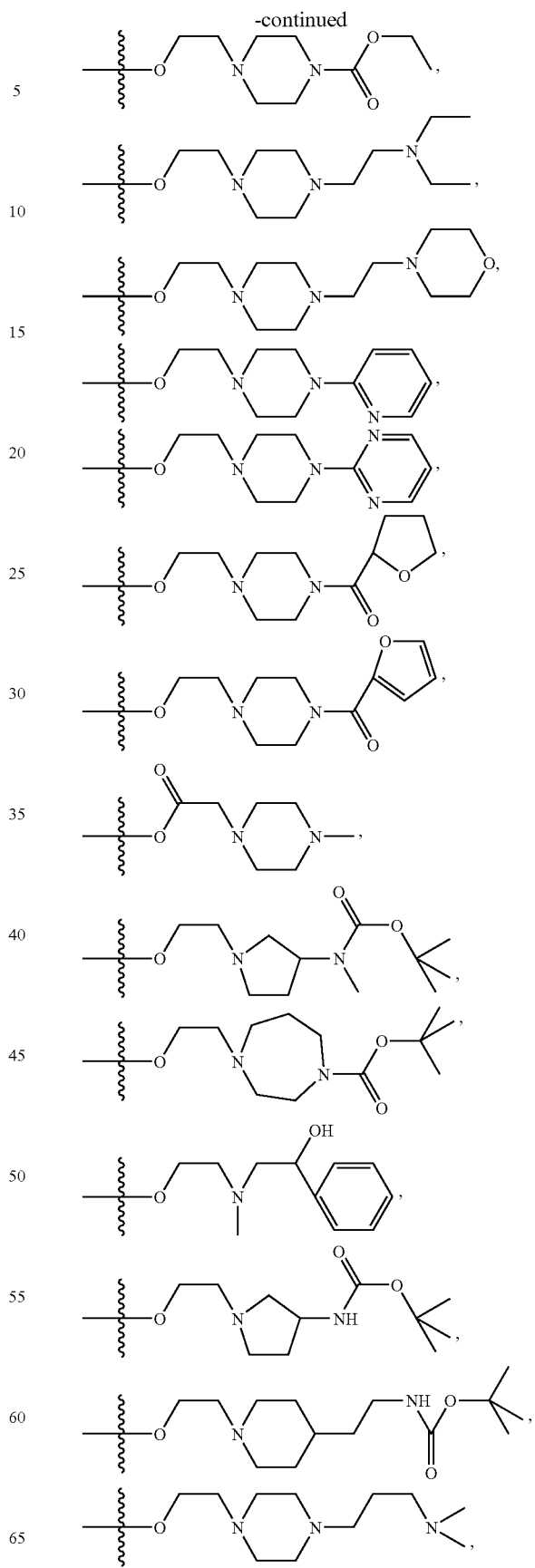

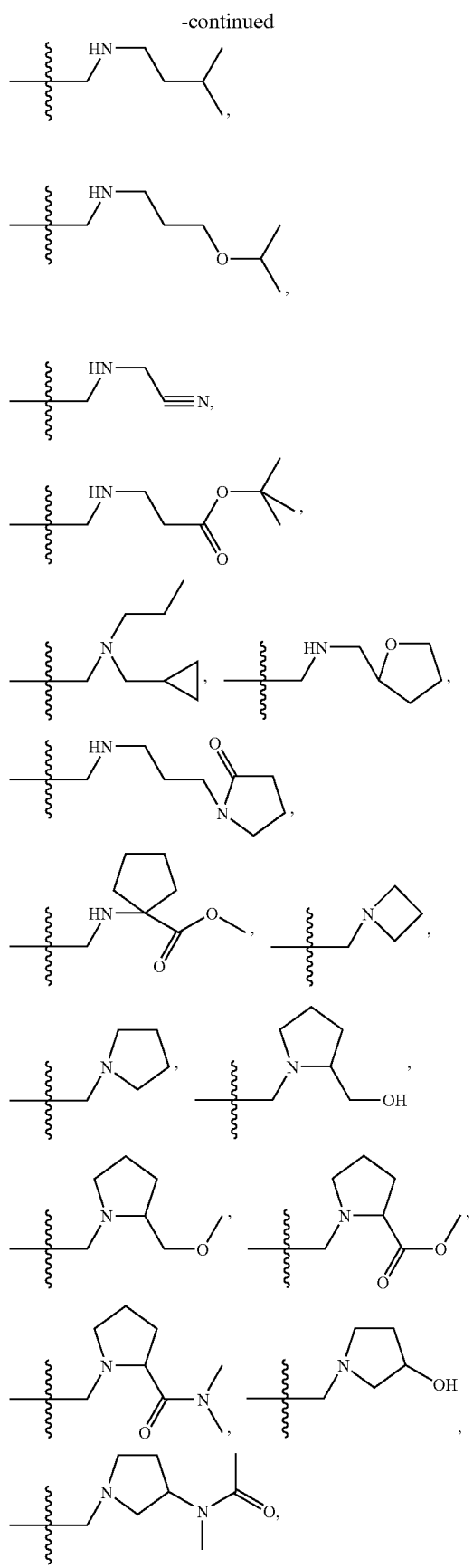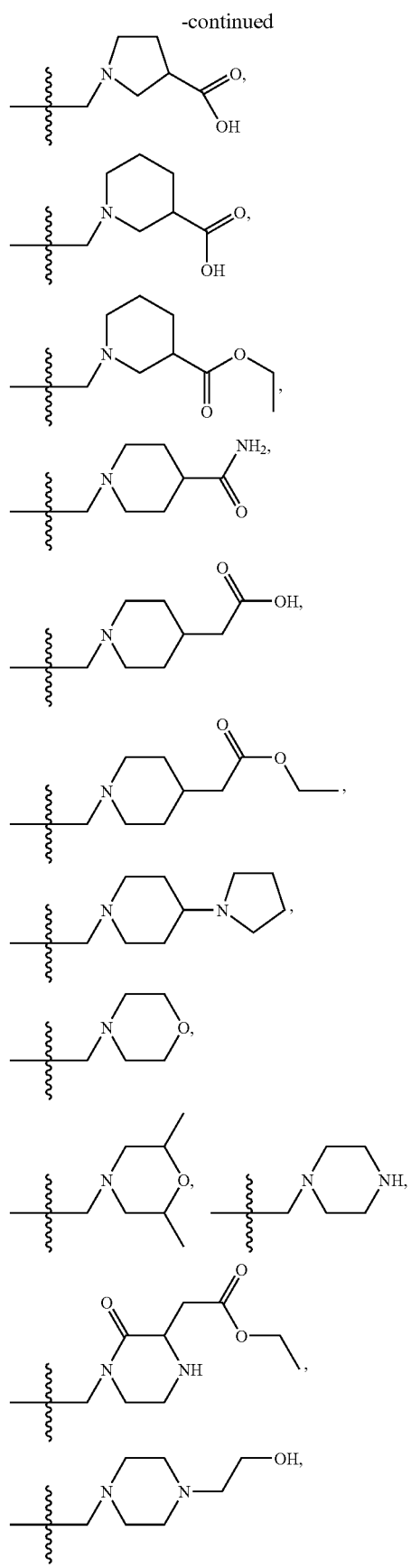

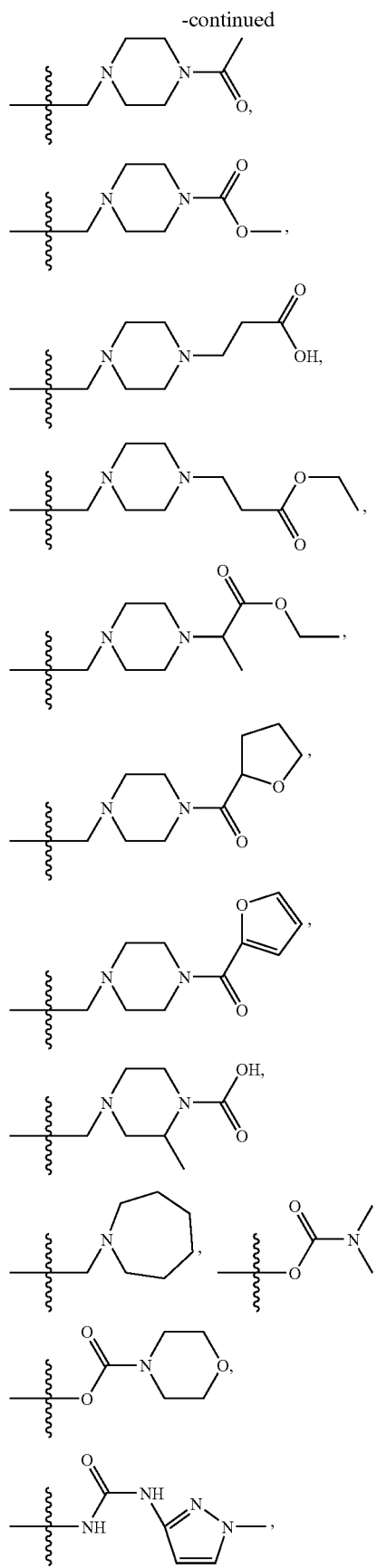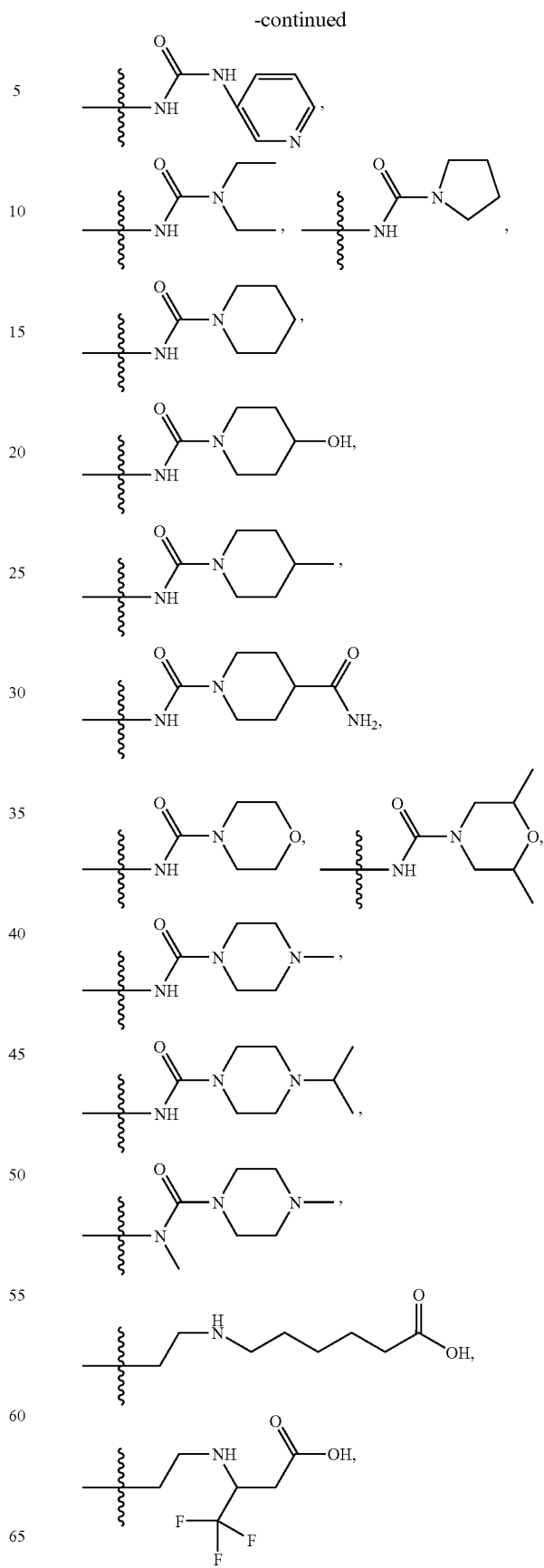

-continued
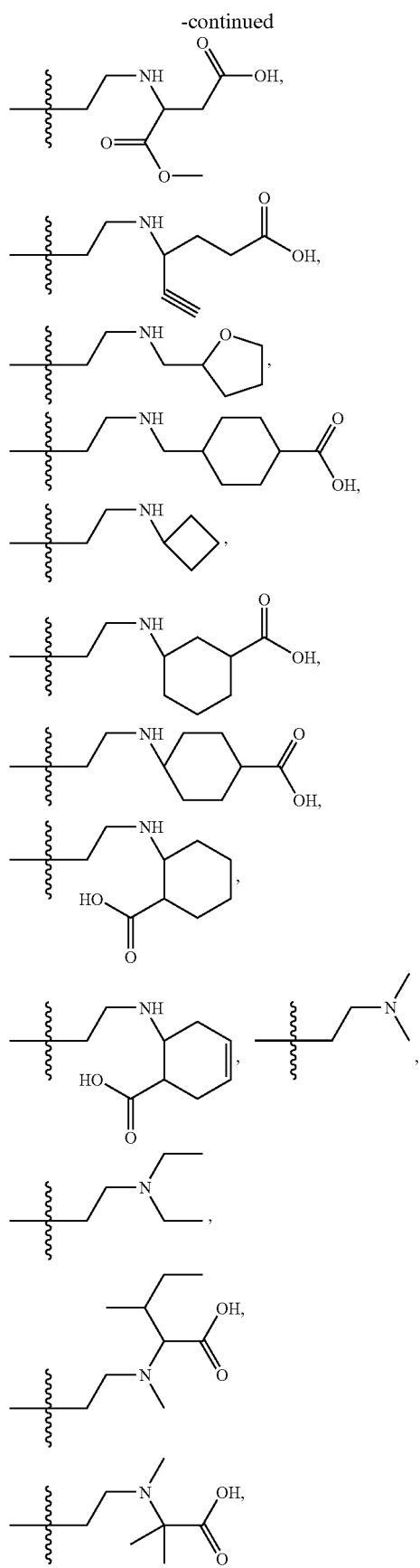
-continued
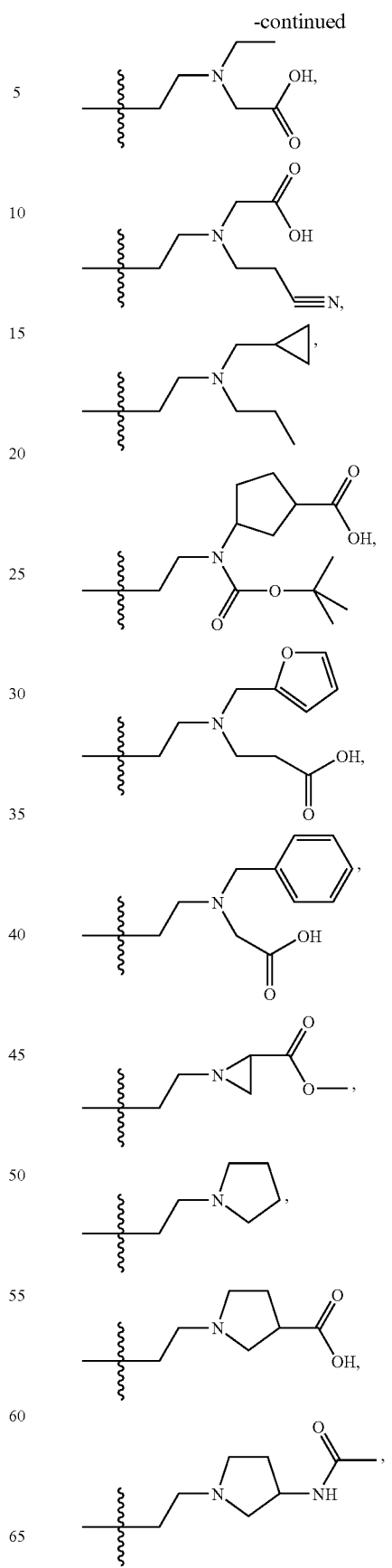

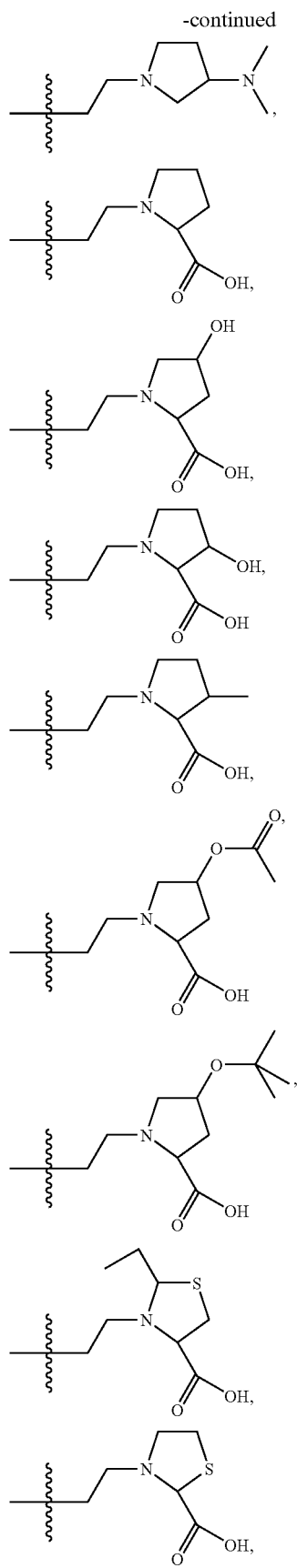
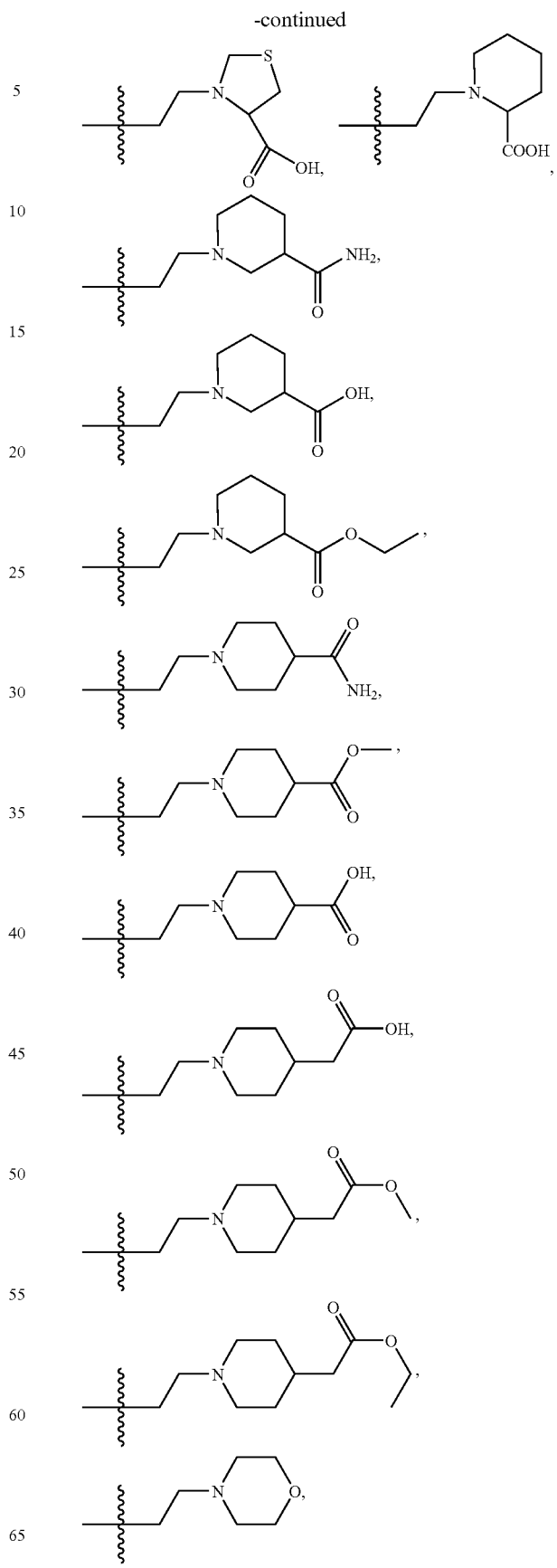

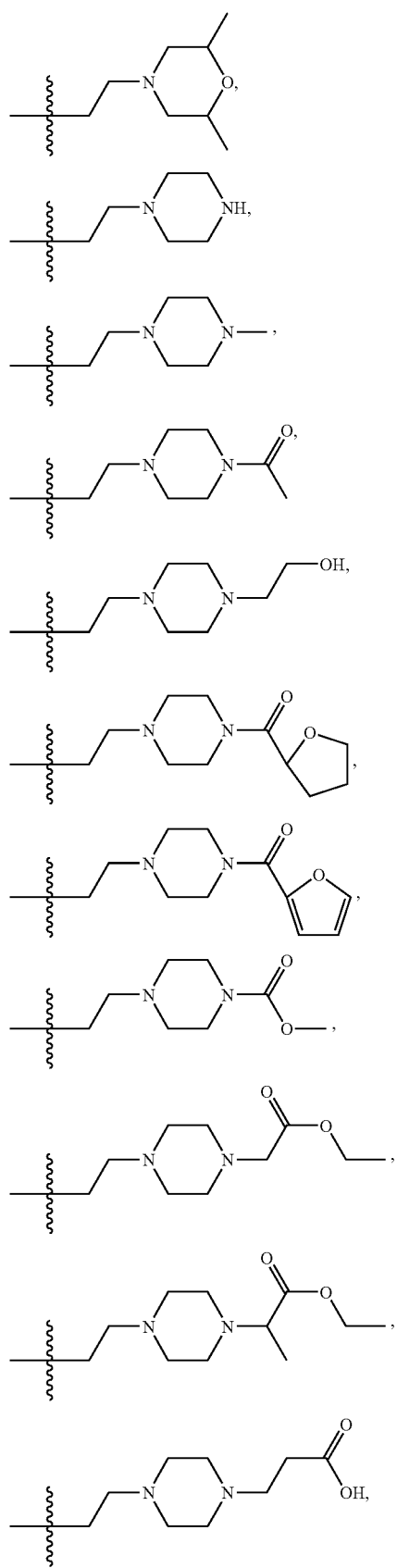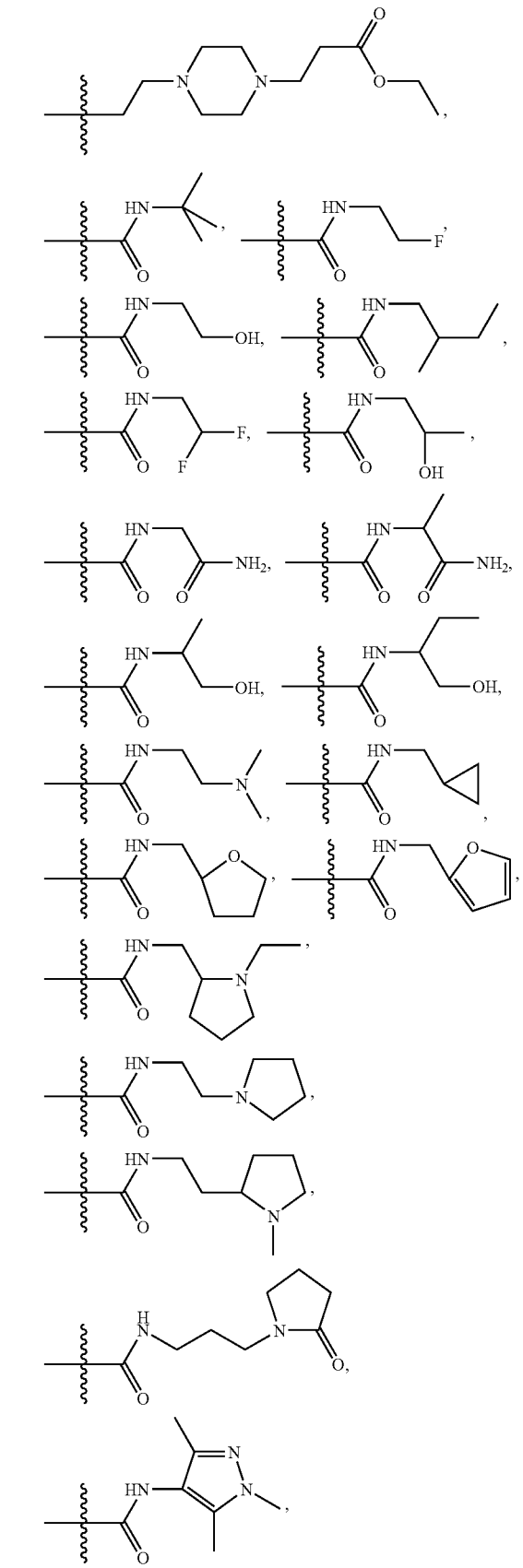

-continued
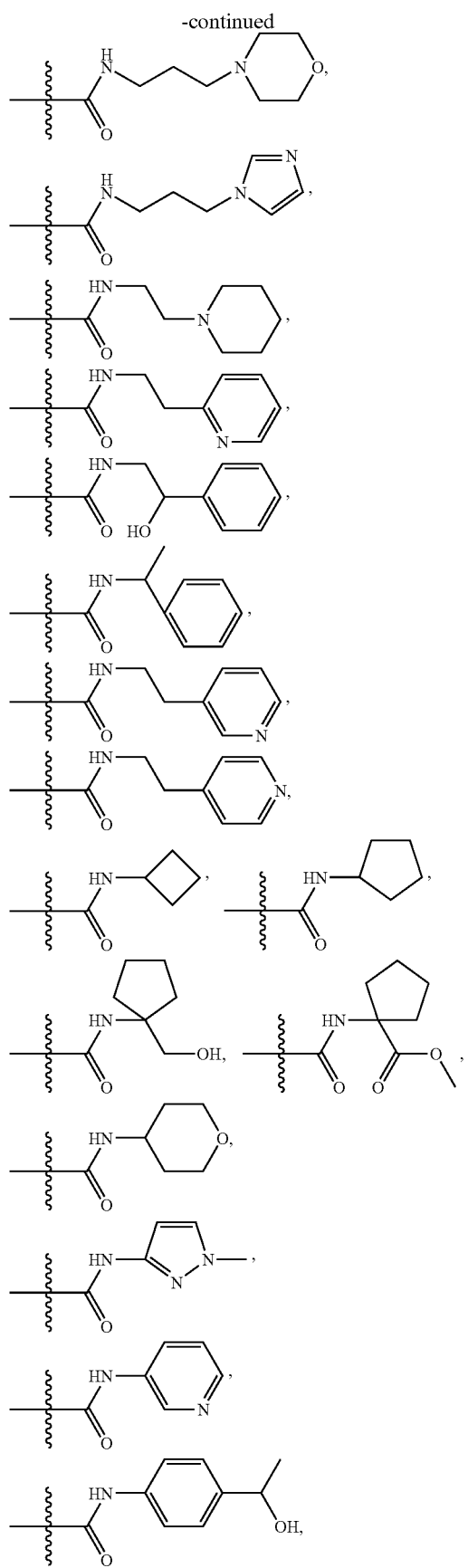
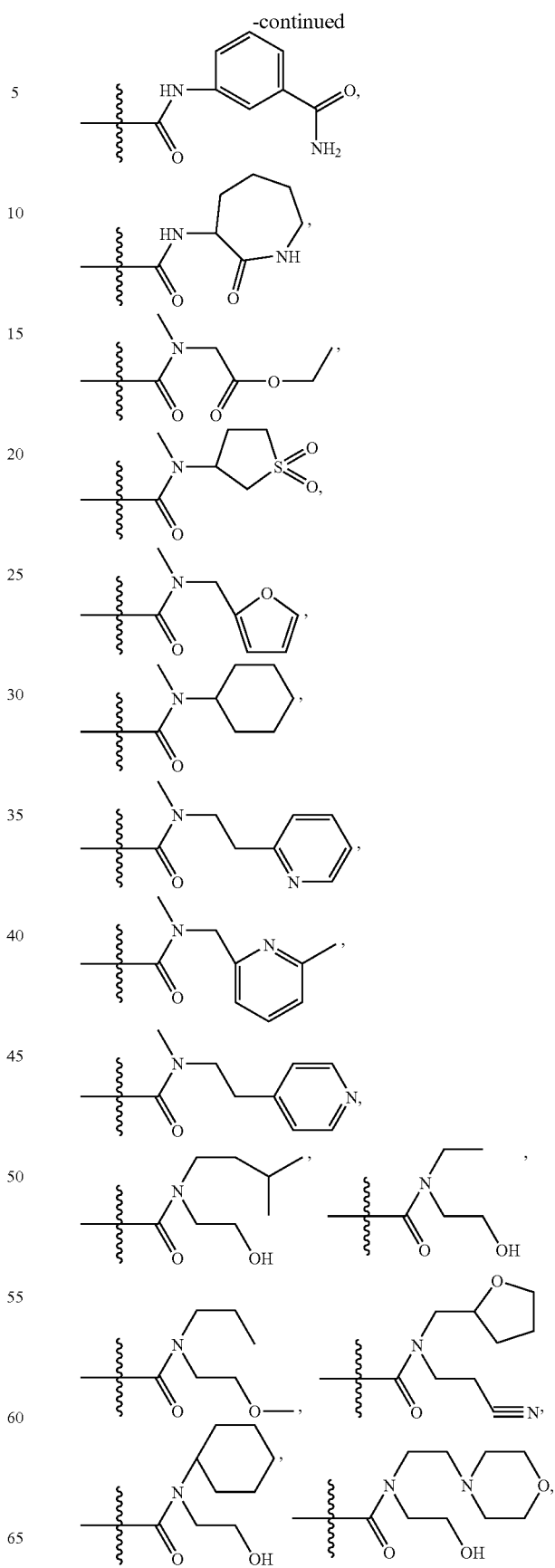

-continued
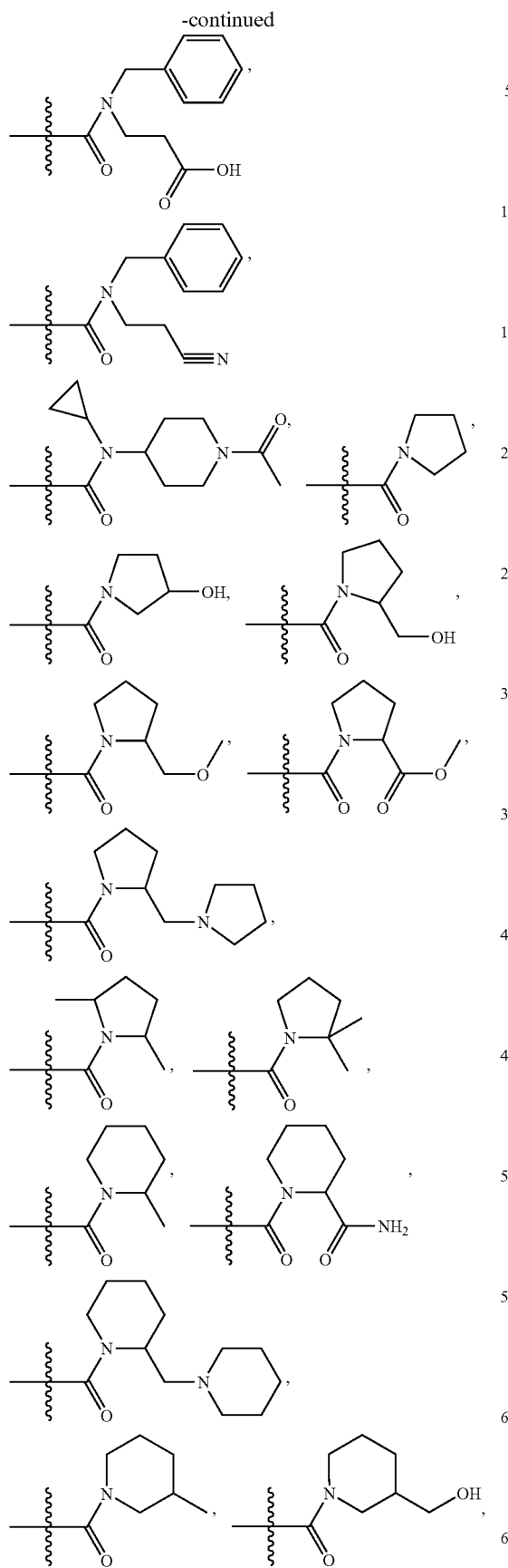
-continued
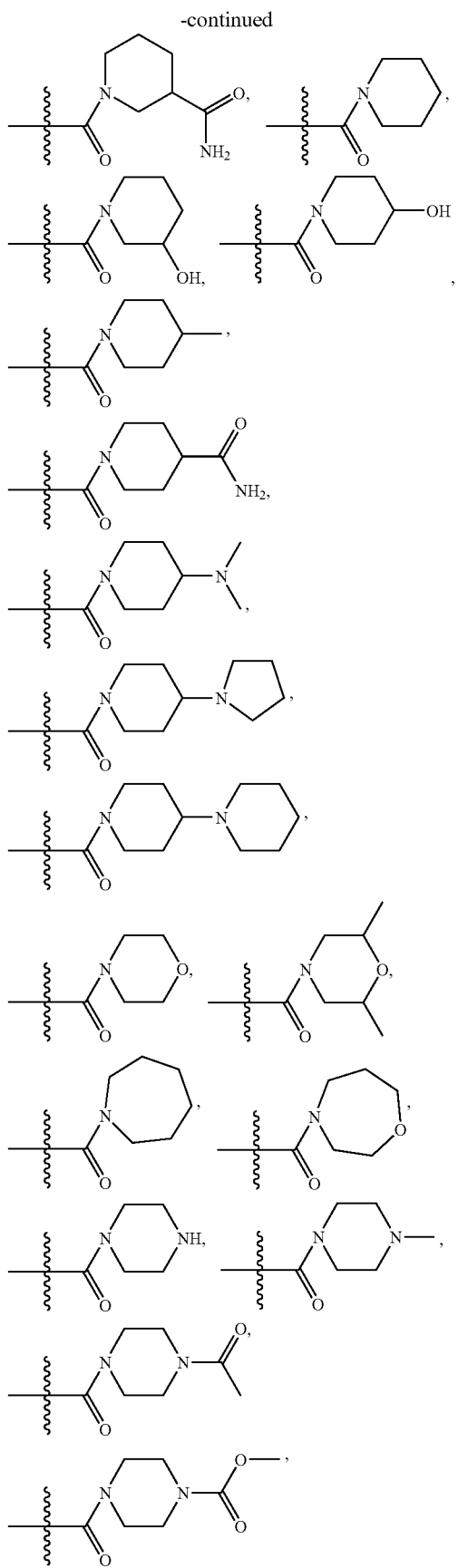

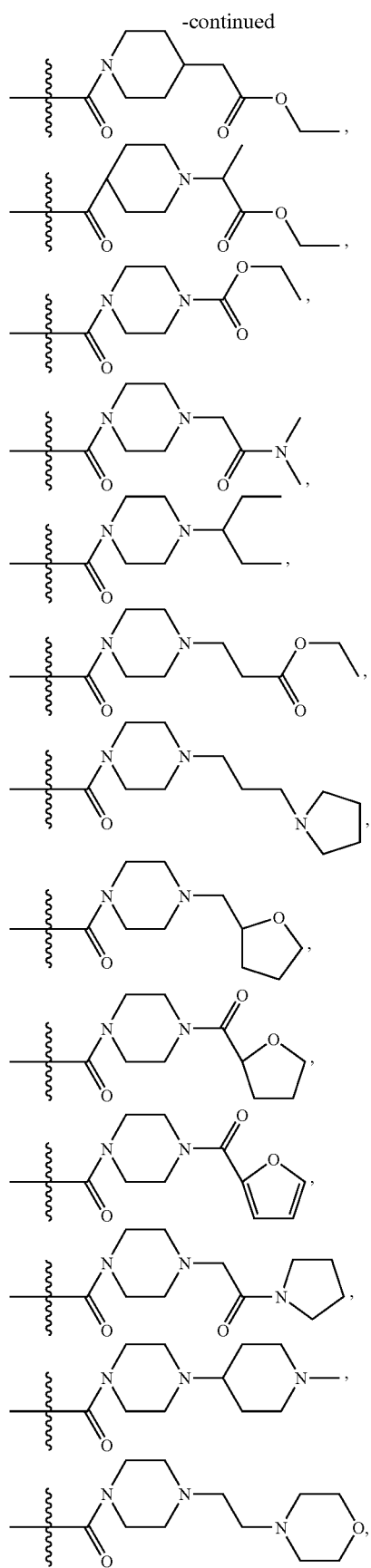
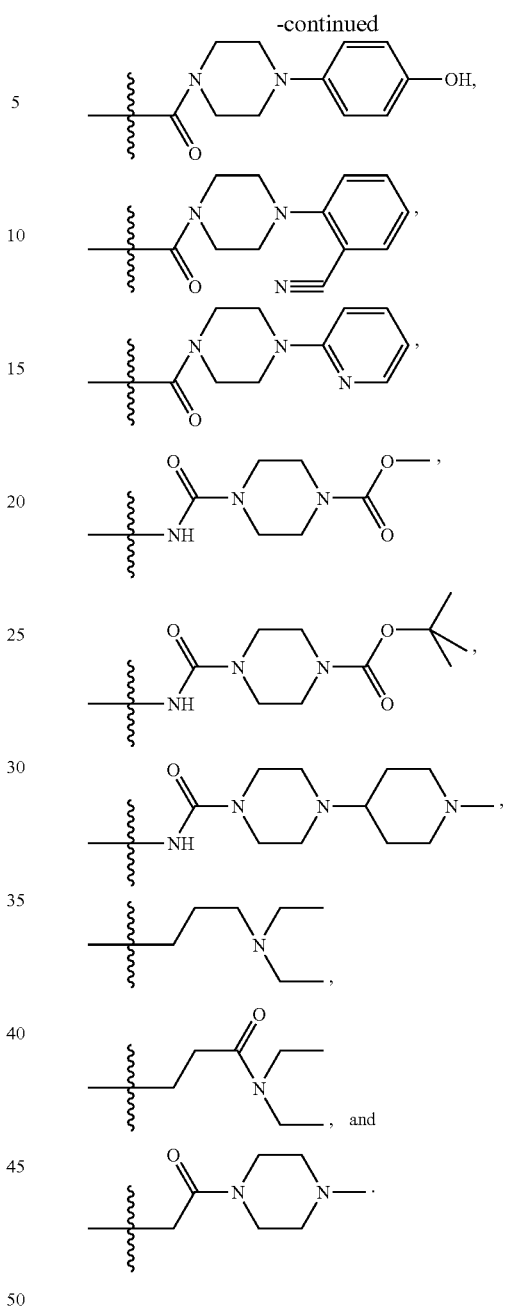
In further or alternative embodiments, Q is selected from the group consisting of
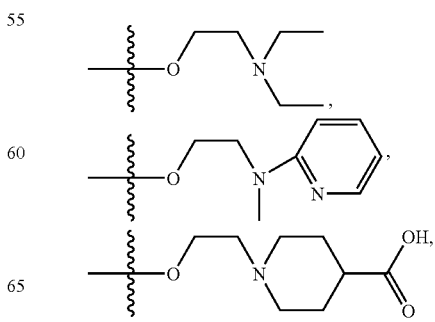

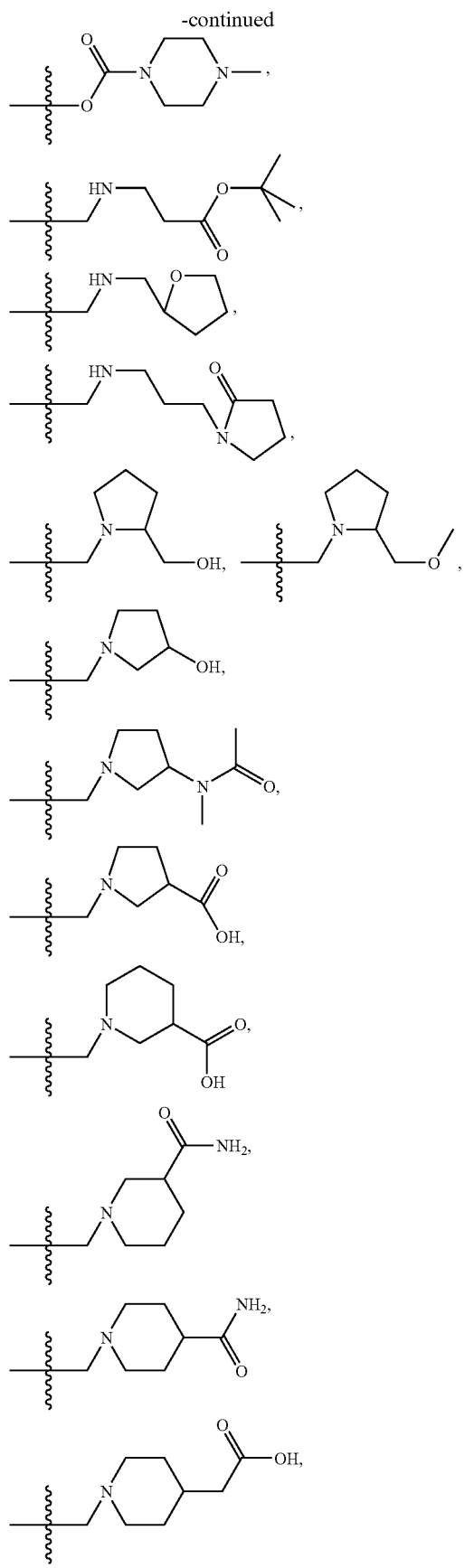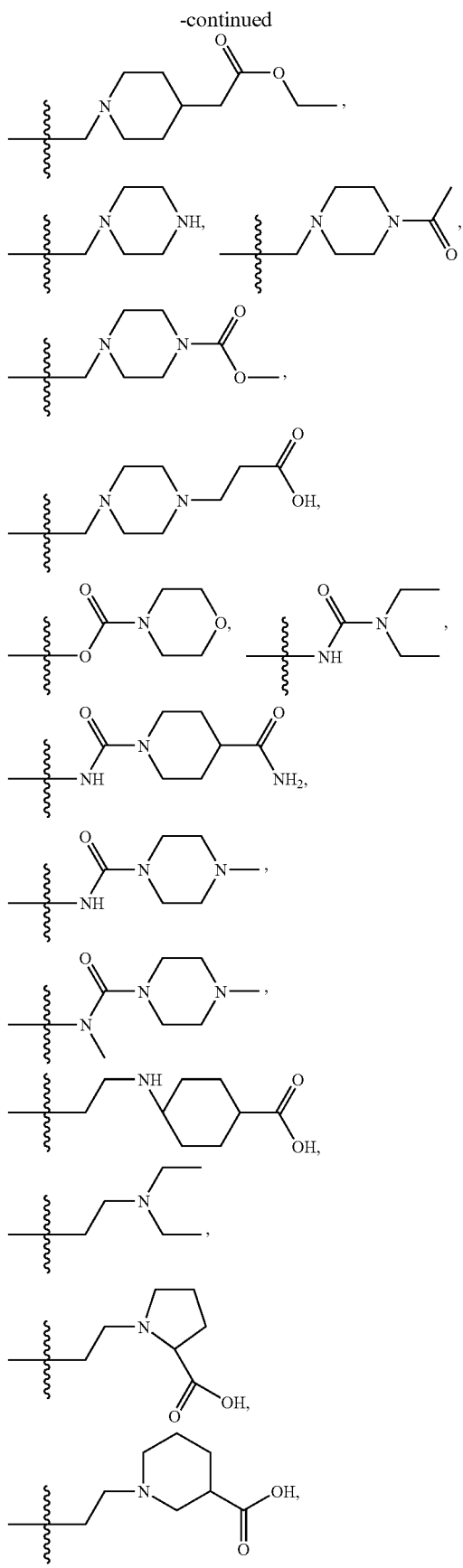

-continued
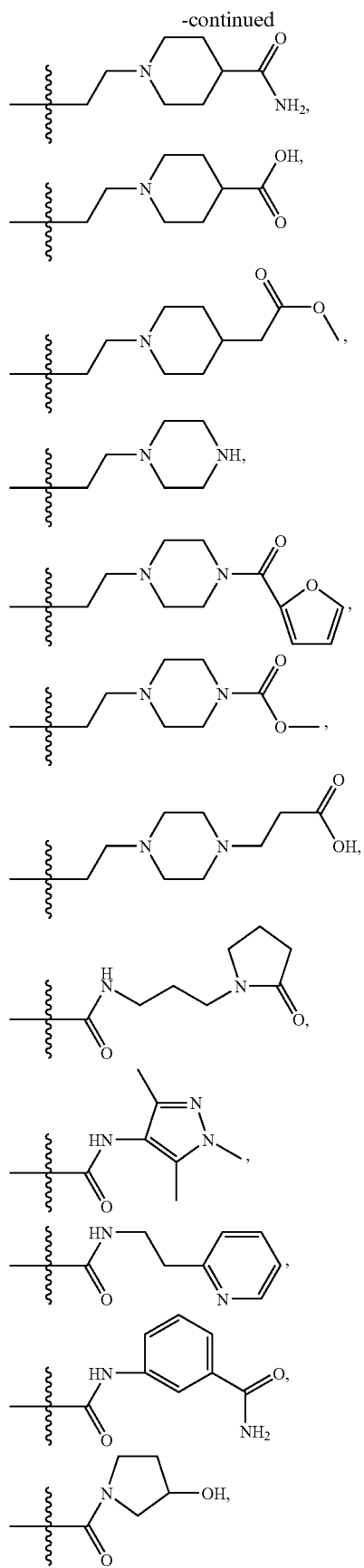
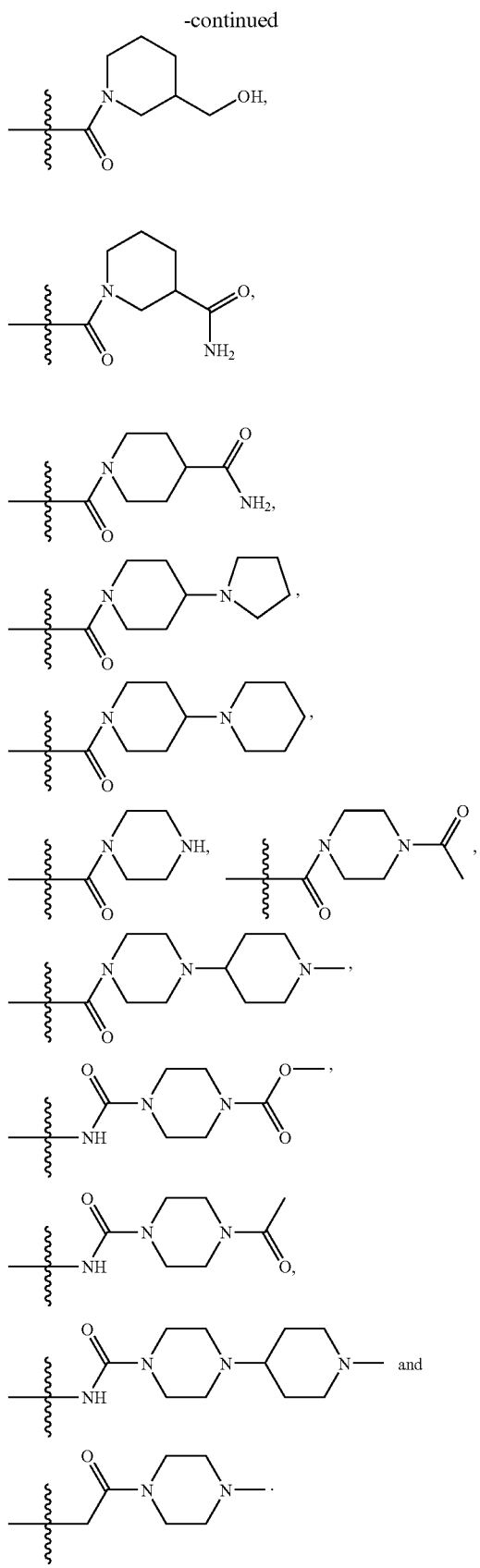

In further or alternative embodiments, Ar is selected from the group consisting of

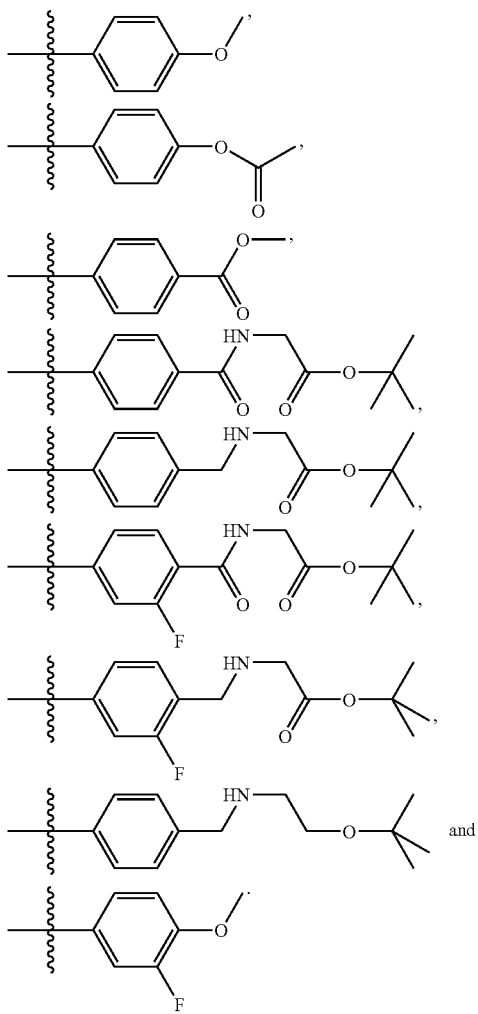

In further or alternative embodiments, the compound is selected from the group consisting of: tert-butyl 2-(4-(2-(4-(2-(diethylamino)ethoxy)phenylamino)pyrimidin-5-yl)-2-fluorobenzamido)acetate, tert-butyl 2-(4-(2-(4-(2-(diethylamino)ethoxy)phenylamino)pyrimidin-5-yl)-2-fluorobenzylamino)acetate, tert-butyl 2-(4-(2-(4-(2-(diethylamino)ethoxy)phenylamino)pyrimidin-5-yl)benzylamino)acetate, 2,2'-(2-(4-(5-(4-methoxyphenyl)pyrimidin-2-ylamino)phenoxy)ethylazanediyl)diethanol, 1-(4-(5-(4-methoxyphenyl)pyrimidin-2-ylamino)phenethyl)piperidine-4-carboxylic acid, tert-butyl 2-(4-(2-(4-(2-(diethylamino)ethoxy)phenylamino)pyrimidin-5-yl)benzamido)acetate, methyl 1-(4-(5-(4-methoxyphenyl)pyrimidin-2-ylamino)phenethyl)piperidine-4-carboxylate, N-(4-(2-(diethylamino)ethyl)phenyl)-5-(4-methoxyphenyl)pyrimidin-2-amine, 1-(2-(4-(5-(4-methoxyphenyl)pyrimidin-2-ylamino)phenoxy)ethyl)piperidine-4-carboxylic acid, N-(4-(2-(diethylamino)ethoxy)phenyl)-5-(4-methoxyphenyl)pyrimidin-2-amine, tert-butyl 2-(4-(2-(4-(2-morpholinoethoxy)phenylamino)pyrimidin-5-yl)benzamido)acetate, tert-butyl 2-(4-(2-(4-(2-(4-carbamoylpiperidin-1-yl)ethoxy)phenylamino)pyrimidin-5-yl)benzamido)acetate, 4-(2-(4-(2-(diethylamino)ethoxy)phenylamino)pyrimidin-5-yl)phenyl acetate, ethyl 2-(2-(diethylamino)ethoxy)-5-(5-(4-methoxyphenyl)pyrimidin-2-ylamino)benzoate, 4-(5-(4-methoxyphenyl)pyrimidin-2-ylamino)phenyl 4-methylpiperazine-1-carboxylate, 5-(4-methoxyphenyl)-N-(4-(2-(methyl(pyridin-2-yl)amino)ethoxy)phenyl)pyrimidin-2-amine, methyl 4-(2-(4-(2-(diethylamino)ethoxy)phenylamino)pyrimidin-5-yl)benzoate, N-(4-(2-(diethylamino)ethoxy)phenyl)-5-(3-fluoro-4-methoxyphenyl)pyrimidin-2-amine, 2-(2-(diethylamino)ethoxy)-4-(5-(4-methoxyphenyl)pyrimidin-2-ylamino)benzoic acid, methyl 2-(2-(diethylamino)ethoxy)-4-(5-(4-methoxyphenyl)pyrimidin-2-ylamino)benzoate, N-(3-(2-(diethylamino)ethoxy)phenyl)-5-(4-methoxyphenyl)pyrimidin-2-anine, N-(3-(2-(diethylamino)ethyl)phenyl)-5-(4-methoxyphenyl)pyrimidin-2-amine, 1-(4-(5-(4-methoxyphenyl)pyrimidin-2-ylamino)benzyl)piperidine-4-carboxamide, 1-(4-(5-(4-methoxyphenyl)pyrimidin-2-ylamino)benzyl)piperidine-3-carboxamide, tert-butyl 3-(4-(5-(4-methoxyphenyl)pyrimidin-2-ylamino)benzylamino)propanoate, 5-(4-methoxyphenyl)-N-(4-(piperazin-1-ylmethyl)phenyl)pyrimidin-2-amine, 1-(4-(4-(5-(4-methoxyphenyl)pyrimidin-2-ylamino)benzyl)piperazin-1-yl)ethanone, (4-(4-(5-(4-methoxyphenyl)pyrimidin-2-ylamino)benzyl)piperazin-1-yl)(tetrahydrofuran-2-yl)methanone, 1-(3-(4-(5-(4-methoxyphenyl)pyrimidin-2-ylamino)benzylamino)propyl)pyrrolidin-2-one, (S)-(1-(4-(5-(4-methoxyphenyl)pyrimidin-2-ylamino)benzyl)pyrrolidin-2-yl)methanol, (R)—N-(4-((2-(methoxymethyl)pyrrolidin-1-yl)methyl)phenyl)-5-(4-methoxyphenyl)pyrimidin-2-amine, 1-(4-(5-(4-methoxyphenyl)pyrimidin-2-ylamino)benzyl)pyrrolidin-3-ol, methyl 1-(4-(5-(4-methoxyphenyl)pyrimidin-2-ylamino)benzylamino)cyclopentanecarboxylate, 4-(4-(5-(4-methoxyphenyl)pyrimidin-2-ylamino)benzyl)-2-methylpiperazine-1-carboxylic acid, 3-(4-(4-(5-(4-methoxyphenyl)pyrimidin-2-ylamino)benzyl)piperazin-1-yl)propanoic acid, 1-(4-(5-(4-methoxyphenyl)pyrimidin-2-ylamino)benzyl)piperidine-3-carboxylic acid, ethyl 2-(1-(4-(5-(4-methoxyphenyl)pyrimidin-2-ylamino)benzyl)piperidin-4-yl)acetate, 2-(1-(4-(5-(4-methoxyphenyl)pyrimidin-2-ylamino)benzyl)piperidin-4-yl)acetic acid, 1-(4-(5-(4-methoxyphenyl)pyrimidin-2-ylamino)benzyl)pyrrolidine-3-carboxylic acid, 3-(5-(4-methoxyphenyl)pyrimidin-2-ylamino)phenyl morpholine-4-carboxylate, 3-(5-(4-methoxyphenyl)pyrimidin-2-ylamino)phenyl 4-methylpiperazine-1-carboxylate, 3-(5-(4-((2-tert-butoxy-2-oxoethylamino)methyl)phenyl)pyrimidin-2-ylamino)phenyl 4-methylpiperazine-1-carboxylate, methyl 4-(4-(5-(4-methoxyphenyl)pyrimidin-2-ylamino)benzyl)piperazine-1-carboxylate, 4-(5-(4-((2-tert-butoxy-2-oxoethylamino)methyl)phenyl)pyrimidin-2-ylamino)phenyl 4-methylpiperazine-1-carboxylate, N-(3-(5-(4-methoxyphenyl)pyrimidin-2-ylamino)phenyl)-4-methylpiperazine-1-carboxamide, 2-(4-(5-(4-methoxyphenyl)pyrimidin-2-ylamino)phenyl)-1-(4-methylpiperazin-1-yl)ethanone, N1-(3-(5-(4-methoxyphenyl)pyrimidin-2-ylamino)phenyl)piperidine-1,4-dicarboxamide, 3-(5-(4-methoxyphenyl)pyrimidin-2-ylamino)benzyl 4-methylpiperazine-1-carboxylate, 4-hydroxy-N-(3-(5-(4-methoxyphenyl)pyrimidin-2-ylamino)phenyl)piperidine-1-carboxamide, N-(4-(5-(4-methoxyphenyl)pyrimidin-2-ylamino)phenyl)-4-methylpiperazine-1-carboxamide, 1-(4-(5-(4-methoxyphenyl)pyrimidin-2-ylamino)phenethyl)piperidine-4-carboxamide, furan-2-yl(4-(4-(5-(4-methoxyphenyl)pyrimidin-2-ylamino)phenethyl)piperazin-1-yl)methanone, 5-(4-methoxyphenyl)-N-(4-(2-(piperazin-1-yl)ethyl)phenyl)pyrimidin-2-amine, N-(3-(5-(4-methoxyphenyl)pyrimidin-2-ylamino)phenyl)-N,4-dimethylpiperazine-1-carboxamide, 1-(4-(5-(4-methoxyphenyl)pyrimidin-2-ylamino)phenethyl) piperidine-3-carboxamide, 1-(4-(5-(4-methoxyphenyl)pyrimidin-2-ylamino)phenethyl)piperidine-3-carboxylic acid, methyl 4-(4-(5-(4-methoxyphenyl)pyrimidin-2-ylamino) phenethyl)piperazine-1-carboxylate, 1-(4-(5-(4-methoxyphenyl)pyrimidin-2-ylamino)phenethyl)piperidine-3-carboxylic acid, 2-(1-(4-(5-(4-methoxyphenyl)pyrimidin-2-ylamino)phenethyl)piperidin-4-yl)acetic acid, methyl 2-(1-(4-(5-(4-methoxyphenyl)pyrimidin-2-ylamino)phenethyl) piperidin-4-yl)acetate, (3-(hydroxymethyl)piperidin-1-yl) (4-(5-(4-methoxyphenyl)pyrimidin-2-ylamino)phenyl) methanone, (3-hydroxypyrrolidin-1-yl)(4-(5-(4-methoxyphenyl)pyrimidin-2-ylamino)phenyl)methanone, 1-(4-(5-(4-methoxyphenyl)pyrimidin-2-ylamino)benzoyl) piperidine-4-carboxamide, 3-(4-(4-(5-(4-methoxyphenyl) pyrimidin-2-ylamino)phenethyl)piperazin-1-yl)propanoic acid, (S)-1-(4-(5-(4-methoxyphenyl)pyrimidin-2-ylamino) phenethyl)pyrrolidine-2-carboxylic acid, 4-(4-(5-(4-methoxyphenyl)pyrimidin-2-ylamino)phenethylamino)cyclohexanecarboxylic acid, 4-(5-(4-methoxyphenyl)pyrimidin-2-ylamino)-N-(3-(2-oxopyrrolidin-1-yl)propyl)benzamide, 1-(4-(5-(4-methoxyphenyl)pyrimidin-2-ylamino)benzoyl) piperidine-3-carboxamide, N-(3-carbamoylphenyl)-4-(5-(4-methoxyphenyl)pyrimidin-2-ylamino)benzamide, 1,4'-bipiperidin-1'-yl(4-(5-(4-methoxyphenyl)pyrimidin-2-ylamino) phenyl)methanone, (4-(5-(4-methoxyphenyl)pyrimidin-2-ylamino)phenyl)(4-(pyrrolidin-1-yl)piperidin-1-yl) methanone, 4-(5-(4-methoxyphenyl)pyrimidin-2-ylamino)-N-(2-(pyridin-2-yl)ethyl)benzamide, 4-(5-(4-methoxyphenyl)pyrimidin-2-ylamino)-N-(1,3,5-trimethyl-1H-pyrazol-4-yl)benzamide, (4-(furan-2-carbonyl) piperazin-1-yl)(3-(5-(4-methoxyphenyl)pyrimidin-2-ylamino)phenyl)methanone, 3-(5-(4-methoxyphenyl) pyrimidin-2-ylamino)-N-(1,3,5-trimethyl-1H-pyrazol-4-yl) benzamide, (3-(5-(4-methoxyphenyl)pyrimidin-2-ylamino) phenyl)(4-(1-methylpiperidin-4-yl)piperazin-1-yl) methanone, 1-(4-(3-(5-(4-methoxyphenyl)pyrimidin-2-ylamino)benzoyl)piperazin-1-yl)ethanone, (3-(5-(4-methoxyphenyl)pyrimidin-2-ylamino)phenyl)(4-(pyrrolidin-1-yl)piperidin-1-yl)methanone, 1,4'-bipiperidin-1'-yl(3-(5-(4-methoxyphenyl)pyrimidin-2-ylamino)phenyl) methanone, 1-(3-(5-(4-methoxyphenyl)pyrimidin-2-ylamino)benzoyl)piperidine-3-carboxamide, N-(3-(5-(4-methoxyphenyl)pyrimidin-2-ylamino)phenyl)-4-(1-methylpiperidin-4-yl)piperazine-1-carboxamide, methyl 4-(3-(5-(4-methoxyphenyl)pyrimidin-2-ylamino)phenylcarbamoyl)piperazine-1-carboxylate, (R)-1-(4-(5-(4-methoxyphenyl)pyrimidin-2-ylamino)phenethyl)piperidine-3-carboxylic acid, (4-(5-(4-methoxyphenyl)pyrimidin-2-ylamino) phenyl)(piperazin-1-yl)methanone, 4-acetyl-N-(3-(5-(4-methoxyphenyl)pyrimidin-2-ylamino)phenyl)piperazine-1-carboxamide, and (3-(5-(4-methoxyphenyl)pyrimidin-2-ylamino)phenyl)(piperazin-1-yl)methanone.

In further or alternative embodiments, Q of the compound having the structure of Formula (1) is selected from the group consisting of

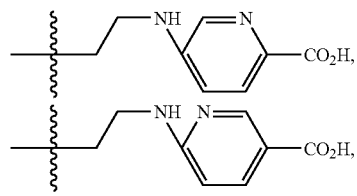

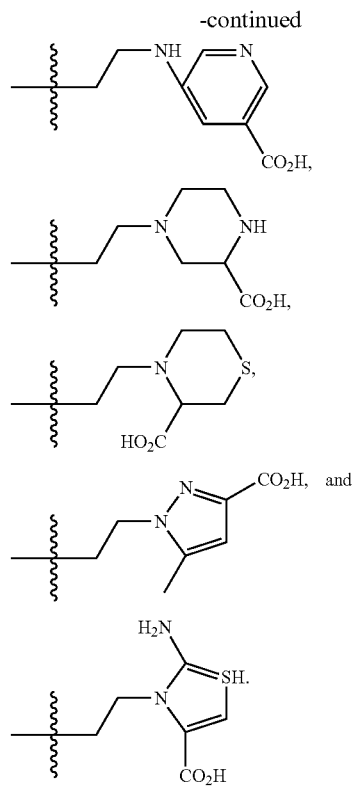

In further or alternative embodiments, Q of the compound having the structure of Formula (1) is selected from the group consisting of

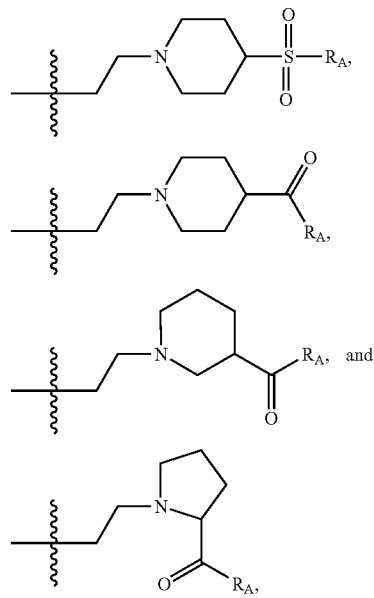

wherein $R_A$ is selected from —$NH_2$, —$NEt_2$, and —NH $(CH_2)_nOH$; and n is 1 to 6.

In further or alternative embodiments, Q of the compound having the structure of Formula (1) is

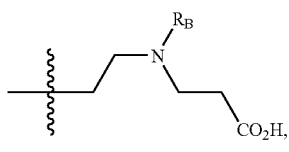

wherein $R_B$ is selected from the group consisting of

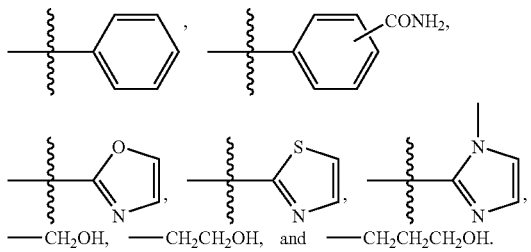

—CH$_2$OH,    —CH$_2$CH$_2$OH,    and    —CH$_2$CH$_2$CH$_2$OH.

In further or alternative embodiments, Q of the compound having the structure of Formula (1) is

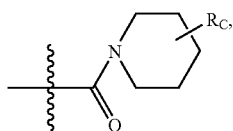

wherein $R_C$ is at 2, 3, or 4 position of the piperidine ring; and $R_C$ is selected from the group consisting of —C(O)NHEt, —C(O)NEt$_2$, c-butyl, c-pentyl, —C(O)NH-thiazole, oxazole, thiazole, —S(O)$_2$NH$_2$, —S(O)$_2$NHEt, and —S(O)$_2$NEt$_2$.

In further or alternative embodiments, Q of the compound having the structure of Formula (1) is selected from the group consisting of

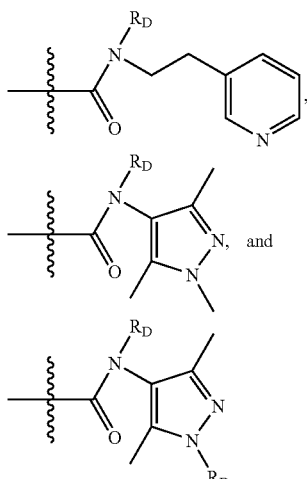

wherein each $R_D$ is independently selected from —(CH$_2$)$_k$OH or —(CH$_2$)$_k$CO$_2$H; and k is 1 to 6.

In further or alternative embodiments, Q of the compound having the structure of Formula (1) is

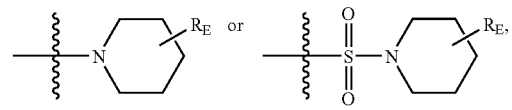

wherein $R_E$ is at 2, 3, or 4 position of the piperidine ring; and $R_E$ is selected from the group consisting of —C(O)NH$_2$, —C(O)NHEt, and —C(O)NEt$_2$.

In further or alternative embodiments, Q of the compound having the structure of Formula (1) is selected from the group consisting of

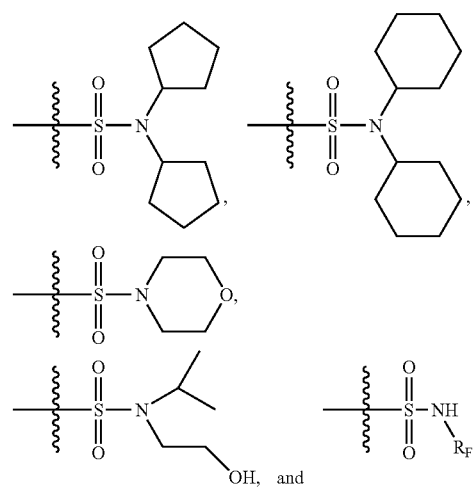

wherein $R_F$ is thiazole, pyrazole, or isoxazole.

In further or alternative embodiments, Q of the compound having the structure of Formula (46) is selected from the group consisting of

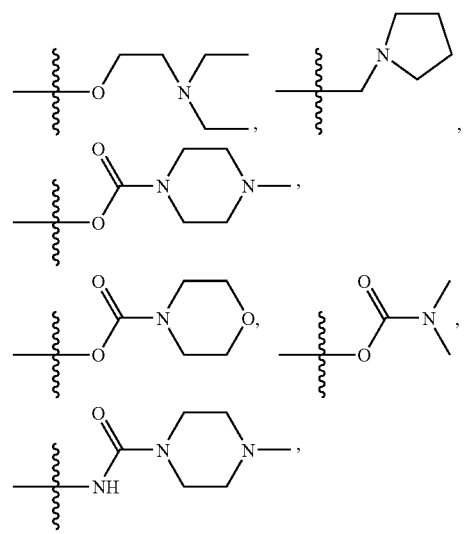

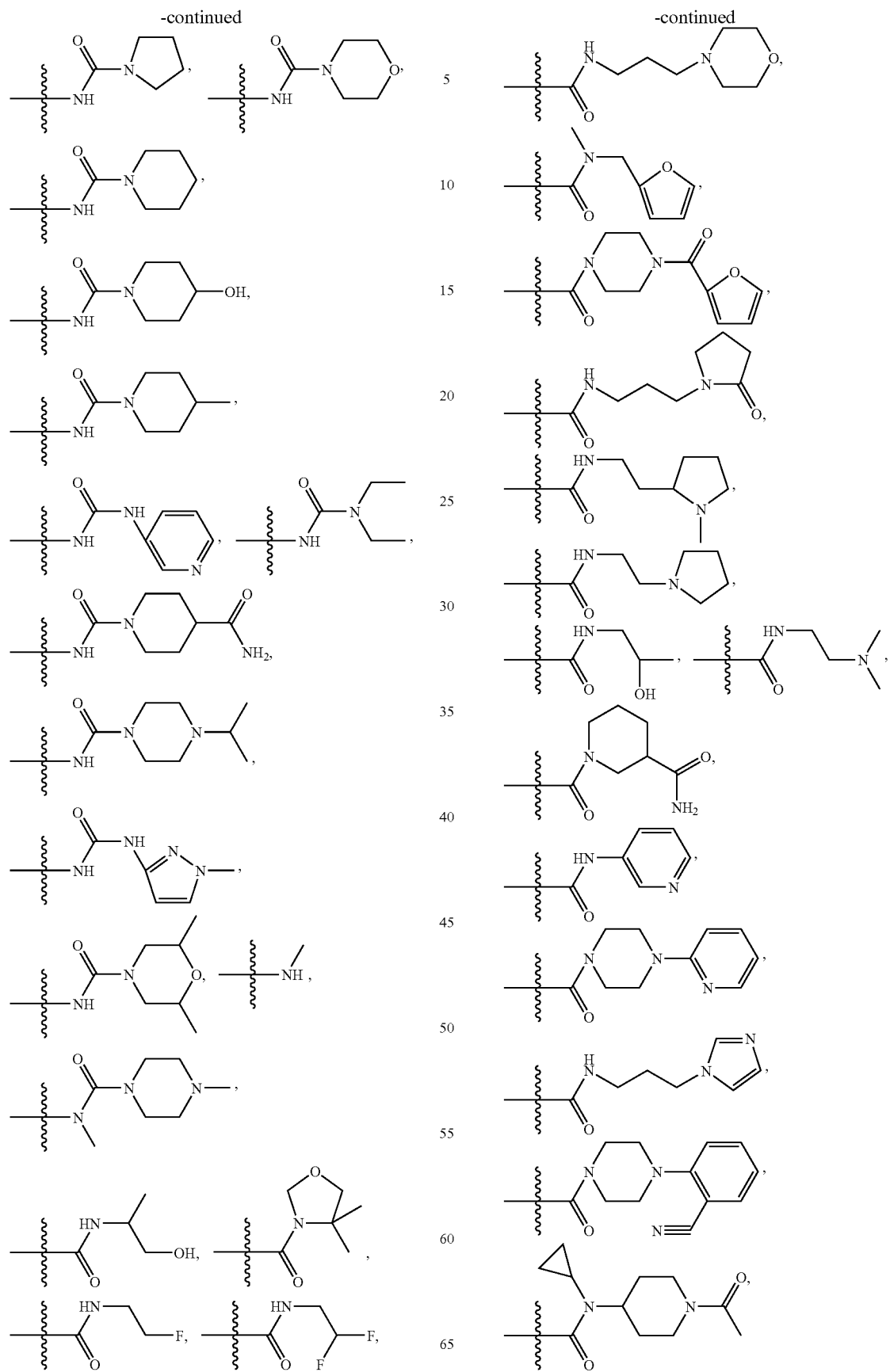

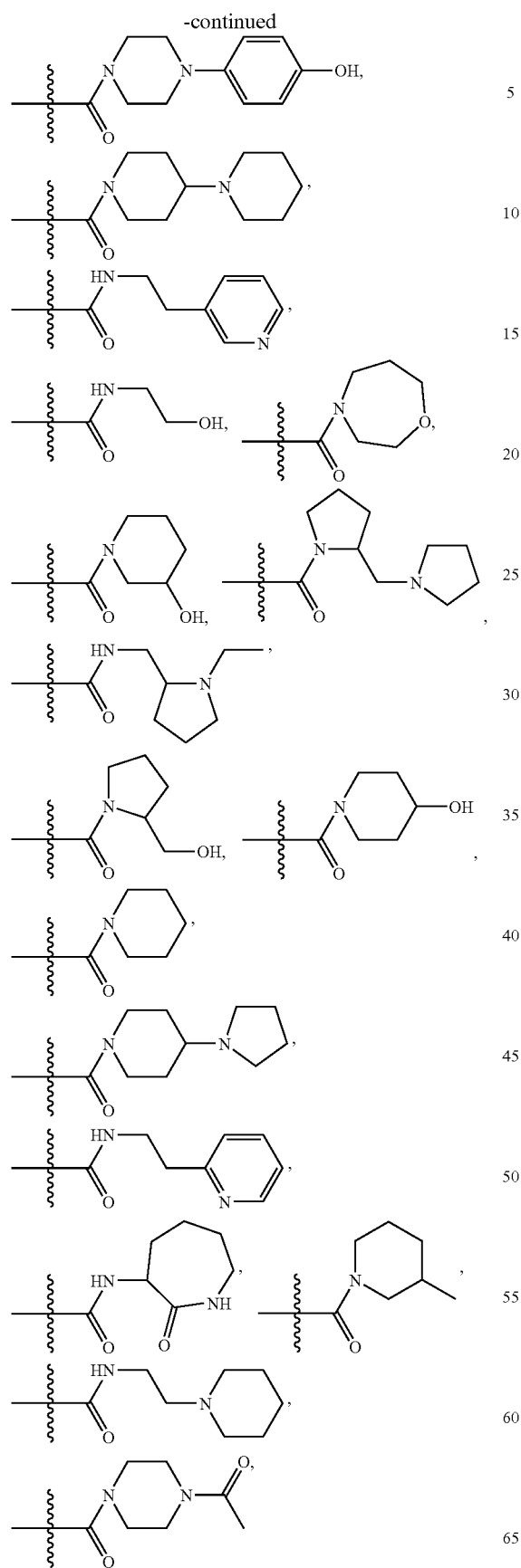
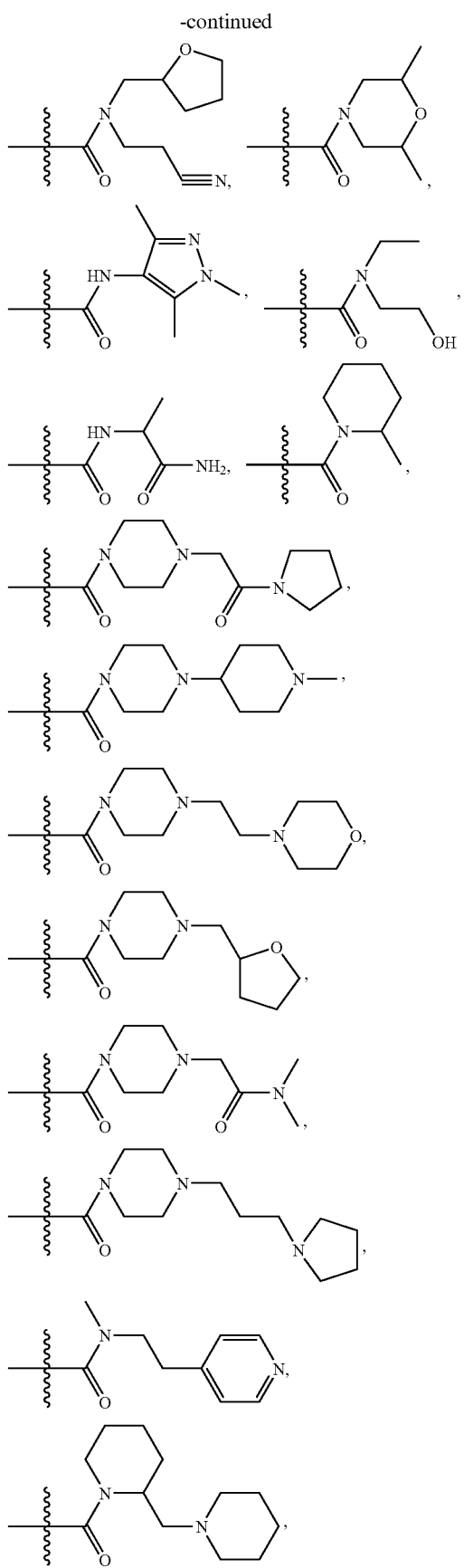

-continued

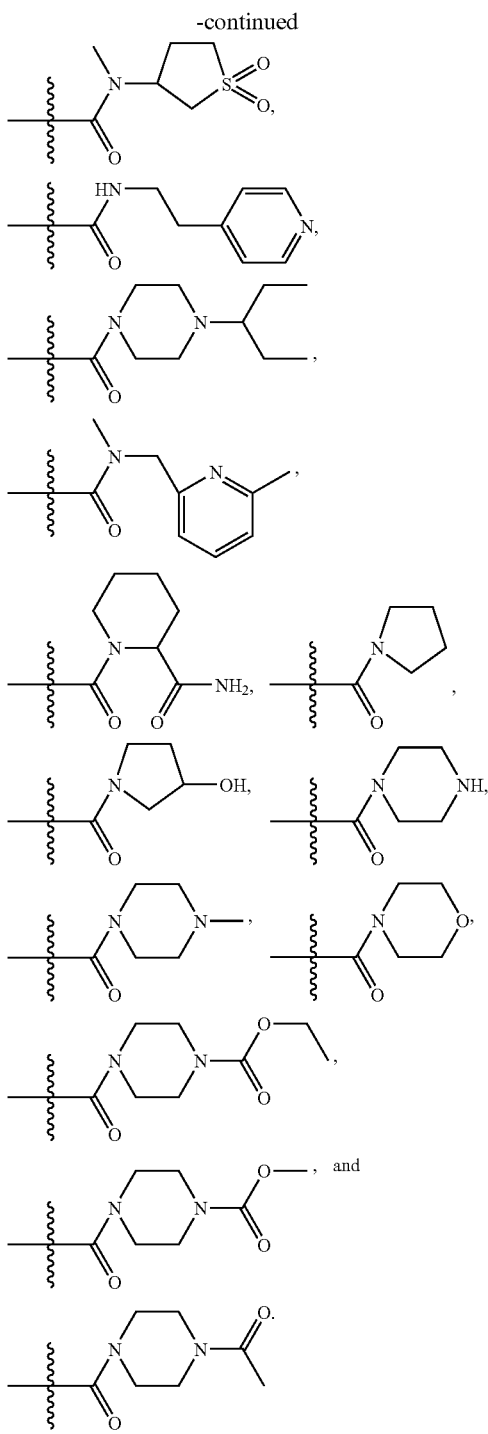

In further or alternative embodiments, Q of the compound having the structure of Formula (46) is selected from the group consisting of

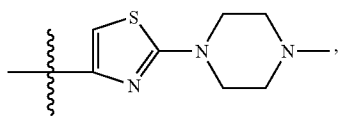

-continued

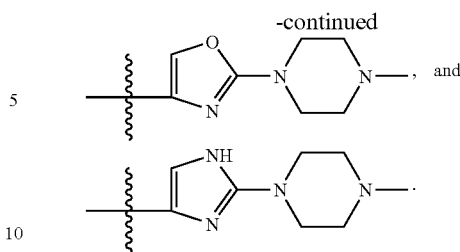

In another aspect are methods of treating a disease or condition in animals in which modulation of c-kit receptor activities can prevent, inhibit or ameliorate the pathology and/or symptomology of the disease or condition, which methods comprise administering to the animal a therapeutically effective amount of a compound having the structure of Formula (A) or Formula (B):

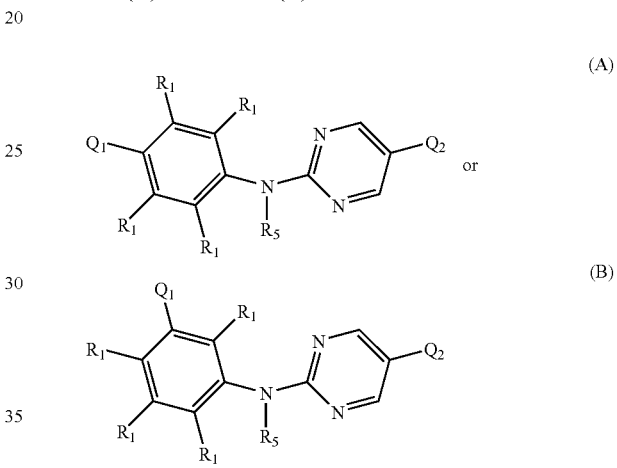

wherein;

$Q_1$ is H, halogen, a group comprising a non-aromatic tertiary amine, a group comprising a non-aromatic secondary amine, or is an optionally substituted moiety selected from the group consisting of: -L-alkyl, -L-cycloalkyl, -L-heteroalkyl, -L-haloalkyl, -L-aryl, -L-heterocycloalkyl, and -L-heteroaryl; wherein L is selected from a bond, —O—, —NH—, —S—, —C(O)—, —C(S)—, —C(O)O—, —C(O)NH—, —S(O)—, —S(O)$_2$—, —OC(O)—, —C(O)NR" (CR"$_2$)$_{1-6}$C(O)O—, —CR"$_2$NR"CR"$_2$C(O)O—, —C(O)—NR"YC(O)O—, —C(O)NR"NR"C(O)O—, and —S(O)NH—; and Y is optionally substituted arylene or heteroarylene;

each $R_1$ is independently selected from the group consisting of H, halogen, and an optionally substituted moiety selected from -L$_1$-alkyl, -L$_1$-cycloalkyl, -L$_1$-heteroalkyl, -L$_1$-haloalkyl, -L-aryl, -L$_1$-heterocycloalkyl, and -L$_1$-heteroaryl; wherein L$_1$ is selected from a bond, —O—, —NH—, —S—, —C(O)—, —C(S)—, —C(O)O—, —C(O)NH—, —S(O)—, —S(O)$_2$—, —C(O)NR"(CR"$_2$)$_{1-6}$C(O)O—, —OC(O)—, —CR"$_2$NR"CR"$_2$C(O)O—, —C(O)—NR"Y'C(O)O—, —C(O)NR"NR"C(O)O—, and —S(O)NH—; and Y' is optionally substituted arylene or heteroarylene;

$Q_2$ is selected from the group consisting of H, halogen, and a group comprising an optionally substituted moiety selected from -L$_6$-alkyl, -L$_6$-cycloalkyl, -L$_6$-heteroalkyl, -L$_6$-haloalkyl, -L$_6$-aromatic carbocycle, -L$_6$-heterocycloalkyl, and -L$_1$-aromatic heterocycle; wherein L$_6$ is selected from a bond, —O—, —NH—, —S—, —C(O)—, —C(S)—, —C(O)O—, —C(O)NH—, —S(O)—, —S(O)$_2$—, —C(O)NR"(CR"$_2$)$_{1-6}$C(O)O—, —OC(O)—, —CR"$_2$NR"CR"$_2$C(O)O—, —C(O)—NR"Y"C(O)O—, —C(O)NR"NR"C(O)O—, and —S(O)NH—; and Y" is optionally substituted arylene or heteroarylene;

each R" is independently H, OH, halogen, C$_{1-6}$alkyl, substituted C$_{1-6}$alkyl, C$_{1-6}$alkoxy, halo-C$_{1-6}$alkyl, halo-C$_{1-6}$alkoxy, aryl, haloaryl, or heteroaryl;

any two R$_1$ groups together may form an optionally substituted 5 to 8-membered heterocyclic, cycloalkyl, or aryl ring;

R$_5$ is selected from the group consisting of H, and an optionally substituted moiety selected from -L$_5$-H, -L$_5$-alkyl, -L$_5$-cycloalkyl, -L$_5$-heteroalkyl, -L$_5$-haloalkyl, -L$_5$-aryl, -L$_5$-heterocycloalkyl, and -L$_5$-heteroaryl, wherein L$_5$ is selected from a bond, —R'O—, —R'N(H)—, —R'S—, —R'C(O)—, —R'C(S)—, —R'C(O)O—, and —R'C(O)NH—;

each R' is independently selected from the group consisting of a bond, alkylene, substituted alkylene, heteroalkylene, substituted heteroalkylene, alkenylene, substituted alkenylene, cycloalkylene, substituted cycloalkylene, heteroalkylene, substituted heteroalkylene, heterocycloalkylene, substituted heterocycloalkylene, arylene, substituted arylene, heteroarylene, substituted heteroarylene, alkarylene, substituted alkarylene, aralkylene, and substituted aralkylene; and any R$_1$ and R$_5$ taken together may form an optionally substituted 5 to 8-membered heterocyclic, cycloalkyl, or aryl ring;

or a pharmaceutically acceptable salt, pharmaceutically acceptable N-oxide, pharmaceutically active metabolite, pharmaceutically acceptable prodrug, or pharmaceutically acceptable solvate thereof.

In a further or alternative embodiment of this aspect, compounds of Formula (A) or Formula (B) are compounds having the structure of Formula (1) or Formula (46):

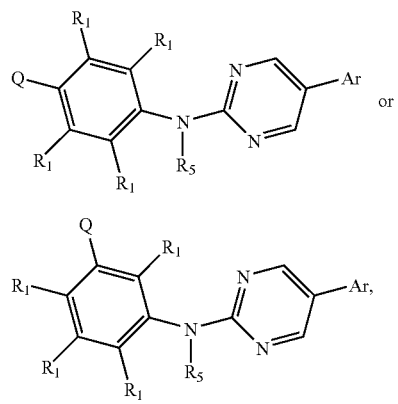

wherein:

Ar is a group comprising a moiety selected from an optionally substituted five-membered aromatic heterocycle, an optionally substituted five-membered aromatic carbocycle, an optionally substituted six-membered aromatic heterocycle, and a substituted, optionally further substituted six-membered aromatic carbocycle;

Q is a group comprising a non-aromatic tertiary amine or a non-aromatic secondary amine, with the proviso that Q is not —NR$_a$R$_b$ or —SO$_2$NR$_a$R$_b$; wherein each of R$_a$ and R$_b$ is independently H or C$_{1-6}$alkyl optionally substituted by mono- or di-alkyl (C$_{1-6}$) amino;

each R$_1$ is independently selected from the group consisting of H, halogen, and an optionally substituted moiety selected from -L$_1$-alkyl, -L$_1$-cycloalkyl, -L$_1$-heteroalkyl, -L$_1$-haloalkyl, -L$_1$-aryl, -L$_1$-heterocycloalkyl, and -L$_1$-heteroaryl; wherein L$_1$ is selected from a bond, —O—, —NH—, —S—, —C(O)—, —C(S)—, —C(O)O—, —C(O)NH—, —S(O)—, —S(O)$_2$—, —C(O)NH(CR"$_2$)$_{1-6}$C(O)O—, —C(O)NR"NR"C(O)O—, and —S(O)NH—;

each R" is independently H, OH, halogen, C$_{1-6}$alkyl, substituted C$_{1-6}$alkyl, C$_{1-6}$alkoxy, halo-C$_{1-6}$alkyl, halo-C$_{1-6}$alkoxy, aryl, haloaryl, or heteroaryl;

or any two adjacent R$_1$ groups together may form an optionally substituted 5 to 8-membered heterocyclic, cycloalkyl, or aryl ring;

R$_5$ is selected from the group consisting of H, and an optionally substituted moiety selected from -L$_5$-H, -L$_5$-alkyl, -L$_5$-cycloalkyl, -L$_5$-heteroalkyl, -L$_5$-haloalkyl, -L$_5$-aryl, -L$_1$-heterocycloalkyl, and -L$_5$-heteroaryl; wherein L$_5$ is selected from a bond, —R'O—, —R'N(H)—, —R'S—, —R'C(O)—, —R'C(S)—, —R'C(O)O—, and —R'C(O)NH—;

each R' is independently selected from the group consisting of a bond, alkylene, substituted alkylene, heteroalkylene, substituted heteroalkylene, alkenylene, substituted alkenylene, cycloalkylene, substituted cycloalkylene, heteroalkylene, substituted heteroalkylene, heterocycloalkylene, substituted heterocycloalkylene, arylene, substituted arylene, heteroarylene, substituted heteroarylene, alkarylene, substituted alkarylene, aralkylene, and substituted aralkylene; and any R$_1$ and R$_5$ taken together may form an optionally substituted 5 to 8-membered heterocyclic, cycloalkyl, or aryl ring;

or a pharmaceutically acceptable salt, pharmaceutically acceptable N-oxide, pharmaceutically active metabolite, pharmaceutically acceptable prodrug, or pharmaceutically acceptable solvate thereof.

In a further or alternative embodiment of this aspect, the method further comprises administration of a therapeutically effective amount of a second substance, wherein the second substance is used in the treatment of a disease or condition selected from the group consisting of a neoplastic disease, an allergy disease, an inflammatory disease, an autoimmune disease, a graft-versus-host disease, a metabolic syndrome, a CNS related disorders, a neurodegenerative disease, a pain condition, a substance abuse disorder, a prion disease, a cancer, a heart disease, a fibrotic disease, idiopathic pulmonary arterial hypertension (IPAH), and primary pulmonary hypertension (PPH).

In further or alternative embodiments, the second substance is selected from the group consisting of a bronchodilator, an anti-inflammatory agent, a leukotriene antagonist, and an IgE blocker. In further or alternative embodiments, the compound of Formula (A) or Formula (B) is administered prior to the second substance. In further or alternative embodiments, the compound of Formula (A) or Formula (B) is administered prior to the second substance. In further or alternative embodiments, the compound of Formula (A) or Formula (B) is administered with the second substance. In further or alternative embodiments, the compound of Formula (A) or Formula (B) is administered after the second substance. In further or alternative embodiments, the compound of Formula (A) or Formula (B) and the second substance are administered in the same pharmaceutical composition.

In further or alternative embodiments, the Ar is a group comprising a substituted, optionally further substituted six-membered aromatic heterocycle. In further or alternative embodiments, said optional substituents are selected from halogen, OH, halogen, $C_{1-6}$alkyl, $C_{1-6}$alkoxy, halo-$C_{1-6}$alkyl, halo-$C_{1-6}$alkoxy, aryl, haloaryl, or heteroaryl. In further or alternative embodiments, the compound is the compound of any of Formula (1) to Formula (54) in various embodiments described above.

In further or alternative embodiments, Ar is selected from the group consisting of

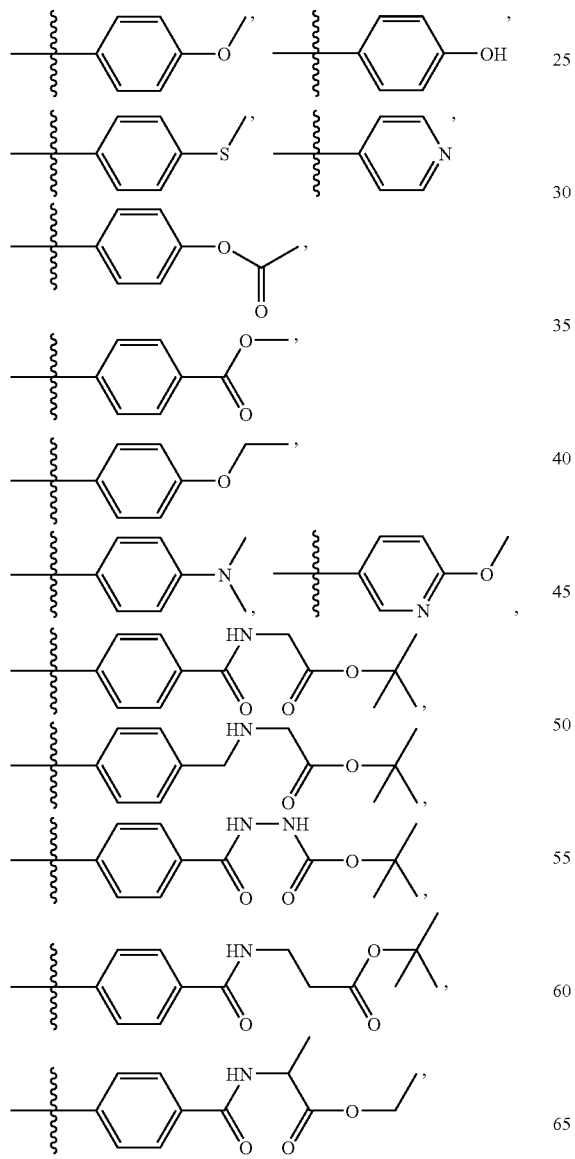

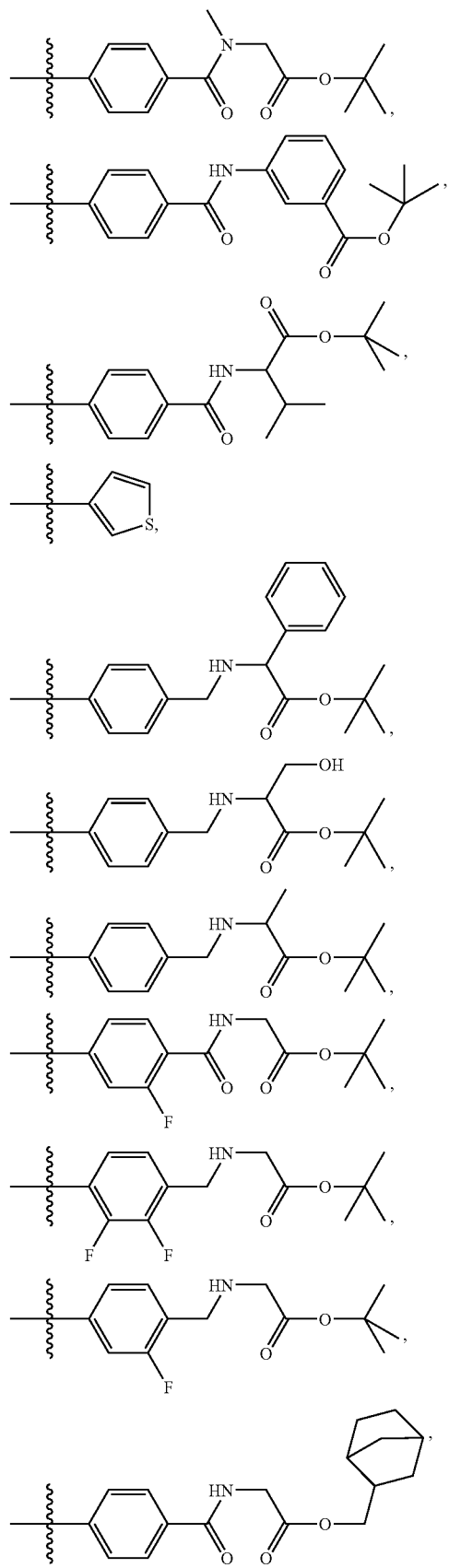

-continued
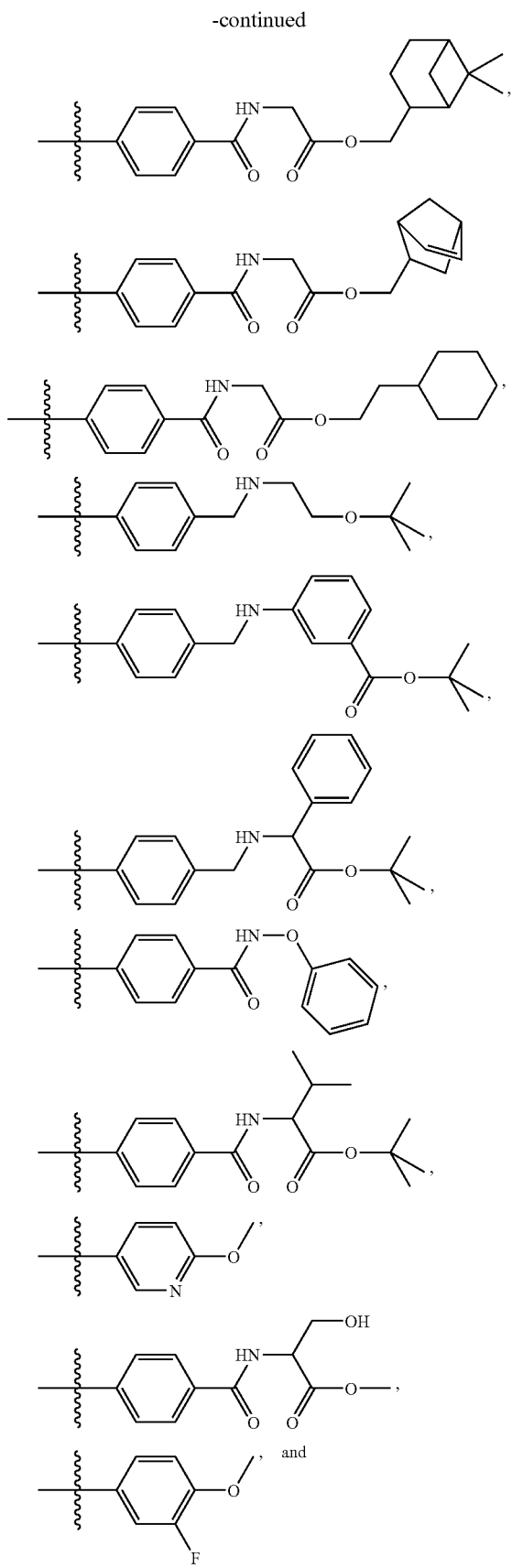
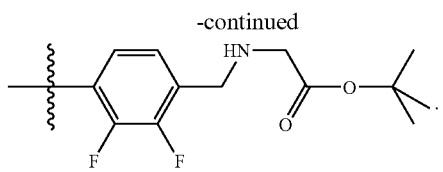
In further or alternative embodiments, Q is selected from the group consisting of
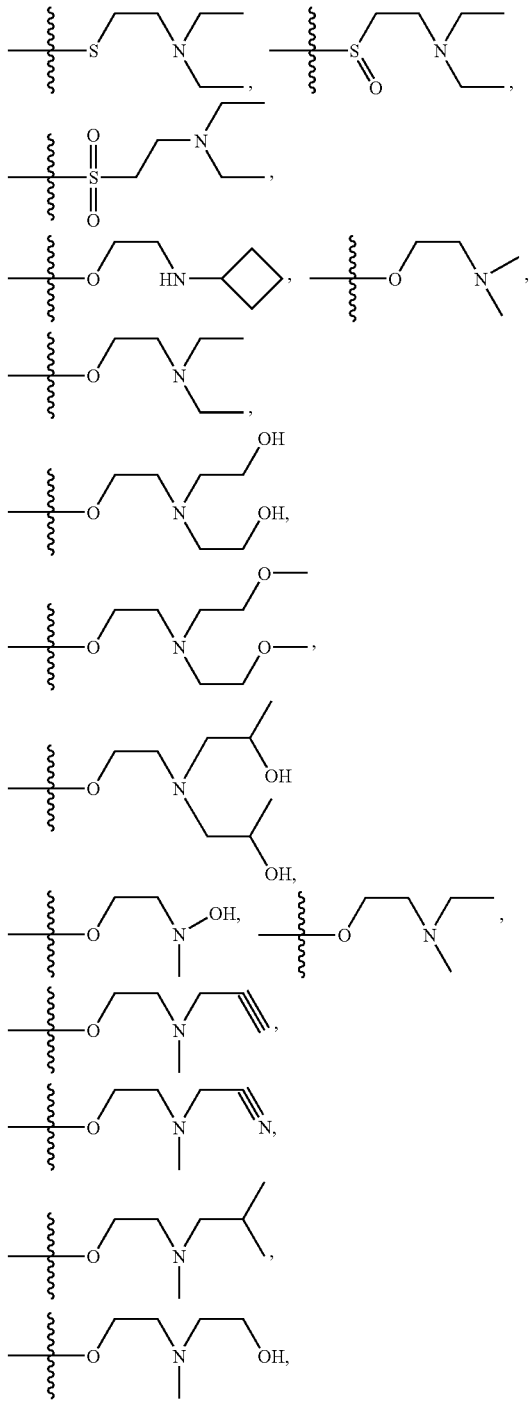

-continued
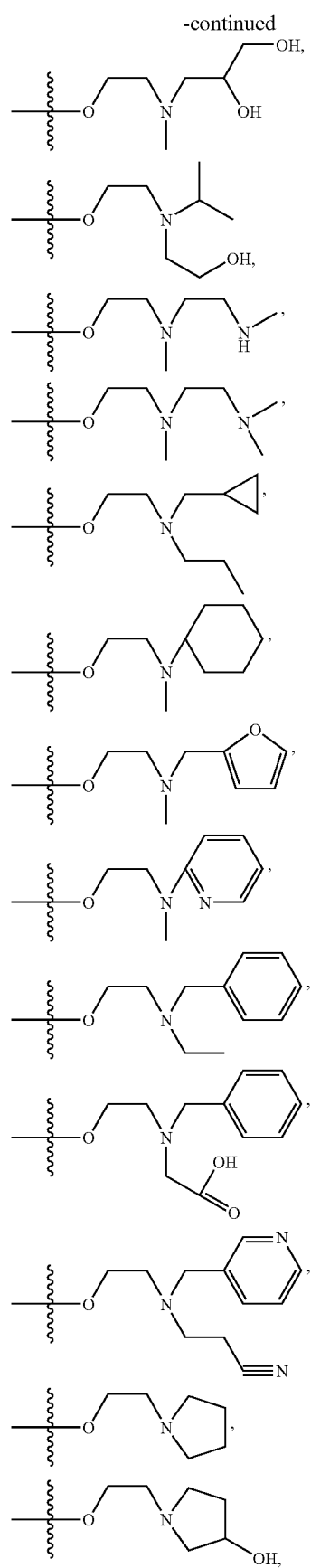
-continued
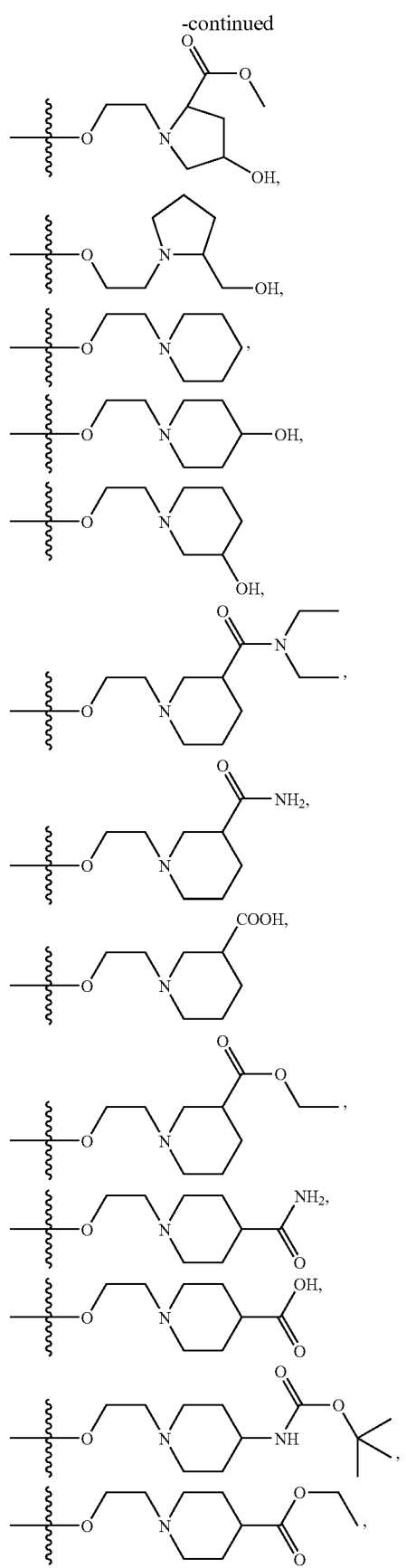

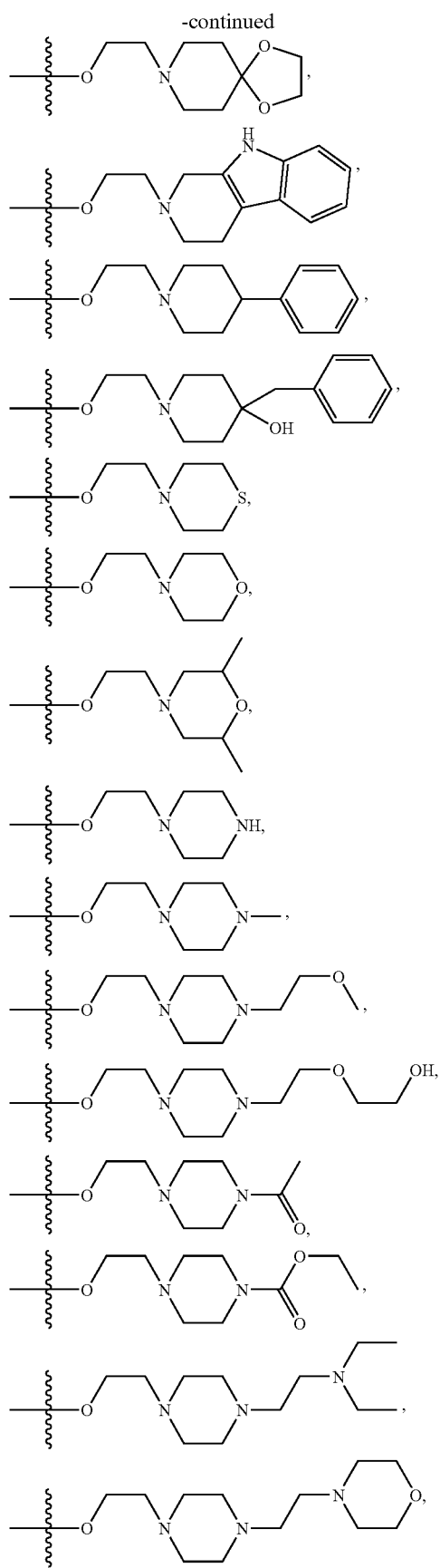
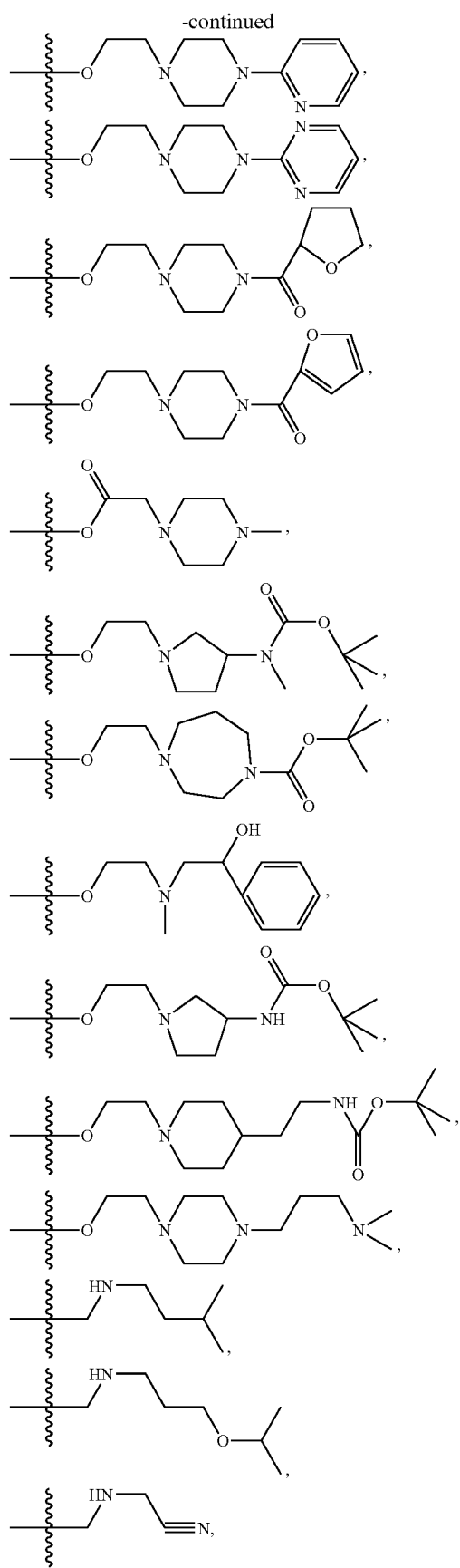

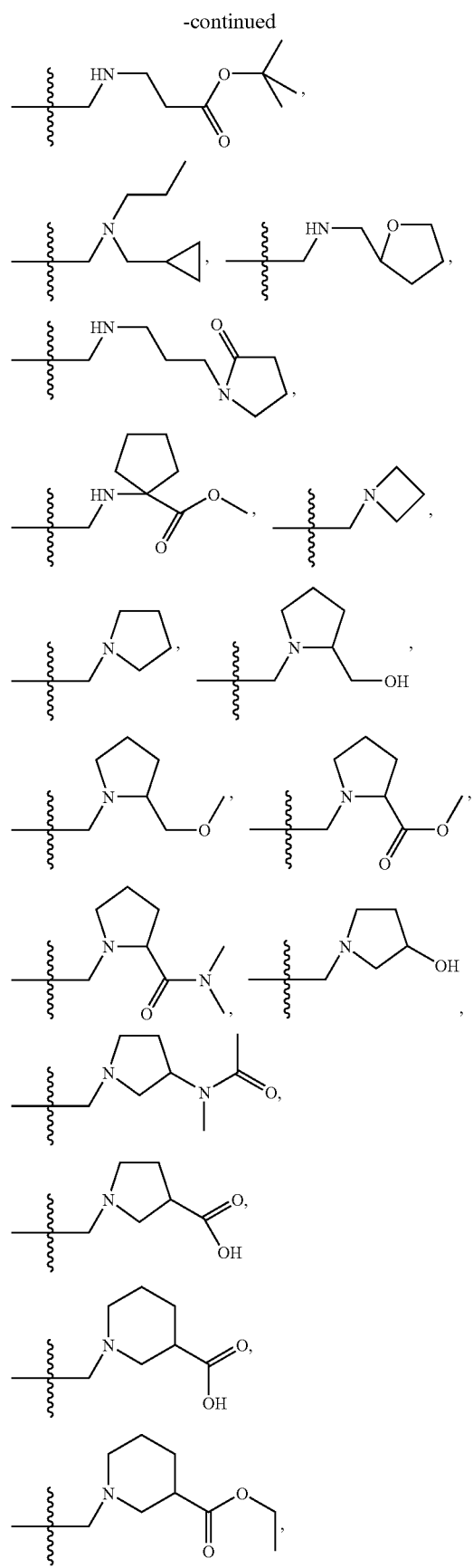
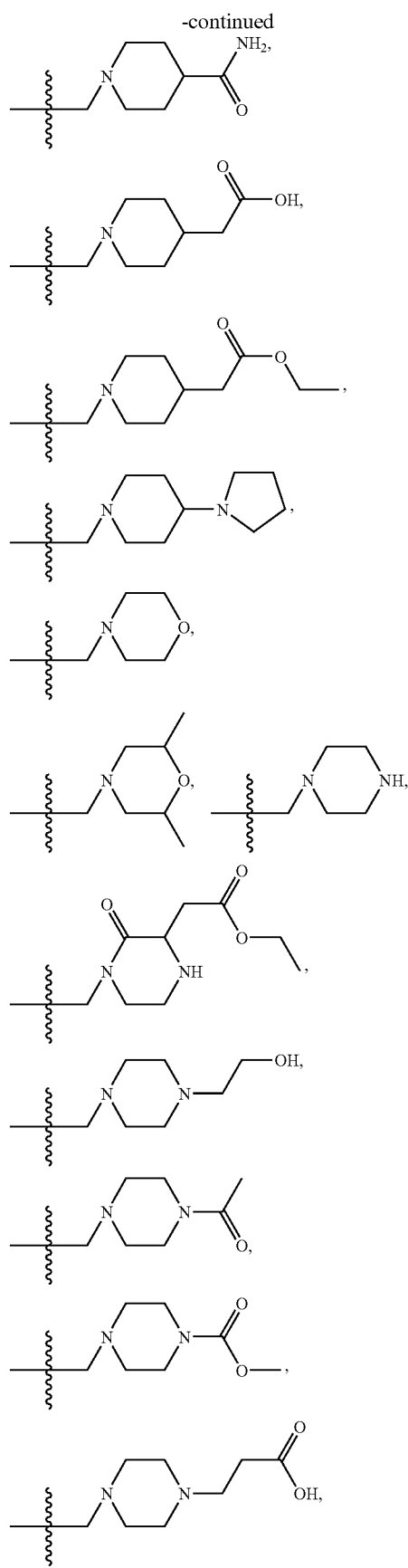

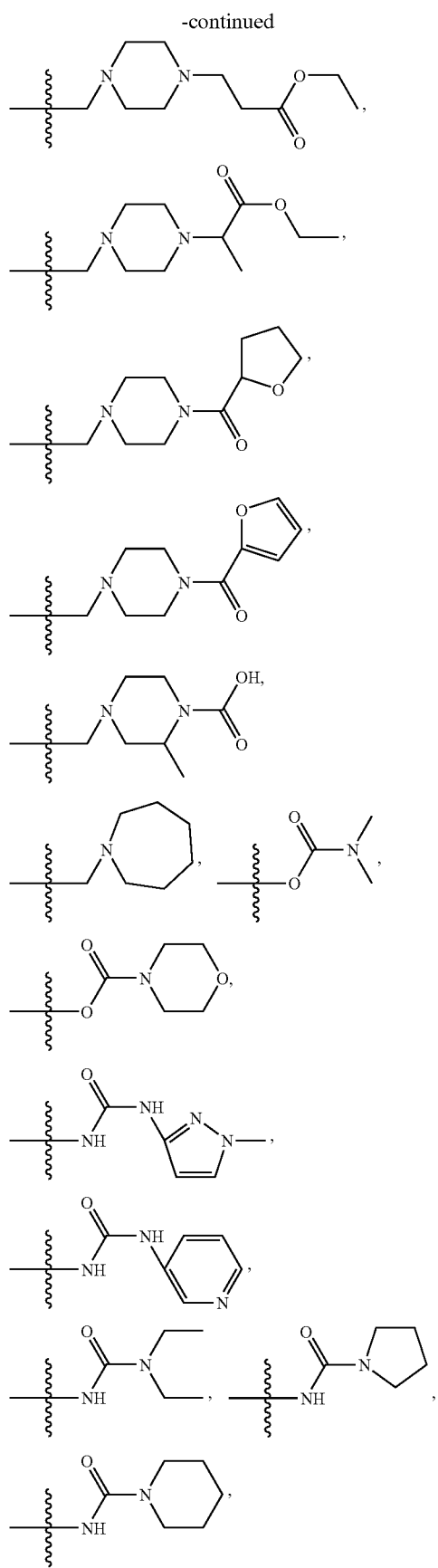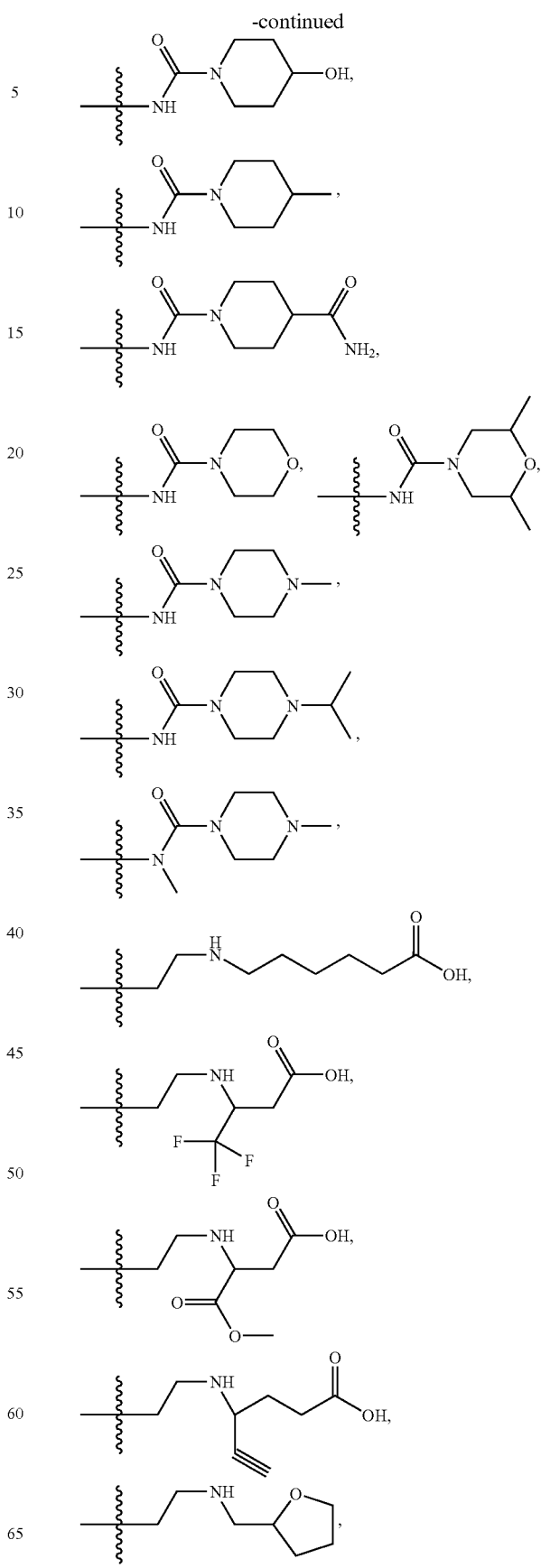

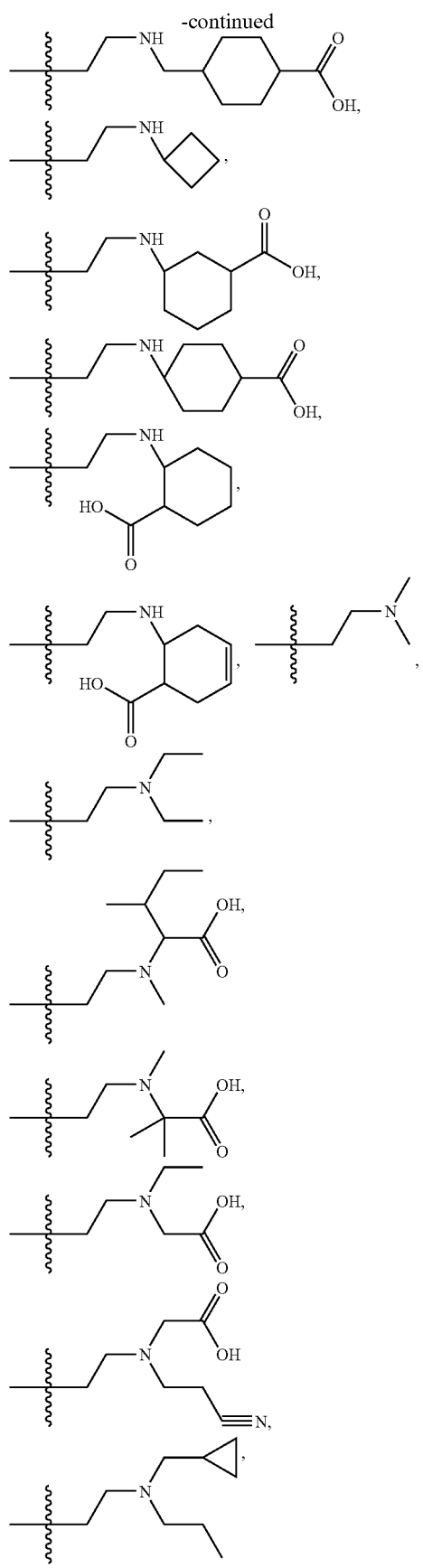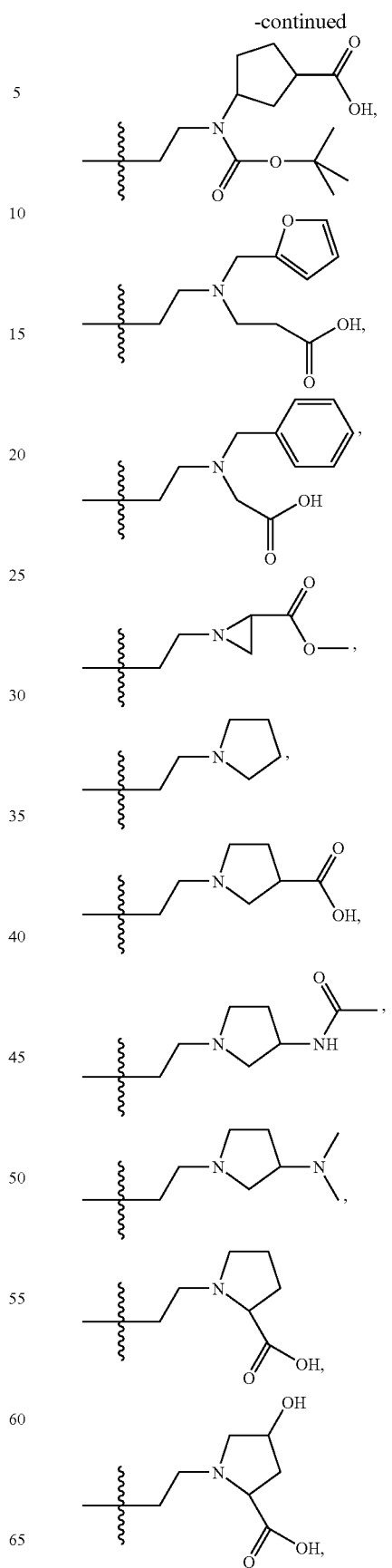

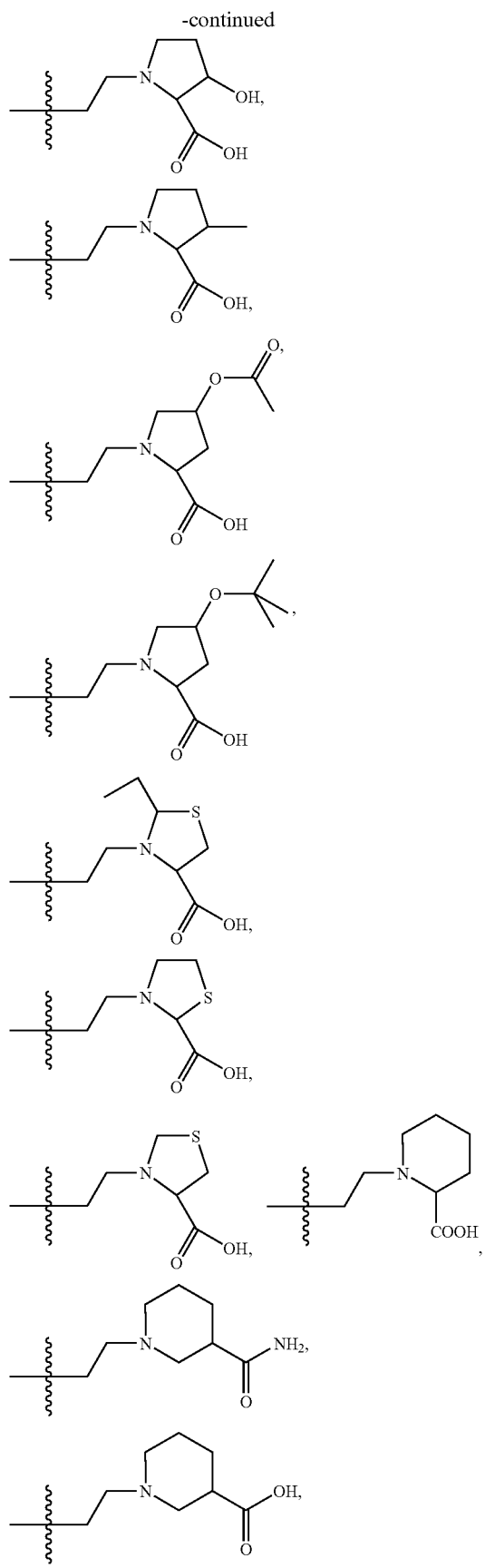
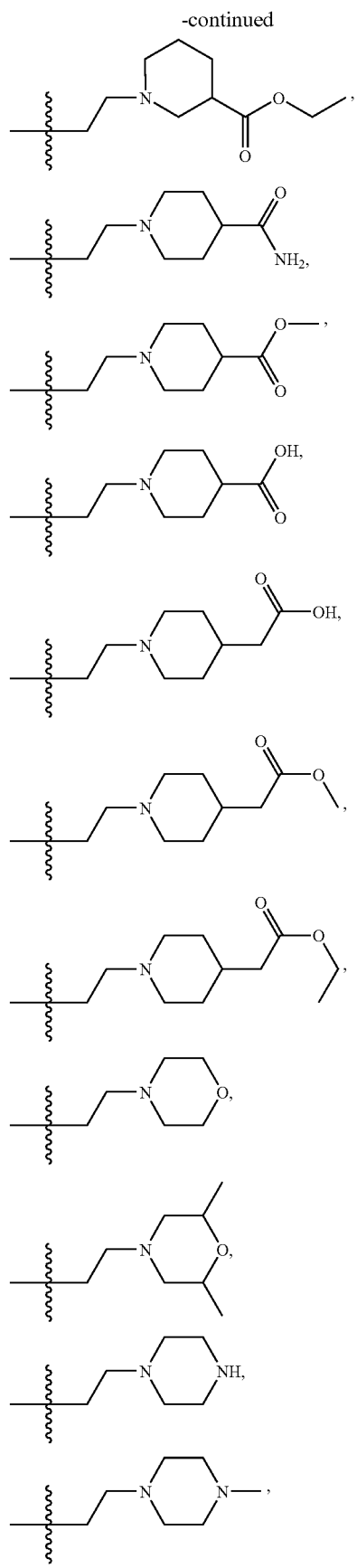

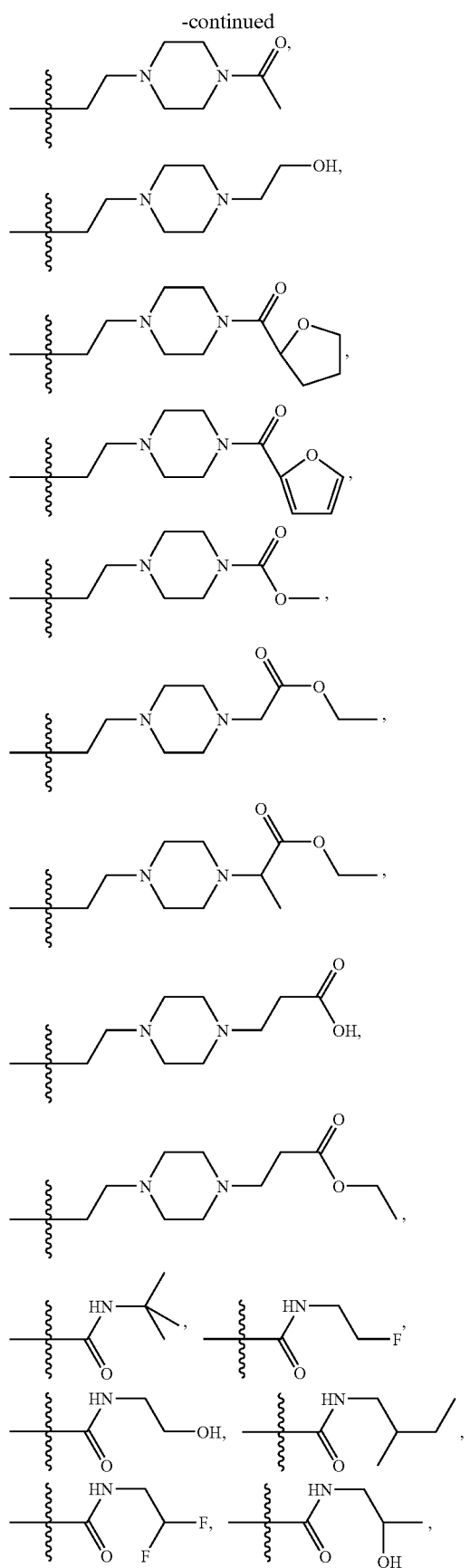
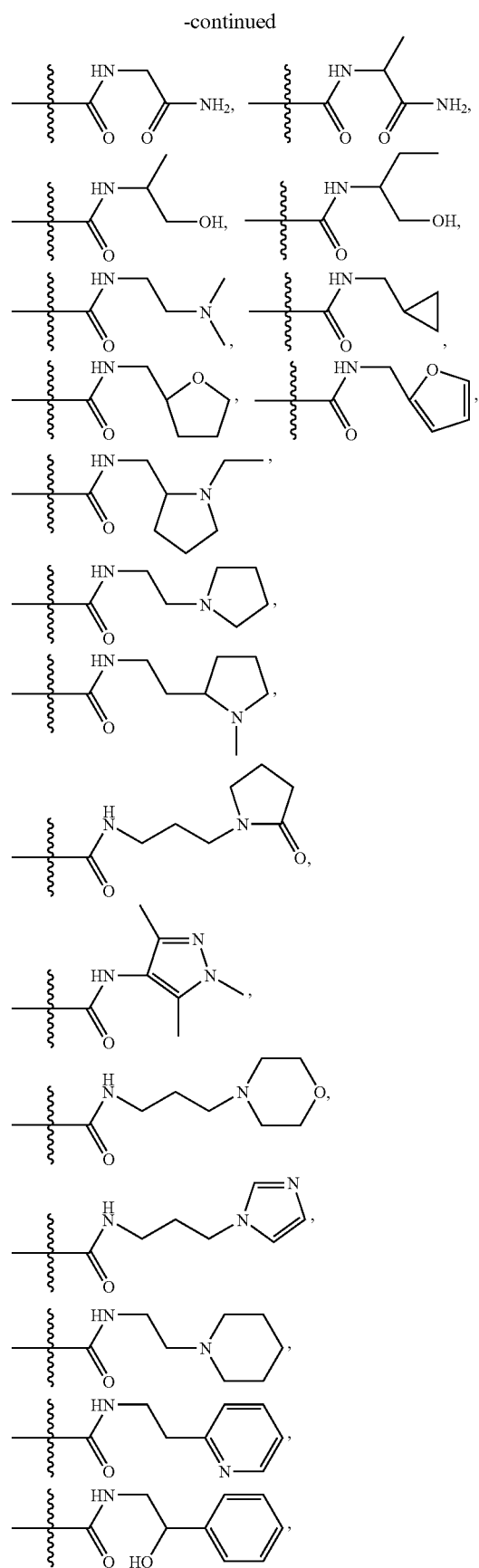

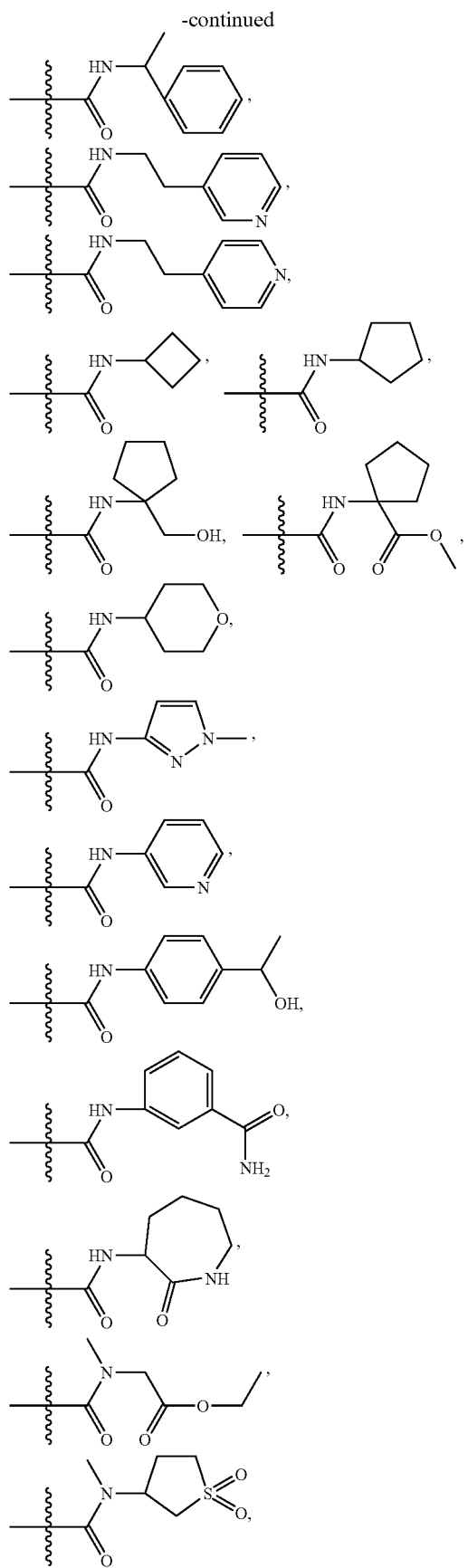
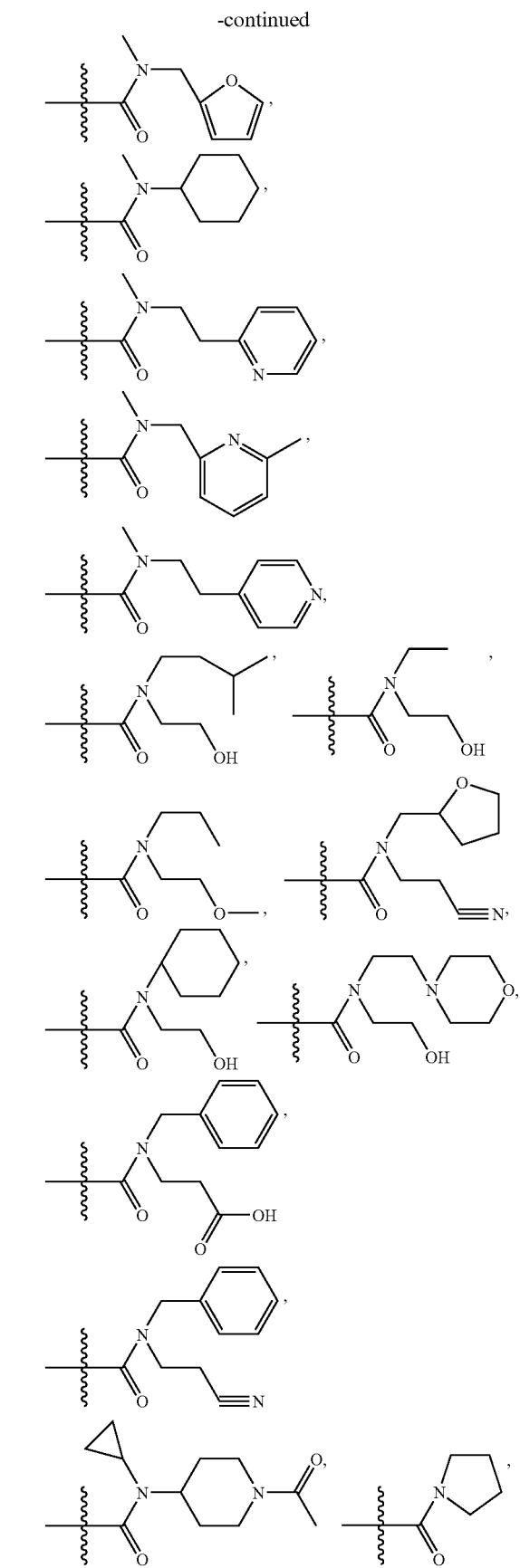

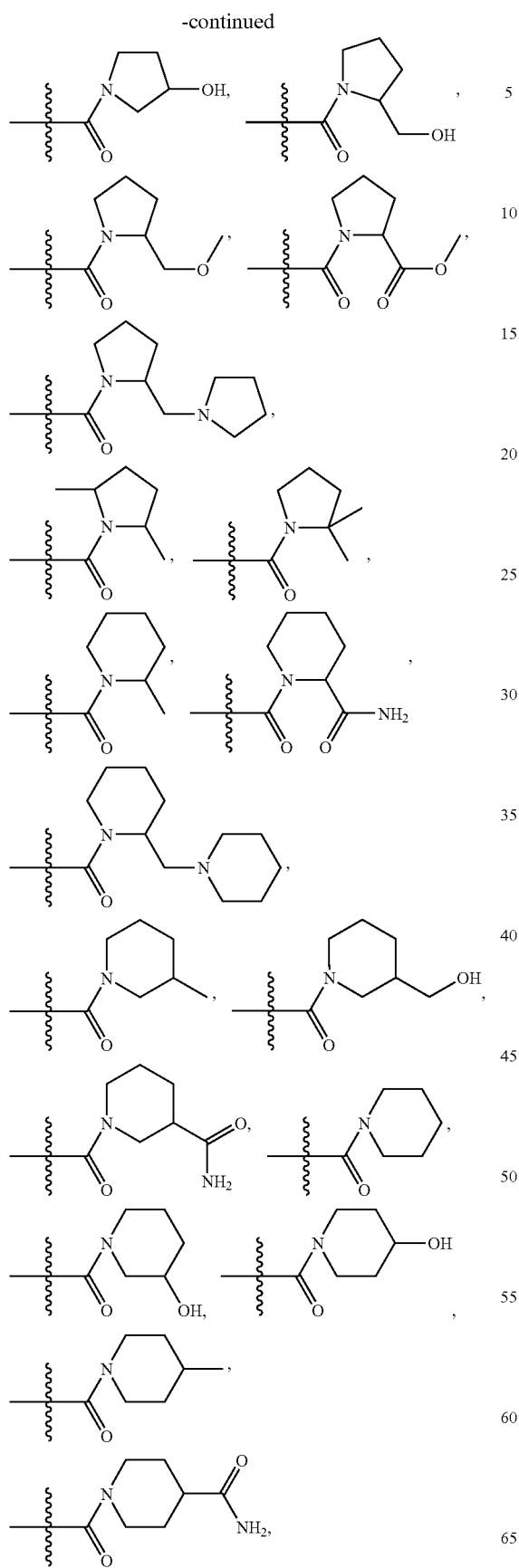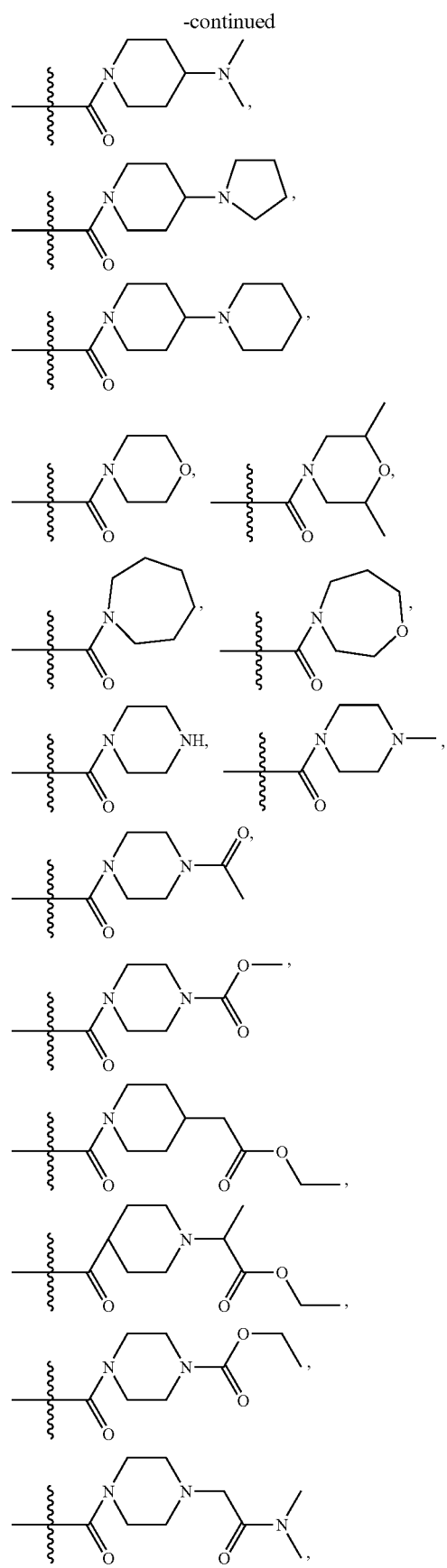

-continued
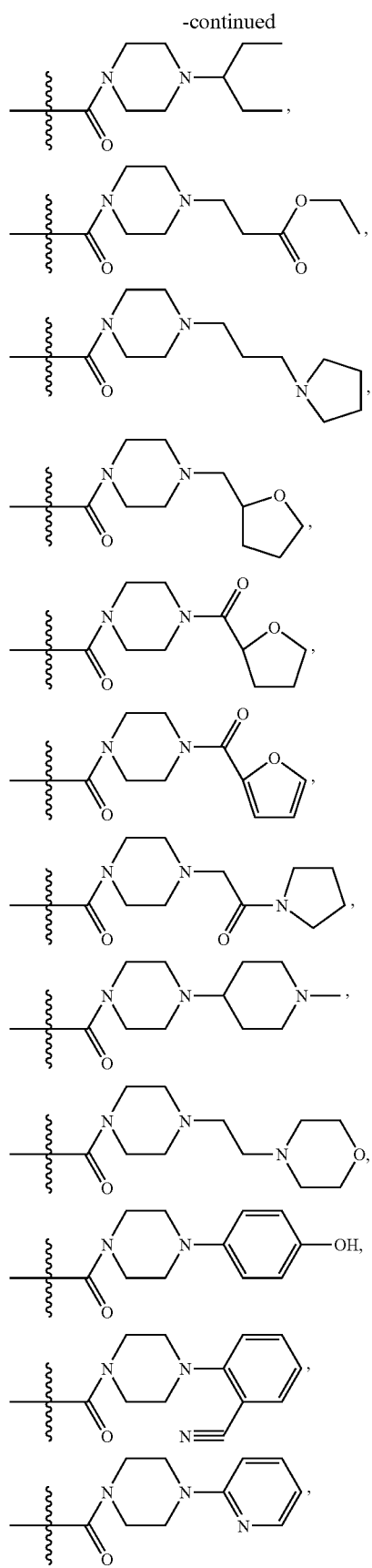
-continued
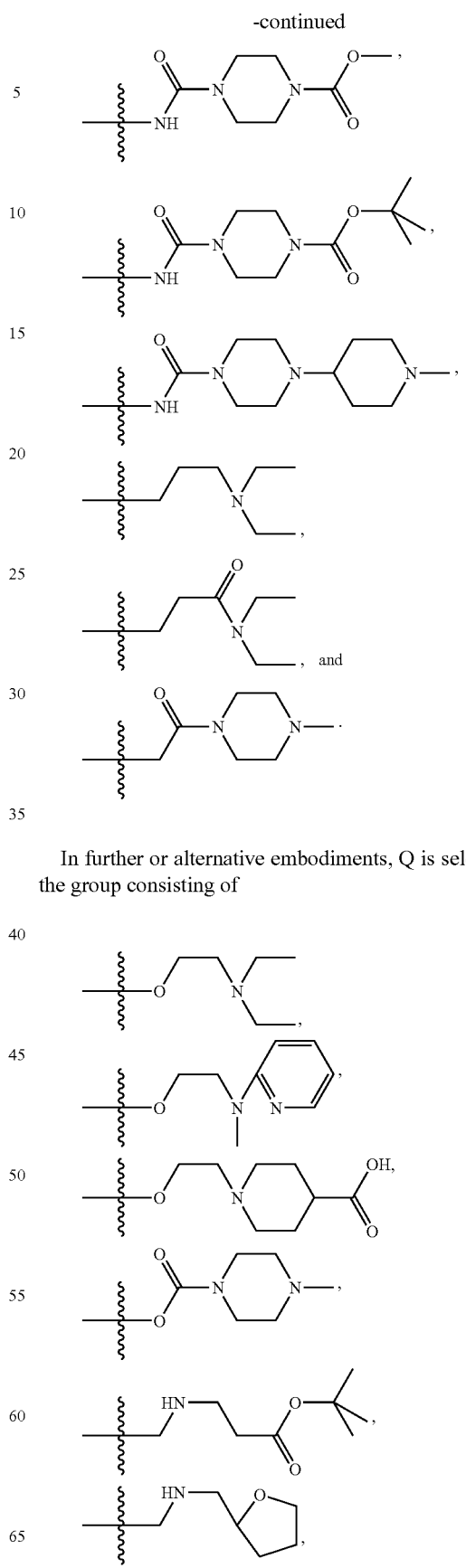
In further or alternative embodiments, Q is selected from the group consisting of 197
-continued
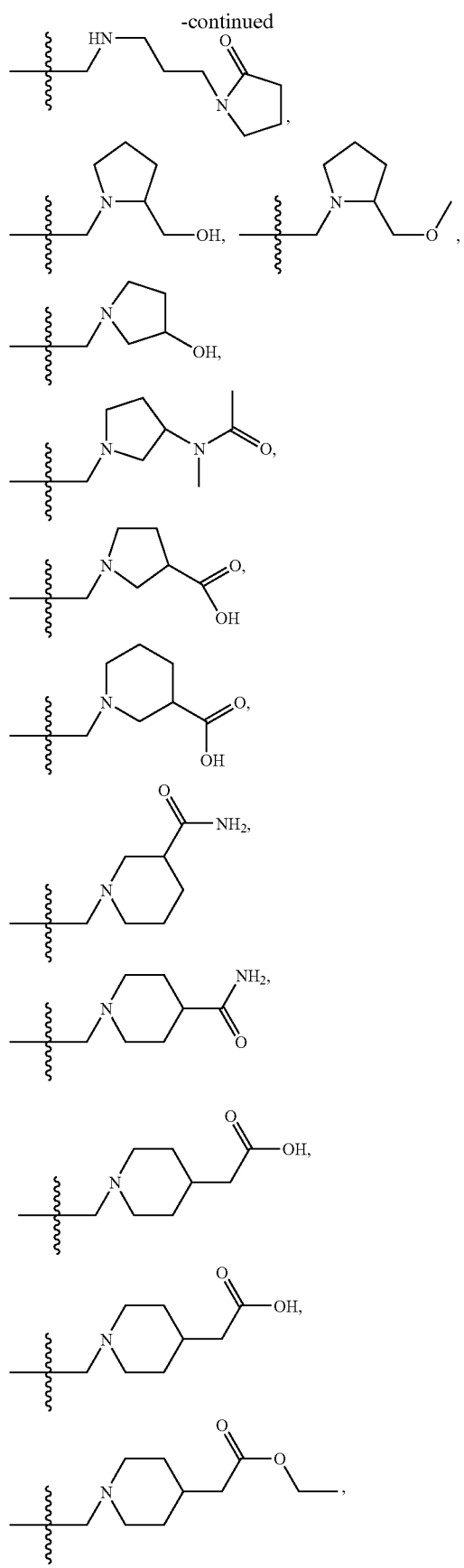
198
-continued
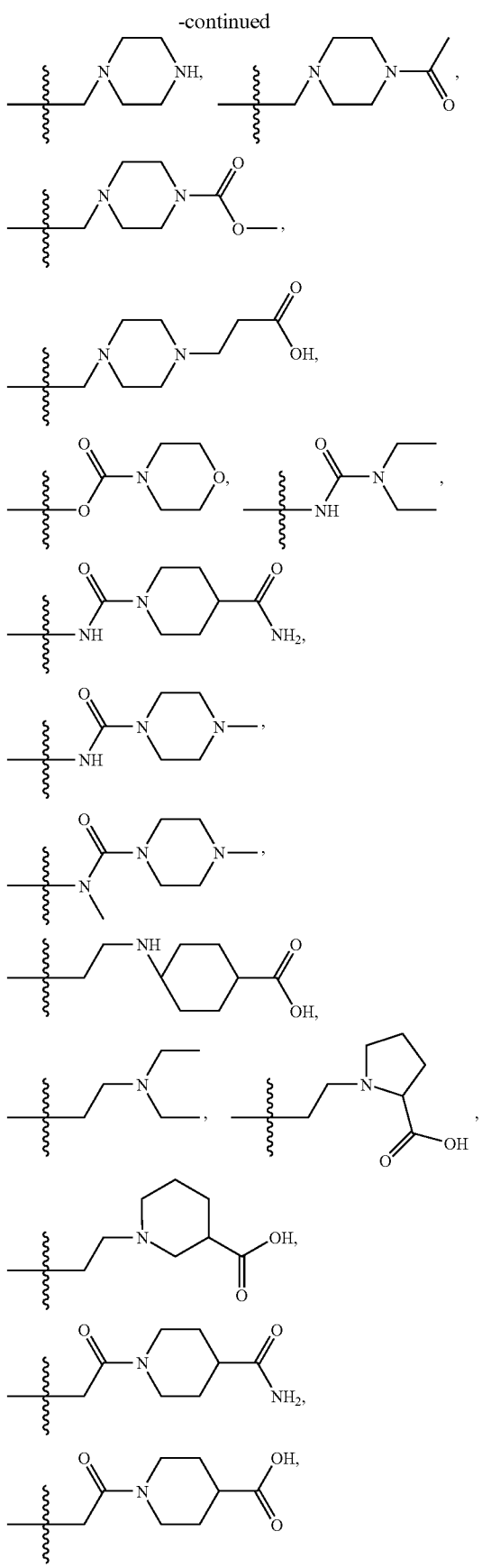

-continued
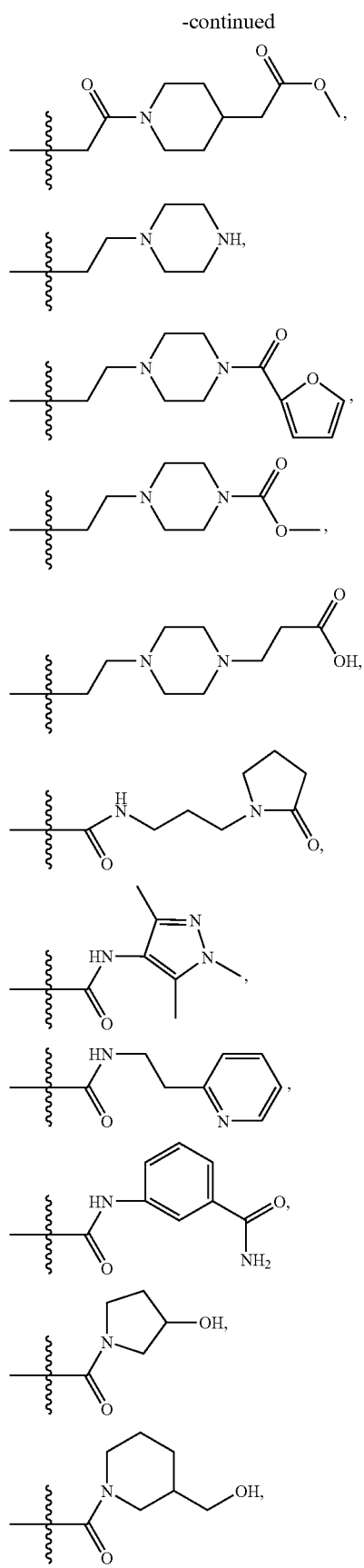
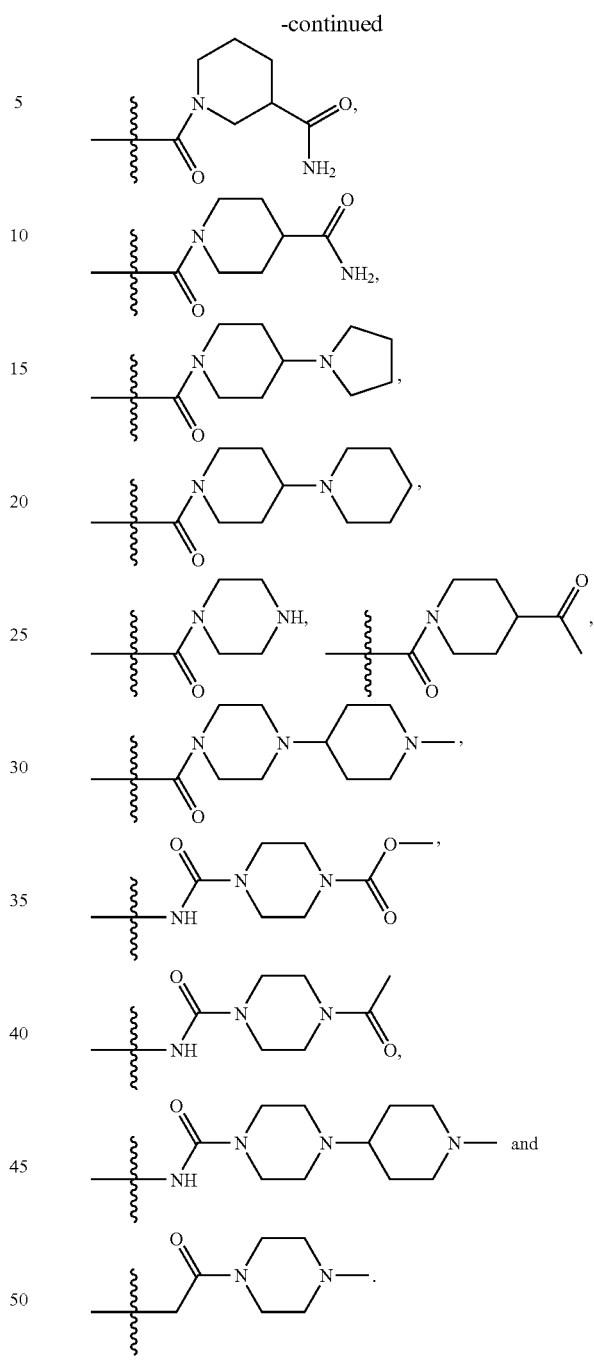
In further or alternative embodiments, Ar is selected from the group consisting of
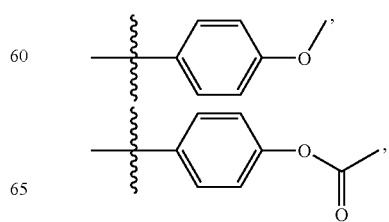

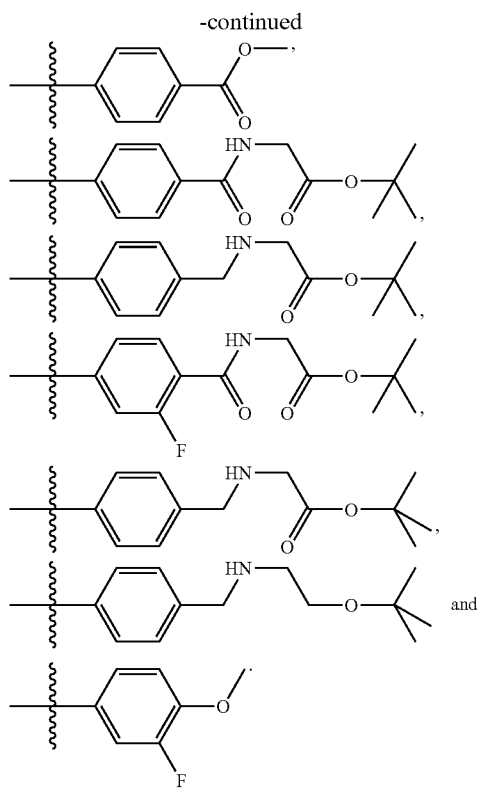

In further or alternative embodiments, the compound is selected from the group consisting of: tert-butyl 2-(4-(2-(4-(2-(diethylamino)ethoxy)phenylamino)pyrimidin-5-yl)-2-fluorobenzamido)acetate, tert-butyl 2-(4-(2-(4-(2-(diethylamino)ethoxy)phenylamino)pyrimidin-5-yl)-2-fluorobenzylamino)acetate, tert-butyl 2-(4-(2-(4-(2-(diethylamino)ethoxy)phenylamino)pyrimidin-5-yl)benzylamino)acetate, 2,2'-(2-(4-(5-(4-methoxyphenyl)pyrimidin-2-ylamino)phenoxy)ethylazanediyl)diethanol, 1-(4-(5-(4-methoxyphenyl)pyrimidin-2-ylamino)phenethyl)piperidine-4-carboxylic acid, tert-butyl 2-(4-(2-(4-(2-(diethylamino)ethoxy)phenylamino)pyrimidin-5-yl)benzamido)acetate, methyl 1-(4-(5-(4-methoxyphenyl)pyrimidin-2-ylamino)phenethyl)piperidine-4-carboxylate, N-(4-(2-(diethylamino)ethyl)phenyl)-5-(4-methoxyphenyl)pyrimidin-2-amine, 1-(2-(4-(5-(4-methoxyphenyl)pyrimidin-2-ylamino)phenoxy)ethyl)piperidine-4-carboxylic acid, N-(4-(2-(diethylamino)ethoxy)phenyl)-5-(4-methoxyphenyl)pyrimidin-2-amine, tert-butyl 2-(4-(2-(4-(2-morpholinoethoxy)phenylamino)pyrimidin-5-yl)benzamido)acetate, tert-butyl 2-(4-(2-(4-(2-(4-carbamoylpiperidin-1-yl)ethoxy)phenylamino)pyrimidin-5-yl)benzamido)acetate, 4-(2-(4-(2-(diethylamino)ethoxy)phenylamino)pyrimidin-5-yl)phenyl acetate, ethyl 2-(2-(diethylamino)ethoxy)-5-(5-(4-methoxyphenyl)pyrimidin-2-ylamino)benzoate, 4-(5-(4-methoxyphenyl)pyrimidin-2-ylamino)phenyl 4-methylpiperazine-1-carboxylate, 5-(4-methoxyphenyl)-N-(4-(2-(methyl(pyridin-2-yl)amino)ethoxy)phenyl)pyrimidin-2-amine, methyl 4-(2-(4-(2-(diethylamino)ethoxy)phenylamino)pyrimidin-5-yl)benzoate, N-(4-(2-(diethylamino)ethoxy)phenyl)-5-(3-fluoro-4-methoxyphenyl)pyrimidin-2-amine, 2-(2-(diethylamino)ethoxy)-4-(5-(4-methoxyphenyl)pyrimidin-2-ylamino)benzoic acid, methyl 2-(2-(diethylamino)ethoxy)-4-(5-(4-methoxyphenyl)pyrimidin-2-ylamino)benzoate, N-(3-(2-(diethylamino)ethoxy)phenyl)-5-(4-methoxyphenyl)pyrimidin-2-amine, N-(3-(2-(diethylamino)ethyl)phenyl)-5-(4-methoxyphenyl)pyrimidin-2-amine, 1-(4-(5-(4-methoxyphenyl)pyrimidin-2-ylamino)benzyl)piperidine-4-carboxamide, 1-(4-(5-(4-methoxyphenyl)pyrimidin-2-ylamino)benzyl)piperidine-3-carboxamide, tert-butyl 3-(4-(5-(4-methoxyphenyl)pyrimidin-2-ylamino)benzylamino)propanoate, 5-(4-methoxyphenyl)-N-(4-(piperazin-1-ylmethyl)phenyl)pyrimidin-2-amine, 1-(4-(4-(5-(4-methoxyphenyl)pyrimidin-2-ylamino)benzyl)piperazin-1-yl)ethanone, (4-(4-(5-(4-methoxyphenyl)pyrimidin-2-ylamino)benzyl)piperazin-1-yl)(tetrahydrofuran-2-yl)methanone, 1-(3-(4-(5-(4-methoxyphenyl)pyrimidin-2-ylamino)benzylamino)propyl)pyrrolidin-2-one, (S)-(1-(4-(5-(4-methoxyphenyl)pyrimidin-2-ylamino)benzyl)pyrrolidin-2-yl)methanol, (R)—N-(4-((2-(methoxymethyl)pyrrolidin-1-yl)methyl)phenyl)-5-(4-methoxyphenyl)pyrimidin-2-amine, 1-(4-(5-(4-methoxyphenyl)pyrimidin-2-ylamino)benzyl)pyrrolidin-3-ol, methyl 1-(4-(5-(4-methoxyphenyl)pyrimidin-2-ylamino)benzylamino)cyclopentanecarboxylate, 4-(4-(5-(4-methoxyphenyl)pyrimidin-2-ylamino)benzyl)-2-methylpiperazine-1-carboxylic acid, 3-(4-(4-(5-(4-methoxyphenyl)pyrimidin-2-ylamino)benzyl)piperazin-1-yl)propanoic acid, 1-(4-(5-(4-methoxyphenyl)pyrimidin-2-ylamino)benzyl)piperidine-3-carboxylic acid, ethyl 2-(1-(4-(5-(4-methoxyphenyl)pyrimidin-2-ylamino)benzyl)piperidin-4-yl)acetate, 2-(1-(4-(5-(4-methoxyphenyl)pyrimidin-2-ylamino)benzyl)piperidin-4-yl)acetic acid, 1-(4-(5-(4-methoxyphenyl)pyrimidin-2-ylamino)benzyl)pyrrolidine-3-carboxylic acid, 3-(5-(4-methoxyphenyl)pyrimidin-2-ylamino)phenyl morpholine-4-carboxylate, 3-(5-(4-methoxyphenyl)pyrimidin-2-ylamino)phenyl 4-methylpiperazine-1-carboxylate, 3-(5-(4-((2-tert-butoxy-2-oxoethylamino)methyl)phenyl)pyrimidin-2-ylamino)phenyl 4-methylpiperazine-1-carboxylate, methyl 4-(4-(5-(4-methoxyphenyl)pyrimidin-2-ylamino)benzyl)piperazine-1-carboxylate, 4-(5-(4-((2-tert-butoxy-2-oxoethylamino)methyl)phenyl)pyrimidin-2-ylamino)phenyl 4-methylpiperazine-1-carboxylate, N-(3-(5-(4-methoxyphenyl)pyrimidin-2-ylamino)phenyl)-4-methylpiperazine-1-carboxamide, 2-(4-(5-(4-methoxyphenyl)pyrimidin-2-ylamino)phenyl)-1-(4-methylpiperazin-1-yl)ethanone, N1-(3-(5-(4-methoxyphenyl)pyrimidin-2-ylamino)phenyl)piperidine-1,4-dicarboxamide, 3-(5-(4-methoxyphenyl)pyrimidin-2-ylamino)benzyl 4-methylpiperazine-1-carboxylate, 4-hydroxy-N-(3-(5-(4-methoxyphenyl)pyrimidin-2-ylamino)phenyl)piperidine-1-carboxamide, N-(4-(5-(4-methoxyphenyl)pyrimidin-2-ylamino)phenyl)-4-methylpiperazine-1-carboxamide, 1-(4-(5-(4-methoxyphenyl)pyrimidin-2-ylamino)phenethyl)piperidine-4-carboxamide, furan-2-yl(4-(4-(5-(4-methoxyphenyl)pyrimidin-2-ylamino)phenethyl)piperazin-1-yl)methanone, 5-(4-methoxyphenyl)-N-(4-(2-(piperazin-1-yl)ethyl)phenyl)pyrimidin-2-amine, N-(3-(5-(4-methoxyphenyl)pyrimidin-2-ylamino)phenyl)-N,4-dimethylpiperazine-1-carboxamide, 1-(4-(5-(4-methoxyphenyl)pyrimidin-2-ylamino)phenethyl)piperidine-3-carboxamide, 1-(4-(5-(4-methoxyphenyl)pyrimidin-2-ylamino)phenethyl)piperidine-3-carboxylic acid, methyl 4-(4-(5-(4-methoxyphenyl)pyrimidin-2-ylamino)phenethyl)piperazine-1-carboxylate, 1-(4-(5-(4-methoxyphenyl)pyrimidin-2-ylamino)phenethyl)piperidine-3-carboxylic acid, 2-(1-(4-(5-(4-methoxyphenyl)pyrimidin-2-ylamino)phenethyl)piperidin-4-yl)acetic acid, methyl 2-(1-(4-(5-(4-methoxyphenyl)pyrimidin-2-ylamino)phenethyl)piperidin-4-yl)acetate, (3-(hydroxymethyl)piperidin-1-yl)(4-(5-(4-methoxyphenyl)pyrimidin-2-ylamino)phenyl)methanone, (3-hydroxypyrrolidin-1-yl)(4-(5-(4- methoxyphenyl)pyrimidin-2-ylamino)phenyl)methanone, 1-(4-(5-(4-methoxyphenyl)pyrimidin-2-ylamino)benzoyl) piperidine-4-carboxamide, 3-(4-(4-(5-(4-methoxyphenyl) pyrimidin-2-ylamino)phenethyl)piperazin-1-yl)propanoic acid, (S)-1-(4-(5-(4-methoxyphenyl)pyrimidin-2-ylamino) phenethyl)pyrrolidine-2-carboxylic acid, 4-(4-(5-(4-methoxyphenyl)pyrimidin-2-ylamino)phenethylamino)cyclohexanecarboxylic acid, 4-(5-(4-methoxyphenyl)pyrimidin-2-ylamino)-N-(3-(2-oxopyrrolidin-1-yl)propyl)benzamide, 1-(4-(5-(4-methoxyphenyl)pyrimidin-2-ylamino)benzoyl) piperidine-3-carboxamide, N-(3-carbamoylphenyl)-4-(5-(4-methoxyphenyl)pyrimidin-2-ylamino)benzamide, 1,4'-bipiperidin-1'-yl(4-(5-(4-methoxyphenyl)pyrimidin-2-ylamino) phenyl)methanone, (4-(5-(4-methoxyphenyl)pyrimidin-2-ylamino)phenyl)(4-(pyrrolidin-1-yl)piperidin-1-yl) methanone, 4-(5-(4-methoxyphenyl)pyrimidin-2-ylamino)-N-(2-(pyridin-2-yl)ethyl)benzamide, 4-(5-(4-methoxyphenyl)pyrimidin-2-ylamino)-N-(1,3,5-trimethyl-1H-pyrazol-4-yl)benzamide, (4-(furan-2-carbonyl) piperazin-1-yl)(3-(5-(4-methoxyphenyl)pyrimidin-2-ylamino)phenyl)methanone, 3-(5-(4-methoxyphenyl) pyrimidin-2-ylamino)-N-(1,3,5-trimethyl-1H-pyrazol-4-yl) benzamide, (3-(5-(4-methoxyphenyl)pyrimidin-2-ylamino) phenyl)(4-(1-methylpiperidin-4-yl)piperazin-1-yl) methanone, 1-(4-(3-(5-(4-methoxyphenyl)pyrimidin-2-ylamino)benzoyl)piperazin-1-yl)ethanone, (3-(5-(4-methoxyphenyl)pyrimidin-2-ylamino)phenyl)(4-(pyrrolidin-1-yl)piperidin-1-yl)methanone, 1,4'-bipiperidin-1'-yl(3-(5-(4-methoxyphenyl)pyrimidin-2-ylamino)phenyl) methanone, 1-(3-(5-(4-methoxyphenyl)pyrimidin-2-ylamino)benzoyl)piperidine-3-carboxamide, N-(3-(5-(4-methoxyphenyl)pyrimidin-2-ylamino)phenyl)-4-(1-methylpiperidin-4-yl)piperazine-1-carboxamide, methyl 4-(3-(5-(4-methoxyphenyl)pyrimidin-2-ylamino)phenylcarbamoyl)piperazine-1-carboxylate, (R)-1-(4-(5-(4-methoxyphenyl)pyrimidin-2-ylamino)phenethyl)piperidine-3-carboxylic acid, (4-(5-(4-methoxyphenyl)pyrimidin-2-ylamino) phenyl)(piperazin-1-yl)methanone, 4-acetyl-N-(3-(5-(4-methoxyphenyl)pyrimidin-2-ylamino)phenyl)piperazine-1-carboxamide, and (3-(5-(4-methoxyphenyl)pyrimidin-2-ylamino)phenyl)(piperazin-1-yl)methanone.

In further or alternative embodiments, Q of the compound having the structure of Formula (1) is selected from the group consisting of

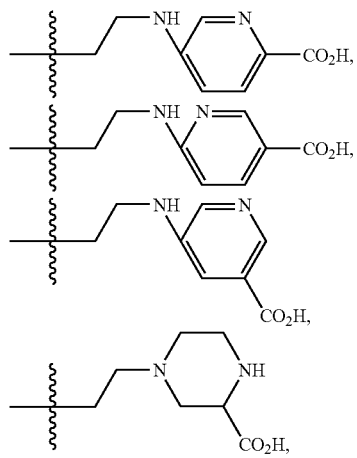

-continued

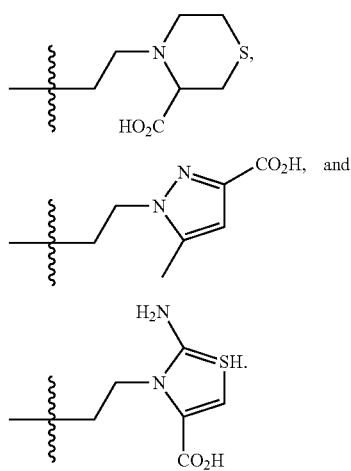

In further or alternative embodiments, Q of the compound having the structure of Formula (1) is selected from the group consisting of

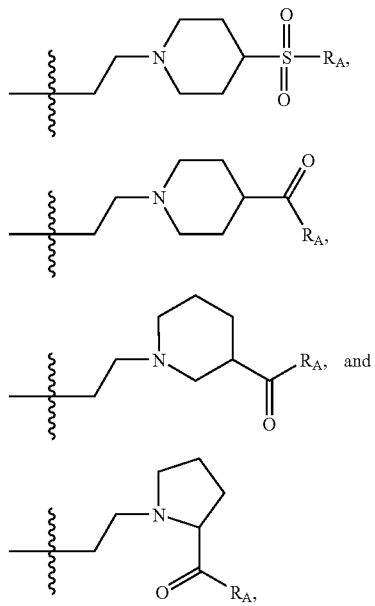

wherein $R_A$ is selected from —$NH_2$, —$NEt_2$, and —NH$(CH_2)_n$OH; and n is 1 to 6.

In further or alternative embodiments, Q of the compound having the structure of Formula (1) is

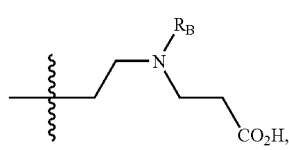

wherein $R_B$ is selected from the group consisting of

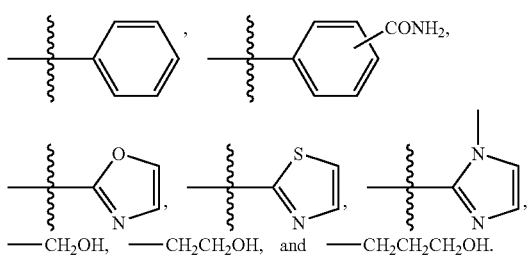

—CH$_2$OH, —CH$_2$CH$_2$OH, and —CH$_2$CH$_2$CH$_2$OH.

In further or alternative embodiments, Q of the compound having the structure of Formula (1) is

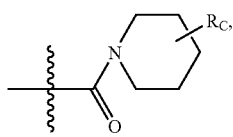

wherein R$_C$ is at 2, 3, or 4 position of the piperidine ring; and R$_C$ is selected from the group consisting of —C(O)NHEt, —C(O)NEt$_2$, c-butyl, c-pentyl, —C(O)NH-thiazole, oxazole, thiazole, —S(O)$_2$NH$_2$, —S(O)$_2$NHEt, and —S(O)$_2$NEt$_2$ In further or alternative embodiments, Q of the compound having the structure of Formula (1) is selected from the group consisting of

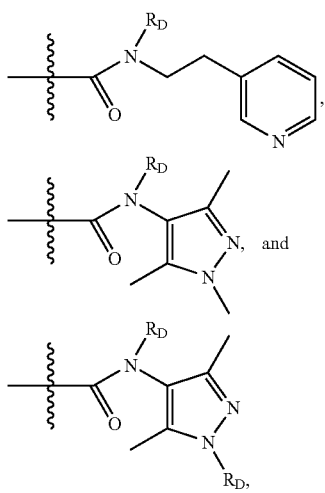

wherein each R$_D$ is independently selected from —(CH$_2$)$_k$OH or —(CH$_2$)$_k$CO$_2$H; and k is 1 to 6.

In further or alternative embodiments, Q of the compound having the structure of Formula (1) is

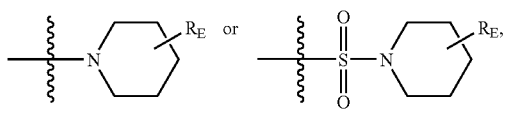

wherein R$_E$ is at 2, 3, or 4 position of the piperidine ring; and R$_E$ is selected from the group consisting of —C(O)NH$_2$, —C(O)NHEt, and —C(O)NEt$_2$.

In further or alternative embodiments, Q of the compound having the structure of Formula (1) is selected from the group consisting of

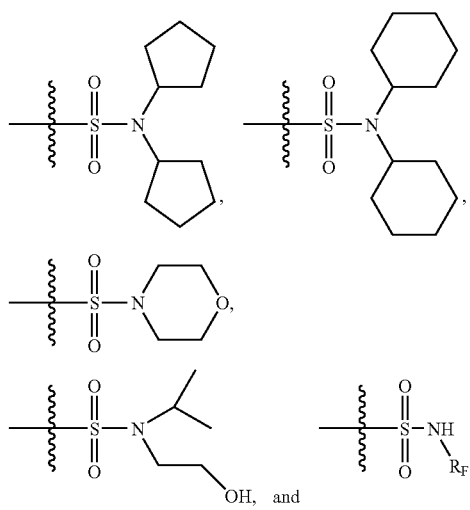

wherein R$_F$ is thiazole, pyrazole, or isoxazole.

In further or alternative embodiments, Q of the compound having the structure of Formula (46) is selected from the group consisting of

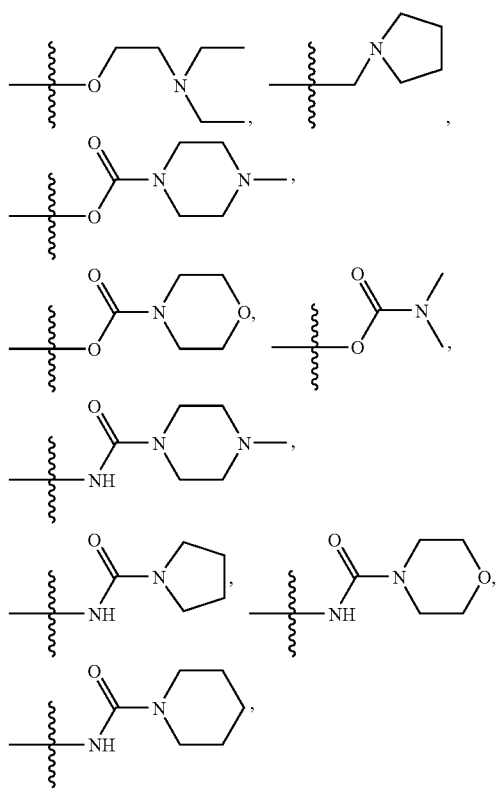

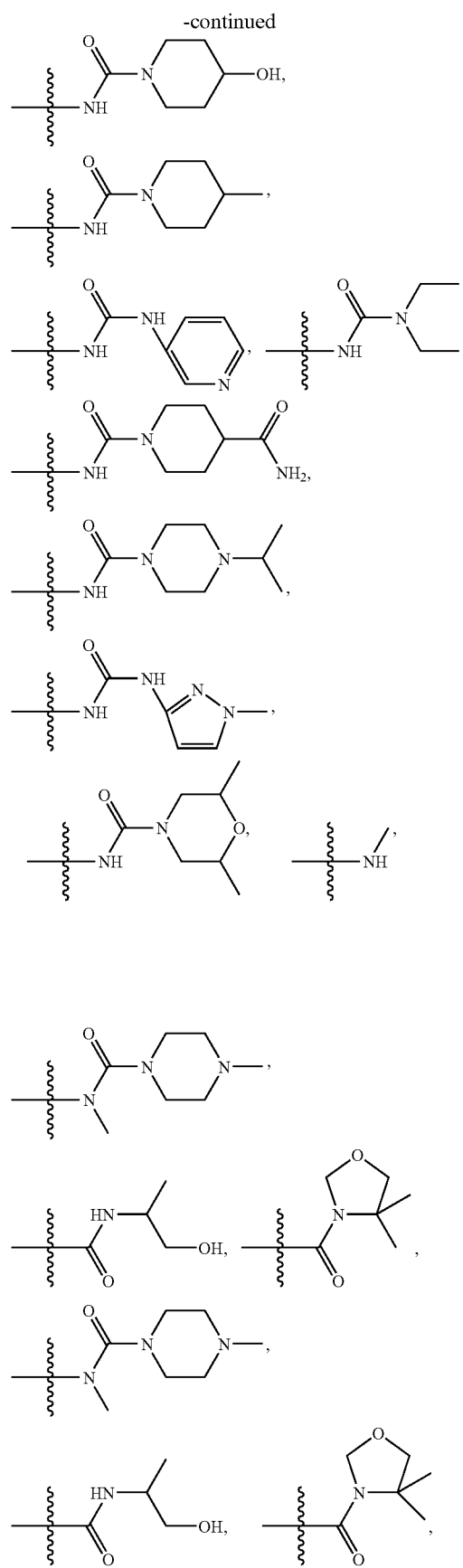
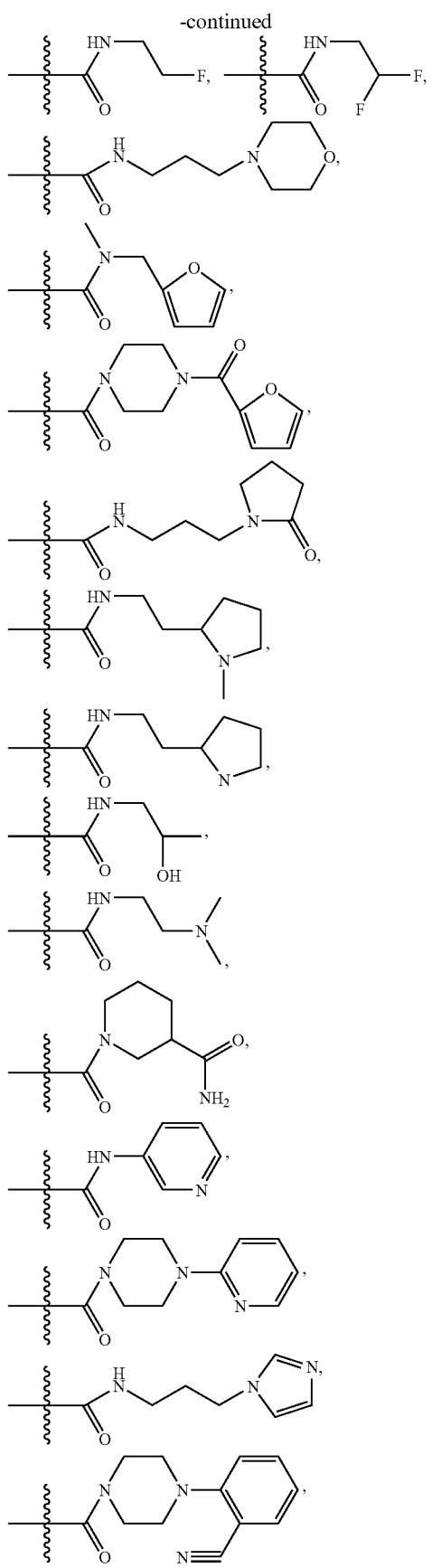

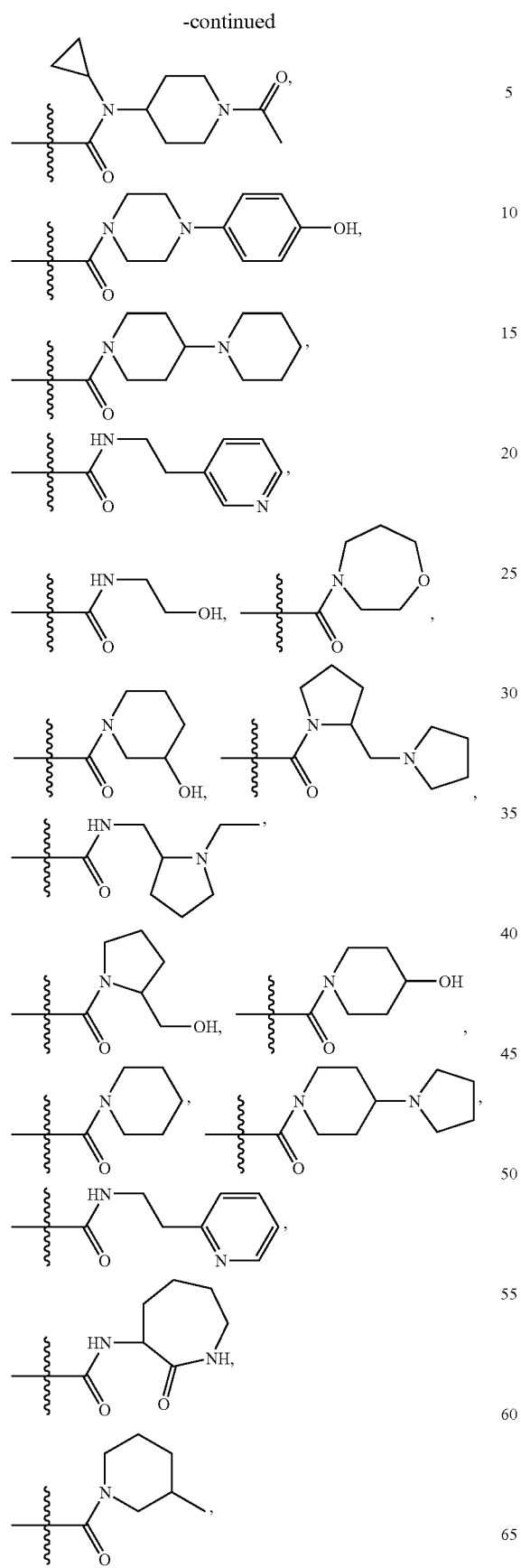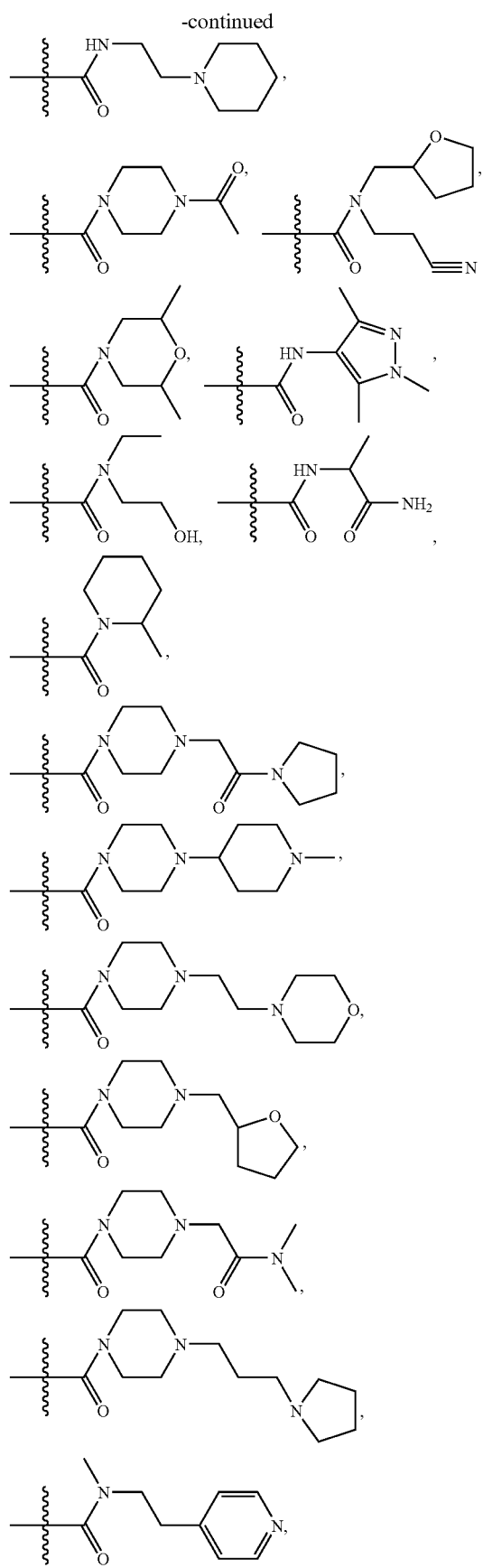

-continued

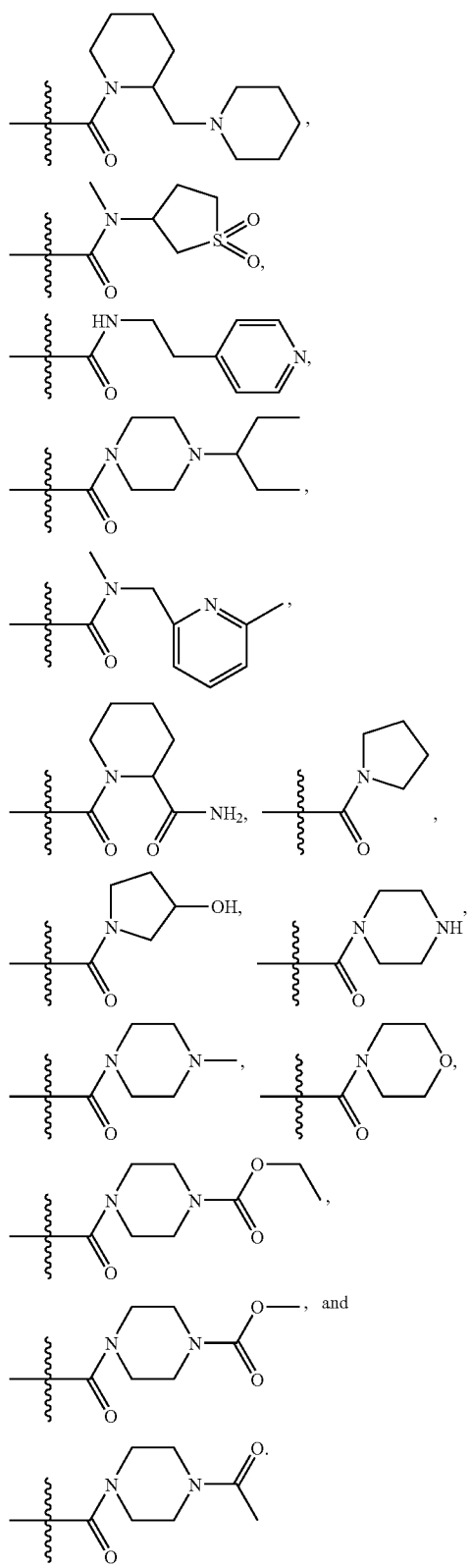

In further or alternative embodiments, Q of the compound having the structure of Formula (46) is selected from the group consisting of

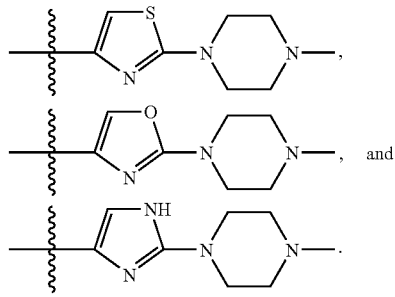, and

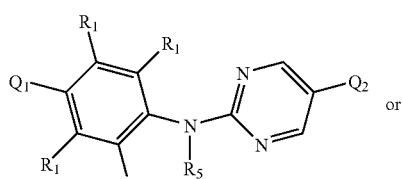

In another aspect are methods of using compounds having the structure of Formula (A) or Formula (B) in the manufacture of a medicament for treating a disease or condition in an animal in which c-kit receptor activity contributes to the pathology and/or symptomology of the disease or condition:

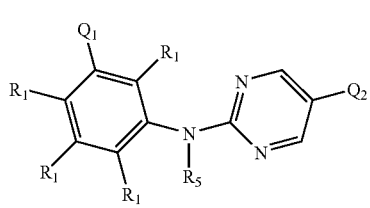

wherein;

$Q_1$ is H, halogen, a group comprising a non-aromatic tertiary amine, a group comprising a non-aromatic secondary amine, or is an optionally substituted moiety selected from the group consisting of: -L-alkyl, -L-cycloalkyl, -L-heteroalkyl, -L-haloalkyl, -L-aryl, -L-heterocycloalkyl, and -L-heteroaryl; wherein L is selected from a bond, —O—, —NH—, —S—, —C(O)—, —C(S)—, —C(O)O—, —C(O)NH—, —S(O)—, —S(O)$_2$—, —OC(O)—, —C(O)NR" (CR"$_2$)$_{1-6}$C(O)O—, —CR"$_2$NR"CR"$_2$C(O)O—, —C(O)—NR"YC(O)O—, —C(O)NR"NR"C(O)O—, and —S(O)NH—; and Y is optionally substituted arylene or heteroarylene;

each $R_1$ is independently selected from the group consisting of H, halogen, and an optionally substituted moiety selected from -$L_1$-alkyl, -$L_1$-cycloalkyl, -$L_1$-heteroalkyl, -$L_1$-haloalkyl, -$L_1$-aryl, -$L_1$-heterocycloalkyl, and -$L_1$-heteroaryl; wherein $L_1$ is selected from a bond, —O—, —NH—, —S—, —C(O)—, —C(S)—, —C(O)O—, —C(O)NH—, —S(O)—, —S(O)$_2$—, —C(O)NR"(CR"$_2$)$_{1-6}$C(O)O—, —OC(O)—, —CR"$_2$NR"CR"$_2$C(O)O—, —C(O)—NR"Y'C(O)O—, —C(O)NR"NR"C(O)O—, and —S(O)NH—; and Y' is optionally substituted arylene or heteroarylene;

$Q_2$ is selected from the group consisting of H, halogen, and a group comprising an optionally substituted moiety selected from -L₆-alkyl, -L₆-cycloalkyl, -L₆-heteroalkyl, -L₆-haloalkyl, -L₆-aromatic carbocycle, -L₆-heterocycloalkyl, and -L₆-aromatic heterocycle; wherein $L_6$ is selected from a bond, —O—, —NH—, —S—, —C(O)—, —C(S)—, —C(O)O—, —C(O)NH—, —S(O)—, —S(O)$_2$—, —C(O)NR"(CR"$_2$)$_{1-6}$C(O)O—, —OC(O)—, —CR"$_2$NR"CR"$_2$C(O)O—, —C(O)—NR"Y"C(O)O—, —C(O)NR"NR"C(O)O—, and —S(O)NH—; and Y" is optionally substituted arylene or heteroarylene;

each R" is independently H, OH, halogen, $C_{1-6}$alkyl, substituted $C_{1-6}$alkyl, $C_{1-6}$alkoxy, halo-$C_{1-6}$alkyl, halo-$C_{1-6}$alkoxy, aryl, haloaryl, or heteroaryl;

any two $R_1$ groups together may form an optionally substituted 5 to 8-membered heterocyclic, cycloalkyl, or aryl ring;

$R_5$ is selected from the group consisting of H, and an optionally substituted moiety selected from -L₅-H, -L₅-alkyl, -L₅-cycloalkyl, -L₅-heteroalkyl, -L₅-haloalkyl, -L₅-aryl, -L₅-heterocycloalkyl, and -L₅-heteroaryl, wherein $L_5$ is selected from a bond, —R'O—, —R'N(H)—, —R'S—, —R'C(O)—, —R'C(S)—, —R'C(O)O—, and —R'C(O)NH—;

each R' is independently selected from the group consisting of a bond, alkylene, substituted alkylene, heteroalkylene, substituted heteroalkylene, alkenylene, substituted alkenylene, cycloalkylene, substituted cycloalkylene, heteroalkylene, substituted heteroalkylene, heterocycloalkylene, substituted heterocycloalkylene, arylene, substituted arylene, heteroarylene, substituted heteroarylene, alkarylene, substituted alkarylene, aralkylene, and substituted aralkylene; and any $R_1$ and $R_5$ taken together may form an optionally substituted 5 to 8-membered heterocyclic, cycloalkyl, or aryl ring;

or a pharmaceutically acceptable salt, pharmaceutically acceptable N-oxide, pharmaceutically active metabolite, pharmaceutically acceptable prodrug, or pharmaceutically acceptable solvate thereof.

In a further or alternative embodiment of this aspect, compounds of Formula (A) or Formula (B) are compounds having the structure of Formula (1) or Formula (46):

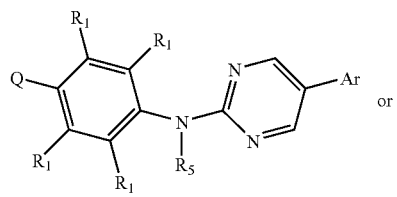

(1)

or

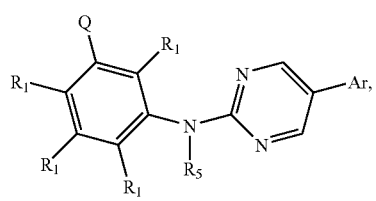

(46)

wherein:
Ar is a group comprising a moiety selected from an optionally substituted five-membered aromatic heterocycle, an optionally substituted five-membered aromatic carbocycle, an optionally substituted six-membered aromatic heterocycle, and a substituted, optionally further substituted six-membered aromatic carbocycle;

Q is a group comprising a non-aromatic tertiary amine or a non-aromatic secondary amine, with the proviso that Q is not —NR$_a$R$_b$ or —SO$_2$NR$_a$R$_b$; wherein each of R$_a$ and R$_b$ is independently H or $C_{1-6}$alkyl optionally substituted by mono- or di-alkyl ($C_{1-6}$) amino;

each $R_1$ is independently selected from the group consisting of H, halogen, and an optionally substituted moiety selected from -L₁-alkyl, -L₁-cycloalkyl, -L₁-heteroalkyl, -L₁-haloalkyl, -L₁-aryl, -L₁-heterocycloalkyl, and -L₁-heteroaryl; wherein $L_1$ is selected from a bond, —O—, —NH—, —S—, —C(O)—, —C(S)—, —C(O)O—, —C(O)NH—, —S(O)—, —S(O)$_2$—, —C(O)NH(CR"$_2$)$_{1-6}$C(O)O—, —C(O)NR"NR"C(O)O—, and —S(O)NH—;

each R" is independently H, OH, halogen, $C_{1-6}$alkyl, substituted $C_{1-6}$alkyl, $C_{1-6}$alkoxy, halo-$C_{1-6}$alkyl, halo-$C_{1-6}$alkoxy, aryl, haloaryl, or heteroaryl;

or any two adjacent $R_1$ groups together may form an optionally substituted 5 to 8-membered heterocyclic, cycloalkyl, or aryl ring;

$R_5$ is selected from the group consisting of H, and an optionally substituted moiety selected from -L₅-H, -L₅-alkyl, -L₅-cycloalkyl, -L₅-heteroalkyl, -L₅-haloalkyl, -L₅-aryl, -L₅-heterocycloalkyl, and -L₅-heteroaryl; wherein $L_5$ is selected from a bond, —R'O—, —R'N(H)—, —R'S—, —R'C(O)—, —R'C(S)—, —R'C(O)O—, and —R'C(O)NH—;

each R' is independently selected from the group consisting of a bond, alkylene, substituted alkylene, heteroalkylene, substituted heteroalkylene, alkenylene, substituted alkenylene, cycloalkylene, substituted cycloalkylene, heteroalkylene, substituted heteroalkylene, heterocycloalkylene, substituted heterocycloalkylene, arylene, substituted arylene, heteroarylene, substituted heteroarylene, alkarylene, substituted alkarylene, aralkylene, and substituted aralkylene; and any $R_1$ and $R_5$ taken together may form an optionally substituted 5 to 8-membered heterocyclic, cycloalkyl, or aryl ring;

or a pharmaceutically acceptable salt, pharmaceutically acceptable N-oxide, pharmaceutically active metabolite, pharmaceutically acceptable prodrug, or pharmaceutically acceptable solvate thereof.

In further or alternative embodiments, the Ar is a group comprising a substituted, optionally further substituted six-membered aromatic heterocycle. In further or alternative embodiments, said optional substituents are selected from halogen, OH, halogen, $C_{1-6}$alkyl, $C_{1-6}$alkoxy, halo-$C_{1-6}$alkyl, halo-$C_{1-6}$alkoxy, aryl, haloaryl, or heteroaryl. In further or alternative embodiments, the compound is the compound of any of Formula (1) to Formula (54) in various embodiments described above.

In further or alternative embodiments, Ar is selected from the group consisting of

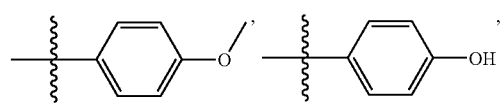

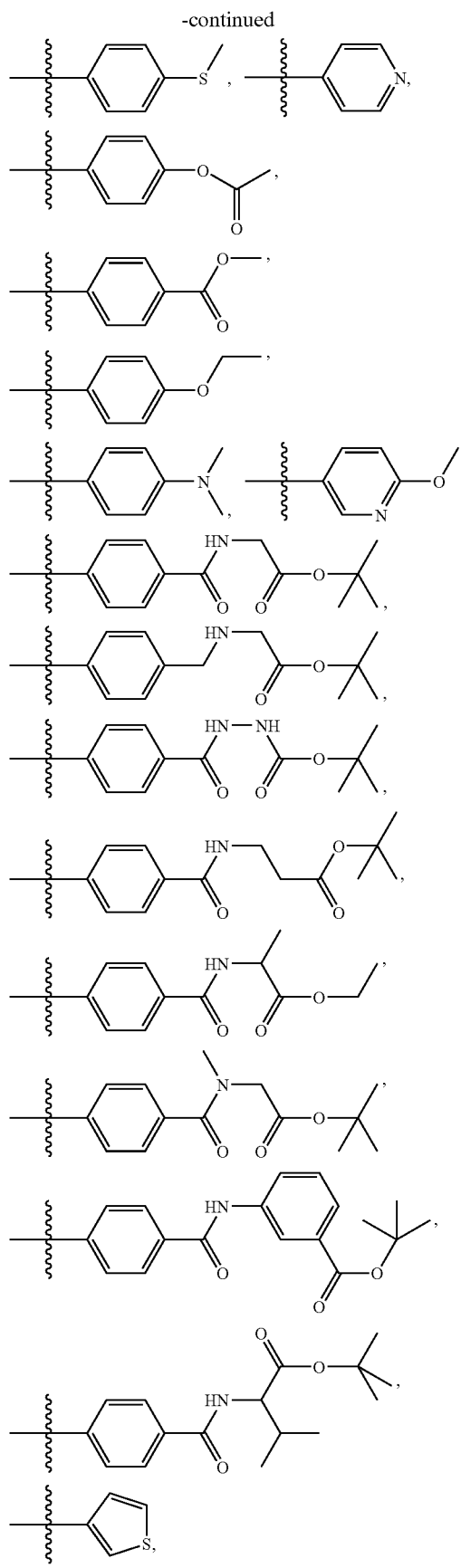
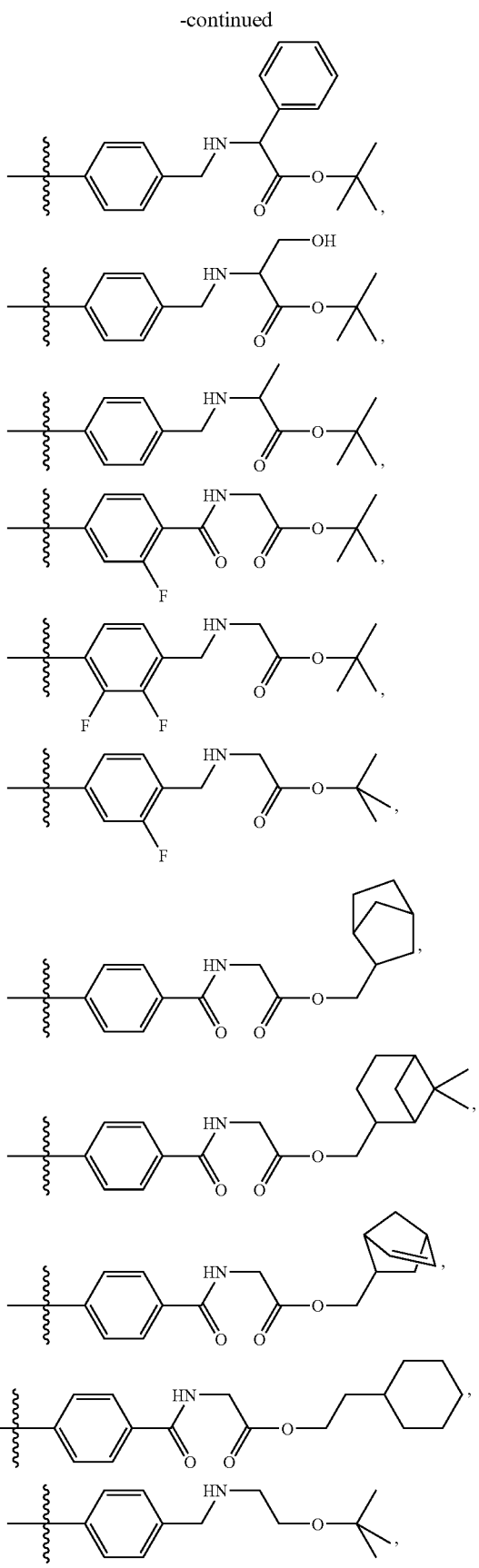

-continued
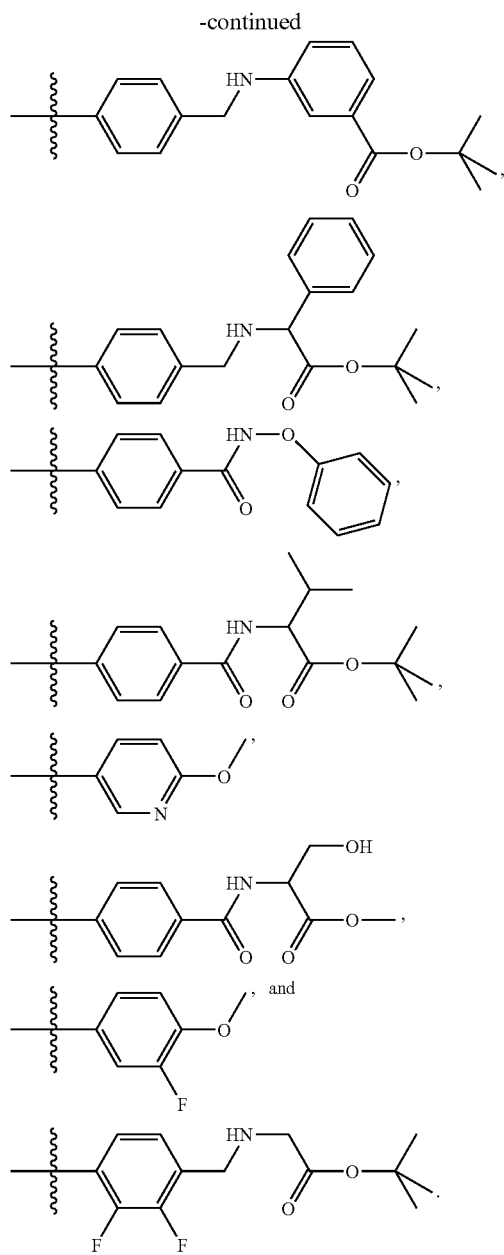
In further or alternative embodiments, Q is selected from the group consisting of
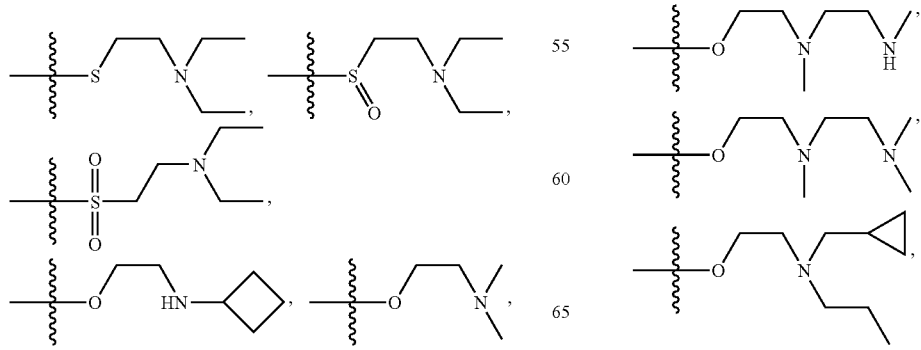
-continued
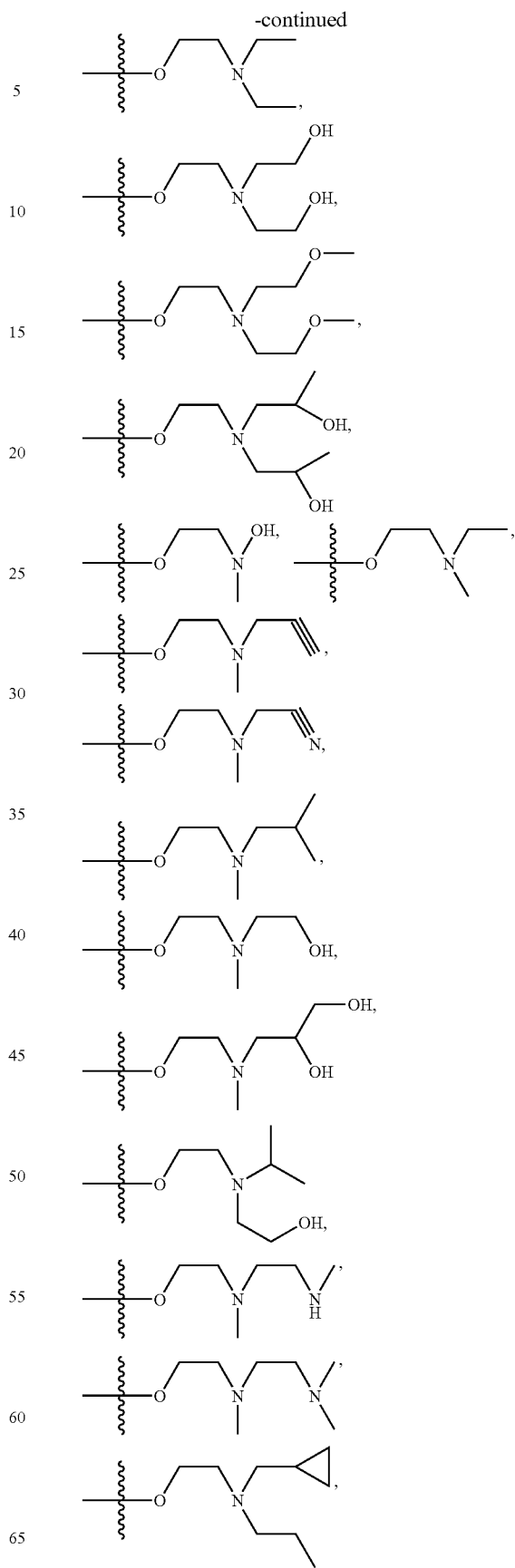

-continued
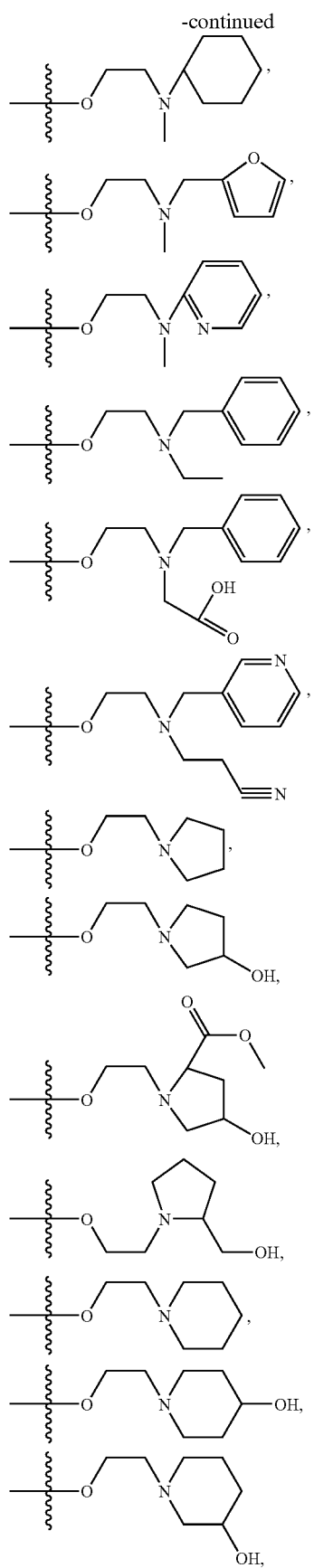
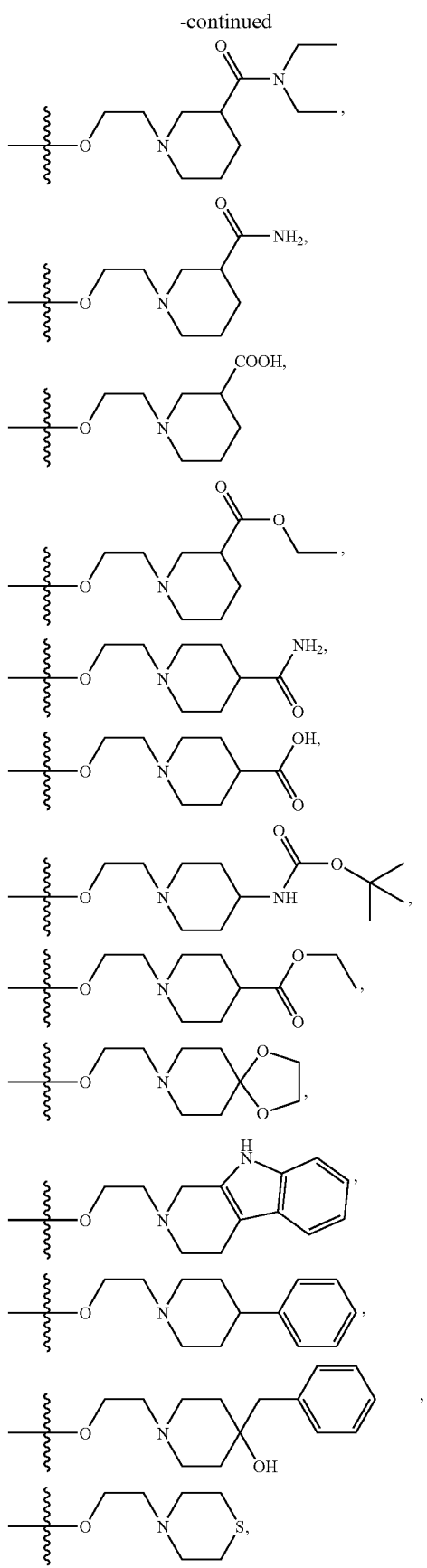

-continued
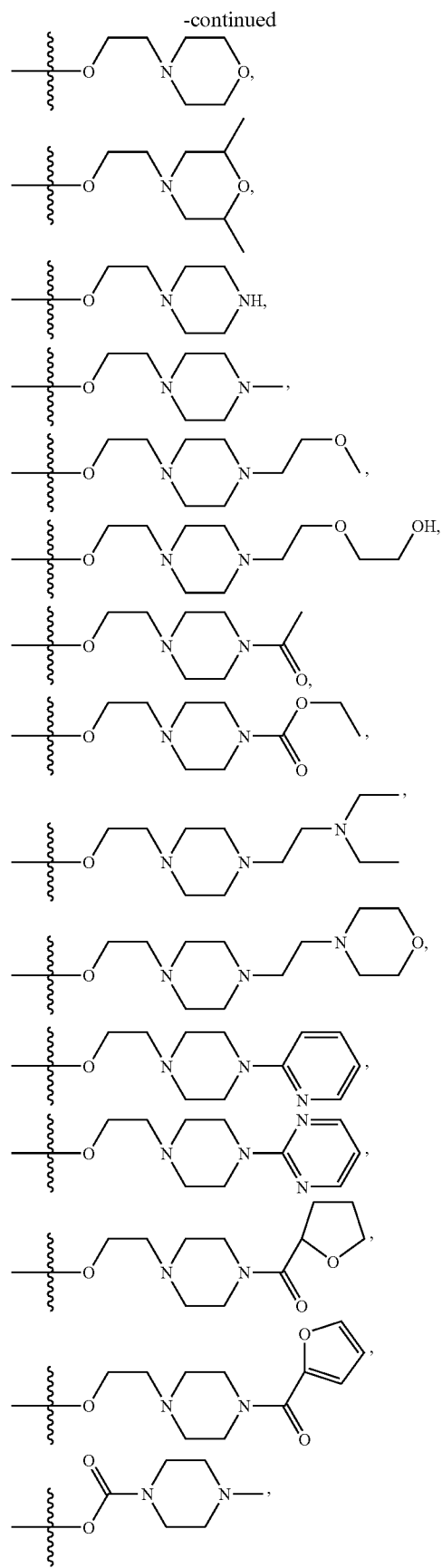
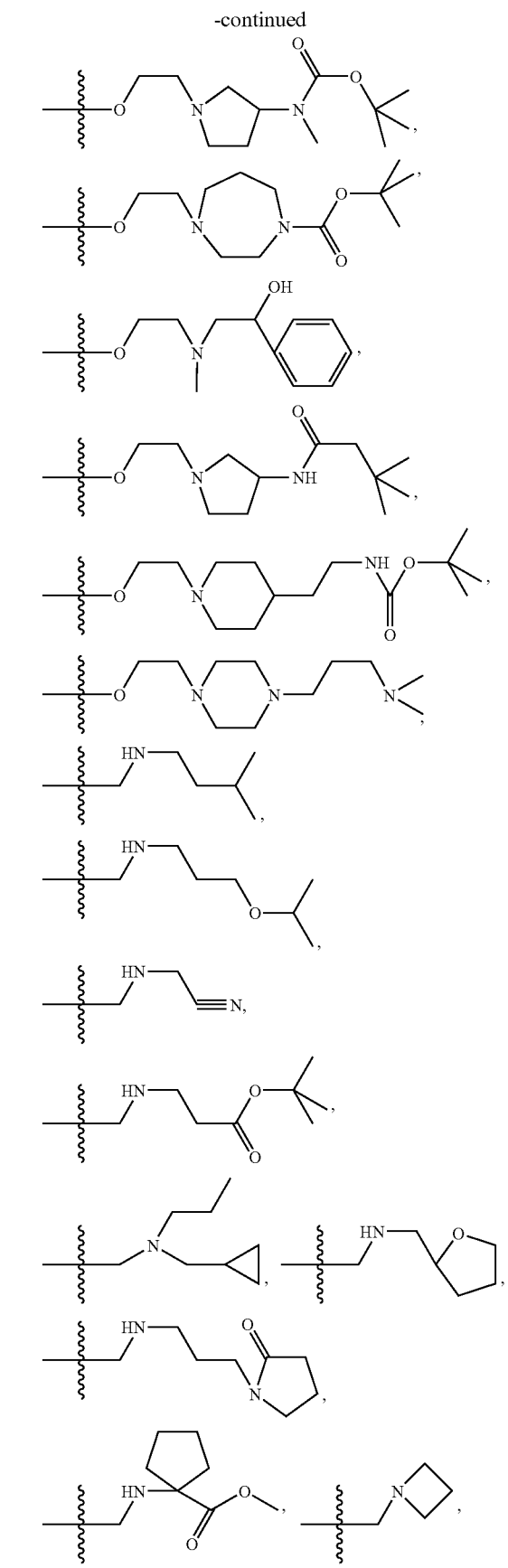

-continued
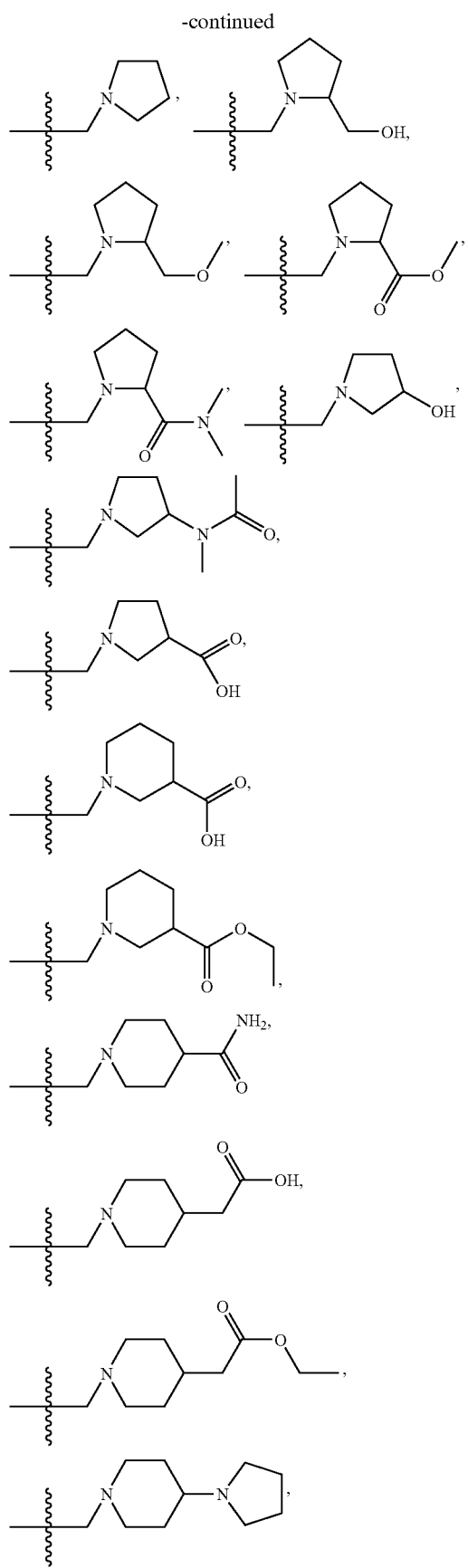
-continued
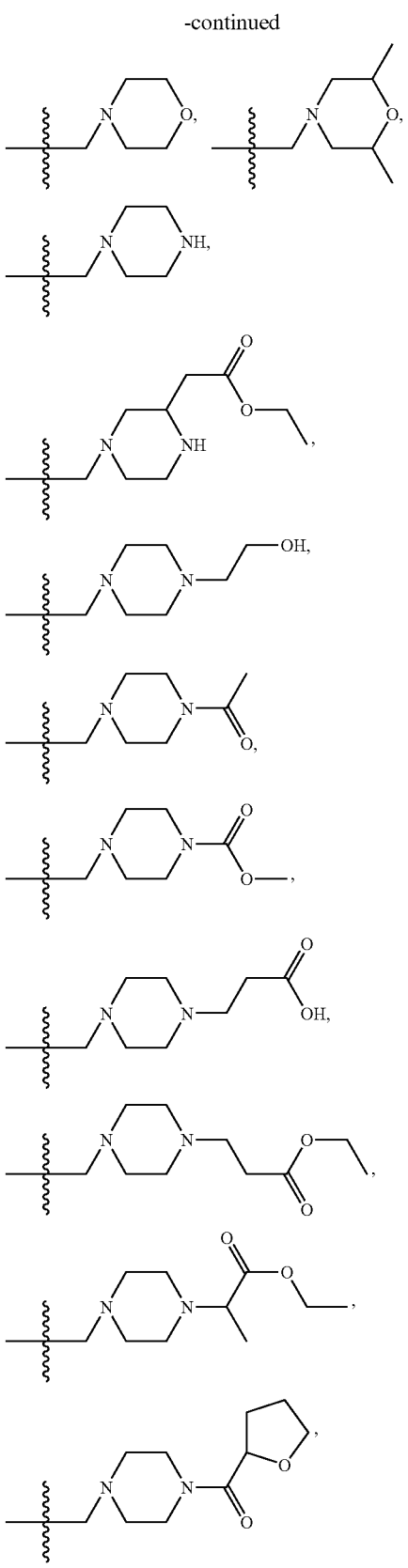

-continued
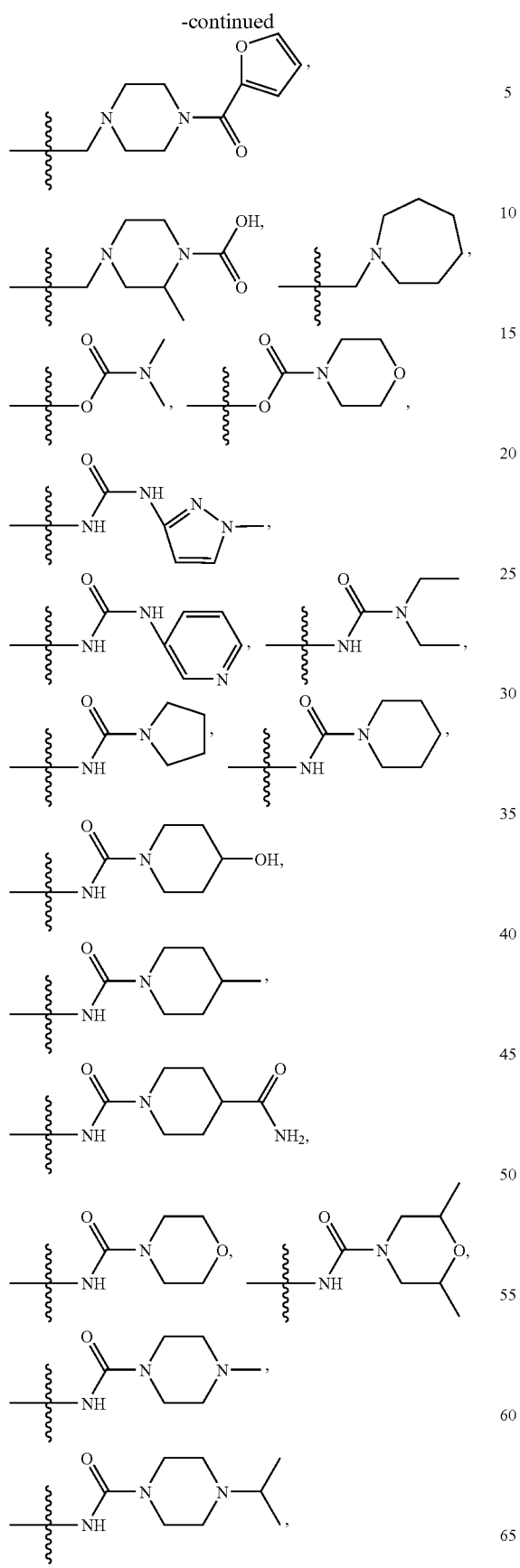
-continued
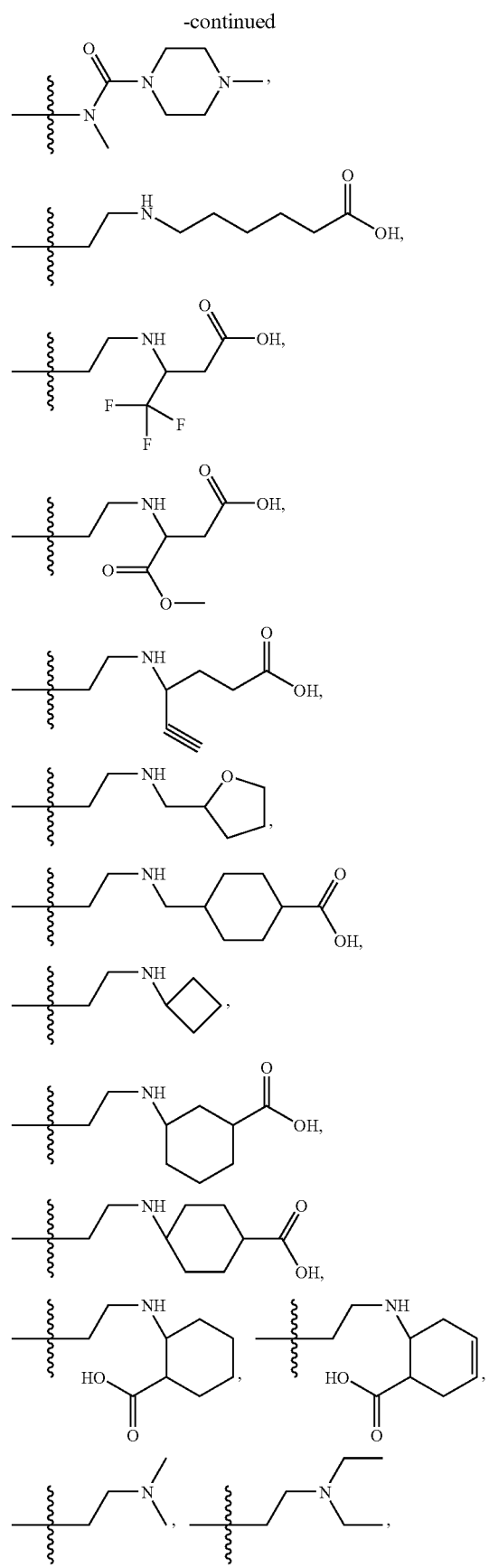

-continued
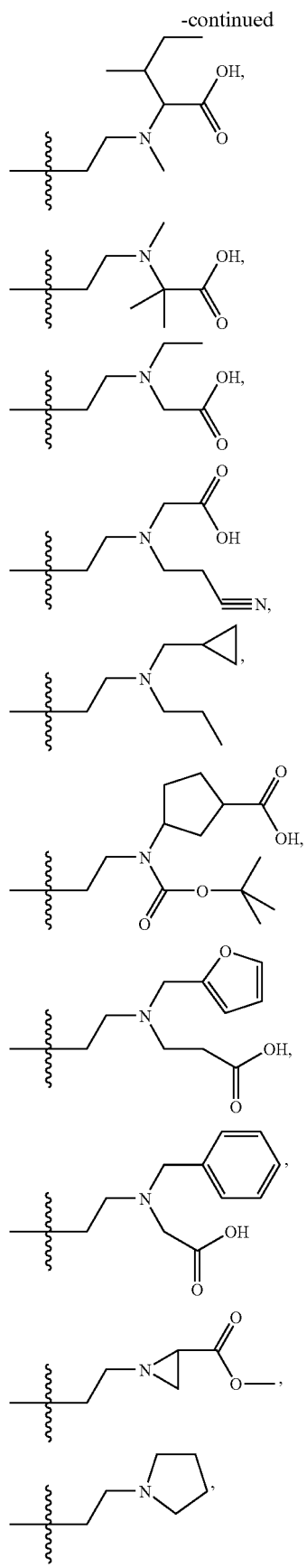
-continued
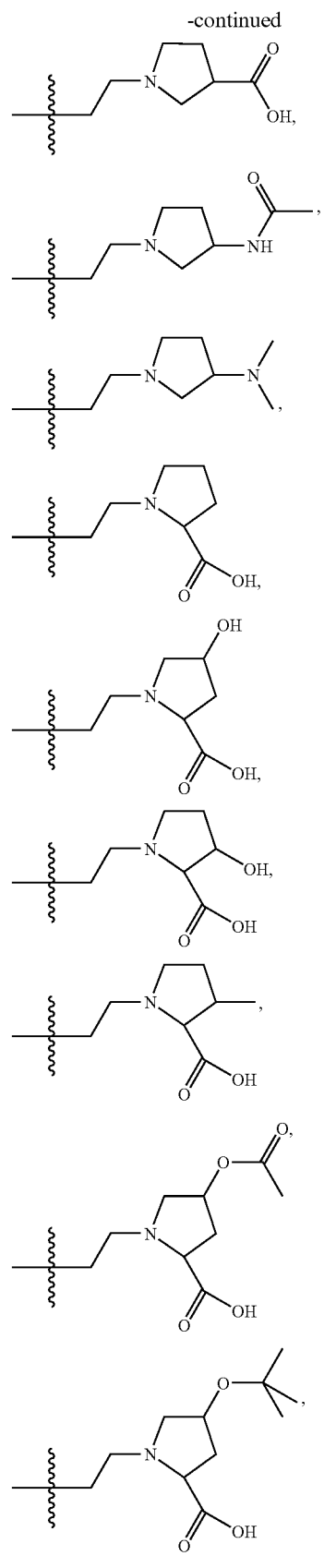

-continued
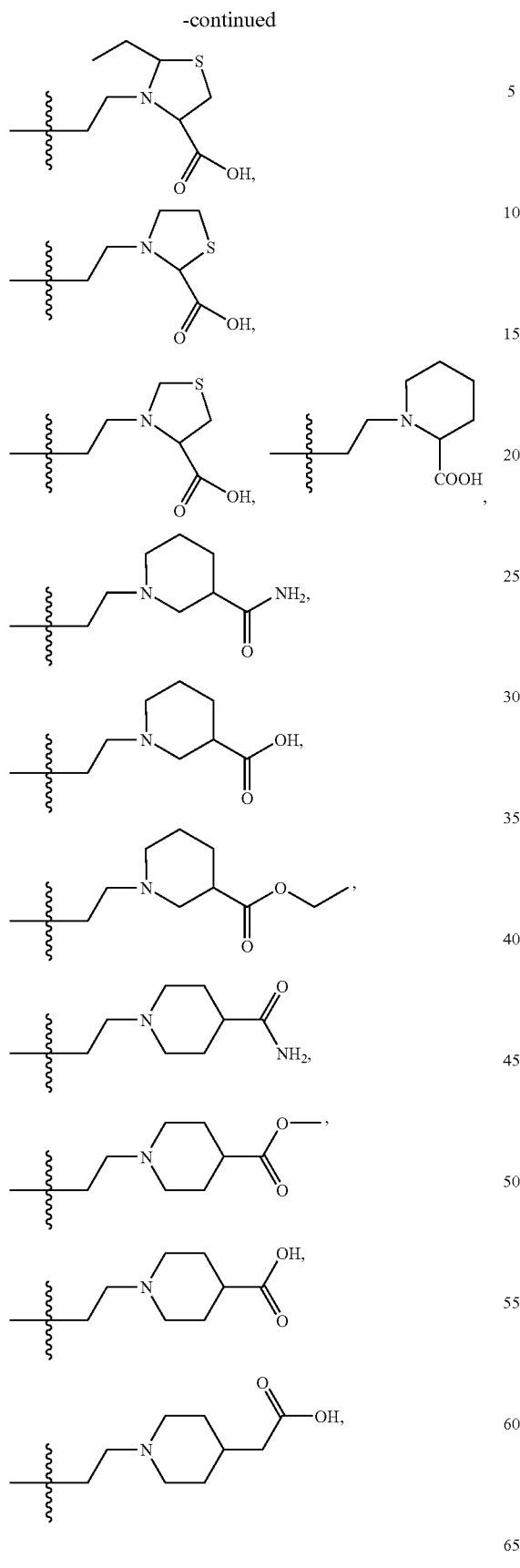
-continued
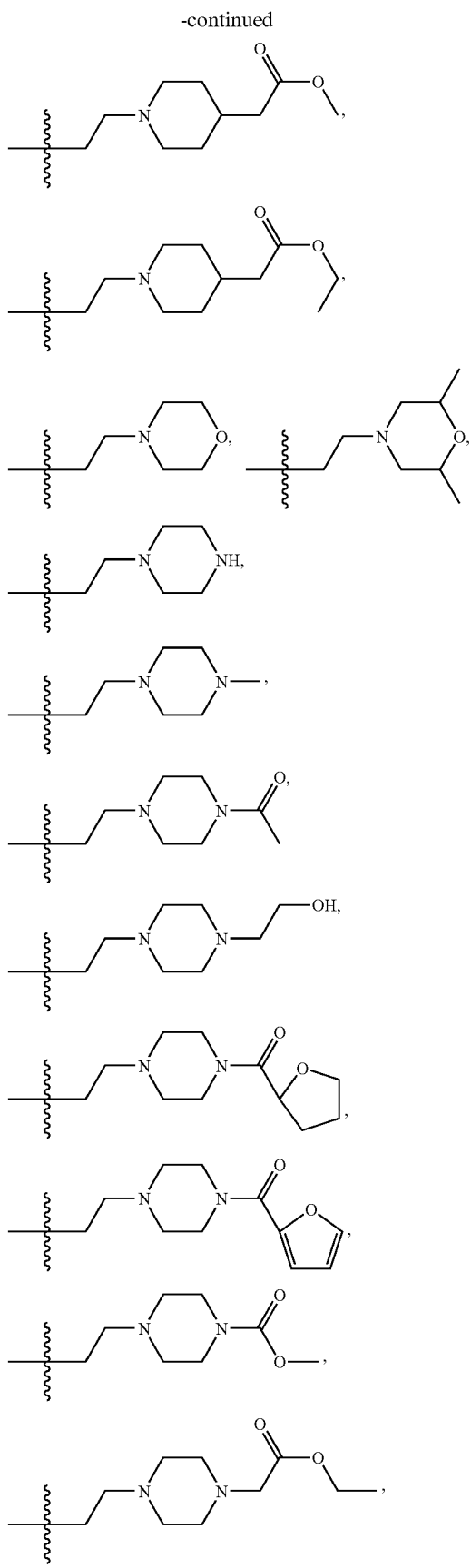

231
-continued
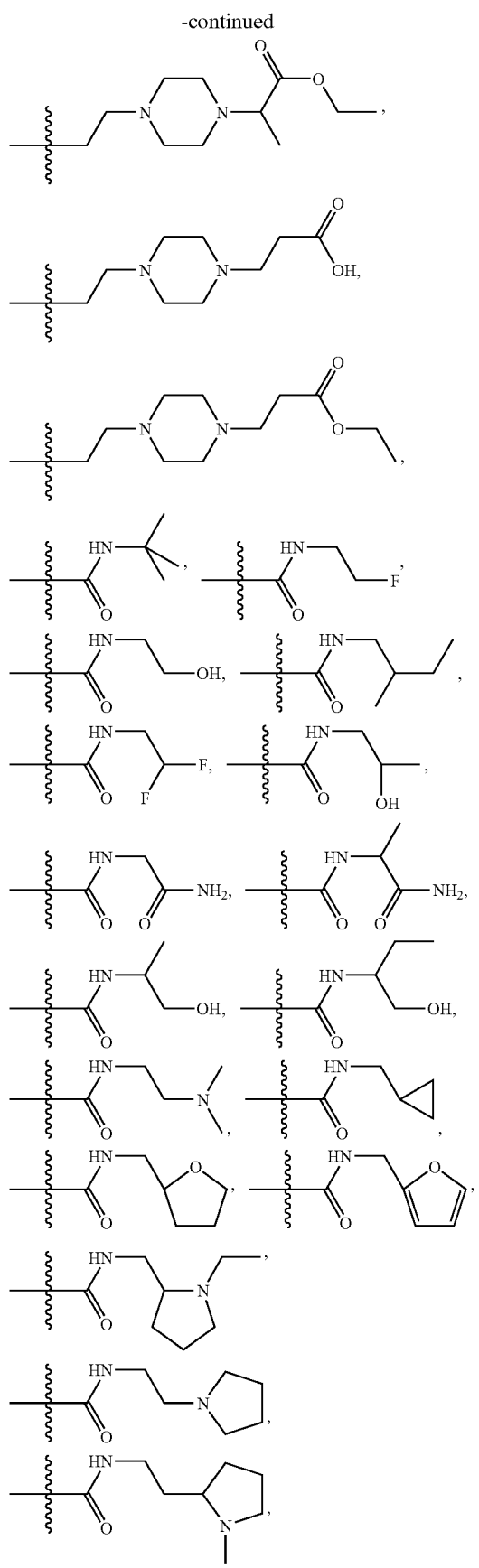
232
-continued
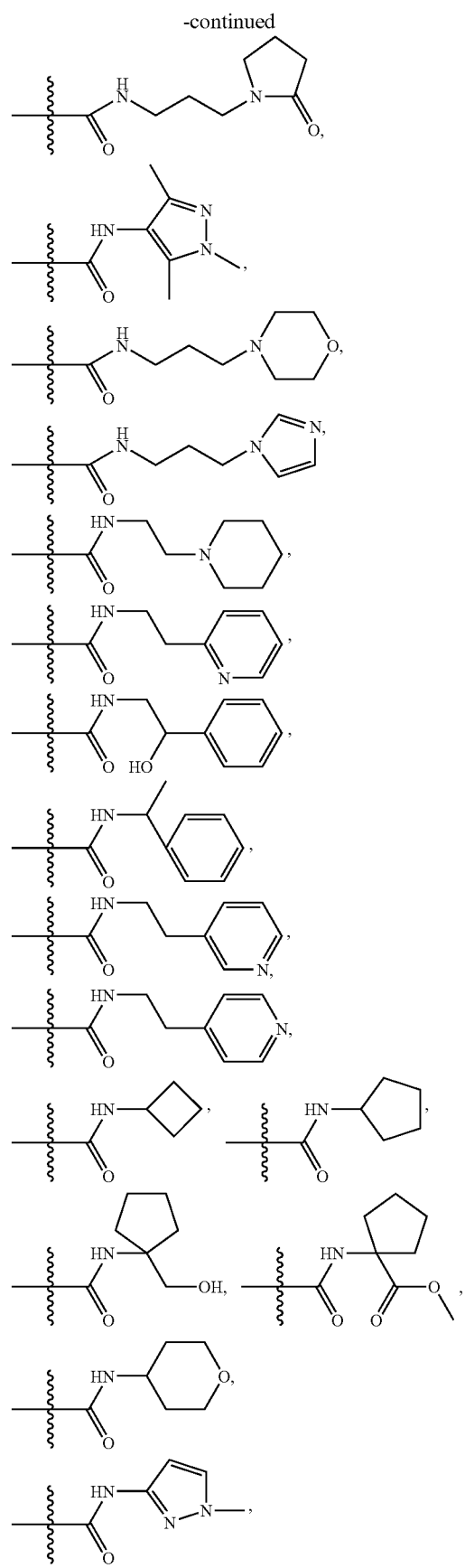

-continued
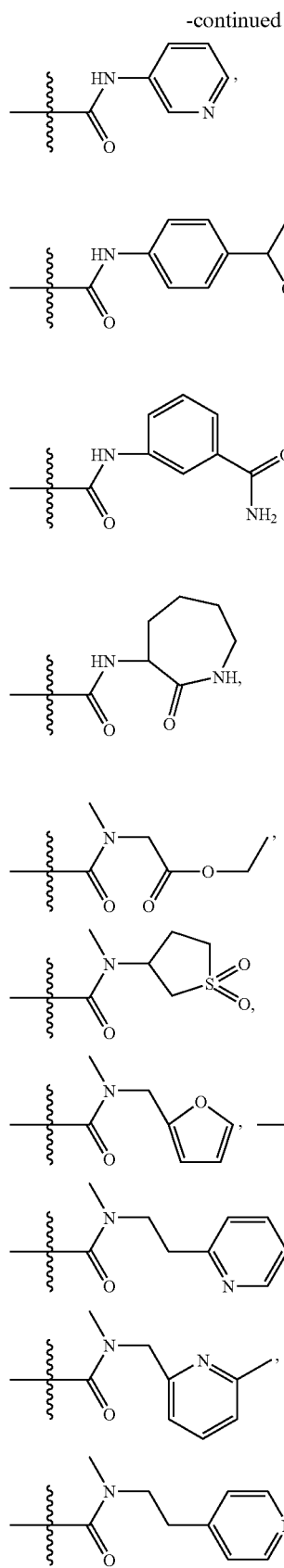
-continued
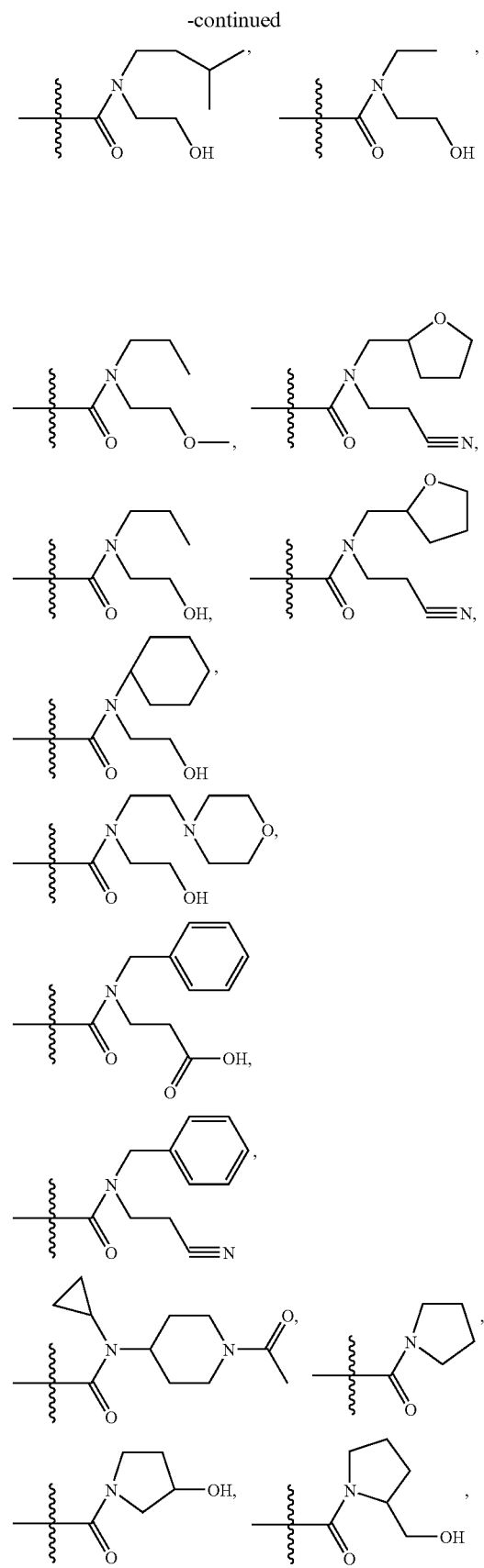

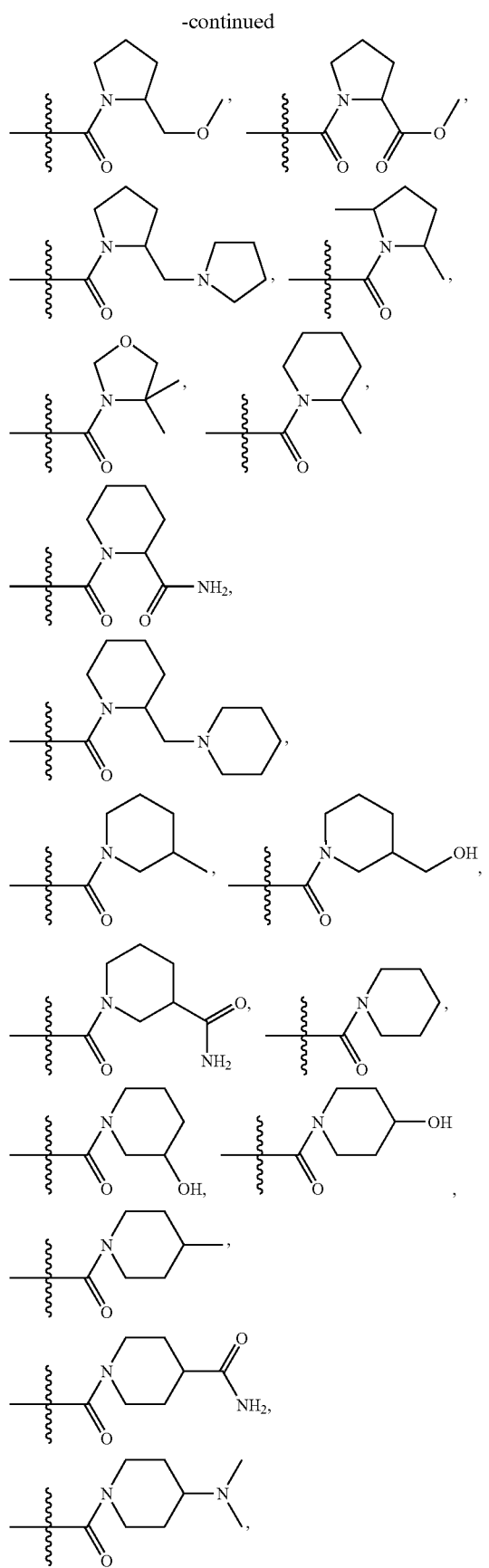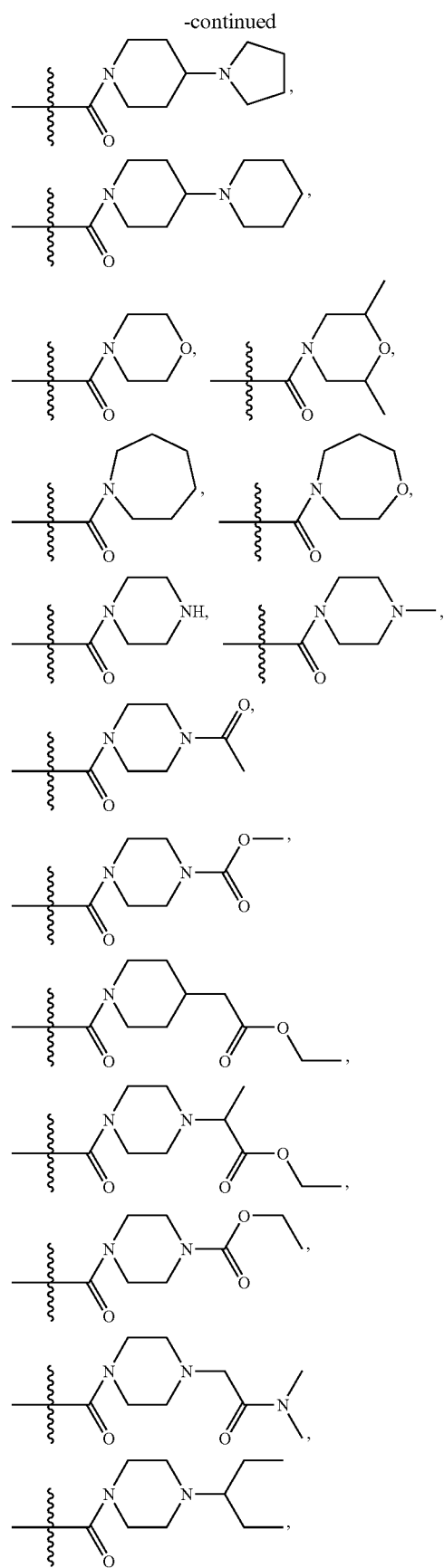

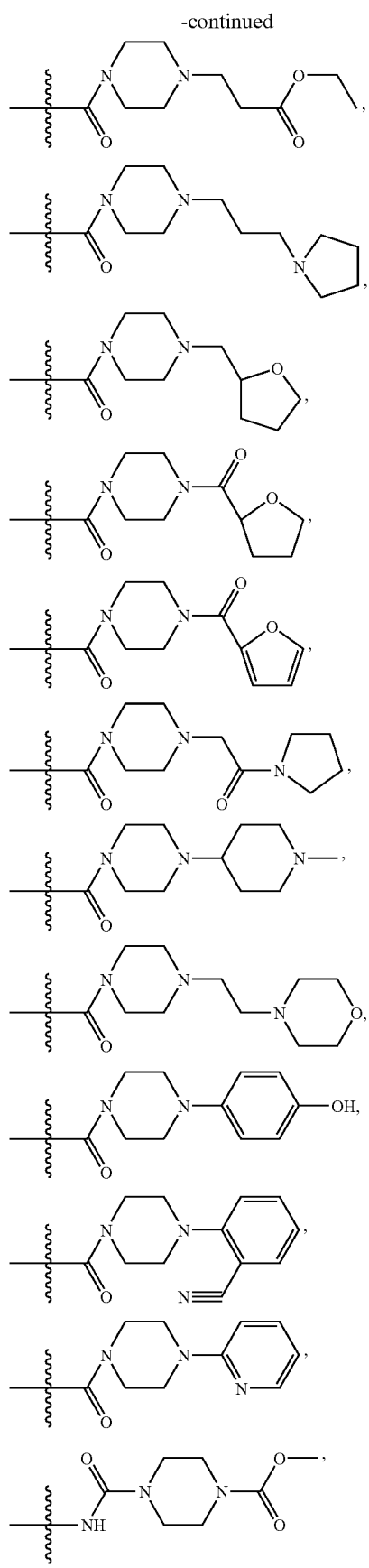
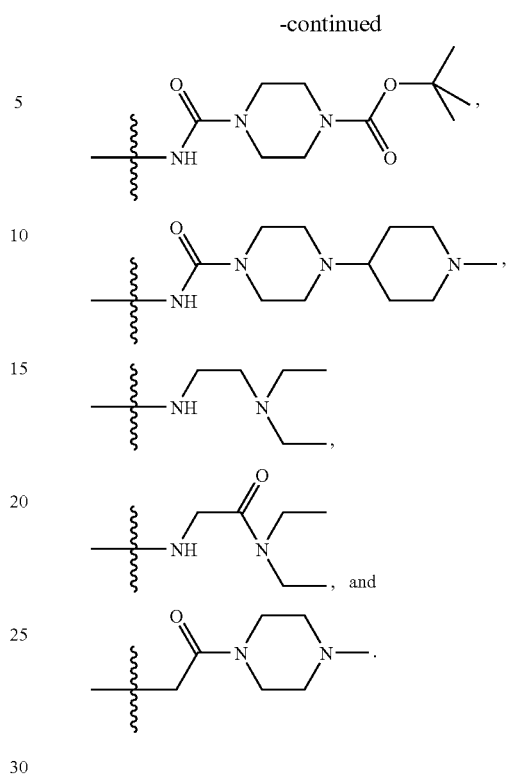
In further or alternative embodiments, Q is selected from the group consisting of
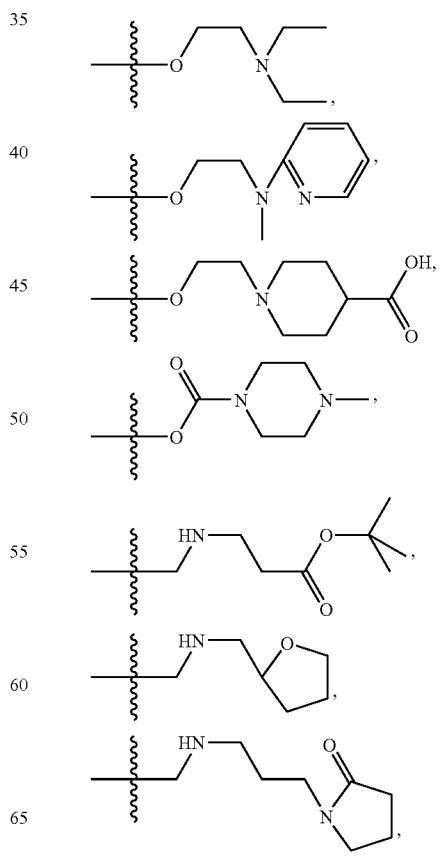

-continued

-continued
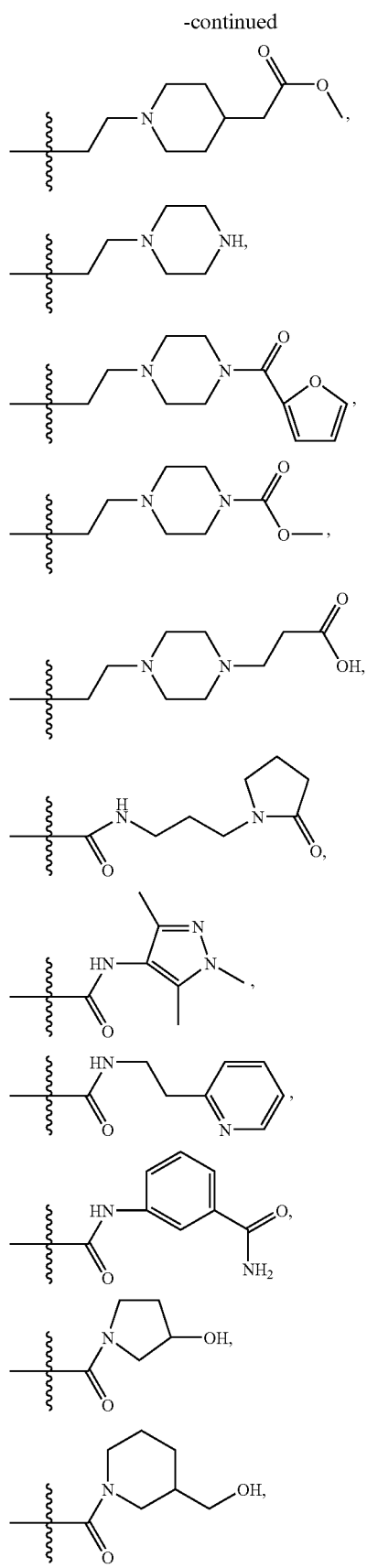
-continued
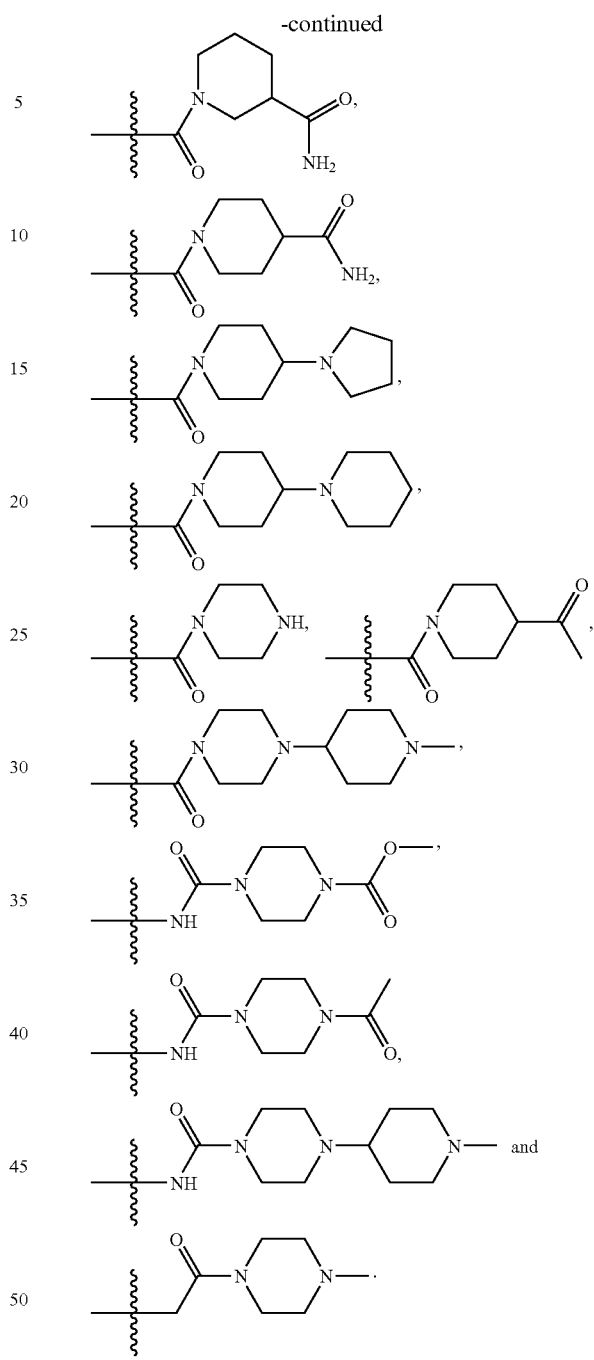
In further or alternative embodiments, Ar is selected from the group consisting of
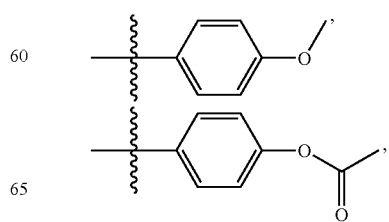

-continued

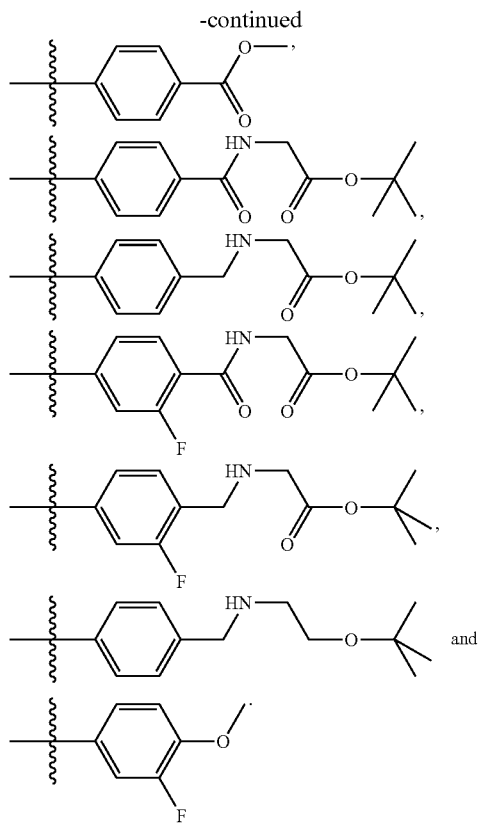

In further or alternative embodiments, the compound is selected from the group consisting of: tert-butyl 2-(4-(2-(4-(2-(diethylamino)ethoxy)phenylamino)pyrimidin-5-yl)-2-fluorobenzamido)acetate, tert-butyl 2-(4-(2-(4-(2-(diethylamino)ethoxy)phenylamino)pyrimidin-5-yl)-2-fluorobenzylamino)acetate, tert-butyl 2-(4-(2-(4-(2-(diethylamino)ethoxy)phenylamino)pyrimidin-5-yl)benzylamino)acetate, 2,2'-(2-(4-(5-(4-methoxyphenyl)pyrimidin-2-ylamino)phenoxy)ethylazanediyl)diethanol, 1-(4-(5-(4-methoxyphenyl)pyrimidin-2-ylamino)phenethyl)piperidine-4-carboxylic acid, tert-butyl 2-(4-(2-(4-(2-(diethylamino)ethoxy)phenylamino)pyrimidin-5-yl)benzamido)acetate, methyl 1-(4-(5-(4-methoxyphenyl)pyrimidin-2-ylamino)phenethyl)piperidine-4-carboxylate, N-(4-(2-(diethylamino)ethyl)phenyl)-5-(4-methoxyphenyl)pyrimidin-2-amine, 1-(2-(4-(5-(4-methoxyphenyl)pyrimidin-2-ylamino)phenoxy)ethyl)piperidine-4-carboxylic acid, N-(4-(2-(diethylamino)ethoxy)phenyl)-5-(4-methoxyphenyl)pyrimidin-2-amine, tert-butyl 2-(4-(2-(4-(2-morpholinoethoxy)phenylamino)pyrimidin-5-yl)benzamido)acetate, tert-butyl 2-(4-(2-(4-(2-(4-carbamoylpiperidin-1-yl)ethoxy)phenylamino)pyrimidin-5-yl)benzamido)acetate, 4-(2-(4-(2-(diethylamino)ethoxy)phenylamino)pyrimidin-5-yl)phenyl acetate, ethyl 2-(2-(diethylamino)ethoxy)-5-(5-(4-methoxyphenyl)pyrimidin-2-ylamino)benzoate, 4-(5-(4-methoxyphenyl)pyrimidin-2-ylamino)phenyl 4-methylpiperazine-1-carboxylate, 5-(4-methoxyphenyl)-N-(4-(2-(methyl(pyridin-2-yl)amino)ethoxy)phenyl)pyrimidin-2-amine, methyl 4-(2-(4-(2-(diethylamino)ethoxy)phenylamino)pyrimidin-5-yl)benzoate, N-(4-(2-(diethylamino)ethoxy)phenyl)-5-(3-fluoro-4-methoxyphenyl)pyrimidin-2-amine, 2-(2-(diethylamino)ethoxy)-4-(5-(4-methoxyphenyl)pyrimidin-2-ylamino)benzoic acid, methyl 2-(2-(diethylamino)ethoxy)-4-(5-(4-methoxyphenyl)pyrimidin-2-ylamino)benzoate, N-(3-(2-(diethylamino)ethoxy)phenyl)-5-(4-methoxyphenyl)pyrimidin-2-amine, N-(3-(2-(diethylamino)ethyl)phenyl)-5-(4-methoxyphenyl)pyrimidin-2-amine, 1-(4-(5-(4-methoxyphenyl)pyrimidin-2-ylamino)benzyl)piperidine-4-carboxamide, 1-(4-(5-(4-methoxyphenyl)pyrimidin-2-ylamino)benzyl)piperidine-3-carboxamide, tert-butyl 3-(4-(5-(4-methoxyphenyl)pyrimidin-2-ylamino)benzylamino)propanoate, 5-(4-methoxyphenyl)-N-(4-(piperazin-1-ylmethyl)phenyl)pyrimidin-2-amine, 1-(4-(4-(5-(4-methoxyphenyl)pyrimidin-2-ylamino)benzyl)piperazin-1-yl)ethanone, (4-(4-(5-(4-methoxyphenyl)pyrimidin-2-ylamino)benzyl)piperazin-1-yl)(tetrahydrofuran-2-yl)methanone, 1-(3-(4-(5-(4-methoxyphenyl)pyrimidin-2-ylamino)benzylamino)propyl)pyrrolidin-2-one, (S)-(1-(4-(5-(4-methoxyphenyl)pyrimidin-2-ylamino)benzyl)pyrrolidin-2-yl)methanol, (R)—N-(4-((2-(methoxymethyl)pyrrolidin-1-yl)methyl)phenyl)-5-(4-methoxyphenyl)pyrimidin-2-amine, 1-(4-(5-(4-methoxyphenyl)pyrimidin-2-ylamino)benzyl)pyrrolidin-3-ol, methyl 1-(4-(5-(4-methoxyphenyl)pyrimidin-2-ylamino)benzylamino)cyclopentanecarboxylate, 4-(4-(5-(4-methoxyphenyl)pyrimidin-2-ylamino)benzyl)-2-methylpiperazine-1-carboxylic acid, 3-(4-(4-(5-(4-methoxyphenyl)pyrimidin-2-ylamino)benzyl)piperazin-1-yl)propanoic acid, 1-(4-(5-(4-methoxyphenyl)pyrimidin-2-ylamino)benzyl)piperidine-3-carboxylic acid, ethyl 2-(1-(4-(5-(4-methoxyphenyl)pyrimidin-2-ylamino)benzyl)piperidin-4-yl)acetate, 2-(1-(4-(5-(4-methoxyphenyl)pyrimidin-2-ylamino)benzyl)piperidin-4-yl)acetic acid, 1-(4-(5-(4-methoxyphenyl)pyrimidin-2-ylamino)benzyl)pyrrolidine-3-carboxylic acid, 3-(5-(4-methoxyphenyl)pyrimidin-2-ylamino)phenyl morpholine-4-carboxylate, 3-(5-(4-methoxyphenyl)pyrimidin-2-ylamino)phenyl 4-methylpiperazine-1-carboxylate, 3-(5-(4-((2-tert-butoxy-2-oxoethylamino)methyl)phenyl)pyrimidin-2-ylamino)phenyl 4-methylpiperazine-1-carboxylate, methyl 4-(4-(5-(4-methoxyphenyl)pyrimidin-2-ylamino)benzyl)piperazine-1-carboxylate, 4-(5-(4-((2-tert-butoxy-2-oxoethylamino)methyl)phenyl)pyrimidin-2-ylamino)phenyl 4-methylpiperazine-1-carboxylate, N-(3-(5-(4-methoxyphenyl)pyrimidin-2-ylamino)phenyl)-4-methylpiperazine-1-carboxamide, 2-(4-(5-(4-methoxyphenyl)pyrimidin-2-ylamino)phenyl)-1-(4-methylpiperazin-1-yl)ethanone, N1-(3-(5-(4-methoxyphenyl)pyrimidin-2-ylamino)phenyl)piperidine-1,4-dicarboxamide, 3-(5-(4-methoxyphenyl)pyrimidin-2-ylamino)benzyl 4-methylpiperazine-1-carboxylate, 4-hydroxy-N-(3-(5-(4-methoxyphenyl)pyrimidin-2-ylamino)phenyl)piperidine-1-carboxamide, N-(4-(5-(4-methoxyphenyl)pyrimidin-2-ylamino)phenyl)-4-methylpiperazine-1-carboxamide, 1-(4-(5-(4-methoxyphenyl)pyrimidin-2-ylamino)phenethyl)piperidine-4-carboxamide, furan-2-yl(4-(4-(5-(4-methoxyphenyl)pyrimidin-2-ylamino)phenethyl)piperazin-1-yl)methanone, 5-(4-methoxyphenyl)-N-(4-(2-(piperazin-1-yl)ethyl)phenyl)pyrimidin-2-amine, N-(3-(5-(4-methoxyphenyl)pyrimidin-2-ylamino)phenyl)-N,4-dimethylpiperazine-1-carboxamide, 1-(4-(5-(4-methoxyphenyl)pyrimidin-2-ylamino)phenethyl)piperidine-3-carboxamide, 1-(4-(5-(4-methoxyphenyl)pyrimidin-2-ylamino)phenethyl)piperidine-3-carboxylic acid, methyl 4-(4-(5-(4-methoxyphenyl)pyrimidin-2-ylamino)phenethyl)piperazine-1-carboxylate, 1-(4-(5-(4-methoxyphenyl)pyrimidin-2-ylamino)phenethyl)piperidine-3-carboxylic acid, 2-(1-(4-(5-(4-methoxyphenyl)pyrimidin-2-ylamino)phenethyl)piperidin-4-yl)acetic acid, methyl 2-(1-(4-(5-(4-methoxyphenyl)pyrimidin-2-ylamino)phenethyl)piperidin- 4-yl)acetate, (3-(hydroxymethyl)piperidin-1-yl)(4-(5-(4-methoxyphenyl)pyrimidin-2-ylamino)phenyl)methanone, (3-hydroxypyrrolidin-1-yl)(4-(5-(4-methoxyphenyl)pyrimidin-2-ylamino)phenyl)methanone, 1-(4-(5-(4-methoxyphenyl)pyrimidin-2-ylamino)benzoyl)piperidine-4-carboxamide, 3-(4-(4-(5-(4-methoxyphenyl)pyrimidin-2-ylamino)phenethyl)piperazin-1-yl)propanoic acid, (S)-1-(4-(5-(4-methoxyphenyl)pyrimidin-2-ylamino)phenethyl)pyrrolidine-2-carboxylic acid, 4-(4-(5-(4-methoxyphenyl)pyrimidin-2-ylamino)phenethylamino)cyclohexanecarboxylic acid, 4-(5-(4-methoxyphenyl)pyrimidin-2-ylamino)-N-(3-(2-oxopyrrolidin-1-yl)propyl)benzamide, 1-(4-(5-(4-methoxyphenyl)pyrimidin-2-ylamino)benzoyl)piperidine-3-carboxamide, N-(3-carbamoylphenyl)-4-(5-(4-methoxyphenyl)pyrimidin-2-ylamino)benzamide, 1,4'-bipiperidin-1'-yl(4-(5-(4-methoxyphenyl)pyrimidin-2-ylamino)phenyl)methanone, (4-(5-(4-methoxyphenyl)pyrimidin-2-ylamino)phenyl)(4-(pyrrolidin-1-yl)piperidin-1-yl)methanone, 4-(5-(4-methoxyphenyl)pyrimidin-2-ylamino)-N-(2-(pyridin-2-yl)ethyl)benzamide, 4-(5-(4-methoxyphenyl)pyrimidin-2-ylamino)-N-(1,3,5-trimethyl-1H-pyrazol-4-yl)benzamide, (4-(furan-2-carbonyl)piperazin-1-yl)(3-(5-(4-methoxyphenyl)pyrimidin-2-ylamino)phenyl)methanone, 3-(5-(4-methoxyphenyl)pyrimidin-2-ylamino)-N-(1,3,5-trimethyl-1H-pyrazol-4-yl)benzamide, (3-(5-(4-methoxyphenyl)pyrimidin-2-ylamino)phenyl)(4-(1-methylpiperidin-4-yl)piperazin-1-yl)methanone, 1-(4-(3-(5-(4-methoxyphenyl)pyrimidin-2-ylamino)benzoyl)piperazin-1-yl)ethanone, (3-(5-(4-methoxyphenyl)pyrimidin-2-ylamino)phenyl)(4-(pyrrolidin-1-yl)piperidin-1-yl)methanone, 1,4'-bipiperidin-1'-yl(3-(5-(4-methoxyphenyl)pyrimidin-2-ylamino)phenyl)methanone, 1-(3-(5-(4-methoxyphenyl)pyrimidin-2-ylamino)benzoyl)piperidine-3-carboxamide, N-(3-(5-(4-methoxyphenyl)pyrimidin-2-ylamino)phenyl)-4-(1-methylpiperidin-4-yl)piperazine-1-carboxamide, methyl 4-(3-(5-(4-methoxyphenyl)pyrimidin-2-ylamino)phenylcarbamoyl)piperazine-1-carboxylate, (R)-1-(4-(5-(4-methoxyphenyl)pyrimidin-2-ylamino)phenethyl)piperidine-3-carboxylic acid, (4-(5-(4-methoxyphenyl)pyrimidin-2-ylamino)phenyl)(piperazin-1-yl)methanone, 4-acetyl-N-(3-(5-(4-methoxyphenyl)pyrimidin-2-ylamino)phenyl)piperazine-1-carboxamide, and (3-(5-(4-methoxyphenyl)pyrimidin-2-ylamino)phenyl)(piperazin-1-yl)methanone.

In further or alternative embodiments, Q of the compound having the structure of Formula (1) is selected from the group consisting of

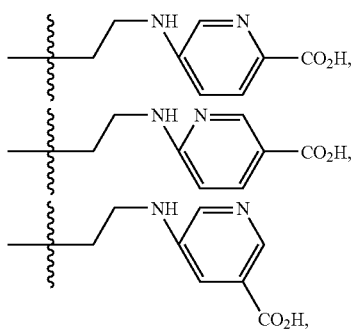

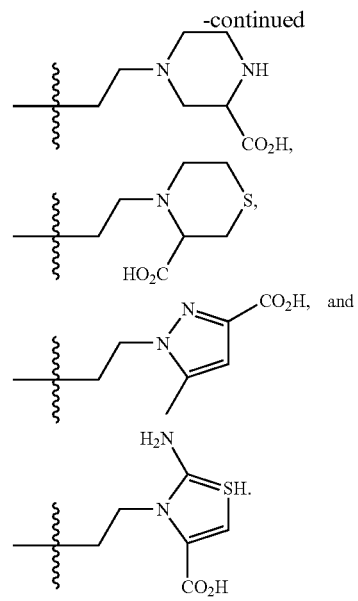

In further or alternative embodiments, Q of the compound having the structure of Formula (1) is selected from the group consisting of

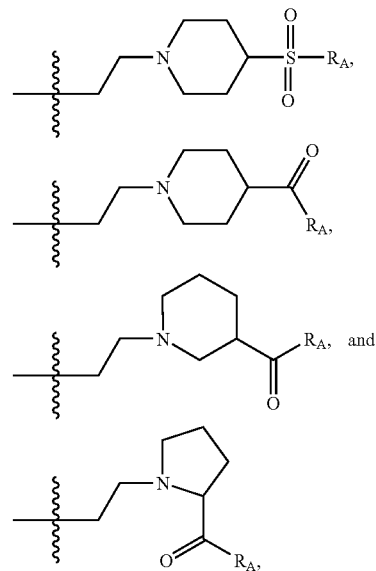

wherein $R_A$ is selected from —$NH_2$, —$NEt_2$, and —NH$(CH_2)_n$OH; and n is 1 to 6.

In further or alternative embodiments, Q of the compound having the structure of Formula (1) is

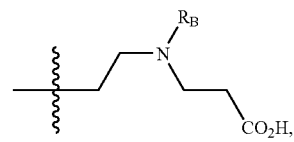

wherein $R_B$ is selected from the group consisting of

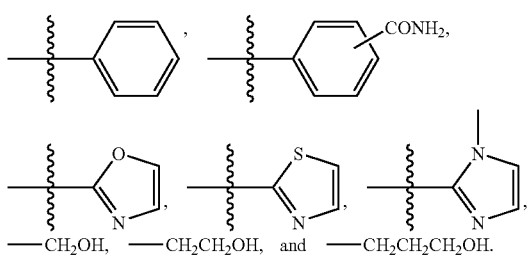

In further or alternative embodiments, Q of the compound having the structure of Formula (1) is

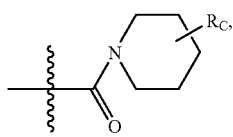

wherein $R_C$ is at 2, 3, or 4 position of the piperidine ring; and $R_C$ is selected from the group consisting of —C(O)NHEt, —C(O)NEt$_2$, c-butyl, c-pentyl, —C(O)NH-thiazole, oxazole, thiazole, —S(O)$_2$NH$_2$, —S(O)$_2$NHEt, and —S(O)$_2$NEt$_2$.

In further or alternative embodiments, Q of the compound having the structure of Formula (1) is selected from the group consisting of

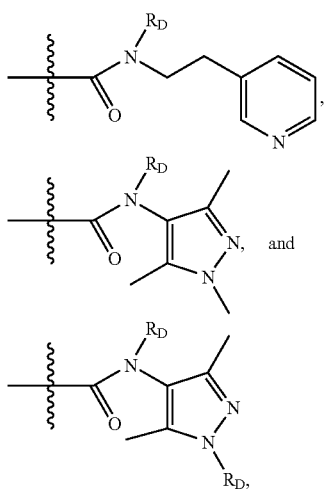

wherein each $R_D$ is independently selected from —(CH$_2$)$_k$OH or —(CH$_2$)$_k$CO$_2$H; and k is 1 to 6.

In further or alternative embodiments, Q of the compound having the structure of Formula (1) is

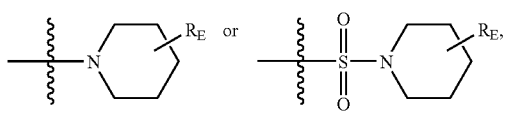

wherein $R_E$ is at 2, 3, or 4 position of the piperidine ring; and $R_E$ is selected from the group consisting of —C(O)NH$_2$, —C(O)NHEt, and —C(O)NEt$_2$.

In further or alternative embodiments, Q of the compound having the structure of Formula (1) is selected from the group consisting of

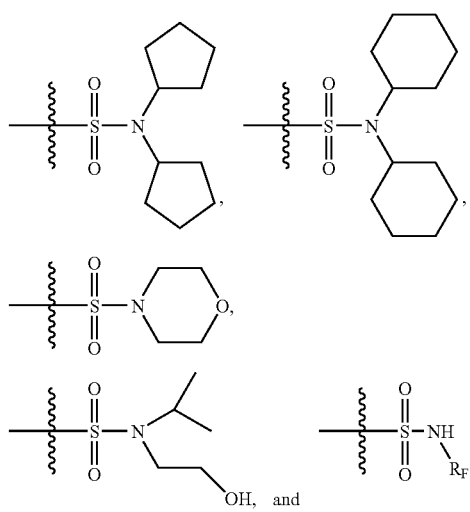

wherein $R_F$ is thiazole, pyrazole, or isoxazole.

In further or alternative embodiments, Q of the compound having the structure of Formula (46) is selected from the group consisting of

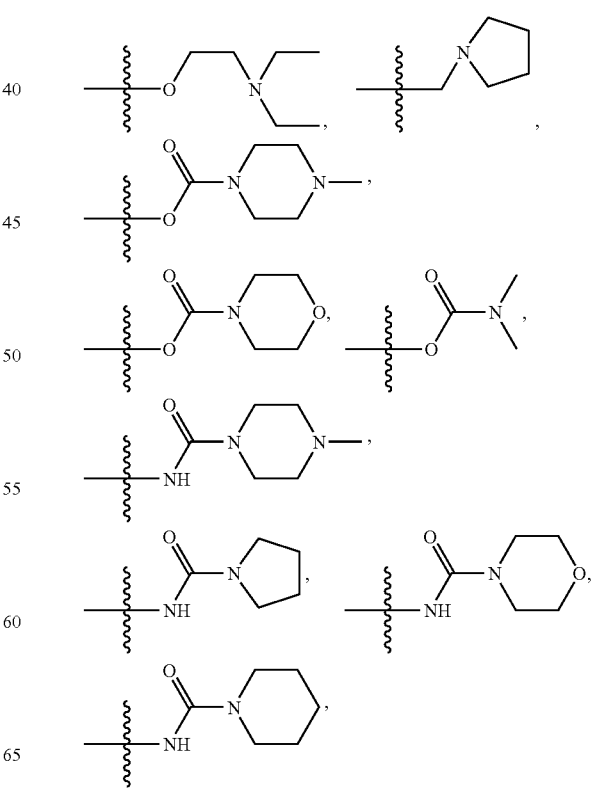

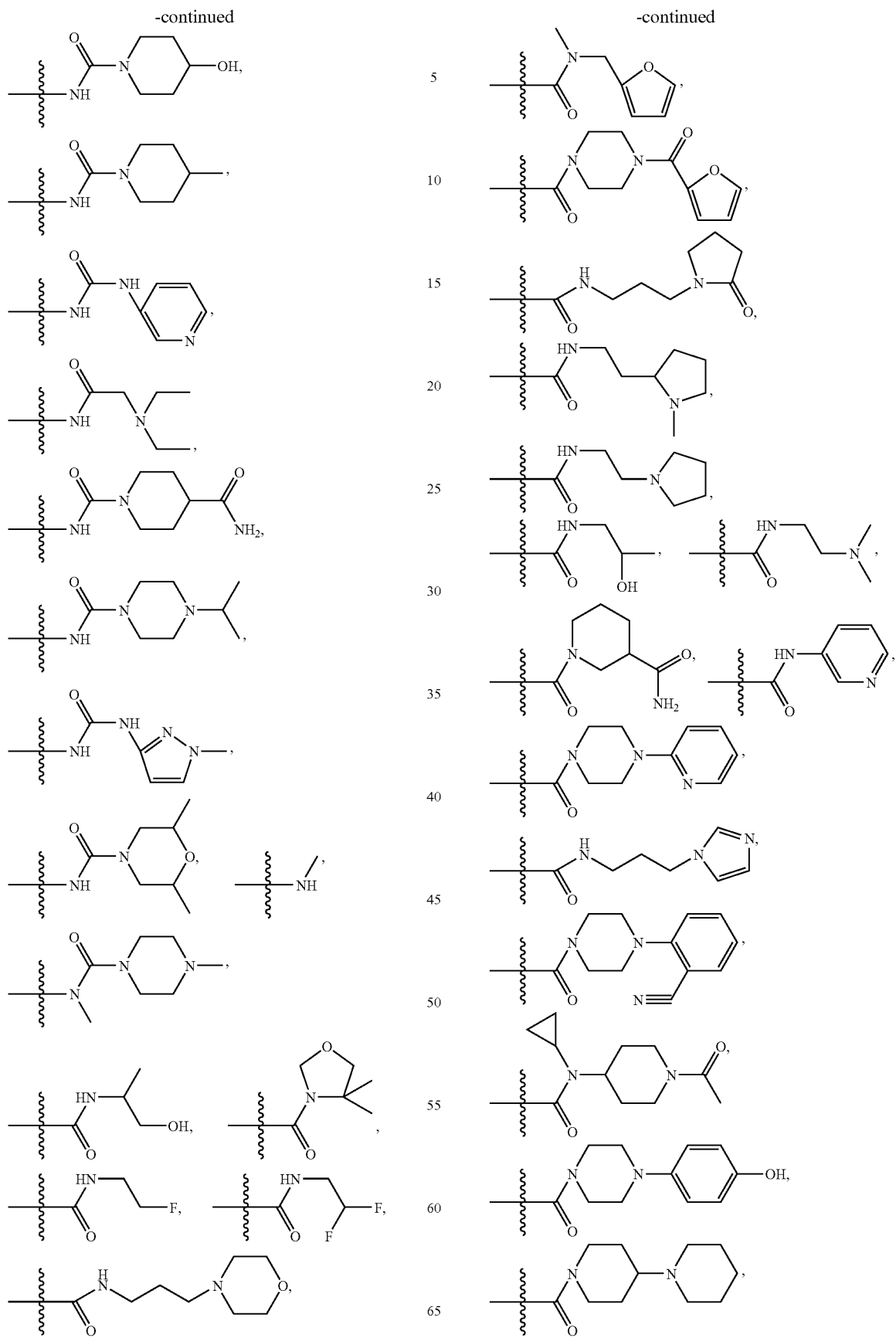

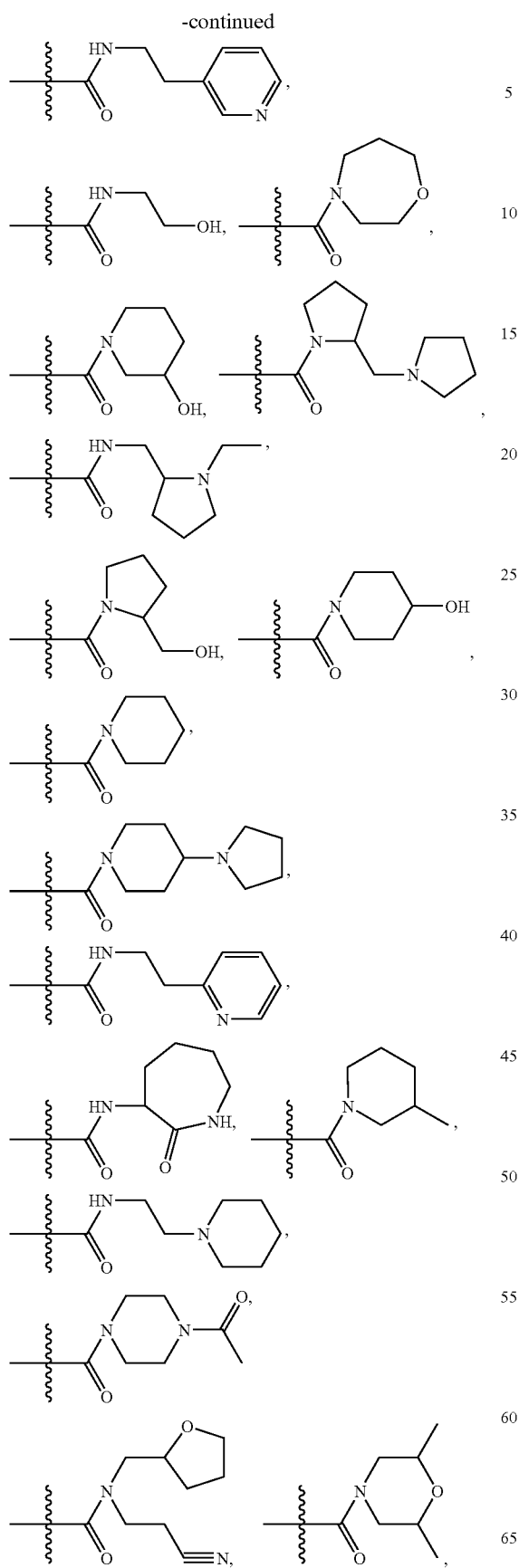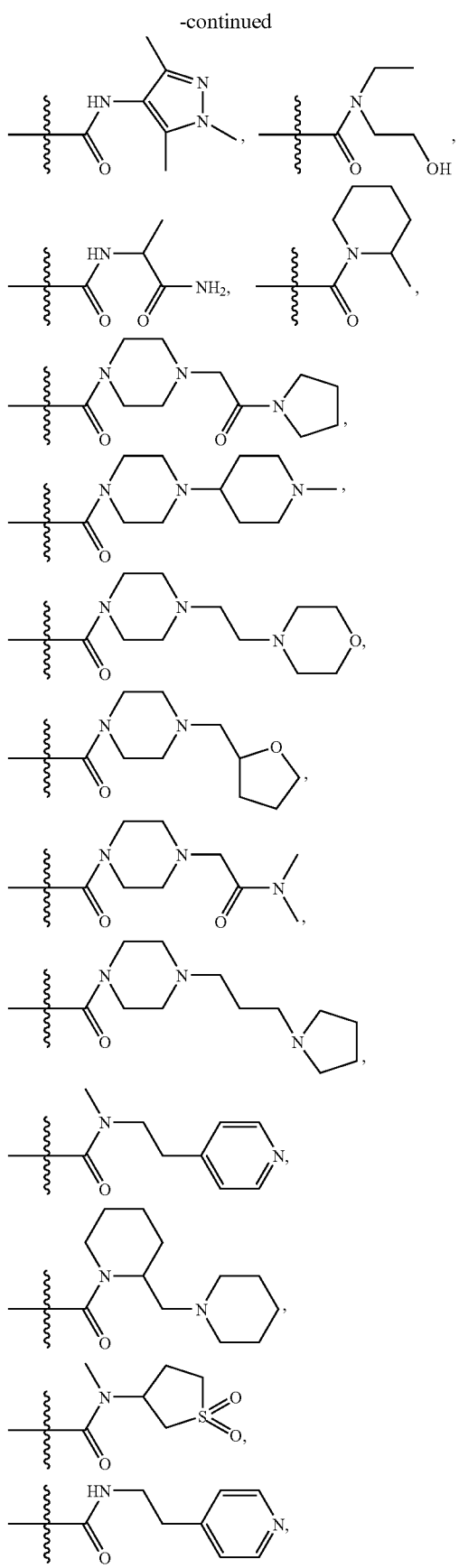

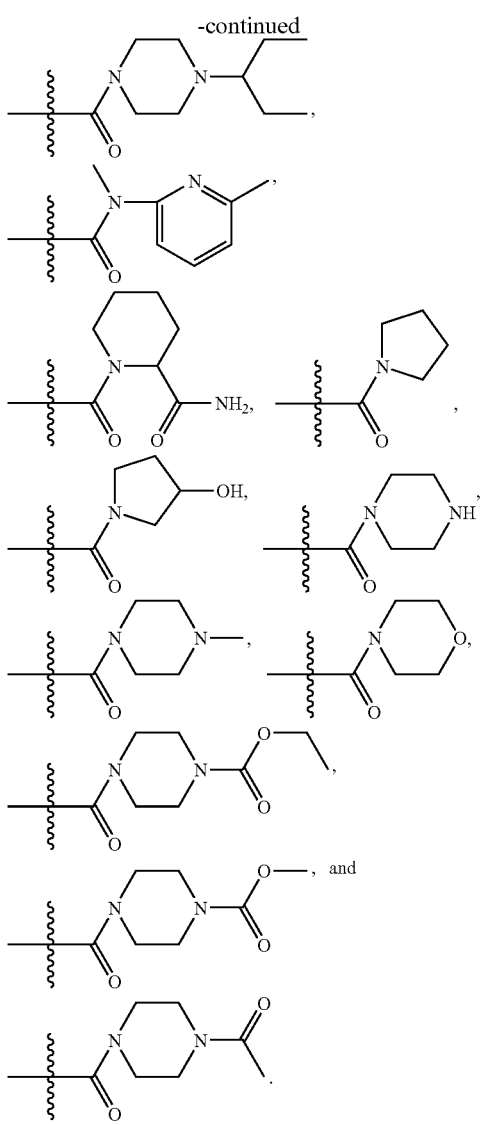

In further or alternative embodiments, Q of the compound having the structure of Formula (46) is selected from the group consisting of

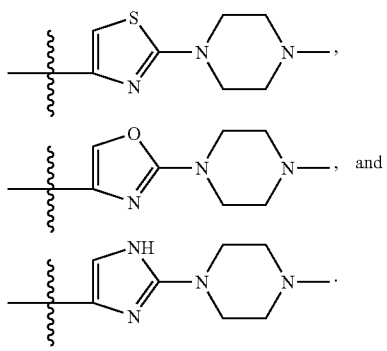

In further or alternative embodiments, the disease is a neoplastic disease. In further or alternative embodiments, the disease is a neoplastic diseases selected from the group consisting of mastocytosis, canine mastocytoma, human gastrointestinal stromal tumor, small cell lung cancer, non-small cell lung cancer, acute myelocytic leukemia, acute lymphocytic leukemia, myelodysplastic syndrome, chronic myelogenous leukemia, colorectal carcinomas, gastric carcinomas, gastrointestinal stromal tumors, testicular cancers, glioblastomas, and astrocytomas.

In further or alternative embodiments, the disease is an allergy disease. In further or alternative embodiments, the disease is an allergic disease selected from the group consisting of asthma, allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation and blood sucking parasitic infestation.

In further or alternative embodiments, the disease is an inflammatory disease. In further or alternative embodiments, the disease is an inflammatory diseases selected from the group consisting of rheumatoid arthritis, conjunctivitis, rheumatoid spondylitis, osteoarthritis, gouty arthritis and other arthritic conditions.

In further or alternative embodiments, the disease is an autoimmune disease. In further or alternative embodiments, the disease is an autoimmune disease selected from the group consisting of multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, dermatomyositis, polymyositis, Sjogren's syndrome, nodular panarteritis, autoimmune enteropathy, and proliferative glomerulonephritis.

In further or alternative embodiments, the disease is a graft-versus-host disease. In further or alternative embodiments, the disease is organ transplantation graft rejection. In further or alternative embodiments, the organ transplantation is kidney transplantation, pancreas transplantation, liver transplantation, heart transplantation, lung transplantation, or bone marrow transplantation.

In further or alternative embodiments, the disease is a metabolic syndrome. In further or alternative embodiments, the disease is a metabolic syndrome selected from type I diabetes, type II diabetes, or obesity.

In further or alternative embodiments, the condition is a CNS related disorder. In further or alternative embodiments, the disease is a CNS related disorders selected from the group consisting of depression, dysthymic disorder, cyclothymic disorder, bipolar depression, severe or "melancholic" depression, atypical depression, refractory depression, seasonal depression, anorexia, bulimia, premenstrual syndrome and post-menopause syndrome, as mental slowing and loss of concentration, pessimistic worry, agitation, self-deprecation and decreased libido, as anxiety disorders including anxiety associated with hyperventilation and cardiac arrhythmias, phobic disorders, obsessive-compulsive disorder, posttraumatic stress disorder, acute stress disorder, and generalized anxiety disorder, as psychiatric disorders such as panic attacks, including psychosis, delusional disorders, conversion disorders, phobias, mania, delirium, dissociative episodes including dissociative amnesia, dissociative fugue and dissociative suicidal behavior, self-neglect, violent or aggressive behavior, trauma, borderline personality, and acute psychosis as schizophrenia including paranoid schizophrenia, disorganized schizophrenia, catatonic schizophrenia, and undifferentiated schizophrenia.

In further or alternative embodiments, the disease is a neurodegenerative disease. In further or alternative embodiments, the disease is a neurodegenerative disease selected from the group consisting of Alzheimer's disease, Parkinson's disease, Huntington's disease, the prion diseases, Motor Neuron Disease (MND), and Amyotrophic Lateral Sclerosis (ALS).

In further or alternative embodiments, the condition is pain. In further or alternative embodiments, the type of pain is selected from the group consisting of acute pain, postoperative pain, chronic pain, nociceptive pain, cancer pain, neuropathic pain, and psychogenic pain syndromes.

In further or alternative embodiments, the condition is a substance use disorder. In further or alternative embodiments, the condition is a substance use disorder selected from the group consisting of drug addiction, drug abuse, drug habituation, drug dependence, withdrawal syndrome and overdose.

In further or alternative embodiments, the disease is a prion disease.

In further or alternative embodiments, the disease is cancer. In further or alternative embodiments, the disease is cancer selected from the group consisting of melanoma, gastrointestinal stromal tumor (GIST), small cell lung cancer, and other solid tumors.

In further or alternative embodiments, the disease is heart disease.

In further or alternative embodiments, the disease is a fibrotic disease. In further or alternative embodiments, the disease is a fibrotic disease selected from the group consisting of hepatitis C (HCV), liver fibrosis, nonalcoholic steatohepatitis (NASH), cirrhosis in liver, pulmonary fibrosis, and bone marrow fibrosis.

In further or alternative embodiments, the disease is idiopathic pulmonary arterial hypertension (IPAH).

In further or alternative embodiments, the disease is primary pulmonary hypertension (PPH).

In another aspect are methods for making the compounds having the structure of Formula (1) comprising admixing a compound of structure:

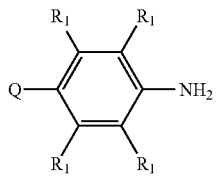

with a compound having the structure:

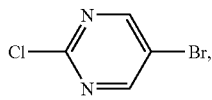

under suitable reaction conditions to yield a compound having the structure of Formula (C):

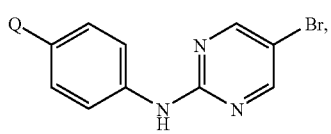

and further admixing the compound having the structure of Formula (C) with a compound of structure: $ArB(OH)_2$, under suitable reaction conditions.

In another aspect are methods for making the compounds having the structure of Formula (1) comprising admixing a compound of structure:

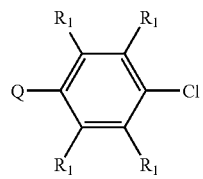

with a compound having the structure:

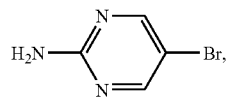

under suitable reaction conditions to yield a compound having the structure of Formula (C):

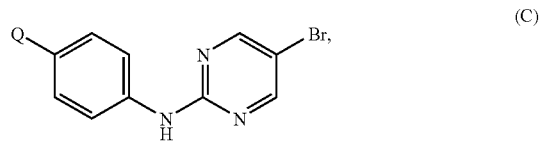

and further admixing the compound having the structure of Formula (C) with a compound of structure: $ArB(OH)_2$, under suitable reaction conditions.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the invention will become apparent to those skilled in the art from this detailed description.

These and other aspects of the present invention will become evident upon reference to the following detailed description. In addition, all patents and other references cited herein which describe in more detail certain procedures or compositions, and are incorporated by reference in their entirety.

DETAILED DESCRIPTION OF THE INVENTION

Certain Chemical Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed.

The term "alkenyl group," as used herein, refers to a hydrocarbon chain having one or more double bonds therein. The double bond of an alkenyl group can be unconjugated or conjugated to another unsaturated group. Suitable alkenyl groups include, but are not limited to, $(C_2-C_8)$alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. The alkenyl moiety may be branched, straight chain, or cyclic (in which case, it would also be known as a "cycloalkenyl" group), and can be unsubstituted or substituted.

The term "alkoxy" as used herein, includes —O-(alkyl), where alkyl is as defined herein. By way of example only, $C_{1-6}$ alkoxy includes, but is not limited to, methoxy, ethoxy, and the like. An alkoxy group can be unsubstituted or substituted.

The term "alkyl," as used herein, refers to a hydrocarbon group having from 1 to 10 carbon atoms and can include straight, branched, cyclic, saturated and/or unsaturated features. Whenever it appears herein, a numerical range such as "1 to 10" refers to each integer in the given range; e.g., "1 to 10 carbon atoms" or "$C_{1-10}$" or "$(C_1-C_{10})$" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated. The alkyl moiety may be a "saturated alkyl" group, which means that it does not contain any alkene or alkyne moieties. Representative saturated alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, sec-butyl, t-butyl, n-pentyl, isopentyl, neopentyl, and n-hexyl, and longer alkyl groups, such as heptyl, and octyl. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. Representative unsaturated alkyl groups include, but are not limited to, ethenyl, propenyl, butenyl and the like. An alkyl group can be unsubstituted or substituted. Substituted alkyl groups include, but are not limited to, halogen-substituted alkyl groups, such as, by way of example only, trifluoromethyl, pentafluoroethyl, and the like.

The term "alkylamine," as used herein, refers to the —N(alkyl)$_x$H$_y$ group, where x and y are selected from the group x=1, y=1 and x=2, y=0. When x=2, the alkyl groups, taken together, can optionally form a cyclic ring system and further when x=2, the alkyl groups can be the same or different. An alkylamine group can be unsubstituted or substituted.

The term "alkynyl" group, as used herein, refers to a hydrocarbon chain having one or more triple bonds therein. The triple bond of an alkynyl group can be unconjugated or conjugated to another unsaturated group. Suitable alkynyl groups include, but are not limited to, $(C_2-C_6)$alkynyl groups, such as ethynyl, propynyl, butynyl, pentynyl, hexynyl, methylpropenyl, 4-methyl-1-butynyl, 4-propyl-2-pentynyl, and 4-butyl-2-hexynyl. The alkynyl moiety may be branched or straight chain, and can be unsubstituted or substituted.

The term "amide," as used herein, refers to a chemical moiety with formula —C(O)NHR or —NHC(O)R, where R is selected from the group consisting of alkyl, cycloalkyl, aryl, and heterocyclic (bonded through a ring carbon). Amides can be formed from any amine or carboxyl side chain on the compounds described herein. The procedures and specific groups to make such amides are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety. An amide group can be unsubstituted or substituted.

The term "aromatic" or "aryl," as used herein, refers to a closed ring structure which has at least one ring having a conjugated pi electron system and includes both carbocyclic aryl and heterocyclic aryl (or "heteroaryl" or "heteroaromatic") groups. The carbocyclic or heterocyclic aromatic group may contain from 5 to 20 ring atoms. The term includes monocyclic or fused-ring polycyclic (i.e., rings which share adjacent pairs of carbon atoms) groups. An aromatic group can be unsubstituted or substituted.

The term "aryloxy," as used herein, includes —O-aryl group, wherein aryl is as defined herein. An aryloxy group can be unsubstituted or substituted.

The term "bond" or "single bond," as used herein, refers to a covalent bond between two atoms, either of which may be part of a larger moiety.

The terms "carbocyclic" or "cycloalkyl," as used herein, refer to a compound which contains one or more covalently closed ring structures, and that the atoms forming the backbone of the ring are all carbon atoms. Such a group may have from 3 to 20 ring carbon atoms and be saturated, partially unsaturated, or fully unsaturated monocyclic, fused bicyclic, spirocyclic, bridged polycyclic or polycyclic ring comprising carbon and hydrogen atoms. Carbocyclic alkyl groups include, but are not limited to, cyclopropyl, cyclobutyl, cyclopentyl, cyclohexyl, cycloheptyl, and cyclooctyl. A carbocyclic aromatic group includes, but is not limited to, phenyl, tolyl, anthracenyl, fluorenyl, indenyl, azulenyl, and naphthyl, as well as benzo-fused carbocyclic moieties such as, by way of example only, dibenzosuberenone, and dibenzosuberone. A carbocyclic group can be unsubstituted or substituted.

The term "ester," as used herein, refers to a chemical moiety with formula —COOR, where R is selected from the group consisting of alkyl, cycloalkyl, aryl, and heterocyclic (bonded through a ring carbon). Any hydroxy or carboxyl side chain on the compounds described herein can be esterified. The procedures and specific groups to make such esters are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety. An ester group can be unsubstituted or substituted.

The terms "heteroalkyl" "heteroalkenyl" and "heteroalkynyl," as used herein, include optionally substituted alkyl, alkenyl and alkynyl moieties and which have one or more skeletal chain atoms selected from an atom other than carbon, e.g., oxygen, nitrogen, sulfur, phosphorus or combinations thereof. A "heteroalkyl" "heteroalkenyl" and "heteroalkynyl" group can be unsubstituted or substituted.

The terms "heteroaryl" or, alternatively, "heteroaromatic," as used herein, refers to an aryl group that includes one or more ring heteroatoms selected from nitrogen, oxygen, sulfur. By way of example, an N-containing "heteroaromatic" or "heteroaryl" moiety refers to an aromatic group in which at least one of the skeletal atoms of the ring is a nitrogen atom. A polycyclic heteroaryl group may be fused or non-fused. A heteroaryl group can be unsubstituted or substituted.

The term "heterocyclic," as used herein, refers to ring structures in which the ring backbone contains at least one atom selected from nitrogen, oxygen, and sulfur. Examples of heterocyclic aromatic groups include, but are not limited to, acridinyl, benzo[1,3]dioxole, benzimidazolyl, benzindazolyl, benzoisooxazolyl, benzokisazolyl, benzofuranyl, benzofurazanyl, benzopyranyl, benzothiazolyl, benzo[b]thienyl, benzothiophenyl, benzothiopyranyl, benzotriazolyl, benzoxazolyl, carbazolyl, carbolinyl, cinnolinyl, furanyl, furazanyl, furopyridinyl, furyl, imidazolyl, indazolyl, indolyl, indolidinyl, indolizinyl, isobenzofuranyl, isoindolyl, isoxazolyl, isoquinolinyl, isothiazolyl, naphthylidinyl, naphthyridinyl, oxadiazolyl, oxazolyl, phenoxazinyl, phenothiazinyl, phenazinyl, phenoxathinyl, thianthrenyl, phenanthridinyl, phenathrolinyl, phthalazinyl, pteridinyl, purinyl, pteridinyl, pyrazyl, pyrazolyl, pyridyl, pyridinyl, pyridazinyl, pyrazinyl, pyrimidinyl, pyrimidyl, pyrrolyl, quinazolinyl, quinolinyl, quinoxalinyl, tetrazolyl, thiadiazolyl, thiazolyl, thienyl, triazinyl, (1,2,3,)- and (1,2,4)-triazolyl and the like. In addition, a heterocyclic group can be unsubstituted or substituted. Examples of non-aromatic heterocyclic groups include, but are not limited to, are azepinyl, azepan-2-onyl, azetidinyl, diazepinyl, dihydrofuranyl, dihydropyranyl, dihydrothienyl, dioxanyl, dioxolanyl, 1,4-dioxa-8-aza-spiro[4.5]dec-8-yl, dithianyl, dithiolanyl, homopiperidinyl, imidazolinyl, imidazolidinyl, indolinyl, indolyl, morpholinyl, oxazepinyl, oxepanyl, oxetanyl, oxylanyl, piperidino, piperidyl, piperidinonyl, piperazinyl, pyranyl, pyrazolinyl, pyrazolidinyl, pyrrolidinyl, pyrrolidinonyl, pyrrolinyl, quinolizinyl, thietanyl, tetrahydrofuranyl, tetrahydroquinolyl, tetrahydrothienyl, tetrahydrothiopyranyl, tetrahydropyridinyl, tetrahydropyranyl, thiazepinyl, thiepanyl, thiomorpholinyl, thioranyl, thioxanyl and the like. The heterocyclic group may be fused or non-fused. The terms referring to the groups also encompass all possible tautomers.

The term "halogen," as used herein, means fluoro, chloro, bromo or iodo. Preferred halogen groups are fluoro, chloro and bromo.

The terms "haloalkyl," "haloalkenyl," "haloalkynyl" and "haloalkoxy" include alkyl, alkenyl, alkynyl and alkoxy structures that are substituted with one or more halogen groups or with combinations thereof.

The term "membered ring," as used herein, can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "moiety," as used herein, refers to a specific segment or functional group of a molecule. Chemical moieties are often recognized chemical entities embedded in or appended to a molecule.

The term "protecting group," as used herein, refers to a chemical moiety which blocks some or all reactive moieties and prevent such groups from participating in chemical reactions until the protective group is removed.

The term "reactant," as used herein, refers to a nucleophile or electrophile used to create covalent linkages.

The term "sulfonyl" refers to the presence of a sulfur atom, which is optionally linked to another moiety such as an alkyl group, an aryl group, or a heterocyclic group. Aryl or alkyl sulfonyl moieties have the formula —$SO_2R'$, wherein R' is alkyl or aryl as defined herein, and include, but are not limited to, methylsulfonyl, ethylsulfonyl and phenylsulfonyl groups. A sulfonyl group can be unsubstituted or substituted. A phenylsulfonyl is optionally substituted with 1 to 3 substituents independently selected from halogen, alkyl, and alkoxy.

Unless otherwise indicated, when a substituent is deemed to be "optionally substituted," it is meant that the substituent is a group that may be substituted with one or more group(s) individually and independently selected from, for example, alkenyl, alkyl, alkoxy, alkylamine, alkylthio, alkynyl, amide, amino, including mono- and di-substituted amino groups, aryl, aryloxy, arylthio, carbonyl, carbocyclic, cyano, cycloalkyl, halogen, heteroalkyl, heteroalkenyl, heteroalkynyl, heteroaryl, heterocyclic, hydroxy, isocyanato, isothiocyanato, mercapto, nitro, O-carbamyl, N-carbamyl, O-thiocarbamyl, N-thiocarbamyl, C-amido, N-amido, S-sulfonamido, N-sulfonamido, C-carboxy, O-carboxy, perhaloalkyl, perfluoroalkyl, silyl, sulfonyl, thiocarbonyl, thiocyanato, trihalomethanesulfonyl, and the protected compounds thereof. The protecting groups that may form the protected compounds of the above substituents are known to those of skill in the art and may be found in references such as Greene and Wuts, Protective Groups in Organic Synthesis, 3$^{rd}$ Ed., John Wiley & Sons, New York, N.Y., 1999, and Kocienski, Protective Groups, Thieme Verlag, New York, N.Y., 1994, which are incorporated herein by reference in their entirety.

Certain Pharmaceutical Terminology

The term "acceptable" with respect to a formulation, composition or ingredient, as used herein, means having no persistent detrimental effect on the general health of the subject being treated.

The term "agonist," as used herein, refers to a molecule such as a compound, a drug, an enzyme activator or a hormone modulator which enhances the activity of another molecule or the activity of a receptor site.

The term "antagonist," as used herein, refers to a molecule such as a compound, a drug, an enzyme inhibitor, or a hormone modulator, which diminishes, or prevents the action of another molecule or the activity of a receptor site.

The term "carrier," as used herein, refers to relatively non-toxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "kit" and "article of manufacture" are used as synonyms.

The term "metabolite," as used herein, refers to a derivative of a compound which is formed when the compound is metabolized.

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulfhydryl groups. Further information on metabolism may be obtained from *The Pharmacological Basis of Therapeutics,* 9th Edition, McGraw-Hill (1996).

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

By "pharmaceutically acceptable," as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which if is contained.

The term "pharmaceutically acceptable salt" of a compound, as used herein, refers to a salt that is pharmaceutically acceptable.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (A) or Formula (B) and a co-agent, are both administered to a patient simultaneously in the form of a single entity or dosage. The term "non-fixed combination" means that the active ingredients, e.g. a compound of Formula (A) or Formula (B) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition," as used herein, refers to a mixture of an active compound with other chemical components, such as carriers, stabilizers, diluents, dispersing agents, suspending agents, thickening agents, and/or excipients.

A "prodrug," as used herein, refers to a drug or compound in which metabolic processes within the body converts the drug or compound into a pharmacological active form.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition.

Illustrative Biological Activity

Presented herein are 5-substituted-2-aminopyrimidine compounds which selectively modulate, regulate, and/or inhibit signal transduction mediated by certain native and/or mutant tyrosine kinases implicated in a variety of human and animal diseases such as cell proliferative, metabolic, allergic, and degenerative disorders. By way of example only, these compounds are potent and selective c-kit inhibitors.

c-Kit Receptor

Mast cells are tissue elements derived from a particular subset of hematopoietic stem cells that express CD34, c-kit and CD13 antigens. Mast cells are characterized by their heterogeneity, not only regarding tissue location and structure but also at the functional and histochemical levels. Immature mast cell progenitors circulate in the bloodstream and differentiate into various tissues. These differentiation and proliferation processes are under the influence of cytokines, one of utmost importance being Stem Cell Factor (SCF), also termed Kit ligand, Steel factor or Mast Cell Growth Factor. The Stem Cell Factor receptor is encoded by the protooncogene, c-kit, which is expressed in hematopoietic progenitor cells, mast cells, germ cells, interstitial cells of Cajal (ICC), and some human tumors, and is also expressed by non hematopoietic cells.

Tyrosine kinases are receptor type or non-receptor type proteins, which transfer the terminal phosphate of ATP to tyrosine residues of proteins thereby activating or inactivating signal transduction pathways. The Stem Cell Factor receptor, c-kit, is a Type III transmembrane receptor protein tyrosine kinase which initiates cell growth and proliferation signal transduction cascades in response to SCF binding. Ligation of c-kit receptor by SCF induces its dimerization followed by its transphorilation, leading to the recruitment and activation of various Intracytoplasmic substrates. These activated substrates induce multiple intracellular signaling pathways responsible for cell proliferation and activation. These proteins are known to be involved in many cellular mechanisms, which in case of disruption, lead to disorders such as abnormal cell proliferation and migration, as well as inflammation.

The activity of the c-kit receptor protein tyrosine kinase is regulated in normal cells, and the normal functional activity of the c-kit gene product is essential for maintenance of normal hematopoeisis, melanogenesis, genetogensis, and growth and differentiation of mast cells. In addition to its importance in normal cellular physiologic activities, c-kit plays a role in the biological aspects of certain human cancers, and unregulated c-kit kinase activity is implicated in the pathogenesis of human cancers, and in certain tumors types. Proliferation of tumor cell growth mediated by c-kit can occur by a specific mutation of the c-kit polypeptide that results in ligand independent activation or by autocrine stimulation of the receptor. In the former case, mutations that cause constitutive activation of c-kit kinase activity in the absence of SCF binding are implicated in malignant human cancers, including germ cell tumors, mast cell tumors, gastrointestinal stromal tumors, small-cell lung cancer, melanoma, breast cancer, acute myelogenous leukemia, neuroblastoma and mastocytosis.

Mast cells present in tissues of patients are implicated in or contribute to the genesis of diseases such as autoimmune diseases (multiple sclerosis, rheumatoid arthritis, inflammatory bowel diseases (IBD)) allergic diseases (allergic sinusitis, allergic rhinitis and asthma), tumor angiogenesis, inflammatory diseases, and interstitial cystitis. In these diseases, mast cells participate in the destruction of tissues by releasing a cocktail of different proteases and mediators such as histamine, neutral proteases, lipid-derived mediators (prostaglandins, thromboxanes and leucotrienes), and various cytokines (IL-1, IL-2, IL-3, IL-4, IL-5, IL-6, IL-8, TNF-A, GM-CSF, MIP-LA, MIP-1b, MIP-2 and IFN-y).

Human are more and more afflicted in modern societies with allergic disorders such as allergic sinusitis, allergic rhinitis and asthma. For example, in the USA alone, it is estimated that more than 87 million people are coping with some form of allergic diseases. The financial burden of the treatments rises to a total of several billion dollars and is due to the recurrence of these diseases. Among these allergic diseases, we can cite allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation, but bronchial asthma is the most prevalent and recurrent disease severely afflicting the human population.

Asthma is characterized by airflow obstruction, bronchial hyperresponsiveness and airway inflammation. Airway inflammation is the major factor in the development and perpetuation of asthma. In allergic asthma, which is the most frequent, especially in children, and better studied form of the disease, allergens are thought to initiate the inflammatory process by inducing a T-lymphocyte mediated response (TH2) that results in the production of allergen-specific IgE. IgE bind to its high-affinity receptor FCERI on pulmonary mast cells triggering a type I (IgE-mediated) immediate allergic response.

Mast cell activation induces diverse effector responses, such as secretion of allergic mediators, proteases, chemokines such as MCP-1 and RANTES, leukotrienes, prostaglandins, neurotrophins, induction of cytokine gene transcription (IL-4, IL-5, IL-6, IL-13, TNFA and GM-CSF). These mediators contribute to creating the asthmatic phenotype by their effects on endothelial cells, smooth muscle cells and fibroblasts and on extracellular matrix, and by recruiting other inflammatory cells.

Different treatments are available to alleviate the symptoms associated with allergic diseases. For instance, treatments for severe allergic diseases such as asthma, include combination of histamine $H_1$-receptor antagonists with antagonists of leukotriene receptors or 5-lipoxygenase inhibitors. However, anti-histamine compounds have been found to be less effective and do not provide a solution to the recurrence of asthma, and the latter treatment only reduces inflammation symptoms associated with allergic diseases and cannot be considered as a cure on the long run. In response to this problem, interleukin-2 (IL-2) has been used to suppress allergic disorders, but the induction of death by apoptosis of a subpopulation of T lymphocytes has many side effects limiting such therapy to the most severe forms of allergic diseases.

Mast cells may play a role in asthma as suggested by the humanized anti-IgE monoclonal antibody treatment. The rationale of anti-IgE therapy is to specifically target IgE with the result of inactivating free anti-IgE and halting further IgE production. In addition, since IgE levels are a major regulator of the level of expression of IgE receptor FceRI, one aim of this therapy is to decrease FceRI expression on mast cells and basophils, and, as a consequence, to decrease the capacity of these cells to be activated. The capacity of the anti-IgE therapy to decrease FceRI expression has been demonstrated on basophils. The decrease in FceRI expression on basophils is associated with a decrease in the capacity of basophils to secrete mediators upon activation. Even though the effect of the anti-IgE therapy on pulmonary mast cells has not been studied because these cells are difficult to harvest. These trials have shown that the anti-IgE therapy is capable of improving some of the parameters of asthma, for example corticosteroid usage. Nevertheless, antibody based therapy is not suitable to repeated treatment of the most recurrent forms of allergic diseases. In addition, compositions comprising tryptase inhibitors for treating mast-cell mediated conditions are may be used, but decreasing the activity of free tryptase released by activated mast cells is not sufficient to block chain reactions caused by the others mast cells released factors. Therefore, there is a need for alternative treatments of allergic diseases and/or conditions which would be more effective on the long term and would be well tolerated, especially in respect to repeated administration.

Non-insulin-dependent diabetes mellitus (NLDDM), also known as type II diabetes, is defined as a chronic disease appearing when insulin is inefficient in promoting glucose uptake by cells, resulting in increased levels of glucose in the blood. This disease affects about 100 million people worldwide, 75% of which are obese at the time of diagnosis.

Diminution in the ability of the cells to respond adequately to insulin is often referred as insulin resistance. Excessive weight and lack of physical activity are regarded as being responsible for inducing insulin resistance. Over many years, the failure of the glucose uptake regulation leads to the development of Type II diabetes and the blood glucose level needs to be regulated with medicinal products. Ultimately, unregulated blood glucose level is responsible for blood vessels, kidney and eye damages, as well as cardiovascular diseases. This tissue damages contribute to mortality in diabetics.

Hypoglycemic agents such as sulfonylureas work by triggering the pancreas to make more insulin, which lower blood glucose. The side effects of sulfonylureas include hypoglycemia, renal and hepatic disease, gastrointestinal disturbances, increased cardiovascular mortality, dermatological reactions, drowsiness and headache. Biguanides lower blood glucose levels by reducing intestinal glucose absorption and hepatic glucose, but not by stimulating insulin secretion. The major side effects of biguanidine are lactic acidosis and increased cardiovascular mortality. Alpha-glucosidase inhibitors decrease the absorption of carbohydrates from the digestive tract, thereby lowering the after-meal glucose level, but gastrointestinal side effects and hypoglycemia are observed. Thiazolidinediones, such as rosiglitazone are PPARgamma agonists and increase the cell's sensitivity to insulin. However, they may be responsible for water retention, liver diseases, cardiovascular diseases, red blood cell abnormalities, and headache.

Because treatment of Type II diabetes requires long term administration of compounds lowering blood glucose level, there is still a great need for improved and safer methods. C-kit inhibitors may also be used in the treatment of type II diabetes. Inhibition of c-kit activity reduces cellular proliferation, depleting the mast cells responsible for diseases and/or conditions, such as allergic diseases, thereby suggesting a role for use of inhibitors of c-kit in the treatment of c-kit dependent diseases and/or conditions, such as diabetes. Described herein are diarylamine compounds, pharmaceutical compositions and medicaments, which include such diarylamine compounds or a pharmaceutically acceptable salt or solvate thereof, that are potent and selective c-kit inhibitors and which selectively modulate, regulate, and/or inhibit signal transduction mediated by certain native and/or mutant tyrosine kinases implicated in a variety of human and animal diseases such as, by way of example only, diabetes.

Neurons propagate a signal in the form of an action potential along its axon to other neurons or to effector cells. Many positive or negative signals are exchanged between neurons and are integrated to produce meaningful firing patterns. The communication between two neurons is based on the action of numerous neurotransmitters on specific receptors located at the synapses. A disruption in the regulation of neurotransmission is responsible for neurologic and psychiatric diseases. Furthermore, the activity of neurotransmitters on their respective receptor is normally time limited so that receptors can respond repeatedly to the next waves of stimuli. In this regard, different mechanisms abolish the action of neurotransmitters, for instance they can be pumped back into the presynaptic nerve terminals by active processes (reuptake), they can be destroyed by enzymes, or they simply diffuse into the surrounding area.

Changes in neurotransmitter synthesis, storage, release, or degradation or changes in the number and affinity of receptors can affect neurotransmission and cause clinical disorders. Among neurotransmitters, glutamate and aspartate are the major excitatory neurotransmitters, whereas aminobutyric acid (GABA) is the major inhibitory neurotransmitter in the brain. The first theory about depression concerned the noradrenergic system (NS) (Shildkraut J. et al. 1965, Am J. Psychiat. 12:, 509-522). At that time, it was observed that tricyclic compounds (ADT) and monoamine-oxidase inhibitors modified the level of noradrenaline. Later on, in 1978, Sulser F. et al., Biochem Pharmacol. 27: 257-261 showed that these antidepressants lead to a decrease in the number of post-synaptic (3-Adrenergis receptors. Therefore, it was thought that depression was due to the deregulation of the noradrenergic pre-synaptic stimuli as well as the post-synaptic receptors (Siever L J. et AL. (1985), Am. J. Psychiat. 142, 1017-1031).

In 1986, Rasmussen et al., Brain Res. 385: 395-400 demonstrated the presence of serotonin (5-hydroxytriptamin, 5-HT) receptors in NA neurones. Treatments with ADT were shown to provoke also a down-regulation of the 5-HT$_2$ receptors in Sugrue M. F. et al, 1981, Pharmacol. Ther. 13: 219-247. As a consequence, it appears that the NA and 5-HT systems play a crucial role in the regulation of mood and behaviour. In the nineties, research has focused on the finding of specific serotonin re-uptake inhibitors (SSRI), such as fluoxetin, parxetin or sertralin (Pinder R. M. et al., 1993, Med. Res. Rev. 13: 259-325). Serotonin (5-hydroxytryptamine, or 5-HT) levels are controlled by the uptake of tryptophan and intraneuronal monoamine oxidase activity. In the meantime, a decrease in the level of HVA, the main catabolic of dopamin (DA), was observed in depressed patients (Kapur S. et al., 1992, Biol. Psychiat. 32: 1-17). GABA was also shown to be involved in the physiopathology of depression since (i) unpolar patients display decreased level of GABA, (ii) some antidepressants induce the release of GABA in vivo and (iii) agonists of GABA receptors have antidepressant effects (Lloyd K. G. et al., 1989, Prog. Neuro-Psycopharmacol. Biol. Psychiat. 13: 341-351).

More recently, it has been reported that other factors may be involved in CNS disorders. For example, it has been observed from 30 to 70% of patients afflicted with melancholia have high level of plasmatic cortisol and escape to the test with dexamethasone described in Caroll B. J. et al., 1981, Arch. Gen. Psychiat. 38: 15. In addition, cortocosteroids modify (i) the expression of serotoninergic receptors and (ii) the activity of tryptophan hydroxylase, which is the key enzyme in the synthesis of 5-HT (Biegon A., 1990, Ann. NY Acad. Sci. 600: 427-431).

Regarding post-partum or post-menopause depression, repeated administration of oestrogene induces a down-regulation of dopaminergic D$_2$ receptors (Munemura M. et al., 1989, Endocrinology 124: 346-355 and Roy E. J. et al., 1990, Brain. Res. Bull. 25: 221-227).

Other neurotransmitters include the well known acetylcholine, norepinephrine which interacts with adrenergic receptors and which is regulated by tyrosine hydroxylase and monoamine oxidase, endorphins which are polypeptides that activate many central neurons and interact with opioid receptors, enkephalins, dynorphins, histamine, vasopressin, vasoactive intestinal peptide, carnosine, bradykinin, cholecystokinin, bombesin, somatostatin, corticotropin releasing factor, neurotensin, and adenosine.

As mentioned above, any imbalance in these neurotransmitters or any deregulation of associated receptors may lead to the development of CNS disorders ranging from psychiatric diseases to migraine, pain, memory loss and nerve cells degeneracy.

As of today, available treatments include selective serotonin reuptake inhibitors (SSRIS) such as fluoxetine, sertraline, paroxetine, and fluvoxamine. Other compounds include nefaxodone which blocks the 5-HT$_2$ receptor and inhibits reuptake of 5-HT and norepinephrine, trazodone which is a 5-HT$_2$ receptor blocker and a 1-noradrenergic blocker, mirtazapine which blocks 2-adrenergic autoreceptors as well as 5-HT$_2$, 5-HT$_3$ and H$_1$ receptors, tricyclic compounds such as imipramine and desipramine, tetracyclic compounds which increase the level of free norepinephrine and of 5-HT, and monoamine oxidase inhibitors (MAOI) which inhibit the oxidative deamination of norepinephrine, dopamine, and 5-HT. We can also cite lithium-antidepressants for treating bipolar disorder.

However, the above mentioned compounds display numerous side effects such as tachycardia, sedation and weight gain. In addition, these compounds are only effective in about 65% of depressed patients, which implies a large population afflicted with the so-called "refractory depression". In some cases, the life of patients is in jeopardy at the extent that hospitalization and electroconvulsive therapy is required, thus showing the seriousness of these diseases.

Schizophrenia is also a serious mental disorder affecting about 1% of western countries population. Antipsychotic (neuroleptic) drugs available include chlorpromazine and haloperidol which show affinity for the dopamine 2 receptor. But, adverse side effects such as sedation, dystonia, tremors and akathisia have been commonly observed and a significant percentage of patients do not respond to the treatments.

Therefore, the problem is to find alternative solutions to provide a relief and a cure for the numerous patients afflicted with these diseases. The activation of mast cells by different stimuli such as stress, trauma, infection as well as neurotransmitters, may participate in the exacerbation of the chemical imbalance causing CNS disorders. More specifically, mast cell degranulation is stimulated by common neurotransmitters such as neurotensin, somatostatin, substance P and acetylcholine, by growth or survival factors, notably NGF, TGFβL Mast cells involved in the response to such stimulus can be brain mast cells but also other mast cells releasing the content of their granules in the blood stream that ultimately reach sensory, motor or brain neurons. Brain mast cells staining is CTMC staining-like but they show the secretory pattern of MC, implying that they constitute a particular subset of mast cells presenting specificities.

Following mast cells activation, released granules liberate various factors capable of modulating and altering neurotransmission and neurons survival. Among such factors, serotonin is important since an increase of the level of free serotonin has been observed in depressed patients. Alternatively, the sudden burst of serotonin may be followed by a period of serotonin shortage, leading to pain and migraine. As a consequence, it is believed that mast cells exacerbate in autocrine or paracrine manner the deregulation of neurotransmission. For example, anxiety or stress-induced release of neurotransmitters such as serotonin activates mast cells, which in turn release the content of their granules, further contributing to the chemical imbalance in the brain leading to CNS disorders.

Other mediators released by mast cells can be categorized into vasoactive, nociceptive, proinflammatory and other neurotransmitters. Taken together, these factors are able to induce great disturbance in the activity of neurons, whether they are sensory, motor, or CNS neurons.

In addition, patients afflicted with mastocytosis are more incline to develop CNS disorders than the normal population. This can be explained by the presence of activating mutations in the c-kit receptor, which induce degranulation of mast cells and a burst of factors contributing to chemical imbalance and neurotransmission alteration.

In some cases, activated mast cells can also participate in the destruction of neuronal tissues by releasing a cocktail of different proteases and mediators categorized into three groups: preformed granule-associated mediators (histamine, proteoglycans, and neutral proteases), lipid-derived mediators (prostaglandins, thromboxanes and leucotrienes), and various cytokines (IL-1, IL-2, IL-3, IL-4, IL-5, IL-6, IL-8, TNF-A, GM-CSF, MIP-LA, MIP-1b, MIP-2 and IFN-y). The liberation by activated mast cells of mediators (TNF-A, histamine, leukotrienes, prostaglandines etc.) as well as proteases may i) induce inflammation and vasodilatation and ii) participate in the neuronal tissue destruction process.

Inhibition of c-kit activity reduces cellular proliferation, depleting the mast cells responsible for diseases and/or conditions, such as allergic diseases, thereby suggesting a role for use of inhibitors of c-kit in the treatment of c-kit dependent diseases and/or conditions, such as CNS disorders. Described herein are diarylamine compounds, pharmaceutical compositions and medicaments, which include such diarylamine compounds or a pharmaceutically acceptable salt or solvate thereof, that are potent and selective c-kit inhibitors and which selectively modulate, regulate, and/or inhibit signal transduction mediated by certain native and/or mutant tyrosine kinases implicated in a variety of human and animal diseases such as, by way of example only, CNS disorders.

Drug dependence is the result of a phenomenon called tolerance, which is the need to increase the dose of the drug to maintain its full effect, and of physical dependence, which is the habituation of the body to a drug. When the intake of a drug is discontinued, individual may experience unpleasant withdrawal syndrome. This syndrome is difficult to qualify or quantify but it can be illustrated by a strong feeling of unmet satisfaction.

This episode has been described by former drug addicted individuals as "a strong scream and complaint emanating from the body", which indicates the seriousness and the difficulties encountered by these individuals. In addition, it must be emphasized that drug addiction is accompanied with or may follow psychiatric disorders such as anxiety, depression, and schizophrenia.

Drugs leading to dependence can be classified into two types. One type is responsible for psychologic dependence such as cocaine, marijuana, amphetamine, and hallucinogens. The other type is more prone to physical dependence, but one must not rule out psychologic dependence, and is exemplified by drugs such as heroin, alcohol and nicotine.

Of course, any drug that acts on the CNS may involve a risk of dependence. For example, one of the side effects of benzodiazepine derivatives is dependence. In animal models, it has been observed that administration of drugs such as opioids, cocaine, amphetamine, nicotine, and benzodiazepines is associated with enhanced dopaminergic transmission. The problem is that the increased level of DA may be followed by a down regulation of DA receptors. This might explain in part the observed withdrawal symptoms that are sometimes associated with depression, mood disorders, insomnia and other unwanted dependence disorders.

Drug addiction may be responsible for, or arise from, job pressure or familial problems resulting in anxiety or depression. At the extreme of the spectrum, it can result in hospitalization for overdose, withdrawal episodes and associated substance use disorders.

Finally, anxyolitics such as benzodiazepines are being consumed more and more, therefore, it is urgent to find solutions for preventing and managing drug dependence and withdrawal symptoms. The socioeconomic consequences of reliable solutions will have a huge impact in modern societies since addiction is often accompanied not only with susceptibility to HIV infection and hepatitis. Consequently, research programs aimed at developing compounds capable of alleviating drug dependence and withdrawal symptoms must be encouraged and considered as a top priority.

Substance abuse and drug addiction introduce changes in neurotransmitter synthesis, storage, release, or in the number and affinity of receptors. This can affect neurotransmission and cause drug dependence and withdrawal symptoms. Among neurotransmitters, example include, but are not limited to, glutamate and aspartate, which are the major excitatory neurotransmitters, aminobutyric acid (GABA), which is the major inhibitory neurotransmitter in the brain and shown to be involved in the physiopathology of depression; serotinin (5-HT); dopamine (DA), which was observed in depressed patients; acetylcholine, norepinephrine which interacts with adrenergic receptors and which is regulated by tyrosine hydroxylase and monoamine oxidase; endorphins, which are polypeptides that activate many central neurons and interact with opioid receptors, and others neurotransmitters such as enkephalins, dynorphins, histamine, vasopressin, vasoactive intestinal peptide, carnosine, bradykinin, cholecystokinin, bombesin, somatostatin, corticotropin releasing factor, neurotensin, and adenosine. As mentioned above, any imbalance in these neurotransmitters or any deregulation of associated receptors due to drug intake may lead to the development of drug dependence and withdrawal symptoms.

It has been identified that mast cells are involved in or contribute to drug dependence and withdrawal symptoms. The activation of mast cells by different drugs, including, but not limited to, salicylic derivatives, morphine derivatives, opioids, heroin, amphetamines, alcohol, nicotine, analgesics, anesthetics, and anxyolitics results in the degranulation of mast cells, which participate in the exacerbation of the chemical imbalance responsible for drug habituation and withdrawal syndrome. In addition, following mast cells activation, released granules liberate various factors capable of modulating and altering neurotransmission. Among such factors, is morphine which is bound or stored in mast cells granules. Also tobacco smoke induces the release of mediators from canine mast cells and modulates prostaglandin production leading to asthma. In addition, patients afflicted with mastocytosis are more incline to develop substance use disorders than the normal population. This can be explained by the presence of activating mutations in the c-kit receptor, which induce degranulation of mast cells and a burst of factors contributing to chemical imbalance and neurotransmission alteration.

Presently, there is no treatment providing relief and help to individuals to withdraw from their addiction are available. C-kit inhibitors may be used for treating substance abuse disorders, particularly drug addiction, drug abuse, drug habituation, drug dependence, withdrawal syndrome and overdose, comprising administering a compound capable of depleting mast cells to a human in need of such treatment.

Inhibition of c-kit activity reduces cellular proliferation, depleting the mast cells responsible for diseases and/or conditions, such as drug dependency, thereby suggesting a role for use of inhibitors of c-kit in the treatment of c-kit dependent diseases and/or conditions, such as drug dependency. Described herein are diarylamine compounds, pharmaceutical compositions and medicaments, which include such diarylamine compounds or a pharmaceutically acceptable salt or solvate thereof, that are potent and selective c-kit inhibitors and which selectively modulate, regulate, and/or inhibit signal transduction mediated by certain native and/or mutant tyrosine kinases implicated in a variety of human and animal diseases such as, by way of example only, drug dependency.

Described herein are diarylamine compounds, pharmaceutical compositions and medicaments, which include such diarylamine compounds or a pharmaceutically acceptable salt or solvate thereof, for treating a disease and/or condition in an animal in which c-kit receptor activity contributes to the pathology and/or symptomology of the disease or condition. Such diseases and/or conditions include, but are not limited to, (i) neoplastic diseases, such as, but not limited to mastocytosis, canine mastocytoma, human gastrointestinal stromal tumor, small cell lung cancer, non-small cell lung cancer, acute myelocytic leukemia, acute lymphocytic leukemia, myelodysplastic syndrome, chronic myelogenous leukemia, colorectal carcinomas, gastric carcinomas, gastrointestinal stromal tumors, testicular cancers, glioblastomas, and astrocytomas; (ii) allergy diseases, such as, but not limited to, asthma, allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation and blood sucking parasitic infestation; (iii) inflammatory diseases, such as, but not limited to, rheumatoid arthritis, conjunctivitis, rheumatoid spondylitis, osteoarthritis, gouty arthritis and other arthritic conditions; (iv) autoimmune diseases, such as, but not limited to, multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, dermatomyositis, polymyositis, Sjogren's syndrome, nodular panarteritis, autoimmune enteropathy, and proliferative glomerulonephritis; (v) graft-versus-host diseases, such as, but not limited to, organ transplantation graft rejection (including, but not limited to, kidney transplantation, pancreas transplantation, liver transplantation, heart transplantation, lung transplantation, and bone marrow transplantation); (vi) metabolic syndromes, such as, but not limited to, type I diabetes, type II diabetes, or obesity; (vii) CNS related disorders, such, as, but not limited to, depression, dysthymic disorder, cyclothymic disorder, bipolar depression, severe or "melancholic" depression, atypical depression, refractory depression, seasonal depression, anorexia, bulimia, premenstrual syndrome and postmenopause syndrome, as mental slowing and loss of concentration, pessimistic worry, agitation, self-deprecation and decreased libido, as anxiety disorders including anxiety associated with hyperventilation and cardiac arrhythmias, phobic disorders, obsessive-compulsive disorder, posttraumatic stress disorder, acute stress disorder, and generalized anxiety disorder, as psychiatric disorders such as panic attacks, including psychosis, delusional disorders, conversion disorders, phobias, mania, delirium, dissociative episodes including dissociative amnesia, dissociative fugue and dissociative suicidal behavior, self-neglect, violent or aggressive behavior, trauma, borderline personality, and acute psychosis as schizophrenia including paranoid schizophrenia, disorganized schizophrenia, catatonic schizophrenia, and undifferentiated schizophrenia; (viii) neurodegenerative diseases, such as, but not limited to, Alzheimer's disease, Parkinson's disease, Huntington's disease, the prion diseases, Motor Neuron Disease (MND), and Amyotrophic Lateral Sclerosis (ALS), (ix) pain, such as, but not limited to, acute pain, postoperative pain, chronic pain, nociceptive pain, cancer pain, neuropathic pain, and psychogenic pain syndromes; (x) substance use disorders, such as, but not limited to, drug addiction, drug abuse, drug habituation, drug dependence, withdrawal syndrome and overdose; (xi) prion diseases; (xii) cancers, such as, but not limited to, melanoma, gastrointestinal stromal tumor (GIST), small-cell lung cancer, germ cell tumors, mast cell tumors, breast cancer, acute myelogenous leukemia, neuroblastoma, mastocytosis, and other solid tumors; (xiii) heart diseases; (xiv) fibrotic diseases, such as, but not limited to, hepatitis C (HCV), liver fibrosis, nonalcoholic steatohepatitis (NASH), cirrhosis in liver, pulmonary fibrosis, and bone marrow fibrosis; (xv) idiopathic pulmonary arterial hypertension (IPAH); and (xvi) primary pulmonary hypertension (PPH).

Compounds

Compounds having the structure of Formula (A) or Formula (B), pharmaceutically acceptable salts, pharmaceutically acceptable N-oxides, pharmaceutically active metabolites, pharmaceutically acceptable prodrugs, and pharmaceutically acceptable solvates thereof, modulate the activity of c-kit receptors; and, as such, are useful for treating diseases or conditions in which aberrant c-kit receptor activity contributes to the pathology and/or symptoms of a disease or condition:

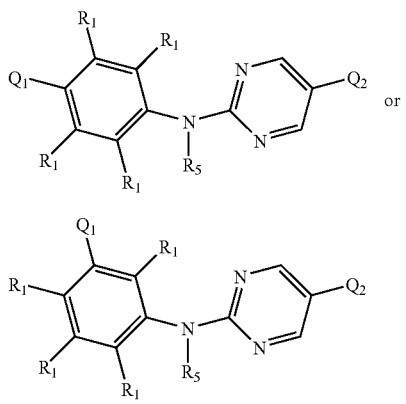

wherein:
Q₁ is H, halogen, a group comprising a non-aromatic tertiary amine, a group comprising a non-aromatic secondary amine, or is an optionally substituted moiety selected from the group consisting of: -L-alkyl, -L-cycloalkyl, -L-heteroalkyl, -L-haloalkyl, -L-aryl, -L-heterocycloalkyl, and -L-heteroaryl; wherein L is selected from a bond, —O—, —NH—, —S—, —C(O)—, —C(S)—, —C(O)O—, —C(O)NH—, —S(O)—, —S(O)₂—, —OC(O)—, —C(O)NR" (CR"₂)₁₋₆C(O)O—, —CR"₂NR"CR"₂C(O)O—, —C(O)—NR"YC(O)O—, —C(O)NR"NR"C(O)O—, and —S(O)NH—; and Y is optionally substituted arylene or heteroarylene;

each R₁ is independently selected from the group consisting of H, halogen, and an optionally substituted moiety selected from -L₁-alkyl, -L₁-cycloalkyl, -L₁-heteroalkyl, -L₁-haloalkyl, -L₁-aryl, -L₁-heterocycloalkyl, and -L₁-heteroaryl; wherein L₁ is selected from a bond, —O—, —NH—, —S—, —C(O)—, —C(S)—, —C(O)O—, —C(O)NH—, —S(O)—, —S(O)₂—, —C(O)NR'"(CR'"₂)₁₋₆C(O)O—, —OC(O)—, —CR"₂NR"CR"₂C(O)O—, —C(O)—NR"Y'C(O)O—, —C(O)NR"NR"C(O)O—, and —S(O)NH—; and Y' is optionally substituted arylene or heteroarylene;

Q₂ is selected from the group consisting of H, halogen, and a group comprising an optionally substituted moiety selected from -L₆-alkyl, -L₆-cycloalkyl, -L₆-heteroalkyl, -L₆-haloalkyl, -L₆-aromatic carbocycle, -L₆-heterocycloalkyl, and -L₆-aromatic heterocycle; wherein L₆ is selected from a bond, —O—, —NH—, —S—, —C(O)—, —C(S)—, —C(O)O—, —C(O)NH—, —S(O)—, —S(O)₂—, —C(O)NR"(CR"₂)₁₋₆C(O)O—, —OC(O)—, —CR"₂NR"CR"₂C(O)O—, —C(O)—NR"Y"C(O)O—, —C(O)NR"NR"C(O)O—, and —S(O)NH—; and Y" is optionally substituted arylene or heteroarylene;

each R" is independently H, OH, halogen, $C_{1-6}$alkyl, substituted $C_{1-6}$alkyl, $C_{1-6}$alkoxy, halo-$C_{1-6}$alkyl, halo-$C_{1-6}$alkoxy, aryl, haloaryl, or heteroaryl;

any two R₁ groups together may form an optionally substituted 5 to 8-membered heterocyclic, cycloalkyl, or aryl ring;

R₅ is selected from the group consisting of H, and an optionally substituted moiety selected from -L₅-H, -L₅-alkyl, -L₅-cycloalkyl, -L₅-heteroalkyl, -L₅-haloalkyl, -L₅-aryl, -L₅-heterocycloalkyl, and -L₅-heteroaryl, wherein L₅ is selected from a bond, —R'O—, —R'N(H)—, —R'S—, —R'C(O)—, —R'C(S)—, —R'C(O)O—, and —R'C(O)NH—;

each R' is independently selected from the group consisting of a bond, alkylene, substituted alkylene, heteroalkylene, substituted heteroalkylene, alkenylene, substituted alkenylene, cycloalkylene, substituted cycloalkylene, heteroalkylene, substituted heteroalkylene, heterocycloalkylene, substituted heterocycloalkylene, arylene, substituted arylene, heteroarylene, substituted heteroarylene, alkarylene, substituted alkarylene, aralkylene, and substituted aralkylene; and any R₁ and R₅ taken together may form an optionally substituted 5 to 8-membered heterocyclic, cycloalkyl, or aryl ring.

Compounds having the structure of Formula (A) or Formula (B) include compounds having the structure of Formula (1) or Formula (46) and pharmaceutically acceptable salts, pharmaceutically acceptable N-oxides, pharmaceutically active metabolites, pharmaceutically acceptable prodrugs, and pharmaceutically acceptable solvates thereof. Such compounds also modulate the activity of c-kit receptors and, as such, are useful for treating diseases or conditions in which aberrant c-kit receptor activity contributes to the pathology and/or symptoms of a disease or condition:

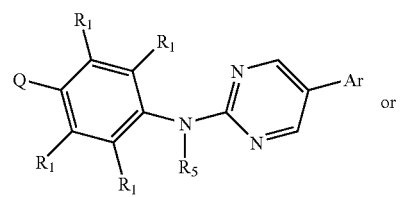

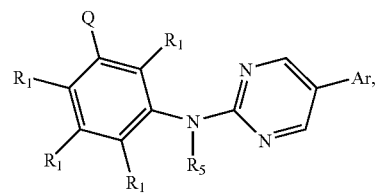

wherein:
Ar is a group comprising a moiety selected from an optionally substituted five-membered aromatic heterocycle, an optionally substituted five-membered aromatic carbocycle, an optionally substituted six-membered aromatic heterocycle, and a substituted, optionally further substituted six-membered aromatic carbocycle;

Q is a group comprising a non-aromatic tertiary amine or a non-aromatic secondary amine, with the proviso that Q is not —NR$_a$R$_b$ or —SO₂NR$_a$R$_b$; wherein each of R$_a$ and R$_b$ is independently H or $C_{1-6}$alkyl optionally substituted by mono- or di-alkyl ($C_{1-6}$) amino;

each R₁ is independently selected from the group consisting of H, halogen, and an optionally substituted moiety selected from -L₁-alkyl, -L₁-cycloalkyl, -L₁-heteroalkyl, -L₁-haloalkyl, -L₁-aryl, -L₁-heterocycloalkyl, and -L₁-heteroaryl; wherein L₁ is selected from a bond, —O—, —NH—, —S—, —C(O)—, —C(S)—, —C(O)O—, —C(O)NH—, —S(O)—, —S(O)₂—, —C(O)NH(CR"₂)₁₋₆C(O)O—, —C(O)NR"NR"C(O)O—, and —S(O)NH—;

each R" is independently H, OH, halogen, $C_{1-6}$alkyl, substituted $C_{1-6}$alkyl, $C_{1-6}$alkoxy, halo-$C_{1-6}$alkyl, halo-$C_{1-6}$alkoxy, aryl, halo aryl, or heteroaryl;

or any two adjacent $R_1$ groups together may form an optionally substituted 5 to 8-membered heterocyclic, cycloalkyl, or aryl ring;

$R_5$ is selected from the group consisting of H, and an optionally substituted moiety selected from -$L_5$-H, -$L_5$-alkyl, -$L_5$-cycloalkyl, -$L_5$-heteroalkyl, -$L_5$-haloalkyl, -$L_5$-aryl, -$L_5$-heterocycloalkyl, and -$L_5$-heteroaryl; wherein $L_5$ is selected from a bond, —R'O—, —R'N(H)—, —R'S—, —R'C(O)—, —R'C(S)—, —R'C(O)O—, and —R'C(O)NH—;

each R' is independently selected from the group consisting of a bond, alkylene, substituted alkylene, heteroalkylene, substituted heteroalkylene, alkenylene, substituted alkenylene, cycloalkylene, substituted cycloalkylene, heteroalkylene, substituted heteroalkylene, heterocycloalkylene, substituted heterocycloalkylene, arylene, substituted arylene, heteroarylene, substituted heteroarylene, alkarylene, substituted alkarylene, aralkylene, and substituted aralkylene; and any $R_1$ and $R_5$ taken together may form an optionally substituted 5 to 8-membered heterocyclic, cycloalkyl, or aryl ring.

Table 1 shows exemplary, non-limiting examples of compounds which have the structure of Formula (A) or Formula (B), and which modulate the activity of c-kit receptors.

TABLE 1

Examplary compounds which modulate the activiry of c-kit receptors.

| # | Structure | MS [M + 1]⁺ |
|---|-----------|-------------|
| 1 | 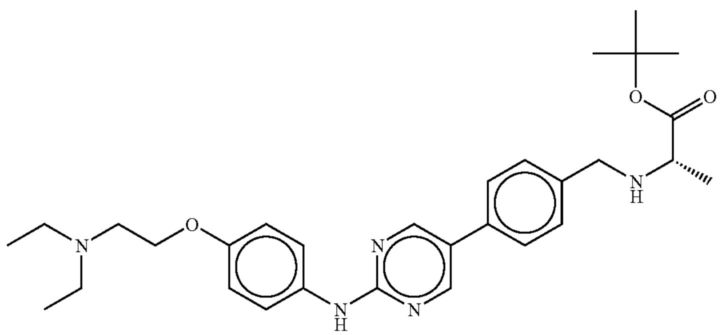 | 520.4 |
| 2 | 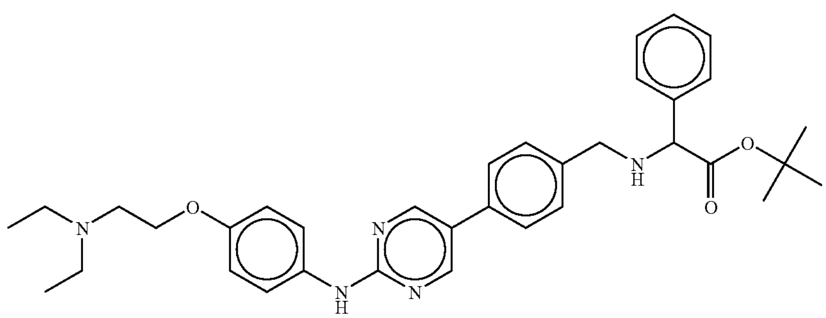 | 582.4 |
| 3 | 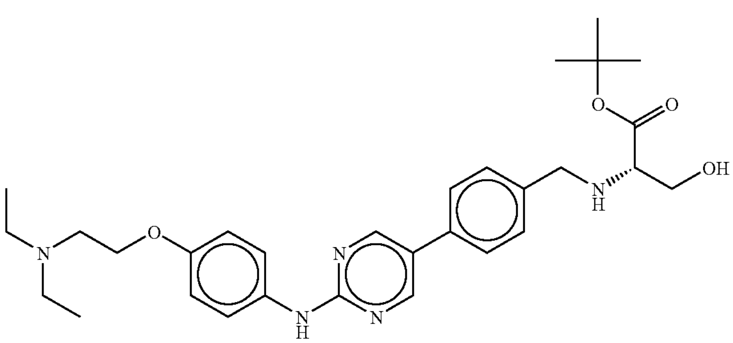 | 536.4 |

TABLE 1-continued

Examplary compounds which modulate the activiry of c-kit receptors.

| # | Structure | MS [M + 1]+ |
|---|---|---|
| 4 | 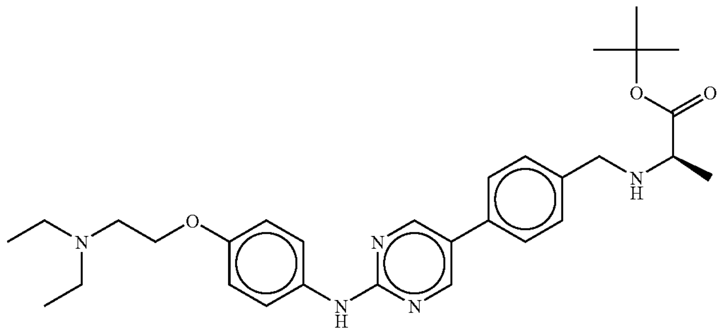 | 520.4 |
| 5 | 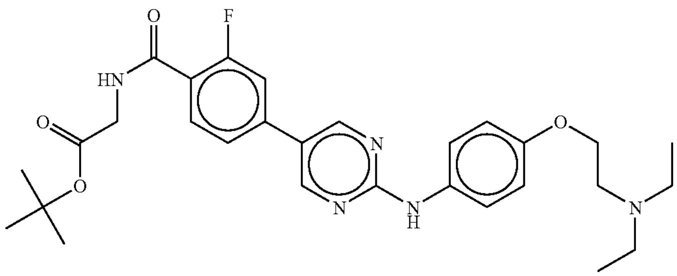 | 538.3 |
| 6 | 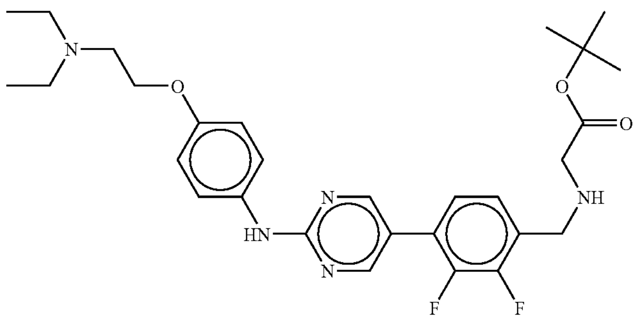 | 542.3 |
| 7 | 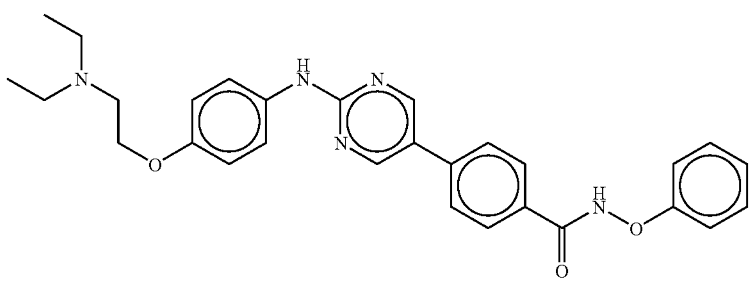 | 498.3 |
| 8 | 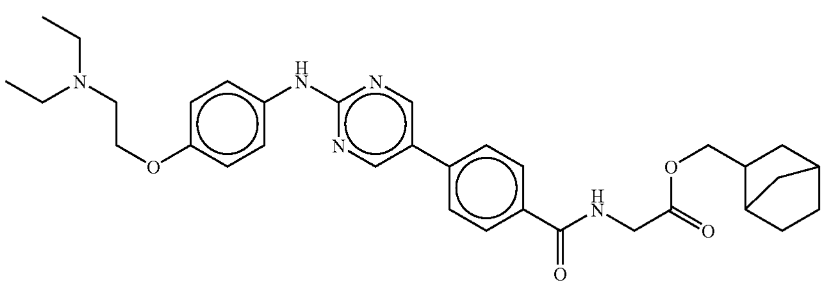 | 572.3 |

TABLE 1-continued
Examplary compounds which modulate the activiry of c-kit receptors.
| # | Structure | MS [M + 1]+ |
|---|---|---|
| 9 | 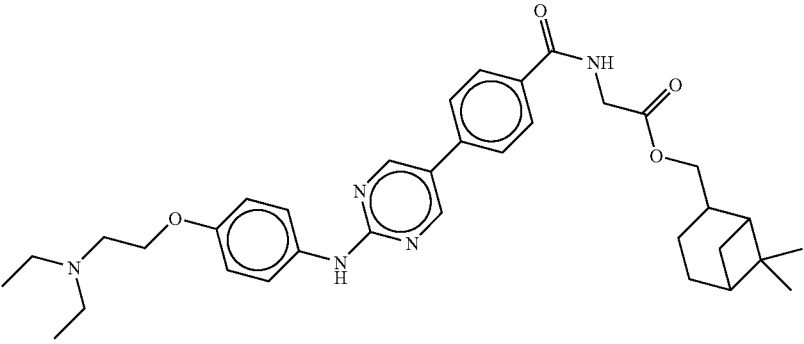 | 600.4 |
| 10 | 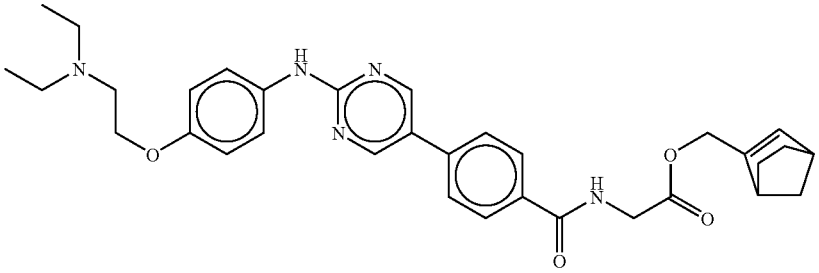 | 570.5 |
| 11 | 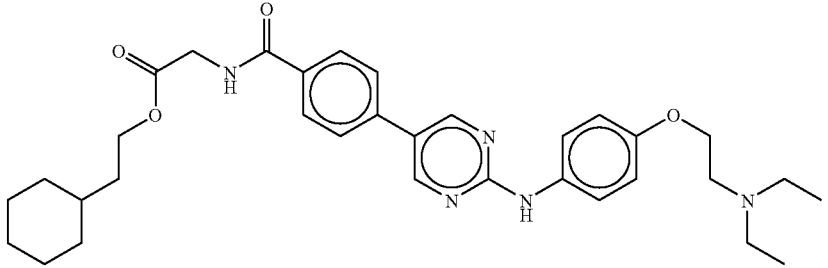 | 574.4 |
| 12 | 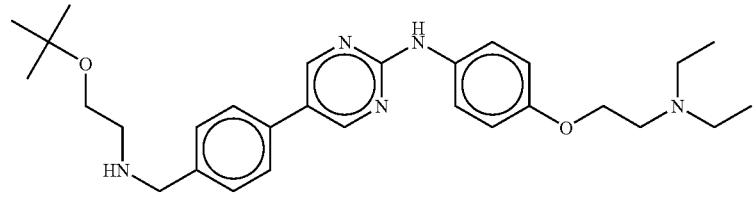 | 492.4 |
| 13 | 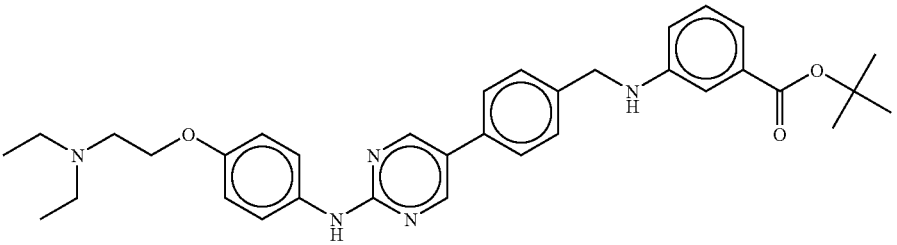 | 568.4 |

TABLE 1-continued

Examplary compounds which modulate the activiry of c-kit receptors.

| # | Structure | MS [M + 1]+ |
|---|---|---|
| 14 | 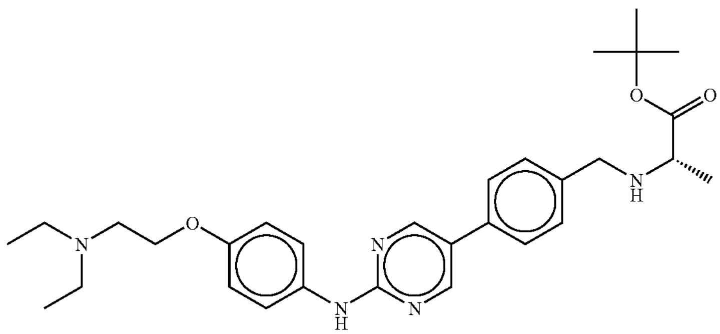 | 520.4 |
| 15 | 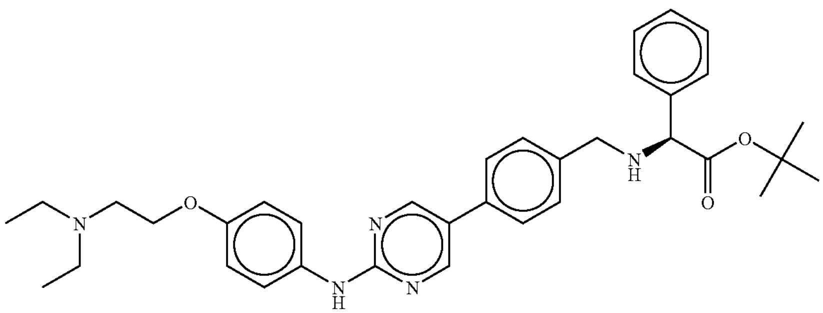 | 582.4 |
| 16 | 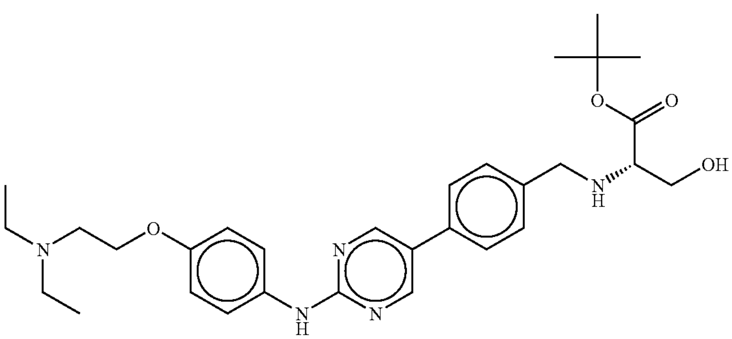 | 536.4 |
| 17 | 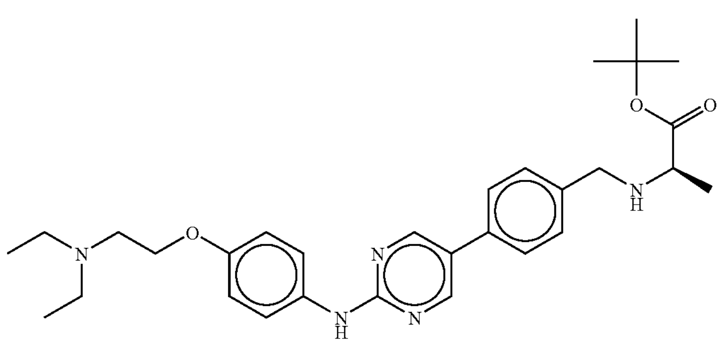 | 520.4 |

TABLE 1-continued

Examplary compounds which modulate the activiry of c-kit receptors.

| # | Structure | MS [M + 1]+ |
|---|---|---|
| 18 | 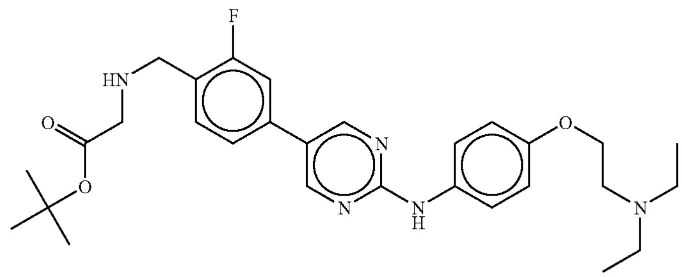 | 524.5 |
| 19 | 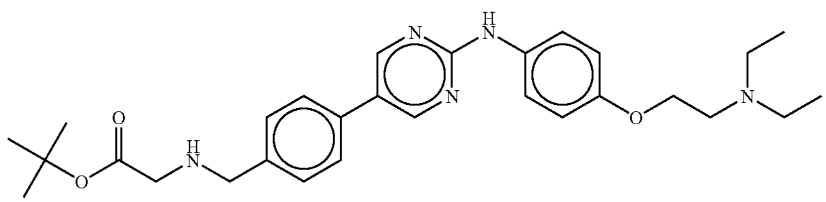 | 506.5 |
| 20 | 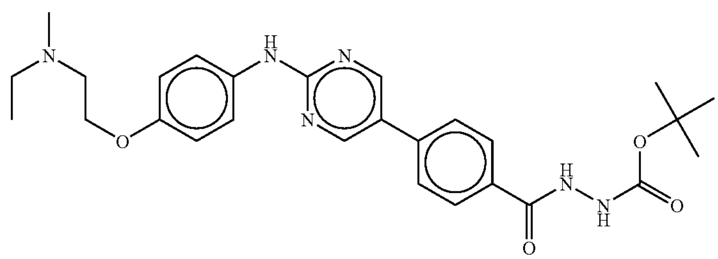 | 521.2 |
| 21 | 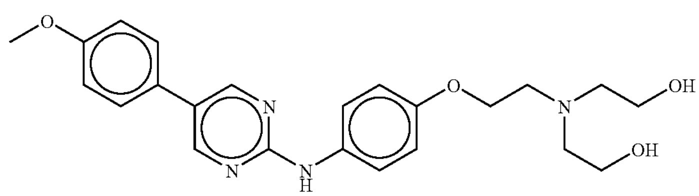 | 425.1 |
| 22 | 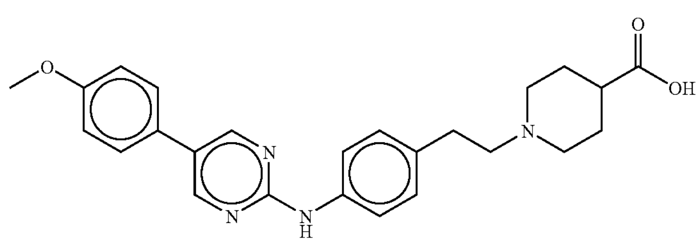 | 433.2 |
| 23 | 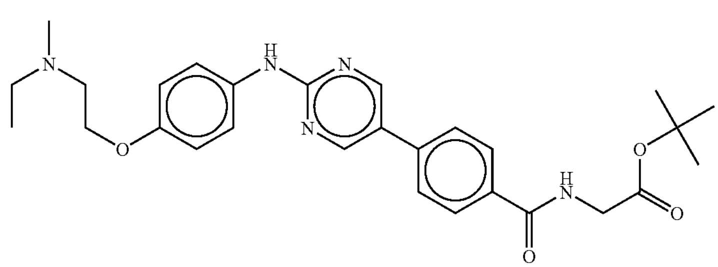 | 520.5 |

TABLE 1-continued

Examplary compounds which modulate the activiry of c-kit receptors.

| # | Structure | MS [M + 1]+ |
|---|---|---|
| 24 | | 447.2 |
| 25 | | 377.2 |
| 26 | | 627.0 |
| 27 | | 534.5 |
| 28 | | 631.6 |
| 29 | | 421.2 |

TABLE 1-continued

Examplary compounds which modulate the activiry of c-kit receptors.

| # | Structure | MS [M + 1]+ |
|---|-----------|-------------|
| 30 | 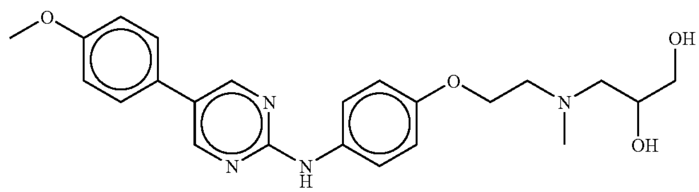 | 425.5 |
| 31 | 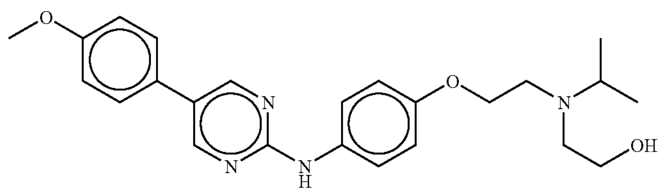 | 423.1 |
| 32 | 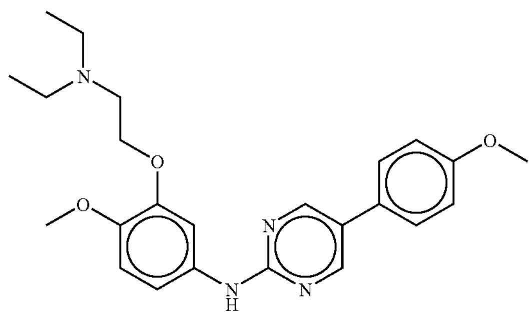 | 423.4 |
| 33 | 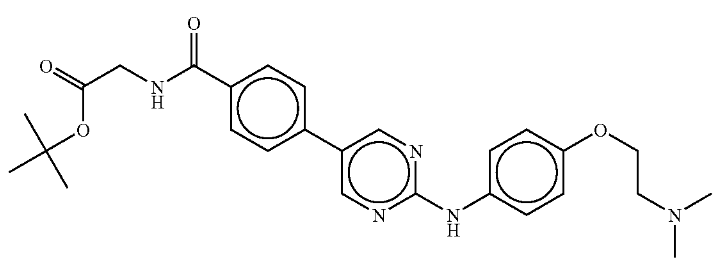 | 492.3 |
| 34 | 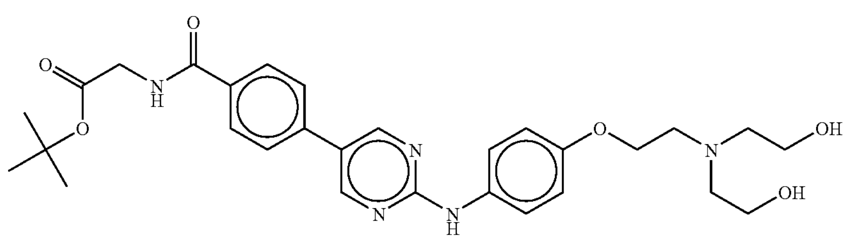 | 552.2 |
| 35 | 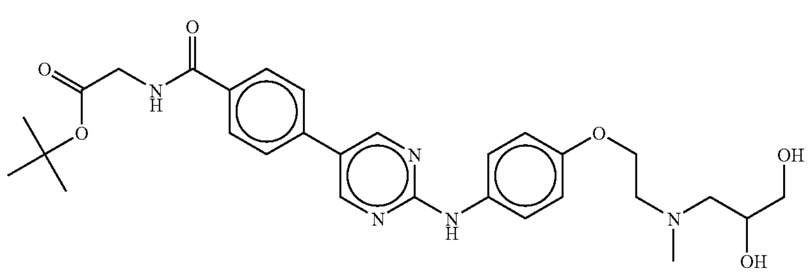 | 552.1 |

TABLE 1-continued

Examplary compounds which modulate the activiry of c-kit receptors.

| # | Structure | MS [M + 1]+ |
|---|-----------|-------------|
| 36 | 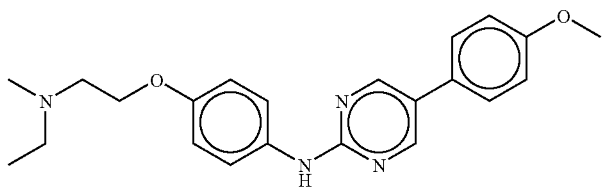 | 379.2 |
| 37 | 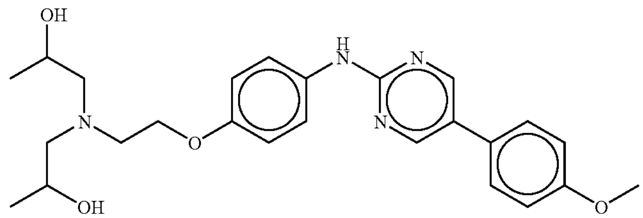 | 453.1 |
| 38 | 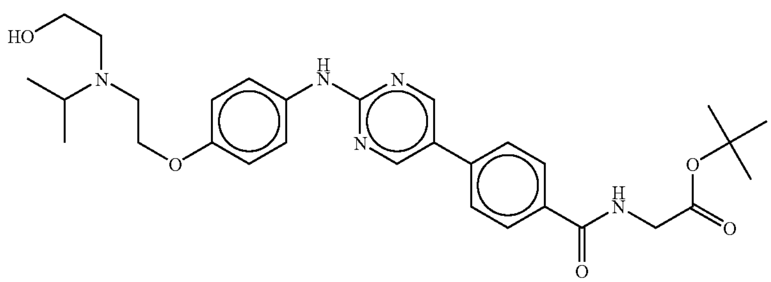 | 550.2 |
| 39 | 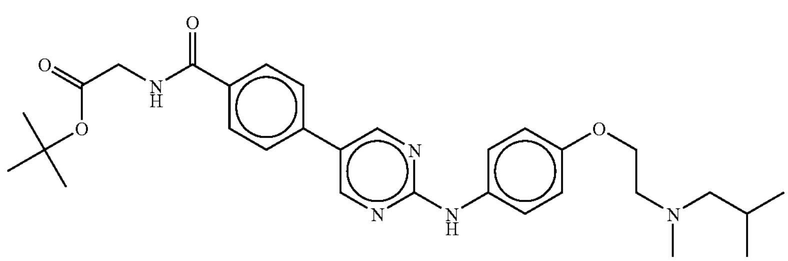 | 534.2 |
| 40 | 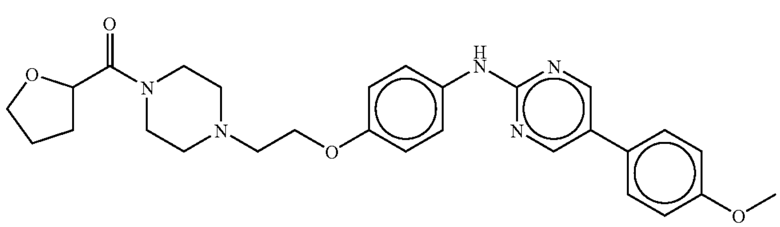 | 504.3 |
| 41 | 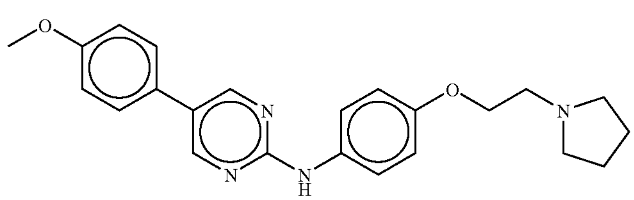 | 391.2 |

TABLE 1-continued

Examplary compounds which modulate the activiry of c-kit receptors.

| # | Structure | MS [M + 1]⁺ |
|---|---|---|
| 42 | 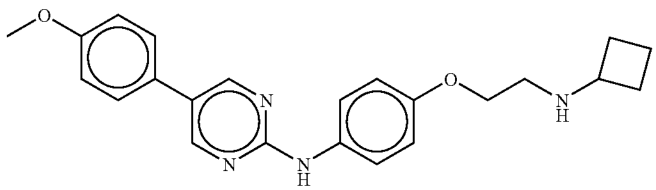 | 391.2 |
| 43 | 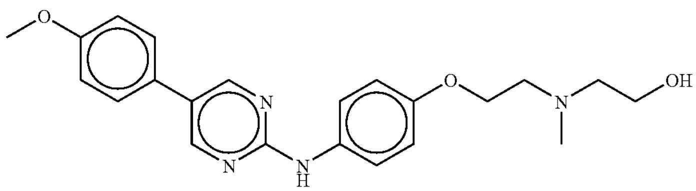 | 395.2 |
| 44 | 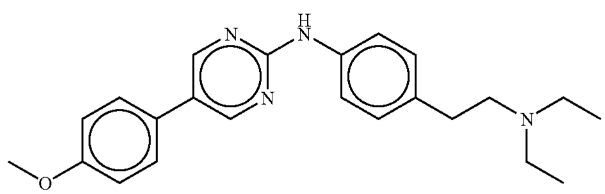 | 377.4 |
| 45 | 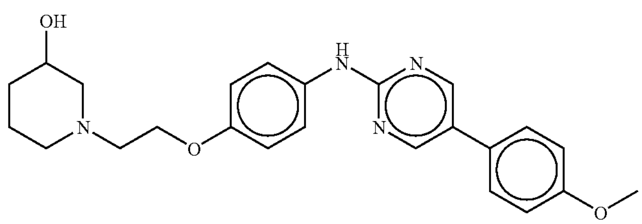 | 421.2 |
| 46 | 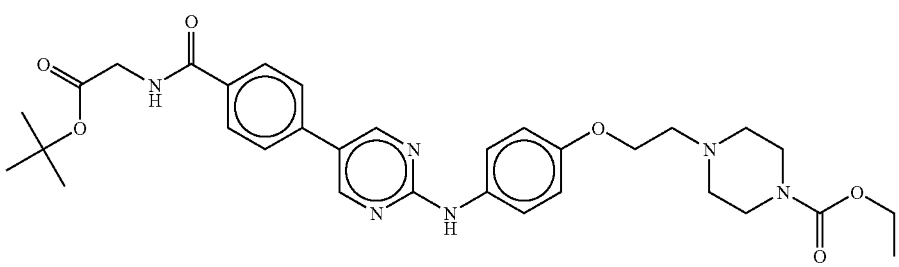 | 605.1 |
| 47 | 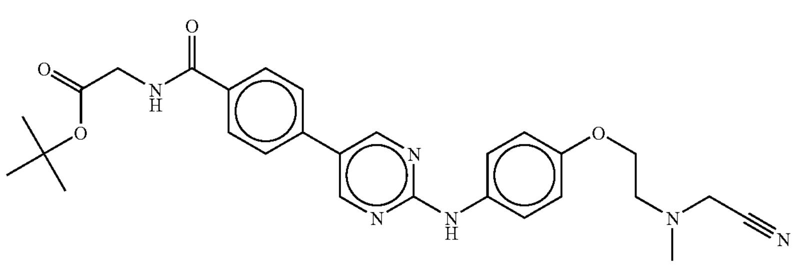 | 517.5 |

TABLE 1-continued

Examplary compounds which modulate the activiry of c-kit receptors.

| # | Structure | MS [M + 1]+ |
|---|---|---|
| 48 | 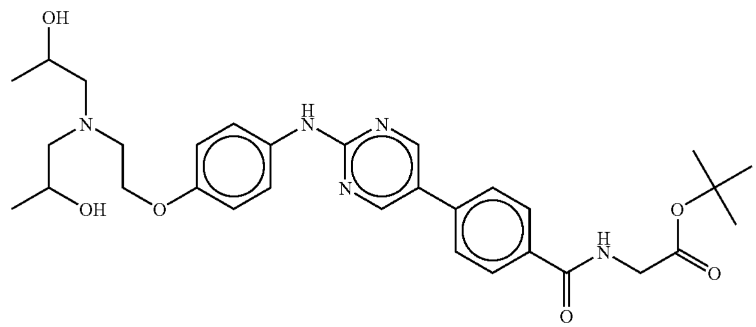 | 580.3 |
| 49 | 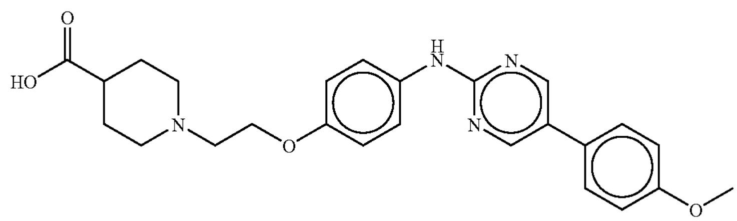 | 449.2 |
| 50 | 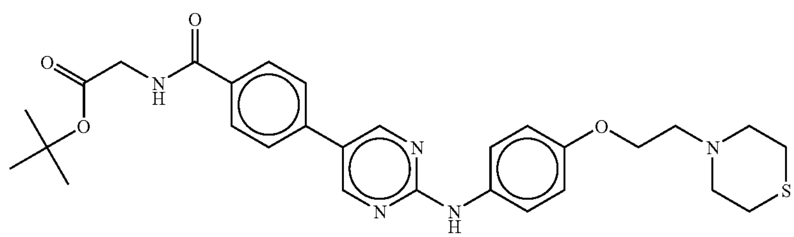 | 550.1 |
| 51 | 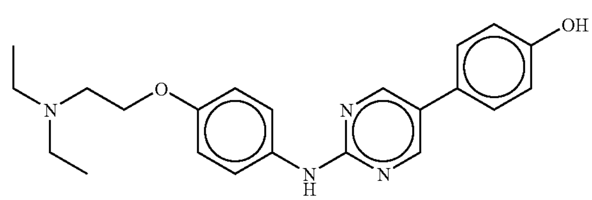 | 379.2 |
| 52 | 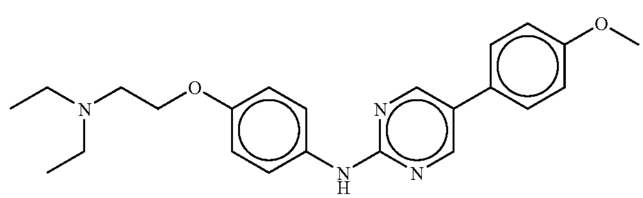 | 393.4 |
| 53 | 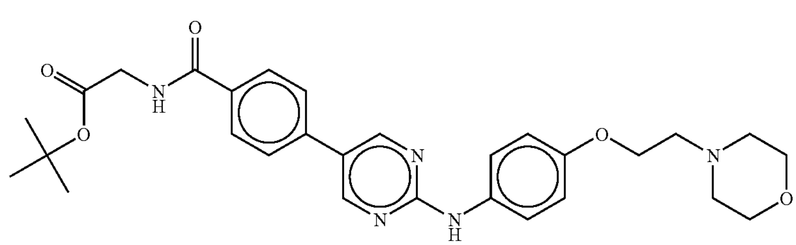 | 534.2 |

TABLE 1-continued

Examplary compounds which modulate the activiry of c-kit receptors.

| # | Structure | MS [M + 1]+ |
|---|---|---|
| 54 | 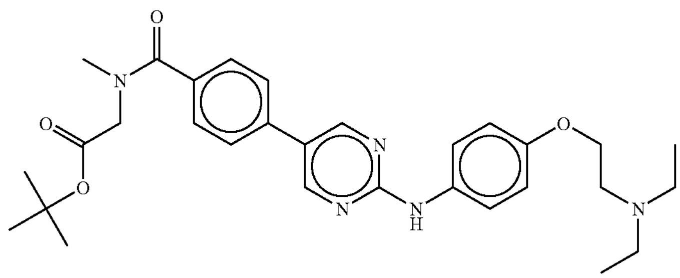 | 534.5 |
| 55 | 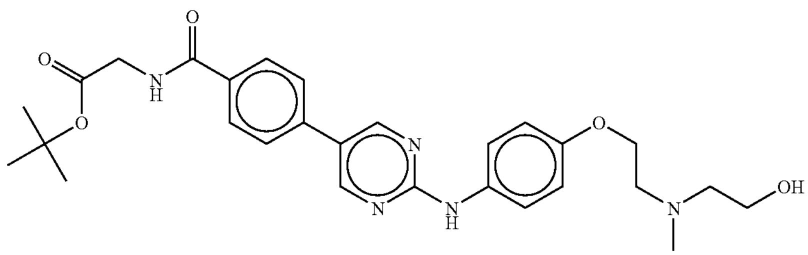 | 522.2 |
| 56 | 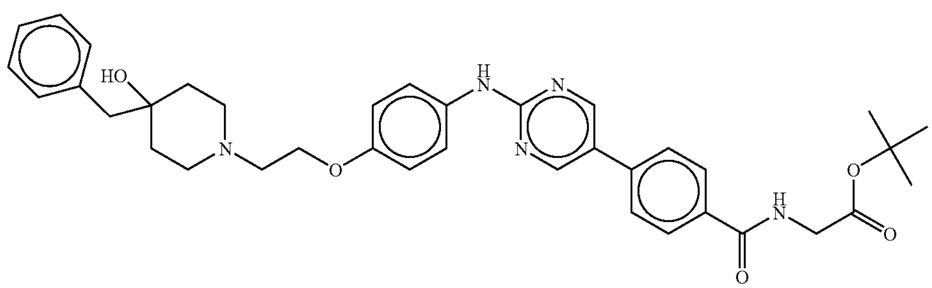 | 638.0 |
| 57 | 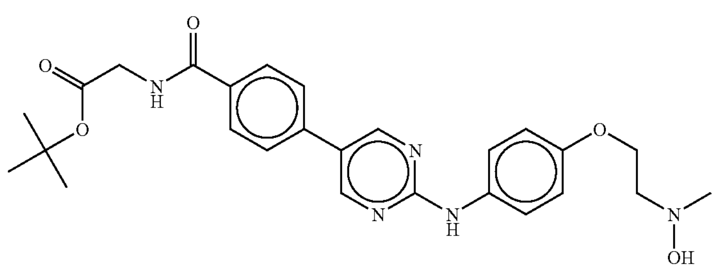 | 494.3 |
| 58 | 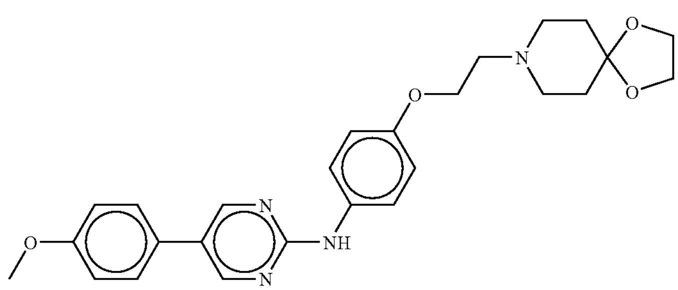 | 463.1 |

TABLE 1-continued

Examplary compounds which modulate the activiry of c-kit receptors.

| # | Structure | MS [M + 1]+ |
|---|---|---|
| 59 | 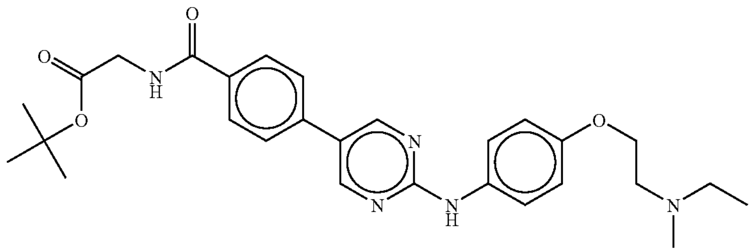 | 506.2 |
| 60 | 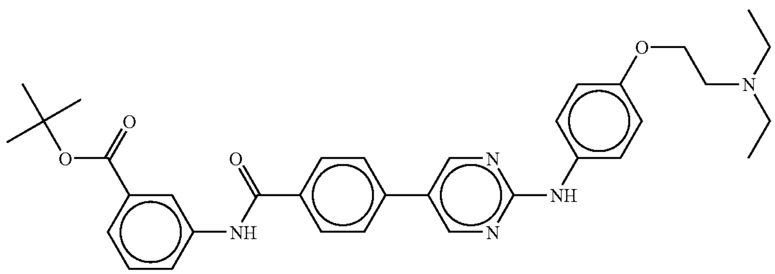 | 582.6 |
| 61 | 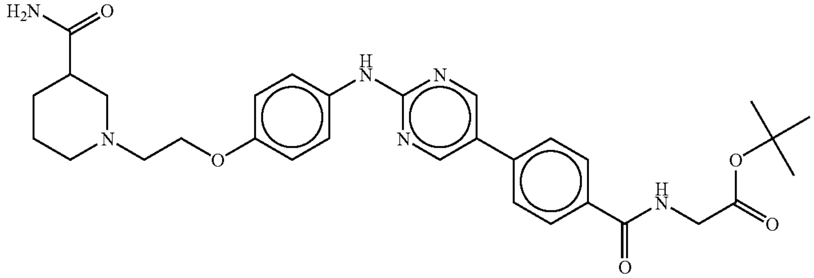 | 575.1 |
| 62 | 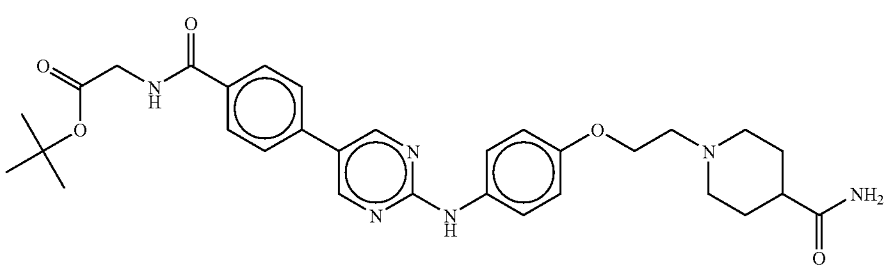 | 575.1 |
| 63 | 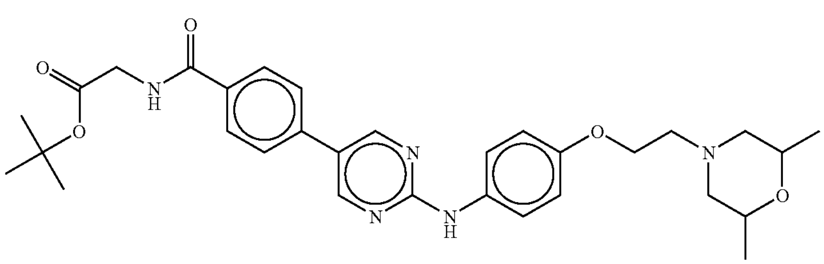 | 562.2 |

TABLE 1-continued

Examplary compounds which modulate the activiry of c-kit receptors.

| # | Structure | MS [M + 1]+ |
|---|-----------|-------------|
| 64 | 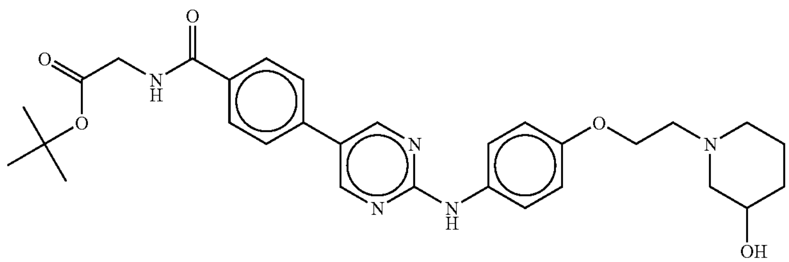 | 548.6 |
| 65 | 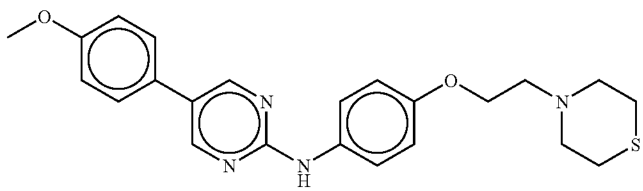 | 423.1 |
| 66 | 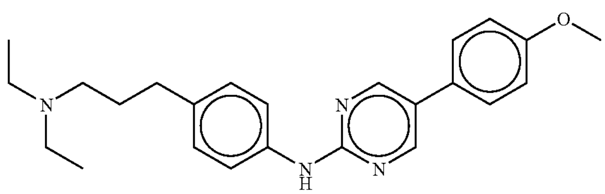 | 391.3 |
| 67 | 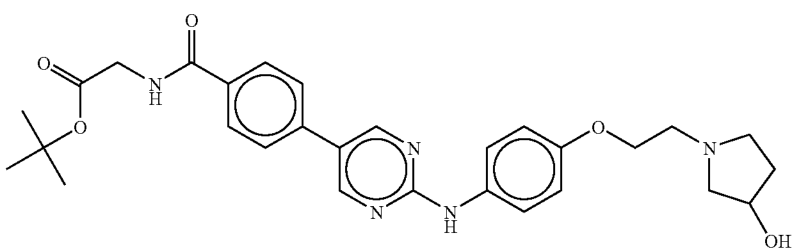 | 534.2 |
| 68 | 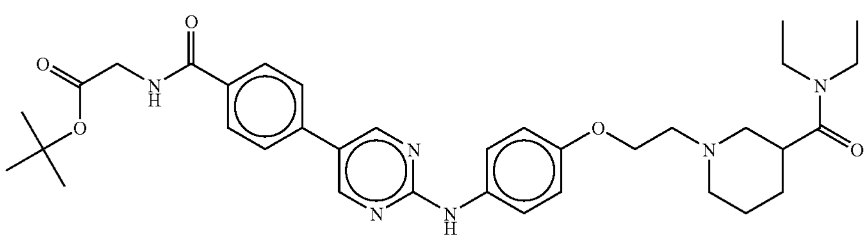 | 631.0 |
| 69 | 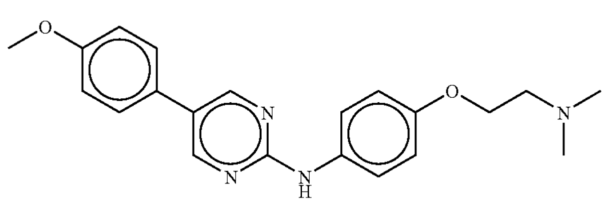 | 365.2 |

TABLE 1-continued

Examplary compounds which modulate the activiry of c-kit receptors.

| # | Structure | MS [M + 1]+ |
|---|---|---|
| 70 | 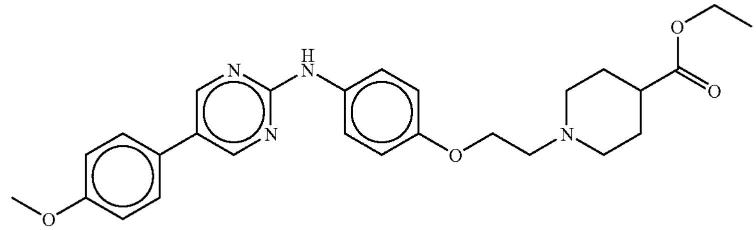 | 477.0 |
| 71 | 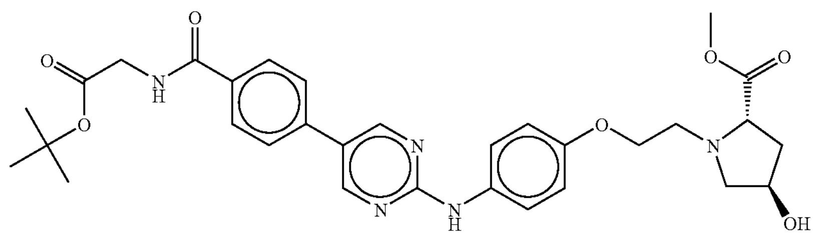 | 592.0 |
| 72 | 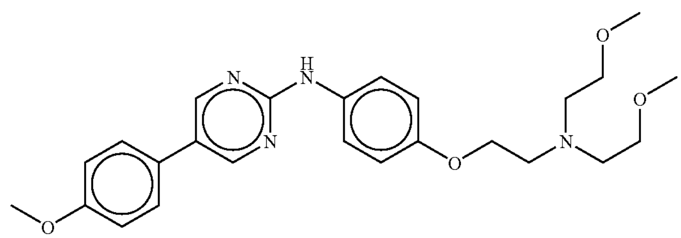 | 453.1 |
| 73 | 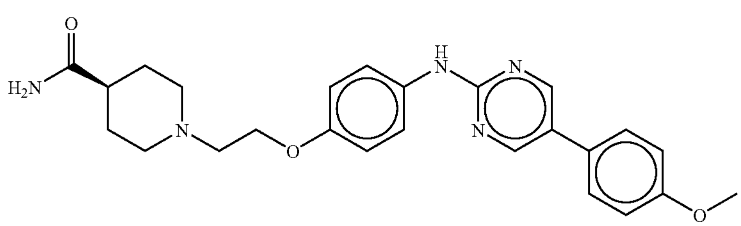 | 448.3 |
| 74 | 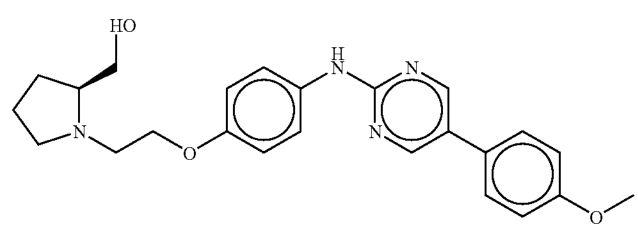 | 421.1 |
| 75 | 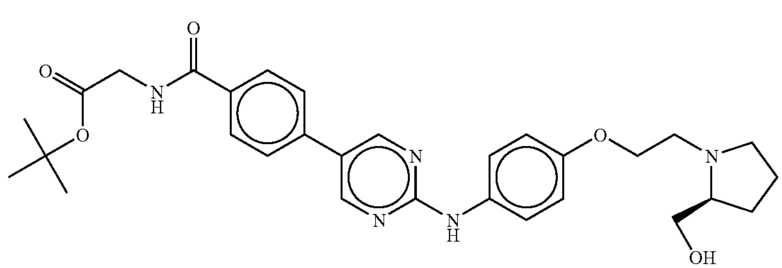 | 548.5 |

TABLE 1-continued

Examplary compounds which modulate the activiry of c-kit receptors.

| # | Structure | MS [M + 1]⁺ |
|---|---|---|
| 76 | 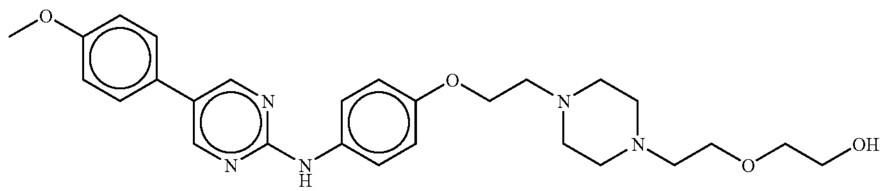 | 494.1 |
| 77 | 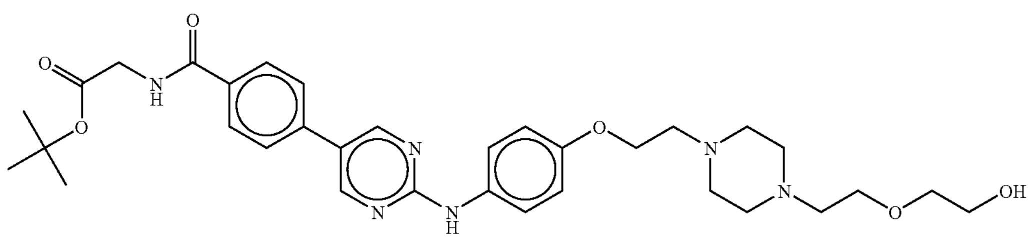 | 621.0 |
| 78 | 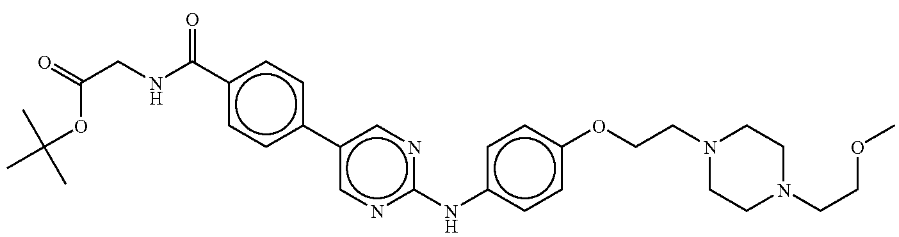 | 591.1 |
| 79 | 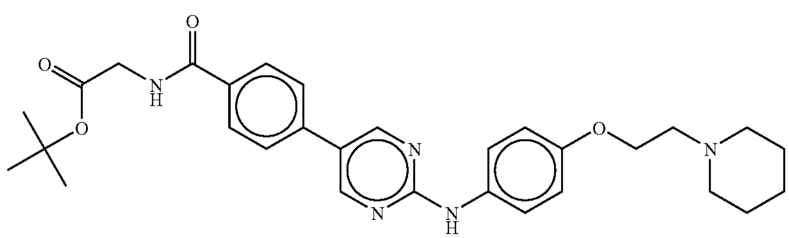 | 532.3 |
| 80 | 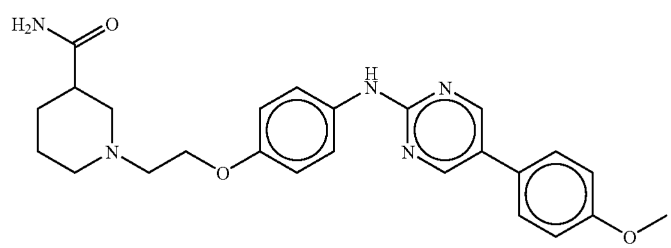 | 448.3 |
| 81 | 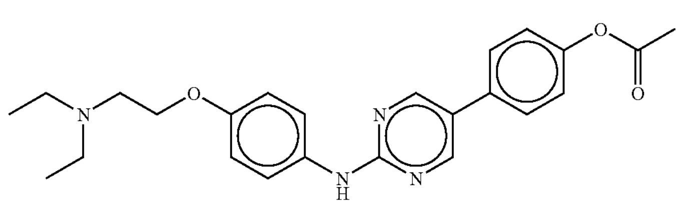 | 421.2 |

TABLE 1-continued
Examplary compounds which modulate the activiry of c-kit receptors.
| # | Structure | MS [M + 1]+ |
|---|---|---|
| 82 | 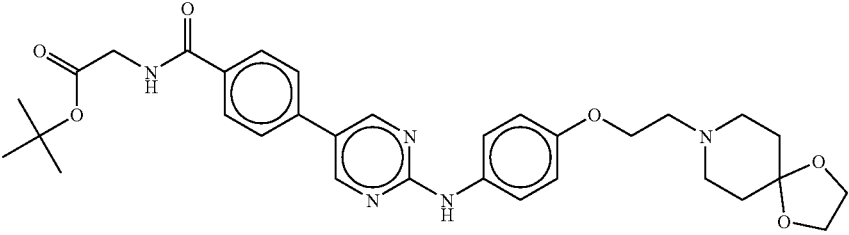 | 590.1 |
| 83 | 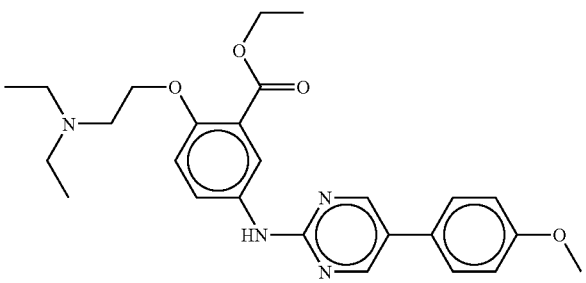 | 465.5 |
| 84 | 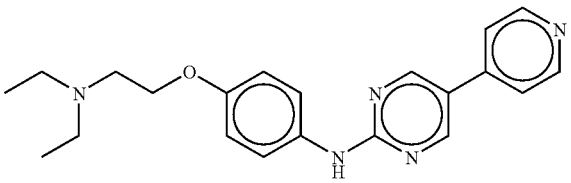 | 364.2 |
| 85 | 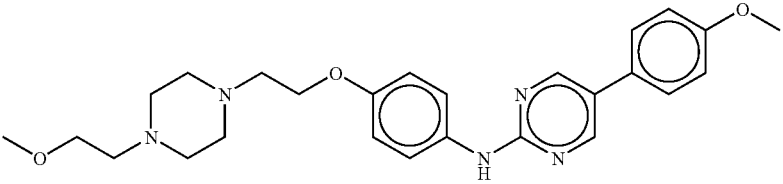 | 464.3 |
| 86 | 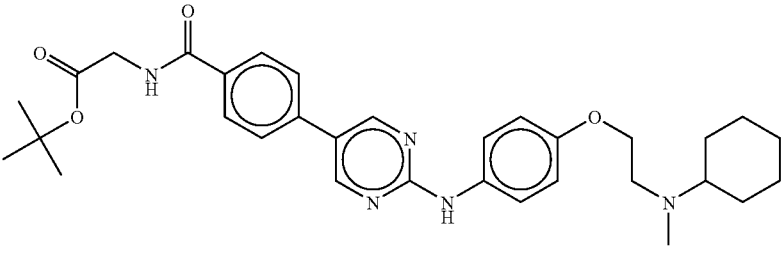 | 560.2 |
| 87 | 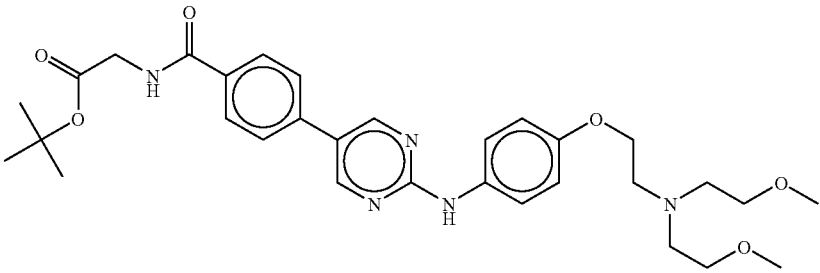 | 580.1 |

TABLE 1-continued
Examplary compounds which modulate the activiry of c-kit receptors.
| # | Structure | MS [M + 1]+ |
|---|---|---|
| 88 | 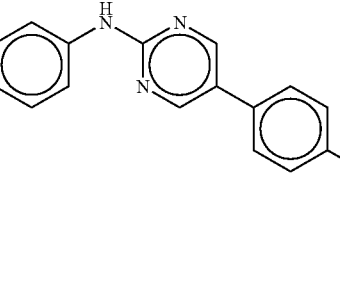 | 560.5 |
| 89 | 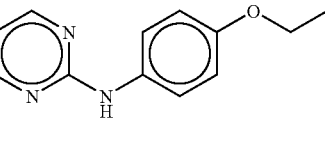 | 407.2 |
| 90 | 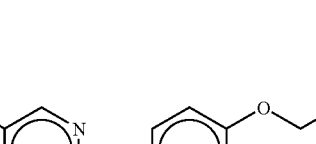 | 647.0 |
| 91 | 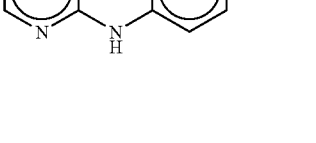 | 604.0 |
| 92 | 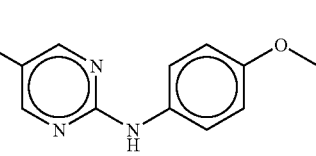 | 435.0 |
| 93 | 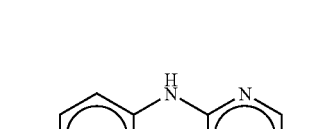 | 407.2 |

TABLE 1-continued

Examplary compounds which modulate the activiry of c-kit receptors.

| # | Structure | MS [M + 1]+ |
|---|---|---|
| 94 | 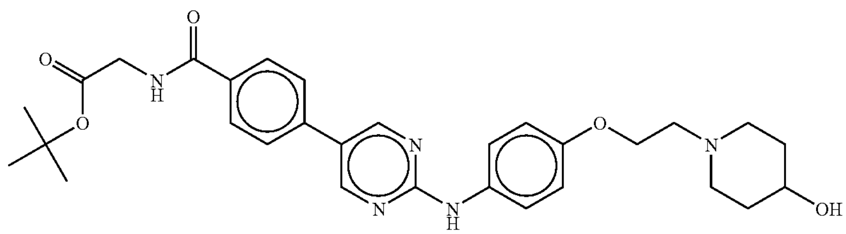 | 548.1 |
| 95 | 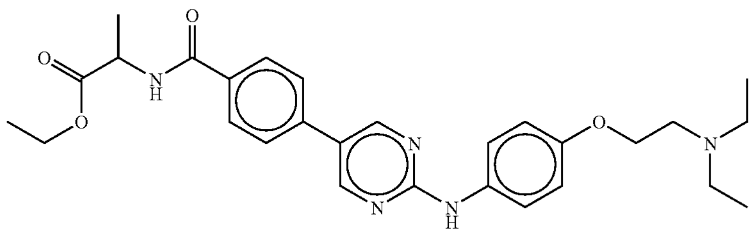 | 506.2 |
| 96 | 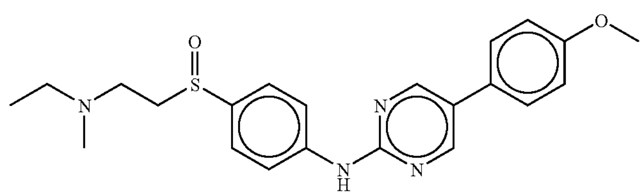 | 425.2 |
| 97 | 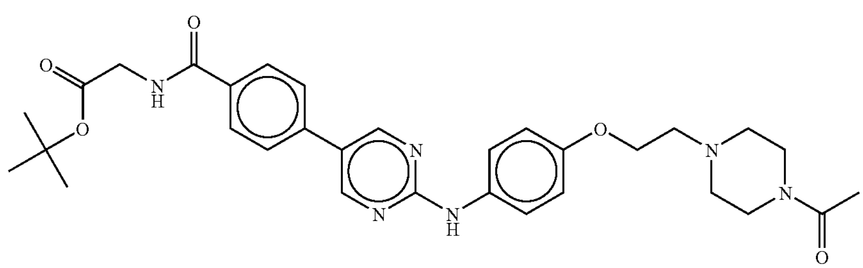 | 575.1 |
| 98 | 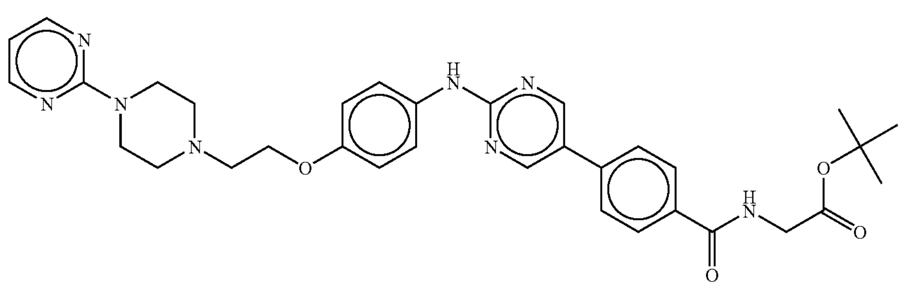 | 611.0 |
| 99 | 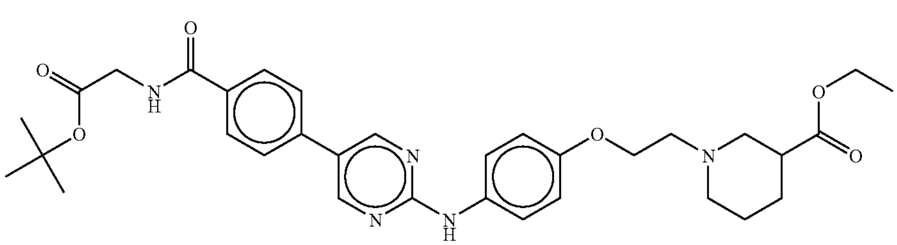 | 604.1 |

TABLE 1-continued
Examplary compounds which modulate the activiry of c-kit receptors.
| # | Structure | MS [M + 1]+ |
|---|---|---|
| 100 | 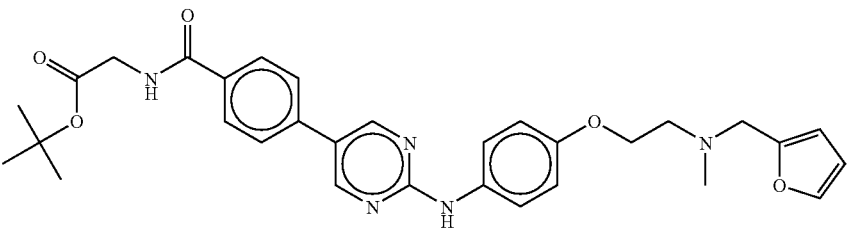 | 558.1 |
| 101 | 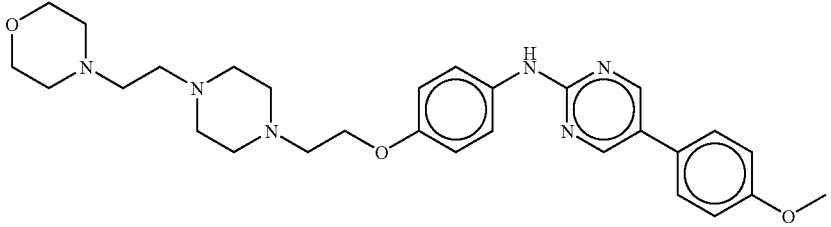 | 519.2 |
| 102 | 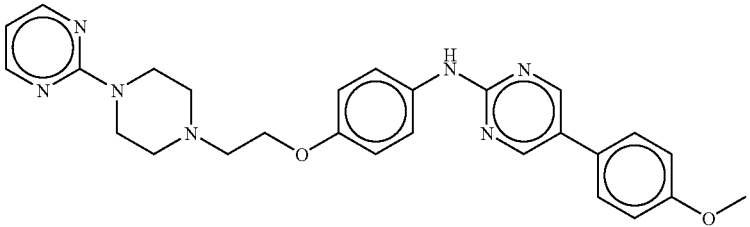 | 484.3 |
| 103 | 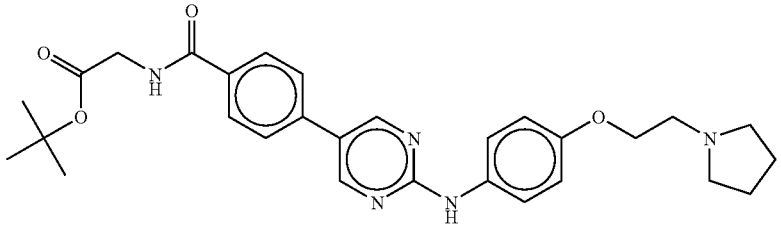 | 518.3 |
| 104 | 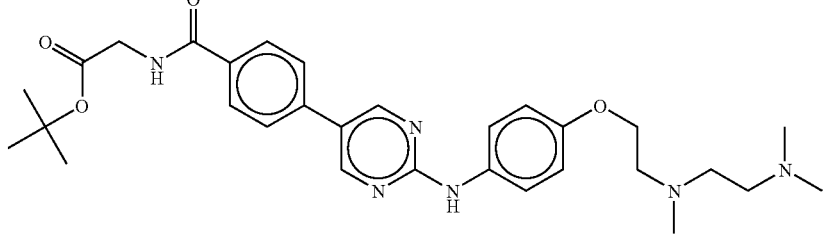 | 549.2 |
| 105 | 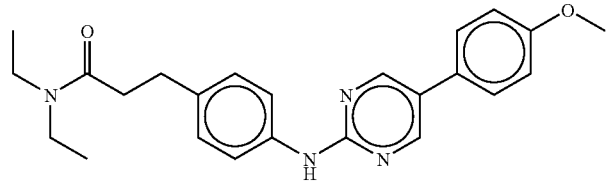 | 406.4 |

TABLE 1-continued
Examplary compounds which modulate the activiry of c-kit receptors.
| # | Structure | MS [M + 1]+ |
|---|-----------|-------------|
| 106 | 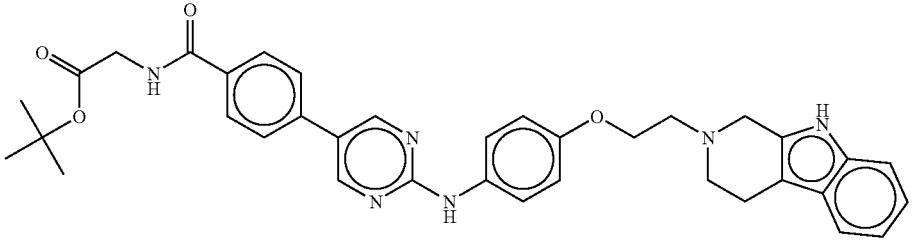 | 619.0 |
| 107 | 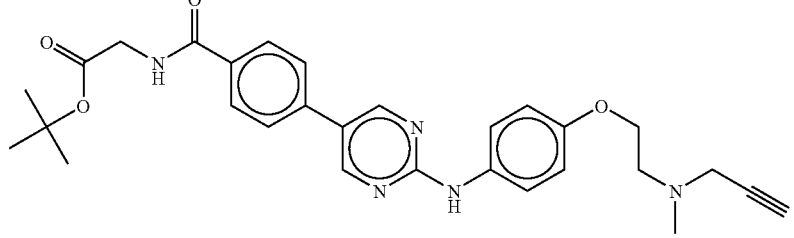 | 516.2 |
| 108 | 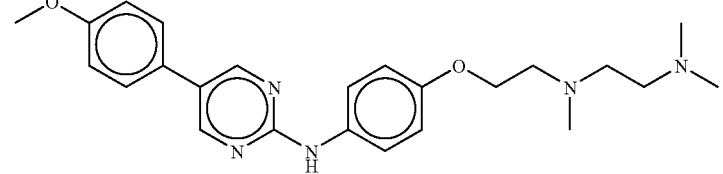 | 422.3 |
| 109 | 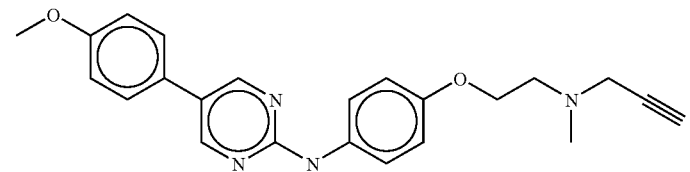 | 389.2 |
| 110 | 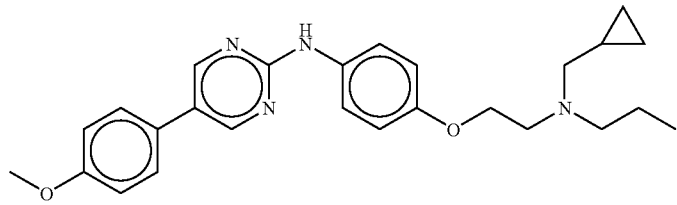 | 433.3 |
| 111 | 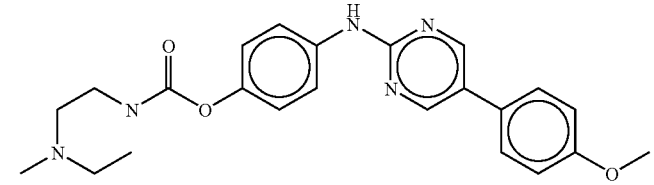 | 420.4 |
| 112 | 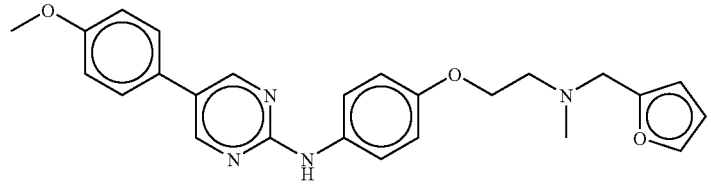 | 431.1 |

TABLE 1-continued
Examplary compounds which modulate the activiry of c-kit receptors.
| # | Structure | MS [M + 1]+ |
|---|---|---|
| 113 | 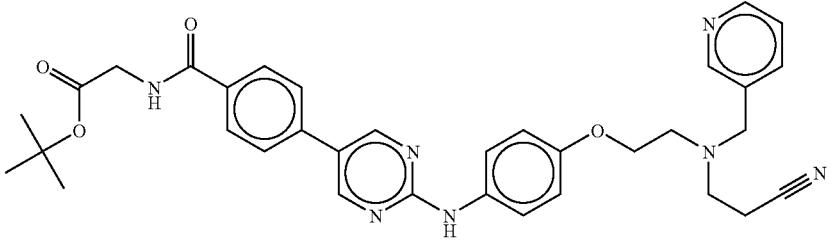 | 608.0 |
| 114 | 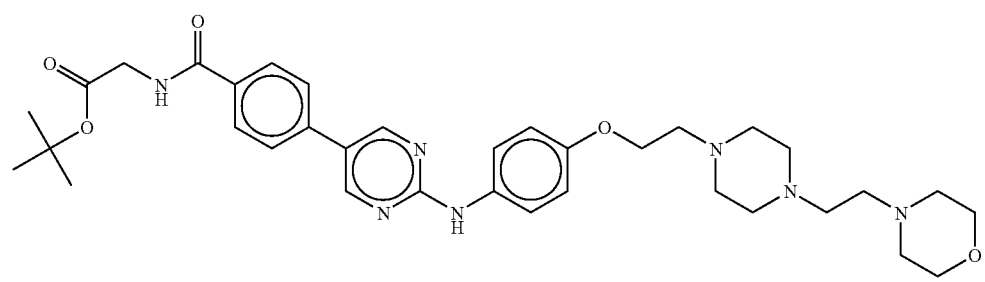 | 646.0 |
| 115 | 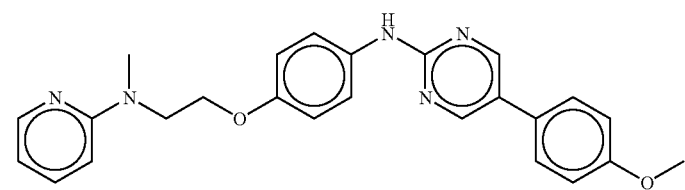 | 428.1 |
| 116 | 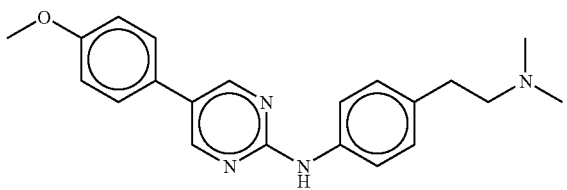 | 349.1 |
| 117 | 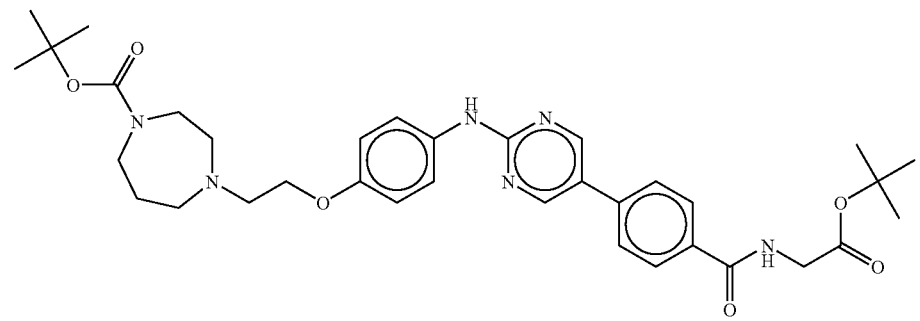 | 647.0 |
| 118 | 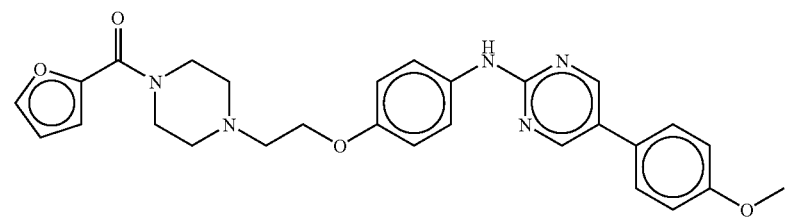 | 500.3 |

TABLE 1-continued

Examplary compounds which modulate the activiry of c-kit receptors.

| # | Structure | MS [M + 1]+ |
|---|---|---|
| 119 | 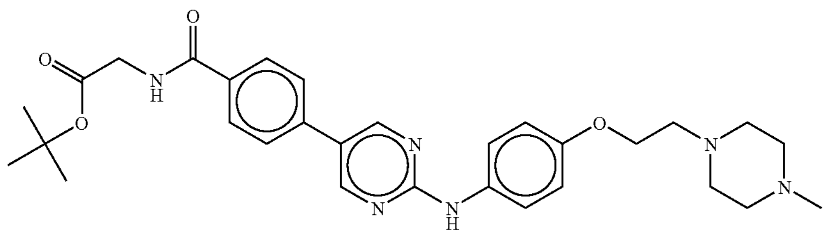 | 547.1 |
| 120 | 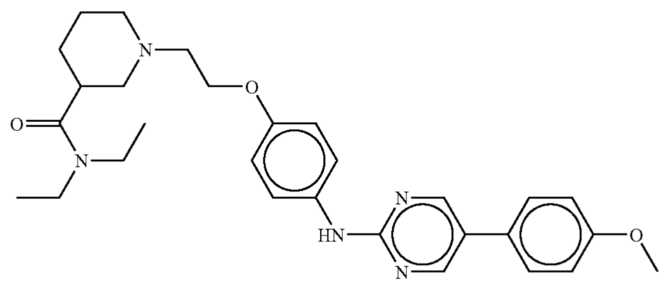 | 504.3 |
| 121 | 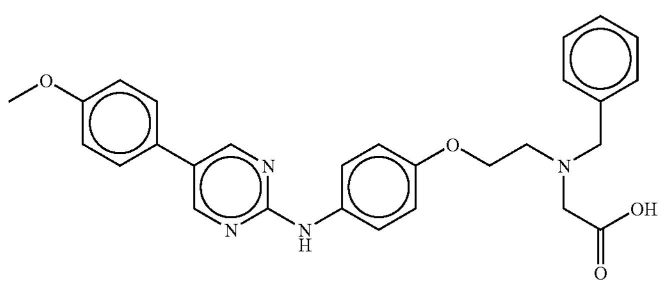 | 485.2 |
| 122 | 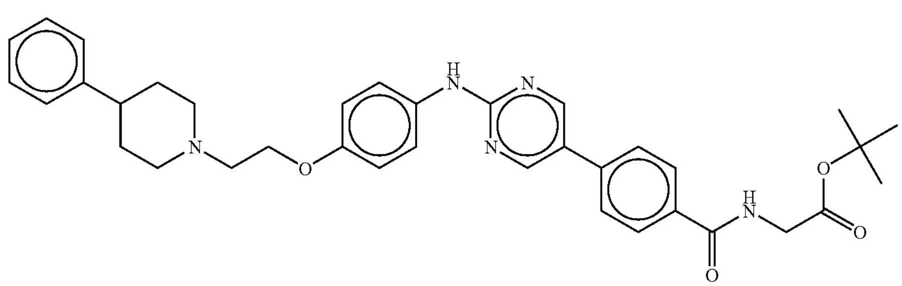 | 608.3 |
| 123 | 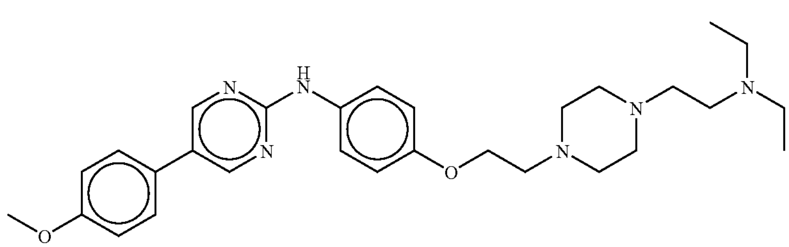 | 505.3 |

TABLE 1-continued

Examplary compounds which modulate the activiry of c-kit receptors.

| # | Structure | MS [M + 1]+ |
|---|---|---|
| 124 | 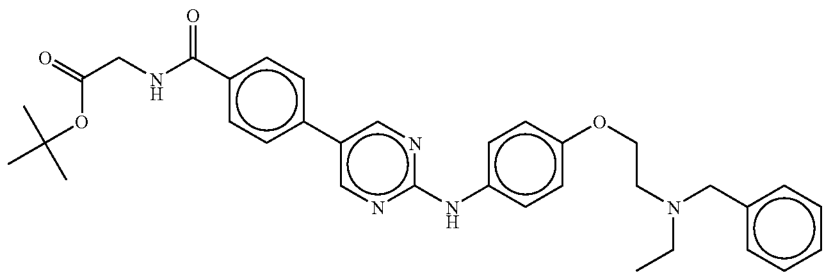 | 582.3 |
| 125 | 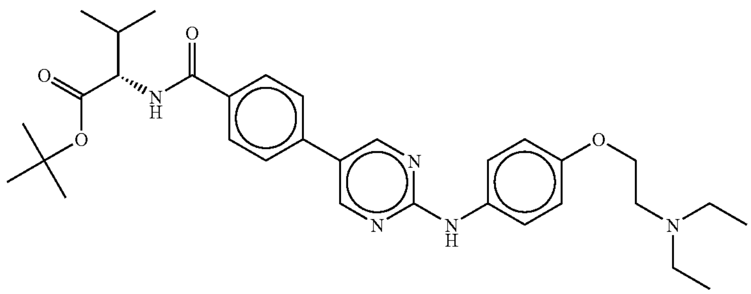 | 562.5 |
| 126 | 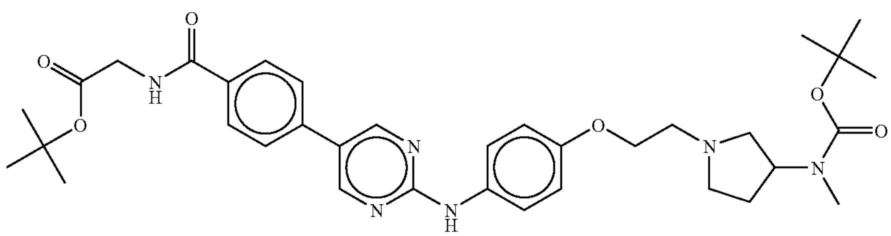 | 647.4 |
| 127 | 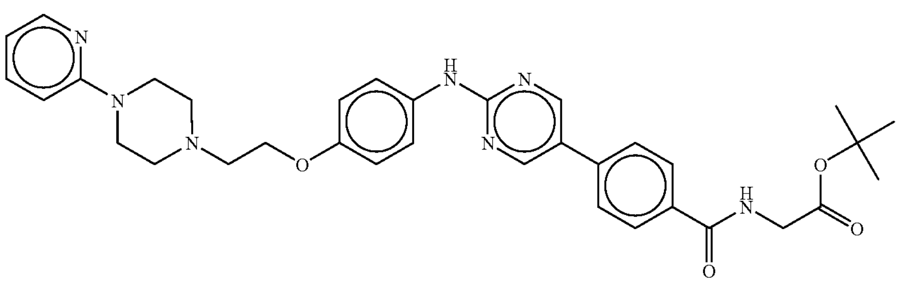 | 610.0 |
| 128 | 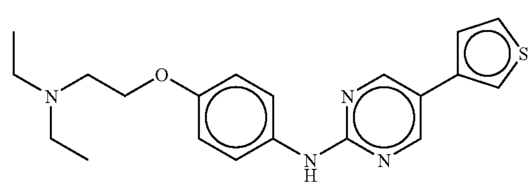 | 369.1 |
| 129 | 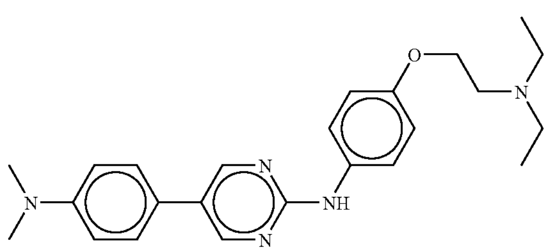 | 406.4 |

TABLE 1-continued
Examplary compounds which modulate the activiry of c-kit receptors.
| # | Structure | MS [M + 1]+ |
|---|---|---|
| 130 | 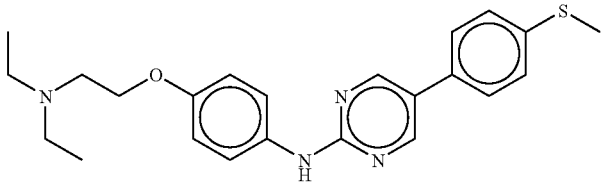 | 409.4 |
| 131 | 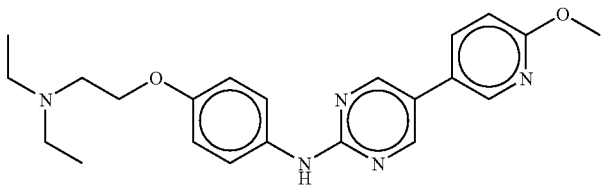 | 394.2 |
| 132 | 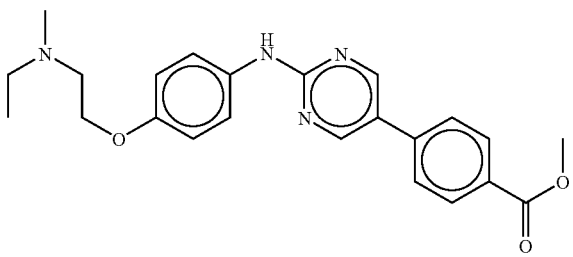 | 421.2 |
| 133 | 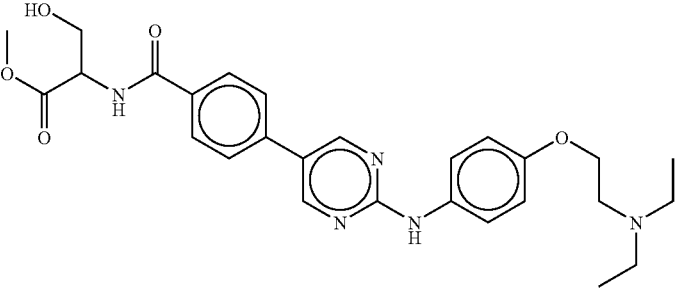 | 508.2 |
| 134 | 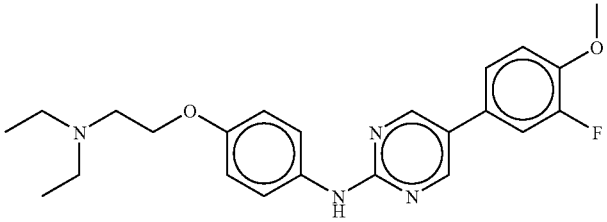 | 411.2 |
| 135 | 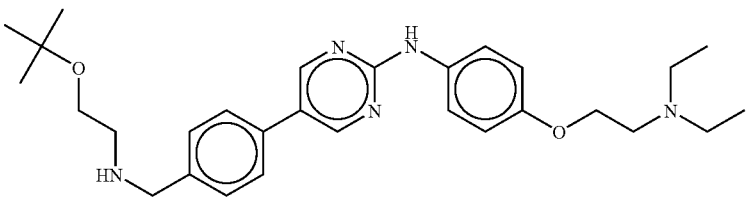 | 492.4 |

TABLE 1-continued
Examplary compounds which modulate the activiry of c-kit receptors.
| # | Structure | MS [M + 1]+ |
|---|---|---|
| 136 | 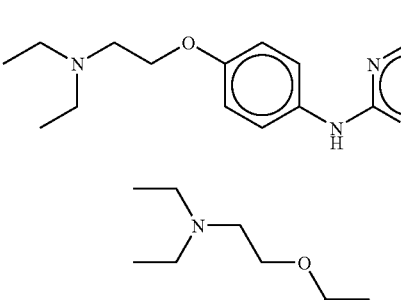 | 568.4 |
| 137 | 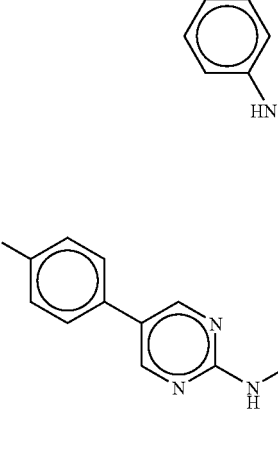 | 542.3 |
| 138 | 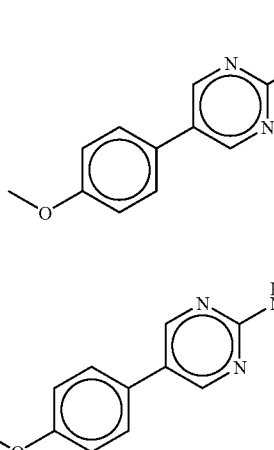 | 471.3 |
| 139 | 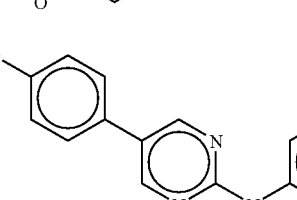 | 408.3 |
| 140 |  | 465.0 |
| 141 | | 520.3 |

TABLE 1-continued

Examplary compounds which modulate the activiry of c-kit receptors.

| # | Structure | MS [M + 1]+ |
|---|---|---|
| 142 | 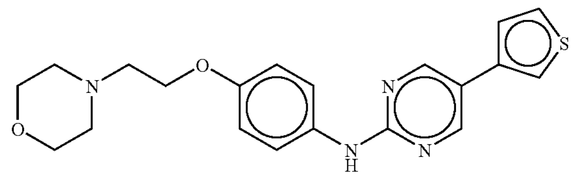 | 383.1 |
| 143 | 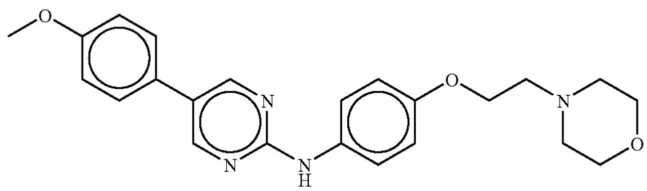 | 407.1 |
| 144 | 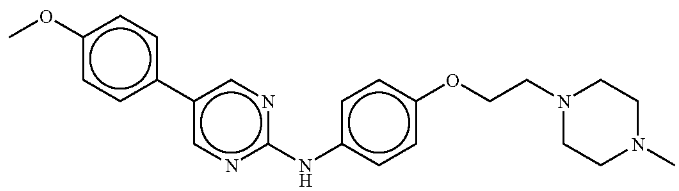 | 420.3 |
| 145 | 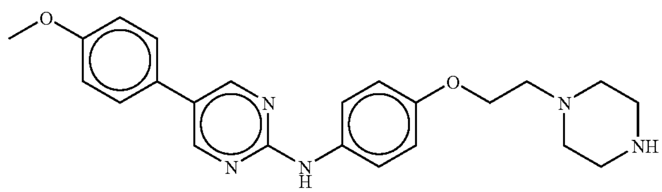 | 406.2 |
| 146 | 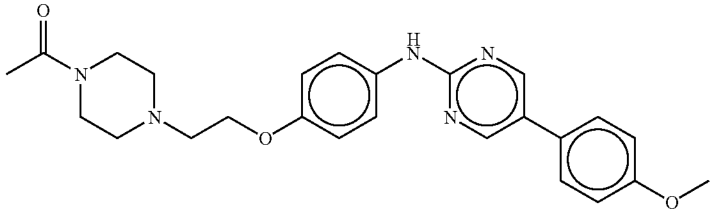 | 448.3 |
| 147 | 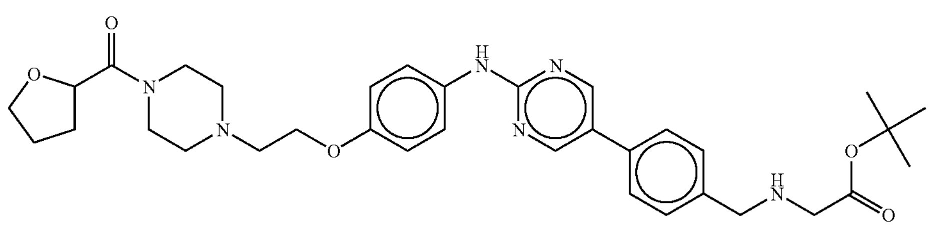 | 617.5 |
| 148 | 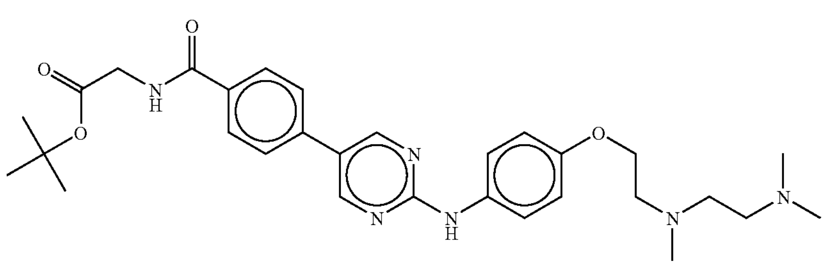 | 549.4 |

TABLE 1-continued
Examplary compounds which modulate the activiry of c-kit receptors.
| # | Structure | MS [M + 1]+ |
|---|---|---|
| 149 | 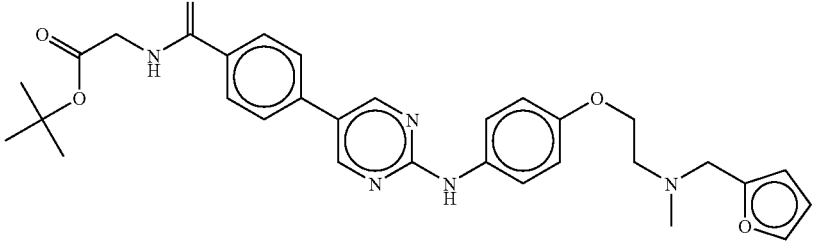 | 558.3 |
| 150 | 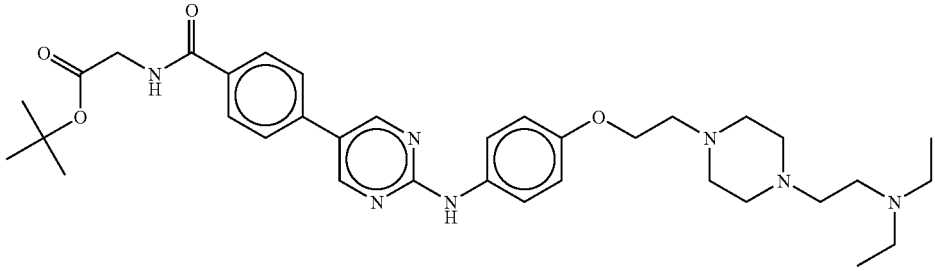 | 632.4 |
| 151 | 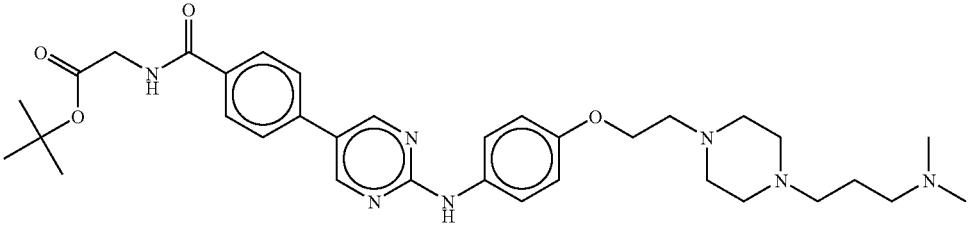 | 618.4 |
| 152 | 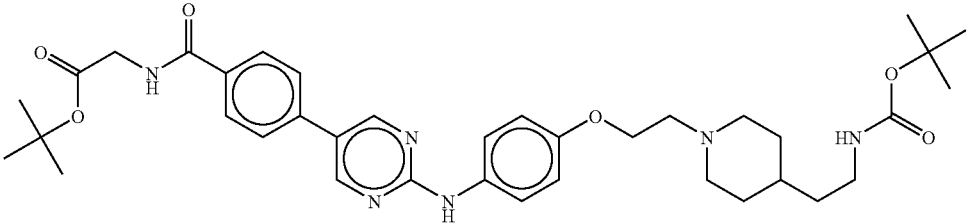 | 675.5 |
| 153 | 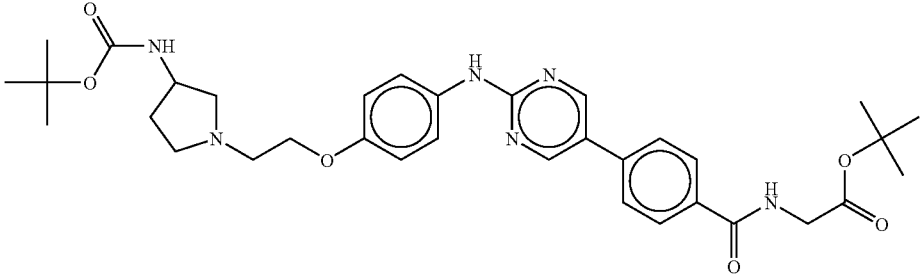 | 633.4 |
| 154 | 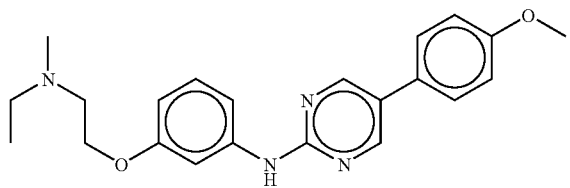 | 393.2 |

TABLE 1-continued

Examplary compounds which modulate the activiry of c-kit receptors.

| # | Structure | MS [M + 1]+ |
|---|---|---|
| 155 | 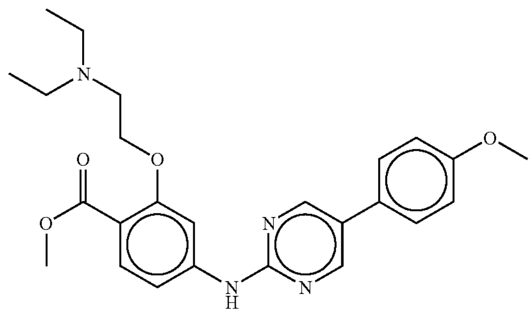 | 451.3 |
| 156 | 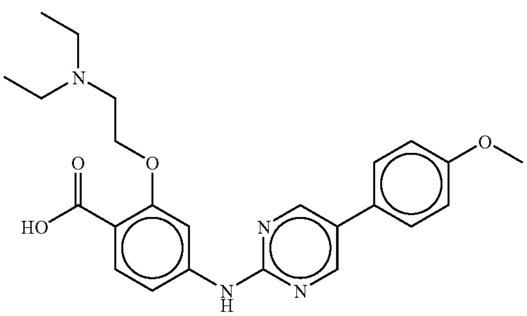 | 437.2 |
| 157 | 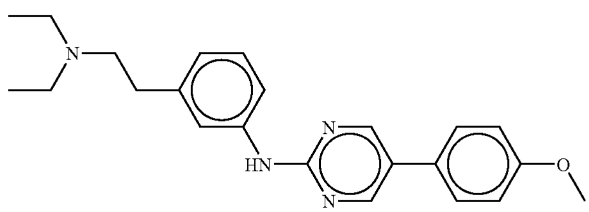 | 377.3 |
| 158 | 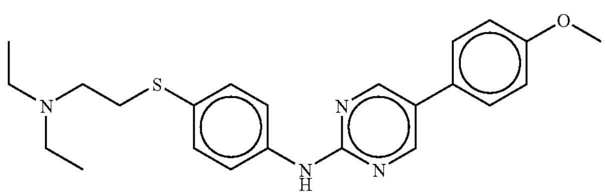 | 409.2 |
| 159 | 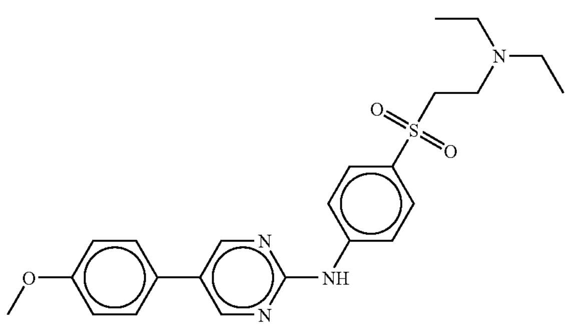 | 441.2 |

TABLE 1-continued

Examplary compounds which modulate the activiry of c-kit receptors.

| # | Structure | MS [M + 1]+ |
|---|---|---|
| 160 | 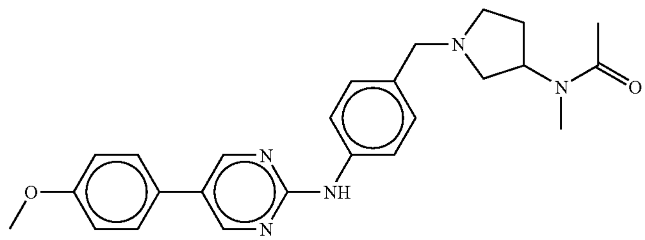 | 423.3 |
| 161 | 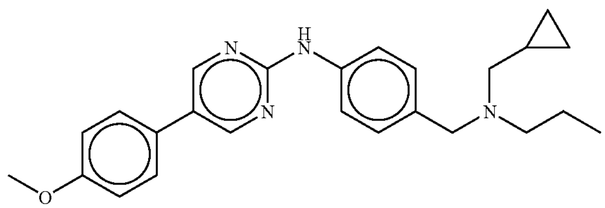 | 403.0 |
| 162 | 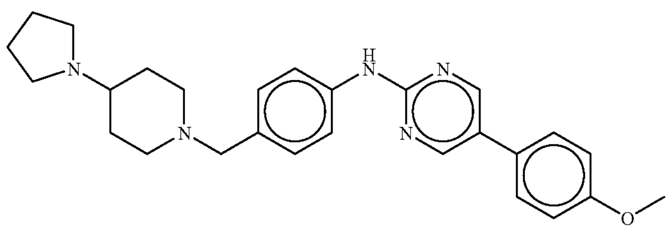 | 444.3 |
| 163 | 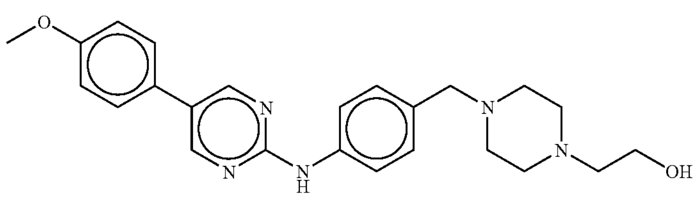 | 420.0 |
| 164 | 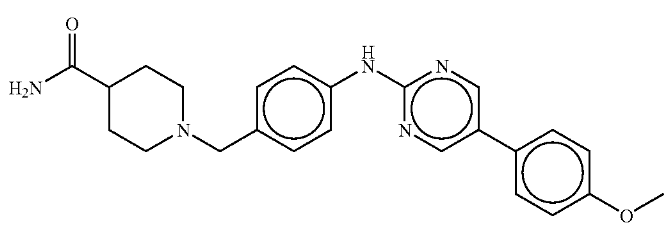 | 418.5 |
| 165 | 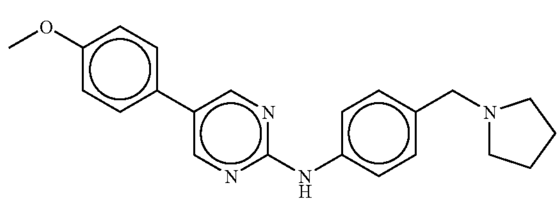 | 361.3 |

TABLE 1-continued

Examplary compounds which modulate the activiry of c-kit receptors.

| # | Structure | MS [M + 1]+ |
|---|-----------|-------------|
| 166 | 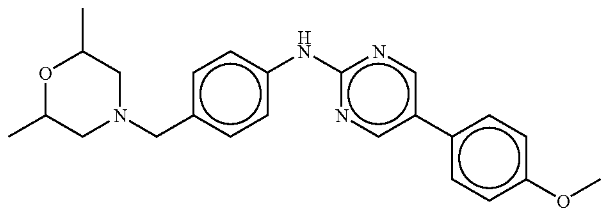 | 405.2 |
| 167 | 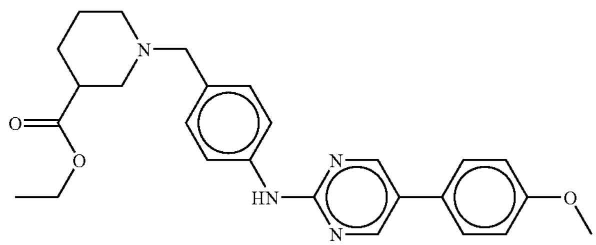 | 447.3 |
| 168 | 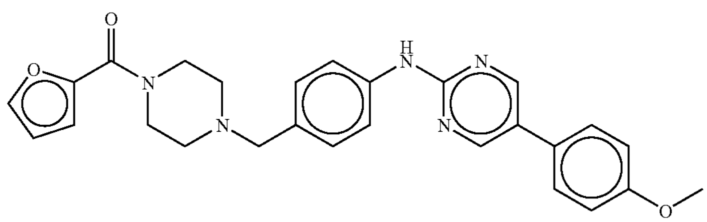 | 470.0 |
| 169 | 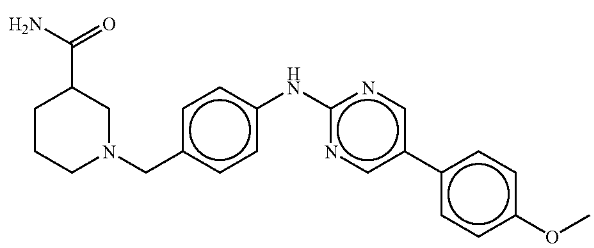 | 418.2 |
| 170 | 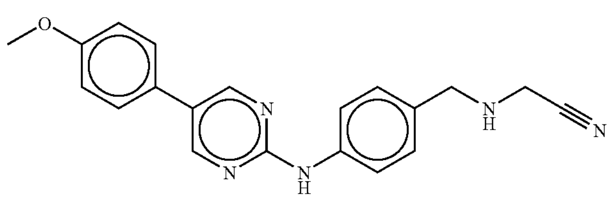 | 346.2 |
| 171 | 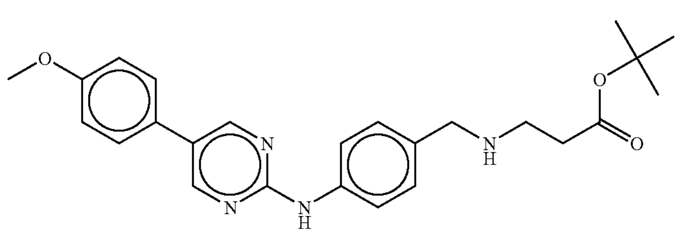 | 435.0 |

TABLE 1-continued
Examplary compounds which modulate the activiry of c-kit receptors.
| # | Structure | MS [M + 1]+ |
|---|-----------|-------------|
| 172 | 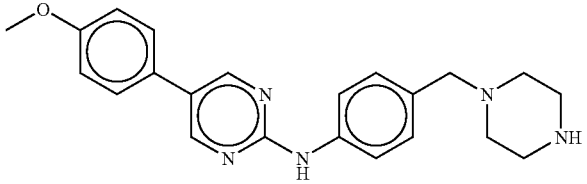 | 376.0 |
| 173 | 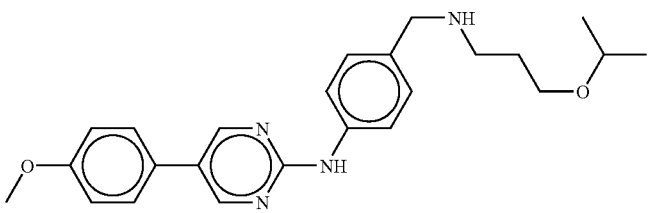 | 407.2 |
| 174 | 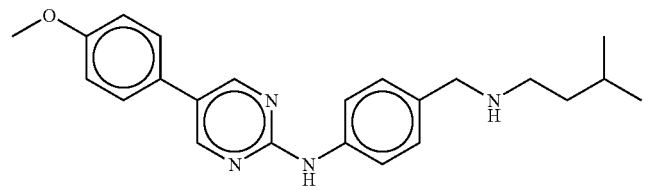 | 462.0 |
| 175 | 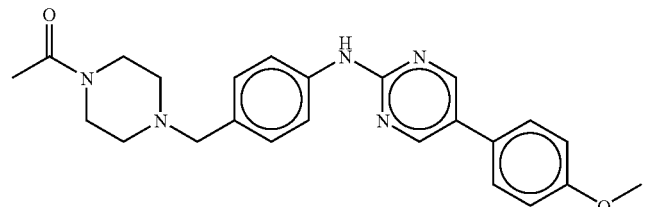 | 418.3 |
| 176 | 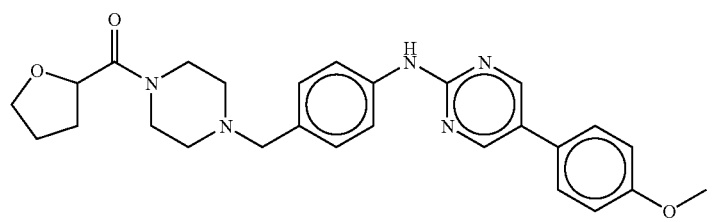 | 474.3 |
| 177 | 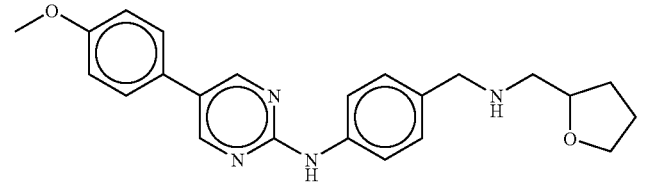 | 391.3 |
| 178 | 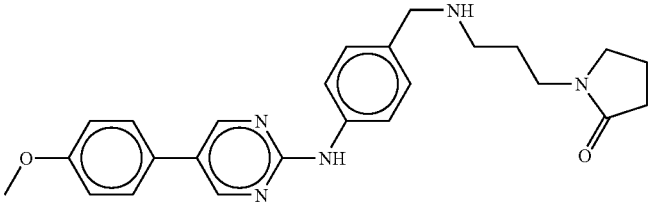 | 432.3 |

TABLE 1-continued

Examplary compounds which modulate the activiry of c-kit receptors.

| # | Structure | MS [M + 1]+ |
|---|---|---|
| 179 | | 389.4 |
| 180 | | 476.3 |
| 181 | | 419.0 |
| 182 | | 391.0 |
| 183 | | 476.3 |
| 184 | | 432.3 |

TABLE 1-continued

Examplary compounds which modulate the activiry of c-kit receptors.

| # | Structure | MS [M + 1]+ |
|---|---|---|
| 185 | 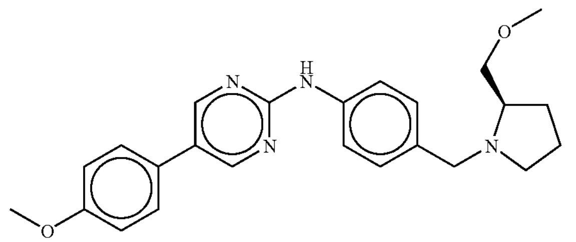 | 405.3 |
| 186 | 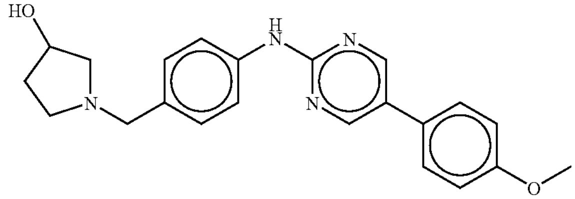 | 377.3 |
| 187 | 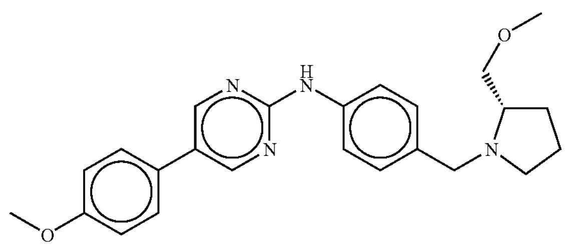 | 405.3 |
| 188 | 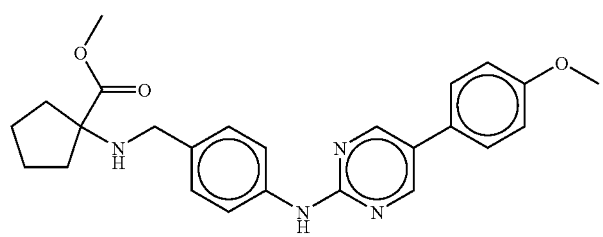 | 433.0 |
| 189 | 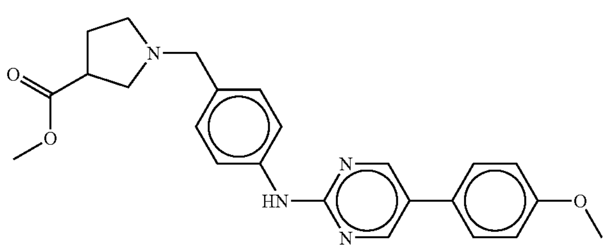 | 419.0 |
| 190 | 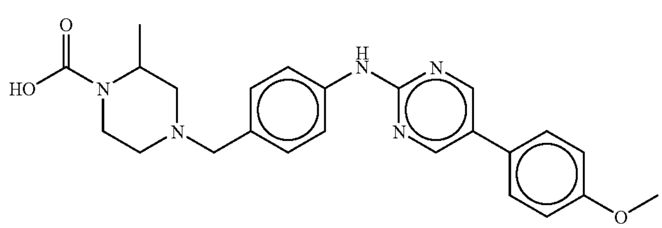 | 434.3 |

TABLE 1-continued

Examplary compounds which modulate the activiry of c-kit receptors.

| # | Structure | MS [M + 1]+ |
|---|---|---|
| 191 | 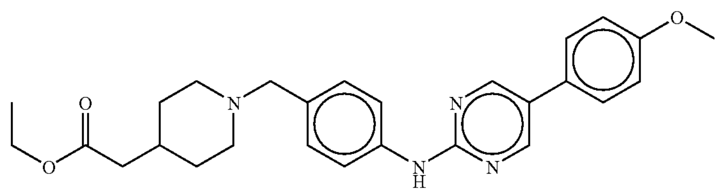 | 461.3 |
| 192 | 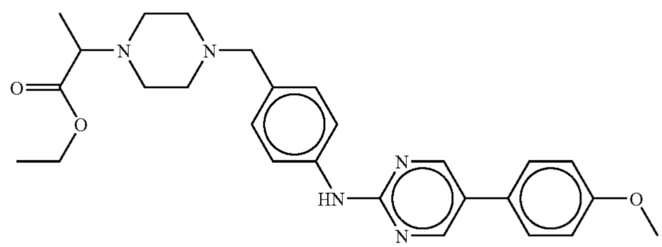 | 476.3 |
| 193 | 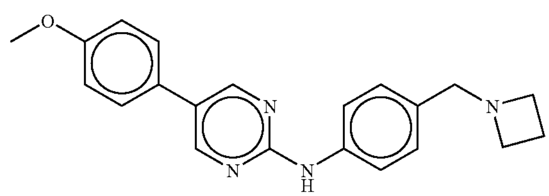 | 347.3 |
| 194 | 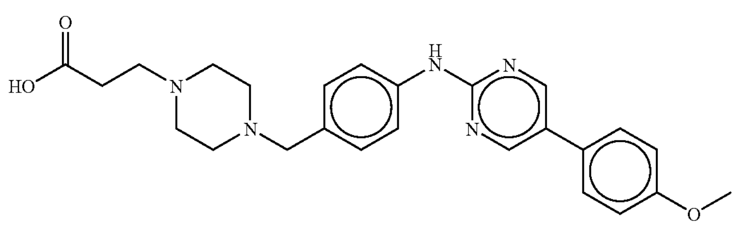 | 448.3 |
| 195 | 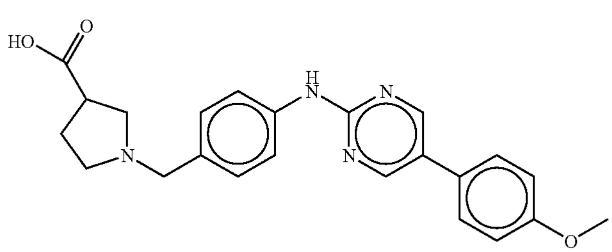 | 405.0 |
| 196 | 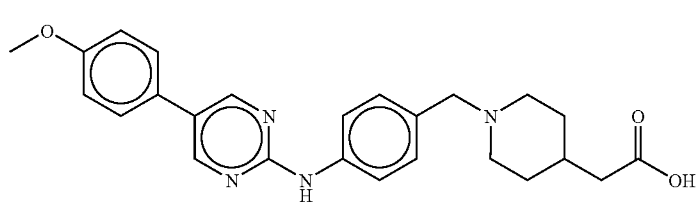 | 433.0 |

TABLE 1-continued

Examplary compounds which modulate the activiry of c-kit receptors.

| # | Structure | MS [M + 1]+ |
|---|---|---|
| 197 | 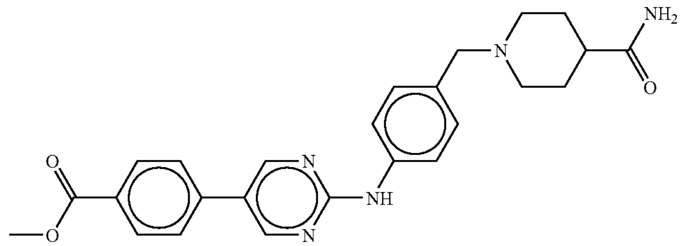 | 446.2 |
| 198 | 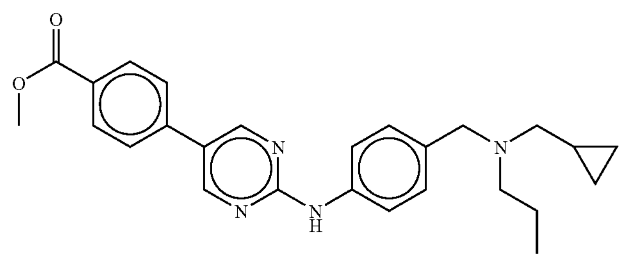 | 431.2 |
| 199 | 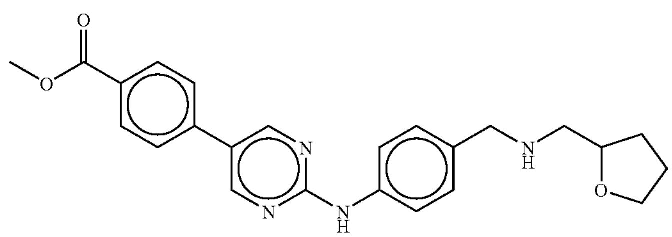 | 419.2 |
| 200 | 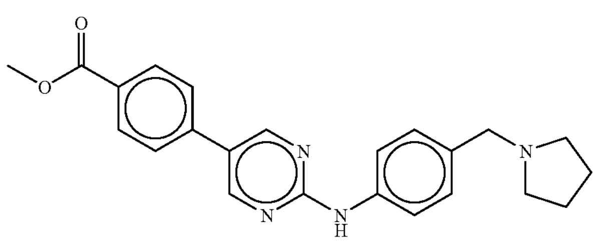 | 389.2 |
| 201 | 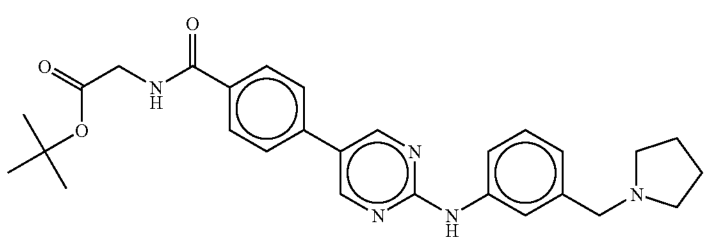 | 488.3 |
| 202 | 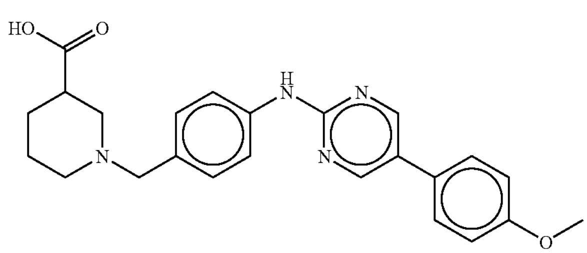 | 419.2 |

TABLE 1-continued
Examplary compounds which modulate the activiry of c-kit receptors.
| # | Structure | MS [M + 1]+ |
|---|---|---|
| 203 | 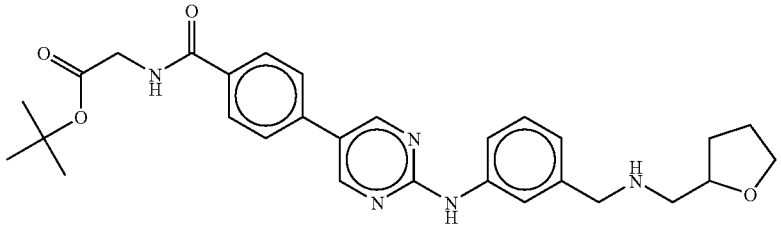 | 518.3 |
| 204 | 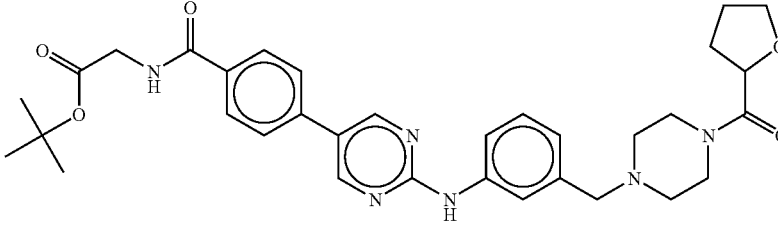 | 601.3 |
| 205 | 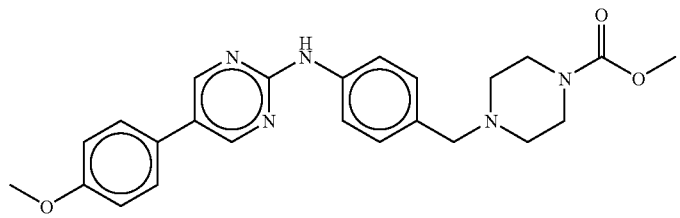 | 434.0 |
| 206 | 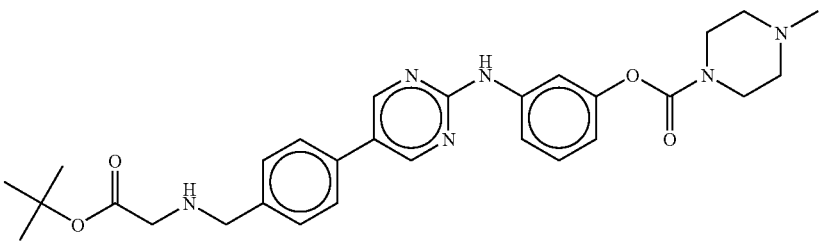 | 533.0 |
| 207 | 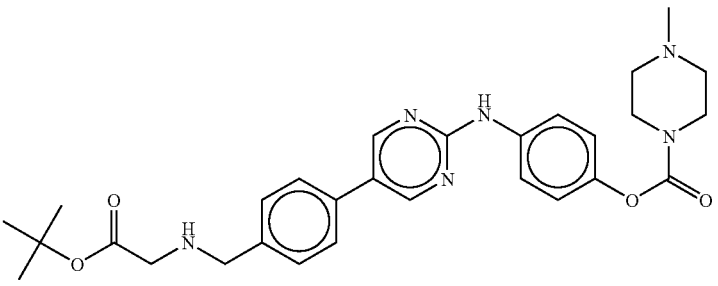 | 533.1 |
| 208 | 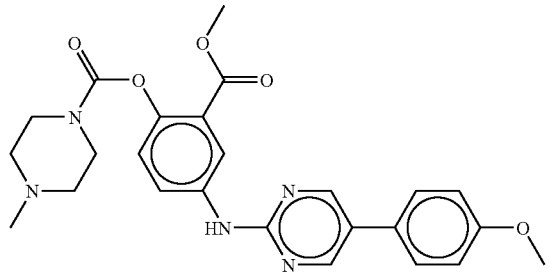 | 478.3 |

TABLE 1-continued

Examplary compounds which modulate the activiry of c-kit receptors.

| # | Structure | MS [M + 1]+ |
|---|---|---|
| 209 | 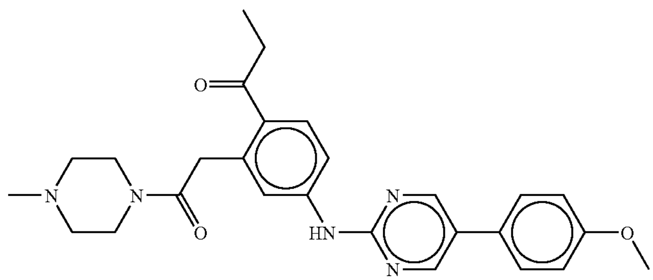 | 478.2 |
| 210 | 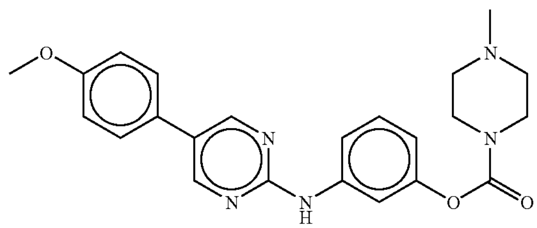 | 420.5 |
| 211 | 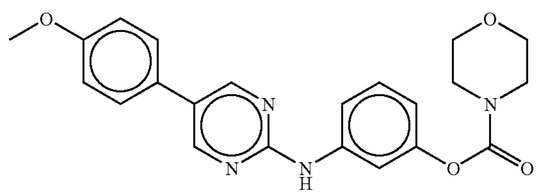 | 407.2 |
| 212 | 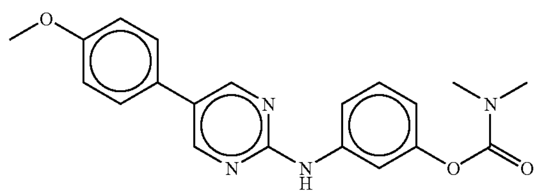 | 365.2 |
| 213 | 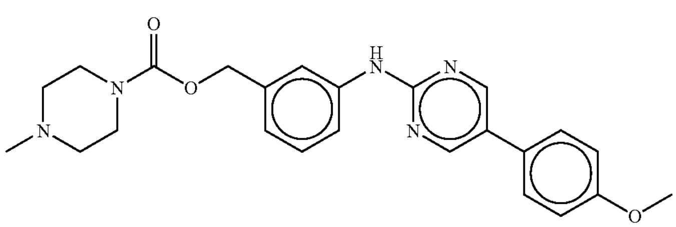 | 434.3 |
| 214 | 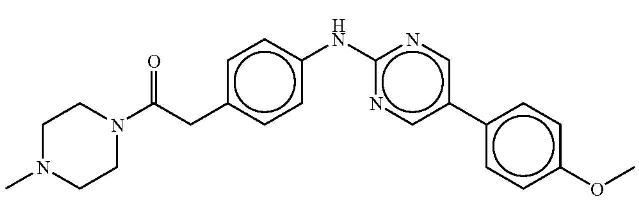 | 418.3 |

TABLE 1-continued
Examplary compounds which modulate the activity of c-kit receptors.
| # | Structure | MS [M + 1]+ |
|---|---|---|
| 215 | 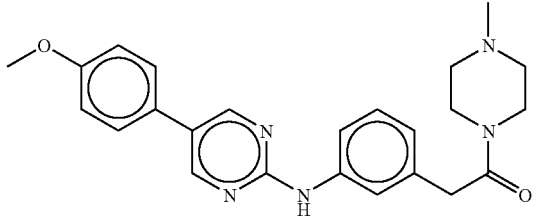 | 419.3 |
| 216 | 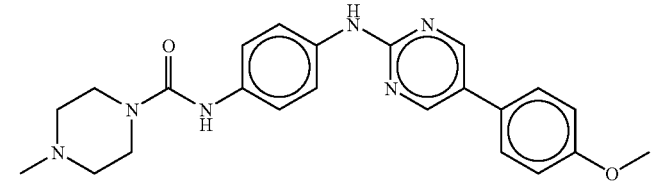 | 419.1 |
| 217 | 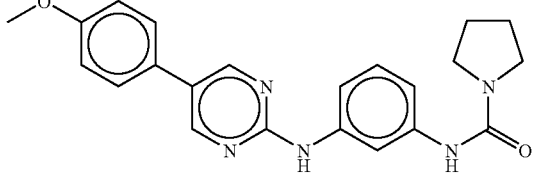 | 390.5 |
| 218 | 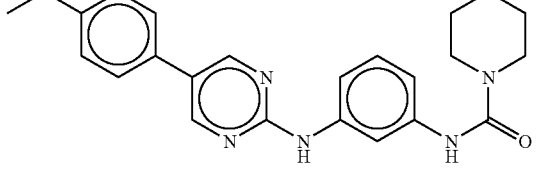 | 406.2 |
| 219 | 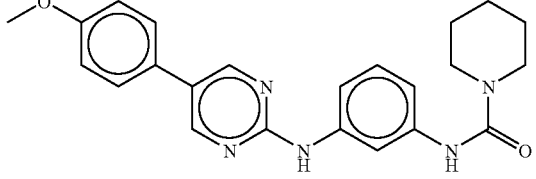 | 404.2 |
| 220 | 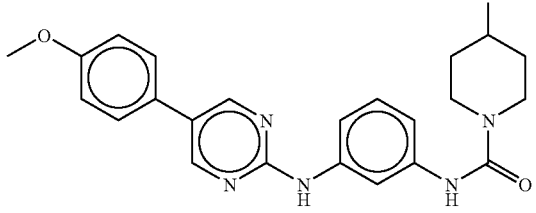 | 420.2 |
| 221 | 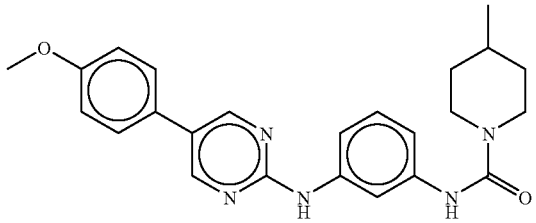 | 418.6 |

TABLE 1-continued

Examplary compounds which modulate the activiry of c-kit receptors.

| # | Structure | MS [M + 1]+ |
|---|---|---|
| 222 | 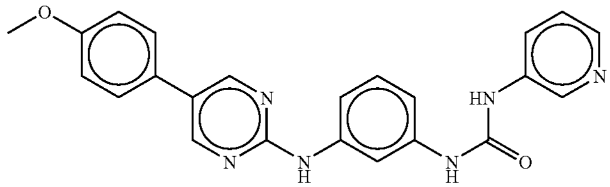 | 413.5 |
| 223 | 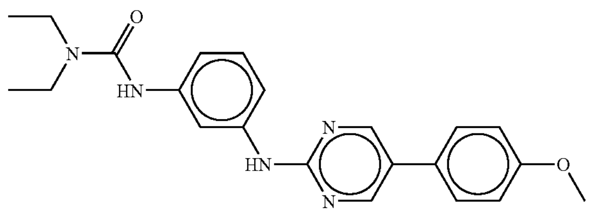 | 392.5 |
| 224 | 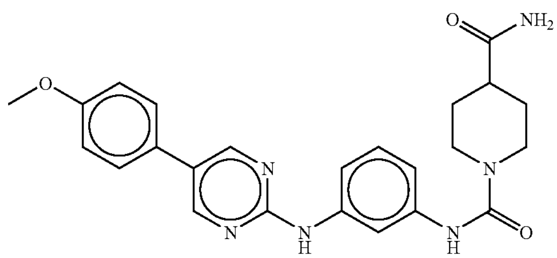 | 447.6 |
| 225 | 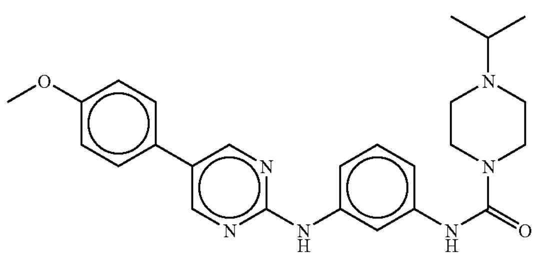 | 447.2 |
| 226 | 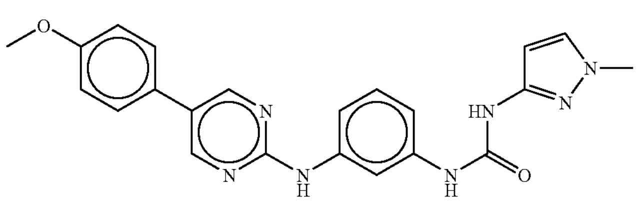 | 416.2 |
| 227 | 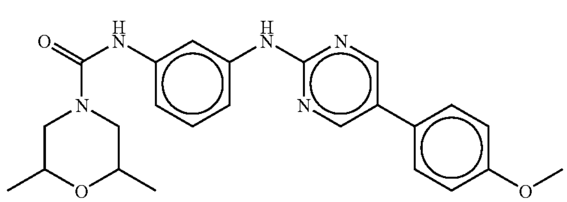 | 434.2 |
| 228 | 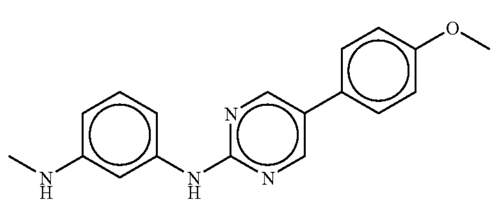 | 307.1 |

TABLE 1-continued

Examplary compounds which modulate the activity of c-kit receptors.

| # | Structure | MS [M + 1]+ |
|---|---|---|
| 230 | 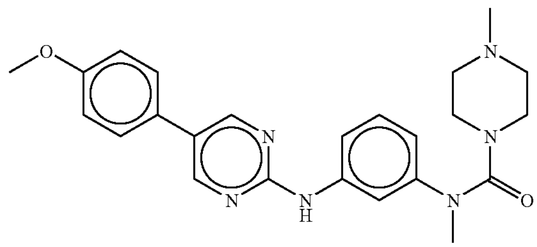 | 433.2 |
| 231 | 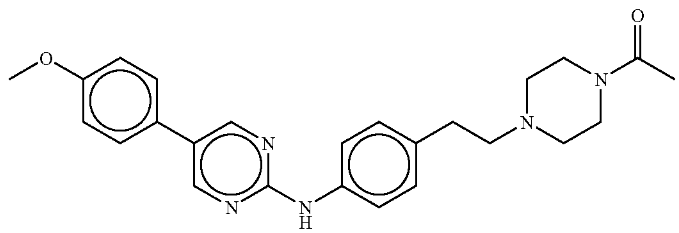 | 432.4 |
| 232 | 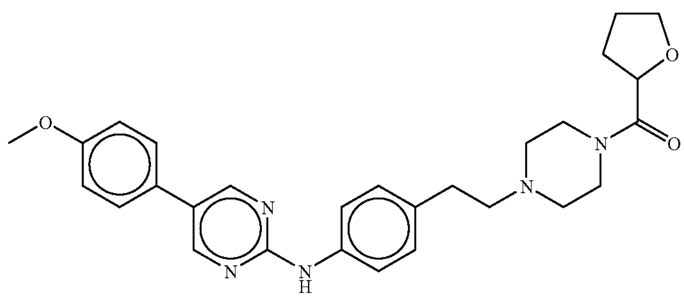 | 488.4 |
| 233 | 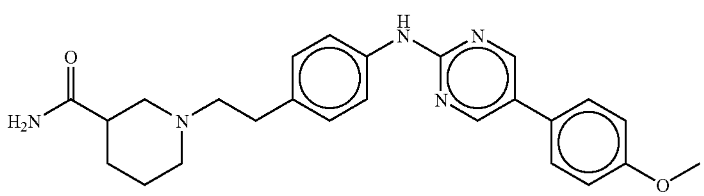 | 432.3 |
| 234 | 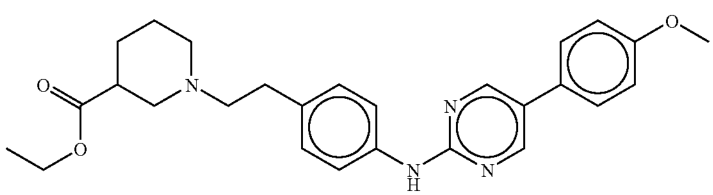 | 461.4 |
| 235 | 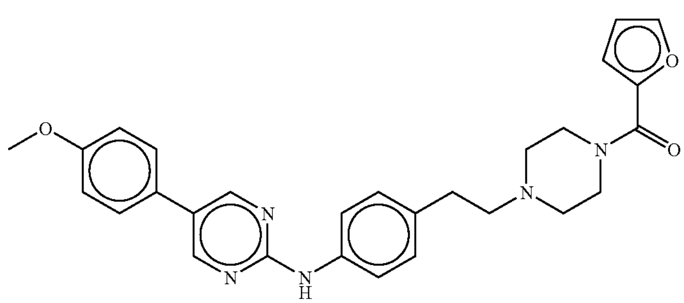 | 484.4 |

TABLE 1-continued

Examplary compounds which modulate the activiry of c-kit receptors.

| # | Structure | MS [M + 1]+ |
|---|---|---|
| 236 | 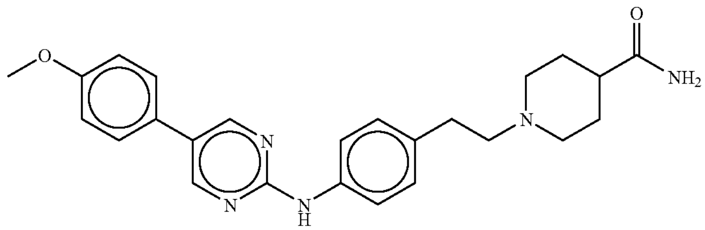 | 432.3 |
| 237 | 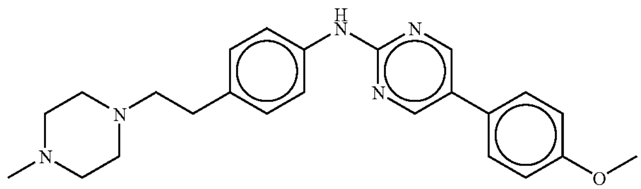 | 404.2 |
| 238 | 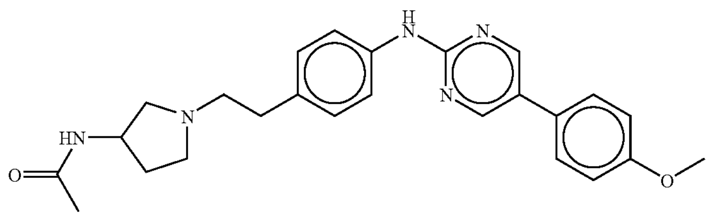 | 432.4 |
| 239 | 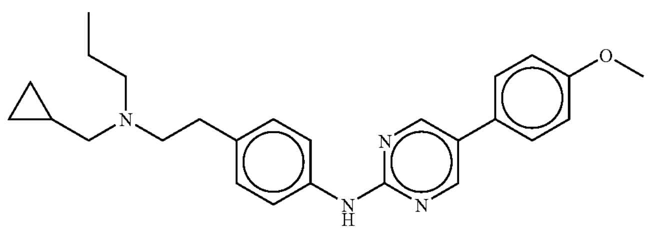 | 417.4 |
| 240 | 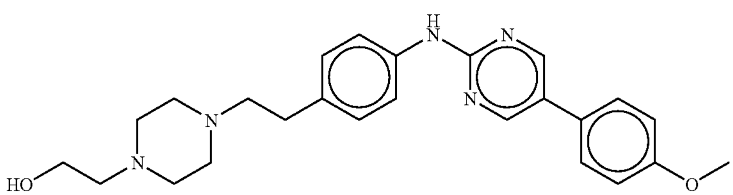 | 434.4 |
| 241 | 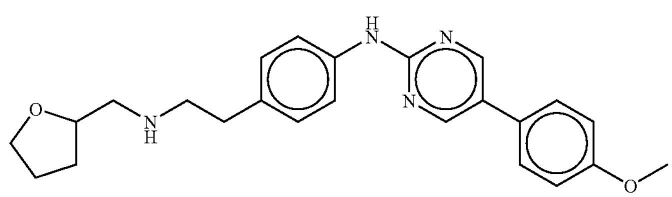 | 405.4 |
| 242 | 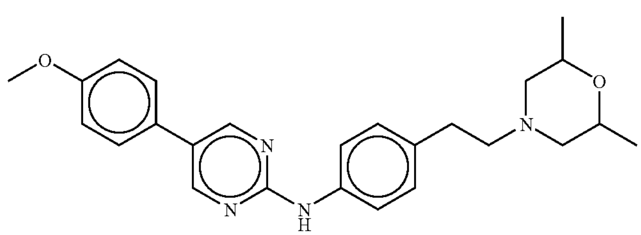 | 419.2 |

TABLE 1-continued

Examplary compounds which modulate the activity of c-kit receptors.

| # | Structure | MS [M + 1]+ |
|---|---|---|
| 243 | 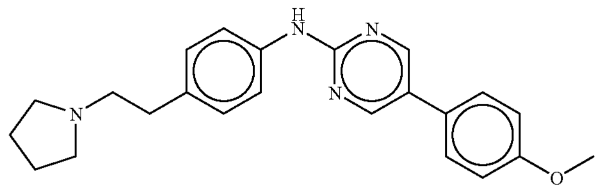 | 375.3 |
| 244 | 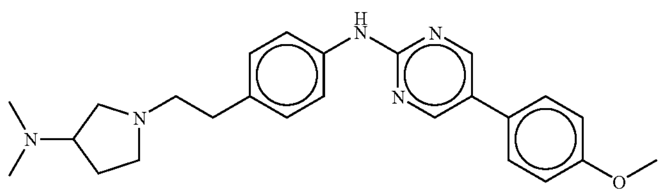 | 418.4 |
| 245 | 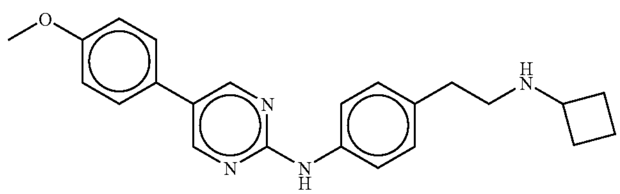 | 375.3 |
| 246 | 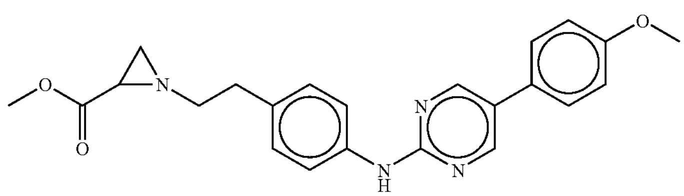 | 405.1 |
| 247 | 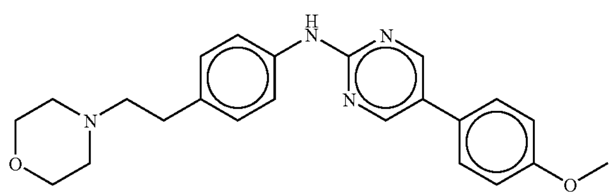 | 391.4 |
| 248 | 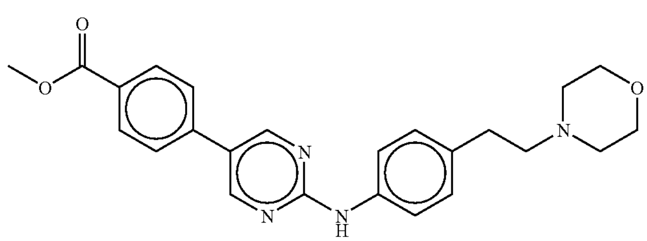 | 419.3 |
| 249 | 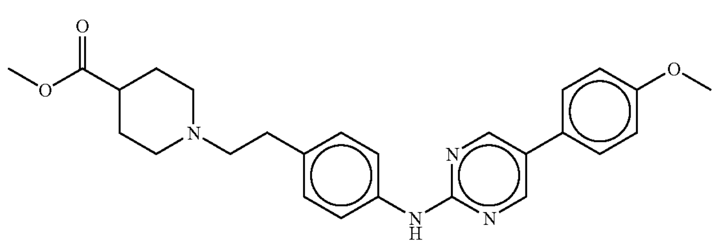 | 447.3 |

TABLE 1-continued
Examplary compounds which modulate the activiry of c-kit receptors.
| # | Structure | MS [M + 1]+ |
|---|---|---|
| 250 | 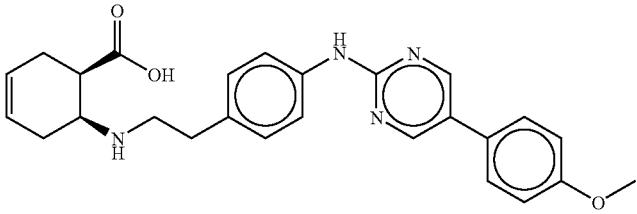 | 445.3 |
| 251 | 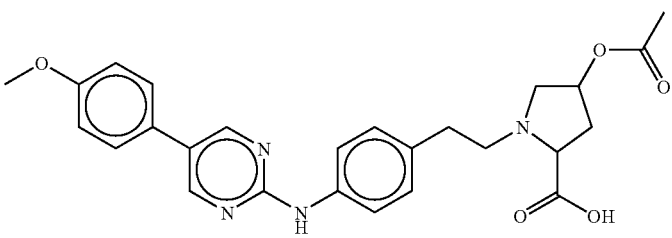 | 477.2 |
| 252 | 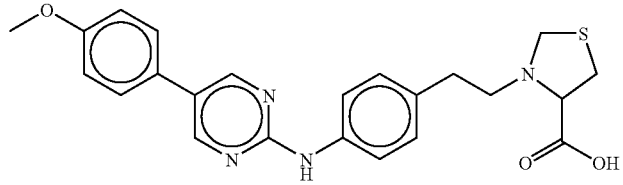 | 437.2 |
| 253 | 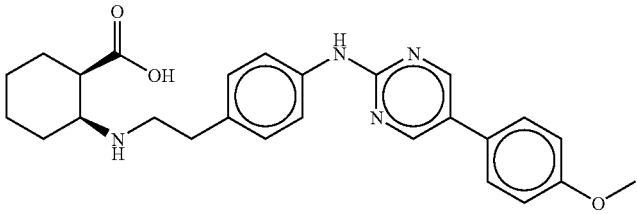 | 447.3 |
| 254 | 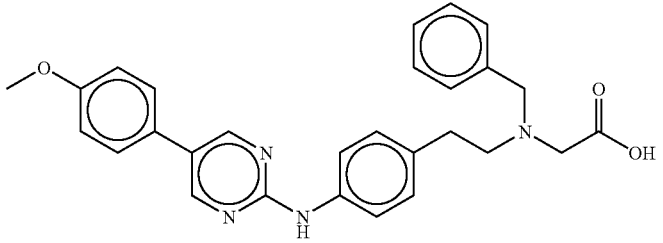 | 469.3 |
| 255 | 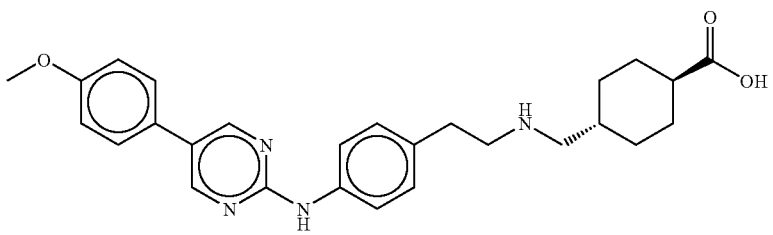 | 461.3 |

TABLE 1-continued

Examplary compounds which modulate the activiry of c-kit receptors.

| # | Structure | MS [M + 1]+ |
|---|---|---|
| 256 | 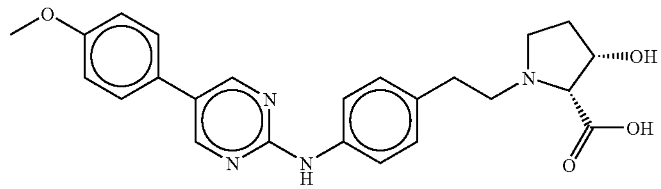 | 435.2 |
| 257 | 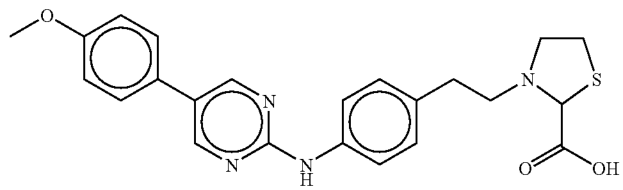 | 437.2 |
| 258 | 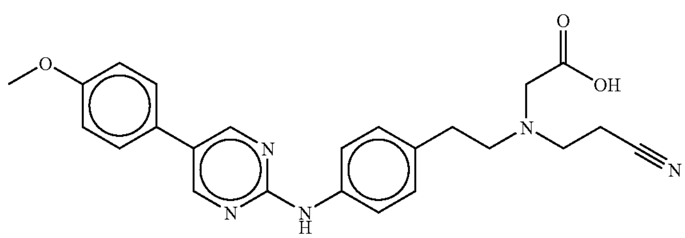 | 432.2 |
| 259 | 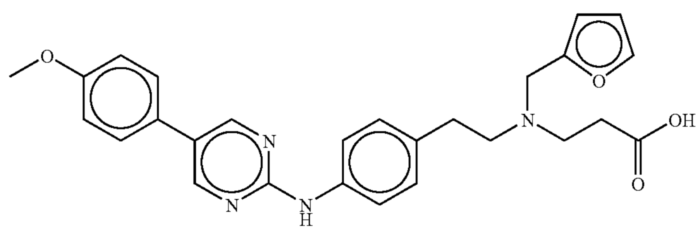 | 473.5 |
| 260 | 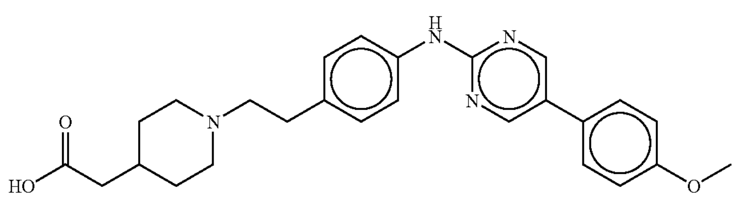 | 447.2 |
| 261 | 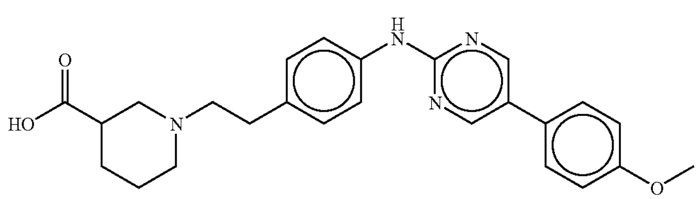 | 433.5 |
| 262 | 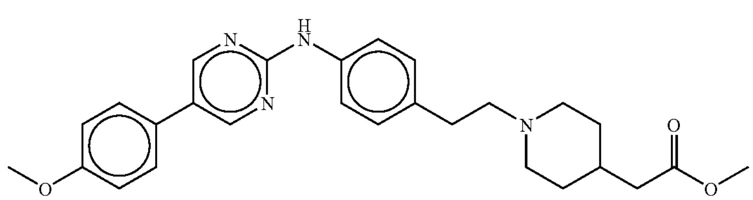 | 461.3 |

TABLE 1-continued

Examplary compounds which modulate the activiry of c-kit receptors.

| # | Structure | MS [M + 1]+ |
|---|---|---|
| 263 | 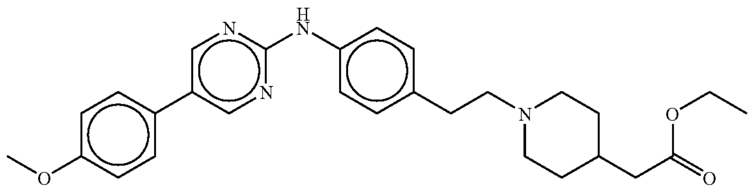 | 475.3 |
| 264 | 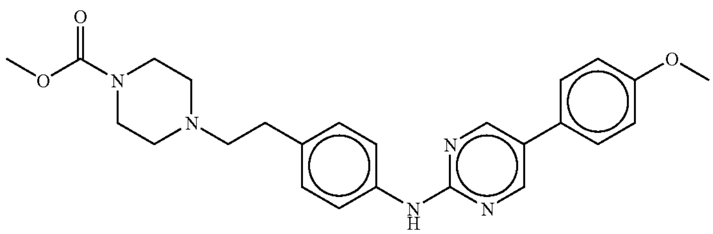 | 448.2 |
| 265 | 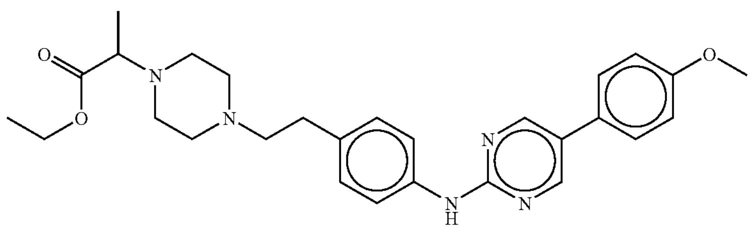 | 490.4 |
| 266 | 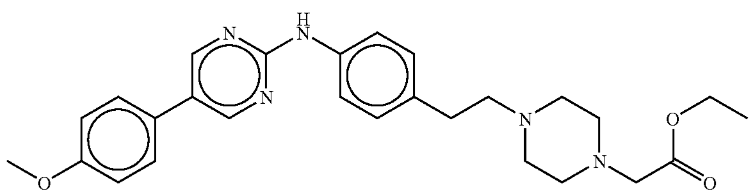 | 476.3 |
| 267 | 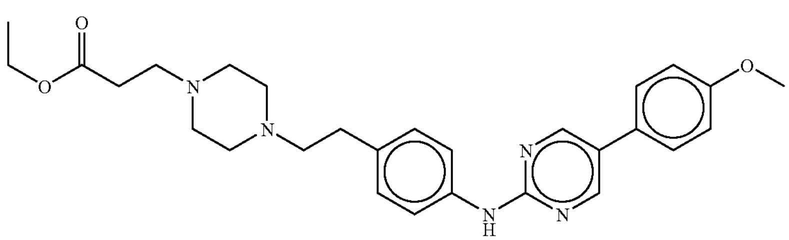 | 490.3 |
| 268 | 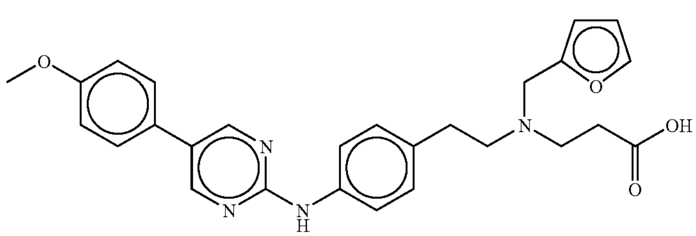 | 473.3 |

TABLE 1-continued

Examplary compounds which modulate the activiry of c-kit receptors.

| # | Structure | MS [M + 1]+ |
|---|---|---|
| 269 | 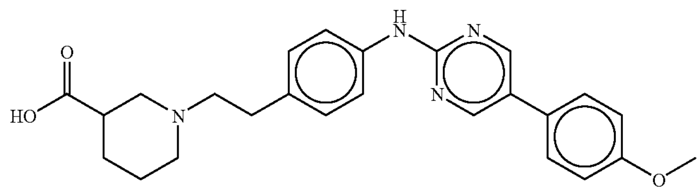 | 433.2 |
| 270 | 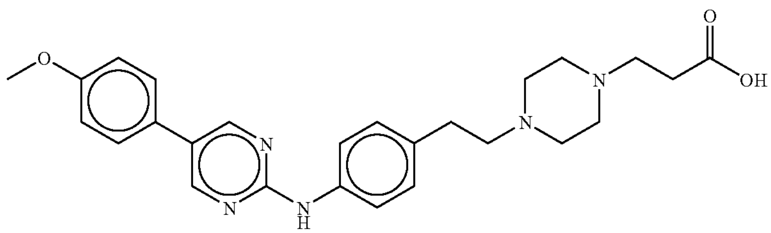 | 462.3 |
| 271 | 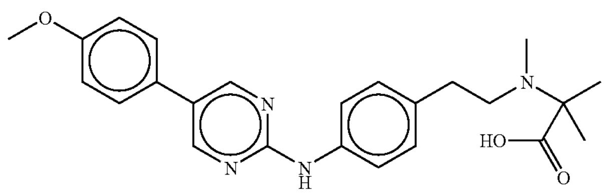 | 421.2 |
| 272 | 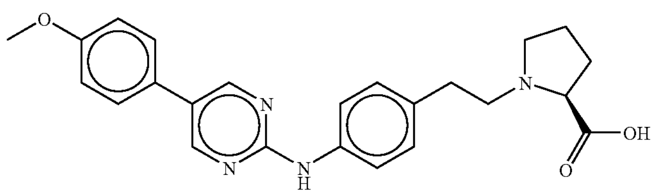 | 419.1 |
| 273 | 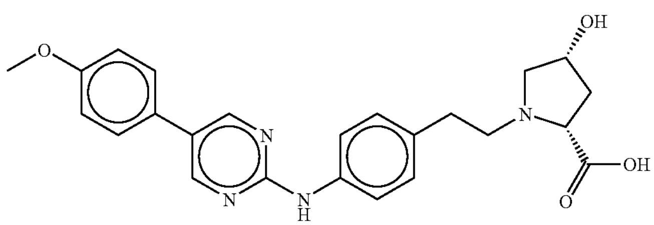 | 435.2 |
| 274 | 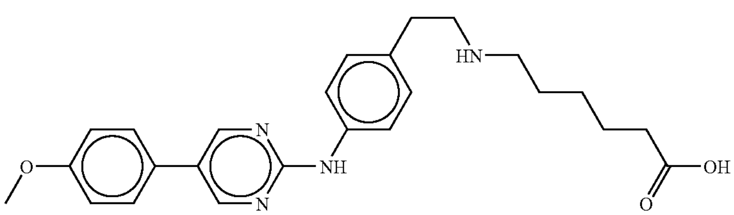 | 435.2 |
| 275 | 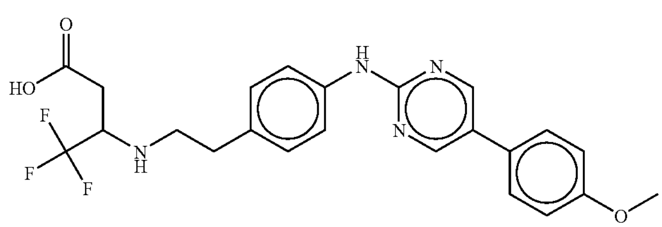 | 461.1 |

TABLE 1-continued

Examplary compounds which modulate the activiry of c-kit receptors.

| # | Structure | MS [M + 1]+ |
|---|-----------|-------------|
| 276 | 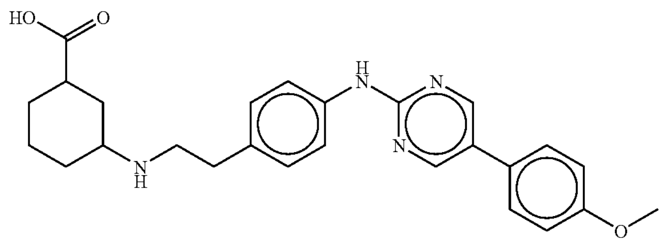 | 447.2 |
| 277 | 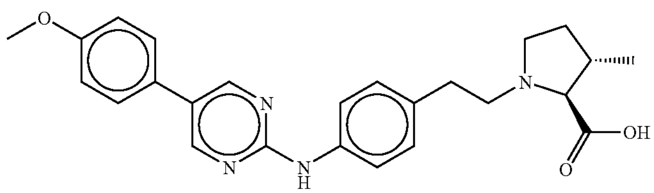 | 433.2 |
| 278 | 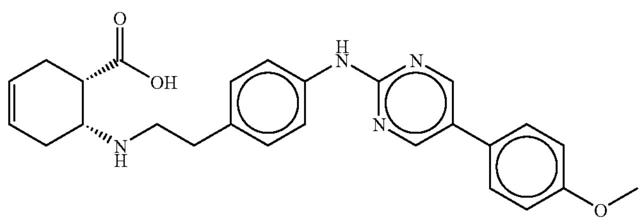 | 445.2 |
| 279 | 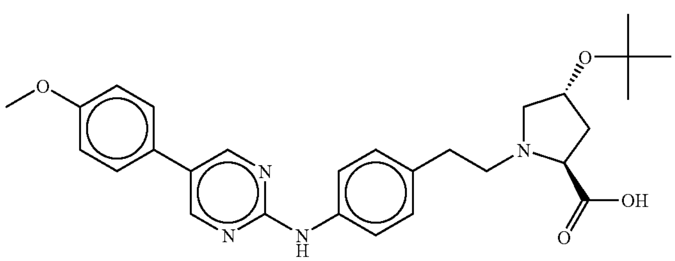 | 491.2 |
| 280 | 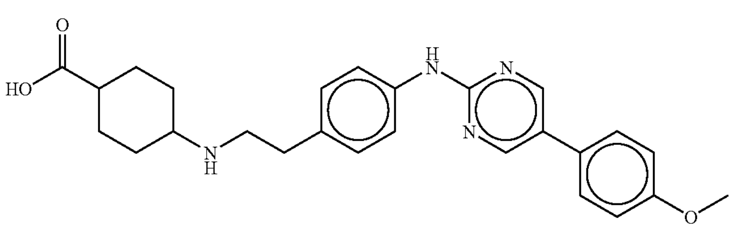 | 447.2 |
| 281 | 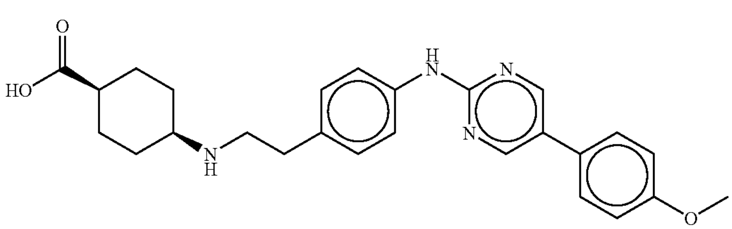 | 447.2 |

TABLE 1-continued

Examplary compounds which modulate the activiry of c-kit receptors.

| # | Structure | MS [M + 1]+ |
|---|---|---|
| 282 | 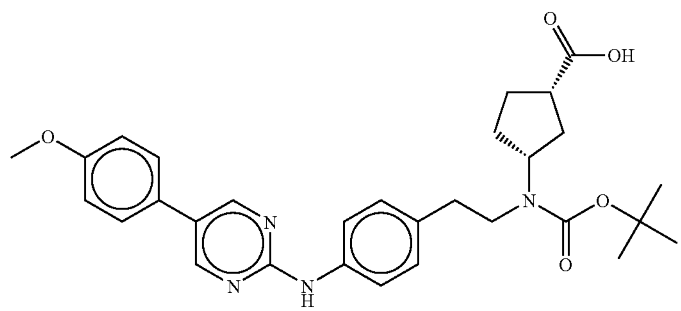 | 533.2 |
| 283 | 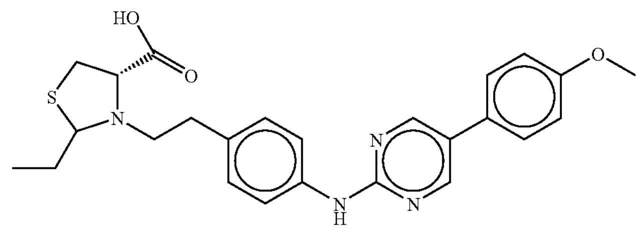 | 465.2 |
| 284 | 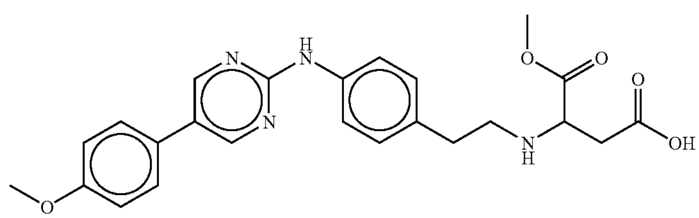 | 451.2 |
| 285 | 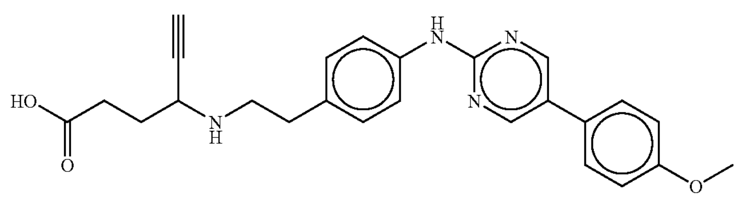 | 431.2 |
| 286 | 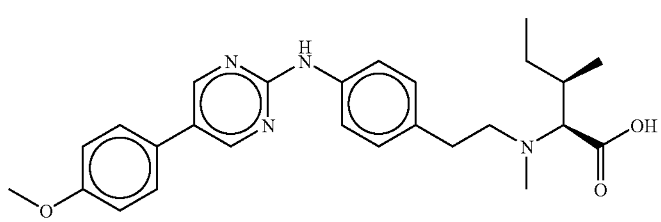 | 499.2 |
| 287 | 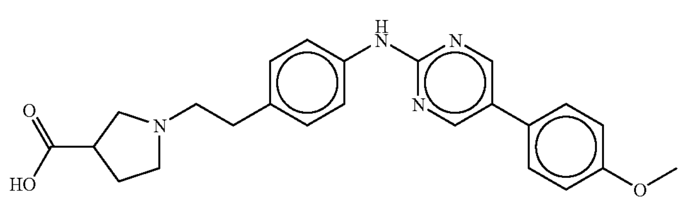 | 419.2 |

TABLE 1-continued
Examplary compounds which modulate the activiry of c-kit receptors.
| # | Structure | MS [M + 1]+ |
|---|---|---|
| 288 | 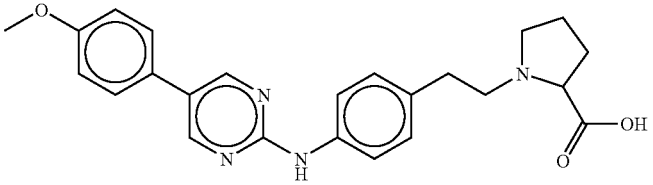 | 419.2 |
| 289 | 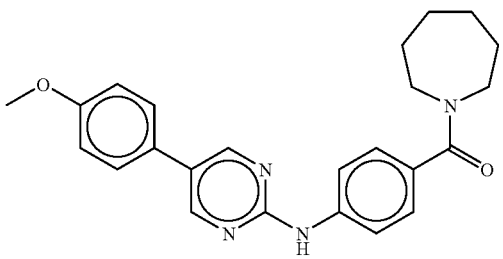 | 403.3 |
| 290 | 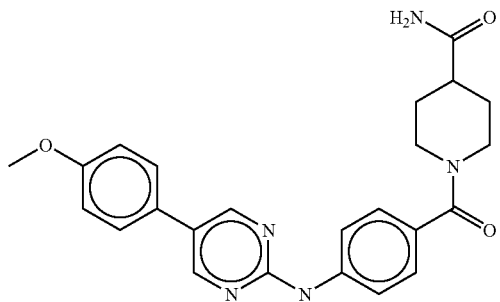 | 432.2 |
| 291 | 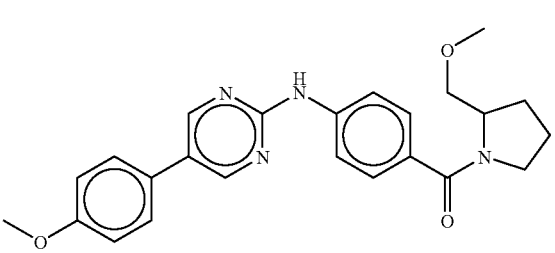 | 419.2 |
| 292 | 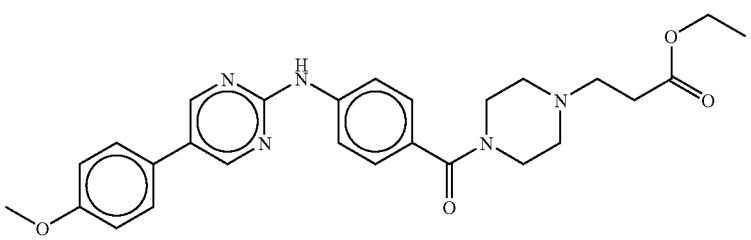 | 490.2 |

TABLE 1-continued

Examplary compounds which modulate the activiry of c-kit receptors.

| # | Structure | MS [M + 1]⁺ |
|---|---|---|
| 293 | 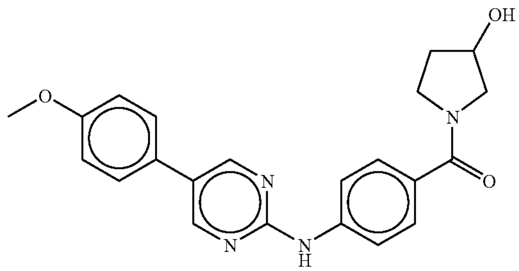 | 391.2 |
| 294 | 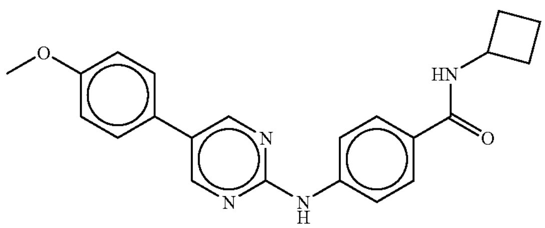 | 375.2 |
| 295 | 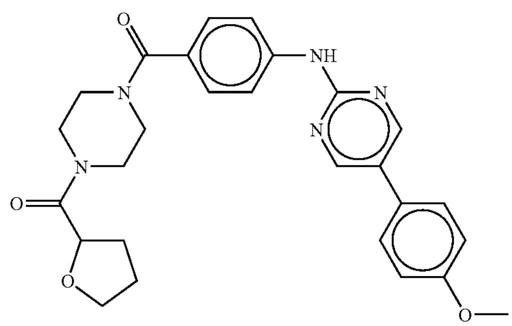 | 488.3 |
| 296 | 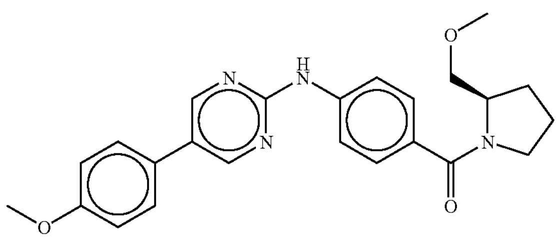 | 419.2 |
| 297 | 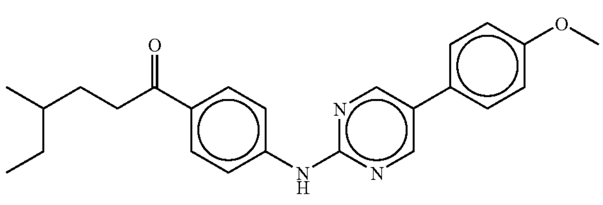 | 391.2 |
| 298 | 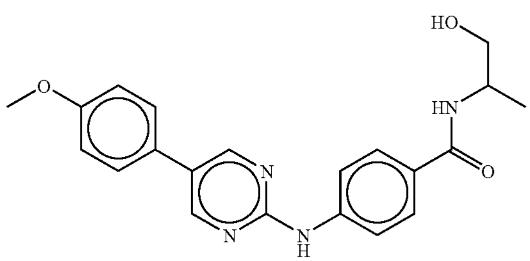 | 379.3 |

TABLE 1-continued

Examplary compounds which modulate the activiry of c-kit receptors.

| # | Structure | MS [M + 1]+ |
|---|---|---|
| 299 | 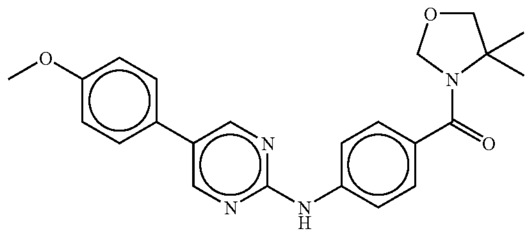 | 405.1 |
| 300 | 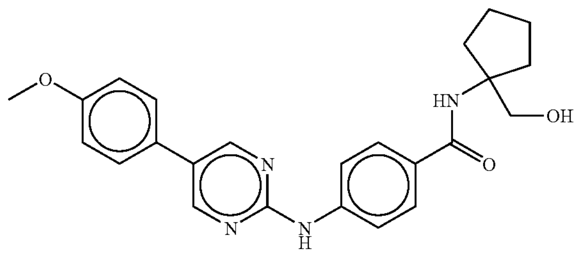 | 419.2 |
| 301 | 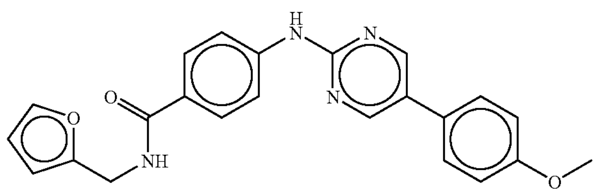 | 401.2 |
| 302 | 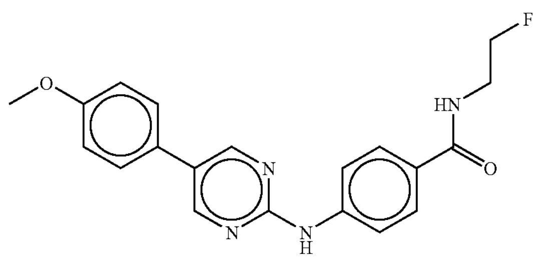 | 367.1 |
| 303 | 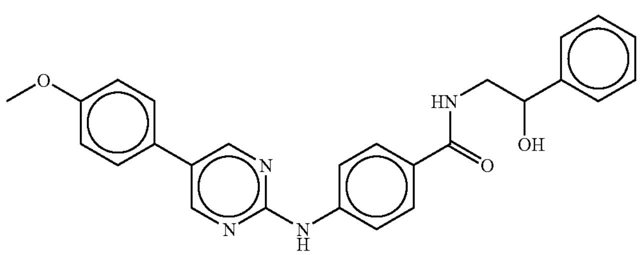 | 441.2 |
| 304 | 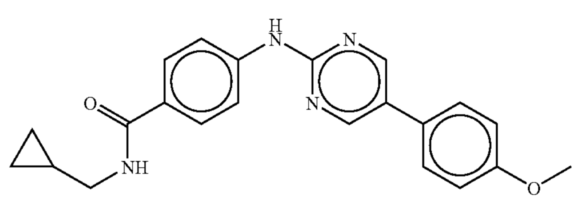 | 375.2 |

TABLE 1-continued

Examplary compounds which modulate the activiry of c-kit receptors.

| # | Structure | MS [M + 1]+ |
|---|---|---|
| 305 | | 419.2 |
| 306 | | 448.3 |
| 307 | | 415.2 |
| 308 | | 403.2 |

TABLE 1-continued

Examplary compounds which modulate the activiry of c-kit receptors.

| # | Structure | MS [M + 1]+ |
|---|---|---|
| 309 | 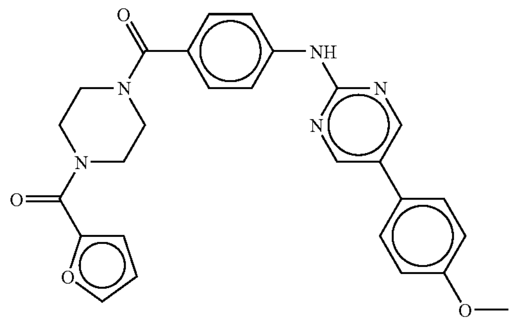 | 484.3 |
| 310 | 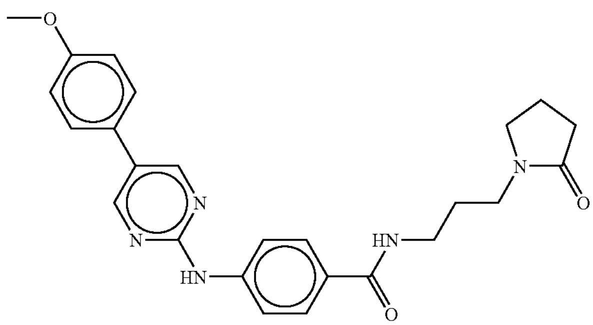 | 446.2 |
| 311 | 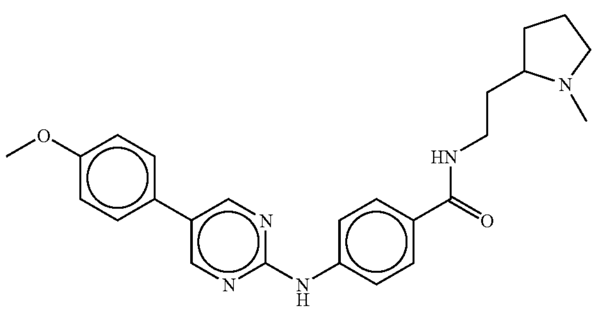 | 432.3 |
| 312 | 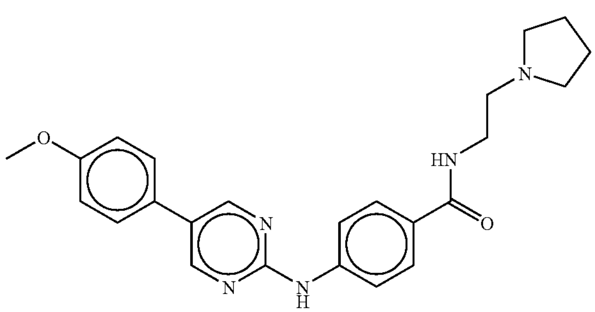 | 418.3 |
| 313 | 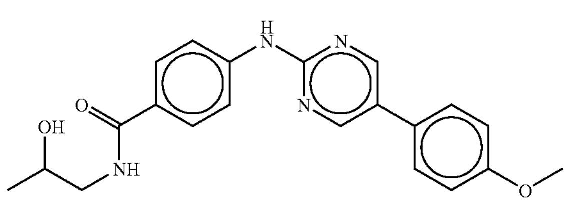 | 379.2 |

TABLE 1-continued

Examplary compounds which modulate the activiry of c-kit receptors.

| # | Structure | MS [M + 1]+ |
|---|---|---|
| 314 | | 392.2 |
| 315 | | 389.2 |
| 316 | | 432.2 |
| 317 | | 398.2 |
| 318 | | 440.2 |

TABLE 1-continued

Examplary compounds which modulate the activiry of c-kit receptors.

| # | Structure | MS [M + 1]+ |
|---|---|---|
| 319 | 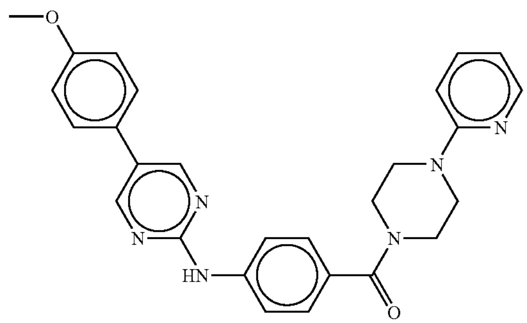 | 467.2 |
| 320 | 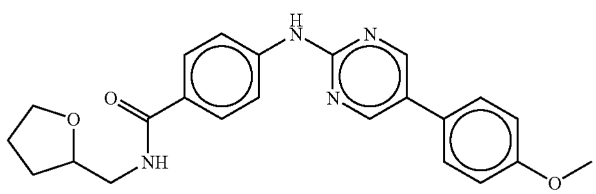 | 405.2 |
| 321 | 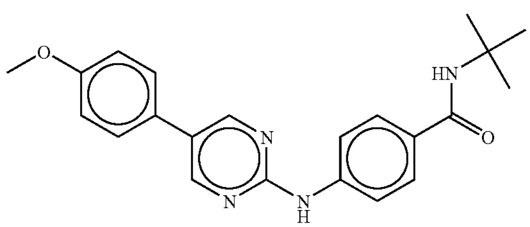 | 377.2 |
| 322 | 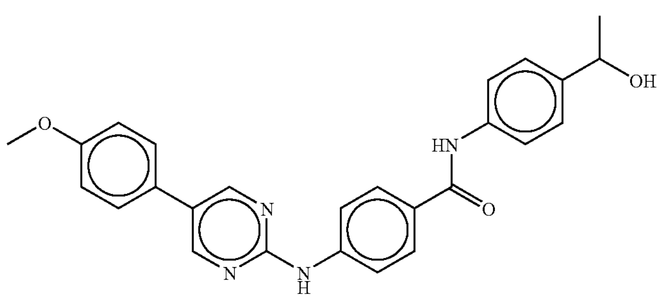 | 441.2 |
| 323 | 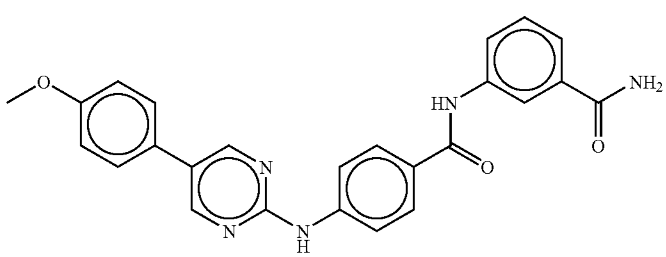 | 440.2 |

TABLE 1-continued

Examplary compounds which modulate the activiry of c-kit receptors.

| # | Structure | MS [M + 1]+ |
|---|---|---|
| 324 | 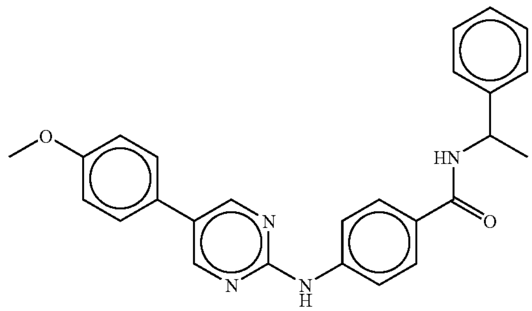 | 425.2 |
| 325 | 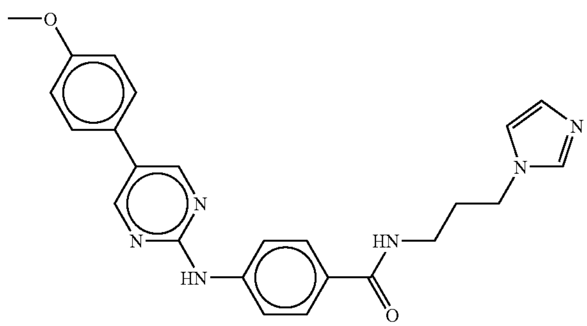 | 429.3 |
| 326 | 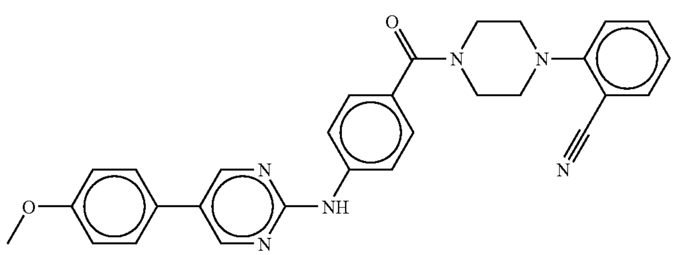 | 491.2 |
| 327 | 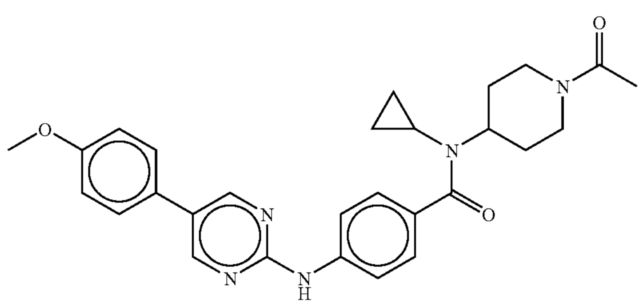 | 486.3 |
| 328 | 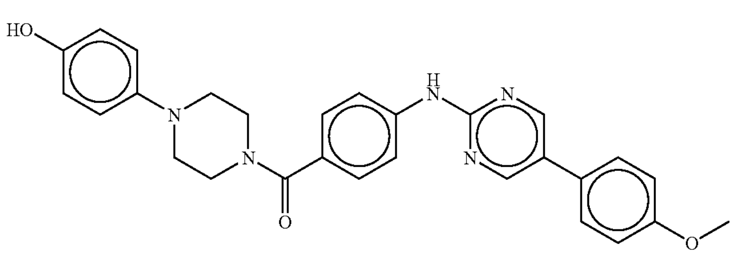 | 482.2 |

TABLE 1-continued

Examplary compounds which modulate the activiry of c-kit receptors.

| # | Structure | MS [M + 1]+ |
|---|---|---|
| 329 | 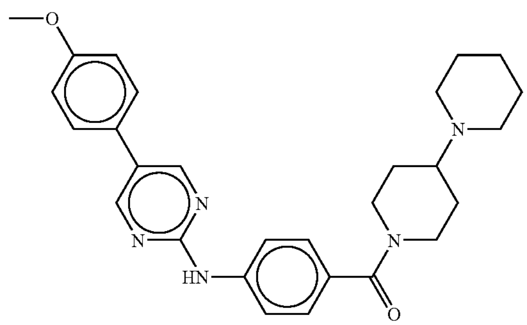 | 472.4 |
| 330 | 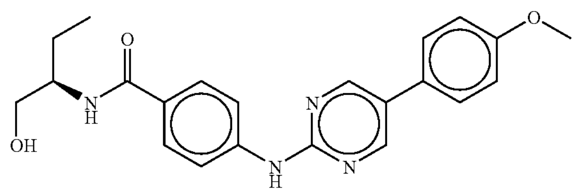 | 393.1 |
| 331 | 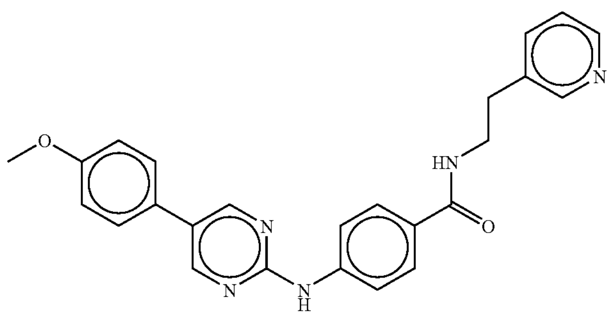 | 426.3 |
| 332 | 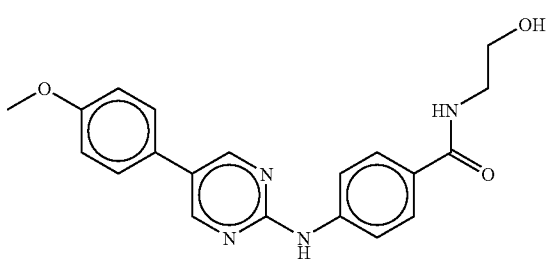 | 365.2 |
| 333 | 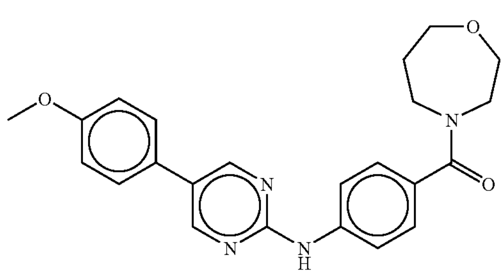 | 405.2 |

TABLE 1-continued

Examplary compounds which modulate the activiry of c-kit receptors.

| # | Structure | MS [M + 1]+ |
|---|-----------|-------------|
| 334 | | 405.2 |
| 335 | | 401.2 |
| 336 | | 405.2 |
| 337 | | 458.4 |
| 338 | | 403.2 |
| 339 | | 421.2 |

TABLE 1-continued

Examplary compounds which modulate the activiry of c-kit receptors.

| # | Structure | MS [M + 1]+ |
|---|---|---|
| 340 | 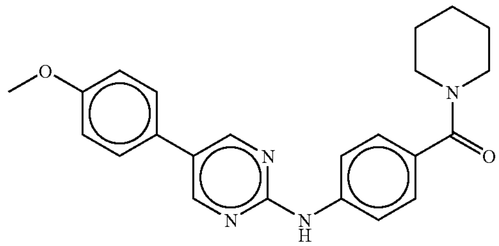 | 389.2 |
| 341 | 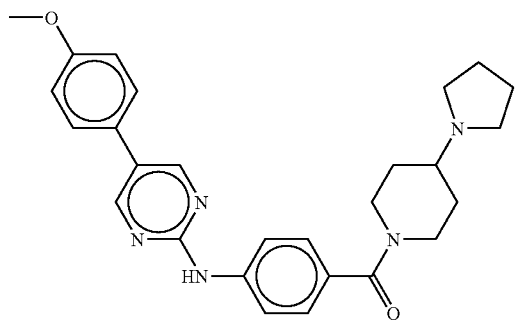 | 458.4 |
| 342 | 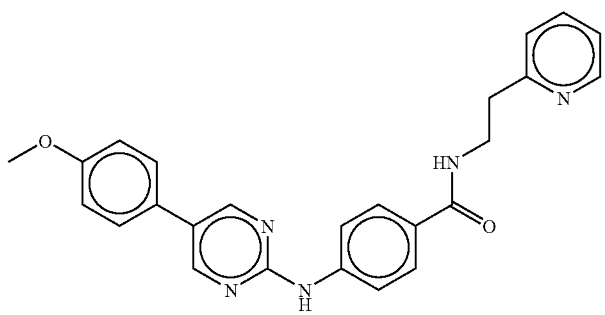 | 426.2 |
| 343 | 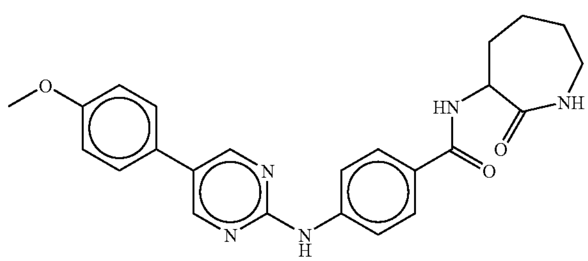 | 432.2 |
| 344 | 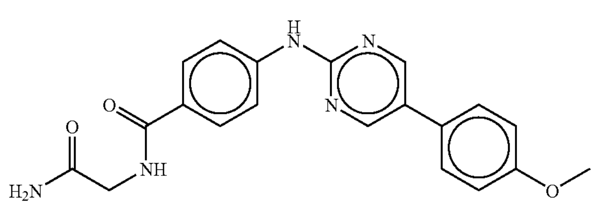 | 378.2 |

TABLE 1-continued

Examplary compounds which modulate the activiry of c-kit receptors.

| # | Structure | MS [M + 1]+ |
|---|---|---|
| 345 | 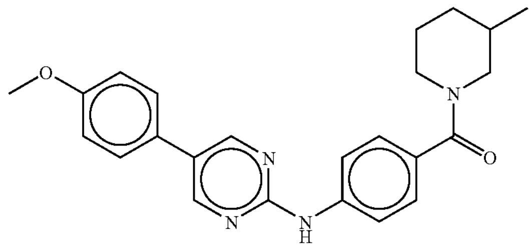 | 403.2 |
| 346 | 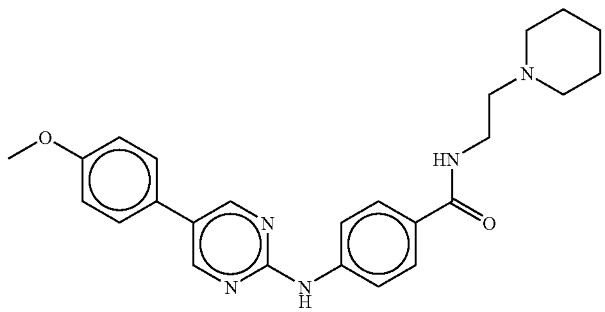 | 432.2 |
| 347 | 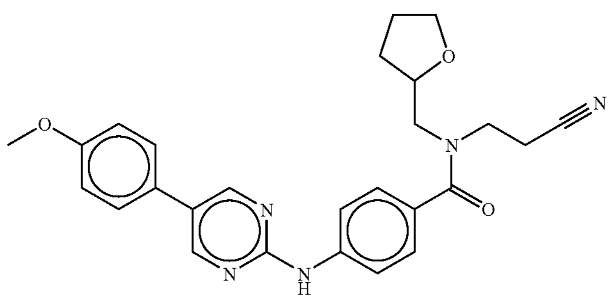 | 458.5 |
| 348 | 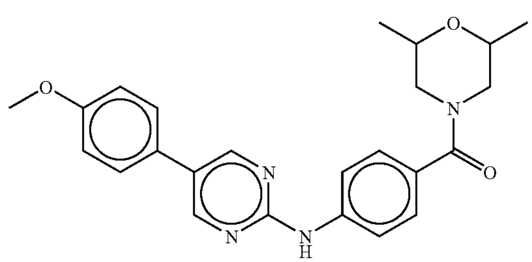 | 419.5 |
| 349 | 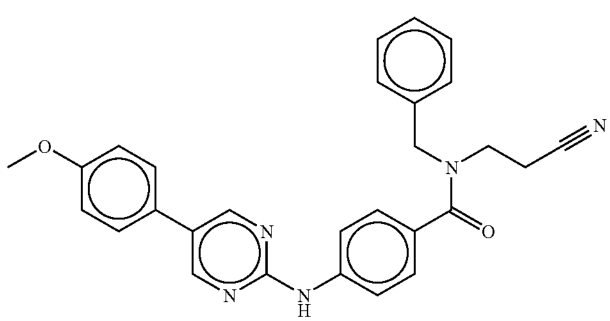 | 464.2 |

TABLE 1-continued

Examplary compounds which modulate the activiry of c-kit receptors.

| # | Structure | MS [M + 1]+ |
|---|---|---|
| 350 | 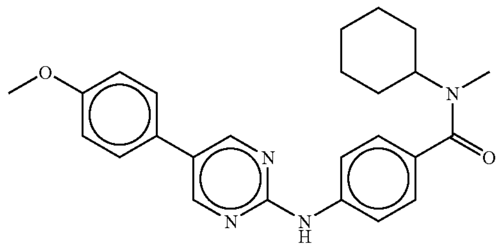 | 417.3 |
| 351 | 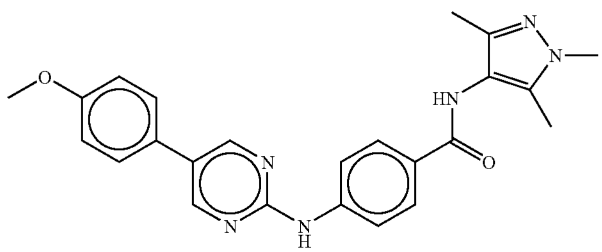 | 429.2 |
| 352 | 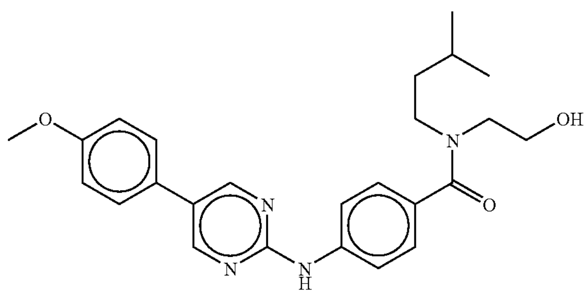 | 435.3 |
| 353 | 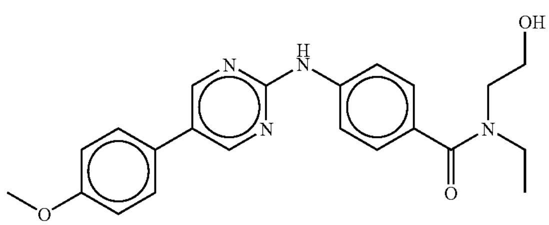 | 393.2 |
| 354 | 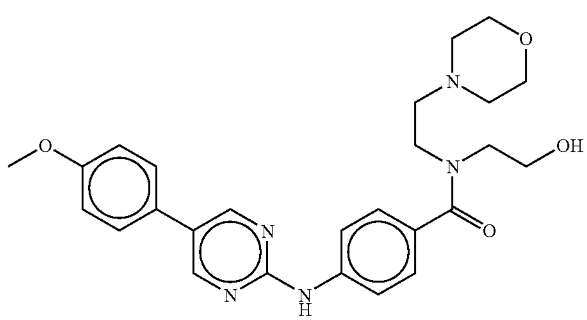 | 478.3 |

TABLE 1-continued

Examplary compounds which modulate the activiry of c-kit receptors.

| # | Structure | MS [M + 1]+ |
|---|---|---|
| 355 | 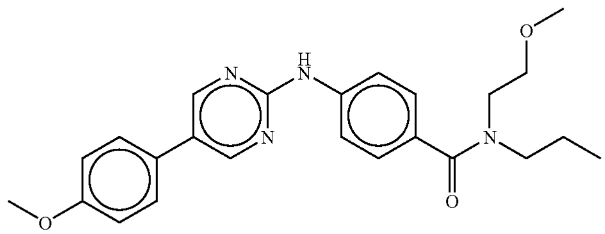 | 421.3 |
| 356 | 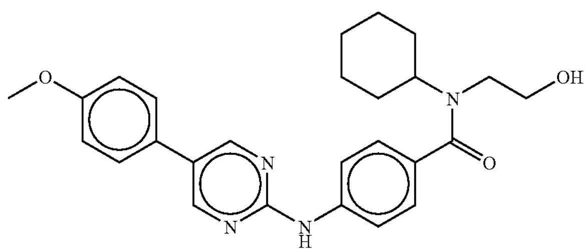 | 447.3 |
| 357 | 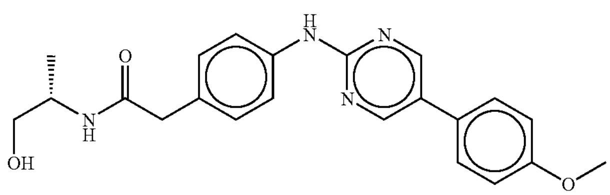 | 379.2 |
| 358 | 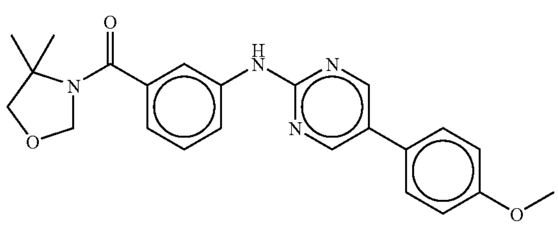 | 405.2 |
| 359 | 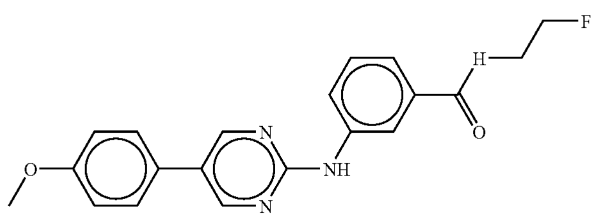 | 367.2 |
| 360 | 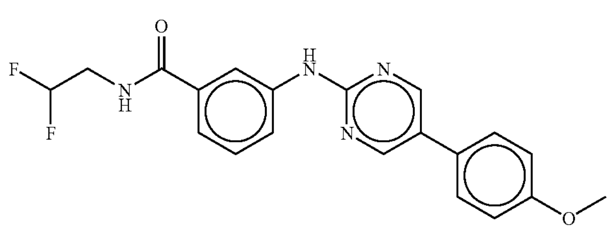 | 385.2 |

TABLE 1-continued
Examplary compounds which modulate the activiry of c-kit receptors.
| # | Structure | MS [M + 1]+ |
|---|-----------|-------------|
| 361 | 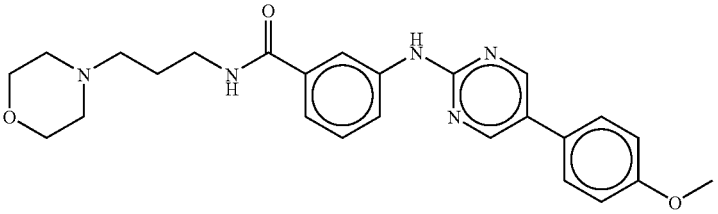 | 448.3 |
| 362 | 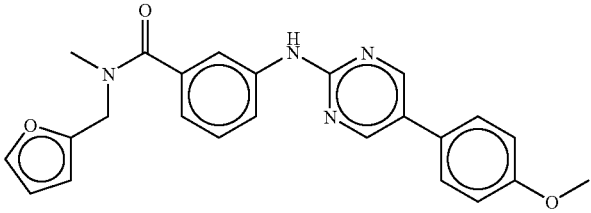 | 415.3 |
| 363 | 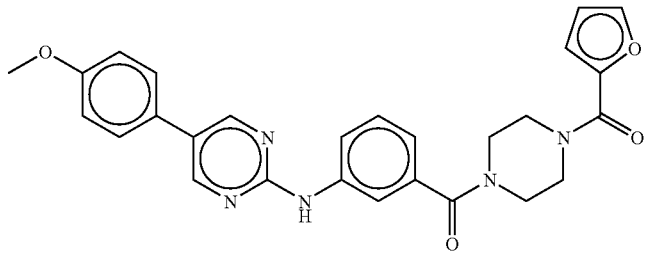 | 484.3 |
| 364 | 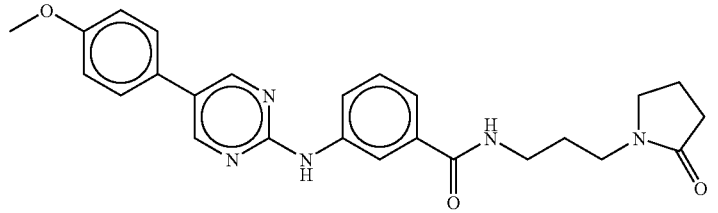 | 446.3 |
| 365 | 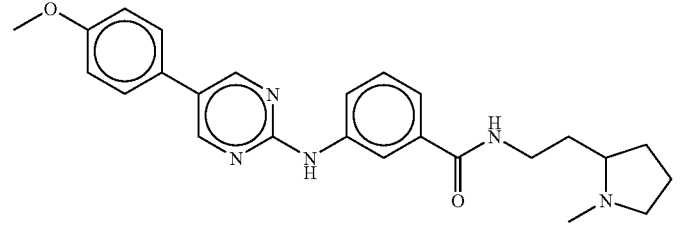 | 432.3 |
| 366 | 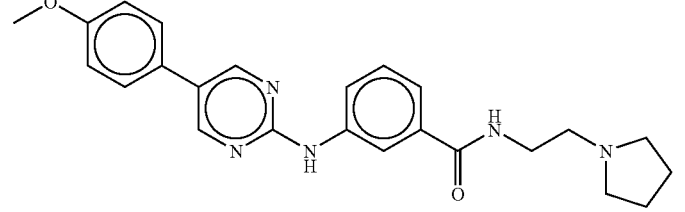 | 418.3 |

TABLE 1-continued

Examplary compounds which modulate the activiry of c-kit receptors.

| # | Structure | MS [M + 1]⁺ |
|---|---|---|
| 367 | 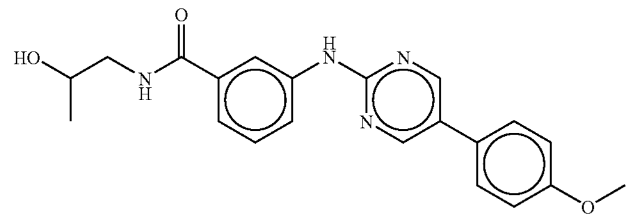 | 379.2 |
| 368 | 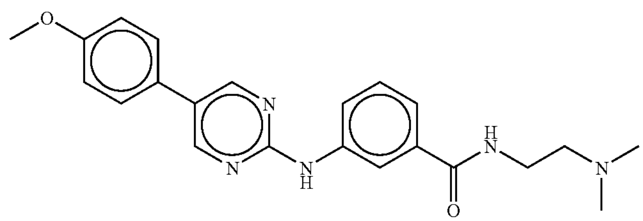 | 392.3 |
| 369 | 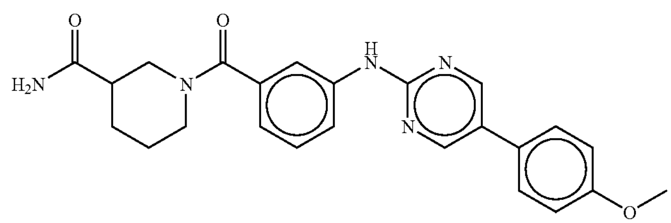 | 432.2 |
| 370 | 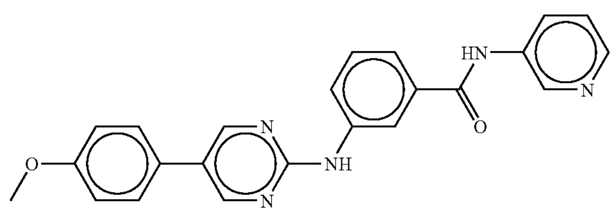 | 398.2 |
| 371 | 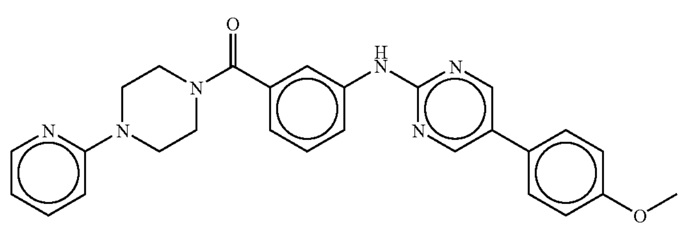 | 467.3 |
| 372 | 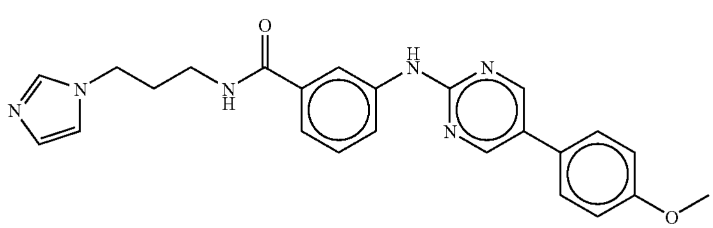 | 429.2 |

TABLE 1-continued
Examplary compounds which modulate the activiry of c-kit receptors.
| # | Structure | MS [M + 1]+ |
|---|---|---|
| 373 | 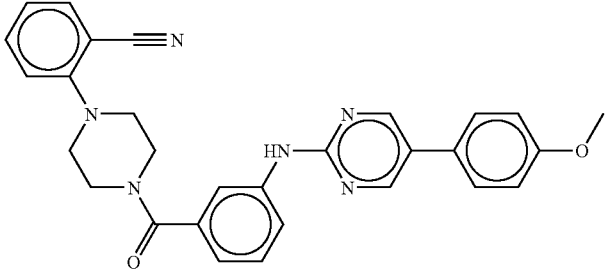 | 491.3 |
| 374 | 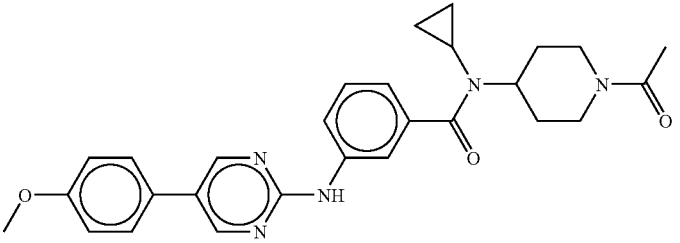 | 486.3 |
| 375 | 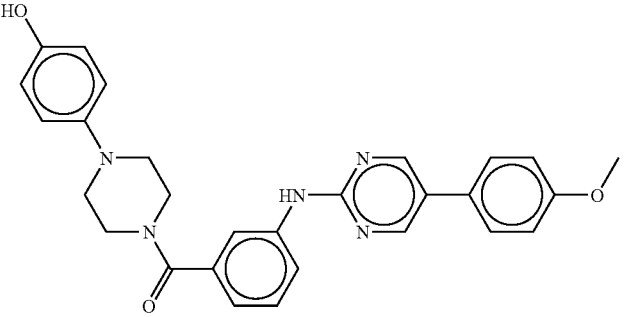 | 482.5 |
| 376 | 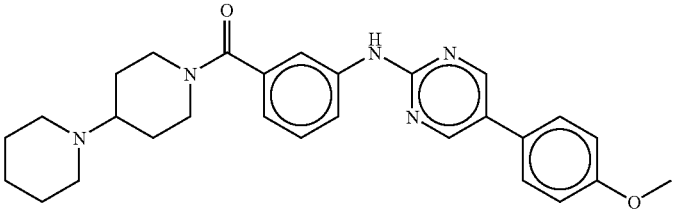 | 472.3 |
| 377 | 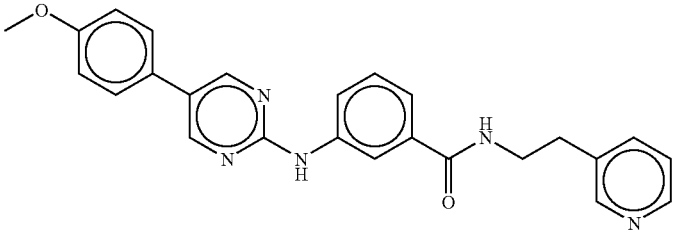 | 426.3 |

TABLE 1-continued

Examplary compounds which modulate the activiry of c-kit receptors.

| # | Structure | MS [M + 1]⁺ |
|---|---|---|
| 378 | 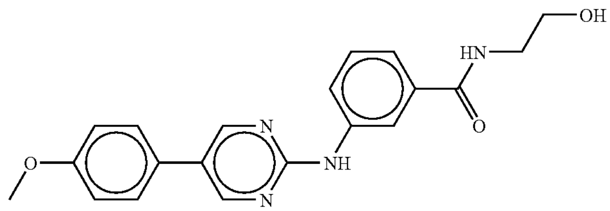 | 365.2 |
| 379 | 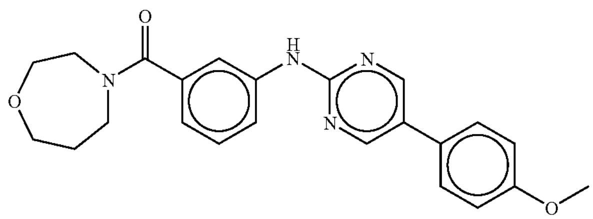 | 405.3 |
| 380 | 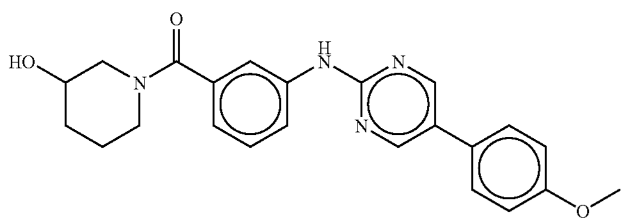 | 405.3 |
| 381 | 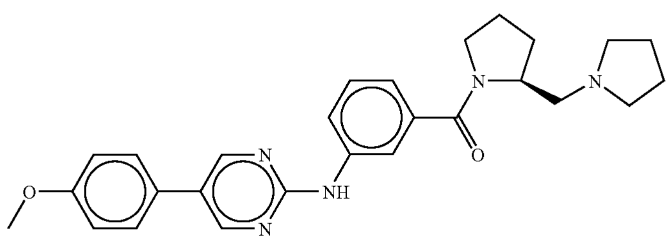 | 458.2 |
| 382 | 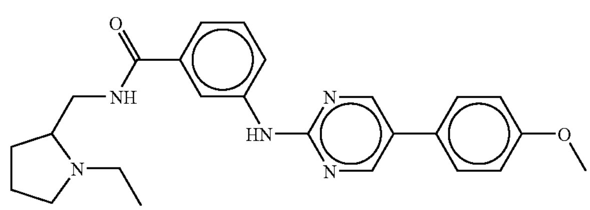 | 432.2 |
| 383 | 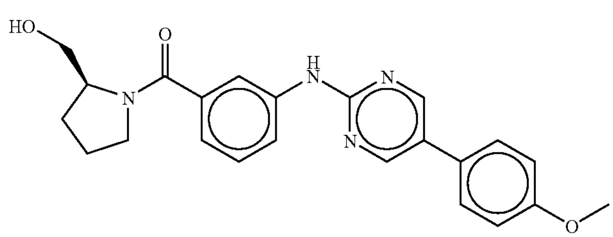 | 405.3 |

TABLE 1-continued

Examplary compounds which modulate the activiry of c-kit receptors.

| # | Structure | MS [M + 1]+ |
|---|---|---|
| 384 | 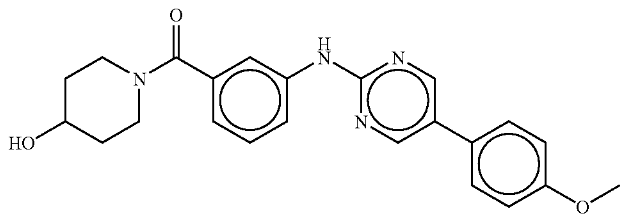 | 405.2 |
| 385 | 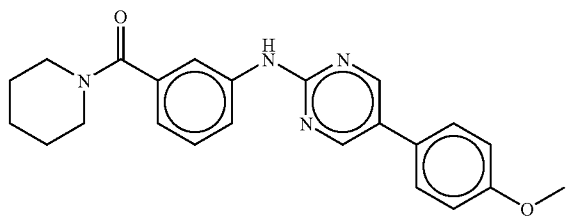 | 389.3 |
| 386 | 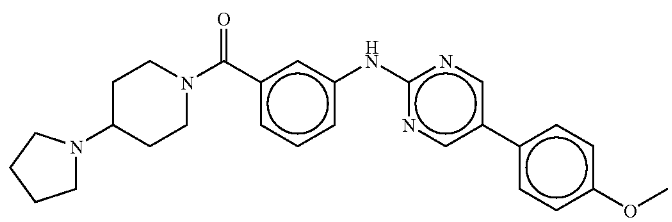 | 458.4 |
| 387 | 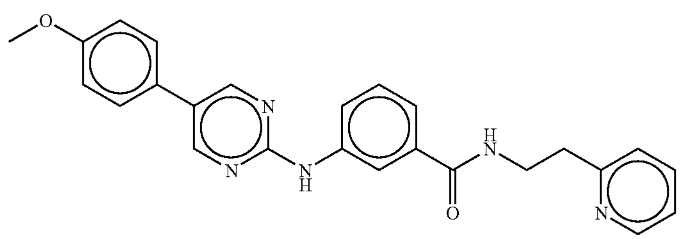 | 426.3 |
| 388 | 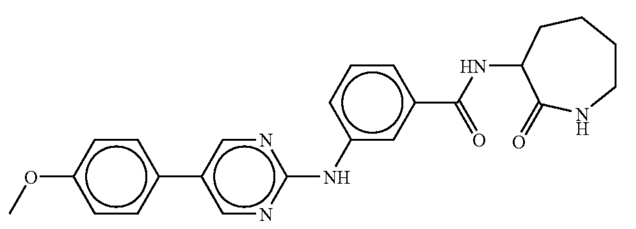 | 432.3 |
| 389 | 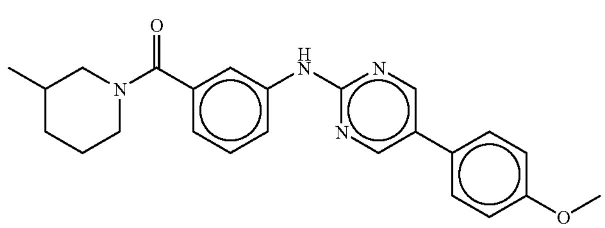 | 403.3 |

TABLE 1-continued

Examplary compounds which modulate the activiry of c-kit receptors.

| # | Structure | MS [M + 1]+ |
|---|-----------|-------------|
| 390 | 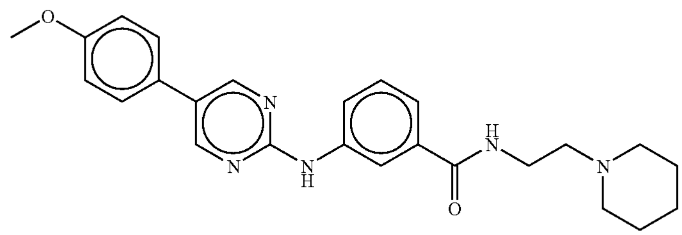 | 432.3 |
| 391 | 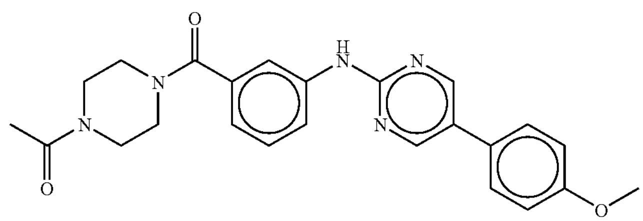 | 432.3 |
| 392 | 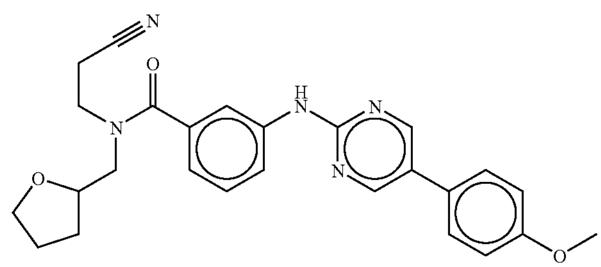 | 458.3 |
| 393 | 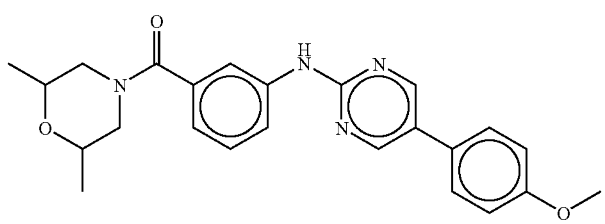 | 419.3 |
| 394 | 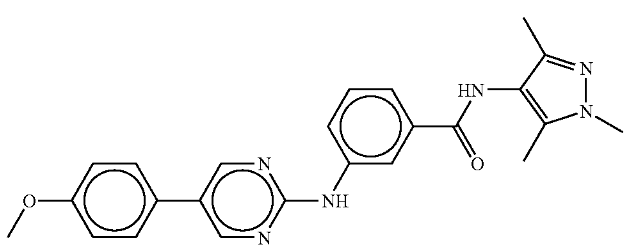 | 429.5 |
| 395 | 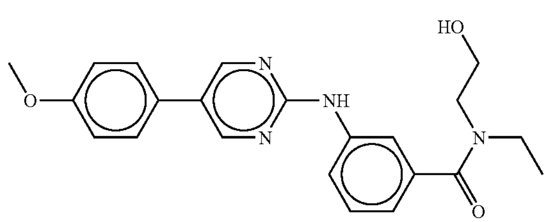 | 393.3 |

TABLE 1-continued
Examplary compounds which modulate the activiry of c-kit receptors.
| # | Structure | MS [M + 1]+ |
|---|---|---|
| 396 | 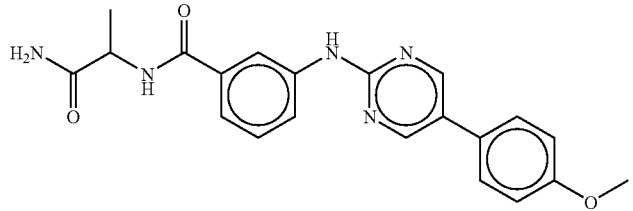 | 392.1 |
| 397 | 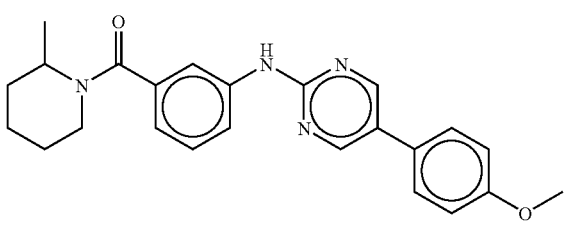 | 403.6 |
| 398 | 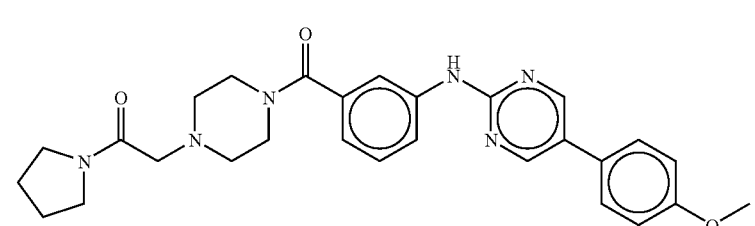 | 501.6 |
| 399 | 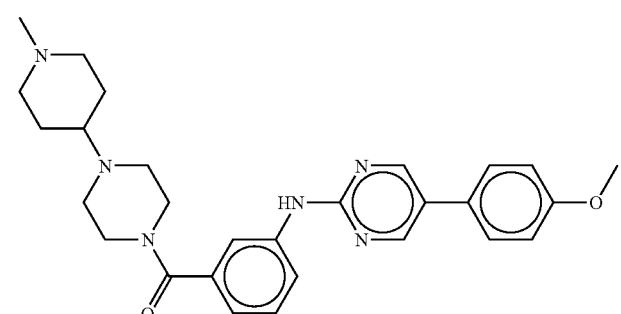 | 487.3 |
| 400 | 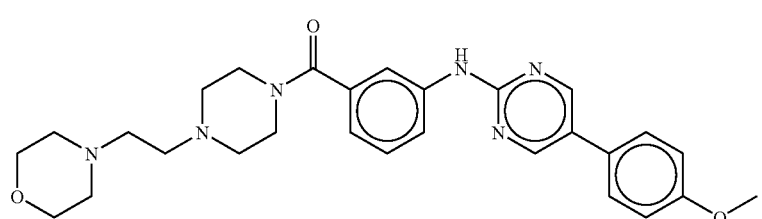 | 503.3 |
| 401 | 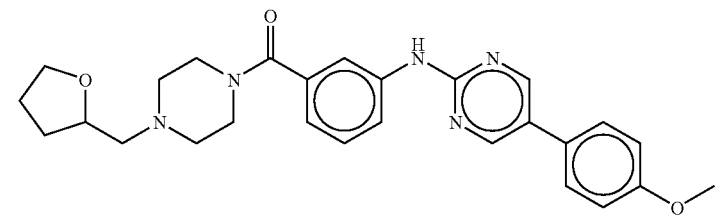 | 474.6 |

TABLE 1-continued
Examplary compounds which modulate the activiry of c-kit receptors.
| # | Structure | MS [M + 1]+ |
|---|---|---|
| 402 | 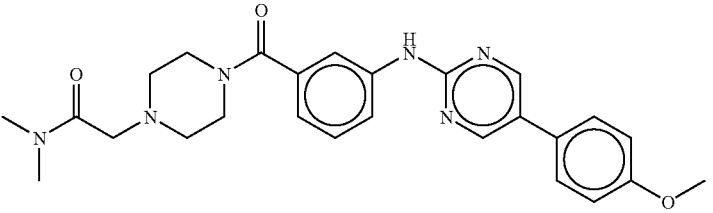 | 475.5 |
| 403 | 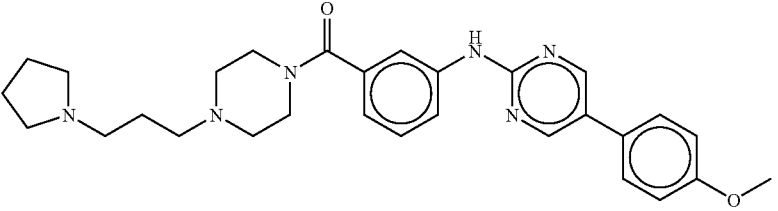 | 501.5 |
| 404 | 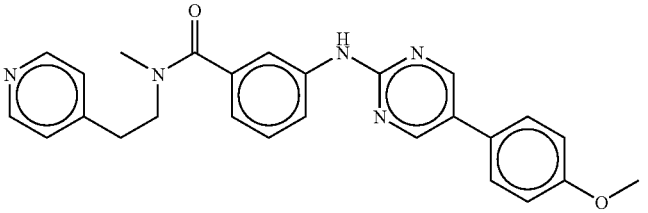 | 440.3 |
| 405 | 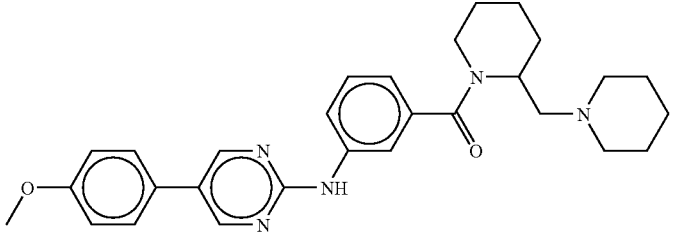 | 486.6 |
| 406 | 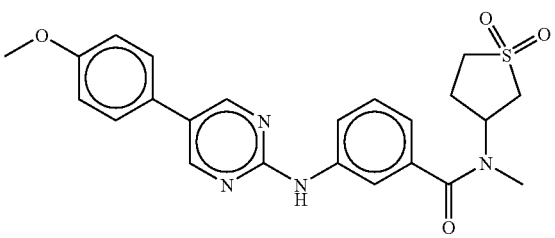 | 453.1 |
| 407 | 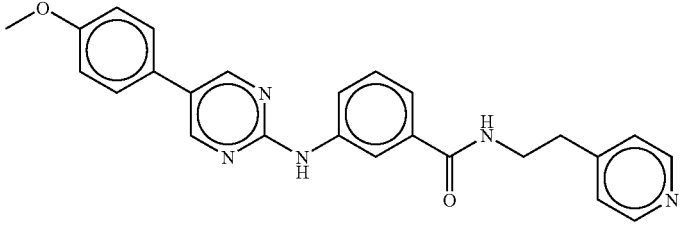 | 426.3 |

TABLE 1-continued
Examplary compounds which modulate the activiry of c-kit receptors.
| # | Structure | MS [M + 1]+ |
|---|---|---|
| 408 | 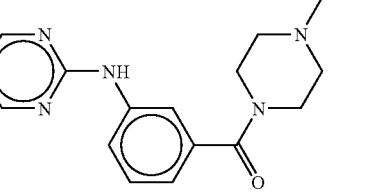 | 460.4 |
| 409 | 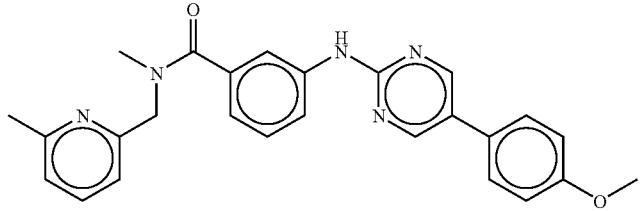 | 440.7 |
| 410 | 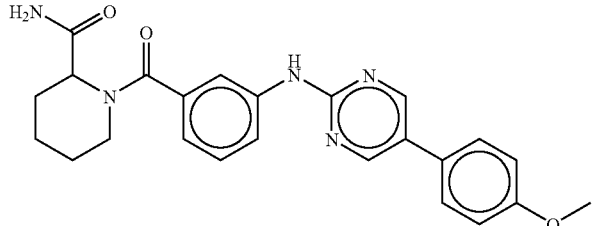 | 432.5 |
| 411 | 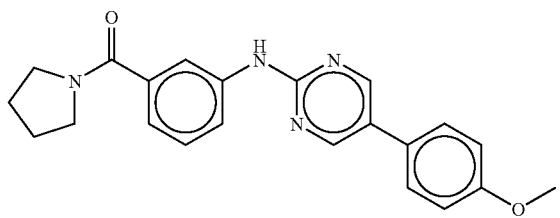 | 375.5 |
| 412 | 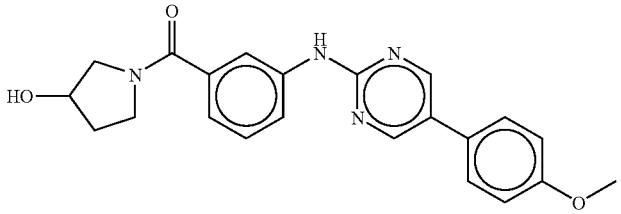 | 391.3 |
| 413 | 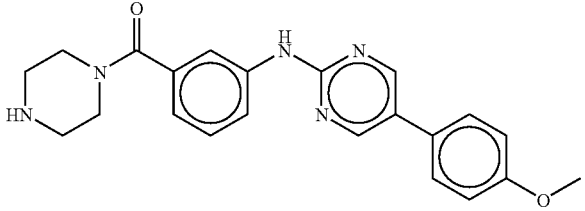 | 390.1 |

TABLE 1-continued
Examplary compounds which modulate the activiry of c-kit receptors.
| # | Structure | MS [M + 1]+ |
|---|---|---|
| 414 | 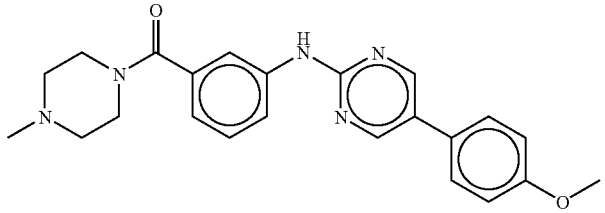 | 404.2 |
| 415 | 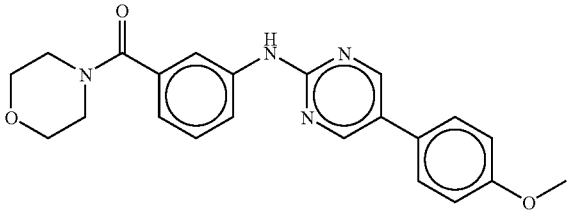 | 391.2 |
| 416 | 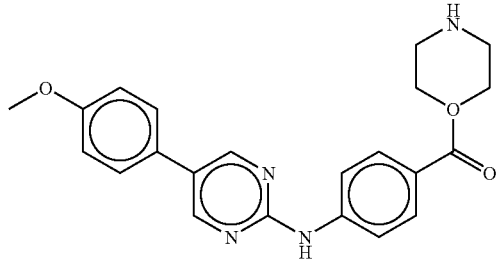 | 390.1 |
| 417 | 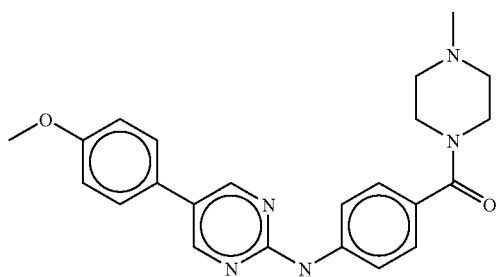 | 404.2 |
| 418 | 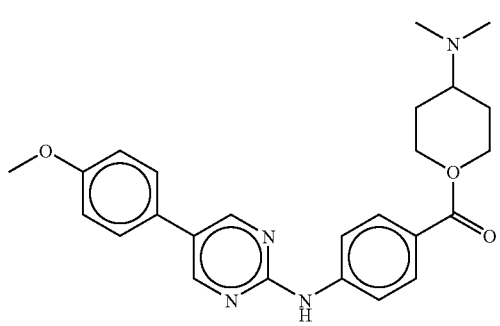 | 391.2 |

TABLE 1-continued
Examplary compounds which modulate the activiry of c-kit receptors.
| # | Structure | MS [M + 1]+ |
|---|---|---|
| 419 | 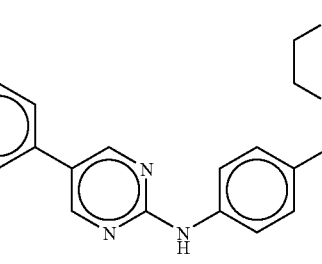 | 432.2 |
| 420 | 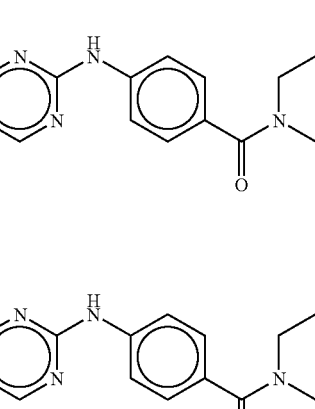 | 462.2 |
| 421 | 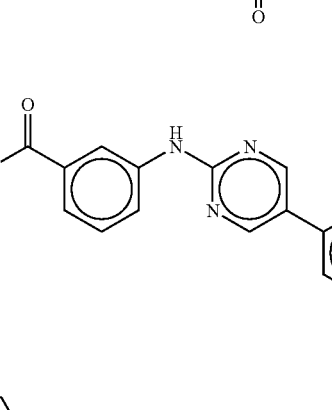 | 448.2 |
| 422 | 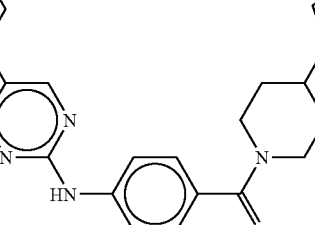 | 483.2 |
| 423 | 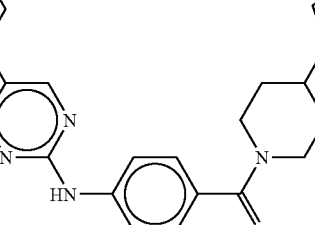 | 458.2 |

TABLE 1-continued

Examplary compounds which modulate the activiry of c-kit receptors.

| # | Structure | MS [M + 1]+ |
|---|---|---|
| 424 | 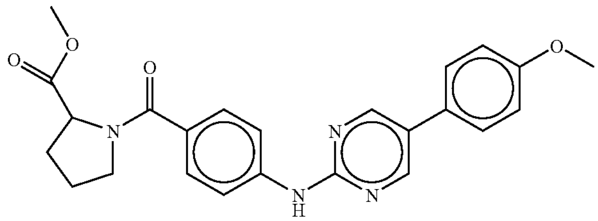 | 433.2 |
| 425 | 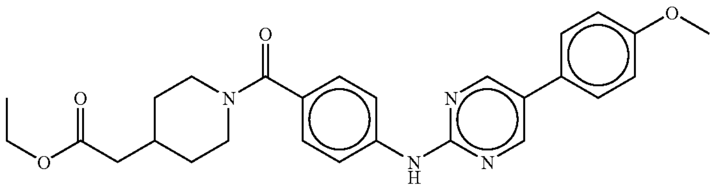 | 475.2 |
| 426 | 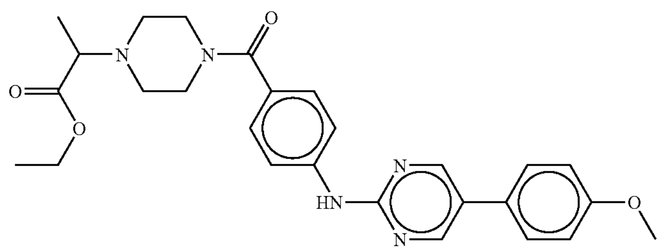 | 490.2 |
| 427 | 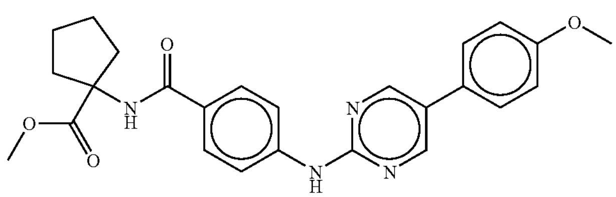 | 447.2 |
| 428 | 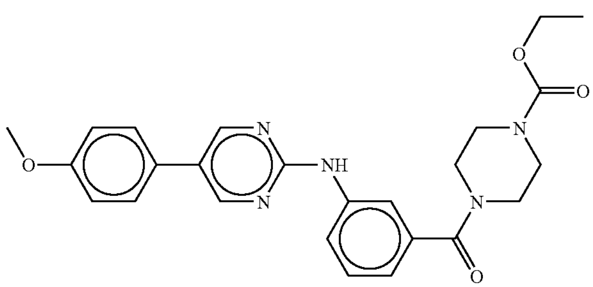 | 432.2 |
| 429 | 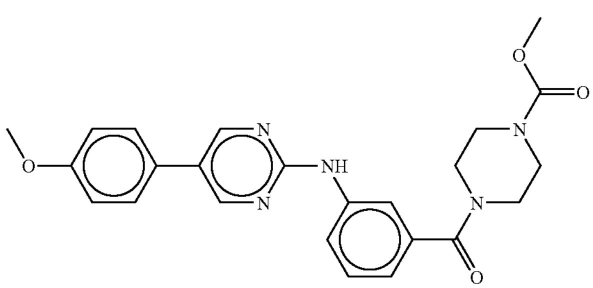 | 462.2 |

TABLE 1-continued
Examplary compounds which modulate the activiry of c-kit receptors.
| # | Structure | MS [M + 1]+ |
|---|---|---|
| 430 | 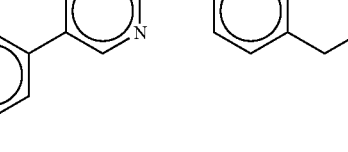 | 407.1 |
| 431 | 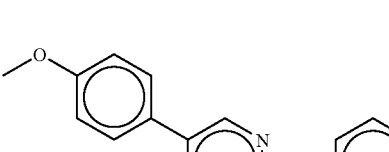 | 375.1 |
| 432 | 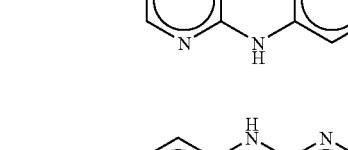 | 433.3 |
| 433 | 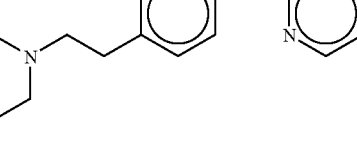 | 447.2 |
| 434 | 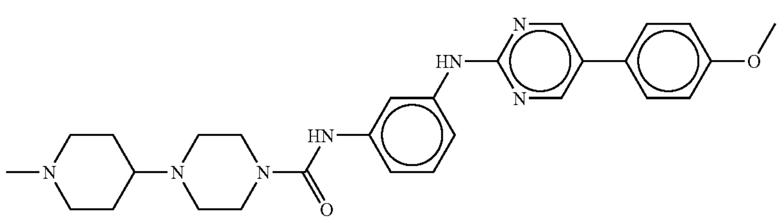 | 502.4 |
| 435 | 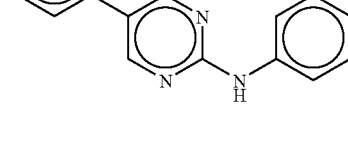 | 463.2 |

TABLE 1-continued

Examplary compounds which modulate the activiry of c-kit receptors.

| # | Structure | MS [M + 1]+ |
|---|---|---|
| 436 | 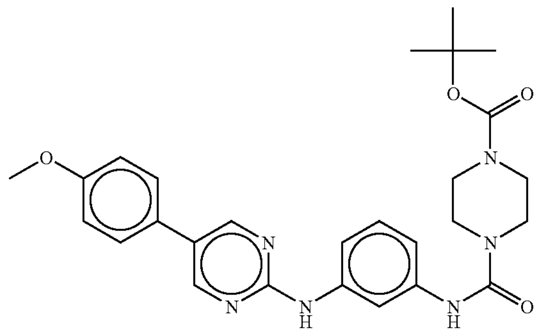 | 505.3 |
| 437 | 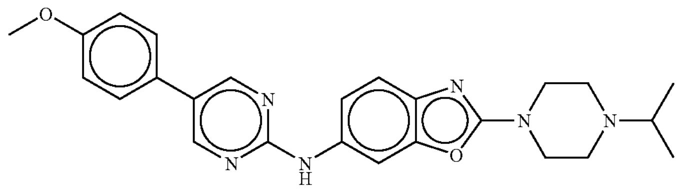 | 445.2 |
| 438 | 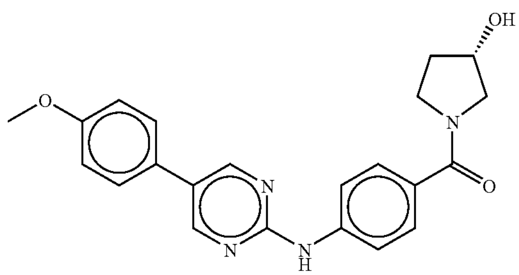 | 391.2 |
| 439 | 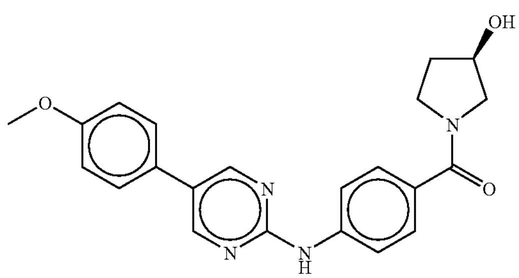 | 391.2 |

Synthesis of the Compounds

Compounds of Formula (A) or Formula (B) and compounds having the structures described in the prior section may be synthesized using standard synthetic techniques known to those of skill in the art or using methods known in the art in combination with methods described herein. In additions, solvents, temperatures and other reaction conditions presented herein may vary according to the practice and knowledge of those of skill in the art.

The starting material used for the synthesis of the compounds of Formula (A) or Formula (B) and compounds having the structures described in the prior section as described herein can be obtained from commercial sources, such as Aldrich Chemical Co. (Milwaukee, Wis.), Sigma Chemical Co. (St. Louis, Mo.), or the starting materials can be synthesized. The compounds described herein, and other related compounds having different substituents can be synthesized using techniques and materials known to those of skill in the art, such as described, for example, in March, ADVANCED ORGANIC CHEMISTRY 4th Ed., (Wiley 1992); Carey and Sundberg, ADVANCED ORGANIC CHEMISTRY 4th Ed., Vols. A and B (Plenum 2000, 2001), and Green and Wuts, PROTECTVE GROUPS IN ORGANIC SYNTHESIS 3rd Ed., (Wiley 1999) (all of which are incorporated by reference in their entirety). General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein. As a guide the following synthetic methods may be utilized.

Formation of Covalent Linkages by Reaction of an Electrophile with a Nucleophile The compounds described herein can be modified using various electrophiles or nucleophiles to form new functional groups or substituents. Table 2 entitled "Examples of Covalent Linkages and Precursors Thereof" lists selected examples of covalent linkages and precursor functional groups which yield and can be used as guidance toward the variety of electrophiles and nucleophiles combinations available. Precursor functional groups are shown as electrophilic groups and nucleophilic groups.

TABLE 2

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |

Use of Protecting Groups

In the reactions described, it may be necessary to protect reactive functional groups, for example hydroxy, amino, imino, thio or carboxy groups, where these are desired in the final product, to avoid their unwanted participation in the reactions. Protecting groups are used to block some or all reactive moieties and prevent such groups from participating in chemical reactions until the protective group is removed. It is preferred that each protective group be removable by a different means. Protective groups that are cleaved under totally disparate reaction conditions fulfill the requirement of differential removal. Protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a $Pd_o$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

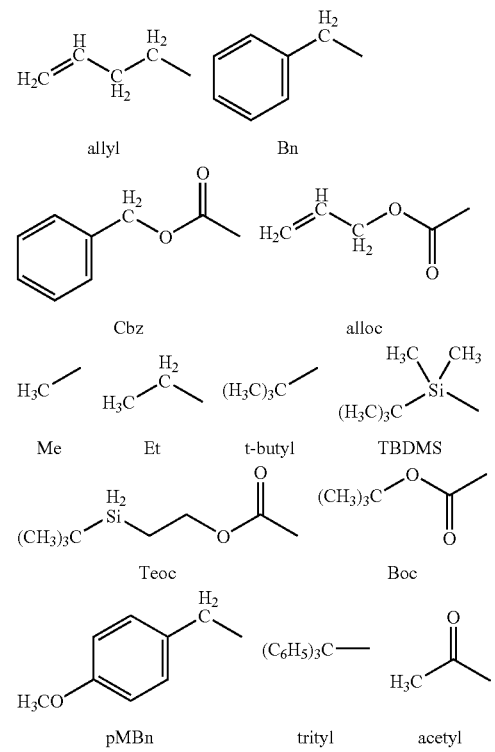

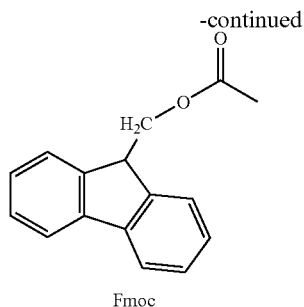

Fmoc

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference in their entirety.

Compounds of Formula (1) can be synthesized according to reaction scheme 1a, wherein amine compounds (A) react with dihalogen compounds (B) to give diaryl compounds (C). Arylation of compounds (C) yield compounds (1).

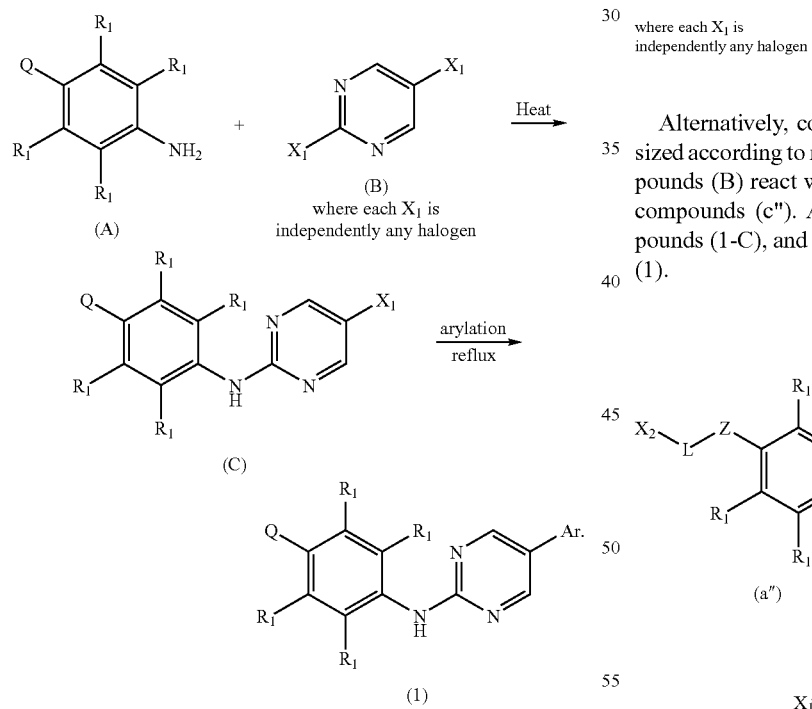

Arylation, by way of example only, may be accomplished by reaction of the halogen functionality with an aryl derivatized boronic acid in the presence of tetrakis(triphenylphosphino) palladium.

Alternatively, compounds of Formula (1) can be synthesized according to reaction scheme 1b, wherein halogen compounds (D) react with amine compounds (E) to give diaryl compounds of (C). Arylation of compounds (C) yield compounds (1).

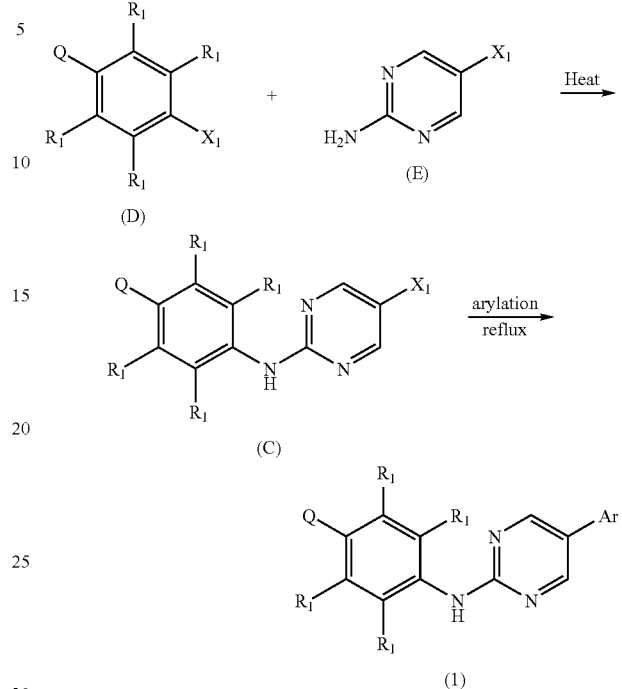

where each $X_1$ is independently any halogen

Alternatively, compounds of Formula (1) can be synthesized according to reaction scheme 1c, wherein halogen compounds (B) react with amine compounds (a″) to give diaryl compounds (c″). Arylation of compounds (c″) yield compounds (1-C), and subsequent amination affords compounds (1).

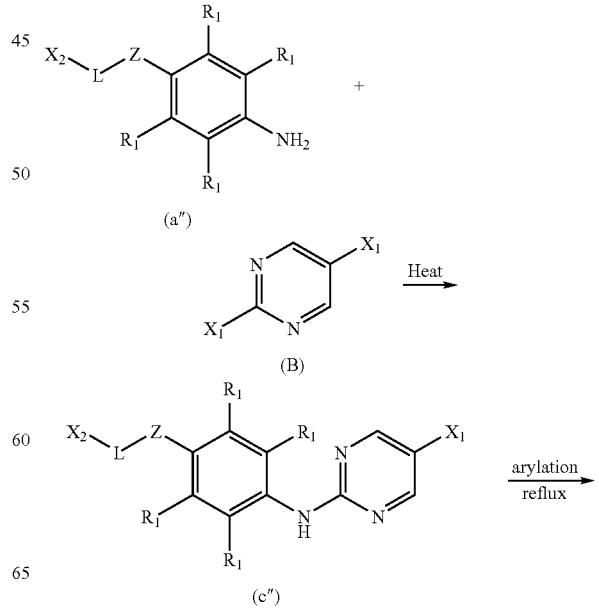

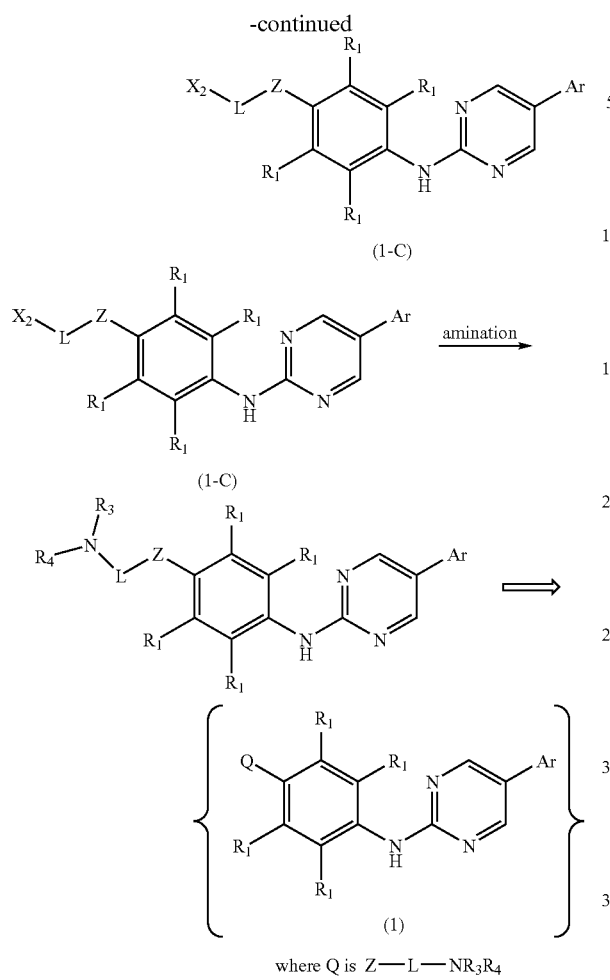

where: each $X_1$ is independently any halogen;
$X_2$ is any halogen, OMes, or OTos wherein, Z is $CR_1R_1$, O, or S, and L is alkylene (substituted or unsubstituted), alkenylene (substituted or unsubstituted), heteroalkylene (substituted or unsubstituted), or heteroalkenylene (substituted or unsubstituted). Amination, by way of example only, may be accomplished by reaction of the halogen functionality with an appropriate amine.

Alternatively, compounds of Formula (1) can be synthesized according to reaction scheme 1d, wherein halogen compounds (d") react with amine compounds (E) to give diaryl compounds (c"). Arylation of compounds (c") yield compounds (1-C), and subsequent amination affords compounds (1).

Scheme 1d where: each $X_1$ is independently any halogen;
$X_2$ is any halogen, OMes, or OTos wherein, Z is $CR_1R_1$, O, or S, and L is alkylene (substituted or unsubstituted), alkenylene (substituted or unsubstituted), heteroalkylene (substituted or unsubstituted), or heteroalkenylene (substituted or unsubstituted).

Alternatively, compounds of Formula (1) can be synthesized according to reaction scheme 1e, wherein dihalogen compounds (B) are arylated to give compounds (b"). Compounds (b") are then reacted with amine compounds (A) to yield compounds (1).

Scheme 1e

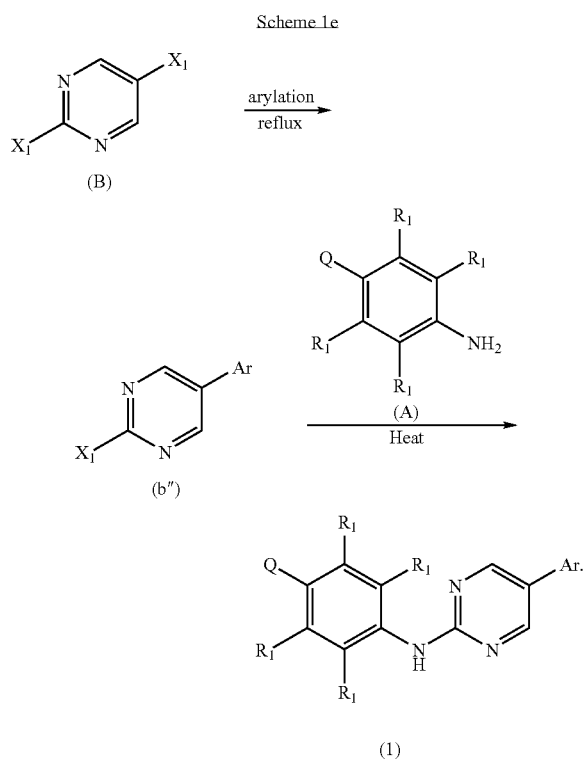

(1)

where each $X_1$ is independently any halogen

Arylation, by way of example only, may be accomplished by reaction of the halogen functionality with an aryl derivatized boronic acid in the presence of tetrakis(triphenylphosphino) palladium.

Alternatively, compounds of Formula (1) can be synthesized according to reaction scheme 1f, wherein compounds (E) are arylated to give compounds (e″). Compounds (e″) are then reacted with amine compounds (D) to yield compounds (1);

Scheme 1f

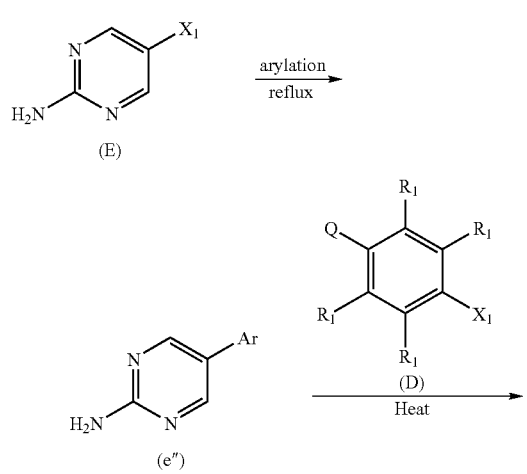

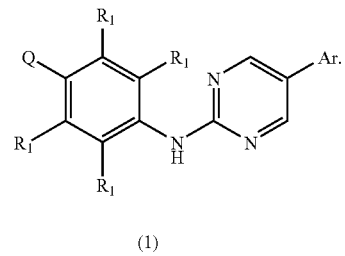

(1)

where each $X_1$ is independently any halogen

Arylation, by way of example only, may be accomplished by reaction of the halogen functionality with an aryl derivatized boronic acid in the presence of tetrakis(triphenylphosphino) palladium.

Alternatively, compounds of Formula (1) can be synthesized according to reaction scheme 1g, wherein dihalogen compounds (B) are arylated giving compounds (b″), which then react with amine compounds (a″) to give compounds (1-C). Subsequent amination of compounds (1-C) affords compounds (1).

Scheme 1g

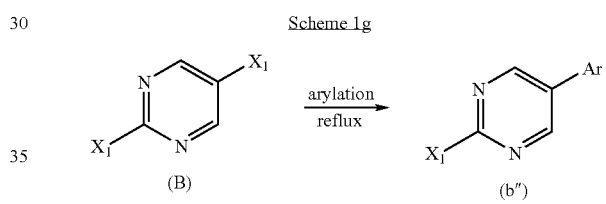

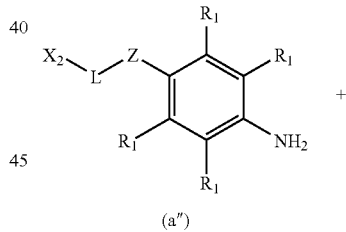

-continued

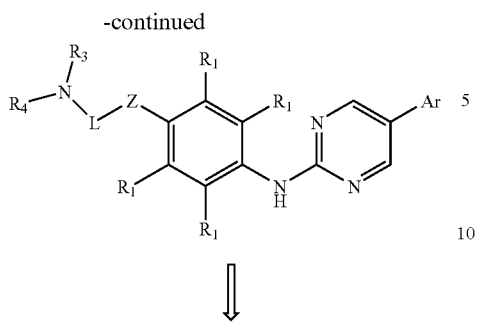

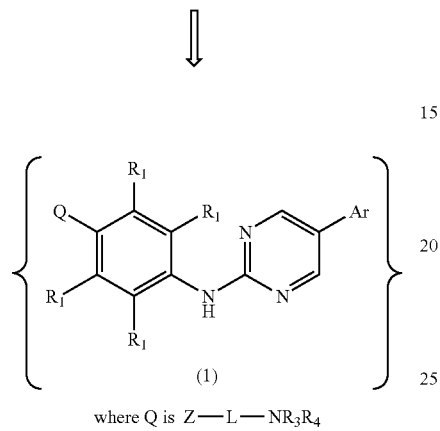

where Q is Z—L—NR₃R₄ where: each X₁ is independently any halogen;
X₂ is any halogen, OMes, or OTos wherein, Z is CR₁R₁, O, or S, and L is alkylene (substituted or unsubstituted), alkenylene (substituted or unsubstituted), heteroalkylene (substituted or unsubstituted), or heteroalkenylene (substituted or unsubstituted). Arylation, by way of example only, may be accomplished by reaction of the halogen functionality with an aryl derivatized boronic acid in the presence of tetrakis(triphenylphosphino) palladium. Amination, by way of example only, may be accomplished by reaction of the halogen functionality with an appropriate amine.

Alternatively, compounds of Formula (1) can be synthesized according to reaction scheme 1 h, wherein halogen compounds (E) are arylated giving compounds (e"), which then react with amine compounds (d") to give compounds (1-C). Subsequent amination of compounds (1-C) affords compounds (1).

Scheme 1h

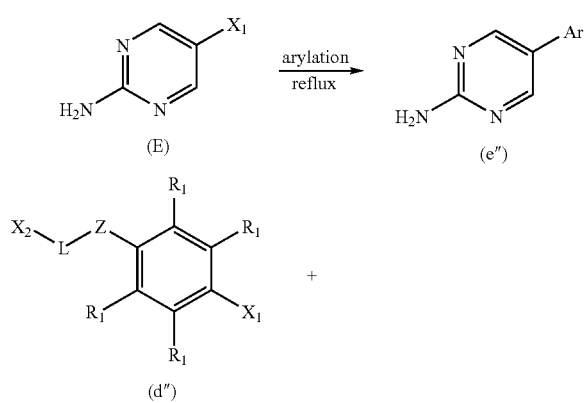

-continued

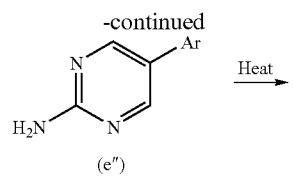

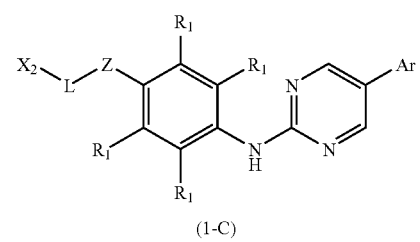

(1-C)

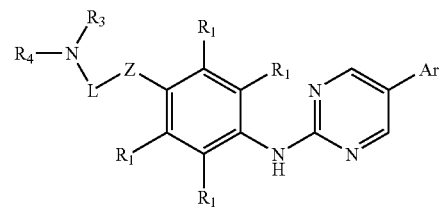

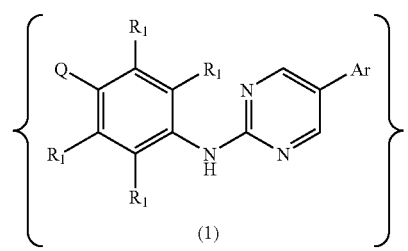

where Q is Z—L—NR₃R₄ where: each X₁ is independently any halogen;
X₂ is any halogen, OMes, or OTos wherein, Z is CR₁R₁, O, or S, and L is alkylene (substituted or unsubstituted), alkenylene (substituted or unsubstituted), heteroalkylene (substituted or unsubstituted), or heteroalkenylene (substituted or unsubstituted). Arylation, by way of example only, may be accomplished by reaction of the halogen functionality with an aryl derivatized boronic acid in the presence of tetrakis(triphenylphosphino) palladium. Amination, by way of example only, may be accomplished by reaction of the halogen functionality with an appropriate amine.

Similarly, compounds of Formula (1) can be synthesized according to reaction scheme 2a, wherein substituted amine compounds (F) react with dihalogen compounds (B) to give diaryl compounds (H). Arylation of compounds (H) yield compounds (1).

Scheme 1a

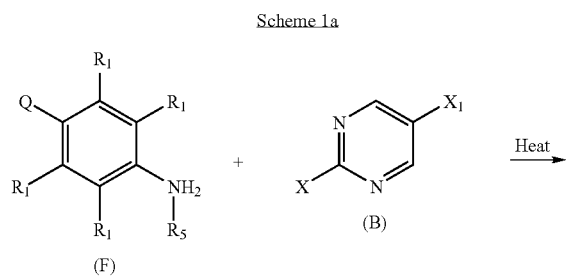

(F) + (B) →(Heat)

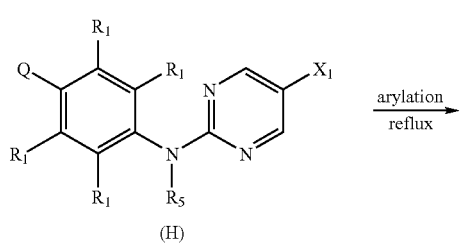

(H) →(arylation reflux)

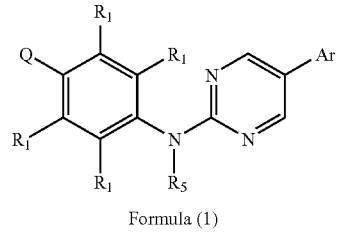

Formula (1)

where each $X_1$ is independently any halogen

Alternatively, compounds of Formula (1) can be synthesized according to reaction scheme 2b, wherein halogen compounds (D) react with substituted amine compounds (I) to give diaryl compounds (H). Arylation of compounds (H) yield compounds of Formula (1).

Scheme 2b

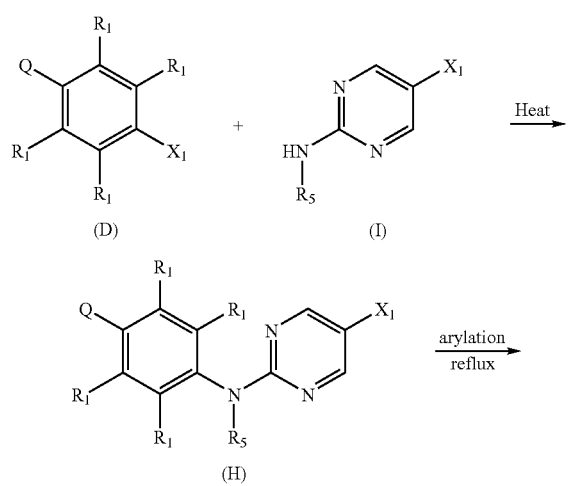

where each $X_1$ is independently any halogen

Alternatively, compounds of Formula (1) can be synthesized according to reaction scheme 2c, wherein halogen compounds (B) react with amine compounds (f″) to give diaryl compounds (h″). Arylation of compounds (h″) yield compounds (2-C), and subsequent amination affords compounds of Formula (1).

Scheme 2c

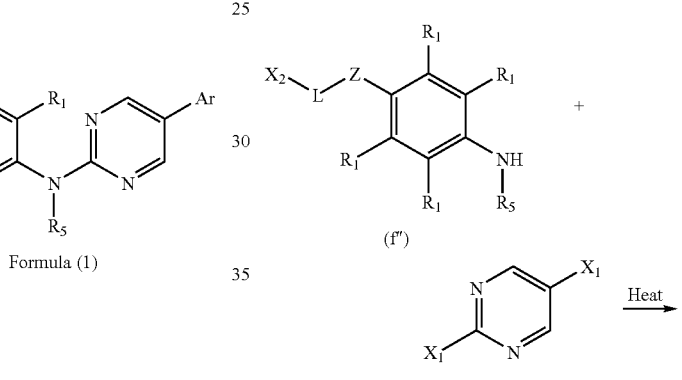

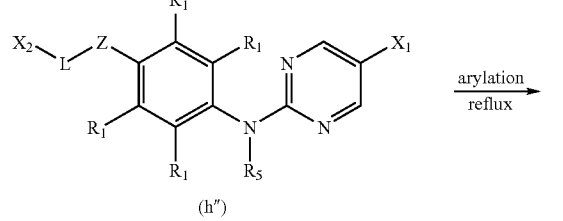

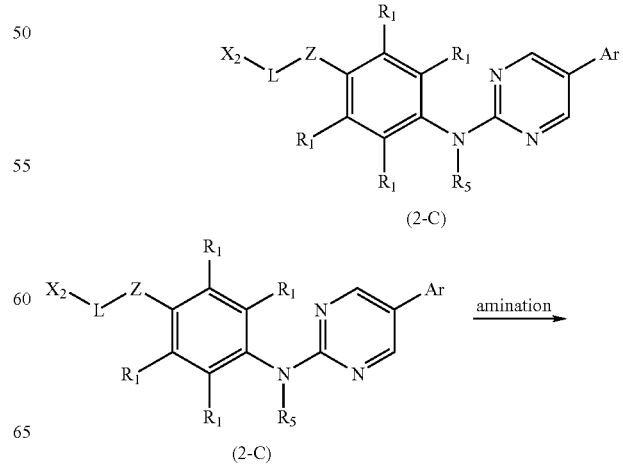

-continued

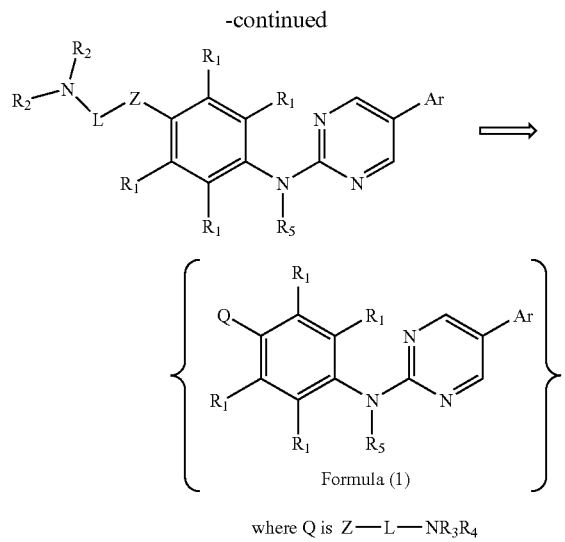

where: each $X_1$ is independently any halogen;
$X_2$ is any halogen, OMes, or OTos wherein, Z is $CR_1R_1$, O, or S, and L is alkylene (substituted or unsubstituted), alkenylene (substituted or unsubstituted), heteroalkylene (substituted or unsubstituted), or heteroalkenylene (substituted or unsubstituted).

Alternatively, compounds of Formula (1) can be synthesized according to reaction scheme 2d, wherein halogen compounds (d") react with amine compounds (E) to give diaryl compounds (c"). Arylation of compounds (c") yield compounds (1-D), and subsequent amination affords compounds of Formula (1).

Scheme 2d

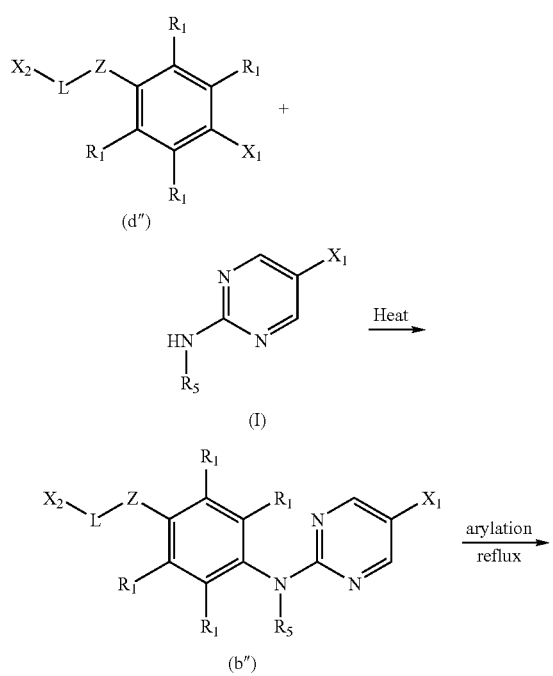

-continued

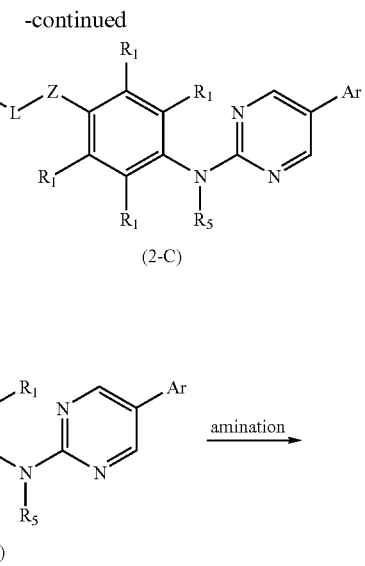

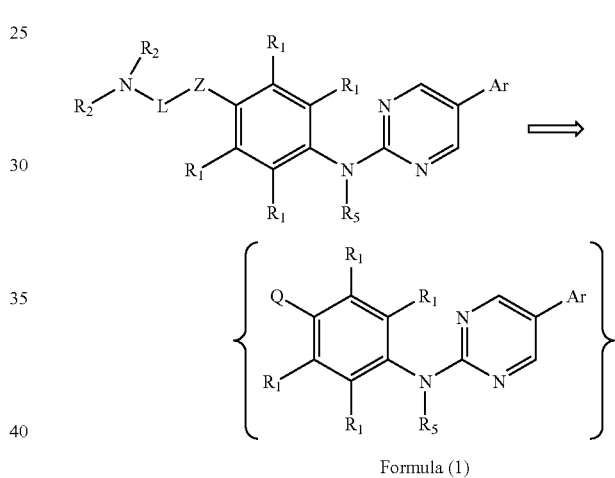

where: each $X_1$ is independently any halogen; $X_2$ is any halogen, OMes, or OTos where Q is Z-L-$NR_3R_4$ wherein, Z is $CR_1R_1$, O, or S, and L is alkylene (substituted or unsubstituted), alkenylene (substituted or unsubstituted), heteroalkylene (substituted or unsubstituted), or heteroalkenylene (substituted or unsubstituted).

Alternatively, compounds of Formula (1) can be synthesized according to reaction scheme 2e, wherein dihalogen compounds (B) are arylated to give compounds (b"), which react with substituted amine compounds (F) to yield compounds of Formula (1).

Scheme 2e

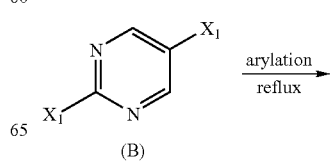

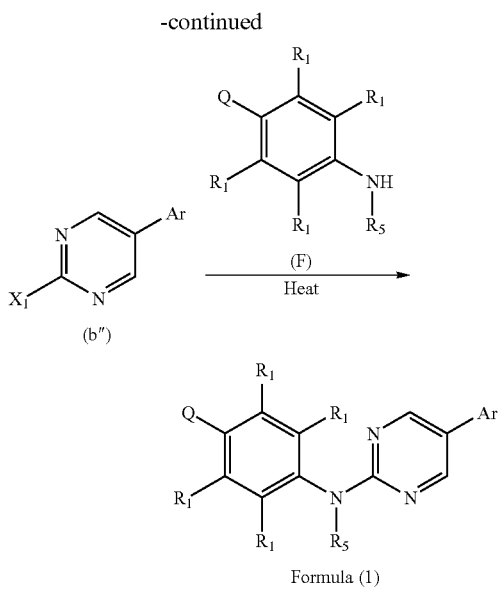

Formula (1)

where each $X_1$ is independently any halogen

Arylation, by way of example only, may be accomplished by reaction of the halogen functionality with an aryl derivatized boronic acid in the presence of tetrakis(triphenylphosphino) palladium.

Alternatively, compounds of Formula (1) can be synthesized according to reaction scheme 2f, wherein compounds (1) are arylated to give compounds (i″). Compounds (i″) are then reacted with amine compounds (D) to yield compounds of Formula (1).

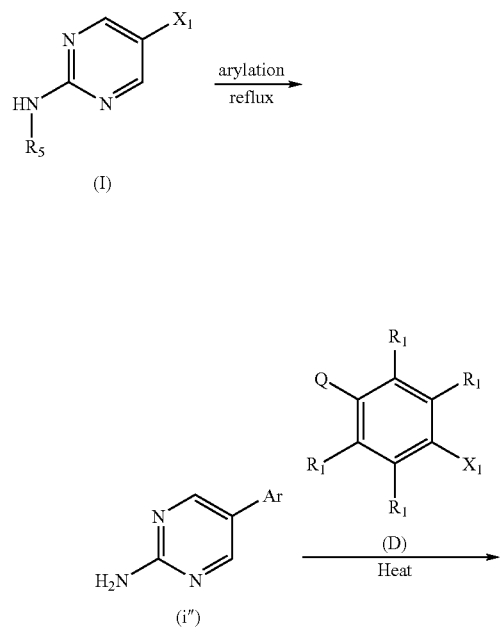

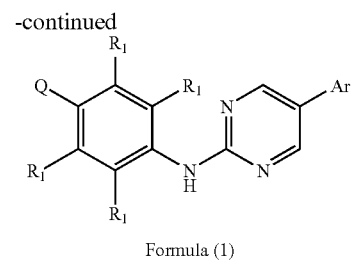

Formula (1)

where each $X_1$ is independently any halogen

Arylation, by way of example only, may be accomplished by reaction of the halogen functionality with an aryl derivatized boronic acid in the presence of tetrakis(triphenylphosphino) palladium.

Alternatively, compounds of Formula (1) can be synthesized according to reaction scheme 2g, wherein dihalogen compounds (B) are arylated giving compounds (b″), which then react with amine compounds (f″) to give compounds (2-C). Subsequent amination of compounds (2-C) affords compounds of Formula (1).

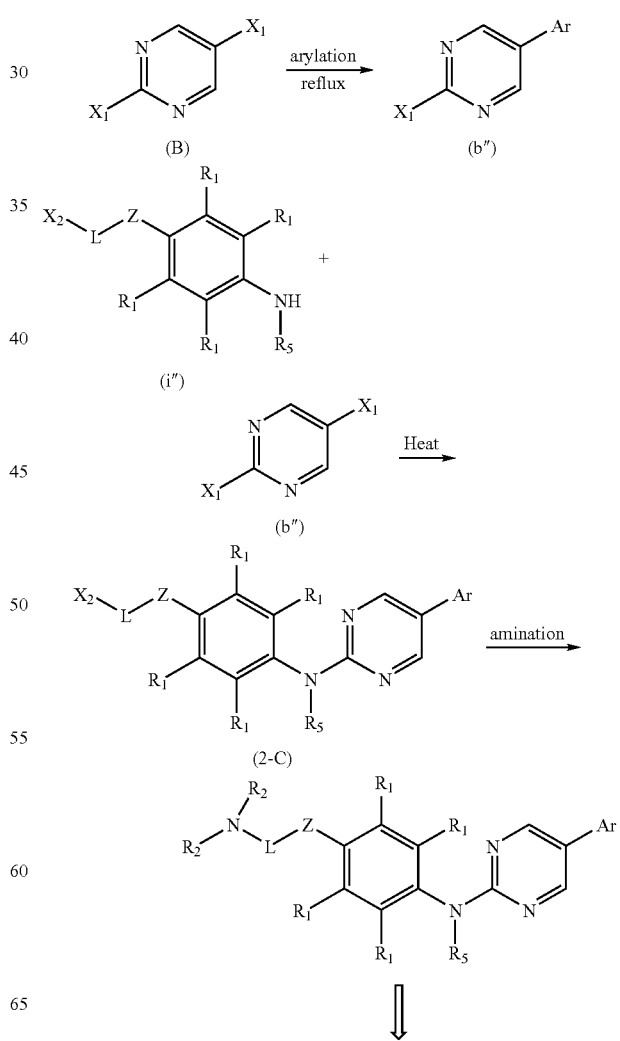

-continued

Formula (1)

where: each $X_1$ is independently any halogen; $X_2$ is any halogen, OMes, or OTos where Q is Z-L-$NR_3R_4$ wherein, Z is $CR_1R_1$, O, or S, and L is alkylene (substituted or unsubstituted), alkenylene (substituted or unsubstituted), heteroalkylene (substituted or unsubstituted), or heteroalkenylene (substituted or unsubstituted). Arylation, by way of example only, may be accomplished by reaction of the halogen functionality with an aryl derivatized boronic acid in the presence of tetrakis(triphenylphosphino) palladium. Amination, by way of example only, may be accomplished by reaction of the halogen functionality with an appropriate amine.

Alternatively, compounds of Formula (1) can be synthesized according to reaction scheme 2h, wherein halogen compounds (1) are arylated giving compounds (i″), which then react with amine compounds (d″) to give compounds (2-C). Subsequent amination of compounds (2-C) affords compounds of Formula (1).

Scheme 2h

-continued

Formula (1)

where: each $X_1$ is independently any halogen; $X_2$ is any halogen, OMes, or OTos where Q is Z-L-$NR_3R_4$ wherein, Z is $CR_1R_1$, O, or S, and L is alkylene (substituted or unsubstituted), alkenylene (substituted or unsubstituted), heteroalkylene (substituted or unsubstituted), or heteroalkenylene (substituted or unsubstituted). Arylation, by way of example only, may be accomplished by reaction of the halogen functionality with an aryl derivatized boronic acid in the presence of tetrakis(triphenylphosphino) palladium. Amination, by way of example only, may be accomplished by reaction of the halogen functionality with an appropriate amine.

The synthesis of amine compounds (A), compounds (a″), compounds (F) and compounds (f″) may be accomplished according to reaction schemes and methodologies known to one skilled in the art used to obtain amine containing compounds. By way of example only, a synthesis of amine compounds (A) is shown in reaction scheme 3a, wherein formation of para-substituted nitrobenzenes results from the addition of halogen containing compounds with reactive nitrobenzenes. Subsequent reduction of such para-substituted nitrobenzene compounds affords amine compounds (A).

Scheme 3a

-continued

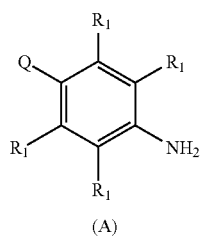

(A)

where Q is Y-L-Z where: Z is O or S; X is halogen; Y is a tertiary amine wherein L is alkylene (substituted or unsubstituted), alkenylene (substituted or unsubstituted), heteroalkylene (substituted or unsubstituted), or heteroalkenylene (substituted or unsubstituted). Reduction, by way of example only, may be accomplished using hydrogen with palladium on carbon as a catalyst.

By way of example only, a synthesis of amine compounds (a″) is shown in reaction scheme 3b, wherein formation of para-substituted nitrobenzene compounds containing terminal halogens results from the addition of di-halogen containing compounds with reactive nitrobenzenes. Subsequent reduction of such para-substituted nitrobenzene compounds affords compounds (a″).

Scheme 3b

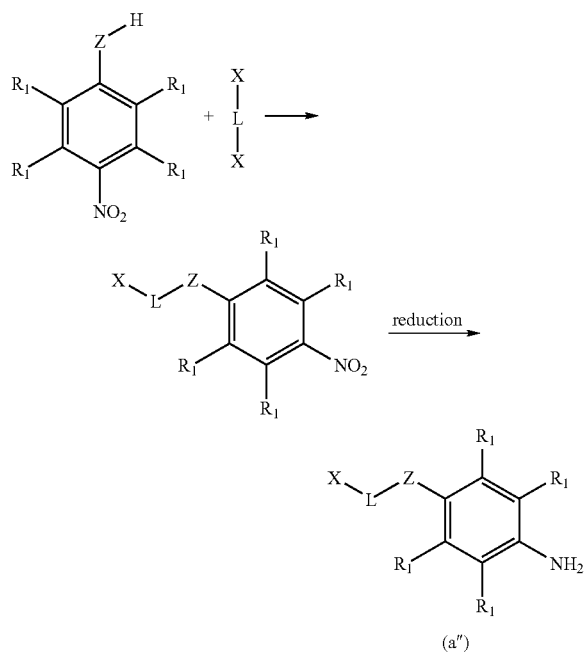

(a″)

where: Z is O or S; X is halogen wherein L is alkylene (substituted or unsubstituted), alkenylene (substituted or unsubstituted), heteroalkylene (substituted or unsubstituted), or heteroalkenylene (substituted or unsubstituted).

By way of example only, a synthesis of amine compounds (A) is shown in reaction scheme 3c, wherein formation of para-substituted protected anilines results from the addition of halogen containing compounds with reactive protected anilines. Subsequent deprotection of such para-substituted protected anilines compounds affords amine compounds (A).

Scheme 3c

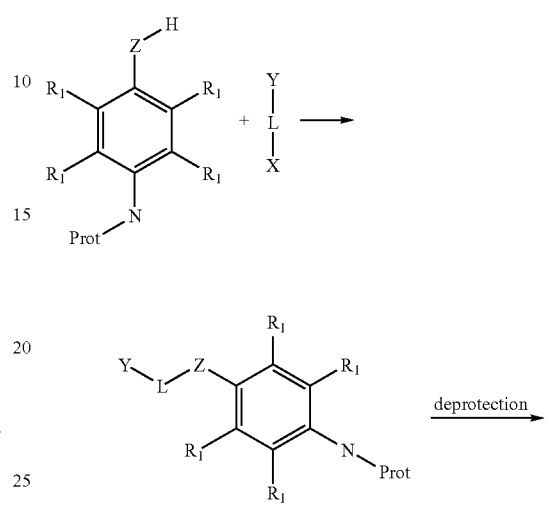

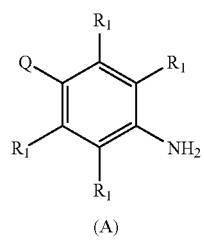

(A)

where: Z is O or S; X is halogen; Y is a tertiary amine; Prot is any amine protecting group where Q is Y-L-Z wherein L is alkylene (substituted or unsubstituted), alkenylene (substituted or unsubstituted), heteroalkylene (substituted or unsubstituted), or heteroalkenylene (substituted or unsubstituted).

By way of example only, a synthesis of amine compounds (F) is shown in reaction scheme 3d, wherein formation of para-substituted nitrobenzenes results from the addition of halogen containing compounds with a reactive nitrobenzene. Reduction of such para-substituted nitrobenzene compounds affords amine compounds (A) and subsequent alkylation of the yields substituted amine compounds (F).

Scheme 3d

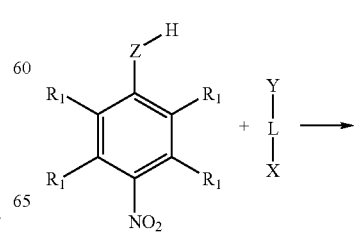

-continued

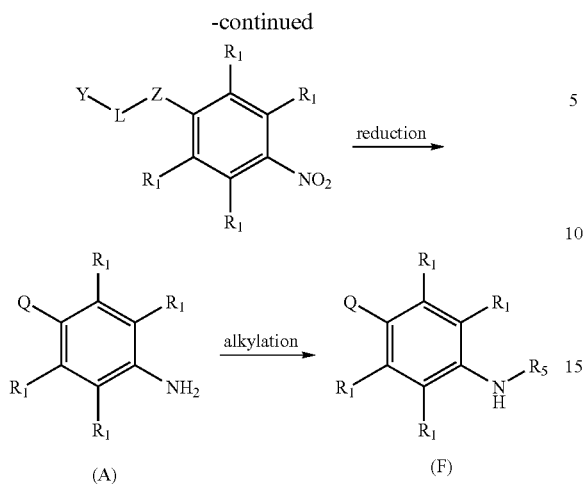

(A)  (F)

wher: Z is O or S; X is halogen; Y is a tertiary amine
where Q is Y-L-Z wherein L is alkylene (substituted or unsubstituted), alkenylene (substituted or unsubstituted), heteroalkylene (substituted or unsubstituted), or heteroalkenylene (substituted or unsubstituted).

By way of example only, a synthesis of amine compounds (f″) is shown in reaction scheme 3e, wherein formation of para-substituted nitrobenzenes compounds containing terminal halogens results from the addition of di-halogen containing compounds with a reactive nitrobenzene. Reduction of such para-substituted nitrobenzene compounds affords compounds (a″) and subsequent alkylation of the yields substituted amine compounds (f″).

Scheme 3e

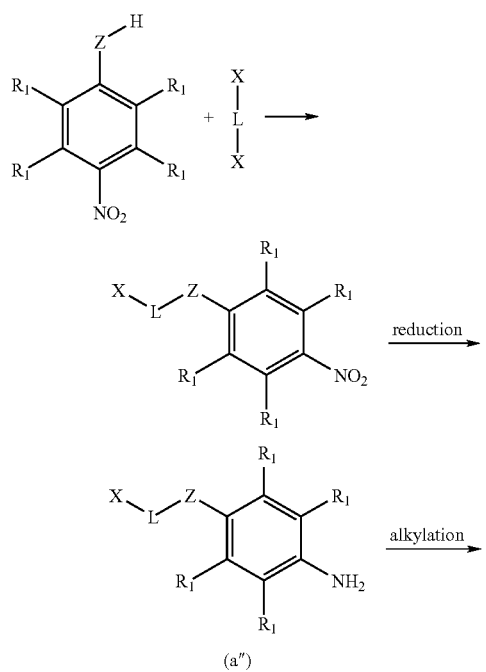

(a″)

-continued

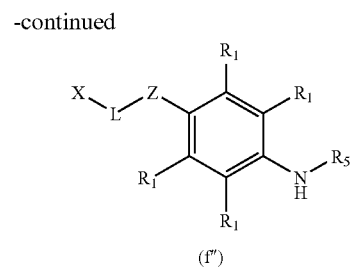

(f″)

wher: Z is O or S; X is halogen; Y is a tertiary amine wherein L is alkylene (substituted or unsubstituted), alkenylene (substituted or unsubstituted), heteroalkylene (substituted or unsubstituted), or heteroalkenylene (substituted or unsubstituted).

The pyrimidine compounds (B), compounds (E) and compounds (1) may be synthesized according to reaction schemes and methodologies known to one skilled in the art, or alternatively they may be purchased. By way of example only, various pyrimidine compounds may be obtained using Pinner Pyrimidine Synthesis as shown in reaction scheme 4a, Scheme 4a

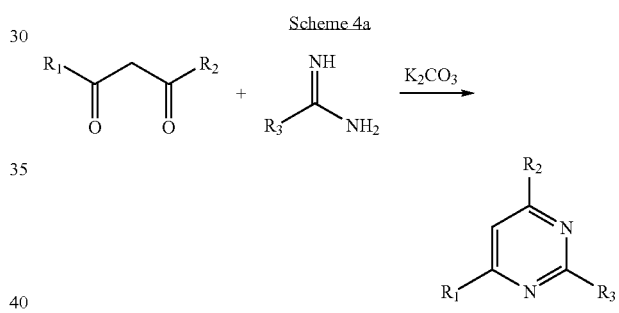

wherein $R_1$ and $R_2$ are independently selected from H, halogen, alkyl, heteroalkyl, cycloalkyl, heterocyloalkyl, aryl and heteroaryl; $R_3$ is $NH_2$, SH, alkyl, or halogen, or the N—C—N type reagent may be urea. This approach may be used in the synthesis of amine compounds (E) as shown in reaction scheme 4b Scheme 4b

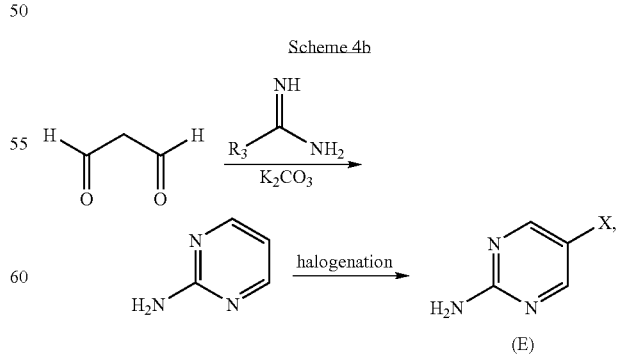

(E)

and the approach may be used to synthesize 2-amino-5-bromopyrimidine as shown in reaction scheme 4c;

Scheme 4c

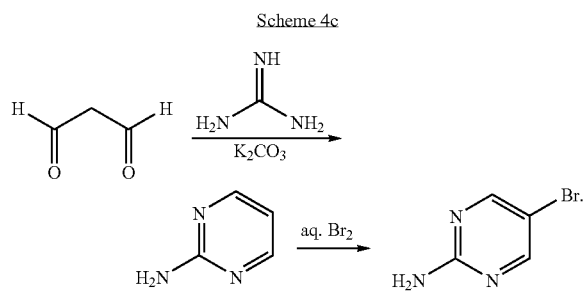

Similarly, amine compounds (1) may be synthesized as shown in reaction scheme 4d and reaction scheme 4e,

Scheme 4d

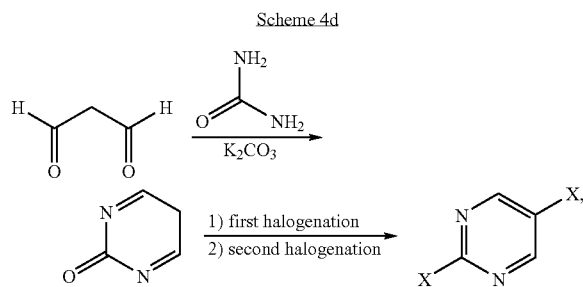

and to synthesize 2-chloro-5-bromopyrimidine as shown in reaction scheme 4c;

Scheme 4e

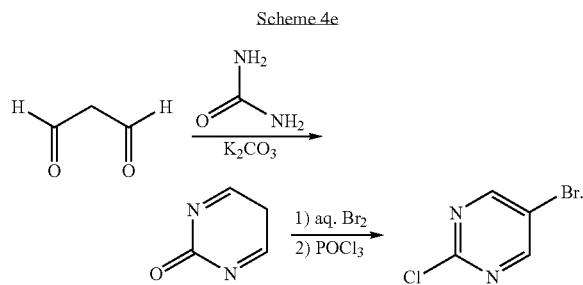

Further Forms of Compounds

For convenience, the form and other characteristics of the compounds described in this section and other parts herein use a single formula, such as "Formula (A) or Formula (B)," by way of example. However, the form and other characteristics of the compounds described herein apply equally well to all formulas presented herein that fall within the scope of Formula (A) or Formula (B). For example, the form and other characteristics of the compounds described herein can be applied to compounds having the structure of any of Formula (1) to Formula (54), as well as to all of the specific compounds that fall within the scope of these generic formula.

Compounds of Formula (A) or Formula (B) can be prepared as a pharmaceutically acceptable salts formed when an acidic proton present in the parent compound either is replaced by a metal ion, for example an alkali metal ion, an alkaline earth ion, or an aluminum ion; or coordinates with an organic base. In addition, the salt forms of the disclosed compounds can be prepared using salts of the starting materials or intermediates.

Compounds of Formula (A) or Formula (B) can be prepared as a pharmaceutically acceptable acid addition salt (which is a type of a pharmaceutically acceptable salt) by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, Q-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

Alternatively, compounds of Formula (A) or Formula (B) can be prepared as a pharmaceutically acceptable base addition salts (which is a type of a pharmaceutically acceptable salt) by reacting the free acid form of the compound with a pharmaceutically acceptable inorganic or organic base, including, but not limited to organic bases such as ethanolamine, diethanolamine, triethanolamine, tromethamine, N-methylglucamine, and the like and inorganic bases such as aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds of Formula (A) or Formula (B) can be conveniently prepared or formed during the processes described herein. By way of example only, hydrates of compounds of Formula (A) or Formula (B) can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Compounds of Formula (A) or Formula (B) include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Compounds of Formula (A) or Formula (B) in unoxidized form can be prepared from N-oxides of compounds of Formula (A) or Formula (B) by treating with a reducing agent, such as, but not limited to, sulfur, sulfur dioxide, triphenyl phosphine, lithium borohydride, sodium borohydride, phosphorus trichloride, tribromide, or the like in a suitable inert organic solvent, such as, but not limited to, acetonitrile, ethanol, aqueous dioxane, or the like at 0 to 80° C.

Compounds of Formula (A) or Formula (B) can be prepared as prodrugs. Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of Formula (A) or Formula (B) which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

Prodrugs may be designed as reversible drug derivatives, for use as modifiers to enhance drug transport to site-specific tissues. The design of prodrugs to date has been to increase the effective water solubility of the therapeutic compound for targeting to regions where water is the principal solvent. See, e.g., Fedorak et al., *Am. J. Physiol.*, 269:G210-218 (1995); McLoed et al., *Gastroenterol*, 106:405-413 (1994); Hochhaus et al., *Biomed. Chrom.*, 6:283-286 (1992); J. Larsen and H. Bundgaard, *Int. J. Pharmaceutics*, 37, 87 (1987); J. Larsen et al., *Int. J. Pharmaceutics*, 47, 103 (1988); Sinkula et al., *J. Pharm. Sci.*, 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987, all incorporated herein in their entirety.

Additionally, prodrug derivatives of compounds of Formula (A) or Formula (B) can be prepared by methods known to those of ordinary skill in the art (e.g., for further details see Saulnier et al., (1994), Bioorganic and Medicinal Chemistry Letters, Vol. 4, p. 1985). By way of example only, appropriate prodrugs can be prepared by reacting a non-derivatized compound of Formula (A) or Formula (B) with a suitable carbamylating agent, such as, but not limited to, 1,1-acyloxyalkylcarbanochloridate, para-nitrophenyl carbonate, or the like. Prodrug forms of the herein described compounds, wherein the prodrug is metabolized in vivo to produce a derivative as set forth herein are included within the scope of the claims. Indeed, some of the herein-described compounds may be a prodrug for another derivative or active compound.

Sites on the aromatic ring portion of compounds of Formula (A) or Formula (B) can be susceptible to various metabolic reactions, therefore incorporation of appropriate substituents on the aromatic ring structures, such as, by way of example only, halogens can reduce, minimize or eliminate this metabolic pathway.

Compounds of Formula (A) or Formula (B) can be optically pure enantiomers or a racemic mixture. Compounds of Formula (A) or Formula (B) can be prepared as their individual stereoisomers by reacting a racemix mixture of the compound with an optically active resolving agent to form a pair of diastereoisomeric compounds, separating the diastereomers and recovering the optically pure enentiomers.

The compounds described herein may be labeled isotopically (e.g. with a radioisotope) or by another other means, including, but not limited to, the use of chromophores or fluorescent moieties, bioluminescent labels, or chemiluminescent labels. The compounds of Formula (A) or Formula (B) may possess one or more chiral centers and each center may exist in the R or S configuration. The compounds presented herein include all diastereomeric, enantiomeric, and epimeric forms as well as the appropriate mixtures thereof. Compounds of Formula (A) or Formula (B) can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds described herein, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chiral chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions," John Wiley And Sons, Inc., 1981, herein incorporated by reference in its entirety.

Additionally, the compounds and methods provided herein may exist as geometric isomers. The compounds and methods provided herein include all cis, trans, syn, anti, entgegen (E), and zusammen (Z) isomers as well as the appropriate mixtures thereof. In some situations, compounds may exist as tautomers. All tautomers are included within the formulas described herein are provided by compounds and methods herein. In additional embodiments of the compounds and methods provided herein, mixtures of enantiomers and/or diastereoisomers, resulting from a single preparative step, combination, or interconversion may also be useful for the applications described herein.

Pharmaceutical Composition/Formulation/Administration

For convenience, the form and other characteristics of the compounds described in this section and other parts herein use a single formula, such as "Formula (A) or Formula (B)," by way of example. However, the form and other characteristics of the compounds described herein apply equally well to all formulas presented herein that fall within the scope of Formula (A) or Formula (B). For example, the form and other characteristics of the compounds described herein can be applied to compounds having the structure of any of Formula (1) to Formula (54), as well as to all of the specific compounds that fall within the scope of these generic formulas.

A pharmaceutical composition, as used herein, refers to a mixture of at least one compound of Formula (A) or Formula (B) with other chemical components, such as carriers, stabilizers, diluents, dispersing agents, suspending agents, thickening agents, and/or excipients. The pharmaceutical composition facilitates administration of the compound to an organism. Pharmaceutical compositions containing compounds of Formula (A) or Formula (B) can be administered in therapeutically effective amounts as pharmaceutical compositions by any conventional form and route known in the art including, but not limited to: intravenous, oral, rectal, aerosol, parenteral, ophthalmic, pulmonary, transdermal, vaginal, otic, nasal, and topical administration.

One may administer the compound in a local rather than systemic manner, for example, via injection of the compound directly into an organ, often in a depot or sustained release formulation. Furthermore, one may administer pharmaceutical composition containing compounds of Formula (A) or Formula (B) in a targeted drug delivery system, for example, in a liposome coated with organ-specific antibody. The liposomes will be targeted to and taken up selectively by the organ. In addition, the pharmaceutical composition containing compounds of Formula (A) or Formula (B) may be provided in the form of a rapid release formulation, in the form of an extended release formulation, or in the form of an intermediate release formulation.

For oral administration, compounds of Formula (A) or Formula (B) can be formulated readily by combining the active compounds with pharmaceutically acceptable carriers or excipients well known in the art. Such carriers enable the compounds described herein to be formulated as tablets, powders, pills, dragees, capsules, liquids, gels, syrups, elixirs, slurries, suspensions and the like, for oral ingestion by a patient to be treated.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal or sublingual administration, the compositions may take the form of tablets, lozenges, or gels formulated in conventional manner. Parental injections may involve for bolus injection or continuous infusion. The pharmaceutical composition of Formula (A) or Formula (B) may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds of Formula (A) or Formula (B) can be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

Formulations suitable for transdermal administration of compounds having the structure of Formula (A) or Formula (B) may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds of Formula (A) or Formula (B) can be accomplished by means of iontophoretic patches and the like. Additionally, transdermal patches can provide controlled delivery of the compounds Formula (A) or Formula (B). The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

For administration by inhalation, the compounds of Formula (A) or Formula (B) may be in a form as an aerosol, a mist or a powder. Pharmaceutical compositions of Formula (A) or Formula (B) are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, such as, by way of example only, gelatin for use in an inhaler or insufflator may be formulated containing a powder mix of the compound and a suitable powder base such as lactose or starch.

The compounds of Formula (A) or Formula (B) may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In practicing the methods of treatment or use provided herein, therapeutically effective amounts of compounds of Formula (A) or Formula (B) provided herein are administered in a pharmaceutical composition to a mammal having a disease or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

Pharmaceutical compositions may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. Pharmaceutical compositions comprising a compound of Formula (A) or Formula (B) may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one pharmaceutically acceptable carrier, diluent or excipient and a compound of Formula (A) or Formula (B) described herein as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds may exist as tautomers. All tautomers are included within the scope of the compounds presented herein. Additionally, the compounds described herein can exist in unsolvated as well as solvated forms with pharmaceutically acceptable solvents such as water, ethanol, and the like. The solvated forms of the compounds presented herein are also considered to be disclosed herein. In addition, the pharmaceutical compositions may include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions can also contain other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The compositions may be in liquid solutions or suspensions, solid forms suitable for solution or suspension in a liquid prior to use, or as emulsions. These compositions may also contain minor amounts of nontoxic, auxiliary substances, such as wetting or emulsifying agents, pH buffering agents, and so forth.

A summary of pharmaceutical compositions described herein may be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins 1999), herein incorporated by reference in their entirety.

Methods of Administration and Treatment Methods

For convenience, the form and other characteristics of the compounds described in this section and other parts herein use a single formula, such as "Formula (A) or Formula (B)," by way of example. However, the form and other characteristics of the compounds described herein apply equally well to all formulas presented herein that fall within the scope of Formula (A) or Formula (B). For example, the form and other characteristics of the compounds described herein can be applied to compounds having the structure of any of Formula (1) to Formula (54), as well as to all of the specific compounds that fall within the scope of these generic formulas.

The compounds of Formula (A) or Formula (B) can be used in the preparation of medicaments for the treatment of diseases or conditions in which c-kit receptor activity contributes to the pathology and/or symptomology of the disease. In addition, a method for treating any of the diseases or conditions described herein in a subject in need of such treatment, involves administration of pharmaceutical compositions containing at least one compound of Formula (A) or Formula (B), or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial).

Compositions containing the compound(s) described herein can be used to treat a disease-state or condition selected from: neoplastic diseases, including, but not limited to, mastocytosis, canine mastocytoma, human gastrointestinal stromal tumor, small cell lung cancer, non-small cell lung cancer, acute myelocytic leukemia, acute lymphocytic leukemia, myelodysplastic syndrome, chronic myelogenous leukemia, colorectal carcinomas, gastric carcinomas, gastrointestinal stromal tumors, testicular cancers, glioblastomas, and astrocytomas; allergic diseases, including, but not limited to, asthma, allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation and blood sucking parasitic infestation; inflammatory diseases including, but not limited to, rheumatoid arthritis, conjunctivitis, rheumatoid spondylitis, osteoarthritis, gouty arthritis and other arthritic conditions; autoimmune diseases, including, but not limited to, multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, dermatomyositis, polymyositis, Sjogren's syndrome, nodular panarteritis, autoimmune enteropathy, and proliferative glomerulonephritis; graft-versus-host disease, including, but not limited to, organ transplantation graft rejection, such as, but not limited to, kidney transplantation, pancreas transplantation, liver transplantation, heart transplantation, lung transplantation, or bone marrow transplantation; metabolic syndrome, including, but not limited to, type I diabetes, type II diabetes, or obesity; CNS related disorders, including, but not limited to, depression, dysthymic disorder, cyclothymic disorder, bipolar depression, severe or "melancholic" depression, atypical depression, refractory depression, seasonal depression, anorexia, bulimia, premenstrual syndrome and post-menopause syndrome, as mental slowing and loss of concentration, pessimistic worry, agitation, self-deprecation and decreased libido, as anxiety disorders including anxiety associated with hyperventilation and cardiac arrhythmias, phobic disorders, obsessive-compulsive disorder, posttraumatic stress disorder, acute stress disorder, and generalized anxiety disorder, as psychiatric disorders such as panic attacks, including psychosis, delusional disorders, conversion disorders, phobias, mania, delirium, dissociative episodes including dissociative amnesia, dissociative fugue and dissociative suicidal behavior, self-neglect, violent or aggressive behavior, trauma, borderline personality, and acute psychosis as schizophrenia including paranoid schizophrenia, disorganized schizophrenia, catatonic schizophrenia, and undifferentiated schizophrenia; neurodegenerative disease, including, but not limited to, Alzheimer's disease, Parkinson's disease, Huntington's disease, the prion diseases, Motor Neuron Disease (MND), and Amyotrophic Lateral Sclerosis (ALS); pain, including, but not limited to, acute pain, postoperative pain, chronic pain, nociceptive pain, cancer pain, neuropathic pain, and psychogenic pain syndromes; substance use disorders, including, but not limited to, drug addiction, drug abuse, drug habituation, drug dependence, withdrawal syndrome and overdose, prion diseases, cancers, heart diseases, fibrotic diseases, idiopathic pulmonary arterial hypertension (IPAH), and primary pulmonary hypertension (PPH); in a patient in need of such treatment, the method comprising administering to the patient an effective amount of a compound described herein, or a tautomer, prodrug, solvate, or salt thereof.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition. In the case wherein the patient's status does improve, upon the doctor's discretion the administration of the compounds may be given continuously or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disease or condition is retained. Patients can, however, require intermittent treatment on a long-term basis upon any recurrence of symptoms.

In certain instances, it may be appropriate to administer therapeutically effective amounts of at least one of the compounds described herein (or a pharmaceutically acceptable salts, pharmaceutically acceptable N-oxides, pharmaceutically active metabolites, pharmaceutically acceptable prodrugs, and pharmaceutically acceptable solvates thereof) in combination with another therapeutic agent. By way of example only, if one of the side effects experienced by a patient upon receiving one of the compounds herein is inflammation, then it may be appropriate to administer an anti-inflammatory agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. In any case, regardless of the disease or condition being treated, the overall benefit experienced by the patient may simply be additive of the two therapeutic agents or the patient may experience a synergistic benefit. For example, synergistic effects can occur with compounds of Formula (A) or Formula (B) and other substances used in the treatment of neoplastic disease, allergy disease, inflammatory disease, autoimmune disease, graft-versus-host disease, metabolic syndrome, CNS related disorders, neurodegenerative disease, pain, substance abuse disorders, prion diseases, cancers, heart diseases, fibrotic diseases, idiopathic pulmonary arterial hypertension (IPAH), or primary pulmonary hypertension (PPH). Examples of such bronchodilators, including, but not limited to, $\beta_2$-agonists, methylxanthines and anticholinerigcs; anti-inflammatory agents, including, but not limited to, corticosteroids and cromolyns, leukotriene antagonists, and IgE blockers, including but not limited to, omalizumab, also known as xolair. Where the compounds described herein are administered in conjunction with other therapies, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is one of the compounds described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; we envision the use of multiple therapeutic combinations.

In addition, the compounds of Formula (A) or Formula (B) may also be used in combination with procedures that may provide additional or synergistic benefit to the patient. By way of example only, patients are expected to find therapeutic and/or prophylactic benefit in the methods described herein, wherein pharmaceutical composition of Formula (A) or Formula (B) and/or combinations with other therapeutics are combined with genetic testing to determine whether that individual is a carrier of a mutant gene that is known to be correlated with certain diseases or conditions.

The compounds of Formula (A) or Formula (B) and combination therapies can be administered before, during or after the occurrence of a disease or condition, and the timing of administering the composition containing a compound can vary. Thus, for example, the compounds can be used as a prophylactic and can be administered continuously to subjects with a propensity to conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over 5 minutes to about 5 hours, a pill, a capsule, transdermal patch, buccal delivery, and the like, or combination thereof. A compound is preferably administered as soon as is practicable after the onset of a disease or condition is detected or suspected, and for a length of time necessary for the treatment of the disease, such as, for example, from about 1 month to about 3 months. The length of treatment can vary for each subject, and the length can be determined using the known criteria. For example, the compound or a formulation containing the compound can be administered for at least 2 weeks, preferably about 1 month to about 5 years, and more preferably from about 1 month to about 3 years.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The daily dosages appropriate for the compounds of Formula (A) or Formula (B) described herein are from about 0.03 to 2.5 mg/kg per body weight. An indicated daily dosage in the larger mammal, including, but not limited to, humans, is in the range from about 0.5 mg to about 100 mg, conveniently administered in divided doses, including, but not limited to, up to four times a day or in retard form. Suitable unit dosage forms for oral administration comprise from about 1 to 50 mg active ingredient. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, for determining the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Kits/Articles of Manufacture

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic.

For example, the container(s) can comprise one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically may comprise one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

ILLUSTRATIVE EXAMPLES

The following examples provide illustrative methods for making and testing the effectiveness and safety of the compounds of Formula (A) or Formula (B). These examples are provided for illustrative purposes only and not to limit the scope of the claims provided herein. All of the methods disclosed and claimed herein can be made and executed without undue experimentation in light of the present disclosure. It will be apparent to those of skill in the art that variations may be applied to the methods and in the steps or in the sequence of steps of the method described herein without departing from the concept, spirit and scope of the claims. All such similar substitutes and modifications apparent to those skilled in the art are deemed to be within the spirit, scope and concept of the appended claims.

Example 1

Synthesis of Substituted Nitro-benzene Compounds

Example 1a

Diethyl-[2-(4-nitro-phenoxy)-ethyl]-amine

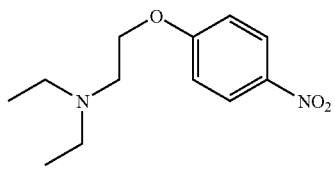

Diethyl-[2-(4-nitro-phenoxy)-ethyl]-amine can be synthesized by the following procedure. To a solution of 4-nitro-phenol (36.0 mmol) in toluene (40 mL) is added cesium carbonate (53.8 mmol) followed by (2-chloro-ethyl)-diethyl-amine hydrochloride (28.7 mmol) and the reaction mixture is heated at 100° C. for 2 h. The reaction mixture is cooled down and the solid is filtered under vacuum and washed with warm toluene. The filtrate is concentrated to afford 3.35 g of diethyl-[2-(4-nitro-phenoxy)-ethyl]-amine (39%) that is used in the next step without further purification. $^1$HNMR (400 MHz, CDC$_3$) δ 8.10-8.08 (m, 2H), 6.86-6.84 (m, 2H), 4.05 (t, J=4.0 Hz, 2H), 2.81 (t, J=4.0 Hz), 2.55 (q, J=8.0 Hz, 4H), 0.98 (t, J=8.0 Hz, 6H). MS (m/z) (M+1)$^+$ 230.3.

Example 1b

Diethyl-[2-(4-nitro-phenylsulfanyl)-ethyl]-amine

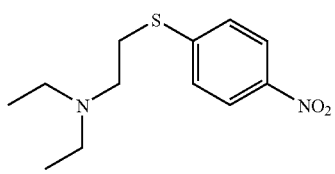

Diethyl-[2-(4-nitro-phenylsulfanyl)-ethyl]-amine can be synthesized by the following procedure. To a solution of 4-nitro-thiophenol (3.6.0 mmol) in toluene (40 mL) is added cesium carbonate (53.8 mmol) followed by (2-chloro-ethyl)-diethyl-amine hydrochloride (28.7 mmol). The reaction mixture is heated at 100° C. for 2 h. The reaction mixture is cooled down and the solid is filtered under vacuum and washed with warm toluene. The filtrate is concentrated to afford diethyl-[2-(4-nitro-phenylsulfanyl)-ethyl]-amine that is used in the next step without further purification. $^1$HNMR (400 MHz, CDCl$_3$) δ 8.23-8.11 (m, 2H), 7.35-7.33 (m, 2H), 3.13 (t, J=8.0 Hz, 2H), 2.77 (t, J=8.0 Hz, 2H), 2.60 (q, J=8.0 Hz, 4H), 1.05 (t, J=8.0 Hz, 6H). MS (m/z) (M+1)$^+$ 255.2.

Example 1c 1-(2-Chloro-ethoxy)-4-nitro-benzene

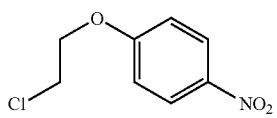

1-(2-Chloro-ethoxy)-4-nitro-benzene can be synthesized by the following procedure. To a solution of 4-nitro-phenol (28.7 mmol) in absolute ethanol (15 mL) is added cesium carbonate (28.7 mmol) followed by 1-bromo-2-chloro-ethane (86.2 mmol). The reaction mixture is heated at 80° C. for 8 h. The reaction mixture is cooled down and quenched with water and extracted with EtOAc. The organic layer is washed with water, brine, dried over Na$_2$SO$_4$, and concentrated to afford an orange residue that upon trituration with EtOH gives 1-(2-chloro-ethoxy)-4-nitro-benzene (66%). MS (m/z) (M+1)$^+$ 202.2.

Example 1d

4-[2-(4-Nitro-phenyl)-ethyl]-morpholine

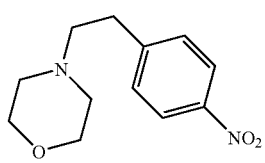

4-[2-(4-Nitro-phenyl)-ethyl]-morpholine can be synthesized by the following procedure. A solution of 1-(2-bromo-ethyl)-4-nitro-benzene (8.7 mmol) in anhydrous DMF (15 mL) and morpholine (17.3 mmol) is heated at 80° C. under a nitrogen atmosphere for 8 h. The reaction mixture is cooled down and quenched with water and extracted with EtOAc. The organic layer is washed with water, brine, dried over Na$_2$SO$_4$, and concentrated to afford 4-[2-(4-nitro-phenyl)-ethyl]-morpholine (93%) as a yellow oil. $^1$HNMR (400 MHz, CDCl$_3$) δ 8.15-8.13 (m, 2H), 7.38-7.36 (m, 2H), 6.86-6.84

(m, 2H), 3.75 (m, 4H), 2.91 (t, J=8.0 Hz, 2H), 2.65 (t, J=8.0 Hz, 4H), 2.55 (m, 4H). MS (m/z) (M+1)⁺ 237.2.

Example 1e

3-Nitrophenyl 4-methylpiperazine-1-carboxylate

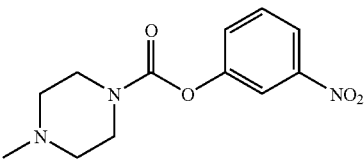

3-Nitrophenyl 4-methylpiperazine-1-carboxylate can be synthesized by the following procedure. A dry flask containing 3-nitro-phenol (28 mmol) and triphosgene (18.7 mmol) in 100 mL dichloromethane is cooled in an ice-water bath. Diisopropylethylamine (28 mmol) is slowly added. The reaction is stirred at rt for 2 h and then refluxed for another 2 h. The mixture is concentrated to dryness. The residue is dissolved in 100 mL of THF and triethylamine (40 mmol) and N-methylpiperazine (30 mmol) are added. The mixture is stirred overnight and concentrated. The residue is dissolved in dichloromethane and washed with 10% NaHCO₃. The organic layer is separated, dried over sodium sulfate, and concentrated. The crude product is used in the next step without further purification.

Example 1f

4-Nitrophenyl 4-methylpiperazine-1-carboxylate

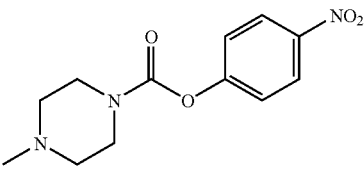

4-Nitrophenyl 4-methylpiperazine-1-carboxylate can be synthesized by the following procedure. A dry flask containing 4-nitro-phenol (28 mmol) and triphosgene (18.7 mmol) in 100 mL dichloromethane is cooled in an ice-water bath. Diisopropylethylamine (28 mmol) is slowly added. The reaction is stirred at rt for 2 h and then refluxed for another 2 h. The mixture is concentrated to dryness. The residue is dissolved in 100 mL of THF and triethylamine (40 mmol) and N-methylpiperazine (30 mmol) are added. The mixture is stirred overnight and concentrated. The residue is dissolved in dichloromethane and washed with 10% NaHCO₃. The organic layer is separated, dried over sodium sulfate, and concentrated. The crude product is used in the next step without further purification.

Examples 1g

Diethyl-[2-(3-nitro-phenoxy)-ethyl]-amine

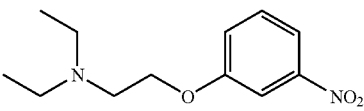

Diethyl-[2-(3-nitro-phenoxy)-ethyl]-amine can be synthesize by the following procedure. To a solution of 3-nitro-phenol (7.2 mmol) in anhydrous EtOH (20 mL), cesium carbonate (10.8 mmol) is added followed by (2-chloro-ethyl)-diethyl-amine hydrochloride (7.0 mmol) and the reaction mixture is refluxed for 12 h. The reaction mixture is cooled down and the solid filtered under vacuum and washed with warm EtOH. The filtrate is concentrated, dissolved in DCM (50 mL), washed with water, brine, dried over Na₂SO₄, and concentrated to afford 1.45 g of the title compound (84%) that is used without further purification. ¹HNMR (400 MHz, CDCl₃) δ 7.82-8.80 (m, 1H), 7.74-7.73 (m, 1H), 7.43-7.38 (m, 1H), 7.23-7.21 (m, 1H), 4.12 (dt, J=8.0 and 4.0 Hz, 2H), 2.91 (dt. J=8.0 and 4.0 Hz, 2H), 2.69-2.63 (m, 4H), 1.11-1.06 (m, 6H). MS (m/z) (M+1)⁺ 239.2.

Examples 1h

2-Hydroxy-4-nitro-benzoic acid methyl ester

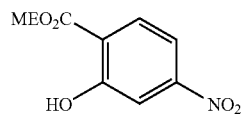

2-Hydroxy-4-nitro-benzoic acid methyl ester can be synthesized by the following procedure. To a suspension of 2-hydroxy-4-nitro-benzoic acid (5.4 mmol) in anhydrous ACN (20 mL), 1,8-diazabicyclo[5.4.0]undec-7-ene (5.4 mmol) is added drop wise followed by methyl iodide (5.4 mmol). The reaction is stirred at rt for 1 h. The solvent is removed under reduced pressure and the yellow residue is dissolved in DCM (50 mL) washed with 2N HCl (2×20 mL), 5% Na₂CO₃ (2×30 mL), brine, dried over Na₂SO₄ and concentrated to afford 2-hydroxy-4-nitro-benzoic acid methyl ester as a pale yellow solid (84%). MS (m/z) (M+1)⁺ 198.1.

Example 1i 2-(2-Diethylamino-ethoxy)-4-[5-(4-methoxy-phenyl)-pyrimidin-2-ylamino]-benzoic acid methyl ester

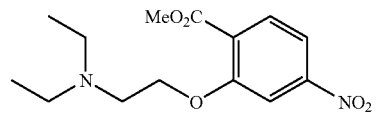

2-(2-Diethylamino-ethoxy)-4-[5-(4-methoxy-phenyl)-pyrimidin-2-ylamino]-benzoic acid methyl ester can be prepared by the following procedure. To a solution of 2-hydroxy-4-nitro-benzoic acid methyl ester (2.5 mmol) in DMF (10 mL), is added cesium carbonate (3.5 mmol) followed by (2-chloro-ethyl)-diethyl-amine hydrochloride (3.5 mmol). The reaction mixture is heated at 80° C. for 8 h. After this time the reaction is cooled down, diluted with water (50 mL) and extracted with EtOAc (3×30 mL). The combined organic layer is washed with water (2×20 mL), brine, dried over Na₂SO₄ and concentrated to afford 2-(2-diethylamino-ethoxy)-4-[5-(4-methoxy-phenyl)-pyrimidin-2-ylamino]-benzoic acid methyl ester (69%) as a yellow oil that is used without further purification. ¹HNMR (400 MHz, DMSO) δ 7.48 (d, J=8 Hz, 1H), 6.20-6.19 (m, 1H), 6.14-6.12 (m, 1H), 5.88 (bs, 21), 3.92 (t, J=8.0 Hz, 2H), 3.64 (s, 3H), 2.77 (t, J=8.0 Hz, 2H), 2.56 (q, J=8.0 Hz, 4H), 10.97 (t, J=8.0 Hz, 6H). MS (m/z) (M+1)$^+$ 267.2.

Example 1j

3-Nitrophenethyl methanesulfonate

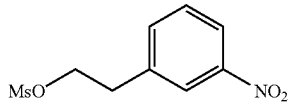

3-Nitrophenethyl methanesulfonate can be synthesized by the following procedure. To a solution of 2-(3-nitrophenyl)ethanol (17.9 mmol) and triethylamine (23.3 mmol) in DCM (50 mL), is added methanesulfonyl chloride (18.8 mmol) in DCM (10 mL) at 0° C. under a nitrogen atmosphere. After the addition is complete, the reaction is allowed to warm to rt and it is stirred for another 2 h. The solvent is removed and the residue is dissolved in DCM (100 mL). The organic layer is washed with water, dried over Na$_2$SO$_4$ and concentrated to afford 3-nitrophenethyl methanesulfonate (98%) that is used without further purification. MS (m/z) (M+1)$^+$ 246.2.

Example 1k

N,N-Diethyl-2-(3-nitrophenyl)ethanamine

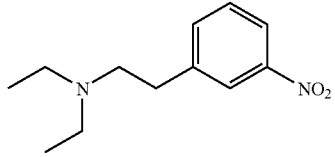

N,N-diethyl-2-(3-nitrophenyl)ethanamine can be prepared by the following procedure. A mixture of diethyl amine (9.0 mmol) and K$_2$CO$_3$ (9.9 mmol) in ACN (50 mL) is refluxed for 1 h under nitrogen atmosphere. To the above mixture, a solution of 3-nitrophenethyl methanesulfonate (8.2 mmol) in ACN (10 mL) is added and the mixture is refluxed for 1 h. The solvent is removed and the residue is dissolved in DCM (100 mL). The organic layer is washed with water, dried over Na$_2$SO$_4$ and concentrated to afford a residue which is purified by silica gel column chromatography (EtOAc:hexane=30:70) to afford N,N-diethyl-2-(3-nitrophenyl)ethanamine (75%). $^1$HNMR (400 MHz, CDCl$_3$) δ 8.04-8.10 (m, 2H), 7.51-7.55 (d, J=7.6 Hz, 1H), 7.43 (t, J=7.8 Hz, 1H), 2.81-2.88 (m, 2H), 2.67-2.74 (m, 2H), 2.59 (q, J=7.2 Hz, 4H), 1.04 (t, J=7.2 Hz, 6H). MS (m/z) (M+1)$^+$ 223.2.

Example 1l 3-nitrobenzyl 4-methylpiperazine-1-carboxylate

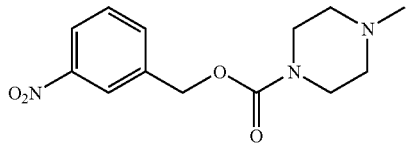

3-nitrobenzyl 4-methylpiperazine-1-carboxylate can be synthesized by the following procedure. To a suspension of NaH (60% weight in mineral oil, 12.0 mmol) in THF (20 mL), is added (3-nitrophenyl)methanol (8.0 mmol) slowly. The reaction mixture is stirred at rt for 5 min. A solution of 4-methylpiperazine-1-carbonyl chloride (10.0 mmol) in THF (5 mL) is added to the above reaction mixture and stirred for 3 h. Upon reaction completion, H$_2$O (1 mL) is added to quench the reaction. The solvent is removed and the residue is dissolved in EtOAc (100 mL). The organic layer is washed with water, dried over Na$_2$SO$_4$ and concentrated to afford a residue which is purified by silica gel column chromatography (EtOAc:hexane=30:70) to afford 3-nitrobenzyl 4-methylpiperazine-1-carboxylate (80%). $^1$HNMR (400 MHz, CDCl$_3$) δ 8.20 (s, 1H), 8.15 (d, J=7.8 Hz, 1H), 7.67 (d, J=7.8 Hz, 1H), 7.53 (t, J=7.8 Hz, 1H), 5.20 (s, 2H), 3.50-3.55 (m, 4H), 2.29 (s, 3H). MS (m/z) (M+1)$^+$ 280.2.

Example 1m 2-(methoxycarbonyl)-5-nitrophenyl 4-methylpiperazine-1-carboxylate

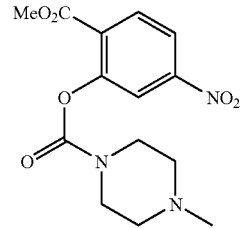

To a dry flask are added 2-hydroxy-4-nitro-benzoic acid methyl ester (40 mmol) (from Example 1h) and triphosgene (26.6 mmol) and DCM (100 mL). The reaction mixture is cooled to 0° C. and diisopropylethylamine (40 mmol) is added slowly. After addition the mixture is warmed to rt. After 1 h at this temperature it is refluxed for 1 h. The mixture is cooled down and the solvents are removed. THF (100 mL), Et$_3$N (80 mmol), and N-methyl piperazine (80 mmol) are added and the mixture is stirred at rt overnight. The solvent is removed and the residue dissolved in EtOAc. Phases are separated upon addition of a 10% solution of NaHCO$_3$. The organic phase is washed with brine, dried on Na$_2$SO$_4$ and evaporated. The crude is used in the following reaction.

Example 1n 2-(2-Diethylamino-ethoxy)-5-nitro-benzoic acid ethyl ester

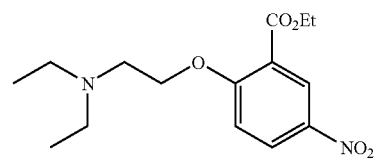

2-(2-Diethylamino-ethoxy)-5-nitro-benzoic acid ethyl ester can be synthesized by the following procedure. A solution of methyl 5-nitrosalicylate (7.61 mmol) in anhydrous EtOH (20 mL) is treated with Cs$_2$CO$_3$ (11.4 mmol) and (2-chloro-ethyl)-diethyl-amine hydrochloride (7.61 mmol). The reaction mixture is stirred at 80° C. for 4 h, then the solvent is removed and the thick oil residue is purified by HPLC (ACN gradient 10-90%) to afford the title compounds (25%). $^1$HNMR (400 MHz, DMSO) δ 9.58 (b.s. 1H), 8.53-8.54 (m, 1H), 8.50-8.47 (m, 1H), 4.58-4.57 (m, 2H), 4.31 (q, J=8.0 Hz, 2H), 3.61-3.60 (m, 2H), 3.32-3.27 (m, 4H), 1.33 (t, J=8.0 Hz, 3H), 1.24 (t, J=8.0 Hz, 6H); MS (m/z) (M+1)$^+$ 311.1.

Example 2

Synthesis of Substituted Aniline Compounds

Example 2a 4-(2-Diethylamino-ethoxy)-phenylamine

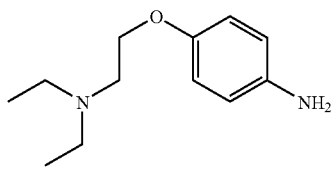

4-(2-Diethylamino-ethoxy)-phenylamine can be synthesized by the following procedure. To a solution of diethyl-[2-(4-nitro-phenoxy)-ethyl]-amine (14.0 mmol) (from Example 1a) in MeOH (20 mL), in a Parr pressure bottle, is added Pd (10% on carbon, 50% wet, 10% weight,). The suspension is shaken at 50 psi of H$_2$ for 2 h. The reaction mixture is filtered through celite. The solvent is removed and the residue is dissolved in MeOH (20 mL) and treated with HCl (1 eq of a 4N solution in dioxane) to afford the 4-(2-diethylamino-ethoxy)-phenylamine as hydrochloride salt (99%). $^1$HNMR (400 MHz, DMSO) δ 6.98-6.91 (m, 4H), 4.30 (t, J=4.0 Hz, 2H), 3.47 (t, J=4.0 Hz), 3.20 (m, 4H), 1.24 (t, J=8.0 Hz, 6H). MS (m/z) (M+1)$^+$ 209.3.

Example 2b 4-(2-Diethylamino-ethylsulfanyl)-phenylamine

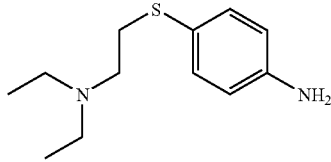

4-(2-Diethylamino-ethylsulfanyl)-phenylamine can be synthesized by the following procedure. A suspension of diethyl-[2-(4-nitro-phenylsulfanyl)-ethyl]-amine (3.9 mmol) (from Example 1b) and SnCl$_2$2H$_2$O (15.7 mmol) in absolute ethanol (30 mL) is heated at 70° C. for 2 h. The solvent is removed under vacuum and the residue is dissolved in 5% NaOH and extracted with EtOAc (3×50 mL). The organic layer is washed with 5% NaOH (1×50 mL), water (1×50 mL), brine, dried over Na$_2$SO$_4$ and concentrated to afford 4-(2-diethylamino-ethylsulfanyl)-phenylamine (91%). $^1$HNMR (400 MHz, CDCl$_3$) δ 8.23-8.11 (m, 2H), 7.35-7.33 (m, 2H), 3.13 (t, J=8.0 Hz, 2H), 2.77 (t, J=8.0 Hz, 2H), 2.60 (q, J=8.0 Hz, 4H), 1.05 (t, J=8.0 Hz, 6H). MS (m/z) (M+1)$^+$ 255.2.

Example 2c 4-(2-Chloro-ethoxy)-phenylamine

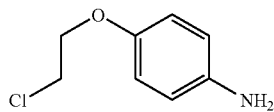

4-(2-Chloro-ethoxy)-phenylamine can be synthesized by the following procedure. A suspension of 1-(2-chloro-ethoxy)-4-nitro-benzene (1.5 mmol) (from Example 1c) and SnCl$_2$.2H$_2$O (5.9 mmol) in absolute ethanol (120 mL) is heated at 70° C. for 2 h. The solvent is removed under vacuum and the residue is dissolved in 5% NaOH and extracted with EtOAc (3×50 mL). The organic layer is washed with 5% NaOH (1×50 mL), water (1×50 mL), brine, and dried over Na$_2$SO$_4$ and reduced to dryness. The dark crude residue is purified by silica chromatography using a mixture of DCM:MeOH:NH$_4$OH=9:1:0.1 to isolate 4-(2-chloro-ethoxy)-phenylamine (90%) which is converted in the hydrochloride salt by treatment with HCl (1 eq of a 4N solution in dioxane). $^1$HNMR (400 MHz, CD$_3$OD) δ 7.35-7.33 (m, 2H), 7.16-7.05 (m, 2H), 4.38 (m, 2H), 3.87 (m, 2H). MS (m/z) (M+1)+173.1.

Example 2d 4-(2-Morpholin-4-yl-ethyl)-phenylamine

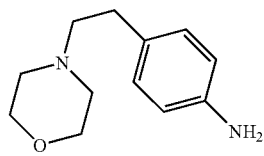

4-(2-Morpholin-4-yl-ethyl)-phenylamine can be synthesized by the following procedure. To a solution of 4-[2-(4-nitro-phenyl)-ethyl]-morpholine (14.0 mmol) (from Example 1d) in MeOH (20 mL), in a Parr pressure bottle, is added Pd (10% on carbon, 50% wet, 10% weight). The reaction mixture is shaken at 50 psi of H$_2$ for 2 h. The reaction mixture is filtered through celite. The solvent is removed to afford 4-(2-morpholin-4-yl-ethyl)-phenylamine. MS (m/z) (M+1)$^+$ 207.2.

Example 2e

3-Aminophenyl 4-methylpiperazine-1-carboxylate

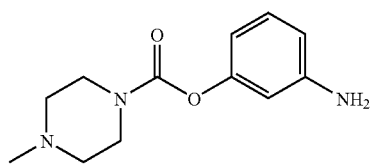

3-Aminophenyl 4-methylpiperazine-1-carboxylate can be synthesized with the following procedure. The crude 3-nitrophenyl 4-methylpiperazine-1-carboxylate (28 mmol) (from Example 1e) is dissolved in MeOH (100 mL) and added Pd (5% on carbon, 50% wet, 10% weight). The flask is charged with a hydrogen balloon and stirred overnight. The mixture is filtered through celite. The filtrate is concentrated and further purified by silica gel column chromatography (DCM:MeOH=30:70) to afford 3-aminophenyl 4-methylpiperazine-1-carboxylate (81%). $^1$HNMR (400 MHz, CDCl$_3$) δ 7.11 (m, 1H), 6.52-6.47 (m, 2H), 6.44 (s, 1H), 3.71 (br, 4H), 3.63 (br, 2H), 2.52 (br, 4H), 2.38 (s, 3H). MS (m/z) (M+1)$^+$ 236.1.

Example 2f 4-aminophenyl 4-methylpiperazine-1-carboxylate

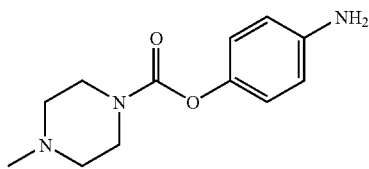

4-Aminophenyl 4-methylpiperazine-1-carboxylate can be synthesized with the following procedure. The crude 4-nitrophenyl 4-methylpiperazine-1-carboxylate (28 mmol) (from Example 1f) is dissolved in MeOH (100 mL) followed by addition of Pd (5% on carbon, 50% wet, 10% weight) The flask is charged with a hydrogen balloon for overnight stirring. The mixture is filtered through celite. The filtrate is concentrated and purified by silica gel column chromatography (DCM:MeOH=30:70) to afford the 4-methyl-piperazine-1-carboxylic acid 4-amino-phenyl ester (80%). $^1$HNMR (400 MHz, CDCl$_3$) δ 6.88 (d, J=7.8 Hz, 2H), 6.55 (d, J=7.8 Hz, 2H), 3.73 (br, 2H), 3.63 (br, 4H), 2.53 (br, 4H), 2.40 (s, 3H). MS (m/z) (M+1)$^+$ 236.1.

Example 2g 3-(2-Diethylamino-ethoxy)-phenylamine

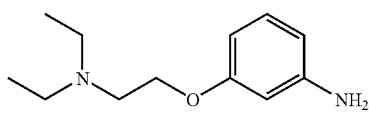

3-(2-Diethylamino-ethoxy)-phenylamine can be prepared by the following procedure. To a solution of diethyl-[2-(3-nitro-phenoxy)-ethyl]-amine (2.72 mmol) (from Example 1g) in EtOH (20 mL) is added SnCl$_2$.2H$_2$O (10.9 mmol). The suspension is refluxed for 2 h. After this time the solvent is removed under reduced pressure. The residue is dissolved in 5% NaOH (50 mL) and extracted with EtOAc (3×50 mL). The organic layer is washed once with 5% NaOH (20 mL), brine, dried over Na$_2$SO$_4$ and concentrated to afford the aniline as a brown oil (80%). MS (m/z) (M+1)$^+$ 209.1.

Example 2h

4-Amino-2-(2-diethylamino-ethoxy)-benzoic acid methyl ester

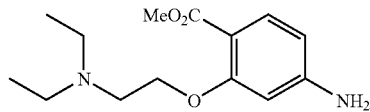

3-(2-Diethylamino-ethoxy)-phenyl-amine can be prepared by the following procedure. In a Parr pressure bottle, a solution of diethyl-[2-(3-nitro-phenoxy)-ethyl]-amine (2.72 mmol) (from Example 11) in MeOH (10 mL) is added Pd (5% on carbon, 50% wet, 10% weight). The suspension is shaken at 40 psi of H$_2$ for 2 h. The reaction is filtered through celite. The solvent is removed under reduced pressure to afford the title compound in quantitative yield. MS (m/z) (M+1)$^+$ 267.1.

Example 2i 3-(2-(diethylamino)ethyl)benzenamine

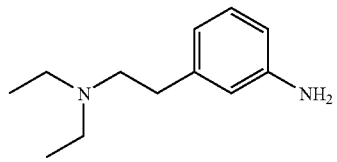

3-(2-(Diethylamino)ethyl)benzenamine can be synthesized by the following procedure. To a solution of N,N-diethyl-2-(3-nitrophenyl)ethanamine (12.2 mmol) (from Example 1k) in MeOH (40 mL) is added Pd (5% on carbon, 50% wet, 10% weight). The suspension is stirred under a balloon of H$_2$ for 2 h. The reaction is filtered through celite. The solvent is removed under reduced pressure to afford the title compound in quantitative yield. $^1$HNMR (400 MHz, CDCl$_3$) δ 7.04-7.09 (m, 1H), 6.58-6.61 (m, 1H), 6.50-6.54 (m, 2H), 3.62 (br, 2H), 2.65-2.70 (m, 4H), 2.61 (q, J=7.2 Hz, 4H), 1.07 (t. J=7.2 Hz, 6H). MS (m/z) (M+1)$^+$ 192.2.

Example 2j 3-aminobenzyl 4-methylpiperazine-1-carboxylate

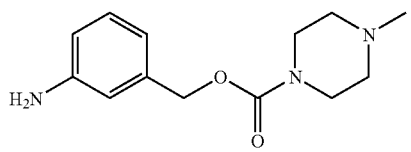

3-Aminobenzyl 4-methylpiperazine-1-carboxylate can be prepared by the following procedure. A suspension of 3-nitrobenzyl 4-methylpiperazine-1-carboxylate (1.5 mmol) (from Example 11) and SnCl$_2$.2H$_2$O (5.9 mmol) in absolute ethanol (120 mL) is heated at 80° C. for 2 h. The solvent is removed under vacuum and the residue is dissolved in 5% NaOH and extracted with EtOAc (3×50 mL). The organic layer is washed with 5% NaOH (1×50 mL), water (1×50 mL), brine, and dried over Na$_2$SO$_4$. The dark crude residue is purified by silica chromatography (DCM:MeOH=70:30) to afford 3-aminobenzyl 4-methylpiperazine-1-carboxylate (90%). $^1$HNMR (400 MHz, CDCl$_3$) δ 7.13 (t, J=7.7 Hz, 1H), 6.71-6.75 (m, 1H), 6.66-6.68 (m, 1H), 6.61-6.65 (m, 1H), 5.03 (s, 2H), 3.70 (br, 2H), 3.52 (t, J=5.0 Hz, 4H), 2.32-2.44 (m, 4H), 2.30 (s, 3H). MS (m/z) (M+1)$^+$ 250.2.

Example 2l 2-(Methoxycarbonyl)-5-aminophenyl 4-methylpiperazine-1-carboxylate

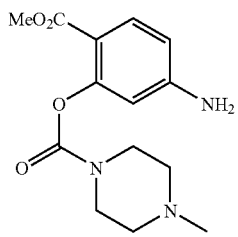

2-(Methoxycarbonyl)-5-aminophenyl 4-methylpiperazine-1-carboxylate can be prepared by the following procedure. The crude 2-(methoxycarbonyl)-5-nitrophenyl 4-methylpiperazine-1-carboxylate (30 mmol) (From Example 1m) is dissolved in MeOH (100 mL) followed by addition of Pd (5% on carbon, 50% wet, 10% weight). The flask is charged with a hydrogen balloon for overnight stirring. The mixture is filtered over celite. The filtrate is concentrated and further purified by silica gel column chromatography (DCM:MeOH=30:70) to afford 2-(methoxycarbonyl)-5-aminophenyl 4-methylpiperazine-1-carboxylate.

Example 2m

5-Amino-2-(2-diethylamino-ethoxy)-benzoic acid ethyl ester

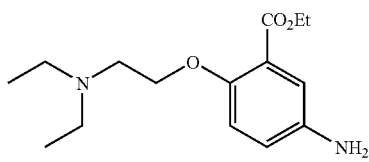

5-Amino-2-(2-diethylamino-ethoxy)-benzoic acid ethyl ester can be synthesized by the following procedure. To 2-(2-Diethylamino-ethoxy)-5-nitro-benzoic acid ethyl ester (1.6 mmol) (from Example 1n) in MeOH (12 mL) in a Parr pressure bottle is added Pd (5% on carbon, 50% wet, 10% weight). The suspension is shaken at 40 psi of H$_2$ for 2 h. The reaction is filtered through celite. The solvent is removed under reduced pressure to afford the title compound in quantitative yield. MS (m/z) (M+1)$^+$ 281.1.

Example 2n

6-Amino-3H-benzooxazol-2-one

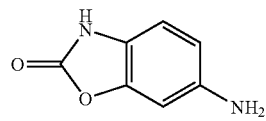

6-Amino-3H-benzooxazol-2-one can be synthesized by the following procedure. A solution of 6-nitro-3H-benzooxazol-2-one (7.22 mmol) in a 1:3 mixture EtOH:MeOH (24 mL) is treated with Pd (5% on carbon, 50% wet, 10% weight). The flask is charged with a hydrogen balloon and stirred overnight. The mixture is filtered over celite and the filtrate is concentrated to afford the 6-amino-benzoxazole-2-one as light brown powder (95%). $^1$HNMR (400 MHz, DMSO-d$_6$) δ 11.06 (b.s., 1H), 6.74 (d, J=8.2 Hz, 1H), 6.49 (d, J=2.0 Hz, 1H), 6.35 (dd, J=2.1 and 8.3 Hz, 1H), 4.96 (s, 2H). MS (m/z) (M+1)$^+$ 151.1.

Example 3

Synthesis of 5-bromo-2-aminopyrimidine compounds

Example 3a (5-Bromo-pyrimidin-2-yl)-[4-(2-diethylamino-ethoxy)-phenyl-amine

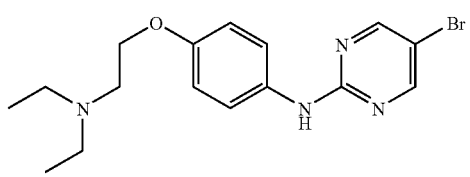

(5-Bromo-pyrimidin-2-yl)-[4-(2-diethylamino-ethoxy)-phenyl-amine can be synthesized by the following procedure. A dry flask charged with 4-(2-diethylamino-ethoxy)-phenylamine (6.1 mmol) (from Example 2a), p-TSA (6.1 mmol), 2-chloro-5-bromo-pyrimidine (6.1 mmol) in NMP (5 mL) is heated in a microwave oven at 210° C. for 15 min. The reaction mixture is diluted with water and extracted with EtOAc (5×70 mL). The organic layer is washed with water, brine, dried over Na$_2$SO$_4$, and concentrated. Purification by silica chromatography (DCM:MeOH NH$_4$OH=95:5:0.1) affords 5-bromo-pyrimidin-2-yl)-[4-(2-diethylamino-ethoxy)-phenyl-amine (50%). $^1$HNMR (400 MHz, CDCl$_3$) δ 8.37 (s, 2H), 7.43-7.40 (m, 2H), 7.02 (s, 1H), 6.91-6.89 (m, 2H), 4.06 (t, J=4.0 Hz, 2H), 2.90 (t, J=4.0 Hz, 2H), 2.67 (q, J=8.0 Hz, 4H), 1.09 (t, J=8.0 Hz, 6H). MS (m/z) (M+1)$^+$ 366.1.

Example 3b (5-Bromo-pyridin-2-yl)-[4-(2-diethylamino-ethylsulfanyl)-phenyl]-amine

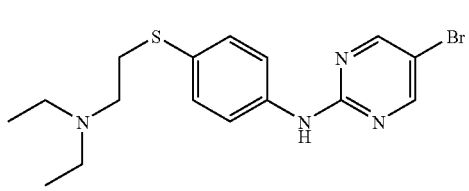

(5-Bromo-pyridin-2-yl)-[4-(2-diethylamino-ethylsulfanyl)-phenyl]-amine can be synthesized by the following procedure. A dry flask charged with 4-(2-diethylamino-ethylsulfanyl)-phenylamine (6.1 mmol) (from Example 2b), p-TSA (6.1 mmol), 2-chloro-5-bromo-pyrimidine (6.1 mmol) in NMP (5 mL) is heated in a microwave oven at 210° C. for 15 min. The reaction mixture is diluted with water and extracted with EtOAc (5×70 mL). The organic layer is washed with water, brine, dried over $Na_2SO_4$, and concentrated. Purification by silica chromatography (DCM:MeOH:$NH_4OH$=95:5:0.1) affords (5-bromo-pyridin-2-yl)-[4-(2-diethylamino-ethylsulfanyl)-phenyl]-amine. MS (m/z) $(M+1)^+$ 282.1.

Example 3c

5-Bromo-pyrimidin-2-yl)-[4-(2-chloro-ethoxy)-phenyl-amine

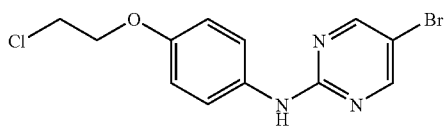

5-Bromo-pyrimidin-2-yl)-[4-(2-chloro-ethoxy)-phenyl-amine can be synthesized by the following procedure. A dry flask charged with 4-(2-chloro-ethoxy)-phenylamine (6.7 mmol) (from Example 2c), p-TSA (6.7 mmol), 2-chloro-5-bromo-pyrimidine (6.7 mmol), and NMP (5 mL) is heated in a microwave oven at 210° C. for 15 min. The reaction mixture is diluted with water and extracted with EtOAc (5×70 mL). The organic layer is washed with water, brine, dried over $Na_2SO_4$, and concentrated. Purification by automated silica chromatography using a mixture of EtOAc:Hexane affords 5-bromo-pyrimidin-2-yl)-[4-(2-chloro-ethoxy)-phenyl-amine (33%). $^1$HNMR (400 MHz, $CDCl_3$) δ 8.35 (s, 2H), 7.39-7.33 (m, 2H), 7.19 (s, 1H), 6.86 (m, 2H), 4.15 (t, J=6.0 Hz, 2H), 3.74 (t, J=6.0 Hz, 2H). MS (m/z) $(M+1)^+$ 329.1.

Example 3d (5-Bromo-pyrimidin-2-yl)-[-(2-morpholin-4-yl-ethyl)-phenyl]-amine

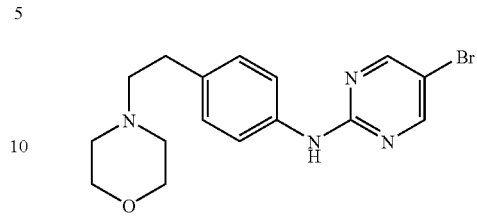

(5-Bromo-pyrimidin-2-yl)-[-(2-morpholin-4-yl-ethyl)-phenyl]-amine can be synthesized by the following procedure. A dry flask charged with 4-(2-morpholin-4-yl-ethyl)-phenylamine (6.1 mmol) (from Example 2d), p-TSA (6.1 mmol), 2-chloro-5-bromo-pyrimidine (6.1 mmol) in NMP (5 mL) is heated in a microwave oven at 210° C. for 15 min. The reaction mixture is diluted with water and extracted with EtOAc (5×70 mL). The organic layer is washed with water, brine, dried over $Na_2SO_4$, and concentrated. Purification by silica chromatography (DCM:MeOH:$NH_4OH$=95:5:0.1) affords (5-bromo-pyrimidin-2-yl)-[-(2-morpholin-4-yl-ethyl)-phenyl]-amine (50%). $^1$HNMR (400 MHz, DMSO-$d_6$) δ 9.75 (S, 1H), 8.58 (s, 2H), 7.60 (d, J=8.4 Hz, 2H), 7.16 (d, J=8.4 Hz, 2H), 3.59 (t, J=4.4 Hz, 4H), 2.69 (t, J=8.0 Hz, 2H), 2.49 (t, J=8.0 Hz, 2H), 2.34 (m, 4H). MS (m/z) $(M+1)^+$ 363.1.

Example 3e (5-Bromo-pyrimidin-2-yl)-[3-(2-diethylamino-ethoxy)-phenyl]-amine

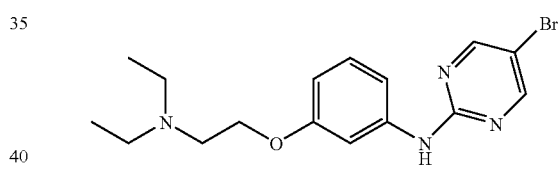

(5-Bromo-pyrimidin-2-yl)-[3-(2-diethylamino-ethoxy)-phenyl]-amine can be synthesized by the following procedure. A 25 ml flask is charged with 3-(2-diethylamino-ethoxy)-phenyl]-amine (1.7 mmol), 2-chloro-5-bromo-pyrimidine (1.7 mmol), p-TSA (1.7 mmol) and NMP (2 mL). The flask is evacuated and irradiated in a microwave oven at 210° C. for 15 min. The reaction mixture is diluted with water and extracted with a EtOAc:THF 4:1 solution (5×50 mL). The organic layer is washed with brine, dried over $Na_2SO_4$, and concentrated. Purification by HPLC (ACN gradient 10-90%) affords the title compounds (63%). MS (m/z) $(M+1)^+$ 366.1.

Example 3f 4-(5-Bromo-pyrimidin-2-ylamino)-benzoic acid methyl ester

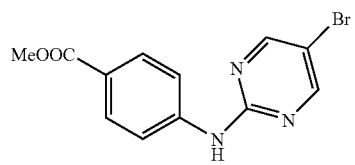

4-(5-Bromo-pyrimidin-2-ylamino)-benzoic acid methyl ester can be synthesized by the following procedure. A 25 ml flask is charged with p-amino methyl benzoate (3.3 mmol) 2-chloro-5-bromo-pyrimidine (3.3 mmol), p-TSA (1.5 mmol) and NMP (2 mL). The flask is evacuated and irradiated in a microwave oven at 210° C. for 15 min. The reaction mixture is diluted with water and extracted with EtOAc (5×50 mL). The organic layer is washed with brine, dried over Na$_2$SO$_4$, and concentrated. Purification by HPLC (ACN gradient 10-90%) affords the title compounds (30%). $^1$HNMR (400 MHz, DMSO-d$_6$) δ 10.34 (s, 1H), 8.70 (s, 2H), 7.92-7.86 (m, 4H), 3.82 (s, 3H). MS (m/z) (M+1)$^+$ 308.1.

Example 3g 5-(5-Bromo-pyrimidin-2-ylamino)-2-methoxy-phenol

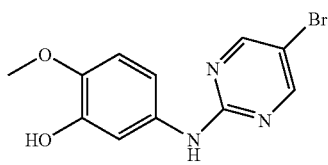

5-(5-Bromo-pyrimidin-2-ylamino)-2-methoxy-phenol can be synthesized by the following procedure. A 25 ml flask is charged with 5-amino-2-methoxy-phenol (3.5 mmol) 2-chloro-5-bromo-pyrimidine (3.5 mmol), p-TSA (1 mmol) and NMP (2 mL). The flask is evacuated and irradiated in a microwave oven at 210° C. for 15 min. The reaction mixture is diluted with water and extracted with DCM (5×50 mL). The organic layer is washed with brine, dried over Na$_2$SO$_4$, and concentrated. Purification by HPLC (ACN gradient 10-90%) affords the title compounds (25%). $^1$HNMR (400 MHz, DMSO-d$_6$) δ 9.56 (s, 1H), 8.51 (s, 2H), 7.18 (d, J, 4 Hz, 1H), 7.02 (dd, J=8.0 and 4.0 Hz, 1H), 6.83 (d, J=8.0 Hz, 1H), 3.72 (s, 3H), 3.17 (s, 1H). MS (m/z) (M+1)$^+$ 297.1.

Example 3h

[4-(5-Bromo-pyrimidin-2-ylamino)-phenyl]-methanol

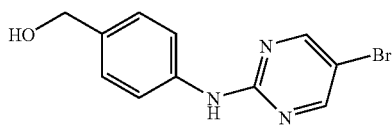

[4-(5-Bromo-pyrimidin-2-ylamino)-phenyl]-methanol can be synthesized by the following procedure. To a solution of 4-aminobenzyl alcohol (8.12 mmol) and 5-bromo-2-chloro-pyrimidine (9.74 mmol) in 2-propanol (20 mL) is added sodium iodide (8.12 mmol) and diisopropylethylamine (16.2 mmol). The reaction mixture is heated in the microwave oven at 200° C. for 15 min. Purification by silica chromatography using hexane:EtOAc=7:3 affords [4-(5-bromo-pyrimidin-2-ylamino)-phenyl]-methanol (44%). $^1$HNMR (400 MHz, CDCl$_3$) δ 8.36 (s, 2H), 7.49 (d, J=8.8 Hz, 2H), 7.28 (d, J=8.4 Hz, 2H) 7.07 (bs, 1H), 4.60 (s, 2H). MS (m/z) (M+1)$^+$ 280.3.

Example 3i

4-Methyl-piperazine-1-carboxylic acid 4-(5-bromo-pyrimidin-2-ylamino)-phenyl ester

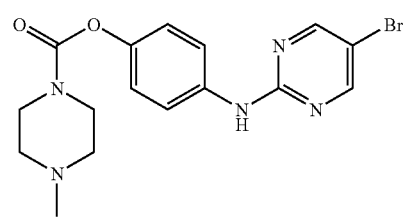

4-Methyl-piperazine-1-carboxylic acid 4-(5-bromo-pyrimidin-2-ylamino)-phenyl ester can be synthesized by the following procedure. To a solution of 4-methyl-piperazine-1-carboxylic acid 4-amino-phenyl ester-(1.06 mmol) (from Example 2f) in NMP (2 mL) are added 5-bromo-2-chloro-pyrimidine (1.06 mmol) and pTSA (1.06 mmol). The flask is evacuated twice and heated in a microwave oven at 210° C. for 10 min. The reaction mix is diluted with water and extracted with DCM. The organic layer is washed with water, brine, dried over Na$_2$SO$_4$ and concentrated. The crude mixture is purified by HPLC (ACN gradient 10-90) to afford 4-methyl-piperazine-1-carboxylic acid 4-(5-bromo-pyrimidin-2-ylamino)-phenyl ester (25%). MS (m/z) (M+1)$^+$ 393.25.

Example 3l 2-(4-(5-Bromopyrimidin-2-ylamino)phenyl)ethanol

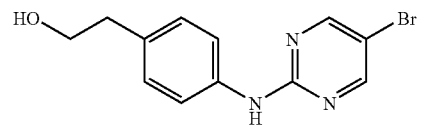

2-(4-(5-Bromopyrimidin-2-ylamino)phenyl)ethanol can be synthesized by the following procedure. A mixture of 2-(4-aminophenyl)ethanol (0.72 mol), 2-chloro-5-bromo-pyrimidine (0.72 mol), NaI (0.72 mol), and diisopropylethylamine (1.45 mol) in n-butanol (400 mL) is heated at reflux overnight. The reaction is cooled to rt and the mixture is diluted with water. The light yellow solid that precipitates is filtered to give 2-(4-(5-bromopyrimidin-2-ylamino)phenyl)ethanol (57%). $^1$HNMR (300 MHz, DMSO-d$_6$) δ 9.722 (s, 1H), 8.52 (s, 2H), 7.55 (m, 2H), 7.09 (d, 2H), 4.64 (m, 1H), 3.52 (m, 2H), 2.65 (m, 2H).

Example 4

Synthesis of 5-substituted-2-chloropyrimidine compounds

Example 4a 4-(2-Chloropyrimidin-5-yl)benzaldehyde

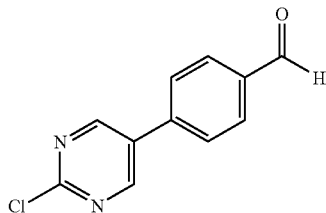

4-(2-Chloropyrimidin-5-yl)benzaldehyde can be synthesized by the following procedure. To a solution of 2-chloro-5-bromo pyrimidine (2.58 mmol) in DMF (2 mL) are added 4-formyl boronic acid (2.84 mmol), K₂CO₃ (5.96 mmol of a 5M aq solution) and Pd(PPh₃)₄ (0.129 mmol). The reaction is evacuated twice and heated at 120° C. for 5 min. The reaction mixture is diluted with a sat. aq NH₄Cl and extracted with DCM (3×50 mL). The organic layer is washed with brine, dried over Na₂SO₄ and concentrated. Purification by silica chromatography using hexane:EtOAc=8:2 affords 4-(2-chloropyrimidin-5-yl)benzaldehyde (53%).

Example 4b

Tert-butyl 2-(4-(2-chloropyrimidin-5-yl)benzylamino)acetate

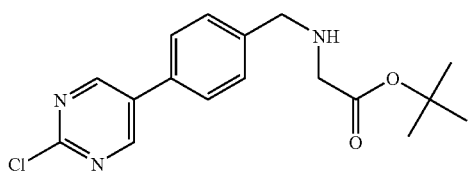

Tert-butyl 2-(4-(2-chloropyrimidin-5-yl)benzylamino)acetate can be synthesized by the following procedure. To a solution of 4-(2-chloropyrimidin-5-yl)benzaldehyde (1.37 mmol) (from Example 4a), phenylglycine tert-butylester (1.37 mmol) and diisopropylethylamine (1.64 mmol) in DCM (20 mL) is added MgSO₄ and the mixture is stirred overnight. MgSO₄ is filtered and the filtrate is diluted with a sat. aq NH₄Cl and extracted with DCM (3×50 mL). The organic layer is washed with brine, dried over Na₂SO₄ and concentrated. Purification by silica chromatography using a hexane EtOAc=8:2 affords tert-butyl 2-(4-(2-chloropyrimidin-5-yl)benzylamino)acetate (33%).

Example 4c

2-Chloro-5-(4-methoxy-phenyl)-pyrimidine

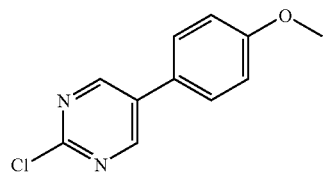

2-Chloro-5-(4-methoxy-phenyl)-pyrimidine can be synthesized by the following procedure. To a solution of 2-chloro-5-bromo pyrimidine (7.7 mmol) in DMF (1.5 mL), 4-methoxy boronic acid (8.9 mmol), K₂CO₃ (16.2 mmol of a 5M aq solution) and Pd(PPh₃)₄ (0.38 mmol) are added. The reaction is evacuated twice and heated at 120° C. for 5 min. After this time the reaction mixture is diluted with a sat. aq NH₄Cl and extracted with DCM (3×50 mL). The organic layer is washed with brine, dried over Na₂SO₄ and concentrated. Purification by silica chromatography using a hexane: EtOAc=8:2 affords 2-chloro-5-(4-methoxy-phenyl)-pyrimidine (59%). ¹HNMR (400 MHz, CDCl₃) δ 8.79 (s, 2H), 7.50 (d, J=8.0 Hz, 2H), 7.05 (d, J=8.0 Hz, 2H), 3.87 (s, 3H). MS (m/z) (M+1)⁺ 221.1.

Example 4d 4-(2-Chloro-pyrimidin-5-yl)-benzoic acid

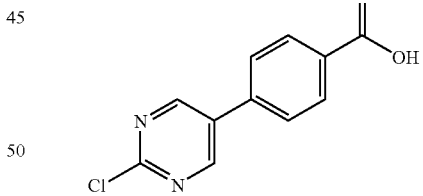

4-(2-Chloro-pyrimidin-5-yl)-benzoic acid can be synthesized by the following procedure. To a solution of 2-chloro-5-bromo pyrimidine (9.9 mmol) in DMF (10 mL) are added benzoic acid-4-boronic acid (10.9 mmol), K₂CO₃ (20.8 mmol of a 5M aq solution) and Pd(PPh₃)₄ (0.49 mmol). The reaction is evacuated twice and heated at 80° C. for 2 h. Addition with water promotes the separation of the desired compound. The solid is washed with water and dried under vacuum to afford 4-(2-chloro-pyrimidin-5-yl)-benzoic acid (51%). MS (m/z) (M+1)⁺ 235.1.

Example 5

Synthesis of 5-substituted-2-aminopyrimidine compounds

Example 5a

[4-(2-Diethylamino-ethoxy)-phenyl]-[5-(4-methoxy-phenyl)-pyrimidin-2-yl]-amine

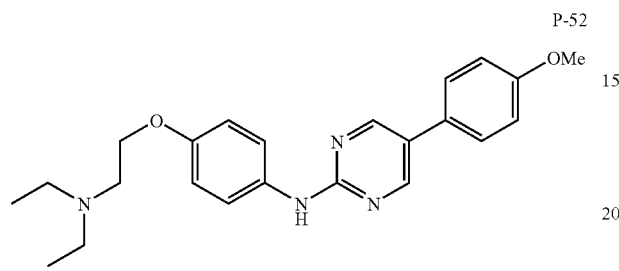

P-52

[4-(2-diethylamino-ethoxy)-phenyl]-[5-(4-methoxy-phenyl)-pyrimidin-2-yl]-amine can be synthesized by the following procedure. To a solution of (5-bromo-pyrimidin-2-yl)-[4-(2-diethylamino-ethoxy)-phenyl-amine (0.32 mmol) (from Example 3a) in glyme (1 mL) is added 4-methoxyphenylboronic acid (0.33 mmol), aqueous potassium carbonate (0.57 mmol), and Pd(PPh$_3$)$_4$ (0.027 mmol). The reaction is heated at reflux for 15 min and the solvent is removed. The residue is dissolved in DCM, washed with sat. aq NH$_4$Cl (2×20 mL), dried over Na$_2$SO$_4$, and concentrated. Purification by HPLC (ACN gradient 10-90%) affords the title compound (47%). The product is dissolved in MeOH and treated with MeSO$_3$H (1 eq) to afford [4-(2-diethylamino-ethoxy)-phenyl]-[5-(4-methoxy-phenyl)-pyrimidin-2-yl]-amine as its mesylate salt (quantitative). $^1$HNMR (400 MHz, MeOD) δ 8.64 (s, 2H), 7.50-7.47 (m, 4H), 7.02-6.96 (m, 4H), 4.29 (t, J=4.8 Hz, 2H), 3.75 (s, 3H), 3.54 (t, J=4.8 Hz, 2H), 3.33-3.24 (m, 4H), 2.61 (s, 3H), 1.30 (t, J=7.2 Hz, 6H). MS (m/z) (M+1)$^+$ 393.3.

Example 5b

[4-(2-Diethylamino-ethylsulfanyl)-phenyl]-[5-(4-methoxy-phenyl)-pyrimidin-2-yl]-amine

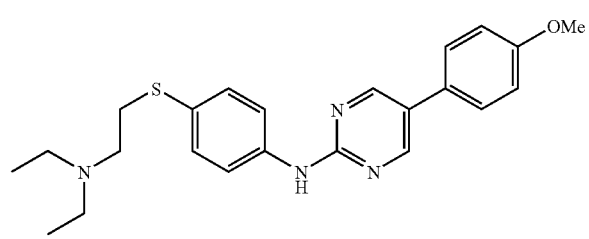

P-158

[4-(2-Diethylamino-ethylsulfanyl)-phenyl]-[5-(4-methoxy-phenyl)-pyrimidin-2-yl]-amine can be synthesized by the following procedure. To a solution of (5-bromo-pyridin-2-yl)-[4-(2-diethylamino-ethylsulfanyl)-phenyl]-amine (0.32 mmol) (from Example 3b) in glyme (1 mL) is added 4-methoxyphenylboronic acid (0.33 mmol), aqueous potassium carbonate (0.57 mmol), and Pd(PPh$_3$)$_4$ (0.027 mmol). The reaction is heated at reflux for 15 min and the solvent is removed. The residue is dissolved in DCM, washed with sat aq NH$_4$Cl. (2×20 mL), dried over Na$_2$SO$_4$, and concentrated. Purification by HPLC (ACN gradient 10-90%) affords the title compound. The product is dissolved in MeOH and treated with MeSO$_3$H (1 eq) to afford [4-(2-diethylamino-ethylsulfanyl)-phenyl]-[5-(4-methoxy-phenyl)-pyrimidin-2-yl]-amine as its mesylate salt (quantitative). $^1$HNMR (400 MHz, CD$_3$OD) δ 8.69 (s, 2H) 7.82-7.80 (m, 2H), 7.55-7.48 (m, 4H), 7.05-7.03 (m, 2H), 3.84 (s, 3H), 3.24-3.18 (m, 8H), 2.70 (s, 3H), 1.25 (t, J=8.0 Hz, 6H). MS (m/z) (M+1)$^+$ 409.2.

Example 5c

[5-(4-Methoxy-phenyl)-pyrimidin-2-yl]-[4-(2-morpholin-4-yl-ethyl)-phenyl]-amine

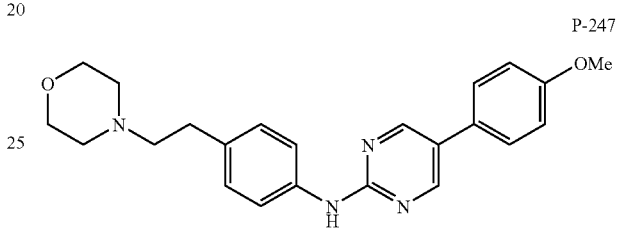

P-247

[5-(4-Methoxy-phenyl)-pyrimidin-2-yl]-[4-(2-morpholin-4-yl-ethyl)-phenyl]-amine can be synthesized by the following procedure. To a solution of (5-bromo-pyrimidin-2-yl)-[-(2-morpholin-4-yl-ethyl)-phenyl]-amine (0.32 mmol) (from Example 3d) in glyme (1 mL) is added 4-methoxyphenylboronic acid (0.33 mmol), aqueous potassium carbonate (0.57 mmol), and Pd(PPh$_3$)$_4$ (0.027 mmol). The reaction is heated at reflux for 15 min and the solvent is then removed. The residue is dissolved in DCM, washed with sat. aq NH$_4$Cl (2×20 mL), dried over Na$_2$SO$_4$, and concentrated. Purification by HPLC (ACN gradient 10-90%) affords [5-(4-methoxy-phenyl)-pyrimidin-2-yl]-[4-(2-morpholin-4-yl-ethyl)-phenyl]-amine which is converted to the corresponding hydrochloride salt by treatment with 4N HCl. $^1$HNMR (400 MHz, CD$_3$OD) δ 8.65 (s, 2H), 7.56-754 (m, 2H), 7.49-7.46 (m, 2H), 7.27-7.25 (m, 2H), 6.97-6.95 (m, 2H), 4.02 (t, J=4.3 Hz, 2H), 3.74 (s, 3H), 3.72 (t, J=4.3 Hz, 2H), 3.48 (d, J=4.3 Hz, 2H), 3.34-3.30 (m, 2H), 3.16-3.10 (m, 2H), 3.03-2.99 (m, 2H). MS (m/z) (M+1)$^+$ 391.2.

Example 5d

[4-(2-Chloro-ethoxy)-phenyl]-[5-(4-methoxy-phenyl)-pyrimidin-2-yl]-amine

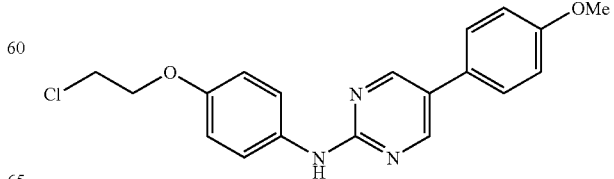

[4-(2-Chloro-ethoxy)-phenyl]-[5-(4-methoxy-phenyl)-pyrimidin-2-yl]-amine can be synthesized by the following procedure. To a solution of 5-bromo-pyrimidin-2-yl)-[4-(2-chloro-ethoxy)-phenyl-amine (0.32 mmol) (from Example 3c) in glyme (1 mL) is added 4-methoxyphenylboronic acid (0.33 mmol), aqueous potassium carbonate (0.57 mmol), and Pd(PPh$_3$)$_4$ (0.027 mmol). The reaction is heated at reflux for 15 min and the solvent is removed. The residue is dissolved in DCM, washed with sat. aq NHCl (2×20 mL), dried over Na$_2$SO$_4$, and concentrated. Purification by HPLC (ACN gradient 10-90%) gives the [4-(2-chloro-ethoxy)-phenyl]-[5-(4-methoxy-phenyl)-pyrimidin-2-yl]-amine. $^1$HNMR (400 MHz, CDCl$_3$) δ 8.53 (s, 2H), 7.50 (d, J=8.8 Hz, 2H), 7.43 (d, J=8.8 Hz, 2H), 6.95 (d, J=8.8 Hz, 2H), 6.86 (d, J=8.8 Hz, 2H), 4.17 (t, J=5.2 Hz, 2H), 3.79-3.77 (m, 5H). MS (m/z) (M+1)$^+$ 356.2.

Example 5e (5-(4-Methoxy-phenyl)-pyrimidin-2-yl]-[4-(2-morpholin-4-yl-ethoxy-phenyl]-amine

P-143

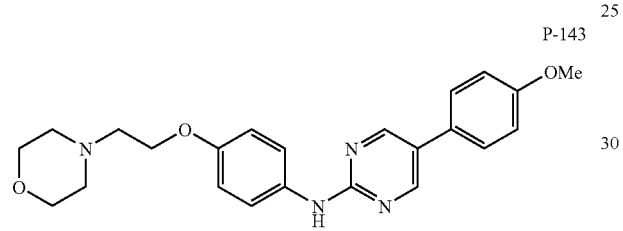

(5-(4-Methoxy-phenyl)-pyrimidin-2-yl]-[4-(2-morpholin-4-yl-ethoxy-phenyl]-amine can be synthesized by the following procedure. A dry flask charged with [4-(2-chloro-ethoxy)-phenyl]-[5-(4-methoxy-phenyl)-pyrimidin-2-yl]-amine (0.14 mmol) (from Example 5d), NaI (0.14 mmol), morpholine (0.14 mmol), diisopropylethylamine (0.14 mmol) and DMF (0.5 mL) is heated in the microwave oven at 200° C. for 8 min. The reaction is diluted with water and extracted with EtOAc (5×20 mL). The organic layer is washed with water, brine, dried over Na$_2$SO$_4$, and concentrated. Purification by HPLC (ACN gradient 10-90%) affords (5-(4-methoxy-phenyl)-pyrimidin-2-yl]-[4-(2-morpholin-4-yl-ethoxy-phenyl]-amine (36%) as a triflate salt. $^1$HNMR (400 MHz, CDCl$_3$) δ 10.04 (s, 1H), 9.58 (s, 2H), 7.73-7.69 (m, 2H), 7.69-7.60 (m, 2H), 7.05-6.96 (m, 4H), 4.62-3.98 (brm 4H), 3.79 (s, 3H), 3.75-3.72 (brm, 2H), 3.61-3.50 (brm, 4H), 3.21 (brm, 2H). MS (m/z) (M+1)$^+$ 407.1.

Example 5f

4-{2-[4-(2-Diethylamino-ethoxy)-phenylamino]-pyrimidin-5-yl}benzaldehyde

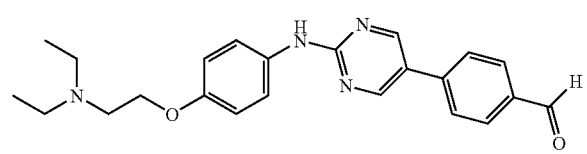

4-{2-[4-(2-Diethylamino-ethoxy)-phenylamino]-pyrimidin-5-yl}-benzaldehyde can be synthesized by the following procedure. To a solution of (5-bromo-pyrimidin-2-yl)-[4-(2-diethylamino-ethoxy)-phenyl]-amine (2 g, 5.48 mmol) (from Example 3a) in THF:water (30 mL: 15 mL) is added 4-formyl-phenylboronic acid (6 mmol), K$_2$CO$_3$ (12 mmol) and Pd(PPh$_3$)$_2$Cl$_2$ (0.25 mmol). The reaction mixture is heated at 65° C. for 2 h. After removal of the THF, the residue is diluted with dichloromethane and water. Then the organic layer is separated, dried over sodium sulfate, and concentrated. Further purification by silica chromatography (DCM: MeOH=20:80) affords the 4-{2-[4-(2-diethylamino-ethoxy)-phenylamino]-pyrimidin-5-yl}-benzaldehyde (80%). MS (m/z) (M+1)$^+$ 391.2.

Example 5g

4-{2-[4-(2-Diethylamino-ethoxy)-phenylamino]-pyrimidin-5-yl}-2-fluoro-benzaldehyde

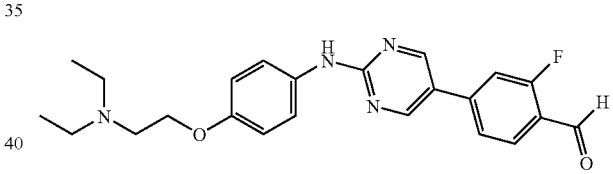

4-{2-[4-(2-Diethylamino-ethoxy)-phenylamino]-pyrimidin-5-yl}-2-fluoro-benzaldehyde can be synthesized by the following procedure. To a solution of (5-bromo-pyrimidin-2-yl)-[4-(2-diethylamino-ethoxy)-phenyl]-amine (5.48 mmol) (from Example 3a) in THF:water (30 mL: 15 mL) is added 3-fluoro-4-formyl-phenyl-boronic acid (6 mmol), K$_2$CO$_3$ (12 mmol) and Pd(PPh$_3$)$_2$Cl$_2$ (0.25 mmol). The reaction mixture is heated at 65° C. for 2 h. After removal of the THF, the residue is diluted with dichloromethane and water. Then the organic layer is separated, dried over sodium sulfate, and concentrated. Further purification by silica chromatography (DCM:MeOH=20:80) affords the 4-{2-[4-(2-diethylamino-ethoxy)-phenylamino]-pyrimidin-5-yl}-2-fluoro-benzaldehyde (75%). MS (m/z) (M+1)$^+$ 409.2.

Example 5h (5-{4-[(2-Tert-Butoxy-ethylamino)-methyl]-phenyl}-
pyrimidin-2-yl)-[4-(2-diethylamino-ethoxy)-phenyl]-
amine

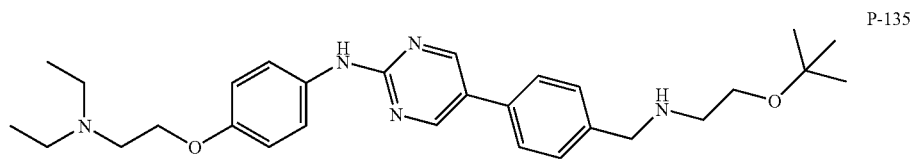

P-135

(5-{4-[(2-Tert-butoxy-ethylamino)-methyl]-phenyl}-pyrimidin-2-yl)-[4-(2-diethylamino-ethoxy)-phenyl]-amine can be synthesized by the following procedure. A solution of 4-{2-[4-(2-diethylamino-ethoxy)-phenylamino]-pyrimidin-5-yl}-benzaldehyde (0.05 mmol) (from Example 5f) and 2-tert-butoxy-ethylamine (0.1 mmol) in 1 mL dichloromethane is stirred at rt for 1 h. Then NaB(OAc)$_3$H (0.15 mmol) is added and the reaction is stirred for 5 h. Purification by preparative LCMS affords (5-{4-[(2-tert-butoxy-ethylamino)-methyl]-phenyl}-pyrimidin-2-yl)-[4-(2-diethylamino-ethoxy)-phenyl]-amine as a TFA salt. MS (m/z) (M+1)$^+$ 492.2.

Example 5i (4-{2-[4-(2-Diethylamino-ethoxy)-phenylamino]-
pyrimidin-5-yl}-2-fluoro-benzylamino)-acetic acid
tert-butyl ester

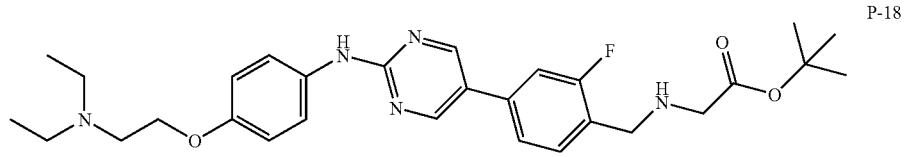

P-18

(4-{2-[4-(2-Diethylamino-ethoxy)-phenylamino]-pyrimidin-5-yl}-2-fluoro-benzylamino)-acetic acid tert-butyl ester can be synthesized by the following procedure. A solution of 4-{2-[4-(2-diethylamino-ethoxy)-phenylamino]-pyrimidin-5-yl}-2-fluoro-benzaldehyde (0.05 mmol) (from Example 5g) and amino-acetic acid tert-butyl ester (0.1 mmol) in 1 mL dichloromethane is stirred at rt for 1 h. Then NaB(OAc)$_3$H (0.15 mmol) is added and the reaction is stirred for 5 h. Purification by preparative LCMS affords (4-{2-[4-(2-diethylamino-ethoxy)-phenylamino]-pyrimidin-5-yl}-2-fluoro-benzylamino)-acetic acid tert-butyl ester as a TFA salt. MS (m/z) (M+1)$^+$ 524.2.

Example 5j

4-Methyl-piperazine-1-carboxylic acid 3-(5-{4-[(tert-butoxycarbonylmethyl-amino)-methyl]-phenyl}-pyrimidin-2-ylamino)-phenyl ester

P-206

4-Methyl-piperazine-1-carboxylic acid 3-(5-{4-[(tert-butoxycarbonylmethyl-amino)-methyl]-phenyl}-pyrimidin-2-ylamino)-phenyl ester can be synthesized with the following procedure.

A mixture of palladium acetate (0.01 mmol), Xantphos (0.012 mmol), potassium tert-butoxide (0.2 mmol), [4-(2-chloro-pyrimidin-5-yl)-benzylamino]-acetic acid tert-butyl ester (0.1 mmol) (from Example 4b) and 3-aminophenyl 4-methylpiperazine-1-carboxylate (from Example 2e) (0.3 mmol) in dioxane (1 mL) is heated at 90° C. for 1 h. Purification is done using preparative LCMS to afford 4-methyl-piperazine-1-carboxylic acid 3-(5-{4-[(tert-butoxycarbonylmethyl-amino)-methyl]-phenyl}-pyrimidin-2-ylamino)-phenyl ester as a TFA salt.
MS (m/z) (M+1)$^+$ 533.0.

Example 5k

4-Methyl-piperazine-1-carboxylic acid 4-(5-{4-[(tert-butoxycarbonylmethyl-amino)-methyl]-phenyl}-pyrimidin-2-ylamino)-phenyl ester

4-Methyl-piperazine-1-carboxylic acid 4-(5-{4-[(tert-butoxycarbonylmethyl-amino)-methyl]-phenyl}-pyrimidin-2-ylamino)-phenyl ester can be synthesized by the following procedure. A mixture of Palladium acetate (0.01 mmol), Xantphos (0.012 mmol), potassium tert-butoxide (0.2 mmol), [4-(2-chloro-pyrimidin-5-yl)-benzylamino]-acetic acid tert-butyl ester (0.1 mmol) (from Example 4b) and 4-aminophenyl 4-methylpiperazine-1-carboxylate (from Example 2f) (0.3 mmol) in dioxane (1 mL) is heated at 90° C. for 1 h. Purification by preparative LCMS to affords 4-methyl-piperazine-1-carboxylic acid 4-(5-{4-[(tertbutoxycarbonylmethyl-amino)-methyl]-phenyl}-pyrimidin-2-ylamino)-phenyl ester as a TFA salt. MS (m/z) (M+1)$^+$ 532.4.

Example 5l

4-[5-(4-Methoxy-phenyl)-pyrimidin-2-ylamino]-benzoic acid

4-[5-(4-Methoxy-phenyl)-pyrimidin-2-ylamino]-benzoic acid can be prepared by the following procedure. To a solution of 4-(5-bromo-pyrimidin-2-ylamino)-benzoic acid

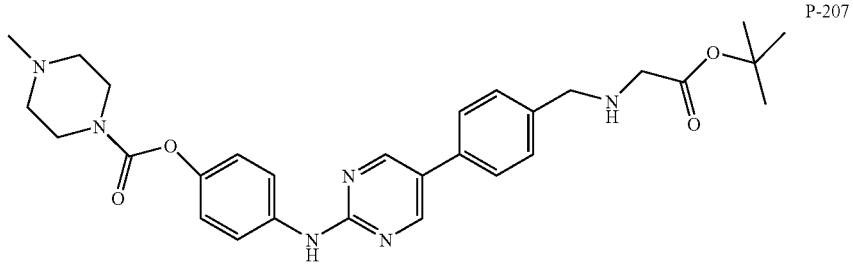

P-207 methyl ester (0.3 mmol) (from Example 3f) in DMF (1.5 mL) are added 4-methoxy boronic acid (0.3 mmol), aq K$_2$CO$_3$ (0.68 mmol) and Pd(PPh$_3$)$_4$ (0.16 mmol). The reaction mixture is evacuated twice and heated at 80° C. for 30 min. After this time the reaction mixture is diluted with a sat. aq NH$_4$Cl and extracted with DCM (3×30 mL). The organic layer is washed with brine, dried over Na$_2$SO$_4$ and concentrated to afford 4-[5-(4-methoxy-phenyl)-pyrimidin-2-ylamino]-benzoic acid methyl ester that upon trituration with MeOH gives an orange solid (95%). MS (m/z) (M+1)$^+$ 336.1. This solid is suspended in a 3:2:1=THF:MeOH:H$_2$O solution (3 mL) and 6N LiOH (0.15 mL) added and stirred at rt for 12 h. At this point the solvent is removed and the residue is dissolved in water and extracted with DCM (3×30 mL). The mixture is adjusted to pH ~2 and extracted with a 3:1=DCM:IPA mixture (5×30 mL). The organic layer is washed with brine, dried over Na$_2$SO$_4$ and concentrated to afford 4-[5-(4-methoxy-phenyl)-pyrimidin-2-ylamino]-benzoic acid as an orange powder (100%) which is used without further purification. $^1$HNMR (400 MHz, DMSO-d$_6$) δ 10.18 (s, 1H), 8.87 (s, 2H), 7.95-7.87 (m, 4H), 7.71 (d, J=8.0 Hz, 2H), 7.06 (d, J=8.0 Hz, 2H), 3.81 (s, 3H). MS (m/z) (M+1)$^+$ 322.1.

Example 5m

1-{4-[5-(4-Methoxy-phenyl)-pyrimidin-2-ylamino]-benzoyl}-piperidine-4-carboxylic acid amide

P-290

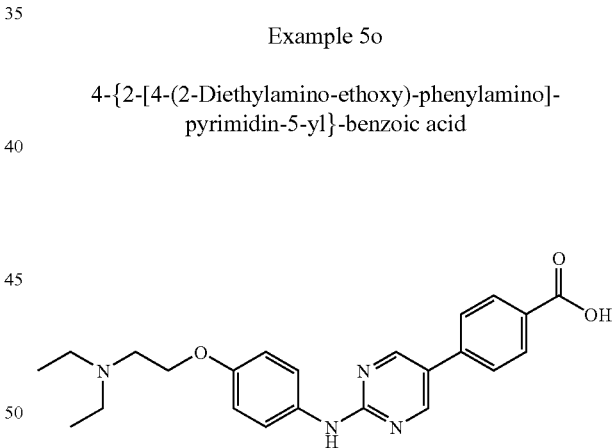

1-{4-[5-(4-Methoxy-phenyl)-pyrimidin-2-ylamino]-benzoyl}-piperidine-4-carboxylic acid amide can be synthesized by the following procedure. To a solution of 4-[5-(4-methoxy-phenyl)-pyrimidin-2-ylamino]-benzoic acid (from Example 51) (0.05 mmol) in anhydrous DMF (1 mL) is added HATU (0.06 mmol), diisopropylethylethylamine (0.12 mmol) and piperidine-4-carboxylic acid amide (0.08 mmol). The reaction mixture is stirred at rt for 8 h. The reaction mixture is purified by HPLC (ACN gradient 10-80%) to afford 1-{4-[5-(4-methoxy-phenyl)-pyrimidin-2-ylamino]-benzoyl}-piperidine-4-carboxylic acid amide (30%) as a fluffy off white solid. MS (m/z) (M+1)$^+$ 432.2.

Example 5n (3-Hydroxy-pyrrolidin-1-yl)-{4-[5-(4-methoxy-phenyl)-pyrimidin-2-ylamino]-phenyl}-methanone

P-293

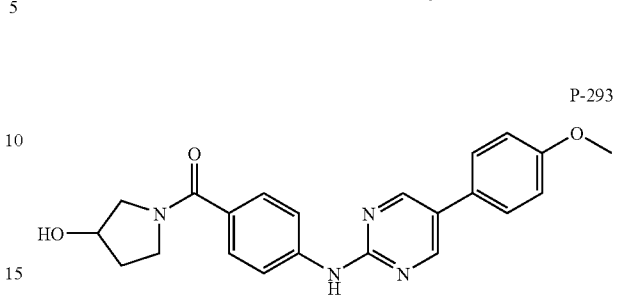

(3-Hydroxy-pyrrolidin-1-yl)-{4-[5-(4-methoxy-phenyl)-pyrimidin-2-ylamino]-phenyl}-methanone can be synthesized by the following procedure. To a solution of 4-[5-(4-methoxy-phenyl)-pyrimidin-2-ylamino]-benzoic acid (from Example 51) (0.05 mmol) in anhydrous DMF (1 mL), HATU (0.06 mmol), diisopropylethylethylamine (0.12 mmol) and pyrrolidin-3-ol (0.08 mmol). The reaction mixture is stirred at rt for 8 h. The reaction mixture is purified by HPLC (ACN gradient 10-80%) to afford the title compound. $^1$HNMR (400MHz, DMSO) δ 10.00 (s, 1H), 8.85 (s, 2H), 7.88-7.85 (m, 2H), 7.69-7.66 (m, 2H), 7.52-7.49 (m, 2H), 7.07-7.05 (m, 2H), 5.01-4.92 (m, 1H), 4.33-4.23 (m, 1H), 3.81 9s, 3H), 3.67-3.45 9m, 4H), 1.94-1.80 (m, 2H). MS (m/z) (M+1)$^+$ 391.2.

Example 5o

4-{2-[4-(2-Diethylamino-ethoxy)-phenylamino]-pyrimidin-5-yl}-benzoic acid

4-{2-[4-(2-Diethylamino-ethoxy)-phenylamino]-pyrimidin-5-yl}-benzoic acid can be synthesized by the following procedure. To a solution of 4-(5-bromo-pyrimidin-2-yl)-[4-(2-diethylamino-ethoxy)-phenyl]-amine (1.1 mmol) (from Example 3a) in DME (2 mL) are added 4-(4,4,5,5-tetramethyl-1,3,2-dioxaborolan-2-yl)benzoic acid (1.3 mmol), K$_2$CO$_3$ aq. (2.3 mmol) and Pd(PPh$_3$)$_4$ (0.11 mmol). The reaction is evacuated and heated at 80° C. for 1 h. The reaction mixture is diluted with a sat. aq NH$_4$Cl and extracted with DCM (3×30 mL). The organic layer is washed with brine, dried over Na$_2$SO$_4$ and concentrated to afford a dark residue that upon trituration with MeOH gives a gray solid (25%) that is used without further purification. MS (m/z) (M+1)$^+$ 407.3.

Example 5p (4-{2-[4-(2-Diethylamino-ethoxy)-phenylamino]-pyrimidin-5-yl}-benzoylamino)-acetic acid tert-butyl ester

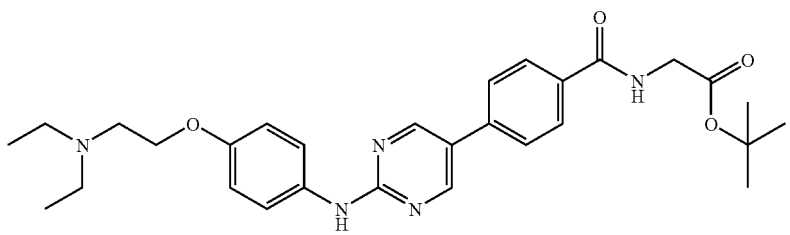

P-23

(4-{2-[4-(2-Diethylamino-ethoxy)-phenylamino]-pyrimidin-5-yl}-benzoylamino)-acetic acid tert-butyl ester can be synthesized by the following procedure. To a solution of 4-{2-[4-(2-diethylamino-ethoxy)-phenylamino]-pyrimidin-5-yl}-benzoic acid (from Example 5o) (0.195 mmol) in anhydrous DMF (1.5 mL) is added HATU (0.273 mmol), diisopropylethylethylamine (0.273 mmol) and glycine tert-butyl ester (0.2 mmol). The mixture is stirred at rt for 8 h. The reaction mixture is quenched with a 10% aq $K_2CO_3$ and extracted with DCM. Purification by HPLC (ACN gradient 10-90%) affords (4-{2-[4-(2-diethylamino-ethoxy)-phenylamino]-pyrimidin-5-yl}-benzoylamino)-acetic acid tert-butyl ester as triflate salt (32%). $^1$HNMR (400 MHz, DMSO-$d_6$) δ 9.78 (s, 1H), 9.40 (bs, 1H), 8.91 (t, J=4 Hz, 1H), 8.89 (s, 2H), 7.97 (d, J, 8 Hz, 2H), 7.85 (d, J=8.0 2H), 7.73 (d, J=8.0 Hz, 2H), 6.99 (d, J=8.0 Hz, 2H), 4.29 (t, J=4.0 Hz, 2H), 3.92 (d, J=4 Hz, 2H), 3.55-3.51 (m, 2H), 3.27-3.22 (m, 4H), 1.25 (t, J=4.0 Hz, 6H). MS (m/z) (M+1)$^+$ 520.2.

Example 5q

[3-(2-Diethylamino-ethoxy)-phenyl]-[5-(4-methoxy-phenyl)-pyrimidin-2-yl]-amine

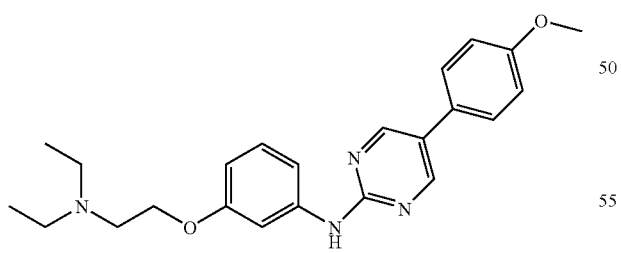

P-154

[3-(2-Diethylamino-ethoxy)-phenyl]-[5-(4-methoxy-phenyl)-pyrimidin-2-yl]-amine can be synthesized by the following procedure. To a solution of (5-bromo-pyrimidin-2-yl)-[3-(2-diethylamino-ethoxy)-phenyl]-amine (0.29 mmol) (from Example 3e) in DME (2 mL) are added 4-methoxy boronic acid (0.35 mmol), aq $K_2CO_3$ (0.66 mmol) and Pd(PPh$_3$)$_4$ (0.029 mmol). The reaction mixture is refluxed for 30 min. After removal of DME, the residue is dissolved in DCM and washed with a sat. aq NH$_4$Cl. The organic layer is dried over Na$_2$SO$_4$ and concentrated under reduced pressure. Purification of the crude by HPLC (ACN gradient 10-90%) affords [3-(2-diethylamino-ethoxy)-phenyl]-[5-(4-methoxy-phenyl)-pyrimidin-2-yl]-amine (70%). $^1$HNMR (400 MHz, DMSO-$d_6$) δ 9.76 (s, 1H), 9.65 (bs 1H), 8.79 (s, 2H), 7.66 (d, J=8.0 Hz, 2H), 7.61 (m, 1H), 7.42 (d, J=8.0 Hz, 1H), 7.24 (t, J=8.0 Hz, 1H), 7.04 (d, J=8.0 HZ, 2H), 6.62 (d, J=8.0 HZ, 1H), 4.34-4.32 (m, 2H), 3.80 (s, 3H), 3.57-3.55 (m, 2H), 3.28-3.23 (m, 4H), 1.26 (t, j=8.0 HZ, 3H). MS (m/z) (M+1)$^+$ 393.2.

Example 5r

3-[5-(4-Methoxy-phenyl)-pyrimidin-2-ylamino]-phenol

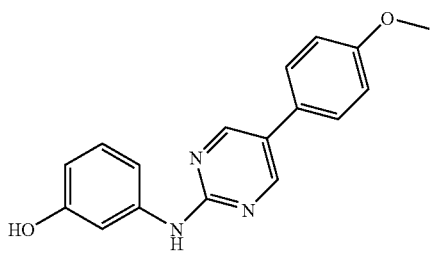

3-[5-(4-Methoxy-phenyl)-pyrimidin-2-ylamino]-phenol can be prepared by the following procedure. A dry flask charged with 3-amino-phenol (0.18 mmol), 2-chloro-5-(4-methoxy-phenyl)-pyrimidine (0.18 mmol) (from Example 4c), diisopropylethylethylamine (0.09 mmol) in NMP is heated in a microwave oven at 210° C. for 10 min. The reaction mixture is diluted with water and extracted with DCM (3×20 mL), washed with brine, dried over Na$_2$SO$_4$ and concentrated. Purification by preparative LCMS (ACN gradient 10-70%) affords 3-[5-(4-methoxy-phenyl)-pyrimidin-2-ylamino]-phenol (22%). $^1$HNMR (400 MHz, DMSO-$d_6$) δ 8.81 (s, 1H), 8.76 (s, 2H), 7.66-7.63 (m, 2H), 7.36 (t, J=4.0 Hz, 1H), 7.19-7.17 (m, 1H), 7.07-7.03 (M, 3H), 6.38-6.35 (M, 1H), 3.80 (s, 3H). MS (m/z) (M+1)$^+$ 294.1.

Example 5s

4-Methyl-piperazine-1-carboxylic acid 3-[5-(4-methoxy-phenyl)-pyrimidin-2-ylamino]-phenyl ester

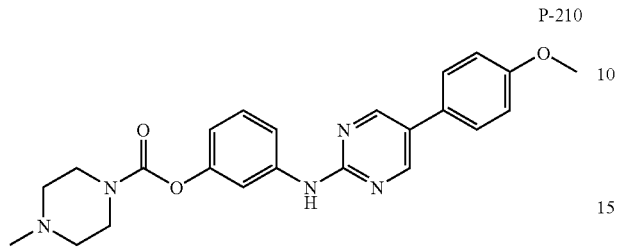

P-210

4-Methyl-piperazine-1-carboxylic acid 3-[5-(4-methoxy-phenyl)-pyrimidin-2-ylamino]-phenyl ester can be synthesized by the following procedure. To a solution of 3-[5-(4-methoxy-phenyl)-pyrimidin-2-ylamino]-phenol (from Example 5r) (0.04 mmol) in DMF is added $Cs_2CO_3$ (0.09 mmol) followed by 4-methyl-piperazine-1-carbonyl chloride (0.9 mmol). The reaction is stirred at rt for 12 h. The reaction mixture is directly purified by preparative LCMS (ACN gradient 10-70%) to afford 4-methyl-piperazine-1-carboxylic acid 3-[5-(4-methoxy-phenyl)-pyrimidin-2-ylamino]-phenyl ester as TFA salt (30%). $^1$HNMR (400 MHz, $CD_3OD$) δ 8.67 (s, 2H), 7.82 (t, J=4.0 Hz, 1H), 7.54-7.52 (m, 2H), 7.47-7.46 (m, 1H), 7.30 (T, J=8.0 Hz, 1H), 7.05-7.02 (m, 2H), 6.78-6.75 (m, 1H), 3.84 (s, 3H), 2.98 (s, 3H). MS (m/z) $(M+1)^+$ 420.2.

Example 5t 2-(2-Diethylamino-ethoxy)-4-[5-(4-methoxy-phenyl)-pyrimidin-2-ylamino]-benzoic acid methyl ester

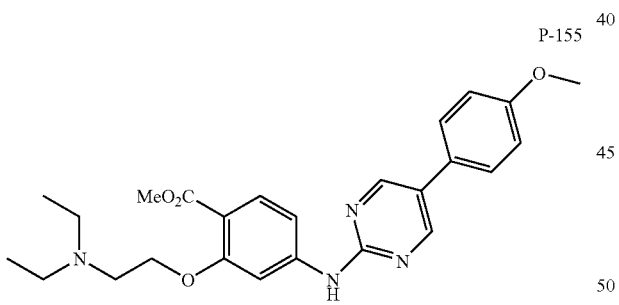

P-155

2-(2-Diethylamino-ethoxy)-4-[5-(4-methoxy-phenyl)-pyrimidin-2-ylamino]-benzoic acid methyl ester can be synthesized by the following procedure. To a solution of 3-(2-diethylamino-ethoxy)-phenylamine (0.2 mmol) (from Example 2h) in anhydrous dioxane (1.5 mL) is added $Pd(OAc)_2$ (0.03 mmol), xantphos (0.03 mmol), potassium tert-butoxide (0.4 mmol) and 2-Cl-5(4-methoxyphenyl)pyrimidine (0.2 mmol) (from Example 4c). The reaction mixture is evacuated twice and heated at 130° C. for 45 min. The reaction mixture is filtered and the filtrate concentrated. Purification by preparative LCMS (ACN gradient 10-40%) and subsequent preparative TLC (DCM:ACN:MeOH:$NH_4OH$=8:1:1:0.1) affords 2-(2-diethylamino-ethoxy)-4-[5-(4-methoxy-phenyl)-pyrimidin-2-ylamino]-benzoic acid methyl ester (20%). MS (m/z) $(M+1)^+$ 451.3.

Example 5u 2-(2-Diethylamino-ethoxy)-4-[5-(4-methoxy-phenyl)-pyrimidin-2-ylamino]-benzoic acid

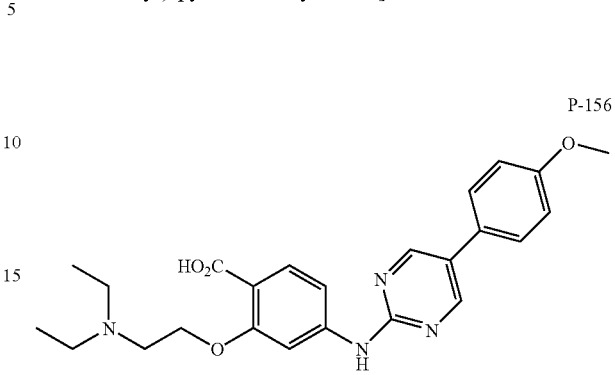

P-156

2-(2-Di ethylamino-ethoxy)-4-[5-(4-methoxy-phenyl)-pyrimidin-2-ylamino]-benzoic acid can be synthesized by the following procedure. To a suspension of 2-(2-diethylamino-ethoxy)-4-[5-(4-methoxy-phenyl)-pyrimidin-2-ylamino]-benzoic acid methyl ester (0.022 mmol) (from example 5t) in a 3:2:1=THF:MeOH:$H_2O$ solution (1 mL) is added 3N LiOH (22 µL) and the mixture is stirred at rt for 12 h then solvent is removed. Purification of the crude by preparative LCMS (ACN gradient 10-50%) affords 2-(2-diethylamino-ethoxy)-4-[5-(4-methoxy-phenyl)-pyrimidin-2-ylamino]-benzoic acid. $^1$HNMR (400 MHz, $CD_3OD$) δ 18.76 (s, 2H), 7.99 (bs, 1H), 7.89 (d, J=8.0 Hz, 2H), 7.57 (d, J=8.0 Hz, 2H), 7.36 (d, J=8.0 Hz, 1H), 7.05 (d, J=8.0 Hz, 2H), 4.53-4.53 (m, 2H), 3.84 (s, 3H), 3.66-3.63 (m, 2H), 3.40-3.37 (m, 4H), 1.38 (t, J=8.0 Hz, 6H). MS (m/z) $(M+1)^+$ 437.1.

Example 5v

2-Methoxy-5-[5-(4-methoxy-phenyl)-pyrimidin-2-ylamino]-phenol

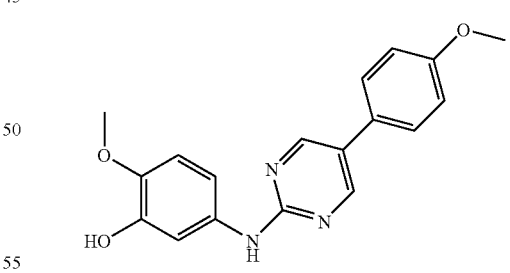

2-Methoxy-5-[5-(4-methoxy-phenyl)-pyrimidin-2-ylamino]-phenol can be synthesized by the following procedure. To a solution of 5-(5-bromo-pyrimidin-2-ylamino)-2-methoxy-phenol (0.34 mmol) (form Example 3g) in DM (1.5 mL) is added 4-methoxy boronic acid (0.41 mmol), $K_2CO_3$ aq. (0.71 mmol) and $Pd(PPh_3)_4$ (0.17 mmol). The reaction is evacuated twice and heated at 85° C. for 30 min. After this time the reaction mixture is diluted with a sat. aq $NH_4Cl$ and extracted with DCM (3×30 mL). The organic layer is washed with brine, dried over Na₂SO₄, concentrated and the crude is purified by HPLC (ACN gradient 20-70%) (67%). MS (m/z) (M+1)⁺ 324.1.

Example 5w

N-(3-(2-(diethylaminoethoxy)-4-methoxyphenyl)-5-(4-methoxyphenyl)pyrimidin-2-amine

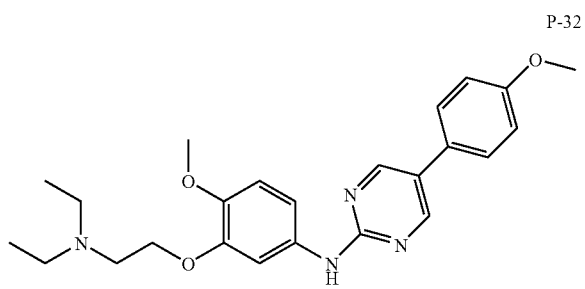

P-32

[3-(2-Diethylamino-ethoxy)-4-methoxy-phenyl]-[5-(4-methoxy-phenyl)-pyrimidin-2-yl]-amine can be synthesized by the following procedure. To a solution of 2-methoxy-5-[5-(4-methoxy-phenyl)-pyrimidin-2-ylamino]-phenol (0.2 mmol) (from Example 5v) in anhydrous DMF (2 mL) is added Cs₂CO₃ (0.28 mmol) and (2-chloro-ethyl)-diethylamine (0.2 mmol). The reaction mixture stirred at 80° C. for 8 h and quenched with water followed by extraction with DCM (3×30 mL). The organic layer is washed with brine, dried over Na₂SO₄ and concentrated. Preparative LCMS purification affords the title compound (78%). MS (m/z) (M+1)⁺ 423.1.

Example 5x 1-(2-{4-[5-(4-Methoxy-phenyl)-pyrimidin-2-ylamino]-phenoxy}-ethyl)-piperidine-4-carboxylic acid

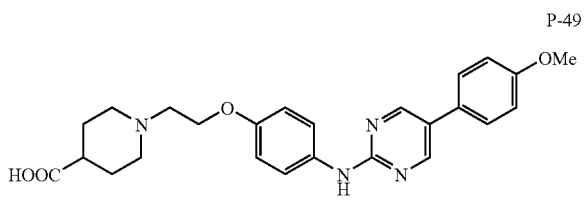

P-49

1-(2-{4-[5-(4-Methoxy-phenyl)-pyrimidin-2-ylamino]-phenoxy}-ethyl)-piperidine-4-carboxylic acid can be synthesized by the following procedure. To a solution of [4-(2-chloro-ethoxy)-phenyl]-[5-(4-methoxy-phenyl)-pyrimidin-2-yl]-amine (0.042 mmol) (from Example 5d) in DMF (1 ml) is added sodium iodide (0.050 mmol) and ethyl isonipecotate (0.084 mmol). The reaction is heated at 120° C. for 12 h. Purification by HPLC (ACN gradient 10-90%) affords 1-(2-{4-[5-(4-methoxy-phenyl)-pyrimidin-2-ylamino]-phenoxy}-ethyl)-piperidine-4-carboxylic acid ethyl ester (50%). MS (m/z) (M+1)⁺ 477.0. This solid is suspended in a 3:2:1=THF:MeOH:H₂O solution (0.5 mL) and 6N LiOH (0.126 mmol) and stirred at rt for 12 h. The reaction mixture is diluted with DMF and purified by HPLC (ACN gradient 10-90%) to afford 1-(2-{4-[5-(4-methoxy-phenyl)-pyrimidin-2-ylamino]-phenoxy}-ethyl)-piperidine-4-carboxylic acid. MS (m/z) (M+1)⁺ 449.2.

Example 5y (4-{2-[4-(2-Chloro-ethoxy)-benzyl]-pyrimidin-5-yl}-benzylamino)-acetic acid tert-butyl ester

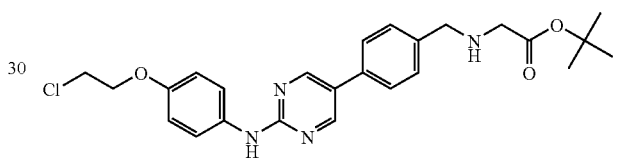

(4-{2-[4-(2-Chloro-ethoxy)-benzyl]-pyrimidin-5-yl}-benzylamino)-acetic acid tert-butyl ester can be synthesized by the following procedure. A mixture of palladium acetate (0.015 mmol), Xantphos (0.018 mmol), potassium tert-butoxide (0.3 mmol), tert-butyl 2-(4-(2-chloropyrimidin-5-yl)benzylamino)acetate (0.15 mmol) (from Example 4b) and 4-(2-chloro-ethoxy)-phenylamine (from Example 2c) (0.45 mmol) in dioxane (2 mL) is heated in the microwave oven at 150° C. for 15 min. Purification by preparative LCMS to afford (4-{2-[4-(2-chloro-ethoxy)-benzyl]-pyrimidin-5-yl}-benzylamino)-acetic acid t-butyl ester as a TFA salt. MS (m/z) (M+1)⁺ 469.2.

Example 5z

{4-[2-(4-{{2-[4-(Tetrahydro-furan-2-carbonyl)-piperazin-1-yl]-ethoxy}-benzyl)-pyrimidin-5-yl]-benzylamino]-acetic acid tert-butyl ester

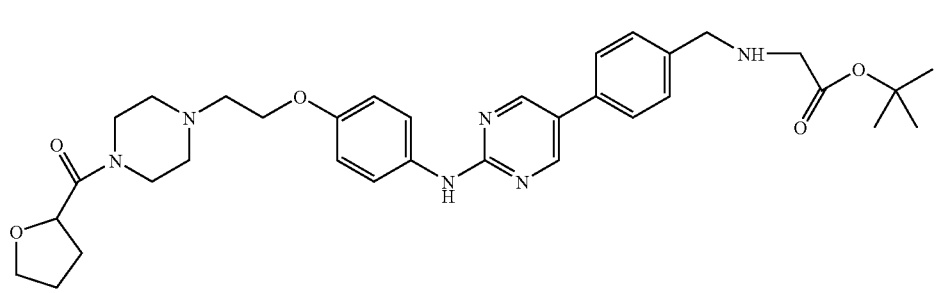

P-147

{4-[2-(4-{{2-[4-(Tetrahydro-furan-2-carbonyl)-piperazin-1-yl]-ethoxy}-benzyl)-pyrimidin-5-yl]-benzylamino]-acetic acid tert-butyl ester can be synthesized by the following procedure. To a solution of (4-{2-[4-(2-chloro-ethoxy)-benzyl]-pyrimidin-5-yl}-benzylamino)-acetic acid tert-butyl ester (0.032 mmol) (from Example 5y) in anhydrous DMF is added sodium iodide (0.0384 mmol) and 1-(tetrahydro-2-furoyl)-piperazine (0.16 mmol). The reaction mixture is heated at 90° C. for 8 h. Purification by preparative LCMS (ACN gradient 10-90%) affords {4-[2-(4-{2-[4-(tetrahydro-furan-2-carbonyl)-piperazin-1-yl]-ethoxy}-benzyl)-pyrimidin-5-yl]-benzylamino}-acetic acid tert-butyl ester (51%). $^1$H NMR (400 MHz, CDCl$_3$) δ 7.66 (d, J=8.0 Hz, 2H), 7.62 (d, J=8.8 Hz, 1H), 7.58 (d, J=8.8 Hz, 2H), 7.51 (d, J=8.0 Hz, 2H), 7.46 (d, J=7.2 Hz, 1H), 6.85 (d, J=9.2 Hz, 2H), 4.3 (m, 4H), 3.85 (m, 4H), 3.76 (m, 3H), 3.52 (m, 4H), 2.35 (m, 4H), 2.0 (m, 4H), 1.48 (s, 9H). MS (m/z) (M+1)$^+$ 617.2.

Example 6

Example 6a

{4-[5-(4-methoxy-phenyl)-pyrimidin-2-ylamino]-phenyl}-methanol

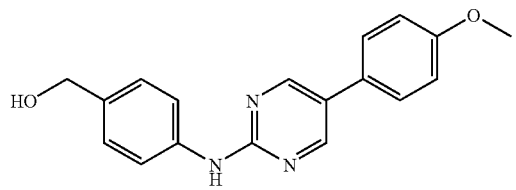

{4-[5-(4-Methoxy-phenyl)-pyrimidin-2-ylamino]-phenyl}-methanol can be synthesized by the following procedure. To a solution of [4-(5-bromo-pyrimidin-2-ylamino)-phenyl]-methanol (7.14 mmol) (from Example 3h) in DMF (56 mL) is added 4-methoxy boronic acid (8.57 mmol), K$_2$CO$_3$ aq (21.4 mmol) and Pd(PPh$_3$)$_4$ (0.714 mmol). The reaction is evacuated twice and heated at 90° C. for 1 h. After this time the reaction mixture is diluted with a sat. aq NH$_4$Cl and extracted with ethyl acetate (3×50 mL). The organic layer is washed with brine, dried over MgSO$_4$ and concentrated. Purification by silica chromatography using a hexane:EtOAc=8:2 affords {4-[5-(4-methoxy-phenyl)-pyrimidin-2-ylamino]-phenyl}-methanol (80%). $^1$H NMR (400 MHz, CDCl$_3$) δ 8.57 (s, 2H), 7.57 (d, J=8 Hz, 2H), 7.45 (bs, 1H), 7.37 (d, J=8.4 Hz, 2H), 7.30 (d, J=8.0 Hz, 2H), 6.94 (d, J=8.4 Hz, 2H), 4.61 (s, 2H), 3.79 (s, 3H). MS (m/z) (M+1) 308.3.

Example 6b

4-[5-(4-Methoxy-phenyl)-pyrimidin-2-ylamino]-benzaldehyde

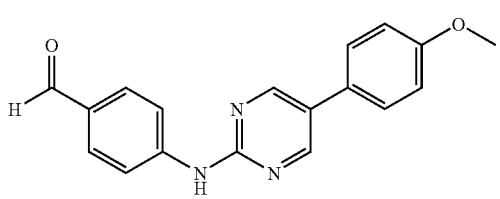

4-[5-(4-Methoxy-phenyl)-pyrimidin-2-ylamino]-benzaldehyde can be synthesized by the following procedure. To a mixture of {4-[5-(4-methoxy-phenyl)-pyrimidin-2-ylamino]-phenyl}-methanol (5.73 mmol) (from Example 5aa) in dioxane is added manganese (IV) oxide (17.2 mmol) and TBAI (0.014 mmol). The reaction mixture is heated in the microwave oven at 130° C. for 30 min. Purification by silica chromatography using hexane:EtOAc=1:1 affords 4-[5-(4-methoxy-phenyl)-pyrimidin-2-ylamino]-benzaldehyde (52%). $^1$H NMR (400 MHz, CDCl$_3$) δ 9.91 (s, 1H), 8.69 (s, 2H), 7.88 (s, 4H), 7.46 (d, J=8.8 Hz, 2H), 7.02 (d, J=8.4 Hz, 2H), 3.87 (s, 3H). MS (m/z) (M+1)$^+$ 306.2.

Example 6c

1-{4-[5-(4-methoxy-phenyl)-pyrimidin-2-ylamino]-benzyl}-piperidine-4-carboxylic acid amide

P-169

1-{4-[5-(4-Methoxy-phenyl)-pyrimidin-2-ylamino]-benzyl}-piperidine-4-carboxylic acid amide can be synthesized by the following procedure. To a solution of 4-[5-(4-Methoxy-phenyl)-pyrimidin-2-ylamino]-benzaldehyde (0.0328 mmol) (from Example 5ab) in dichloromethane (1 mL) is added isonipecotamide (0.0768 mmol) and sodium sulfate. The reaction mixture is stirred at rt for 1 h. Then NaB(OAc)$_3$H (0.0984 mmol) is added and the reaction is stirred for 8 h. Purification by preparative LCMS affords 1-{4-[5-(4-Methoxy-phenyl)-pyrimidin-2-ylamino]-benzyl}-piperidine-4-carboxylic acid amide (55%) as a TFA salt. $^1$H NMR (400 MHz, CD$_3$OD) δ 8.72 (s, 2H), 7.91 (d, J=8.4 Hz, 2H), 7.56 (d, J=8.8 Hz, 2H), 7.44 (d, J=8.8 Hz, 2H), 7.05 (d, J=8.8 Hz, 2H), 4.28 (s, 2H), 3.86 (s, 3H), 3.58 (m, 2H), 3.03 (m, 2H), 2.55 (m, 1H), 2.10 (m, 2H), 1.93 (m, 2H). MS (m/z) (M+1)$^+$ 418.2.

Example 6d (1-{4-[5-(4-Methoxy-phenyl)-pyrimidin-2-ylamino]-benzyl}-piperidin-4-yl)-acetic acid

P-196

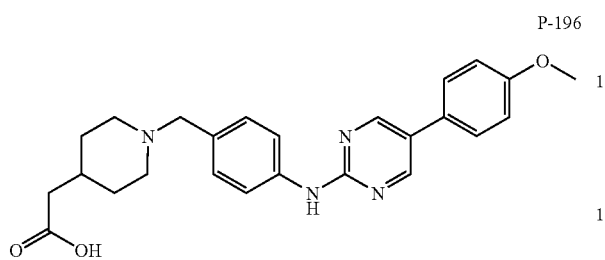

(1-{4-[5-(4-Methoxy-phenyl)-pyrimidin-2-ylamino]-benzyl}-piperidin-4-yl)-acetic acid can be synthesized by the following procedure. A mixture of 4-[5-(4-methoxy-phenyl)-pyrimidin-2-ylamino]-benzaldehyde (0.0656 mmol) (from Example 5ab), 2-(piperidin-4-yl)acetic acid ethyl ester (0.197 mmol) and sodium sulfate in dichloromethane (1 ml) is stirred at rt for 1 h. Then NaB(OAc)$_3$H (0.197 mmol) is added and the reaction is stirred for 8 h. Purification by preparative LCMS affords (1-{4-[5-(4-methoxy-phenyl)-pyrimidin-2-ylamino]-benzyl}-piperidin-4-yl)-acetic acid ethyl ester as a TFA salt (46%). MS (m/z) (M+1)$^+$ 461.3. This solid is suspended in a 3:2:1=THF:MeOH:H$_2$O solution (0.6 mL) and 6N LiOH is added (0.09 mmol). The mixture is stirred at rt for 12 h. The reaction mixture is diluted in DMF and purified by HPLC (ACN gradient 10-90%) to afford (1-{4-[5-(4-methoxy-phenyl)-pyrimidin-2-ylamino]-benzyl}-piperidin-4-yl)-acetic acid (54%). $^1$H NMR (400 MHz, CD$_3$OD) δ 8.70 (s, 2H), 7.88 (d, J=8.0 Hz, 2H), 7.54 (d, J=8.4 Hz, 2H), 7.42 (d, J=8.4 Hz, 2H), 7.03 (d, J=8.4 Hz, 2H), 4.25 (s, 2H), 3.84 (s, 3H), 3.5 (m, 2H), 3.3 (m, 2H), 2.3 (m, 2H), 2.04 (m, 3H), 1.49 (m, 2H). MS (m/z) (M+1)$^+$ 433.2.

Example 6e

2-{4-[5-(4-Methoxy-phenyl)-pyrimidin-2-ylamino]-phenyl}-ethanol

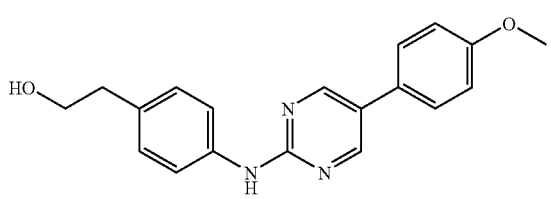

2-{4-[5-(4-Methoxy-phenyl)-pyrimidin-2-ylamino]-phenyl}-ethanol can be synthesized by the following procedure. To a solution of 2-(4-(5-bromopyrimidin-2-ylamino)phenyl)ethanol (0.204 mol) (from Example 31) in DMF (200 mL) is added 4-methoxyphenylboronic acid (0.214 mol), aq K$_2$CO$_3$ (0.408 mol) and Pd(PPh$_3$)$_4$ (172 mmol). The reaction is heated at reflux for 1 h, cooled to rt and the solvent evaporated. The residue is dissolved in dichloromethane, washed with sat. aq NH$_4$Cl (2×200 mL), dried over Na$_2$SO$_4$, and concentrated. Purification by silica chromatography (petroleum ether:EtOAc=1:1) affords 2-{4-[5-(4-Methoxy-phenyl)-pyrimidin-2-ylamino]-phenyl}-ethanol (46%). $^1$HNMR (300 MHz, DMSO-d$_6$) δ 8.59 (s, 2H), 7.57 (d, J=8.4 Hz, 2H), 7.43 (d, J=9.0 Hz, 2H), 7.23 (d, J=8.4 Hz, 2H), 6.99 (d, J=9 Hz, 2H), 3.85 (m, 5H), 2.86 (m, 2H).

Example 6f

Methanesulfonic acid 2-{4-[5-(4-methoxy-phenyl)-pyrimidin-2-ylamino]-phenyl}-ethyl ester

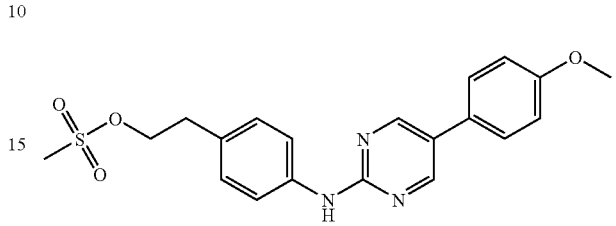

Methanesulfonic acid 2-{4-[5-(4-methoxy-phenyl)-pyrimidin-2-ylamino]-phenyl}-ethyl ester can be synthesized by the following procedure. To a solution of 2-{4-[5-(4-methoxy-phenyl)-pyrimidin-2-ylamino]-phenyl}-ethanol (6.22 mmol) in dichloromethane (30 mL) is added triethylamine (9.33 mmol) and methanesulfonyl chloride (7.47 mmol). The reaction mixture is stirred at rt for 1.5 h. The reaction is diluted with H$_2$O (10 mL) and washed with Na$_2$CO$_3$ solution (3×10 mL). The organic layer is washed with brine, dried over MgSO$_4$ and concentrated to afford methanesulfonic acid 2-{4-[5-(4-methoxy-phenyl)-pyrimidin-2-ylamino]-phenyl}-ethyl ester (99%). $^1$H NMR (400 MHz, CD$_2$Cl$_2$) δ 8.54 (s, 2H), 7.56 (d, J=8.8 Hz, 2H), 7.39 (d, J=8.8 Hz, 2H), 7.29 (bs, 1H), 7.14 (d, J=8.4 Hz, 2H), 6.92 (d, J=8.8 Hz, 2H), 4.31 (t, J=6.8 Hz, 2H), 3.76 (s, 3H), 2.95 (t, J=6.8 Hz, 2H), 2.79 (s, 3H). MS (m/z) (M+1)$^+$ 400.4.

Example 6g 1-(2-{4-[5-(4-Methoxy-phenyl)-pyrimidin-2-ylamino]-phenyl}-ethyl)-piperidine-3-carboxylic acid amide

P-316

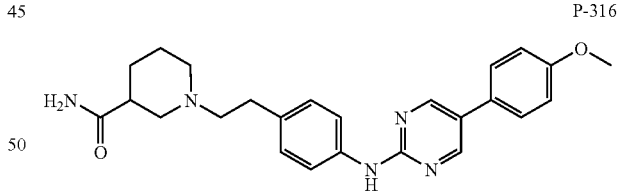

1-(2-{4-[5-(4-Methoxy-phenyl)-pyrimidin-2-ylamino]-phenyl}-ethyl)-piperidine-3-carboxylic acid amide can be synthesized according to the following procedure. To a solution of methanesulfonic acid 2-{4[5-(4-methoxy-phenyl)-pyrimidin-2-ylamino]-phenyl}-ethyl ester (0.050 mmol) in anhydrous DMF is added nipecotamide (0.25 mmol) and heated at 100° C. for 8 h. Purification by preparative LCMS affords 1-(2-{4-[5-(4-methoxy-phenyl)-pyrimidin-2-ylamino]-phenyl}-ethyl)-piperidine-3-carboxylic acid amide (80%). $^1$H NMR (400 MHz, DMSO-d$_6$) δ 9.71 (s, 1H), 8.76 (s, 2H), 7.75 (d, J=8.4 Hz, 2H), 7.64 (d, J=8.8 Hz, 2H), 7.20 (d, J=9.2 Hz, 2H), 7.04 (d, J=8.8 Hz, 2H), 3.80 (s, 3H) 3.55 (m, 2H), 3.3 (m, 2H), 2.95 (m, 4H), 2.6 (m, 1H), 1.95 (m, 2H), 1.70 (m, 2H). MS (m/z) (M+1)$^+$ 432.3.

Example 6h

4-[2-(3-Hydroxymethyl-phenylamino)-pyrimidin-5-yl]-benzoic acid

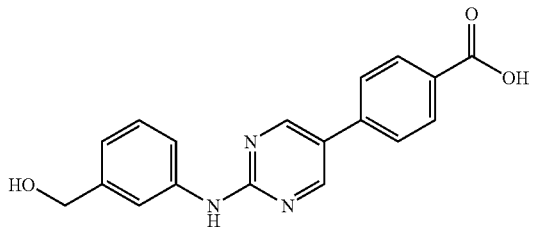

4-[2-(3-Hydroxymethyl-phenylamino)-pyrimidin-5-yl]-benzoic acid can be synthesized according to the following procedure. To a solution of 3-amino benzyl alcohol (8.1 mmol) in NMP (8 mL), in a microwave vial, is added 4-(2-chloro-pyrimidin-5-yl)-benzoic acid (8.1 mmol) (from Example 4d) and p-TSA (5.2 mmol). The vial is evacuated twice and then heated in a microwave oven at 210° C. for 15 min. The reaction mixture is quenched with water, the precipitated solid is filtered, washed with additional water, then EtOAc and dried under vacuum to afford 4-[2-(3-hydroxymethyl-phenylamino)-pyrimidin-5-yl]-benzoic acid (68%). $^1$H NMR (400 MHz, DMSO-$d_6$) δ 9.89 (s, 1H), 8.92 (s, 2H), 8.03-8.01 (m, 2H), 7.88-7.86 (m, 2H), 7.76 (b.s, 1H), 7.70-68 (m, 1H), 7.26-7.24 (m, 1H) 6.94-6.92 (m, 1H), 4.49 (m, 2H). MS (m/z) (M+1)$^+$ 322.2.

Example 6i

{4-[2-(3-Hydroxymethyl-phenylamino)-pyrimidin-5-yl]-benzoylamino}-acetic acid tert-butyl ester

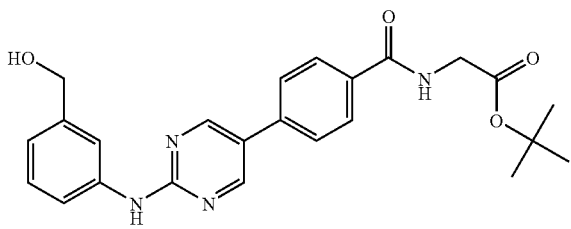

{4-[2-(3-Hydroxymethyl-phenylamino)-pyrimidin-5-yl]-benzoylamino}-acetic acid tert-butyl ester can be synthesized according to the following procedure. A solution of 4-[2-(3-hydroxymethyl-phenylamino)-pyrimidin-5-yl]-benzoic (from Example 5ah) (1.7 mmol), HATU (2.39 mmol), diisopropylethylamine (2.5 mmol), and glycine t-butyl ester in anhydrous DMF, is stirred at rt for 8 h. After this time the reaction mixture is purified by HPLC (ACN gradient 10-90) to afford 4-[2-(3-hydroxymethyl-phenylamino)-pyrimidin-5-yl]-benzoylamino}-acetic acid tert-butyl ester (39%). MS (m/z) (M+1)$^+$ 435.1.

Example 6j

{4-[2-(3-Formyl-phenylamino)-pyrimidin-5-yl]-benzoylamino}-acetic acid tert-butyl ester

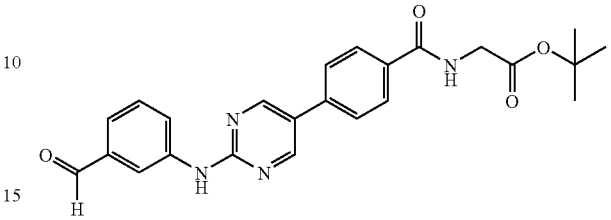

{4-[2-(3-Formyl-phenylamino)-pyrimidin-5-yl]-benzoylamino}-acetic acid tert-butyl ester can be synthesized by the following procedure. To a mixture of {4-[2-(3-hydroxymethyl-phenylamino)-pyrimidin-5-yl]-benzoylamino}-acetic acid tert-butyl ester (0.39 mmol) (from example 5ai) in dioxane is added manganese (IV) oxide (1.95 mmol) and TBAI (0.014 mmol). The reaction mixture is heated in the microwave oven at 150° C. for 30 min. The reaction mixture is filtered and the filtrated is concentrated under reduced pressure to afford {4-[2-(3-formyl-phenylamino)-pyrimidin-5-yl]-benzoylamino}-acetic acid tert-butyl ester (71%). MS (m/z) (M+1)$^+$ 433.2.

Example 6k

{4-[2-(3-Pyrrolidin-1-ylmethyl-phenylamino)-pyrimidin-5-yl]-benzoylamino}-acetic acid tert-butyl ester

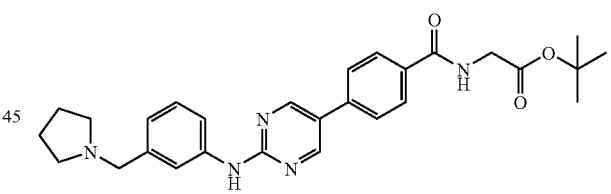

P-201

{4-[2-(3-Pyrrolidin-1-ylmethyl-phenylamino)-pyrimidin-5-yl]-benzoylamino}-acetic acid tert-butyl ester can be synthesized by the following procedure. To a solution {4-[2-(3-formyl-phenylamino)-pyrimidin-5-yl]-benzoylamino}-acetic acid tert-butyl ester (0.046 mmol) (from Example 5aj) in dichloromethane (1 mL) is added pyrrolidine (0.138 mmol) and sodium sulfate. The reaction mixture is stirred at rt for 1 h. Then NaB(OAc)$_3$H (0.138 mmol) is added and the reaction is stirred for 8 h. After this time the reaction mixture is purified by preparative LCMS to afford {4-[2-(3-pyrrolidin-1-ylmethyl-phenylamino)-pyrimidin-5-yl]-benzoylamino}-acetic acid tert-butyl ester (55%) as a TFA salt. $^1$H NMR (400 MHz, DMSO-$d_6$) δ 10.05 (s, 1H), 8.94-8.92 (m, 3H), 7.99-7.85 (m, 6H), 7.41 (m, 1H), 7.14-7.12 (m, 1H), 4.35 (d, J=4.0 Hz, 2), 3.93 (d, J=4.0 Hz, 2H), 3.41-3.40 (m, 2H), 3.15-3.10 (m, 2H), 2.15-2.10 (m, 2H), 1.90-1.89 (m, 2H), 1.43 (s, 9H). MS (m/z) (M+1)$^+$ 488.3.

Example 6l

4-Methyl-piperazine-1-carboxylic acid 4-[5-(4-methoxy-phenyl)-pyrimidin-2-ylamino]-phenyl ester

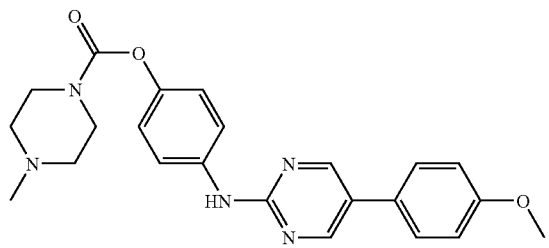

P-111

4-Methyl-piperazine-1-carboxylic acid 4-[5-(4-methoxy-phenyl)-pyrimidin-2-ylamino]-phenyl ester can be synthesized by the following procedure. A suspension of 4-methyl-piperazine-1-carboxylic acid 4-amino-phenyl ester (0.166 mmol) (from example 31), 4-methoxy phenyl boronic acid (0.199 mmol), $K_2CO_3$ (0.36 mmol) and $Pd(PPh_3)_4$ (0.0166 mmol) in a 5:1 mixture of $DME:H_2O$ (1.5 mL) is heated at 80° C. for 10 min. The reaction mixture is cooled to rt, diluted with dichloromethane, washed with $NH_4Cl$, and dried under reduced pressure. The crude is purified by a short silica column using a mixture 9.5:0.5:0.1=$DCM:MeOH:NH_4OH$ to afford 4-methyl-piperazine-1-carboxylic acid 4-[5-(4-methoxy-phenyl)-pyrimidin-2-ylamino]-phenyl ester as white powder (86%). $^1H$ NMR (400 MHz, $CDCl_3$) δ 8.53 (s, 2H), 7.57 (d, J=8.0 Hz, 2H), 7.37 (d, J=8.0 Hz, 2H), 7.12 (b.s, 1H), 7.0.2 (m, 2H), 6.95 (m, 2H), 3.79 (s, 3H), 3.71-3.69 (m, 4H), 2.51-2.50 (m, 4H). MS (m/z) (M+1)$^+$ 420.2.

A methanolic solution of this solid is treated with 1 equivalent of $MeSO_3H$ and lyophilized to afford the correspondent mesylate salt as yellow solid in quantitative yield. $^1H$ NMR (400 MHz, $CD_3OD$) δ 8.48 (s, 2H), 7.55-7.52 (m, 2H), 7.35-7.33 (m, 2H), 6.93-6.90 (m, 2H), 6.85-6.83 (m, 2H), 4.30-4.28 (m, 2H), 3.64 (s, 3H), 3.41-3.40 (m, 2H), 2.94-2.91 (m, 4H), 2.79 (s, 3H). MS (m/z) (M+1)$^+$ 420.2.

Example 6m

N-(3-(2-(diethylaminoethylphenyl)-5-(4-methoxyphenylpyrimidin-2-amine

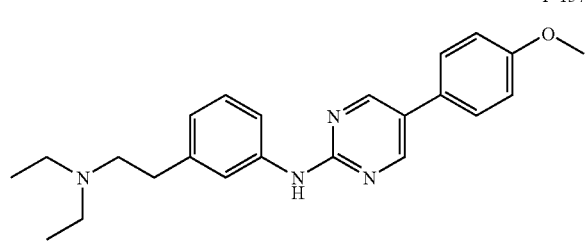

P-157

N-(3-(2-(diethylamino)ethyl)phenyl)-5-(4-methoxyphenyl)pyrimidin-2-amine can be prepared by the following procedure. To a mixture of 2-chloro-5-(4-methoxy-phenyl)-pyrimidine (0.40 mmol) (from Example 4c) and 3-(2-(diethylamino)ethyl)benzenamine (0.40 mmol) (from example 21) in 0.5 mL of 1,4-dioxane is added p-TSA monohydrate (1.2 mmol). The reaction mixture is heated at 90° C. overnight. The crude mixture is purified by preparative LCMS to afford N-(3-(2-(diethylamino)ethyl)phenyl)-5-(4-methoxyphenyl)pyrimidin-2-amine as a TFA salt. $^1H$ NMR (400 MHz, $CD_3OD$) δ 12.24 (s, 1H), 10.95 (s, 1H), 8.67 (s, 2H), 7.50-7.60 (m, 2H), 7.26-7.44 (m, 3H), 7.04-7.12 (m, 1H), 6.96-7.02 (m, 2H), 3.81 (s, 3H), 3.42 (m, 2H), 3.04-3.26 (m, 6H), 1.39 (m, 6H). MS (m/z) (M+1)$^+$ 377.2.

Example 6n 3-(5-(4-methoxyphenyl)pyrimidin-2-ylamino)benzyl 4-methylpiperazine-1-carboxylate

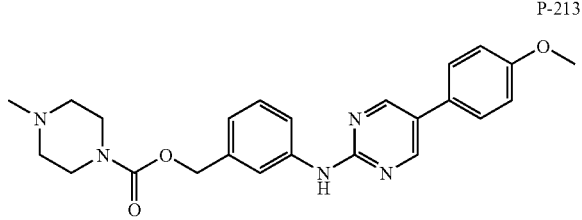

P-213

3-(5-(4-methoxyphenyl)pyrimidin-2-ylamino)benzyl 4-methylpiperazine-1-carboxylate can be prepared by the following procedure. To a mixture of 2-chloro-5-(4-methoxyphenyl)-pyrimidine (0.40 mmol) (from Example 4c) and 3-aminobenzyl 4-methylpiperazine-1-carboxylate (0.40 mmol) (from Example 2j) in 1,4-dioxane (0.5 mL) is added p-TSA monohydrate (1.2 mmol). The reaction mixture is heated at 90° C. overnight. The crude mixture is purified by preparative LCMS to afford 3-(5-(4-methoxyphenyl)pyrimidin-2-ylamino)benzyl 4-methylpiperazine-1-carboxylate as a TFA salt. $^1H$ NMR (400 MHz, $CD_3OD$) δ 11.15 (s, 1H), 8.61 (s, 2H), 7.72-7.77 (m, 1H), 7.30-7.38 (m, 3H), 7.04-7.07 (m, 1H), 6.95-7.00 (m, 2H), 4.20 (s, 2H), 3.70-4.10 (m, 4H), 3.80 (s, 3H), 3.30-3.52 (m, 4H), 2.75 (s, 3H). MS (m/z) (M+1)$^+$ 434.2.

Example 6o (4-{2-[4-(2-Diethylamino-ethoxy)-phenylamino]-pyrimidin-5-yl}-benzylamino)-acetic acid tert-butyl ester

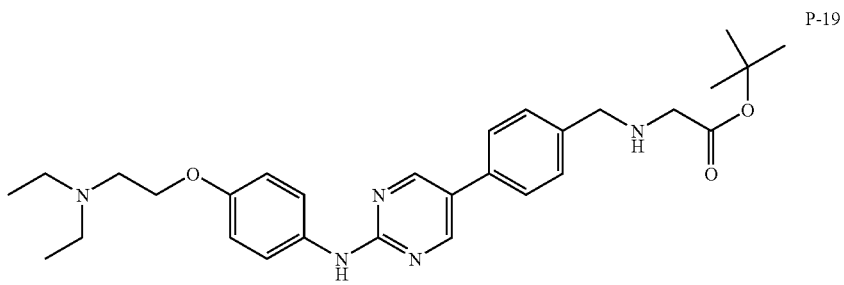

P-19

(4-{2-[4-(2-Diethylamino-ethoxy)-phenylamino]-pyrimidin-5-yl}-benzylamino)-acetic acid tert-butyl ester can be prepared by the following procedure. A mixture of 4-{2-[4-(2-diethylamino-ethoxy)-phenylamino]-pyrimidin-5-yl}-benzaldehyde (from Example 5f) (0.02 mol), triethylamine (0.06 mmol) and tert-butyl glycine ester (0.04 mmol) in THF (0.1 mL) is stirred at ambient temperature for 0.5 h in the presence of excess anhydrous $Na_2SO_4$. $NaBH(OAc)_3$ (0.1 mmol) is added and the mixture is further stirred for 1 h. MeOH is added and the resultant crude mixture is purified by preparative LCMS to yield the title compound. $^1$H NMR (400 MHz, $D_2O$) δ 8.68 (s, 2H), 7.71 (d, J=8.4 Hz, 2H), 7.58 (d, J=8.3 Hz, 2H), 7.42 (d, J=9 Hz, 2H), 7.07 (d, J=9.1 Hz, 2H), 4.4 (d, J=5.1 Hz, 2H), 4.34 (s, 2H), 3.91 (s, 2H), 3.62 (t, J=4.8 Hz, 2H), 3.34 (m, 4H), 1.46 (s, 9H), 1.34 (t, J=7.3, Hz, 6H). MS (m/z) (M+1)$^+$ 506.3.

Example 6p

[4-(2-Dimethylamino-ethyl)-phenyl]-[5-(4-methoxy-phenyl)-pyrimidin-2-yl]-amine

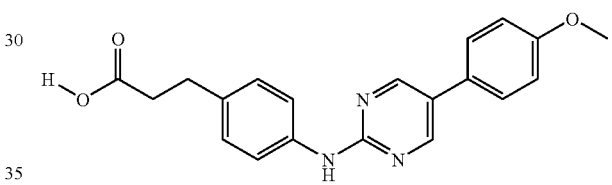

P-116

[4-(2-Dimethylamino-ethyl)-phenyl]-[5-(4-methoxy-phenyl)-pyrimidin-2-yl]-amine can be prepared by the following procedure. A mixture of 4-(2-dimethylamino-ethyl)-phenylamine (0.1 mmol), p-TSA (0.05 mmol) and 2-chloro-5-(4-methoxy-phenyl)-pyrimidine (from Example 4c) (0.1 mmol) in NMP (0.2 mL) is heated by microwave at 215° C. for 15 min to afford the crude mixture which is purified by preparative LCMS to yield the title compound. $^1$H NMR (400 MHz, CDCl$_3$) δ 12.1 (s, 1H), 11.5 (s, 1H), 8.67 (s, 2H), 7.63 (d, J=8.3 Hz, 1H), 7.41 (d, J=8.6 Hz, 2H), 7.19 (d, J=8.3 Hz, 2H), 7.04 (d, J=8.7 Hz, 2H), 3.87 (s, 3H), 3.01 (m, 2H), 2.82 (s, 6H), 2.09 (m, 2H). MS (m/z) (M+1)$^+$ 349.2.

Example 6q

3-{4-[5-(4-methoxy-phenyl)-pyrimidin-2-ylamino]-phenyl}-propionic acid

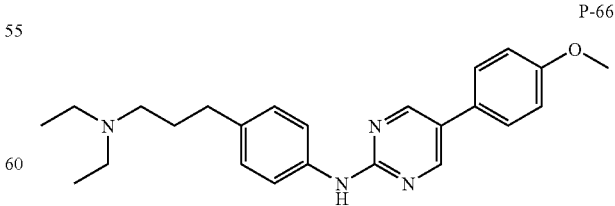

3-{4-[5-(4-methoxy-phenyl)-pyrimidin-2-ylamino]-phenyl}-propionic acid can be prepared by the following procedure. 3-(4-Amino-phenyl)-propionic acid (1.0 mmol), p-TSA (0.25 mmol) and 2-chloro-5-(4-methoxy-phenyl)-pyrimidine (from Example 4c) (1.0 mmol) are dissolved in NMP (2 mL) and heated by microwave at 215° C. for 15 min to afford the crude 3-{4-[5-(4-methoxy-phenyl)-pyrimidin-2-ylamino]-phenyl}-propionic acid. MS (m/z) (M+1)$^+$ 350.2.

Example 6r

[4-(3-Diethylamino-propyl)-phenyl]-[5-(4-m[ethoxy-phenyl)-pyrimidin-2-yl]-amine

P-66

4-(3-Diethylamino-propyl)-phenyl]-[S-(4-methoxy-phenyl)-pyrimidin-2-yl]-amine can be prepared by the following procedure. Diethylamine (10 mmol), EDC (25 mmol) and DMAP (0.1 mmol) are dissolved in dichloromethane (3 mL)

and added to the crude 3-{4-[5-(4-methoxy-phenyl)-pyrimidin-2-ylamino]-phenyl}-propionic acid dissolved in NMP (from example 5ao) at rt. After 3 h, sat. aq NH₄Cl is added and the mixture is extracted with EtOAc. The combined extracts are dryed over anhydrous Na₂SO₄ and solvent is removed. Purification by preparative HPLC yields N,N-diethyl-3-{4-[5-(4-methoxy-phenyl)-pyrimidin-2-ylamino]-phenyl}-propionamide.

N,N-Diethyl-3-{4-[5-(4-methoxy-phenyl)-pyrimidin-2-ylamino]-phenyl}-propionamide (0.1 mmol) is heated at reflux with lithium aluminium hydride in THF (1.0 M, 1.0 mmol) for 4 h. MeOH is added at rt to quench the reaction. Purification by preparative LCMS affords the title compound. $^{1}$H NMR (400 MHz, CDCl₃) δ 12.4 (s, 1H), 8.62 (s, 2H), 8.59 (s, 1H), 7.61 (d, J=8.3 Hz, 2H), 7.43 (d, J=8.6 Hz, 2H), 7.17 (d, J=8.2 Hz, 2H), 7.02 (d, J=8.6 Hz, 2H), 3.86 (s, 3H), 3.1 (m, 4H), 3.96 (s, 1H), 3.0 (m, 2H), 2.71 (t, J=7.2, 2H), 2.06 (m, 2H), 1.27 (t, J=7.3 Hz, 6H). MS (m/z) (M+1)$^{+}$ 391.2.

Example 6s

Synthesis of 4-{2-[4-(2-diethylamino-ethoxy)-phenylamino]-pyrimidin-5-yl}-2-fluoro-benzoic acid

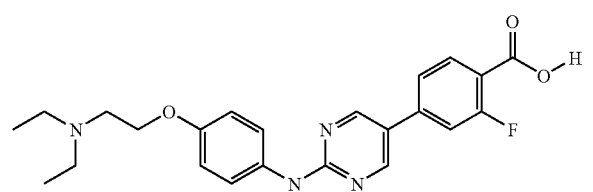

4-{2-[4-(2-Diethylamino-ethoxy)-phenylamino]-pyrimidin-5-yl}-2-fluoro-benzoic acid can be prepared by the following procedure. (5-Bromo-pyrimidin-2-yl)-[4-(2-diethylamino-ethoxy)-phenyl-amine (from Example 3a) (1 mmol), Pd(PPh₃)₄ (0.1 mmol), 3-fluoro-4-methoxycarbonyl-benzeneboronic acid (1.5 mmol) are dissolved in 2 mL of DMF. After purging with nitrogen, Na₂CO₃ (0.4 mL of a 5M aq solution) is added and the mixture is heated in the microwave at 120° C. for 20 min. The resultant mixture is diluted with EtOAc and water. After extraction with EtOAc and drying with anhydrous Na₂SO₄, the solvent is removed to afford the crude mixture which is purified by preparative HPLC to yield 4-{2-[4-(2-diethylamino-ethoxy)-phenylamino]-pyrimidin-5-yl}-2-fluoro-benzoic acid. MS (m/z) (M+1)$^{+}$ 425.2.

Example 6t

Synthesis of tert-butyl 2-(4-(2-(4-(2-(diethylamino)ethoxy)phenylamino)pyrimidin-5-yl)-2-fluorobenzamido)acetate

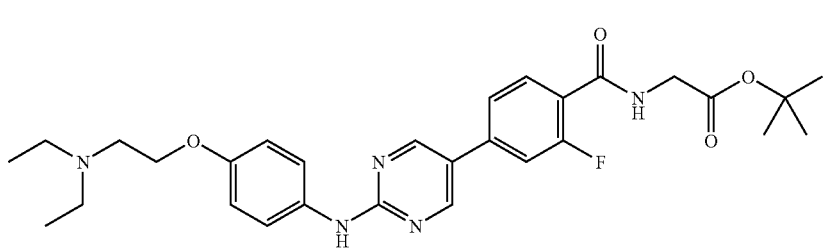

Tert-butyl 2-(4-(2-(4-(2-(diethylamino)ethoxy)phenylamino)pyrimidin-5-yl)-2-fluorobenzamido)-acetate can be prepared by the following procedure. 4-{2-[4-(2-diethylamino-ethoxy)-phenylamino]-pyrimidin-5-yl}-2-fluoro-benzoic acid (from Example 5) (0.05 mmol), HATU (0.075 mmol), amino-acetic acid tert-butyl ester (0.05 mmol) and diisopropylethylamine (0.1 mmol) in DMF (0.1 mL) are stirred at rt for 2 h. Purification by preparative LCMS affords the title compound. $^{1}$H NMR (400 MHz, CDCl₃) δ 11.8 (s, 1H), 10.6 (s, 1H), 8.72 (s, 2H), 8.25 (t, J=8.1 Hz, 1H), 7.6 (d, J=4.1 Hz, 2H), 7.41 (t, J=8.1 Hz, 1H), 7.28 (m, 1H), 6.95 (d, J=8.7 Hz, 2H), 4.52 (s, 2H), 4.2 (d, J=4.6 Hz, 2H), 3.5 (s, 2H), 3.3 (m, 4H), 2.73 (m, 2H), 1.52 (s, 9H), 1.46 (t, J=7.1 Hz, 6H). MS (m/z) (M+1)$^{+}$ 538.3.

Example 6u

N'-(4-{2-[4-(2-Diethylamino-ethoxy)-phenylamino]-pyrimidin-5-yl}-benzoyl)-hydrazinecarboxylic acid tert-butyl ester

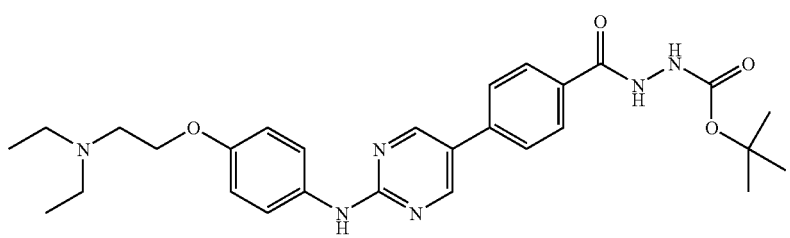

N'-(4-{2-[4-(2-Diethylamino-ethoxy)-phenylamino]-pyrimidin-5-yl}-benzoyl)-hydrazinecarboxylic acid tert-butyl ester can be prepared by the following procedure. 4-{2-[4-(2-Diethylamino-ethoxy)-phenylamino]-pyrimidin-5-yl}-benzoic acid (from Example 5o) (0.3 mmol), hydrazinecarboxylic acid tert-butyl ester (0.36 mmol), EDC (0.42 mmol) and DMAP (0.03 mmol) in DMF:THF (0.5:0.5 mL) are stirred at rt for 1 h. The resultant mixture is diluted with EtOAc and water. After further extraction with EtOAc and drying of the combined organic phases with anhydrous $Na_2SO_4$, the solvent is removed to afford the crude mixture which is purified by silica chromatography (10% MeOH in DCM) to yield the title compound. $^1$H NMR (400 MHz, CDCl$_3$) δ 8.6 (s, 2H), 7.89 (d, J=8.3 Hz, 1H), 7.56 (d, J=8.3 Hz, 2H), 7.51 (d, J=9 Hz, 2H), 7.22 (s, 1H), 6.92 (d, J=9 Hz, 2H), 4.1 (t, J=6.2 Hz, 2H), 3.02 (s, 1M), 2.91 (t, J=6.2 Hz, 2H), 2.68 (dd, J=14.3, 7.1 Hz, 4H), 1.51 (s, 9H), 1.1 (t, J=7.1 Hz, 6H). MS (m/z) (M+1)$^+$ 521.2.

Example 6v

4-{2-[4-(2-Diethylamino-ethoxy)-phenylamino]-pyrimidin-5-yl}-N-phenoxy-benzamide

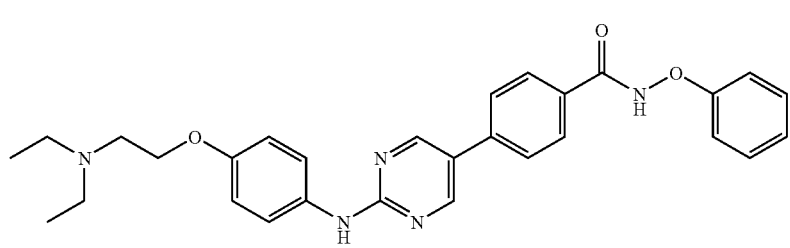

P-7

4-{2-[4-(2-Diethylamino-ethoxy)-phenylamino]-pyrimidin-5-yl}-N-phenoxy-benzamide can be prepared by the following procedure. 4-{2-[4-(2-Diethylamino-ethoxy)-phenylamino]-pyrimidin-5-yl}-benzoic acid from (Example 5o) (0.03 mmol), o-phenyl-hydroxylamine (0.04 mmol), HATU (0.04 mmol) and diisopropylethylamine (0.1 mmol) in DMF (0.1 mL) are stirred at rt for 1 h. The resultant mixture is purified by preparative LCMS to yield title compound. $^1$H NMR (400 MHz, CDCl$_3$) δ 9.28 (s, 1H), 8.68 (d, J=7.2 Hz, 2H), 8.15 (d, J=8.3 Hz, 1H), 8.01 (d, J=8.3 Hz, 1H), 7.57-7.6 (m, 5H), 7.35 (dd, J=8.6, 7.5 Hz, 1H), 7.2 (d, J=7.8 Hz, 1H), 7.08 (t, J=7.3 Hz, 1H), 6.91 (dd, J=8.9, 5.3 Hz, 2H), 4.39 (dd, J=9.1, 4.6 Hz, 2H), 3.96 (s, 1H), 3.52 (dd, J=8.7, 3.7 Hz, 2H), 3.3 (m, 4H), 1.39 (dt, J=7.3, 1.3 Hz, 6H). MS (m/z) (M+1)$^+$ 498.2.

Example 6w 5-(4-methoxyphenyl)-N-(3-nitrophenyl)pyrimidin-2-amine

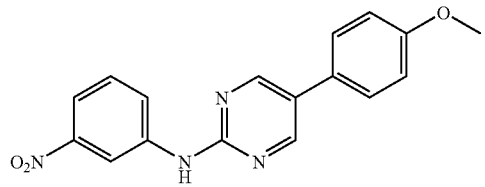

5-(4-methoxyphenyl)-N-(3-nitrophenyl)pyrimidin-2-amine can be prepared by the following procedure. 2-Chloro-5-(4-methoxy-phenyl)-pyrimidine (3.0 mmol) (from Example 4c), 3-nitroaniline (3.0 mmol) and p-TSA (0.9 mmol) are dissolved in NMP (3 mL) and heated at 215° C. for 15 min by microwave. The reaction mixture is partitioned with NaHCO$_3$/EtOAc. The organic layer is washed with brine, dried over magnesium sulfate, filtered and the solvent is removed. The crude product is purified by silica chromatography with hexanes:EtOAc (2:1) as the eluant (31%). MS (m/z) (M+1)$^+$ 323.2.

Example 6x

N1-(5-(4-methoxyphenyl)pyrimidin-2-yl)benzene-1,3-diamine

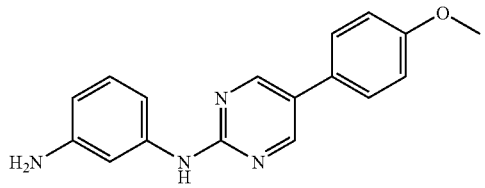

N1-(5-(4-methoxyphenyl)pyrimidin-2-yl)benzene-1,3-diamine can be prepared by the following procedure. To a solution 5-(4-methoxyphenyl)-N-(3-nitrophenyl)pyrimidin-2-amine (0.9 mmol) (from Example 5au) in EtOH (50 mL) is added Pd (10% on carbon, 50% wet, 10% weight). The reaction vessel is evacuated and backfilled with hydrogen. The contents are stirred under a hydrogen atmosphere for 8 h, filtered through celite and reduced to dryness (70%). MS (m/z) (M+1)$^+$ 293.2.

Example 6y

N-(3-(5-(4-methoxyphenylpyrimidin-2-ylamino)phenyl)-4-methylpiperazine-1-carboxamide

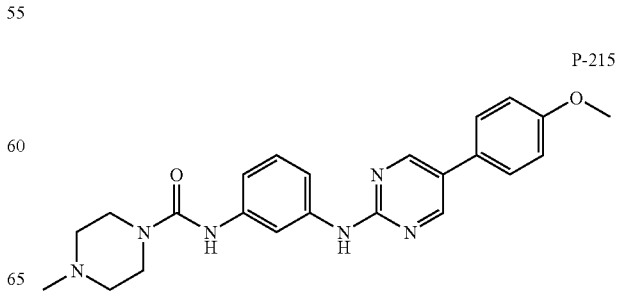

P-215

N-(3-(5-(4-methoxyphenyl)pyrimidin-2-ylamino)phenyl)-4-methylpiperazine-1-carboxamide can be prepared by the following procedure. To a solution of N1-(5-(4-methoxyphenyl)pyrimidin-2-yl)benzene-1,3-diamine (0.34 mmol) (From Example 5av) in THF (7 mL) are added diisopropylethylamine (0.75 mmol) and triphosgene (0.10 mmol). After stirring for 30 min at rt, 1-methylpiperazine (1.02 mmol) is added and stirring is continued for 1 h. The reaction is partitioned between dichloromethane and water. The organic layer is washed with brine, dried over magnesium sulfate, filtered and the solvent is removed. The crude product is crystallized from dichloromethane to afford the desired product as a white crystalline solid (50%). $^1$H NMR (400 MHz, DMSO-$d_6$) δ 9.63 (s, 1H), 8.76 (s, 2H), 8.49 (s, 1H), 7.83 (t, J=2.0 Hz, 1H), 7.64 (d, J=8.4 Hz, 2H), 7.37 (d, J=7.0 Hz, 1H), 7.13 (t, J=8.0 Hz, 1H), 7.05 (d, J=7.0 Hz, 1H), 7.04 (d, J=8.0 Hz, 2H), 3.80 (s, 3H), 3.44 (bs, 4H), 2.33 (bs, 4H), 2.22 (s, 3H). MS (m/z) (M+1)$^+$ 419.2.

Example 6z-1

Methyl 1-(4-(5-(4-methoxyphenyl)pyrimidin-2-ylamino)phenethyl)piperidine-4-carboxylate

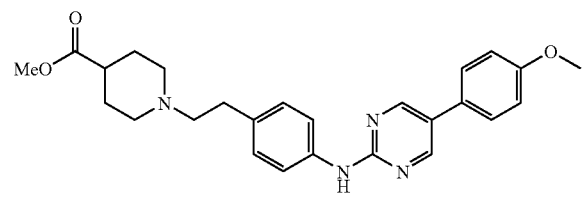

P-24

Methyl 1-(4-(5-(4-methoxyphenyl)pyrimidin-2-ylamino)phenethyl)piperidine-4-carboxylate can be prepared by the following procedure. A solution of methanesulfonic acid 2-{4-[5-(4-methoxy-phenyl)-pyrimidin-2-ylamino]-phenyl}-ethyl ester (10.0 mmol) (from Example 5af) and methyl piperidine-4-carboxylate (50.0 mmol) in DMF (60 mL) is heated at 100° C. for 8 h. The reaction is cooled to rt and poured into water (600 mL). The white precipitate is filtered, washed with water and air dried. The crude precipitate is purified by silica chromatography with dichloromethane methanol (3%) as eluant (77%). $^1$H NMR (400 MHz, DMSO-$d_6$) δ 9.63 (s, 1H), 8.76 (s, 2H), 7.67 (d, J=8.4 Hz, 2H), 7.64 (d, J=8.4 Hz, 2H), 7.13 (d, J=8.2 Hz, 2H), 7.04 (d, J=8.2 Hz, 2H), 3.80 (s, 3H), 3.60 (s, 3H), 2.86 (bd, J=10.0 Hz, 2H), 2.67 (bt, J=8.4 Hz, 2H), 2.41 (dt, J=8.4 Hz, 1H), 2.31 (m, 1H), 2.01 (bt, J=10.0 Hz, 2H), 1.81 (bd, J=10.0 Hz, 2H), 1.57 (m, 2H). MS (m/z) (M+1)$^+$ 447.4.

Example 6z-2

1-(4-(5-(4-methoxyphenyl pyrimidin-2-ylamino)phenethyl)piperidine-4-carboxylic acid hydrochloride

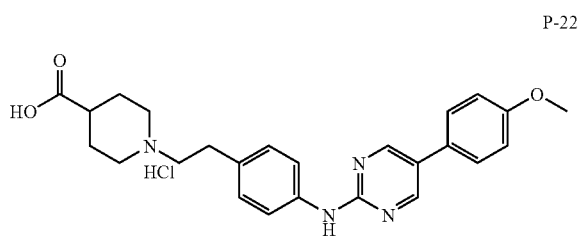

P-22

1-(4-(5-(4-methoxyphenyl)pyrimidin-2-ylamino)phenethyl)piperidine-4-carboxylic acid hydrochloride can be prepared by the following procedure. To a solution of methyl 1-(4-(5-(4-methoxyphenyl)pyrimidin-2-ylamino)phenethyl)piperidine-4-carboxylate (3.9 mmol) (from Example 5ay) in methanol:THF:water=3:2:1 (38 mL total) is added LiOH (2.0 mL of a 6N solution) and the mixture is stirred at rt for 12 h. The reaction is reduced to 50% of its volume, water (100 mL) is added and the contents are neutralized with 3M HCl. The resulting white precipitate is filtered, triturated repeatedly with acetonitrile, and dried under vacuum (96%). The white precipitate is suspended in acetonitrile (30 mL) and treated with HCl (3.7 mL of a 4M solution in dioxane). After stirring for 1 h the reaction is reduced to dryness and dried under vacuum to yield a bright yellow precipitate (99%). $^1$H NMR (400 MHz, DMSO-$d_6$) δ 10.71 (bs, 1H), 9.76 (s, 1H), 8.78 (s, 2H), 7.75 (d, J=8.4 Hz, 2H), 7.65 (d, J=8.4 Hz, 2H), 7.20 (d, J=8.2 Hz, 2H), 7.04 (d, J=8.2 Hz, 2H), 3.80 (2, 3H), 3.57 (m, 2H), 3.21 (m, 2H), 3.01 (m, 4H), 2.06 (m, 2H), 1.92 (m, 2H). MS (m/z) (M+1)$^+$ 469.1.

Example 7

Example 7a 2-(methoxycarbonyl)-5-(5-(4-methoxyphenyl)pyrimidin-2-ylamino)phenyl 4-methylpiperazine-1-carboxylate

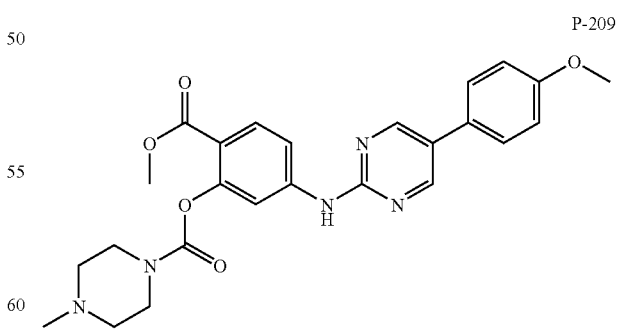

P-209

2-(methoxycarbonyl)-5-(5-(4-methoxyphenyl)pyrimidin-2-ylamino)phenyl 4-methylpiperazine-1-carboxylate can be prepared by the following procedure. To a flask under nitrogen atmosphere containing dry dioxane (8 mL) are added Pd(OAc)$_2$ (0.1 mmol), Xantphos (0.12 mmol) followed by 2-(methoxycarbonyl)-5-aminophenyl 4-methylpiperazine-1-carboxylate (1 mmol) (from Example 21), 2-chloro-5-(4-methoxy-phenyl)-pyrimidine (1.5 mmol) (from Example 4c) and KOtBu (1.5 mol). The reaction mixture is heated at 90° C. for 2 h and the crude is purified by preparative LCMS to yield 2-(methoxycarbonyl)-5-(5-(4-methoxyphenyl)pyrimidin-2-ylamino)phenyl 4-methylpiperazine-1-carboxylate (76%). MS (m/z) (M+1)$^+$ 478.2.

Example 7b 2-(2-Diethylamino-ethoxy)-5-[5-(4-methoxy-phenyl)-pyrimidin-2-ylamino]-benzoic acid ethyl ester

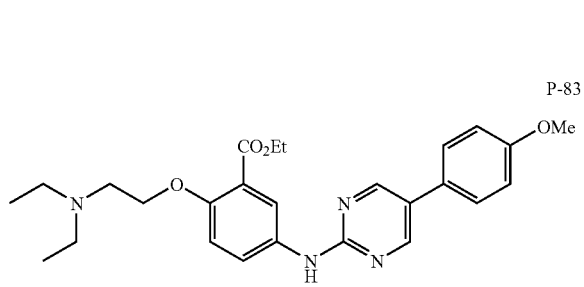

P-83

2-(2-Diethylamino-ethoxy)-5-[5-(4-methoxy-phenyl)-pyrimidin-2-ylamino]-benzoic acid ethyl ester synthesized by the following procedure. A 15 ml flask is charged with 5-amino-2-(2-diethylamino-ethoxy)-benzoic acid ethyl ester (0.19 mmol), 2-chloro-5-(4-methoxy-phenyl)-pyrimidine (0.19 mmol), p-TSA (0.22 mmol) and NMP (2 mL). The flask is evacuated and irradiated in a microwave oven at 210° C. for 15 min. The reaction mixture is diluted with water and extracted with DCM (5×50 mL). The organic layer is washed with brine, dried over Na$_2$SO$_4$, and concentrated. Purification by preparative LCMS (ACN gradient 10-70%) affords the title compounds (20%) as TFA salt. $^1$HNMR (400 MHz, DMSO-d$_6$) δ 9.77 (s, 1H), 9.29 (b.s 1H), 8.78 (s, 2H), 8.14-8.15 (m, 1H), 7.98-7.95 (m, 1H), 7.66-7.64 (m, 2H), 7.21-7.18 (m, 1H), 7.05-7.03 (m, 2H), 4.37-4.35 (m, 2H), 4.28- (q, J=8.0 Hz, 2H), 3.80 (s, 3H), 3.55-3.54 (m, 2H), 3.32-3.27 (m, 4H), 1.32 (t, J=8.0 Hz, 3H), 1.24 (t, J=8.0 Hz, 6H). MS (m/z) (M+1)$^+$ 465.2.

Example 7c 2-(3-(5-(4-methoxyphenyl)pyrimidin-2-ylamino)phenyl)acetic acid

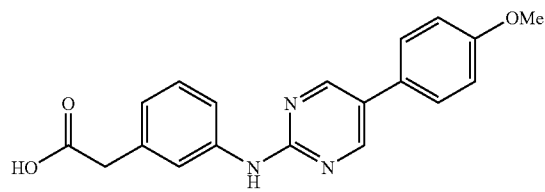

2-(3-(5-(4-methoxyphenyl)pyrimidin-2-ylamino)phenyl) acetic acid can be prepared by the following procedure. To a mixture of 2-chloro-5-(4-methoxy-phenyl)-pyrimidine (1.0 mmol) (from Example 4c) and 2-(3-aminophenyl)acetic acid (1.0 mmol) in 1,4-dioxane (2 mL) is added p-TSA monohydrate (1.0 mmol). The reaction mixture is heated at 90° C. for 5 h. After the reaction is complete, the solvent is removed. The residue is dissolved in EtOAc and washed with water, dried over MgSO$_4$ and concentrated to afford a pale yellow solid which is used in the next step without purification. MS (m/z) (M+1)$^+$ 336.1.

Example 7d 2-(3-(5-(4-methoxyphenyl)pyrimidin-2-ylamino) phenyl)-1-(4-methylpiperazin-1-yl)ethanone

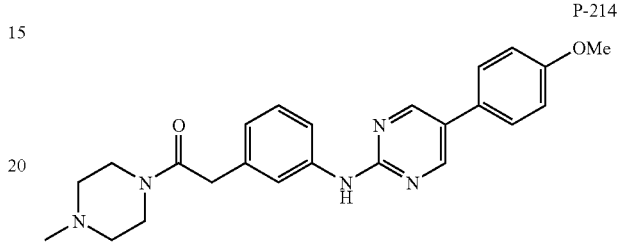

P-214

2-(3-(5-(4-methoxyphenyl)pyrimidin-2-ylamino)phenyl)-1-(4-methylpiperazin-1-yl)ethanone can be prepared by the following procedure. A mixture of 2-(3-(5-(4-methoxyphenyl)pyrimidin-2-ylamino)phenyl)acetic acid (from Example 5bc) (0.05 mmol), HATU (0.075 mmol), 1-methylpiperazine (0.05 mmol) and diisopropylethylamine (0.1 mmol) in DMF (0.5 mL) is stirred at rt for 2 h. Purification with preparative LCMS affords the title compound. MS (m/z) (M+1)$^+$ 418.2.

Example 7e

6-[5-(4-Methoxy-phenyl)-pyrimidin-2-ylamino]-3H-benzooxazol-2-one

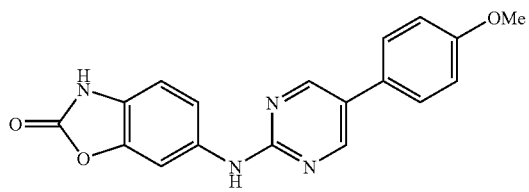

6-[5-(4-Methoxy-phenyl)-pyrimidin-2-ylamino]-3H-benzooxazol-2-one can be synthesized by the following procedure. A dry flask charged with 6-amino-3H-benzooxazol 2-one (2.03 mmol) (from Example 2n), p-TSA (0.61 mmol), 2 5-(4-methoxy-phenyl)-pyrimidin-2-ylamine (2.03 mmol), and NMP (5 mL) is heated by microwave at 210° C. for 15 min. The reaction mixture is diluted with water and extracted with EtOAc (3×20 mL). The organic layer is washed with water, brine, dried over Na$_2$SO$_4$, and concentrated. The crude oil is titrated with hexane to afford the title compound as an off white solid (40%). $^1$HNMR (400 MHz, DMSO-d$_6$) δ 11.47 (s, 1H), 9.79 (s, 1H), 8.78 (s, 2H), 7.94 (b.s, 1H), 7.65 (d, J=2.0 Hz, 2H), 7.44-7.41 (m, 3H), 7.05-7.01 (m, 3H), 3.89 (s, 3H). MS (m/z) (M+1)$^+$ 335.2.

Example 7f

6-[5-(4-Methoxy-phenyl)-pyrimidin-2-ylamino]-3H-benzooxazole-2-thione

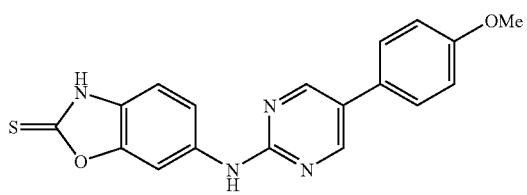

6-[5-(4-Methoxy-phenyl)-pyrimidin-2-ylamino]-3H-benzooxazole-2-thione can be prepared by the following procedure. A dry flask charged with 6-[5-(4-methoxy-phenyl)-pyrimidin-2-ylamino]-3H-benzooxazol-2-one (0.45 mmol) (from Example 5be), Lawesson's reagent (1.8 mmol), and a 5:1 mixture of THF:toluene (6 ml) is heated by microwave at 160° C. for 45 min. The reaction mixture is diluted with water and extracted with EtOAc (3×20 mL). The organic layer is washed with water, brine, dried over $Na_2SO_4$, and concentrated. The crude mixture is purified by silica chromatography using a 9:1 mixture DCM:MeOH as eluent to afford 6-[5-(4-methoxy-phenyl)-pyrimidin-2-ylamino]-3H-benzooxazole-2-thione as a yellow solid (48% based on recovered starting material). $^1$HNMR (400 MHz, DMSO-$d_6$) δ 10.0 (s, 1H), 8.82 (s, 2H), 8.19 (b.s, 1H), 7.68-7.66 (m, 2H), 7.57 (dd, J=2.0 and 8.0 Hz, 1H), 7.19 (d, J=8.0 Hz, 1H), 7.05 (d, J=8.0 Hz, 2H), 3.89 (s, 3H). MS (m/z) (M+1)$^+$ 351.2.

Example 7g

[2-(4-Isopropyl-piperazin-1-yl)-benzooxazol-6-yl]-[5-(4-methoxy-phenyl)-pyrimidin-2-yl]-amine

P-443

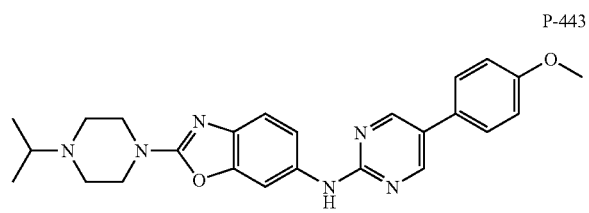

[2-(4-Isopropyl-piperazin-1-yl)-benzooxazol-6-yl]-[5-(4-methoxy-phenyl)-pyrimidin-2-yl]-amine can be synthesized by the following procedure. A dry flask charged with 6-[5-(4-methoxy-phenyl)-pyrimidin-2-ylamino]-3H-benzooxazole-2-thione (0.034 mmol) (from example 5bf), N-isopropyl piperazine (1 mL), and THF (0.5 mL) is heated by microwave at 150° C. for 10 min. Purification by preparative LCMS affords the title compound as TFA salt. $^1$HNMR (400 MHz, CD$_3$OD) δ 8.65 (s, 2H), 8.12 (bs, 1H), 7.55 (d, J=8.0 Hz, 2H), 7.3-7.30 (m, 2H), 7.05-7.03 (m, 2H), 5.46 (b.m 2H), 3.84 (s, 3H), 3.67-3.32 (m, 5H), 1.43 (d, J=8.0 Hz, 6H). MS (m/z) (M+1)$^+$ 445.8.

Example 7h

{4-[5-(4-Methoxy-phenyl)-pyrimidin-2-ylamino]-phenyl}-acetaldehyde

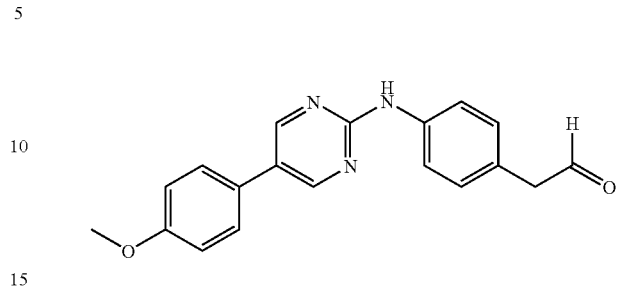

{4-[5-(4-Methoxy-phenyl)-pyrimidin-2-ylamino]-phenyl}-acetaldehyde can be synthesized by the following procedure. Dess-Martin reagent (4.35 mmol) is suspended in anhydrous THF (20 mL) and NaHCO$_3$ (10 mmol) is added. The suspension is stirred at rt for 15 min then a solution of 2-{4-[5-(4-methoxy-phenyl)-pyrimidin-2-ylamino]-phenyl}-ethanol (from Example 5ae) (3.11 mmol) in THF (10 mL) is added. The stirring is continued for 15 min, after that the reaction mixture is diluted with EtOAc and washed with a 5% NaHCO$_3$ solution (1×50 mL), brine (1×50 mL), dried over Na$_2$SO$_4$, and concentrated to afford a light brown solid. The crude is purified by HPLC (ACN 30-90% gradient) to afford {4-[5-(4-methoxy-phenyl)-pyrimidin-2-ylamino]-phenyl}-acetaldehyde as off white solid (70%). $^1$HNMR (400 MHz, DMSO-d$_6$) δ 9.75 (s, 1H), 9.67 (s, 1H), 8.78 (s, 2H), 7.77 (d, J=8.0 Hz, 2H), 7.65 (d, J=8.0 Hz, 2H), 7.15 (d, J=8.0 Hz, 2H), 7.04 (d, J=8.0 Hz, 2H), 3.80 (s, 3H), 3.69 (s, 2H). MS (m/z) (M+1)$^+$ 320.2.

Example 7i (R)-1-(2-{4-[5-(4-Methoxy-phenyl)-pyrimidin-2-ylamino]-phenyl}-ethyl)-piperidine-3-carboxylic acid

P-438

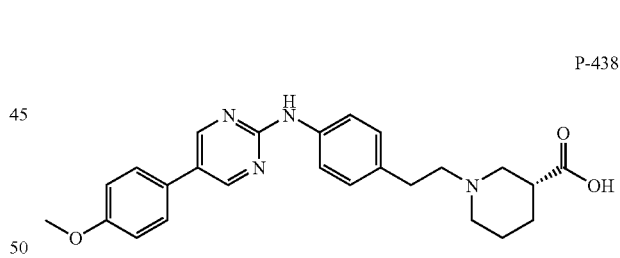

(R)-1-(2-{4-[5-(4-Methoxy-phenyl)-pyrimidin-2-ylamino]-phenyl}-ethyl)-piperidine-3-carboxylic acid can be synthesized by the following procedure. To a solution of {4-[5-(4-methoxy-phenyl)-pyrimidin-2-ylamino]-phenyl}-acetaldehyde (0.31 mmol) in DCM (10 mL) (R)-nipecotic acid (0.44 mmol) is added. The solution is stirred at rt for 1 h then NaB(OAc)$_3$H is added at once and the stirring is continued for an additional hour. The solvent is removed under reduced pressure and the residue is purified by HPLC (ACN gradient 10-90%) to afford the title compound. $^1$HNMR (600 MHz, DMSO-d$_6$) δ 10.43 (b.s, 1H), 9.71 (s, 1H), 8.78 (s, 2H), 7.74 (d, J=8.3 Hz, 1H), 7.63 (d, J=8.0 Hz, 2H), 7.19 (d, J=8.7 Hz, 2H), 7.03 (d, J=8.0 Hz, 2H), 3.79 (s, 3H), 3.69-3.67 (m, 2H), 3.56-3.53 (m, 2H), 3.29-3.25 (m, 2H), 3.02-2.95 (m, 2H), 2.91-2.86 (m, 2H), 2.07-20.4 (m, 1H), 1.91-1.83 (m, 2H). MS (m/z) (M+1)$^+$ 433.1.

513

The exemplary compounds given in Table 1 can be synthesized according to the conditions described in examples 1-7.

Example 8

Pharmaceutical Compositions

Example 8a

Parenteral Composition

To prepare a parenteral pharmaceutical composition suitable for administration by injection, 100 mg of a water-soluble salt of a compound of Formula (A) or Formula (B) is dissolved in DMSO and then mixed with 10 mL of 0.9% sterile saline. The mixture is incorporated into a dosage unit form suitable for administration by injection.

Example 8b

Oral Composition

To prepare a pharmaceutical composition for oral delivery, 100 mg of a compound of Formula (A) or Formula (B) is mixed with 750 mg of lactose. The mixture is incorporated into an oral dosage unit, such as a hard gelatin capsule, which is suitable for oral administration.

Example 8c

Inhalation Composition

To prepare a pharmaceutical composition for inhalation delivery, 25 mg of a compound of Formula (A) or Formula (B) is mixed with 2 mL of 95% ethanol and 100 mL of 0.9% sodium chloride solution. The mixture is incorporated into an inhalation delivery unit, such as a nebulizer, which is suitable for inhalation administration.

Example 8d

Suppository Composition

To prepare a pharmaceutical composition for rectal delivery [such as twelve 1.8 g. cocoa butter base, medicated suppositories containing 300 mg of a compound of Formula (A) or Formula (B)], 3.6 g. of a compound of Formula (A) or Formula (B) is mixed with 18 g. of cocoa butter. The mixture is gently fused and the resulting melt is poured into molds to form suppositories suitable for rectal administration.

Example 9

Functional Assay of c-kit Inhibition

The compounds described herein are tested for inhibition of SCF dependent proliferation using Mo7e cells which endogenously express c-kit in a 96 well format. Briefly, two-fold serially diluted test compounds ($C_{max}=10\,\mu M$) are evaluated for their antiproliferative activity on Mo7e cells stimulated with human recombinant SCF. After 48 hour incubation at 37° C., cell viability is measured by using a MTT calorimetric assay from Promega.

Exemplary test compounds are evaluated using the functional assay described above for inhibition of the c-kit receptor. The ability of compounds of Formula (A) or Formula (B) to antagonize 50% of the specified c-kit receptor yields $IC_{50}$ values for the compounds tested. In certain embodiments compounds of Formula (A) or Formula (B) have $IC_{50}$ values greater than about 10 µM, while in other embodiments compounds of Formula (A) or Formula (B) have $IC_{50}$ values between about 1 µM and about 10 M. In still other embodiments, compounds of Formula (A) or Formula (B) have $IC_{50}$ values between about 0.1 µM and about 1 µM. While in even further embodiments, compounds of Formula (A) or Formula (B) have $IC_{50}$ values less than about 0.1 µM.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A pharmaceutical composition comprising a therapeutically effective amount of a compound having the structure of Formula (1) or Formula (46):

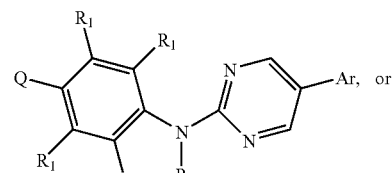

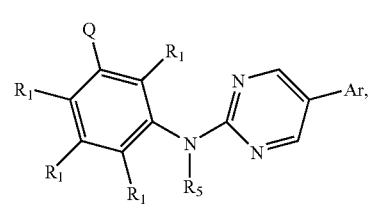

wherein:

Ar is a group comprising a moiety selected from an optionally substituted five-membered aromatic heterocycle, an optionally substituted five-membered aromatic carbocycle, an optionally substituted six-membered aromatic heterocycle, and a substituted, optionally further substituted phenyl;

Q is a group comprising a non-aromatic tertiary amine or a non-aromatic secondary amine, with the proviso that Q is not —$NR_aR_b$ or —$SO_2NR_aR_b$; wherein each of $R_a$ and $R_b$ is independently H or $C_{1-6}$alkyl optionally substituted by mono- or di-alkyl ($C_{1-6}$) amino;

each $R_1$ is independently an optionally substituted moiety selected from -$L_1$-H or -$L_1$-$C_{1-6}$alkyl; wherein $L_1$ is selected from a bond, —O—, —NH—, —S—, —C(O)—, —C(S)—, —C(O)O—, —C(O)NH—, —S(O)—, —S(O)$_2$—, —C(O)NH(CR"$_2$)$_{1-6}$C(O)O—, —C(O)NR"NR"C(O)O—, and —S(O)NH—;

each R" is independently H, OH, halogen, $C_{1-6}$alkyl, substituted $C_{1-6}$alkyl, $C_{1-6}$alkoxy, halo-$C_{1-6}$alkyl, halo-$C_{1-6}$alkoxy, aryl, haloaryl, or heteroaryl;

or any two adjacent $R_1$ groups together may form an optionally substituted 5 to 8-membered heterocyclic, cycloalkyl, or aryl ring;

R$_5$ is H or C$_{1-6}$alkyl;

or a pharmaceutically acceptable salt, or pharmaceutically acceptable N-oxide thereof, in admixture with one or more pharmaceutically acceptable excipients.

2. The pharmaceutical composition eel of claim 1, wherein the Ar is a group comprising a substituted, optionally further substituted six-membered-aromatic heterocycle.

3. The pharmaceutical composition of claim 1, wherein said optional substituents are selected from halogen, OH, C$_{1-6}$alkyl, C$_{1-6}$alkoxy, halo-C$_{1-6}$alkyl, halo-C$_{1-6}$alkoxy, aryl, haloaryl, or heteroaryl.

4. The pharmaceutical composition of claim 1, wherein Ar is selected from the group consisting of

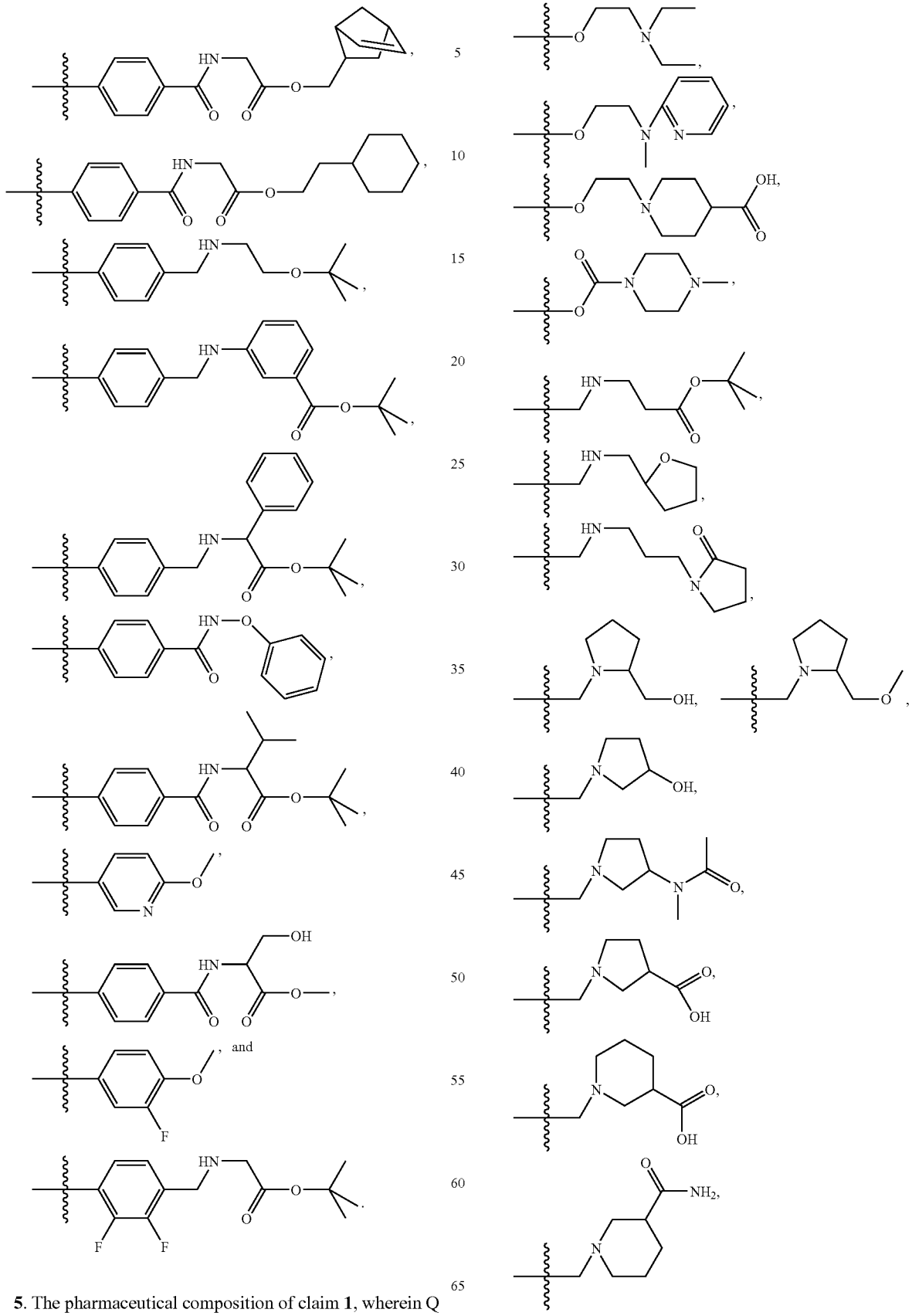
5. The pharmaceutical composition of claim 1, wherein Q is selected from the group consisting of

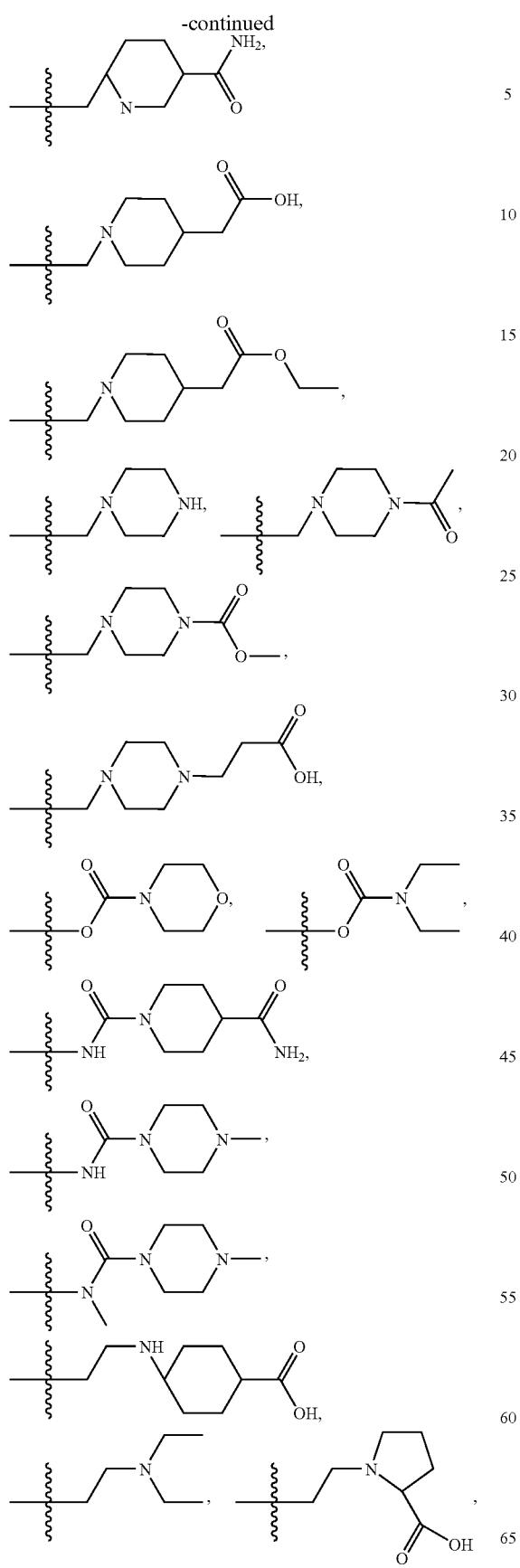
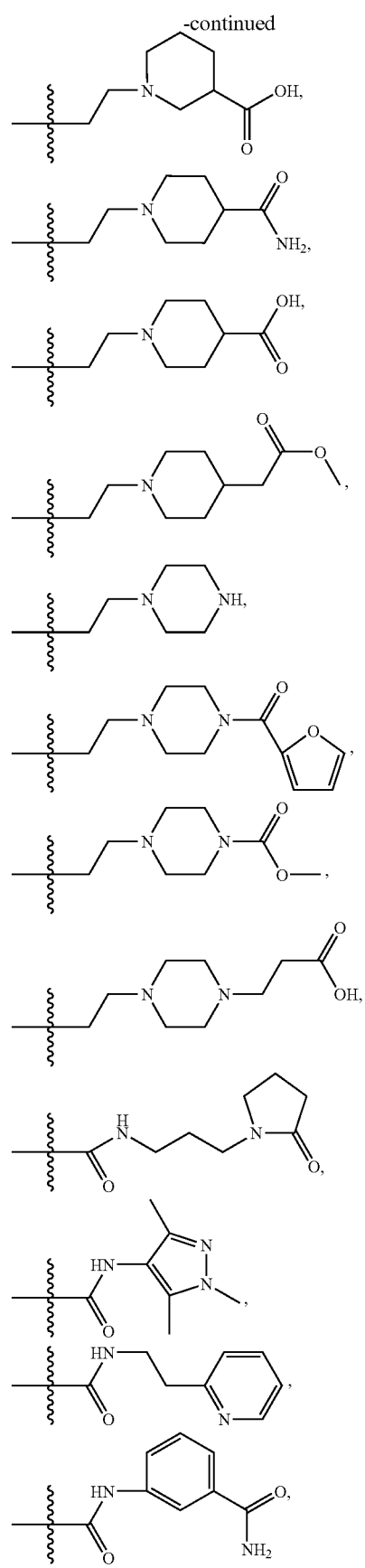

6. The pharmaceutical composition of claim 5, wherein Ar is selected from the group consisting of

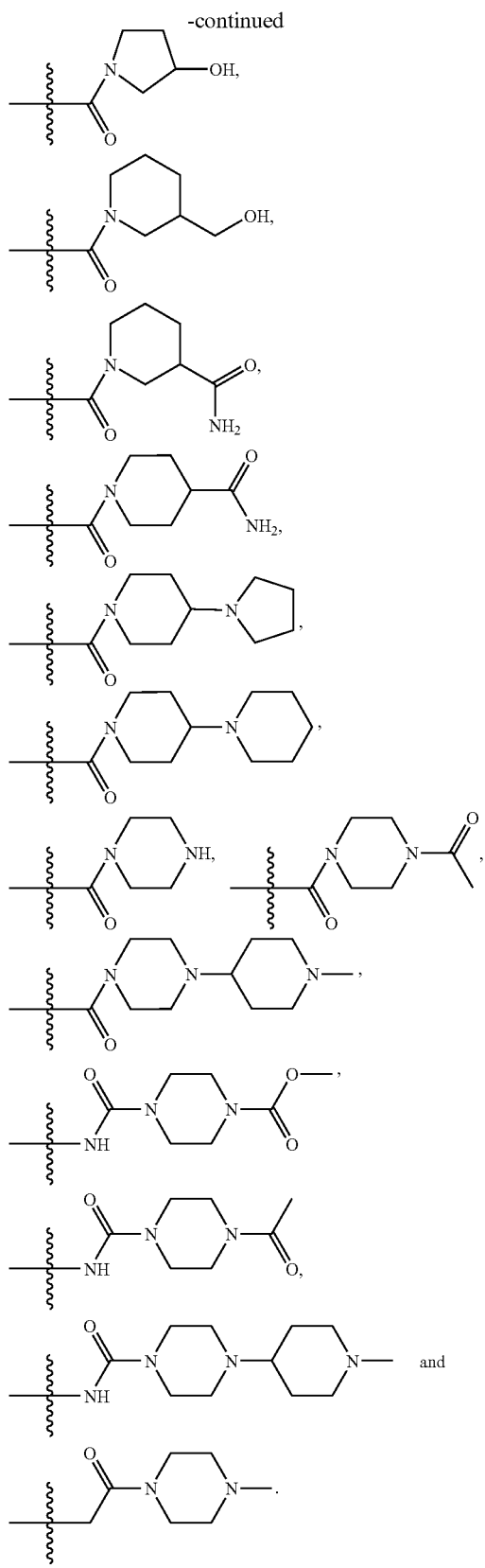

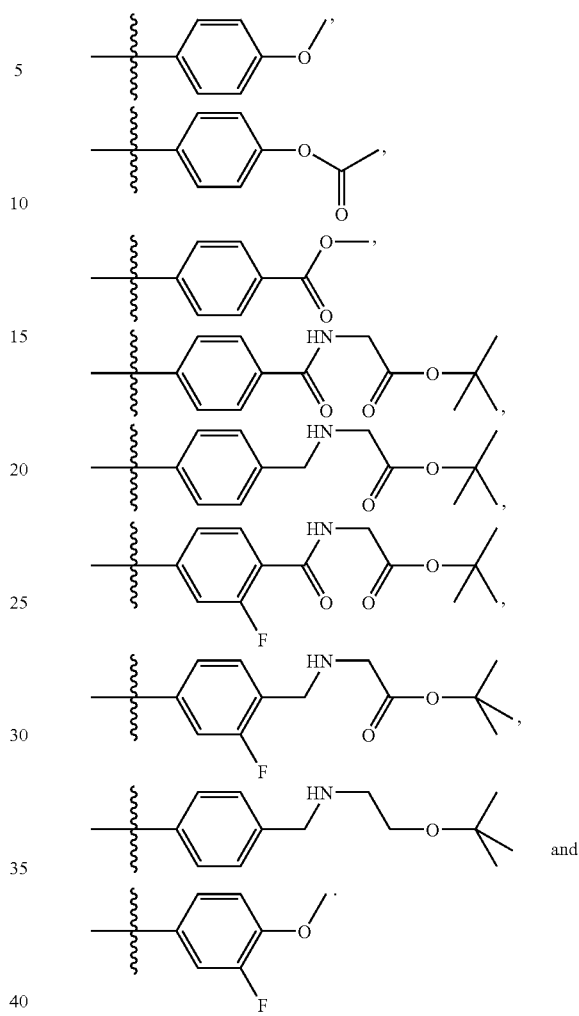

7. The pharmaceutical composition of claim 6, wherein the compound is selected from the group consisting of:
  tert-butyl 2-(4-(2-(4-(2-diethylamino)ethoxy)phenylamino)pyrimidin-5-yl)-2-fluorobenzamido)acetate,
  tert-butyl 24-(2-(4-(2-diethylaminoethoxy)phenylamino)pyrimidin-5-yl)-2-fluorobenzylamino)acetate,
  tert-butyl 2-(4-(2-(4-(2-(diethylamino)ethoxy)phenylamino)pyrimidin-5-yl)benzylamino)acetate,
  2,2'-2-(4-(5-(4-methoxyphenylpyrimidin-2-ylamino)phenoxy)ethylazanediyl)diethanol,
  1-(4-(5-(4-methoxyphenyl)pyrimidin-2-ylamino)phenethyl)piperidine-4-carboxylic acid,
  tert-butyl 2-(4-(2-(4-(2-(diethylamino)ethoxy)phenylamino)pyrimidin-5-yl)benzamido)acetate,
  methyl 1-(4-(5-(4-methoxyphenyl)pyrimidin-2-ylamino)phenethyl)piperidine-4-carboxylate,
  N-(4-(2-diethylamino)ethyl)phenyl)-5-(4-methoxyphenyl)pyrimidin-2-amine,
  1-(2-(4-(5-(4-methoxyphenyl)pyrimidin-2-ylamino)phenoxy)ethyl)piperidine-4-carboxylic acid,
  N-(4-(2-(diethylamino)ethoxy)phenyl)-5-methoxyphenyl)pyrimidin-2-amine,
  tert-butyl 2-(4-(4-(2-(4-(2-morpholinoethoxy)phenylamino)pyrimidin-5-yl)benzamido)acetate, tert-butyl-2-(4-(2-(4-(2-(4-carbamoylpiperidin-1-yl)ethoxy)phenylamino)pyrimidin-5-yl)benzamido)acetate,
4-(2-(4-(2-(diethylamino)ethoxy)phenylamino)pyrimidin-5-yl)phenyl acetate,
ethyl 2-(2-(diethylamino)ethoxy)-5-(5-(4-methoxyphenyl)pyrimidin-2-ylamino)benzoate,
4-(5-(4-methoxyphenyl)pyrimidin-2-ylamino)phenyl 4-methylpiperazine-1-carboxylate,
5-(4-methoxyphenyl)-N-(4-(2-(methyl(pyridin-2-yl)amino)ethoxy)phenyl)pyrimidin-2-amine,
methyl 4-(2-(4-(2-(diethylamino)ethoxy)phenylamino)pyrimidin-5-yl)benzoate,
N-(4-(2-(diethylamino)ethoxy)phenyl)-5-(3-fluoro-4-methoxyphenyl)pyrimidin-2-amine,
2-(2-(diethylamino)ethoxy)-4-(5-(4-methoxyphenyl)pyrimidin-2-ylamino)benzoic acid,
methyl 2-(2-(diethylamino)ethoxy)-4-(5-(4-methoxyphenyl)pyrimidin-2-ylamino)benzoate,
N-(3-(2-(diethylamino)ethoxy)phenyl)-5-(4-methoxyphenyl)pyrimidin-2-amine,
N-(3-(2-(diethylamino)ethenyl)-5-(4 methoxyphenyl)pyrimidin-2-amine,
1-(4-(5-(4-methoxyphenyl)pyrimidin-2-ylamino)benzyl)piperidine-4-carboxamide,
1-(4-(5-(4-methoxyphenyl)pyrimidin-2-ylamino)benzyl piperidine-3-carboxamide,
tert-butyl 3-(4-(5-(4-methoxyphenyl)pyrimidin-2-ylamino)benzylamino)propanoate,
5-(4-methoxyphenyl)-N-(4-(piperazin-1-ylmethyl)phenyl)pyrimidin-2-amine,
1-(4-(4-(4-(5-(4-methoxyphenyl)pyrimidin-2-ylamino)benzyl)piperazin-1-yl)ethanone,
(4-(4-(5-(4-methoxyphenyl)pyrimidin-2-ylamino)benzyl)piperazin-1-yl)tetrahydrofuran-2-yl)methanone,
1-(3-(4-(5-(4-methoxyphenyl)pyrimidin-2-ylamino)benzylamino)propyl)pyrrolidin-2-one,
(S)-1-(4-(5-(4-methoxyphenyl)pyrimidin-2-ylamino)benzyl)pyrrolidin-2-ylmethanol,
(R)—N-(4-((2-(methoxymethyl)pyrrolidin-1-yl)methyl)phenyl)-5-(4-methoxyphenyl)pyrimidin-2-amine,
1-(4-(5-(4-methoxyphenyl)pyrimidin-2'-ylamino)benzyl)pyrrolidin-3-ol,
methyl 1-(4-(5-(4-methoxyphenyl)pyrimidin-2-ylamino)benzylamino)cyclopentanecarboxylate,
4-(4-(5-(4-methoxyphenyl)pyrimidin-2-ylamino)benzyl)-2-methylpiperazine-1-carboxylic acid,
3-(4-(4-(5-(4-methoxyphenyl)pyrimidin-2-ylamino)benzyl)piperazin-1-yl)propanoic acid,
1-(4-(5-(4-methoxyphenyl)pyrimidin-2-ylamino)benzyl)piperidine-3-carboxylic acid,
ethyl-2-(1-(4-(5-(4-methoxyphenyl)pyrimidin-2-ylamino)benzyl)piperidin-4-yl)acetate,
2-(1-(4-(5-(4-methoxyphenyl)pyrimidin-2-ylamino)benzyl)piperidin-4-yl)acetic acid,
1-(4-(5-(4-methoxyphenyl)pyrimidin-2-ylamino)benzyl)pyrrolidine-3-carboxylic acid,
3-(5-(4-methoxyphenyl)pyrimidin-2-ylamino)phenyl morpholine-4 carboxylate,
3-(5-(4-methoxyphenyl)pyrimidin-2-ylamino)phenyl 4-methylpiperazine-1-carboxylate,
3-(5-(4-((2-tert-butoxy-2-oxoethylamino)methyl)phenyl)pyrimidin-2-ylamino)phenyl 4-methylpiperazine-1-carboxylate,
methyl 4)-4-(5-(4-methoxyphenyl)pyrimidin-2-ylamino)benzyl)piperazine-1-carboxylate,
4-(5-(4-((2-tert-butoxy-2-oxoethylamino)methyl)phenyl)pyrimidin-2-ylamino)phenyl 4-methylpiperazine-1-carboxylate,
N-(3-(5-(4-methoxyphenyl)pyrimidin-2-ylamino)phenyl)-4-methylpiperazine-1-carboxamide,
2-(4-(5-(4-methoxyphenyl)pyrimidin-2-ylamino)phenyl)-1-(4-methylpiperazin-1-yl)ethanone,
N1-(3-(5-(4-methoxyphenyl)pyrimidin-2-ylamino)phenyl)piperidine-1,4-dicarboxamide,
3-(5-(4-methoxyphenyl)pyrimidin-2-ylamino)benzyl 4-methylpiperazine-1-carboxylate,
4-hydroxy-N-(3-(5-(4-methoxyphenyl)pyrimidin-2-ylamino)phenyl)piperidine-1-carboxamide,
N-(4-(5 (4-methoxyphenyl)pyrimidin-2-ylamino)phenyl)-4-methylpiperazine-1-carboxamide,
1-(4-(4-(5-(4-methoxyphenylpyrimidin-2-ylamino)phenethyl)piperidine-4-carboxamide,
furan-2-yl(4-(4-(5-(4-methoxyphenylpyrimidin-2-ylamino)phenethyl)piperazin-1-yl)methanone,
5-(4-methoxyphenyl)-N-(4-(2-(piperazin-1-yl)ethyl)phenyl)pyrimidin-2-amine,
N-(3-(5-(4-methoxyphenyl)pyrimidin-2-ylamino)phenyl)-N,4-dimethylpiperazine-1-carboxamide,
1-(4-(5-(4-methoxyphenyl)pyrimidin-2-ylamino)phenethyl)piperidine-3-carboxamide,
1-(4-(5-(4-methoxyphenyl)pyrimidin-2-ylamino)phenethyl)piperidine-3-carboxylic acid,
methyl 4-(4-(5-(4-(4-methoxyphenyl)pyrimidin-2-ylamino)phenethyl)piperazine-1-carboxylate,
1-(4-(5-(4-methoxyphenyl)pyrimidin-2-ylamino)phenethyl)piperidine-3-carboxylic acid,
2-(1-(4-(5-(4-methoxyphenyl)pyrimidin-2-ylamino)phenethyl)piperidin-4-yl)acetic acid,
methyl 2-(1-(4-(5-(4-methoxyphenyl)pyrimidin-2-ylamino)phenethyl)piperidin-4-yl)acetate,
(3-(hydroxymethyl)piperidin-1-yl)(4-(4-(5-(4-methoxyphenyl)pyrimidin-2-ylamino)phenyl)methanone,
(3-hydroxypyrrolidin-1-yl)(4-(5-(4-methoxyphenyl)pyrimidin-2-ylamino)phenyl)methanone,
1-(4-(5-(4-methoxyphenyl)pyrimidin-2-ylamino)benzoyl)piperidine-4-carboxamide,
3-(4-(4-(5-(4-methoxyphenyl)pyrimidin-2-ylamino)phenethyl)piperazin-1-yl)propanoic acid,
(S)-1-(4-(5-(4-methoxyphenyl)pyrimidin-2-ylamino)phenethyl)pyrrolidine-2-carboxylic acid,
4-(4-(5-(4-methoxyphenyl)pyrimidin-2-ylamino)phenethylamino)cyclohexanecarboxylic acid,
4-(5-(4-methoxyphenyl)pyrimidin-2-ylamino)-N-(3-(2-oxopyrrolidin-1-yl)propyl)benzamide,
1-(4-(5-(4-methoxyphenyl)pyrimidin-2-ylamino)benzoyl)piperidine-3-carboxamide,
N-(3-carbamoylphenyl)-4-(5-(4-methoxyphenyl)pyrimidin-2-ylamino)benzamide,
1,4'-bipiperidin-1'-yl(4-(5-(4-methoxyphenyl)pyrimidin-2-ylamino)phenyl)methanone,
(4-(5-(4-methoxyphenyl)pyrimidin-2-yl-amino)phenyl)(4-(pyrrolidin-1-yl)piperidin-1-yl)methanone,
(4-(5-(4-methoxyphenyl)pyrimidin-2-ylamino)-N-(2-(pyridin-2-yl)ethyl)benzamide,
(4-(5-(4-methoxyphenyl)pyrimidin-2-ylamino)-N-(1,3,5-trimethyl-1H-pyrazol-4-yl)benzamide,
(4-(furan-2-carbonyl piperazin-1-yl)(3-(5-(4-methoxyphenyl)pyrimidin-2-ylamino)phenyl) methanone,
3-(5-(4-methoxyphenyl)pyrimidin-2-ylamino)-N-(1,3,5-trimethyl-1H-pyrazol-4-yl)benzamide,
(3-(5-(4-methoxyphenyl)pyrimidin-2-ylamino)phenyl)(4-(1-methylpiperidin-4-yl)piperazin-1-yl)methanone, 1-(4-(3-(5-(4-methoxyphenyl)pyrimidin-2-ylamino)benzoyl)piperazin-1-yl)ethanone,
(3-(5-(4-methoxyphenyl)pyrimidin-2-ylamino)phenyl)(4-(pyrrolidin-1-yl)piperidin-1-yl)methanone,
1,4'-bipiperidin-1'-yl(3-(5-(4-methoxyphenyl)pyrimidin-2-ylamino)phenyl)methanone,
1-(3-(5-(4-methoxyphenyl)pyrimidin-2-ylamino)benzoyl)piperidin-3-carboxamide,
N-(3-(5-(4-methoxyphenyl)pyrimidin-2-ylamino)phenyl)-4-(1-methylpiperidin-4-yl)piperazine-1-carboxamide,
methyl 4-(3-(5-(4-methoxyphenyl)pyrimidin-2-ylamino)phenylcarbamoyl)piperazine-1-carboxylate,
(R)-1-(4-(5-(4-methoxyphenyl)pyrimidin-2-ylamino)phenethyl)piperidine-3-carboxylic acid,
(4-(5-(4-methoxyphenyl)pyrimidin-2-ylamino)phenyl)(piperazin-1-yl)methanone,
4-acetyl-N-(3-(5-(4-methoxyphenyl)pyrimidin-2-ylamino)phenyl)piperazine-1-carboxamide, and
(3-(5-(4-methoxyphenyl)pyrimidin-2-ylamino)phenyl)(piperazin-1-yl)methanone.

8. The pharmaceutical composition of claim 1, wherein the compound having the structure of Formula (1) is selected from Formula (2), Formula (3), or Formula (44):

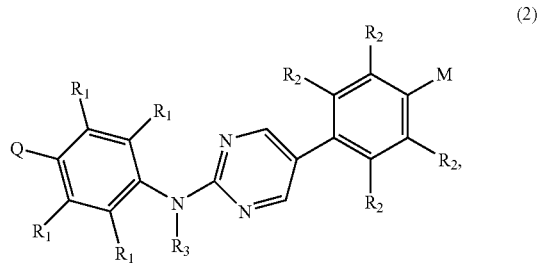

(2)

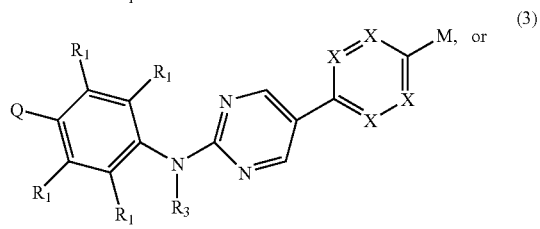

(3)

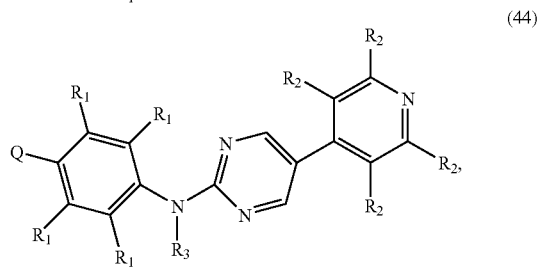

(44)

wherein:
M is selected from the group consisting of H, OH, SH, NO$_2$, CN, NR"$_2$, and an optionally substituted moiety selected from -L$_7$-alkyl, -L$_7$-cycloalkyl, -L$_7$-heteroalkyl, -L$_7$-haloalkyl, -L$_7$-aryl, -L$_7$-heterocycloalkyl, and -L$_7$-heteroaryl; wherein L$_7$ is selected from a bond, —O—, —NH—, —S—, —C(O)—, —C(S)—, —C(O)O—, —C(O)NH—, —S(O)—, —S(O)$_2$—, —OC(O)—, —C(O)NR"(CR"$_2$)$_{1-6}$C(O)O—, —CR"$_2$NR"CR"$_2$C(O)O—, —C(O)NR"Y$^1$C(O)O—, —C(O)NR"NR"C(O)O—, —S(O)NH—, —C(O)NR"CR"$_2$C(O)W—, —CR"$_2$NR"WO—, —CR"$_2$NR"Y$^1$C(O)O—, and —C(O)NR"O—; W is C$_{1-6}$alkylene; Y$^1$ is optionally substituted arylene or optionally substituted heteroarylene; wherein said optional substituents are selected from halogen, OH, C$_{1-6}$alkyl, C$_{1-6}$alkoxy, halo-C$_{1-6}$alkyl and halo-C$_{1-6}$alkoxy; provided that M is not H in Formula (2);

each R" is independently H, OH, halogen, C$_{1-6}$alkyl, substituted C$_{1-6}$alkyl, C$_{1-6}$alkoxy, halo-C$_{1-6}$alkyl, halo-C$_{1-6}$alkoxy, aryl, haloaryl, or heteroaryl;

each X is independently selected from N or CR$_2$, provided that at least one but no more than 2X groups are N;

each R$_2$ is independently selected from the group consisting of H, OH, halogen, and an optionally substituted moiety selected from -L$_2$-alkyl, -L$_2$-cycloalkyl, -L$_2$-heteroalkyl, -L$_2$-haloalkyl, -L$_2$-aryl, -L$_2$-heterocycloalkyl, and -L$_2$-heteroaryl; wherein L$_2$ is selected from a bond, —O—, —NH—, —S—, —C(O)—, —C(S)—, —C(O)O—, —C(O)NH—, —S(O)—, —S(O)$_2$—, —C(O)NR"(CR"$_2$)$_{1-6}$C(O)O—, —OC(O)—, —CR"$_2$NR"CR"$_2$C(O)O—, —C(O)NR"NR"C(O)O—, and —S(O)NH—; wherein said optional substituents are selected from halogen, OH, C$_{1-6}$alkyl, C$_{1-6}$alkoxy, halo-C$_{1-6}$alkyl, and halo-C$_{1-6}$alkoxy;

or any two adjacent R$_2$ groups together may form an optionally substituted 5 to 8-membered heterocyclic, cycloalkyl, or aryl ring;

or a pharmaceutically acceptable salt, or pharmaceutically acceptable N-oxide thereof, in admixture with one or more pharmaceutically acceptable excipients.

9. The pharmaceutical composition of claim 1, wherein the compound having the structure of Formula (46) is selected from Formula (47), Formula (48), or Formula (49):

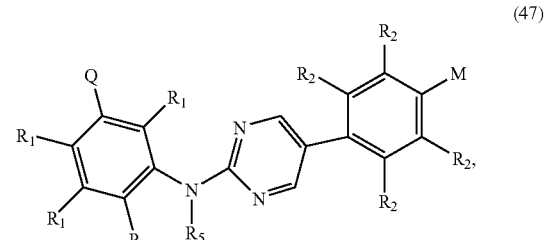

(47)

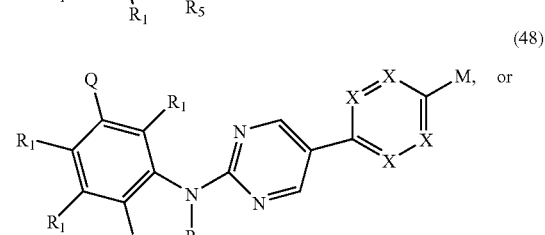

(48)

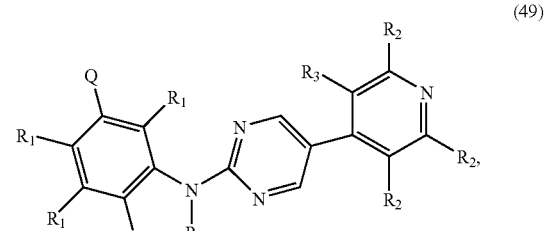

(49)

wherein:

M is selected from the group consisting of H, OH, SH, NO₂, CN, NR"₂, and an optionally substituted moiety selected from -L₇-alkyl, -L₇-cycloalkyl, -L₇-heteroalkyl, -L₇-haloalkyl, -L₇-aryl, -L₇-heterocycloalkyl, and -L₇-heteroaryl; wherein L₇ is selected from a bond, —O—, —NH—, —S—, —C(O)—, —C(S)—, —C(O)O—, —C(O)NH—, —S(O)—, —S(O)₂—, —OC(O)—, —C(O)NR"(CR"₂)₁₋₆C(O)O—, —CR"₂NR"CR"₂C(O)O—, —C(O)NR"Y¹C(O)O—, —C(O)NR"NR"C(O)O—, —S(O)NH—, —C(O)NR"CR"₂C(O)W—, —CR"₂NR"WO—, —CR"₂NR"Y¹C(O)O—, and —C(O)NR"O—; W is C₁₋₆alkylene; Y¹ is optionally substituted arylene or optionally substituted heteroarylene; wherein said optional substituents are selected from halogen, OH, C₁₋₆alkyl, C₁₋₆alkoxy, halo-C₁₋₆alkyl and halo-C₁₋₆ alkoxy; provided that M is not H in Formula (47);

each R" is independently H, OH, halogen, C₁₋₆alkyl, substituted C₁₋₆alkyl, C₁₋₆alkoxy, halo-C₁₋₆alkyl, halo-C₁₋₆ alkoxy, aryl, haloaryl, or heteroaryl;

each X is independently selected from N or CR₂, provided that at least one but no more than 2X groups are N;

each R₂ is independently selected from the group consisting of H, OH, halogen, and an optionally substituted moiety selected from -L₂-alkyl, -L₂-cycloalkyl, -L₂-heteroalkyl, -L₂-haloalkyl, -L₂-aryl, -L₂-heterocycloalkyl, and -L₂-heteroaryl; wherein L₂ is selected from a bond, —O—, —NH—, —S—, —C(O)—, —C(S)—, —C(O)O—, —C(O)NH—, —S(O)—, —S(O)₂—, —C(O)NR" (CR"₂)₁₋₆C(O)O—, —OC(O)—, —CR"₂NR"CR"₂C(O)O—, —C(O)NR"NR"C(O)O—, and —S(O)NH—; wherein said optional substituents are selected from halogen, OH, C₁₋₆alkyl, C₁₋₆alkoxy, halo-C₁₋₆alkyl, and halo-C₁₋₆alkoxy;

or any two adjacent R₂ groups together may form an optionally substituted 5 to 8-membered heterocyclic, cycloalkyl, or aryl ring;

or a pharmaceutically acceptable salt, or pharmaceutically acceptable N-oxide thereof, in admixture with one or more pharmaceutically acceptable excipients.

10. The pharmaceutical composition of any of claims 1-4, 8 and 9, wherein Q is selected from the group consisting of

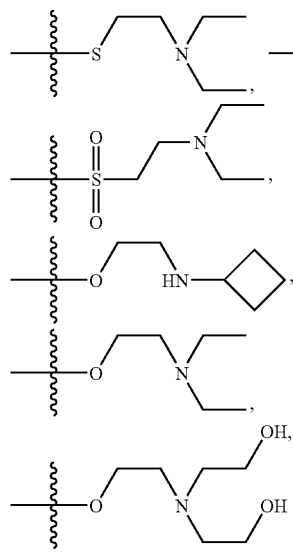

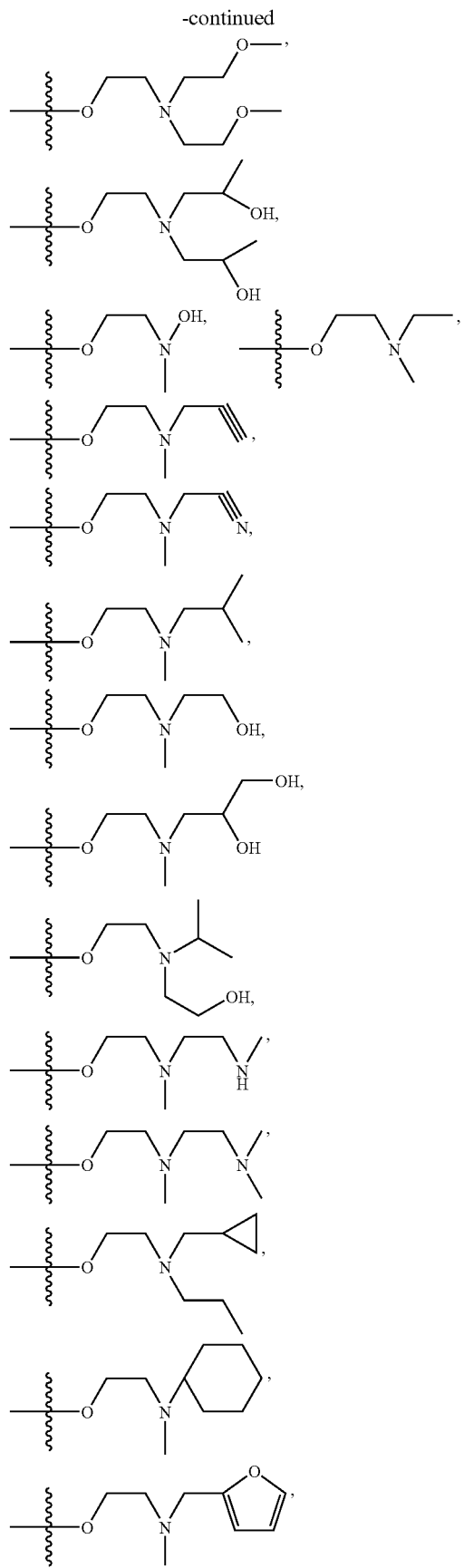

-continued
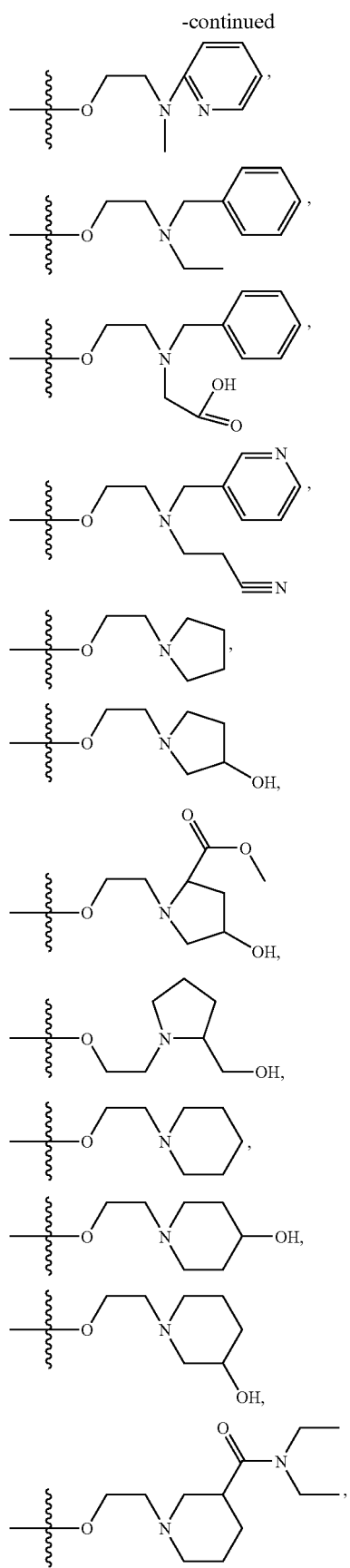
-continued
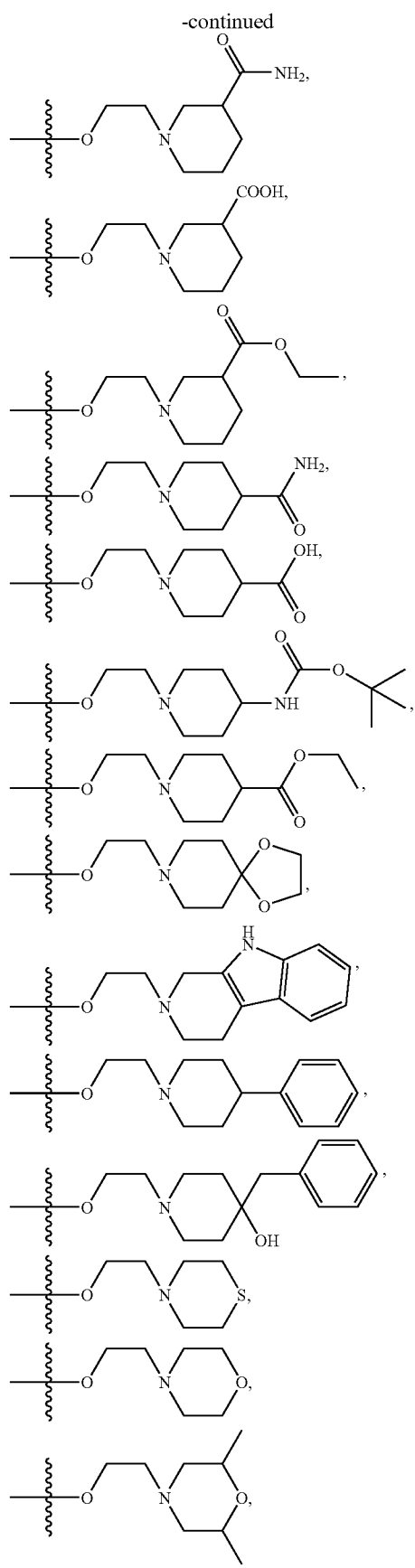

531
-continued
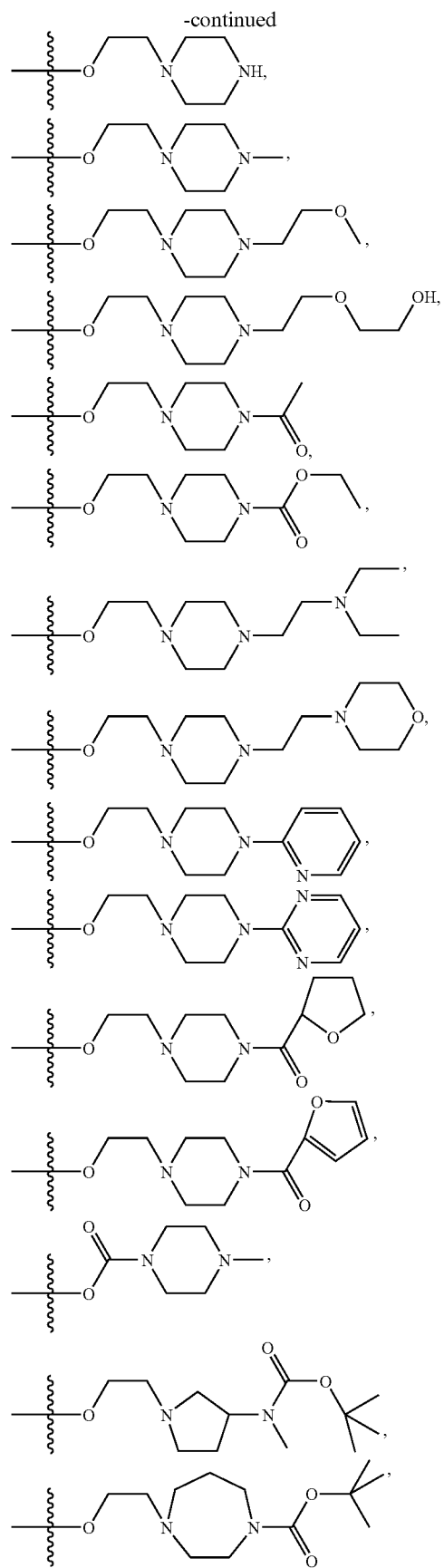
532
-continued
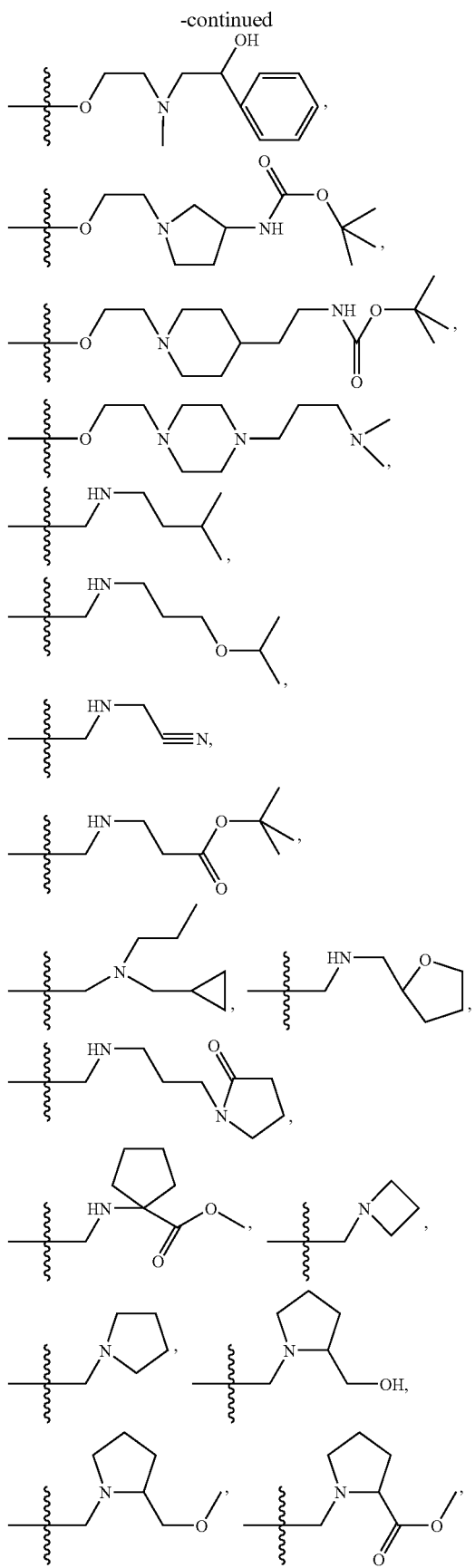

-continued

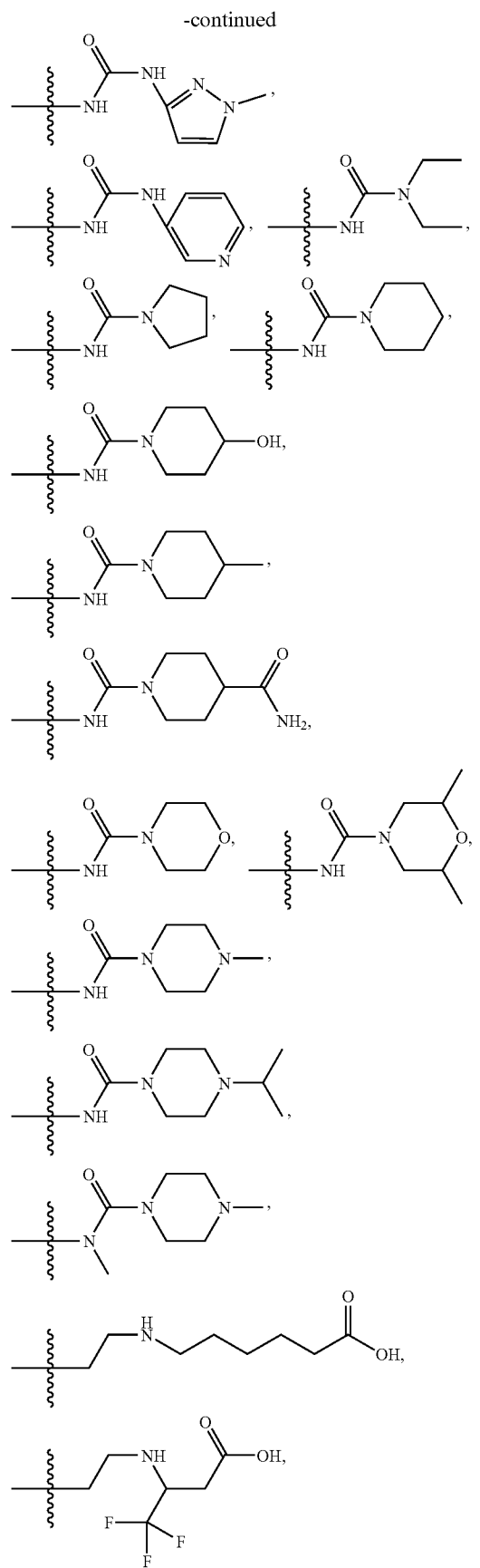
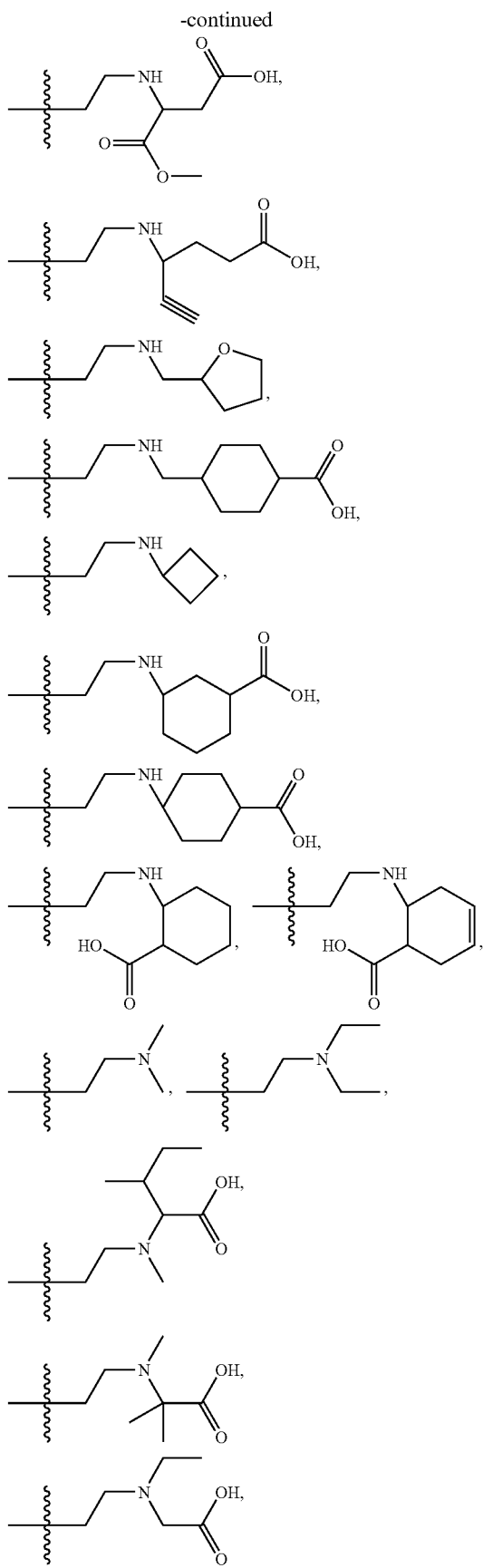

-continued
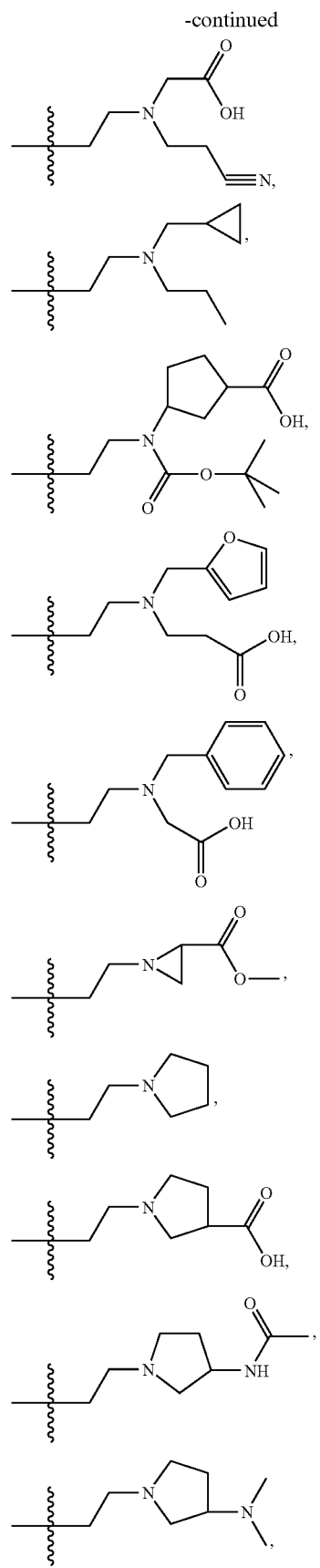
-continued
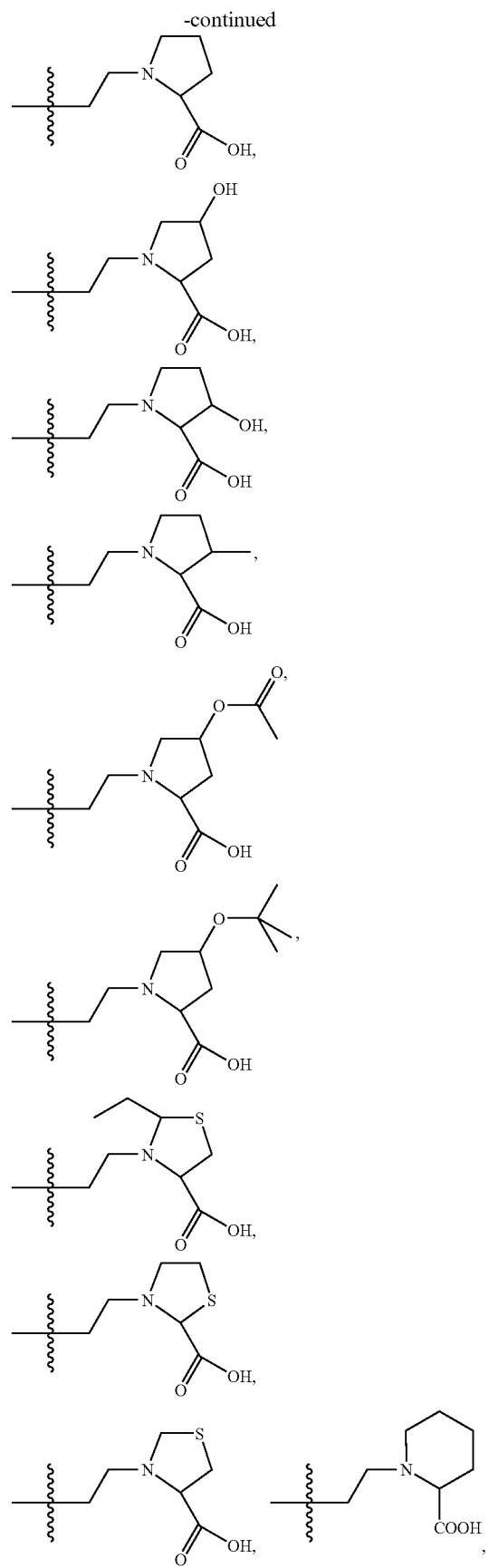

539
-continued
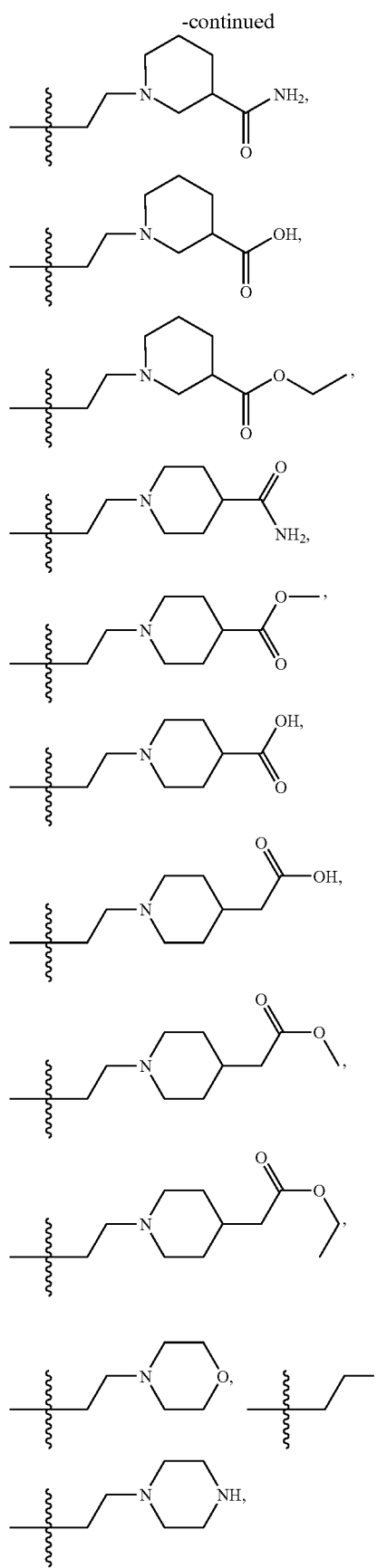
540
-continued
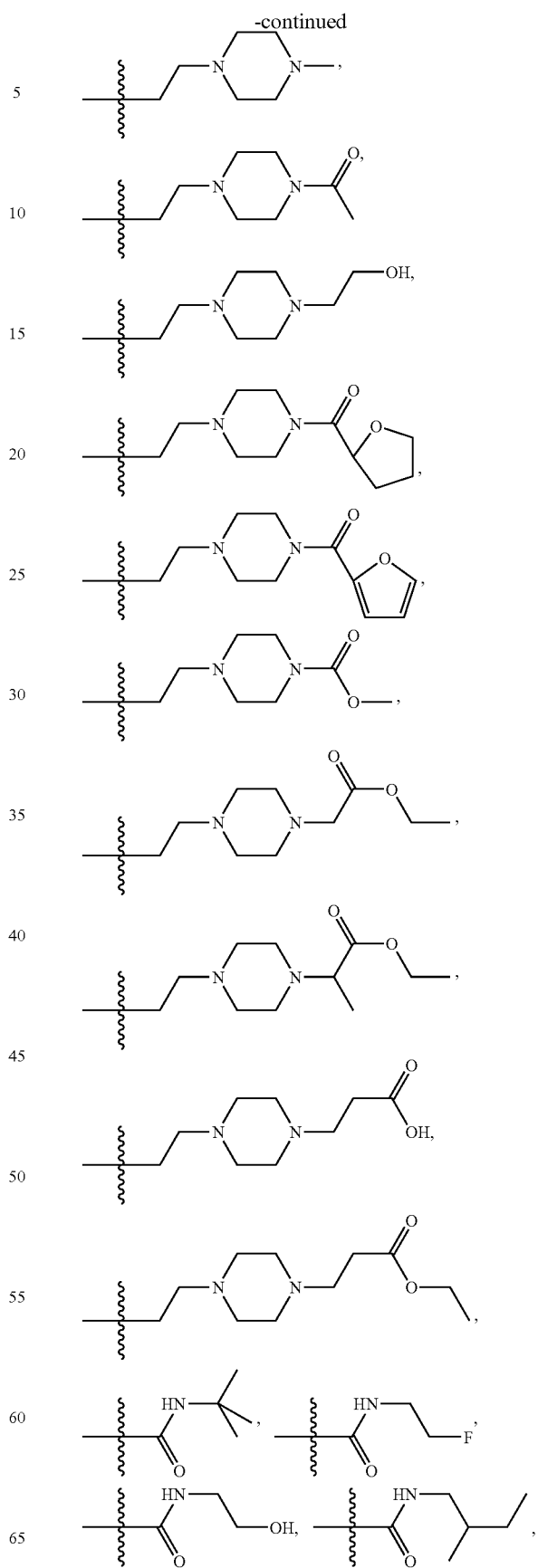

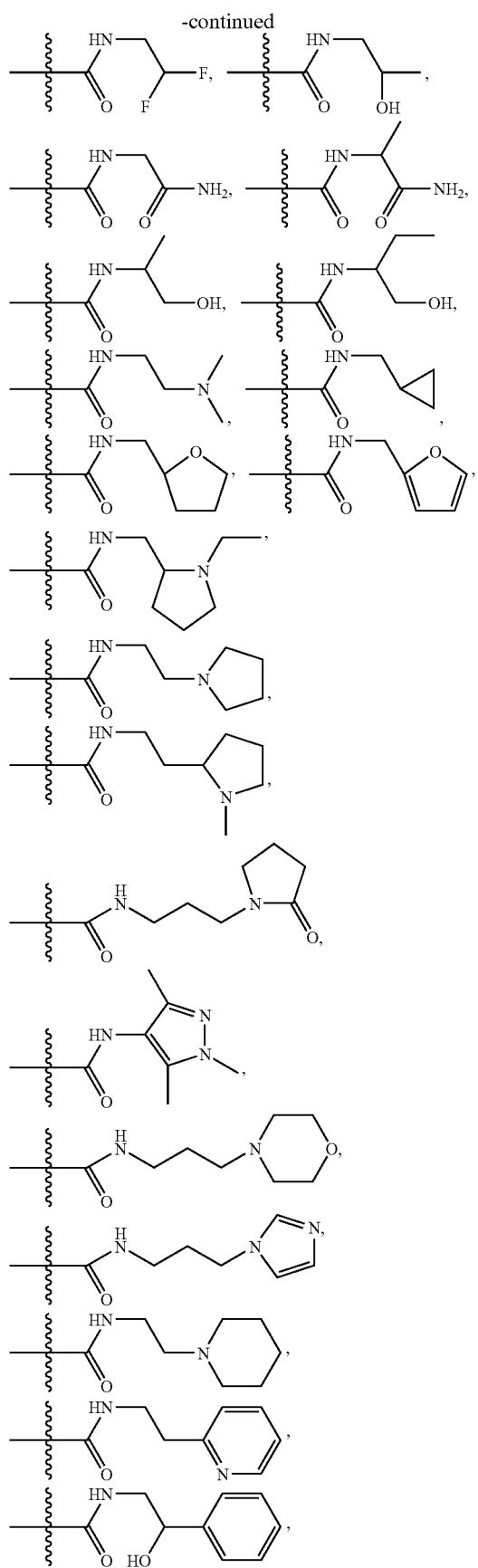
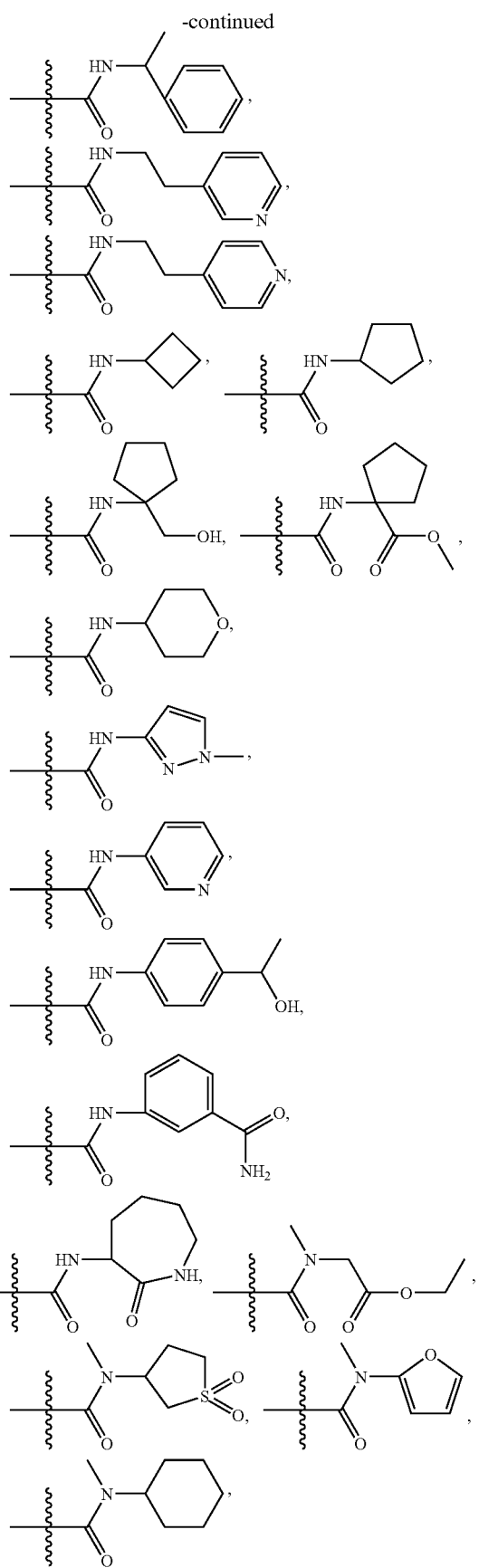

-continued
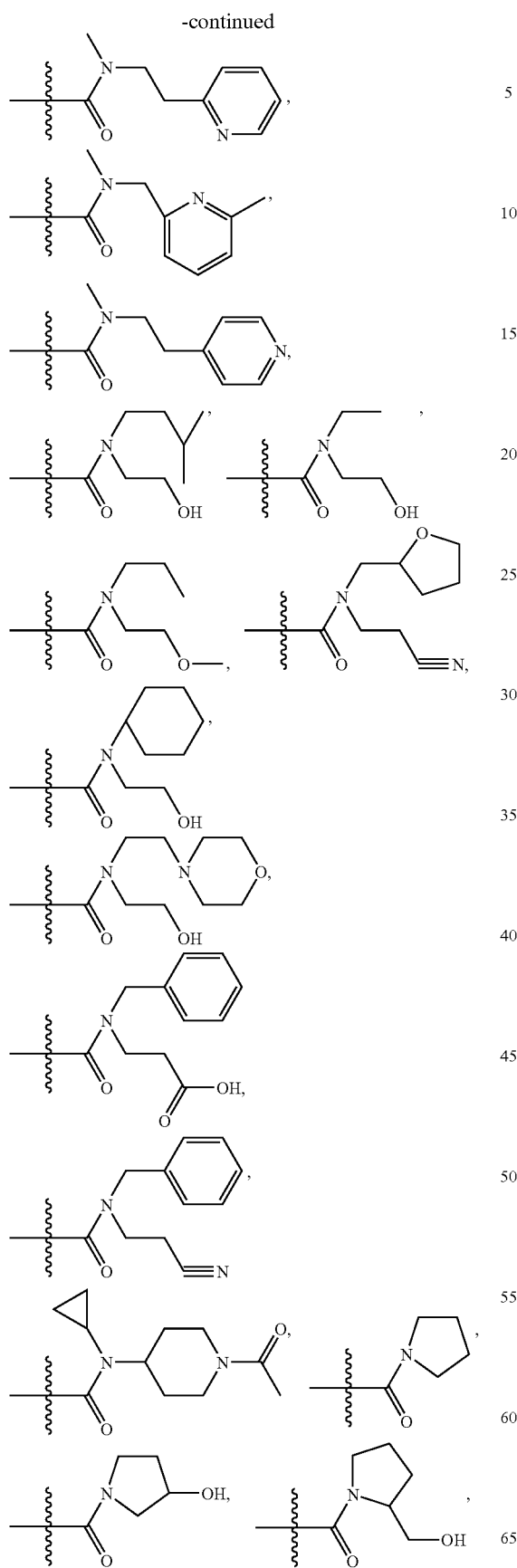
-continued
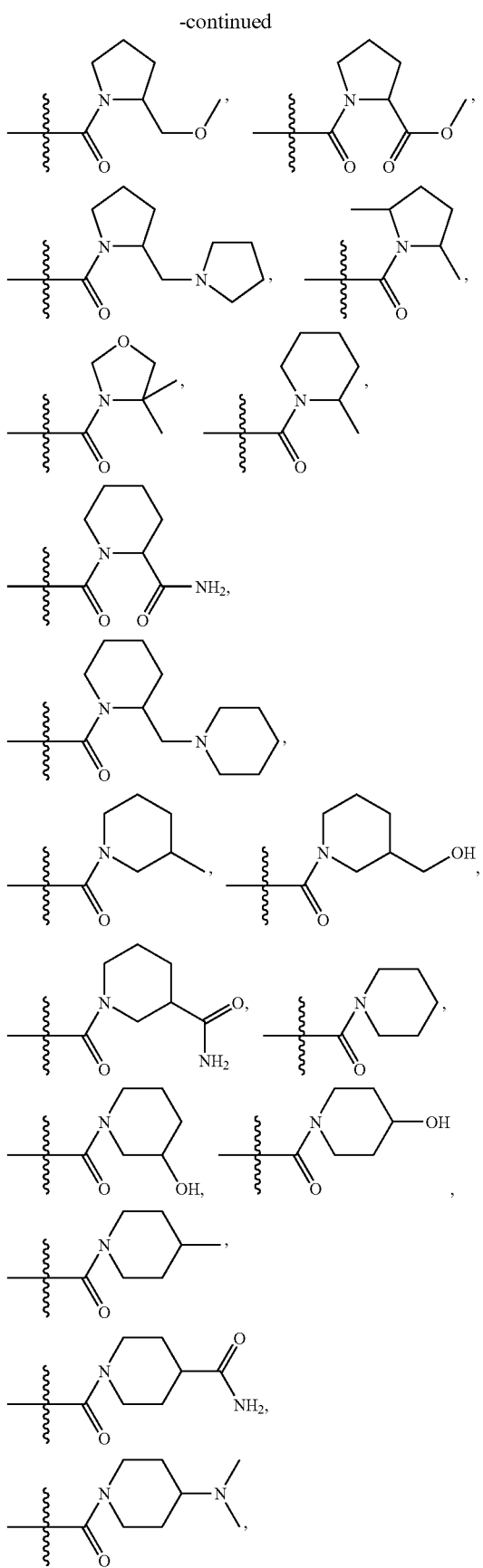

545
-continued
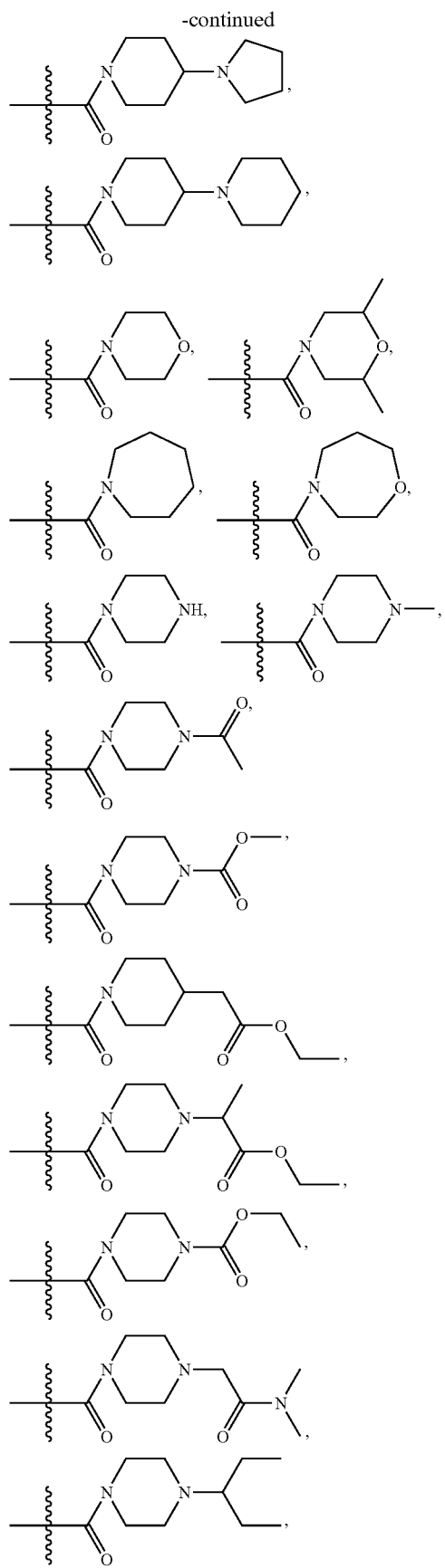
546
-continued
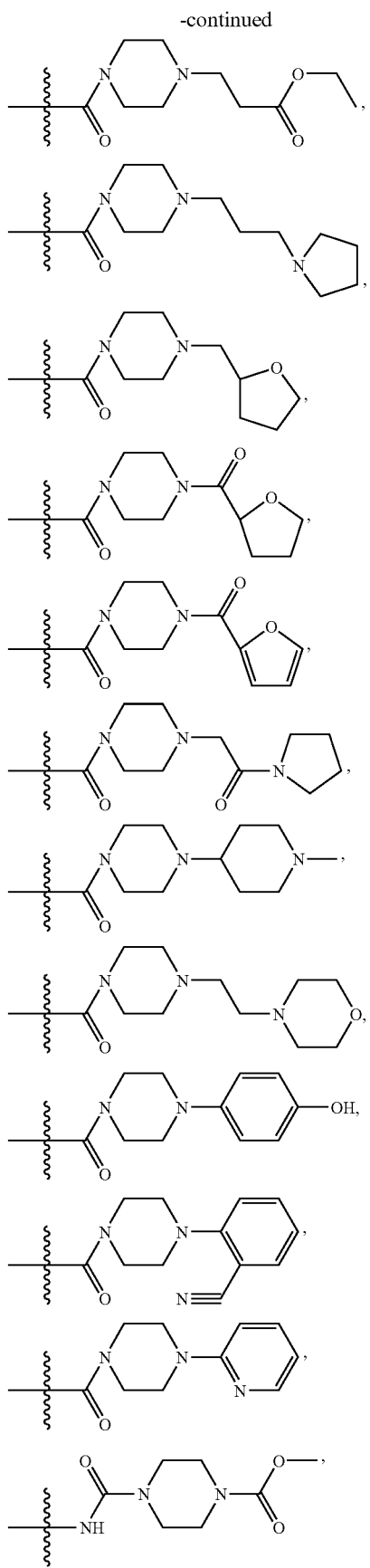

547

-continued

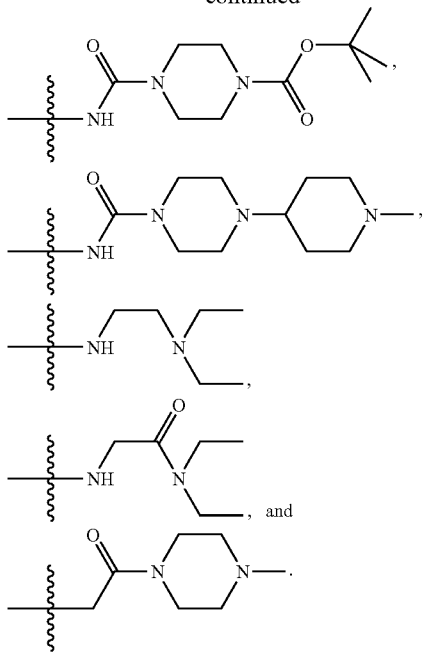

11. The pharmaceutical composition of claim 1, wherein the compound having the structure of Formula (1) is selected from Formula (23), Formula (24), or Formula (45):

(23)

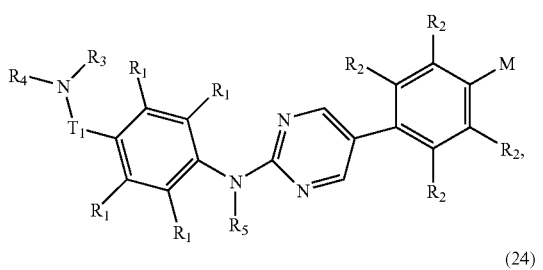

(24)

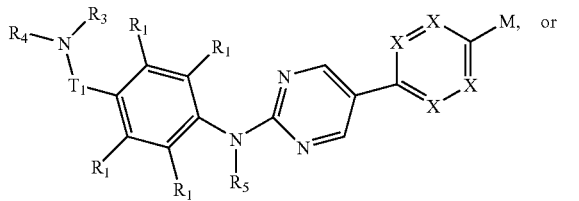

(45)

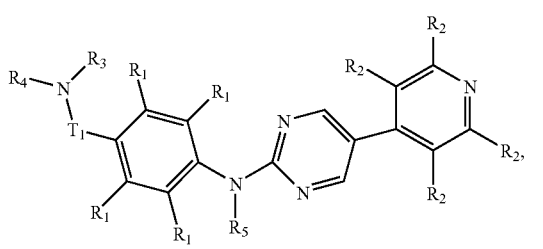

wherein:
M is selected from the group consisting of H, OH, SH, $NO_2$, CN, $NR''_2$, and an optionally substituted moiety

548 selected from -$L_7$-alkyl, -$L_7$-cycloalkyl, -$L_7$-heteroalkyl, -$L_7$-haloalkyl, -$L_7$-aryl, -$L_7$-heterocycloalkyl, and -$L_7$-heteroaryl; wherein $L_7$ is selected from a bond, —O—, —NH—, —S—, —C(O)—, —C(S)—, —C(O)O—, —C(O)NH—, —S(O)—, —S(O)_2—, —OC(O)—, —C(O)NR''(CR''_2)_{1-6}C(O)O—, —CR''_2NR''CR''_2C(O)O—, —C(O)NR''Y^1C(O)O—, —C(O)NR''NR''C(O)O—, —S(O)NH—, —C(O)NR''CR''_2C(O)W—, —CR''_2NR''WO—, —CR''_2NR''Y^1C(O)O—, and —C(O)NR''O—; W is $C_{1-6}$alkylene; $Y^1$ is optionally substituted arylene or optionally substituted heteroarylene; wherein said optional substituents are selected from halogen, OH, $C_{1-6}$alkyl, $C_{1-6}$alkoxy, halo-$C_{1-6}$alkyl and halo-$C_{1-6}$alkoxy; provided that M is not H in Formula (23);

each R'' is independently H, OH, halogen, $C_{1-6}$alkyl, substituted $C_{1-6}$alkyl, $C_{1-6}$alkoxy, halo-$C_{1-6}$alkyl, halo-$C_{1-6}$alkoxy, aryl, haloaryl, or heteroaryl;

each X is independently selected from N or $CR_2$, provided that at least one but no more than 2X groups are N;

each $R_2$ is independently selected from the group consisting of H, OH, halogen, and an optionally substituted moiety selected from -$L_2$-alkyl, -$L_2$-cycloalkyl, -$L_2$-heteroalkyl, -$L_2$-haloalkyl, -$L_2$-aryl, -$L_2$-heterocycloalkyl, and -$L_2$-heteroaryl; wherein $L_2$ is selected from a bond, —O—, —NH—, —S—, —C(O)—, —C(S)—, —C(O)O—, —C(O)NH—, —S(O)—, —S(O)_2—, —C(O)NR''(CR''_2)_{1-6}C(O)O—, —OC(O)—, —CR''_2NR''CR''_2C(O)O—, —C(O)NR''NR''C(O)O—, and —S(O)NH—; wherein said optional substituents are selected from halogen, OH, $C_{1-6}$alkyl, $C_{1-6}$alkoxy, halo-$C_{1-6}$alkyl, and halo-$C_{1-6}$alkoxy;

or any two adjacent $R_2$ groups together may form an optionally substituted 5 to 8-membered heterocyclic, cycloalkyl, or aryl ring;

each of $R_3$ and $R_4$ is independently an optionally substituted-moiety selected from -Z, -$L_3$-Z, -$L_3$-H, -$L_3$-alkyl, -$L_3$-cycloalkyl, -$L_3$-heteroalkyl, -$L_3$-haloalkyl, -$L_3$-aryl, -$L_3$-heterocycloalkyl, and -$L_3$-heteroaryl; wherein $L_3$ is selected from a bond, —C(S)—, —C(O)O—, C(O)NR'''—, —(CR''_2)_{1-6}—, —CR'''_2S(O)—, —CR'''_2S(O)_2—, —CR'''_2S(O)NR'''—, —CR'''_2C(O)NR'''—, —(CR'''_2)_{1-6}NR'''—, —(CR''_2)_{1-6}O—, —(CR'''_2)_{1-6}C(O)O—, —$Y^2$C(O)O—, and an optionally substituted $C_{1-6}$alkylene;

wherein:
said optional substituents are selected from halogen, —H, =O, —$Y^3$, $C_{1-6}$alkyl, $C_{1-6}$alkoxy, halogen or OH substituted $C_{1-6}$alkyl, halogen or OH substituted $C_{1-6}$alkoxy, —(CR'''_2)_{1-6}C(O)OR_6, —C(O)NR'''_2, —C(O)R_6, or —C(O)OR_6;

$Y^2$ is an optionally substituted cycloalkyl ring or optionally substituted non-aromatic heterocyclic ring; wherein said optional substituents are selected from $C_{1-6}$alkyl, halogen, —OH, =O, and —CN;

$Y^3$ is optionally substituted aryl, optionally substituted heteroaryl, optionally substituted cycloalkyl, or optionally substituted non-aromatic heterocycle; wherein said optional substituents are selected from $C_{1-6}$alkyl, halogen, —OH, =O, and —CN;

Z is —H, —OH, —CN, —COOR''', —NR'''_2, or —C≡CR''';

each R''' is independently H, alkyl, or substituted alkyl;

or two R''' together may form a 3-6 membered cycloalkyl or heterocyclic ring;

or $R_3$ and $R_4$ taken together with the N atom to which they are attached may form an optionally substituted 3 to 8-membered heterocyclic ring;

wherein:

said optional substituents are selected from halogen, —OH, =O, —$Y^3$, $C_{1-6}$alkyl, $C_{1-6}$alkoxyl, halogen or OH substituted $C_{1-6}$alkyl, halogen or OH substituted $C_{1-6}$alkoxy, —(CR'''$_2$)$_{1-6}Y^4$, —(CR'''$_2$)$_{1-6}$OR$_6$, —C(O)NR'''R$_6$, —C(O)OR$_6$, —OR$_6$, —NR'''C(O)OR$_6$, —NR'''C(O)R$_6$, —(CR'''$_2$)$_{1-6}$C(O)OR$_6$, —(CR'''$_2$)$_{1-6}$NR'''C(O)OR$_6$, —(CR'''$_2$)$_{1-6}$NR$_7$R$_8$, —S(O)$_2$NR'''$_2$, —C(O)R$_6$, —OC(O)R$_6$, —NR$_7$R$_8$, —(CR'''$_2$)$_{1-6}$C(O)NR$_7$R$_8$, —S(O)$_2$R$_A$, or —C(O)R$_A$;

$Y^4$ is aryl, heteroaryl, cycloalkyl, or non-aromatic heterocycle;

$R_A$ is selected from —NH$_2$, —NEt$_2$, and —NH(CH$_2$)$_{1-6}$OH;

$R_6$ is H, alkyl, substituted alkyl, cycloalkyl, non-aromatic heterocycle, aryl, or heteroaryl;

each of $R_7$ and $R_8$ is independently H, OH, halogen, $C_{1-6}$alkyl, $C_{1-6}$alkoxy, halo-$C_{1-6}$alkyl, or halo-$C_{1-6}$alkoxy;

or $R_7$ and $R_8$ taken together with the N atom to which they are attached may form a 3 to 6-membered heterocyclic ring;

$T_1$ is an optionally substituted moiety selected from -L$_4$-, -alkylene-L$_4$-, -L$_4$-alkylene-, -L$_4$-cycloalkylene-, -L$_4$-heteroalkylene-, -L$_4$-haloalkylene-, -L$_4$-arylene-, -L$_4$-heteroarylene-, and -L$_4$-heterocycloalkylene-; wherein $L_4$ is selected from a bond, —O—, —NH—, —S—, —CR''$_2$—, —NR'''C(O)—, —C(O)—, —C(S)—, —C(O)O—, —C(O)NR'''—, —S(O)—, —S(O)$_2$—, —OC(O)—, —C(O)NR'''(CR''$_2$)$_{1-6}$C(O)O—, —C(O)NR'''(CR''$_2$)$_{1-6}$C(O)—, —CR''$_2$NR'''CR''$_2$C(O)O—, —C(O)NR'''NR'''C(O)O—, —C(O)NR'''(CR''$_2$)$_{1-6}$—, —CR''$_2$C(O)—, and —S(O)NH—; wherein said optional substituents are selected from halogen, OH, $C_{1-6}$alkyl, $C_{1-6}$alkoxy, halo-$C_{1-6}$alkyl, halo-$C_{1-6}$alkoxy, aryl, haloaryl, and heteroaryl;

or a pharmaceutically acceptable salt, or pharmaceutically acceptable N-oxide thereof, in admixture with one or more pharmaceutically acceptable excipients.

12. The pharmaceutical composition of claim 1, wherein the compound having the structure of Formula (46) is selected from Formula (50), Formula (51), or Formula (52):

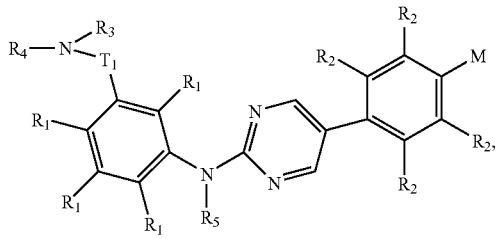

(50)

-continued

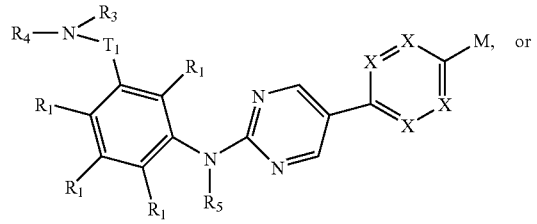

(51)

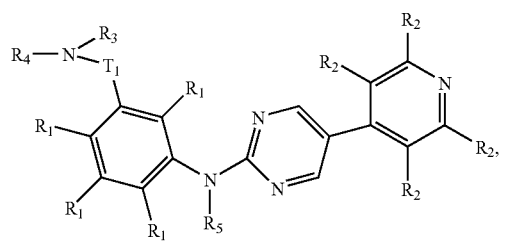

(52)

wherein:

M is selected from the group consisting of H, OH, SH, NO$_2$, CN, NR''$_2$, and an optionally substituted moiety selected from -L$_7$-alkyl, -L$_7$-cycloalkyl, -L$_7$-heteroalkyl, -L$_7$-haloalkyl, -L$_7$-aryl, -L$_7$-heterocycloalkyl, and -L$_7$-heteroaryl; wherein $L_7$ is selected from a bond, —O—, —NH—, —S—, —C(O)—, —C(S)—, —C(O)O—, —C(O)NH—, —S(O)—, —S(O)$_2$—, —OC(O)—, —C(O)NR''(CR''$_2$)$_{1-6}$C(O)O—, —CR''$_2$NR''CR''$_2$C(O)O—, —C(O)NR''Y$^1$C(O)O—, —C(O)NR''NR''C(O)O—, —S(O)NH—, —C(O)NR''CR''$_2$C(O)W—, —CR''$_2$NR''WO—, —CR''$_2$NR''Y$^1$C(O)O—, and —C(O)NR''O—; W is $C_{1-6}$alkylene; $Y^1$ is optionally substituted arylene or optionally substituted heteroarylene; wherein said optional substituents are selected from halogen, OH, $C_{1-6}$alkyl, $C_{1-6}$alkoxy, halo-$C_{1-6}$alkyl and halo-$C_{1-6}$alkoxy; provided that M is not H in Formula (23);

each R'' is independently H, OH, halogen, $C_{1-6}$alkyl, substituted $C_{1-6}$alkyl, $C_{1-6}$alkoxy, halo-$C_{1-6}$alkyl, halo-$C_{1-6}$alkoxy, aryl, haloaryl, or heteroaryl;

each X is independently selected from N or CR$_2$, provided that at least one but no more than 2X groups are N;

each $R_2$ is independently selected from the group consisting of H, OH, halogen, and an optionally substituted moiety selected from -L$_2$-alkyl, -L$_2$-cycloalkyl, -L$_2$-heteroalkyl, -L$_2$-haloalkyl, -L$_2$-aryl, -L$_2$-heterocycloalkyl, and -L$_2$-heteroaryl; wherein $L_2$ is selected from a bond, —O—, —NH—, —S—, —C(O)—, —C(S)—, —C(O)O—, —C(O)NH—, —S(O)—, —S(O)$_2$—, —C(O)NR''(CR''$_2$)$_{1-6}$C(O)O—, —OC(O)—, —CR''$_2$NR''CR''$_2$C(O)O—, —C(O)NR''NR''C(O)O—, and —S(O)NH—; wherein said optional substituents are selected from halogen, OH, $C_{1-6}$alkyl, $C_{1-6}$alkoxy, halo-$C_{1-6}$alkyl, and halo-$C_{1-6}$alkoxy;

or any two adjacent $R_2$ groups together may form an optionally substituted 5 to 8-membered heterocyclic, cycloalkyl, or aryl ring;

each of $R_3$ and $R_4$ is independently an optionally substituted-moiety selected from -Z, -L$_3$-Z, -L$_3$-H, -L$_3$-alkyl, -L$_3$-cycloalkyl, -L$_3$-heteroalkyl, -L$_3$-haloalkyl, -L$_3$-aryl, -L$_3$-heterocycloalkyl, and -L$_3$-heteroaryl; wherein $L_3$ is selected from a bond, —C(S)—, —C(O)O—, C(O)

NR'''—, —(CR'''$_2$)$_{1-6}$—, —CR'''$_2$S(O)—, —CR'''$_2$S(O)$_2$—, —CR'''$_2$S(O)NR'''—, —CR'''$_2$C(O)NR'''—, —(CR'''$_2$)$_{1-6}$NR'''—, —(CR'''$_2$)$_{1-6}$O—, —(CR'''$_2$)$_{1-6}$C(O)O—, —Y$^2$C(O)O—, and an optionally substituted C$_{1-6}$alkylene;
wherein:
said optional substituents are selected from halogen, —H, =O, —Y$^3$, C$_{1-6}$alkyl, C$_{1-6}$alkoxy, halogen or OH substituted C$_{1-6}$alkyl, halogen or OH substituted C$_{1-6}$alkoxy, —(CR'''$_2$)$_{1-6}$C(O)OR$_6$, —C(O)NR'''$_2$, —C(O)R$_6$, or —C(O)OR$_6$;
Y$^2$ is an optionally substituted cycloalkyl ring or optionally substituted non-aromatic heterocyclic ring; wherein said optional substituents are selected from C$_{1-6}$alkyl, halogen, —OH, =O, and —CN;
Y$^3$ is optionally substituted aryl, optionally substituted heteroaryl, optionally substituted cycloalkyl, or optionally substituted non-aromatic heterocycle; wherein said optional substituents are selected from C$_{1-6}$alkyl, halogen, —OH, =O, and —CN;
Z is —H, —OH, —CN, —COOR''', —NR'''$_2$, or —C≡CR''';
each R''' is independently H, alkyl, or substituted alkyl;
or two R''' together may form a 3-6 membered cycloalkyl or heterocyclic ring;
or R$_3$ and R$_4$ taken together with the N atom to which they are attached may form an optionally substituted 3 to 8-membered heterocyclic ring;
wherein:
said optional substituents are selected from halogen, —OH, =O, —Y$^3$, C$_{1-6}$alkyl, C$_{1-6}$alkoxyl, halogen or OH substituted C$_{1-6}$alkyl, halogen or OH substituted C$_{1-6}$alkoxy, —(CR'''$_2$)$_{1-6}$Y$^4$, —(CR'''$_2$)$_{1-6}$OR$_6$, —C(O)NR'''R$_6$, —C(O)OR$_6$, —OR$_6$, —NR'''C(O)OR$_6$, —NR'''C(O)R$_6$, —(CR'''$_2$)$_{1-6}$C(O)OR$_6$, —(CR'''$_2$)$_{1-6}$NR'''C(O)OR$_6$, —(CR'''$_2$)$_{1-6}$NR$_7$R$_8$, —S(O)$_2$NR'''$_2$, —C(O)R$_6$, —OC(O)R$_6$, —NR$_7$R$_8$, —(CR'''$_2$)$_{1-6}$C(O)NR$_7$R$_8$, —S(O)$_2$R$_4$, or —C(O)R$_4$;
Y$^4$ is aryl, heteroaryl, cycloalkyl, or non-aromatic heterocycle;

R$_4$ is selected from —NH$_2$, —NEt$_2$, and —NH(CH$_2$)$_{1-6}$OH;
R$_6$ is H, alkyl, substituted alkyl, cycloalkyl, non-aromatic heterocycle, aryl, or heteroaryl;
each of R$_7$ and R$_8$ is independently H, OH, halogen, C$_{1-6}$alkyl, C$_{1-6}$alkoxy, halo-C$_{1-6}$alkyl, or halo-C$_{1-6}$alkoxy;
or R$_7$ and R$_8$ taken together with the N atom to which they are attached may form a 3 to 6-membered heterocyclic ring;
T$_1$ is an optionally substituted moiety selected from -L$_4$-, -alkylene-L$_4$-, -L$_4$-alkylene-, -L$_4$-cycloalkylene-, -L$_4$-heteroalkylene-, -L$_4$-haloalkylene-, -L$_4$-arylene-, -L$_4$-heteroarylene-, and -L$_4$-heterocycloalkylene-; wherein L$_4$ is selected from a bond, —O—, —NH—, —S—, —CR''$_2$—, —NR'''C(O)—, —C(O)—, —C(S)—, —C(O)O—, —C(O)NR'''—, —S(O)—, —S(O)$_2$—, —OC(O)—, —C(O)NR'''(CR''$_2$)$_{1-6}$C(O)O—, —C(O)NR'''(CR''$_2$)$_{1-6}$C(O)—, —CR''$_2$NR'''CR''$_2$C(O)O—, —C(O)NR'''NR''C(O)O—, —C(O)NR'''(CR''$_2$)$_{1-6}$—, —CR''$_2$C(O)—, and —S(O)NH—; wherein said optional substituents are selected from halogen, OH, C$_{1-6}$alkyl, C$_{1-6}$alkoxy, halo-C$_{1-6}$alkyl, halo-C$_{1-6}$alkoxy, aryl, haloaryl, and heteroaryl;
or a pharmaceutically acceptable salt, or pharmaceutically acceptable N-oxide thereof, in admixture with one or more pharmaceutically acceptable excipients.

13. The pharmaceutical composition of any of claims 8, 9, 11 and 12, wherein each R$_2$ is H.

14. The pharmaceutical composition of claim 11, wherein the compound having the structure of Formula (23) is

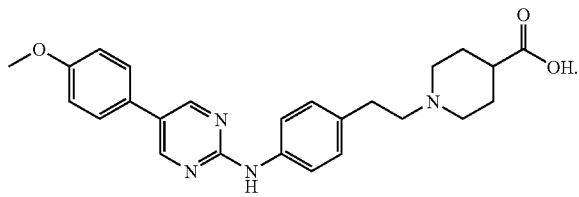

* * * * *